(12) United States Patent
Kawakami et al.

(10) Patent No.: US 9,136,479 B2
(45) Date of Patent: *Sep. 15, 2015

(54) ORGANIC COMPOUND, ANTHRACENE DERIVATIVE, AND LIGHT-EMITTING ELEMENT, LIGHT-EMITTING DEVICE, AND ELECTRONIC DEVICE USING THE ANTHRACENE DERIVATIVE

(71) Applicant: Semiconductor Energy Laboratory Co., Ltd., Atsugi-shi, Kanagawa-ken (JP)

(72) Inventors: Sachiko Kawakami, Isehara (JP); Nobuharu Ohsawa, Zama (JP); Satoshi Seo, Kawasaki (JP); Hiroki Suzuki, Atsugi (JP)

(73) Assignee: Semiconductor Energy Laboratory Co., Ltd., Atsugi-shi, Kanagawa-ken (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/327,584

(22) Filed: Jul. 10, 2014

(65) Prior Publication Data

US 2015/0004731 A1 Jan. 1, 2015

Related U.S. Application Data

(60) Continuation of application No. 13/958,789, filed on Aug. 5, 2013, now Pat. No. 8,816,098, which is a continuation of application No. 13/568,159, filed on Aug. 7, 2012, now Pat. No. 8,530,672, which is a
(Continued)

(30) Foreign Application Priority Data

Mar. 23, 2007 (JP) .................. 2007-077981

(51) Int. Cl.
*H01L 21/02* (2006.01)
*H01L 51/50* (2006.01)
(Continued)

(52) U.S. Cl.
CPC .......... *H01L 51/0052* (2013.01); *C07D 209/58* (2013.01); *C07D 209/86* (2013.01);
(Continued)

(58) Field of Classification Search
CPC ....... H01L 21/02; H01L 51/50; C07D 209/82
See application file for complete search history.

(56) References Cited

U.S. PATENT DOCUMENTS 5,811,834 A 9/1998 Tamano et al.
6,099,996 A 8/2000 Yanus et al.
(Continued)

FOREIGN PATENT DOCUMENTS

CN 001526689 A 9/2004
CN 001653857 A 8/2005
(Continued)

OTHER PUBLICATIONS

International Search Report (Application No. PCT/JP2006/306775) Dated May 2, 2006.
(Continued)

*Primary Examiner* — Samantha Shterengarts
(74) *Attorney, Agent, or Firm* — Eric J. Robinson; Robinson Intellectual Property Law Office, P.C.

(57) ABSTRACT

Objects of the present invention are to provide novel anthracene derivatives and novel organic compounds; a light-emitting element that has high emission efficiency; a light-emitting element that is capable of emitting blue light with high luminous efficiency; a light-emitting element that is capable of operation for a long time; and a light-emitting device and an electronic device that have lower power consumption. An anthracene derivative represented by a general formula (1) and an organic compound represented by a general formula (17) are provided. A light-emitting element that has high emission efficiency can be obtained by use of the anthracene derivative represented by the general formula (1). Further, a light-emitting element that has a long life can be obtained by use of the anthracene derivative represented by the general formula (1).

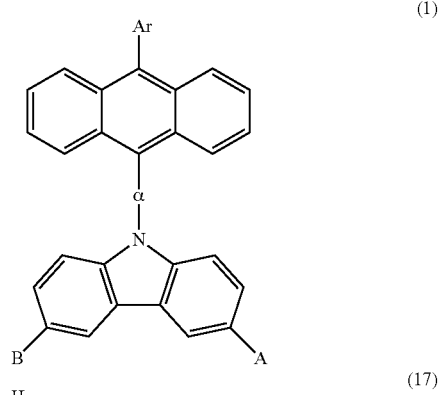

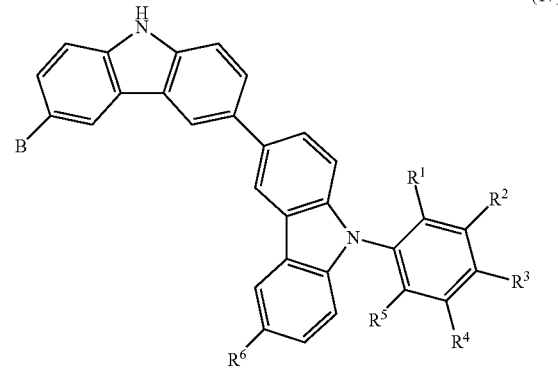

22 Claims, 71 Drawing Sheets

Related U.S. Application Data division of application No. 13/348,019, filed on Jan. 11, 2012, now Pat. No. 8,278,655, which is a continuation of application No. 12/760,076, filed on Apr. 14, 2010, now Pat. No. 8,134,147, which is a continuation of application No. 12/071,997, filed on Feb. 28, 2008, now Pat. No. 7,723,722.

(51) Int. Cl.

| | | |
|---|---|---|
| *C07D 209/82* | (2006.01) | |
| *H01L 51/00* | (2006.01) | |
| *C07D 209/86* | (2006.01) | |
| *C07D 403/04* | (2006.01) | |
| *C07D 403/10* | (2006.01) | |
| *C07D 403/14* | (2006.01) | |
| *C09K 11/06* | (2006.01) | |
| *C07D 209/58* | (2006.01) | |
| *H01L 51/56* | (2006.01) | |

(52) U.S. Cl.
CPC ............ *C07D403/04* (2013.01); *C07D 403/10* (2013.01); *C07D 403/14* (2013.01); *C09K 11/06* (2013.01); *H01L 51/006* (2013.01); *H01L 51/0061* (2013.01); *H01L 51/0072* (2013.01); *H01L 51/56* (2013.01); *C09K 2211/1007* (2013.01); *C09K 2211/1011* (2013.01); *C09K 2211/1029* (2013.01); *H01L 51/0059* (2013.01); *H01L 51/50* (2013.01); *H01L 51/5088* (2013.01); *Y10S 428/917* (2013.01)

(56) References Cited

U.S. PATENT DOCUMENTS

| | | |
|---|---|---|
| 6,482,986 B1 | 11/2002 | Boigegrain et al. |
| 6,617,051 B1 | 9/2003 | Higashi et al. |
| 6,627,333 B2 | 9/2003 | Hatwar |
| 6,713,566 B1 | 3/2004 | Marcuccio et al. |
| 6,815,094 B2 | 11/2004 | Lee et al. |
| 6,852,429 B1 | 2/2005 | Li et al. |
| 6,905,788 B2 | 6/2005 | Tyan et al. |
| 6,984,462 B2 | 1/2006 | Kim et al. |
| 7,132,456 B2 | 11/2006 | Gillig et al. |
| 7,148,502 B2 | 12/2006 | Yamazaki et al. |
| 7,161,185 B2 | 1/2007 | Yamazaki et al. |
| 7,252,894 B2 | 8/2007 | Yu et al. |
| 7,270,893 B2 | 9/2007 | Fukuda et al. |
| 7,387,845 B2 | 6/2008 | Saitoh et al. |
| 7,541,097 B2 | 6/2009 | Seo et al. |
| 7,629,060 B2 | 12/2009 | Oshiyama et al. |
| 7,641,986 B2 | 1/2010 | Lo et al. |
| 7,651,787 B2 | 1/2010 | Seo et al. |
| 7,704,912 B2 | 4/2010 | Reetz et al. |
| 7,723,722 B2 | 5/2010 | Kawakami et al. |
| 7,740,954 B2 | 6/2010 | Burn et al. |
| 7,745,988 B2 | 6/2010 | Sasaki et al. |
| 7,790,892 B2 | 9/2010 | Ikeda et al. |
| 7,834,538 B2 | 11/2010 | Yamazaki et al. |
| 7,985,491 B2 | 7/2011 | Kubota et al. |
| 8,025,988 B2 | 9/2011 | Burn et al. |
| 8,039,122 B2 | 10/2011 | Kawakami et al. |
| 8,080,934 B2 | 12/2011 | Kido et al. |
| 8,084,146 B2 | 12/2011 | Murase et al. |
| 8,482,193 B2 | 7/2013 | Kido et al. |
| 8,530,672 B2 | 9/2013 | Kawakami et al. |
| 2001/0052751 A1 | 12/2001 | Wakimoto et al. |
| 2003/0189401 A1 | 10/2003 | Kido et al. |
| 2003/0205696 A1 | 11/2003 | Thoms et al. |
| 2003/0215667 A1 | 11/2003 | Xie |
| 2004/0086745 A1 | 5/2004 | Iwakuma et al. |
| 2004/0161633 A1 | 8/2004 | Seo et al. |
| 2005/0116622 A1 | 6/2005 | Lo et al. |
| 2006/0068221 A1 | 3/2006 | Saitoh et al. |
| 2006/0115680 A1 | 6/2006 | Hwang et al. |
| 2007/0049760 A1 | 3/2007 | Kawakami et al. |
| 2007/0075632 A1 | 4/2007 | Kawakami et al. |
| 2007/0106103 A1 | 5/2007 | Ikeda et al. |
| 2007/0247063 A1 | 10/2007 | Murase et al. |
| 2008/0107918 A1 | 5/2008 | Egawa et al. |
| 2009/0015140 A1 | 1/2009 | Kawakami et al. |
| 2009/0102360 A1 | 4/2009 | Kawakami et al. |
| 2010/0069647 A1 | 3/2010 | Suzuki et al. |
| 2010/0076201 A1 | 3/2010 | Suzuki et al. |
| 2011/0037061 A1 | 2/2011 | Yamazaki et al. |
| 2011/0050118 A1 | 3/2011 | Egawa et al. |
| 2012/0007066 A1 | 1/2012 | Kawakami et al. |
| 2012/0138907 A1 | 6/2012 | Murase et al. |

FOREIGN PATENT DOCUMENTS

| | | |
|---|---|---|
| CN | 001984897 A | 6/2007 |
| CN | 101200634 A | 6/2008 |
| EP | 1351558 A | 10/2003 |
| EP | 1748045 A | 1/2007 |
| EP | 1829871 A | 9/2007 |
| EP | 1864962 A | 12/2007 |
| EP | 2450356 A | 5/2012 |
| JP | 11-144876 A | 5/1999 |
| JP | 2003-031371 A | 1/2003 |
| JP | 2003-167550 A | 6/2003 |
| JP | 2003-229273 A | 8/2003 |
| JP | 2003-317966 A | 11/2003 |
| JP | 2004-087396 A | 3/2004 |
| JP | 2004-091334 A | 3/2004 |
| JP | 2004-178895 A | 6/2004 |
| JP | 2004-311415 A | 11/2004 |
| JP | 2005-521210 | 7/2005 |
| JP | 2007-039431 A | 2/2007 |
| JP | 2007-063501 A | 3/2007 |
| JP | 2007-131722 A | 5/2007 |
| JP | 2008-195841 A | 8/2008 |
| TW | 200306762 | 11/2003 |
| TW | 200503577 | 1/2005 |
| WO | WO-01/23353 | 4/2001 |
| WO | 2003-238534 A | 8/2003 |
| WO | WO-03/079736 | 9/2003 |
| WO | WO-2004/020547 | 3/2004 |
| WO | WO-2005/113531 | 12/2005 |
| WO | WO-2006/104044 | 10/2006 |
| WO | WO-2006/104221 | 10/2006 |
| WO | WO-2007/026626 | 3/2007 |

OTHER PUBLICATIONS

Written Opinion (Application No. PCT/JP2006/306775) Dated May 2, 2006.
International Search Report (Application No. PCT/JP2007/066706) Dated Oct. 16, 2007.
Written Opinion (Application No. PCT/JP2007/066706) Dated Oct. 16, 2007.
International Search Report (Application No. PCT/JP2009/062568) Dated Aug. 11, 2009.
Written Opinion (Application No. PCT/JP2009/062568) Dated Aug. 11, 2009.
Search Report (Application No. 09169453.9) Dated Nov. 3, 2009.
Search Report (Application No. 06730723.1) Dated Jan. 26, 2010.
Office Action (Application No. 200680018801.4) Dated Apr. 15, 2010.
Li.J et al., "CuI/DABCO-Catalyzed Cross-Coupling Reactions of Aryl Halides with Arylboronic Acids", Eur. J. Org. Chem(European Journal of Organic Chemistry), 2006, pp. 2063-2066.
Kim.S et al., "Synthesis and Hole-Transporting Properties of Phenyl-Carbazyl Derivatives", Mol. Cryst. Liq. Cryst. (Molecular Crystals and Liquid Crystals), 2008, vol. 491, pp. 133-144, Taylor & Francis.
Grisorio.R et al., "Novel Bifluorene Based Conjugated Systems: Synthesis and Properties", Tetrahedron, 2006, vol. 62, pp. 627-634.
Notice from JPO and IDS from 3rd Party for counterpart JP application (Application No. JP2008-071125) Dated Jul. 12, 2011.

(56) References Cited

OTHER PUBLICATIONS

Promarak.V et al., "Synthesis and Properties of Stable Amorphous Hole-Transporting molecules for electroluminescent devices", Tetrahedron Letters, 2006, vol. 47, No. 50, pp. 8949-8952.
Search Report (Application No. 08003826.8) Dated Jul. 14, 2008.
Li.Z et al., "Synthesis and Functional Properties of End-Dendronized Oligo(9,9-diphenyl)fluorenes", Organic Letters, Mar. 9, 2006, vol. 8, No. 7, pp. 1499-1502.
Chinese Office Action (Application No. 200810086266.7) Dated Jul. 26, 2011.
Taiwanese Office Action (Application No. 97108908) Dated Jul. 17, 2013.
Thomas.K et al., "Quinoxalines Incorporating Triarylamines: Potential Electroluminescent Materials With Tunable mission Characteristics", Chem. Mater. (Chemistry of Materials), 2002, vol. 14, No. 6, pp. 2796-2802.
Thomas.K et al., "Green and Yellow Electroluminescent Dipolar Carbazole Derivatives: Features and Benefits of Electron-Withdrawing Segments", Chem. Mater. (Chemistry of Materials), 2002, vol. 14, No. 9, pp. 3852-3859.
Thomas.K et al., "New Carbazole-Oxadiazole Dyads for Electroluminescent Devices: Influence of Acceptor Substituents on Luminescent and Theramal Properties", Chem. Mater. (Chemistry of Materials), 2004, vol. 16, No. 25, pp. 5437-5444.
Thomas.K et al., "Cyanocarbazole Derivatives for High-Performance Electroluminescent Devices", Adv. Funct. Mater. (Advanced Functional Materials), Apr. 1, 2004, vol. 14, No. 4, pp. 387-392.
Chakrabarty.M et al., "An Expedient Synthesis of 5,11-Dimethylindolo[3,2-b]-carbazole, A Potent Ligand for the Receptor for TCDD", 1996, vol. 26, No. 16, pp. 3015-3023.
Paliulis.O et al., "Synthesis of Conjugated Carbazole Trimers and Pentamers by Suzuki Coupling", Macromolecular Chemistry and Physics(Macromol. chem. phys.), Sep. 19, 2003, vol. 204, No. 14, pp. 1706-1712.
Korean Office Action (Application No. 2014-0135541) Dated Jan. 12, 2015.
Chinese Office Action (Application No. 201310190127.X) Dated Mar. 26, 2015.

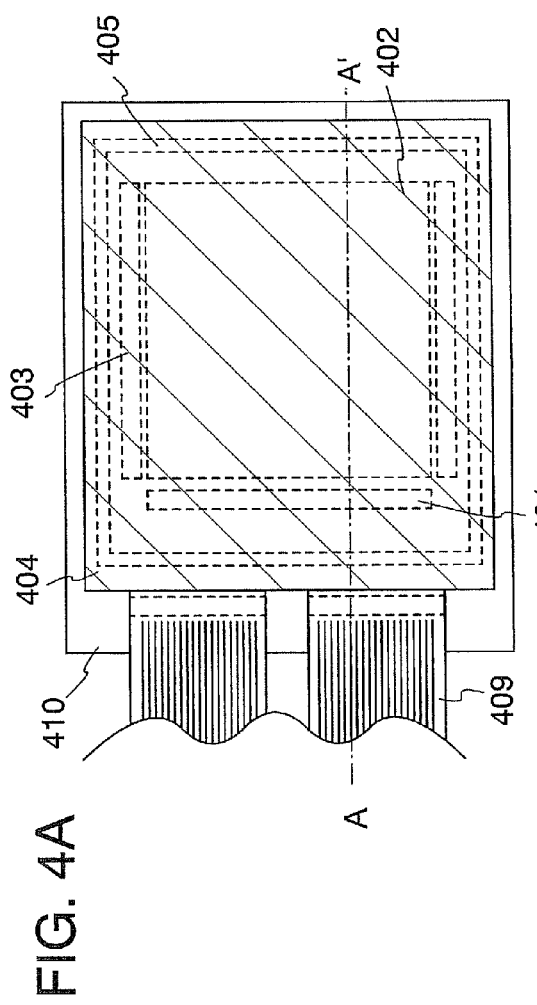
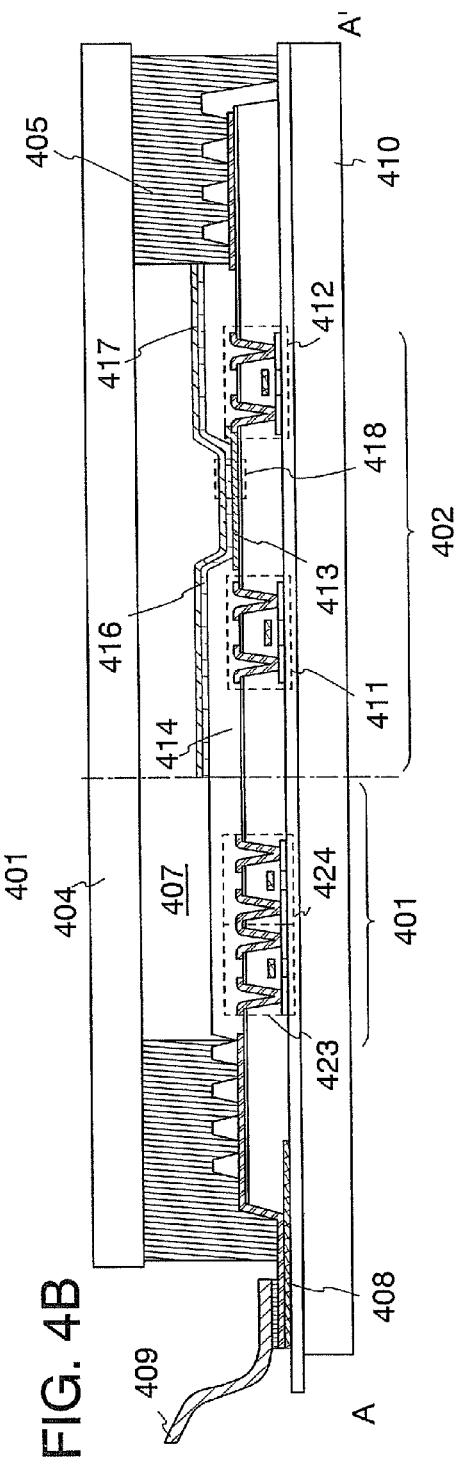
FIG. 4A
FIG. 4B

ORGANIC COMPOUND, ANTHRACENE DERIVATIVE, AND LIGHT-EMITTING ELEMENT, LIGHT-EMITTING DEVICE, AND ELECTRONIC DEVICE USING THE ANTHRACENE DERIVATIVE

BACKGROUND OF THE INVENTION

1. Field of the Invention

The present invention relates to organic compounds, anthracene derivatives, and light-emitting elements, light-emitting devices, and electronic devices each of which use the anthracene derivatives.

2. Description of the Related Art

Light-emitting elements that use light-emitting materials have advantages of being thin, being lightweight, and the like, and are expected to be applied to next-generation displays. Further, since the light-emitting elements are self-light-emitting elements, the light-emitting elements are superior to liquid crystal displays (LCDs) because they have high visibility without a problem such as a viewing angle.

A basic structure of a light-emitting element is a structure in which a light-emitting layer is included between a pair of electrodes. It is said that, when a voltage is applied to such a light-emitting element, holes injected from an anode and electrons injected from a cathode are recombined with each other in a luminescent center of the light-emitting layer to excite molecules, and the molecular excitons release energy in returning to a ground state, whereby light is emitted. It is to be noted that excited states generated by the recombination include a singlet state and a triplet state. The light emission can be obtained in either of the excited states. In particular, the light emission occurring when the singlet-excited state directly returns to the ground state is referred to as fluorescence, and the light emission occurring when the triplet-excited state returns to the ground state is referred to as phosphorescence.

With such light-emitting elements, there are a lot of material-related problems for improvement of element characteristics. In order to solve the problems, improvement of an element structure, development of materials, and the like have been carried out.

For example, in Patent Document 1: United States Patent Application Publication No. 2005-0260442, an anthracene derivative that emits green light is described. However, Patent Document 1 discloses only the emission spectrum of the anthracene derivative but not the device performance for when the anthracene derivative was applied to a light-emitting element.

Also, in Patent Document 2: Japanese Published Patent Application No. 2004-91334, a light-emitting element in which an anthracene derivative is used for a charge transporting layer is described. However, in Patent Document 2, there is no description of the life of the light-emitting element.

If commercialization is considered, extending the life of the light-emitting element is an important issue. Further, the development of light-emitting elements with much higher levels of performance is desired.

SUMMARY OF THE INVENTION

In view of the foregoing problems, objects of the present invention are to provide novel organic compounds and anthracene derivatives.

Another object of the present invention is to provide a light-emitting element that has emission efficiency. Further, another object of the present invention is to provide a light-emitting element that emits blue light at high luminous efficiency. Another object of the present invention is to provide a light-emitting device that is capable of operation for a long time.

Another object of the present invention is to provide a light-emitting device and electronic device that have reduced power consumption.

As a result of diligent study, the inventors have found that the problems can be solved with an anthracene derivative represented by a general formula (1) given below. Thus, one aspect of the present invention is an anthracene derivative represented by the general formula (1) given below.

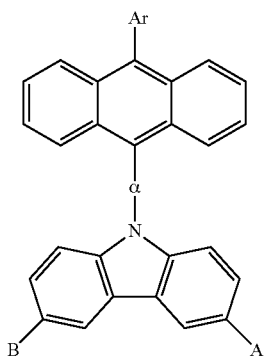

(1)

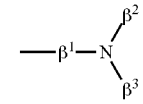

(2-1)

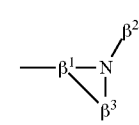

(2-2)

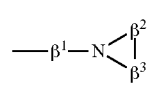

(2-3)

In the general formula (1), Ar represents an aryl group having 6 to 25 carbon atoms; α represents an arylene group having 6 to 25 carbon atoms; A is represented by any of the above structural formulae (2-1) to (2-3); $\beta^1$ to $\beta^3$ each represent a substituted or unsubstituted benzene ring; and B is any of hydrogen, an alkyl group having 1 to 4 carbon atoms, an aryl group having 6 to 25 carbon atoms, a halogen group, and a haloalkyl group or is represented by any of the above structural formulae (2-1) to (2-3).

A more preferable aspect of the present invention is an anthracene derivative represented by the above general formula (1) in which $\beta^1$ is an unsubstituted benzene ring.

One aspect of the present invention is an anthracene derivative represented by a general formula (3) given below.

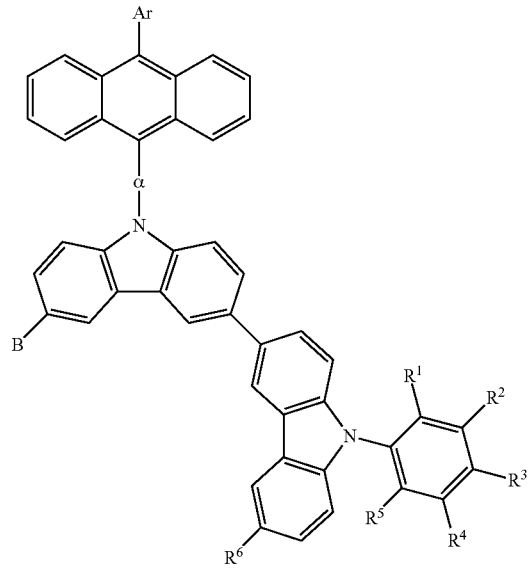

(3)

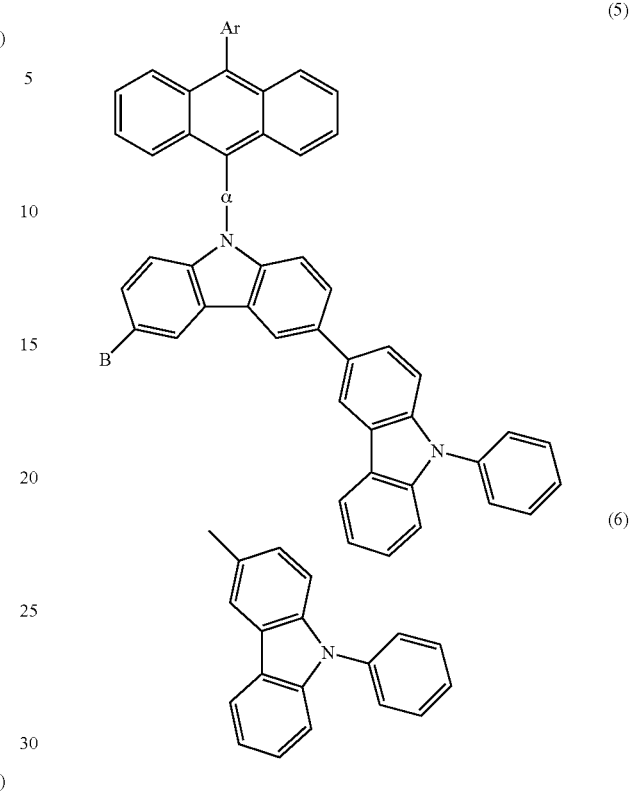

(5)

(6)

In the general formula (5), Ar represents an aryl group having 6 to 25 carbon atoms; α represents an arylene group having 6 to 25 carbon atoms; and B represents any of hydrogen, an alkyl group having 1 to 4 carbon atoms, an aryl group having 6 to 25 carbon atoms, a halogen group, and a haloalkyl group or is represented by the above structural formula (6).

One aspect of the present invention is an anthracene derivative represented by a general formula (7) given below.

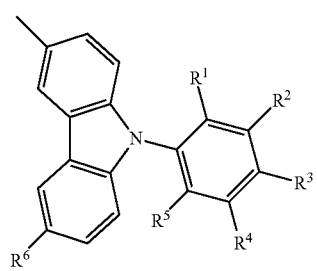

(4)

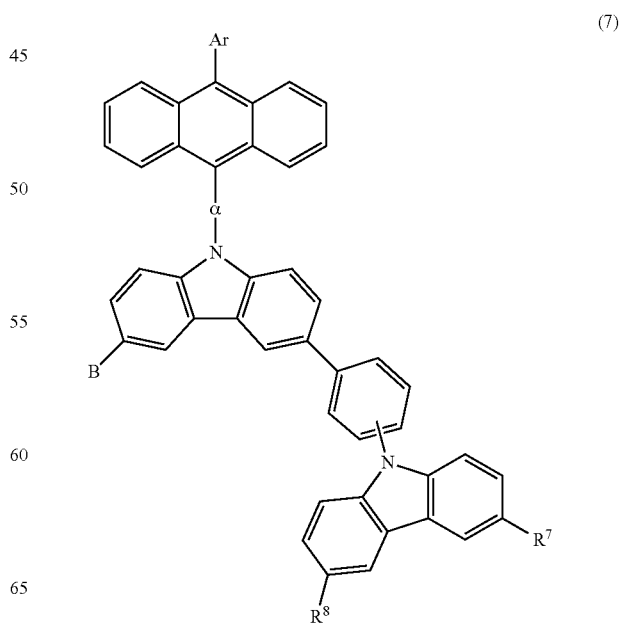

(7)

In the general formula (3), Ar represents an aryl group having 6 to 25 carbon atoms; a represents an arylene group having 6 to 25 carbon atoms; $R^1$ to $R^6$ each represent any of hydrogen, an alkyl group having 1 to 4 carbon atoms, a halogen group, a haloalkyl group, and an aryl group having 6 to 25 carbon atoms and may be the same or different from one another; and B represents any of hydrogen, an alkyl group having 1 to 4 carbon atoms, an aryl group having 6 to 25 carbon atoms, a halogen group, and a haloalkyl group or is represented by the above structural formula (4). In the structural formula (4), $R^1$ to $R^6$ each represent any of hydrogen, an alkyl group having 1 to 4 carbon atoms, a halogen group, a haloalkyl group, and an aryl group having 6 to 25 carbon atoms and may be the same or different from one another.

One aspect of the present invention is an anthracene derivative represented by a general formula (5) given below.

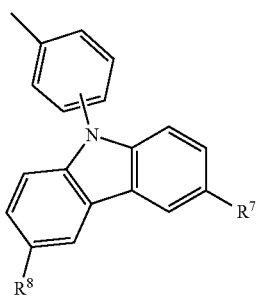

(8)

In the general formula (7), Ar represents an aryl group having 6 to 25 carbon atoms; α represents an arylene group having 6 to 25 carbon atoms; $R^7$ and $R^8$ each represent any of hydrogen, an alkyl group having 1 to 4 carbon atoms, a halogen group, a haloalkyl group, and an aryl group having 6 to 25 carbon atoms and may be the same or different from one another; B represents any of hydrogen, an alkyl group having 1 to 4 carbon atoms, an aryl group having 6 to 25 carbon atoms, a halogen group, and a haloalkyl group or is represented by the above structural formula (8); and, in the above structural formula (8), $R^7$ and $R^8$ each represent any of hydrogen, an alkyl group having 1 to 4 carbon atoms, a halogen group, a haloalkyl group, and an aryl group having 6 to 25 carbon atoms and may be the same or different from one another.

One aspect of the present invention is an anthracene derivative represented by a general formula (9) given below.

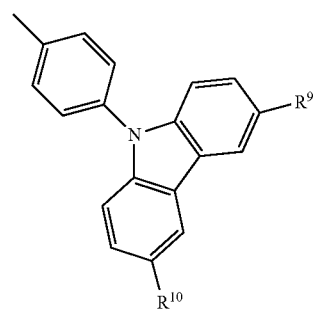

(10)

In the general formula (9), Ar represents an aryl group having 6 to 25 carbon atoms; α represents an arylene group having 6 to 25 carbon atoms; $R^9$ and $R^{10}$ each represent any of hydrogen, an alkyl group having 1 to 4 carbon atoms, a halogen group, a haloalkyl group, and an aryl group having 6 to 25 carbon atoms and may be the same or different from one another; B represents any of hydrogen, an alkyl group having 1 to 4 carbon atoms, an arylene group having 6 to 25 carbon atoms, a halogen group, and a haloalkyl group or is represented by the above structural formula (10); and, in the above structural formula (10), $R^9$ and $R^{10}$ each represent any of hydrogen, an alkyl group having 1 to 4 carbon atoms, a halogen group, a haloalkyl group, and an aryl group having 6 to 25 carbon atoms and may be the same or different from one another.

One aspect of the present invention is an anthracene derivative represented by a general formula (11) given below.

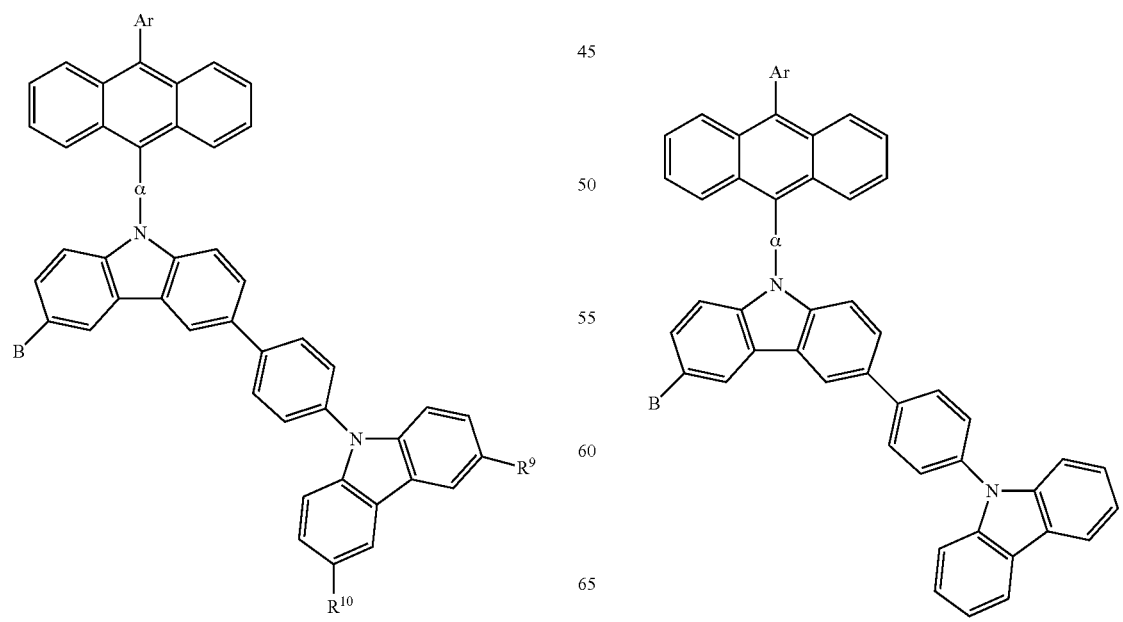

-continued (12)

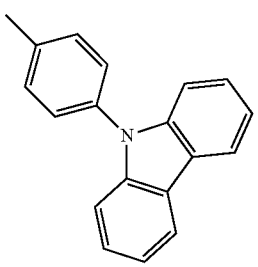

In the general formula (11), Ar represents an aryl group having 6 to 25 carbon atoms; α represents an arylene group having 6 to 25 carbon atoms; and B represents any of hydrogen, an alkyl group having 1 to 4 carbon atoms, an aryl group having 6 to 25 carbon atoms, a halogen group, and a haloalkyl group or is represented by the above structural formula (12).

One aspect of the present invention is an anthracene derivative represented by a general formula (13) given below.

(13)

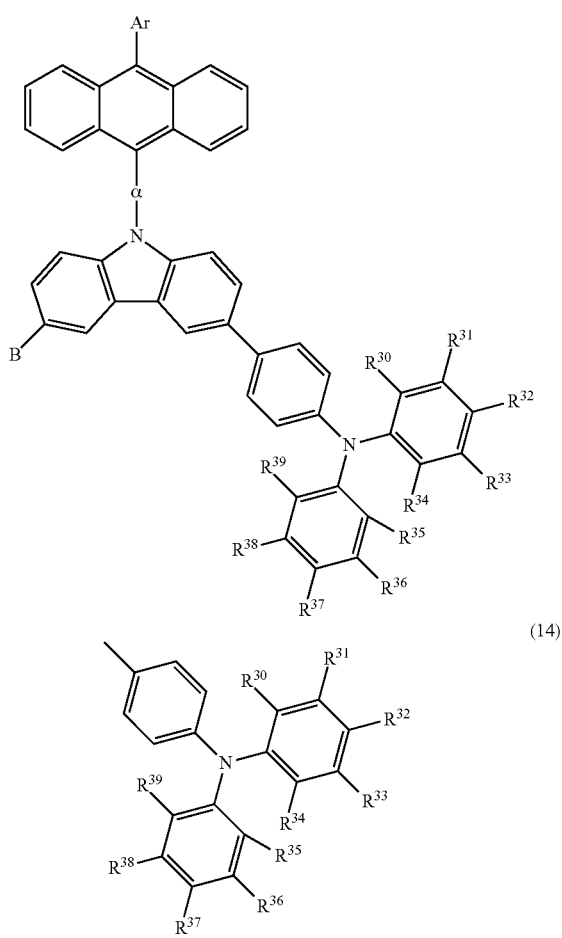

(14)

In the general formula (13), Ar represents an aryl group having 6 to 25 carbon atoms; α represents an arylene group having 6 to 25 carbon atoms; $R^{30}$ to $R^{39}$ each represent any of hydrogen, an alkyl group having 1 to 4 carbon atoms, a halogen group, a haloalkyl group, and an aryl group having 6 to 25 carbon atoms and may be the same or different from one another; and B represents any of hydrogen, an alkyl group having 1 to 4 carbon atoms, an aryl group having 6 to 25 carbon atoms, a halogen group, and a haloalkyl group or is represented by the above structural formula (14). In the structural formula (14), $R^{30}$ to $R^{39}$ each represent any of hydrogen, an alkyl group having 1 to 4 carbon atoms, a halogen group, a haloalkyl group, and an aryl group having 6 to 25 carbon atoms and may be the same or different from one another.

One aspect of the present invention is an anthracene derivative represented by a general formula (15) given below.

(15)

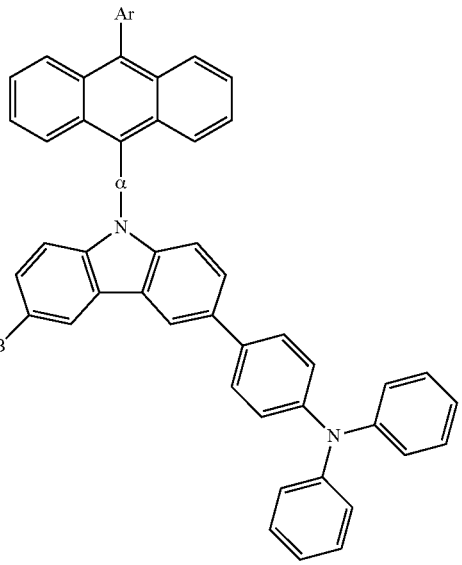

(16)

In the general formula (15), Ar represents an aryl group having 6 to 25 carbon atoms; α represents an arylene group having 6 to 25 carbon atoms; and B represents any of hydrogen, an alkyl group having 1 to 4 carbon atoms, an aryl group having 6 to 25 carbon atoms, a halogen group, and a haloalkyl group or is represented by the above structural formula (16).

One aspect of the present invention is a light-emitting element including any of the above anthracene derivatives.

The light-emitting element of the present invention thus obtained can be made to have a long life, and therefore, a light-emitting device (e.g., an image display device) using such light-emitting element can be made to have a long life. Thus, the present invention also covers the light-emitting device and an electronic device each of which uses the light-emitting element of the present invention.

The light-emitting device of the present invention includes a light-emitting element including any of the above-described anthracene derivatives, and a control circuit configured to control light emission from the light-emitting element. The light-emitting device in this specification includes an image display device that uses a light-emitting element. Further, the category of the light-emitting device also includes a module in which a tape automated bonding (TAB) tape or a tape carrier package (TCP) is attached to a light-emitting element; a module in which a printed wiring board is provided at an end of a TAB tape or a TCP; and a module in which an integrated circuit (IC) is directly mounted on a light-emitting element by a chip on glass (COG) method. Moreover, a light-emitting device used in a lighting device or the like is also included.

Further, an electronic device that uses the light-emitting element of the present invention in its display portion is also included in the category of the present invention. Accordingly, one aspect of the present invention is an electronic device having a display portion, where the display portion includes the above-described light-emitting element and a control circuit configured to control light emission from the light-emitting element.

Furthermore, the present invention covers also organic compounds used for synthesis of the anthracene derivatives of the present invention because the organic compounds used for synthesis of the anthracene derivatives of the present invention are novel materials. Accordingly, one aspect of the present invention is an organic compound represented by a general formula (17) given below.

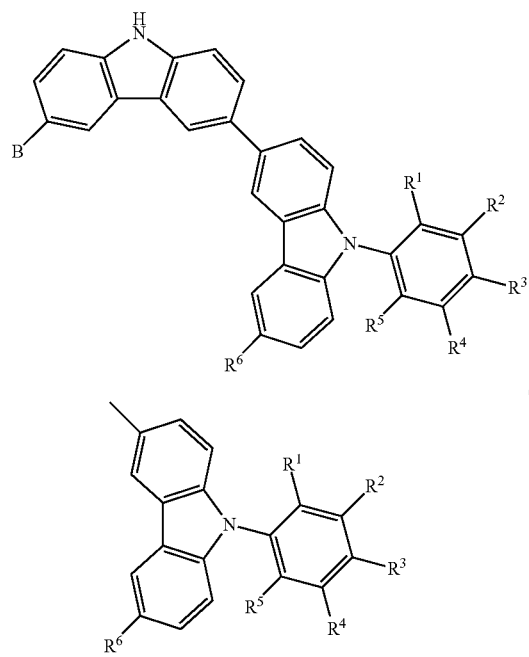

In the general formula (17), $R^1$ to $R^6$ each represent any of hydrogen, an alkyl group having 1 to 4 carbon atoms, a halogen group, a haloalkyl group, and an aryl group having 6 to 25 carbon atoms and may be the same or different from one another; and B represents any of hydrogen, an alkyl group having 1 to 4 carbon atoms, an aryl group having 6 to 25 carbon atoms, a halogen group, and a haloalkyl group or is represented by the above structural formula (18). In the structural formula (18), $R^1$ to $R^6$ each represent any of hydrogen, an alkyl group having 1 to 4 carbon atoms, an aryl group having 6 to 25 carbon atoms, a halogen group, and a haloalkyl group, and may be the same or different from one another.

One aspect of the present invention is an organic compound represented by a general formula (19) given below.

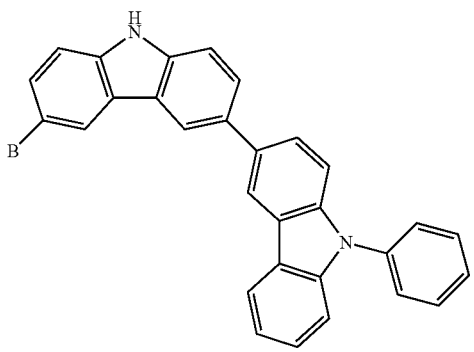

In the general formula (19), B represents any of hydrogen, an alkyl group having 1 to 4 carbon atoms, an aryl group having 6 to 25 carbon atoms, a halogen group, and a haloalkyl group or is represented by the above structural formula (20).

One aspect of the present invention is an organic compound represented by a general formula (21) given below.

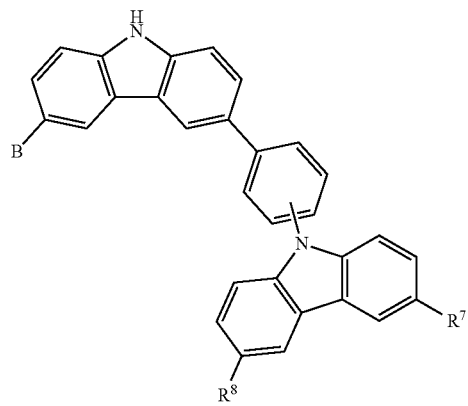

In the general formula (21), $R^7$ and $R^8$ each represent any of hydrogen, an alkyl group having 1 to 4 carbon atoms, a halogen group, a haloalkyl group, and an aryl group having 6 to 25 carbon atoms and may be the same or different from one another; B represents any of hydrogen, an alkyl group having 1 to 4 carbon atoms, an aryl group having 6 to 25 carbon atoms, a halogen group, and a haloalkyl group or is represented by the above structural formula (22); and, in the above structural formula (22), $R^7$ and $R^8$ each represent any of hydrogen, an alkyl group having 1 to 4 carbon atoms, a halogen group, a haloalkyl group, and an aryl group having 6 to 25 carbon atoms and may be the same or different from one another.

One aspect of the present invention is an organic compound represented by a general formula (23) given below.

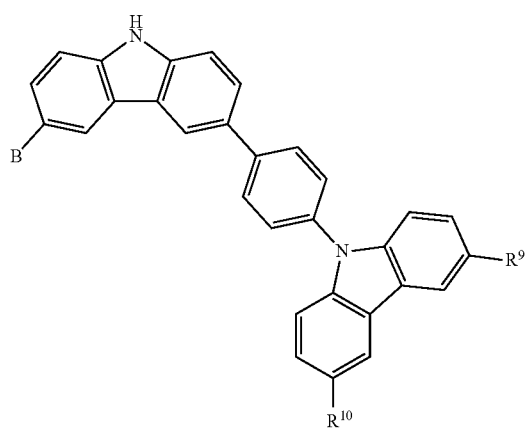

(23)

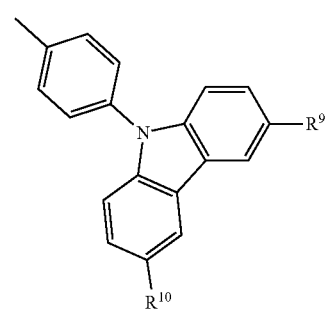

(24)

In the general formula (23), $R^9$ and $R^{10}$ each represent any of hydrogen, an alkyl group having 1 to 4 carbon atoms, a halogen group, a haloalkyl group, and an aryl group having 6 to 25 carbon atoms and may be the same or different from one another; B represents any of hydrogen, an alkyl group having 1 to 4 carbon atoms, an aryl group having 6 to 25 carbon atoms, a halogen group, and a haloalkyl group or is represented by the above structural formula (24); and, in the above structural formula (24), $R^9$ and $R^{10}$ each represent any of hydrogen, an alkyl group having 1 to 4 carbon atoms, a halogen group, a haloalkyl group, and an aryl group having 6 to 25 carbon atoms and may be the same or different from one another.

One aspect of the present invention is an organic compound represented by a general formula (25) given below.

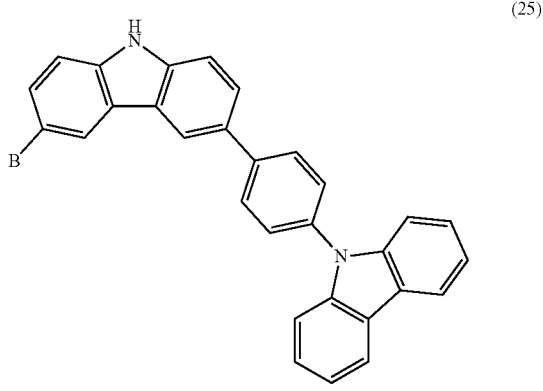

(25)

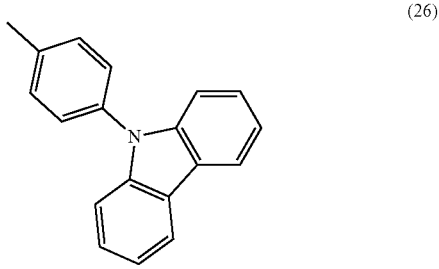

(26)

In the general formula (25), B represents any of hydrogen, an alkyl group having 1 to 4 carbon atoms, an aryl group having 6 to 25 carbon atoms, a halogen group, and a haloalkyl group or is represented by the above structural formula (26).

One aspect of the present invention is an organic compound represented by a general formula (27) given below.

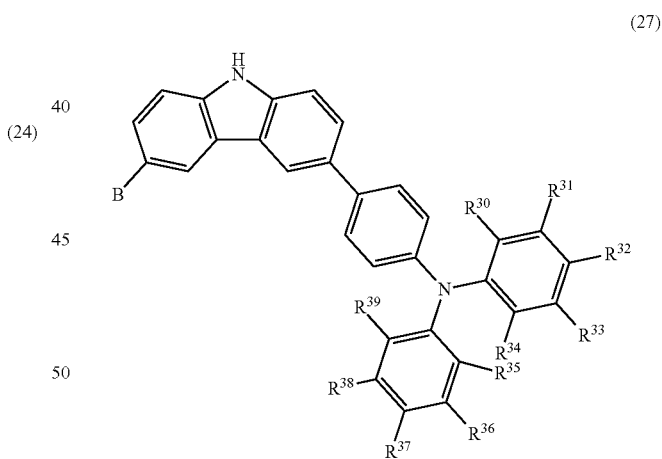

(27)

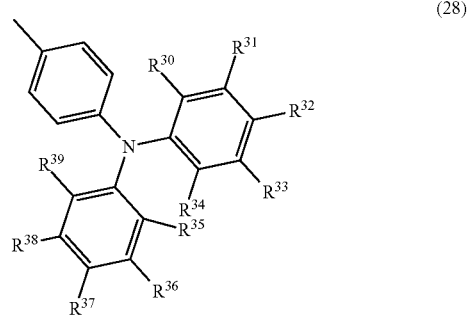

(28)

In the general formula (27), $R^{30}$ to $R^{39}$ each represent any of hydrogen, an alkyl group having 1 to 4 carbon atoms, a halogen group, a haloalkyl group, and an aryl group having 6 to 25 carbon atoms and may be the same or different from one another; and B represents any of hydrogen, an alkyl group having 1 to 4 carbon atoms, an aryl group having 6 to 25 carbon atoms, a halogen group, and a haloalkyl group or is represented by the above structural formula (28). In the structural formula (28), $R^{30}$ to $R^{39}$ each represent any of hydrogen, an alkyl group having 1 to 4 carbon atoms, a halogen group, a haloalkyl group, and an aryl group having 6 to 25 carbon atoms and may be the same or different from one another.

One aspect of the present invention is an organic compound represented by a general formula (29) given below.

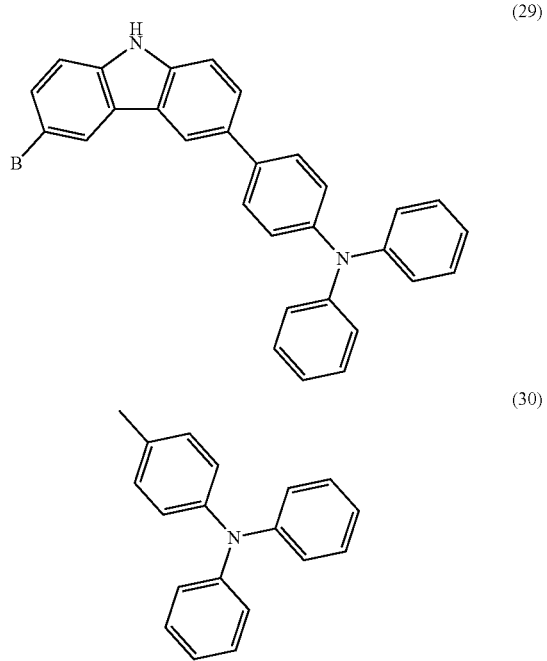

In the general formula (29), B represents any of hydrogen, an alkyl group having 1 to 4 carbon atoms, an aryl group having 6 to 25 carbon atoms, a halogen group, and a haloalkyl group or is represented by the above structural formula (30).

The anthracene derivatives of the present invention emit light at high efficiency. Therefore, by use of any of the anthracene derivatives of the present invention in a light-emitting element, a light-emitting element with high emission efficiency can be obtained. Also, by use of any of the anthracene derivatives of the present invention in a light-emitting element, the light-emitting element with a long life can be obtained.

Further, by use of any of the anthracene derivatives of the present invention, a light-emitting device and electronic device each having a long life can be obtained.

BRIEF DESCRIPTION OF THE DRAWINGS

In the accompanying drawings:
FIGS. 4A and 4B illustrate a light-emitting device of the present invention.

DETAILED DESCRIPTION OF THE INVENTION

Figure 1:
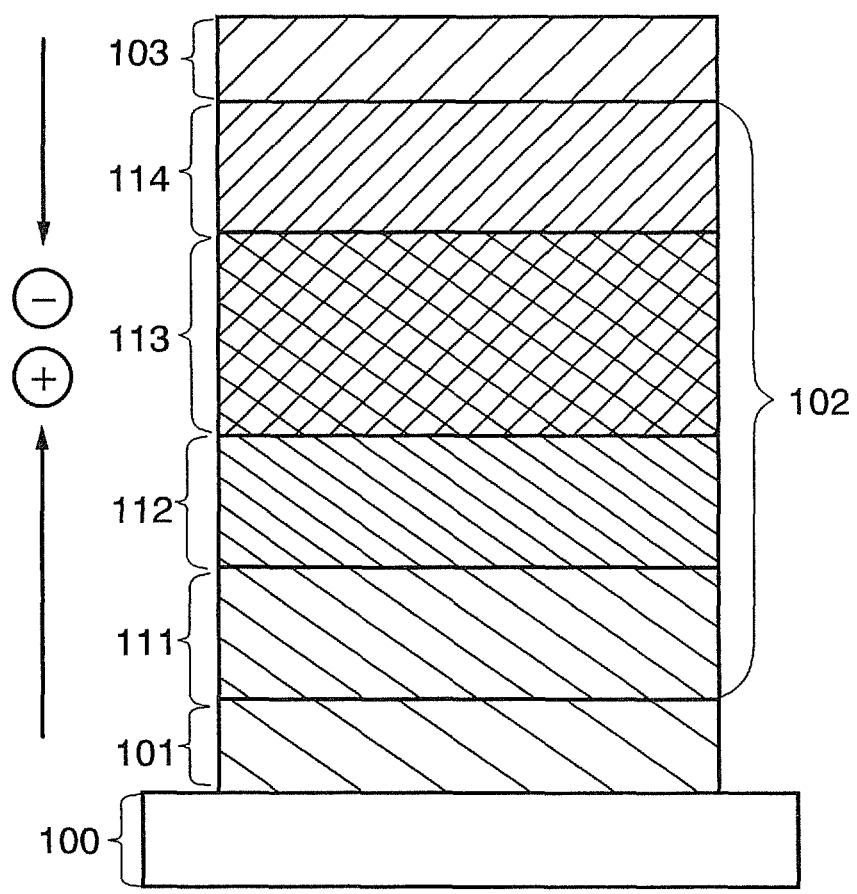
FIG. 1 illustrates a light-emitting element of the present invention.

Hereinafter, embodiment modes and examples of the present invention are described using the accompanying drawings. It is to be noted that the present invention can be carried out in many a variety of modes. It is easily understood by those skilled in the art that a variety of changes may be made in forms and details without departing from the spirit and the scope of the present invention. Therefore, the present invention should not be limited to the description of the embodiment modes and examples below.

(Embodiment Mode 1)

In this embodiment mode, anthracene derivatives of the present invention are described.

An anthracene derivative of the present invention is represented by a general formula (31).

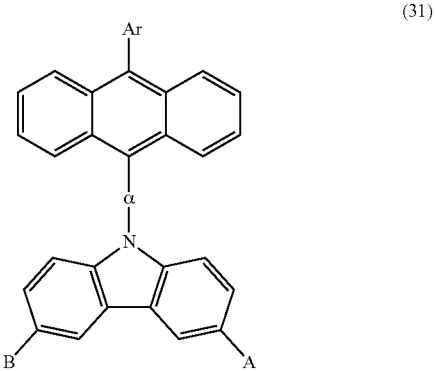

(31)

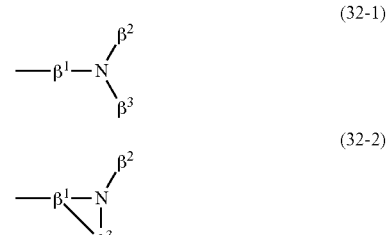

(32-1)

(32-2)

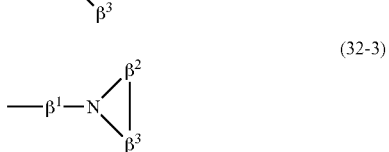

(32-3)

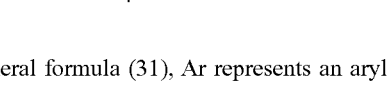

In the above general formula (31), Ar represents an aryl group having 6 to 25 carbon atoms; α represents an arylene group having 6 to 25 carbon atoms; A is represented by any of the above structural formulae (32-1) to (32-3); $\beta^1$ to $\beta^3$ each represent a substituted or unsubstituted benzene ring; and B is any of hydrogen, an alkyl group having 1 to 4 carbon atoms, an aryl group having 6 to 25 carbon atoms, a halogen group, and a haloalkyl group or is represented by any of the above structural formulae (32-1) to (32-3).

In the general formula (31), as examples of the substituent represented by Ar, substituents represented by structural formulae (33-1) to (33-9) are given.

(33-1)

(33-2) 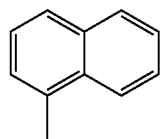
(33-3) 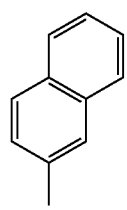
(33-4) 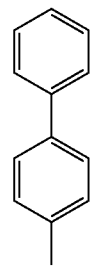
(33-5) 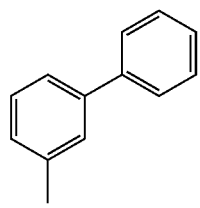
(33-6) 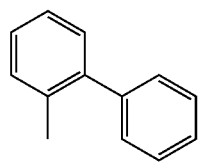
(33-7) 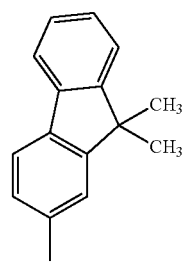
(33-8) 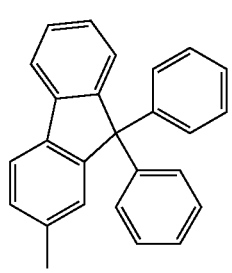
(33-9) 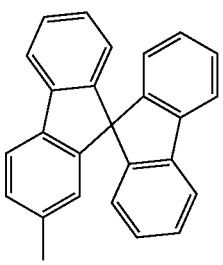
In the general formula (31), as examples of the substituent represented by α, substituents represented by structural formulae (34-1) to (34-9) are given.
(34-1) 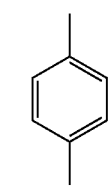
(34-2) 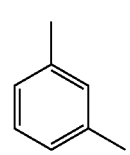
(34-3) 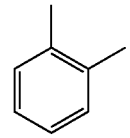
(34-4) 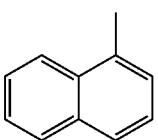
(34-5) 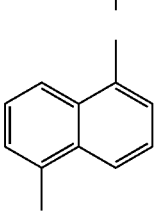
(34-6) 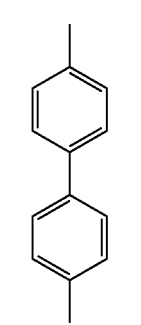

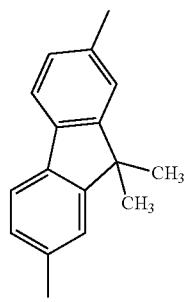
(34-7)

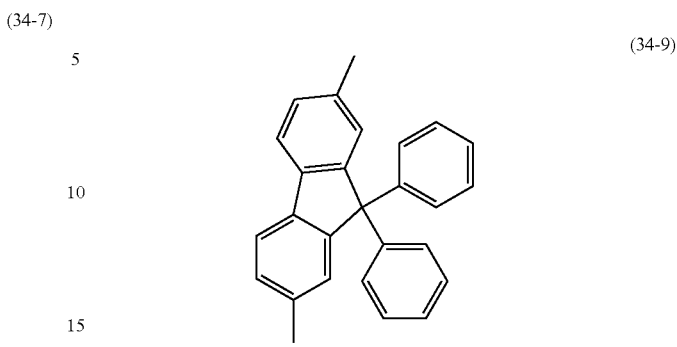
(34-9)

(34-8)

In the above general formula (31), Ar and α each may be substituted with either an alkyl group having 1 to 4 carbon atoms or an alkoxy group having 1 to 4 carbon atoms. The solubility of the anthracene derivative of the present invention is increased, whereby a light-emitting element can be fabricated by a wet process. Examples of the above alkyl group having 1 to 4 carbon atoms include a methyl group, an ethyl group, and a butyl group. Examples of the above alkoxy group having 1 to 4 carbon atoms include a methoxy group, an ethoxy group, and a butoxy group.

Examples of the anthracene derivatives of the present invention include, but are not limited to, anthracene derivatives represented by structural formulae (101) to (414) given below.

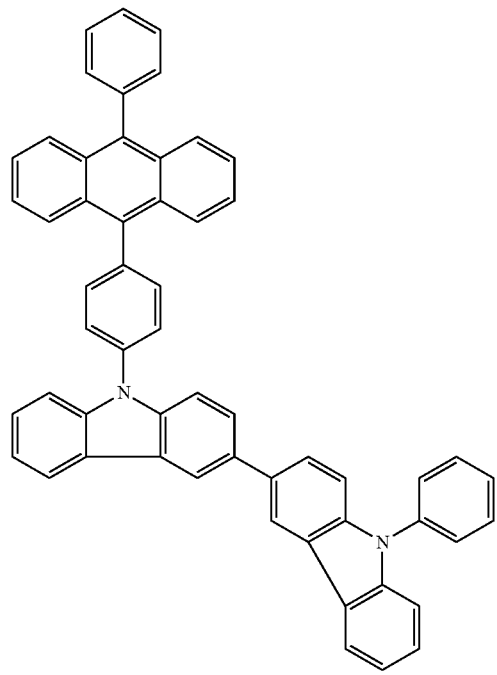
(101)

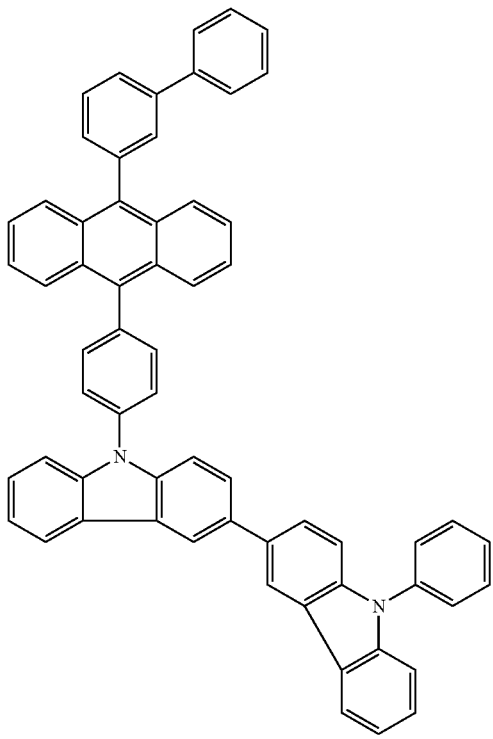
(102)

(103)
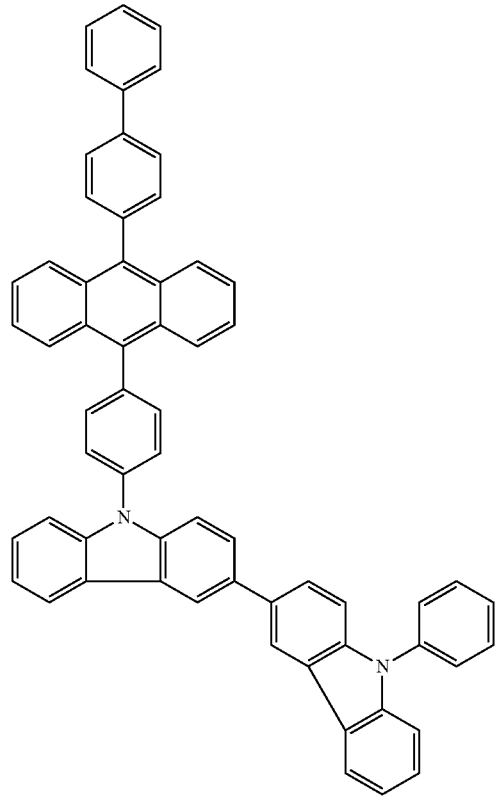
(104)
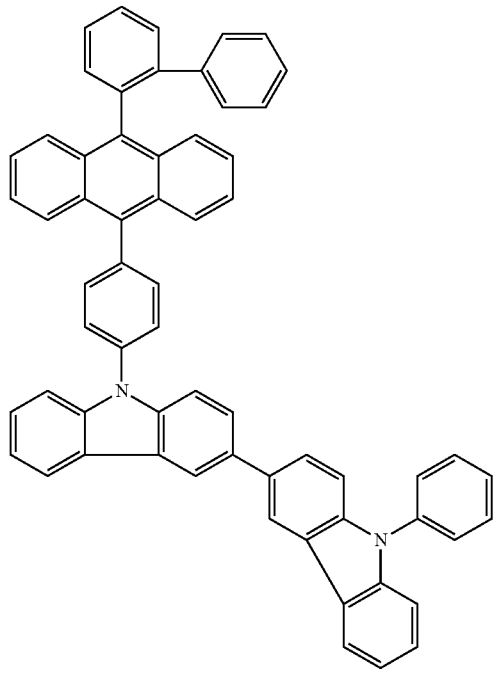
(105)
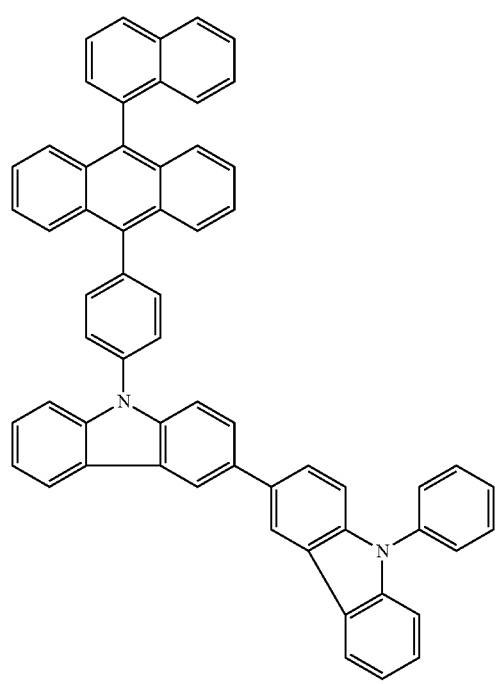
(106)
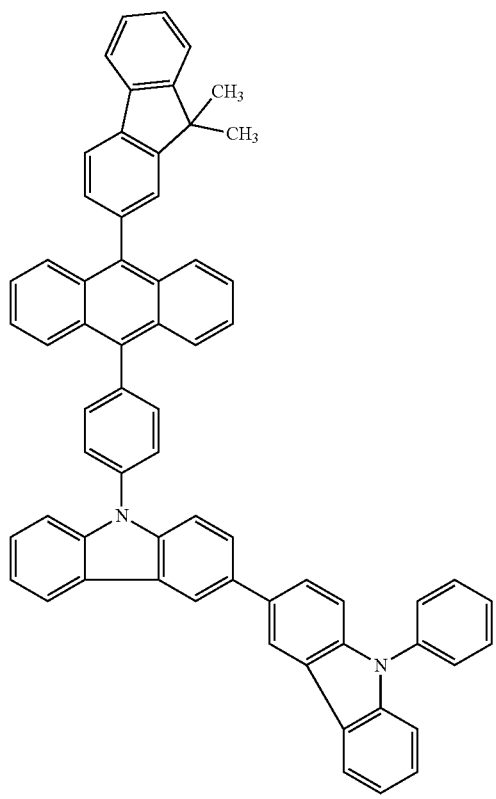

-continued
(107)
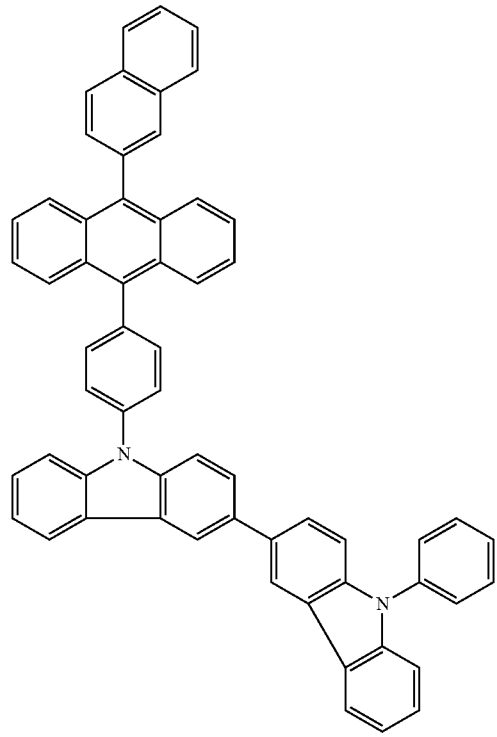
(108)
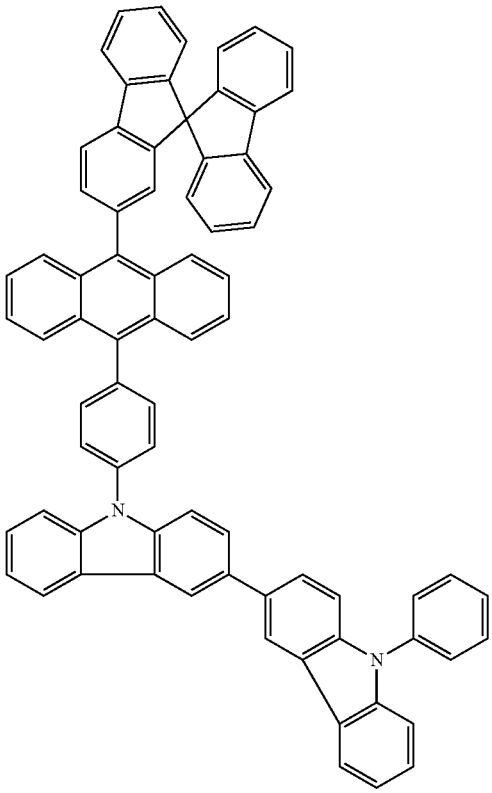
(109)
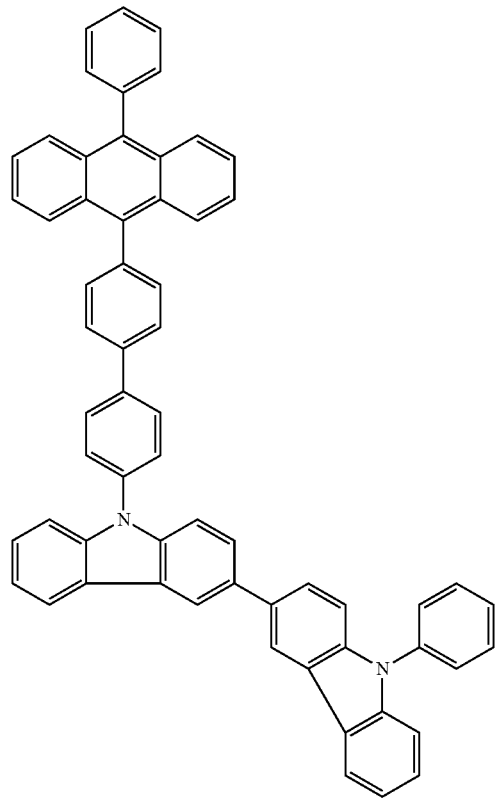
(110)
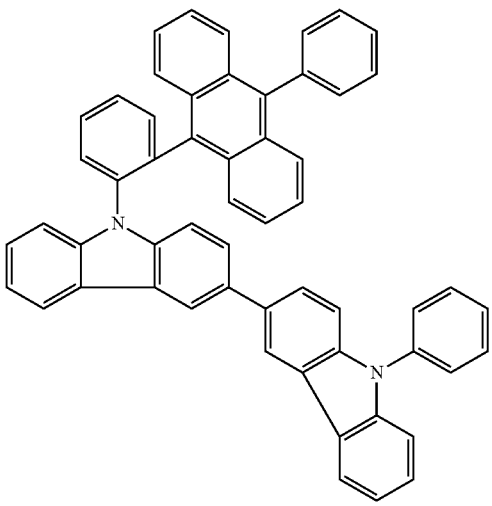

-continued
(111)
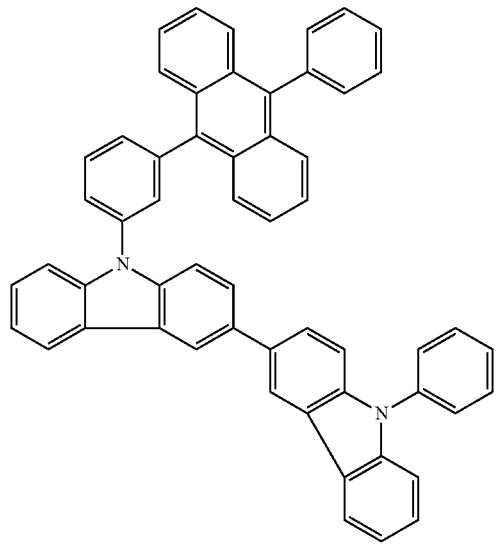
(112)
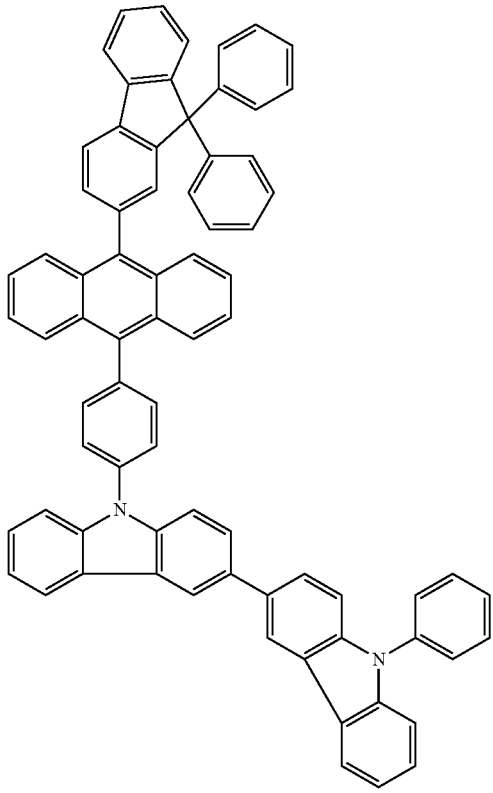
(113)
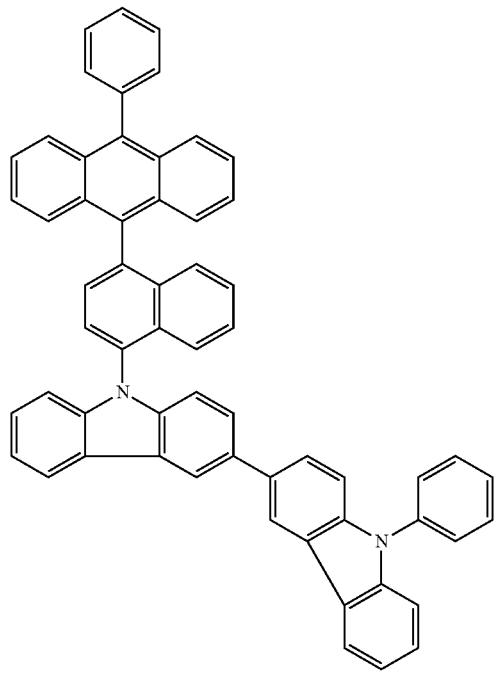
(114)
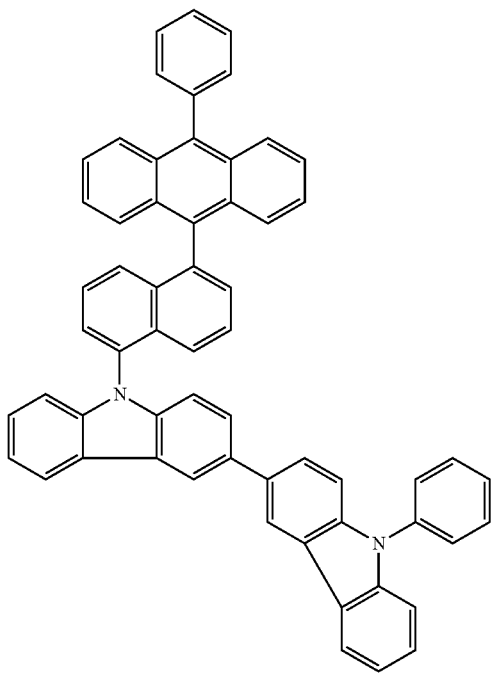

(115)
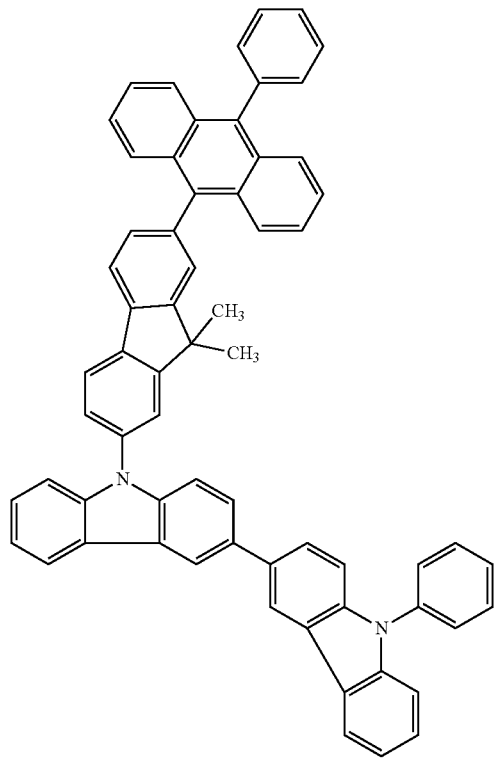
(116)
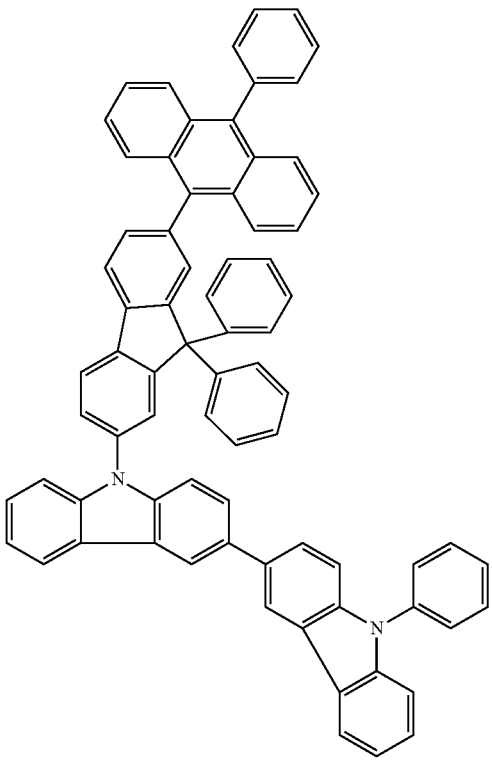
(117)
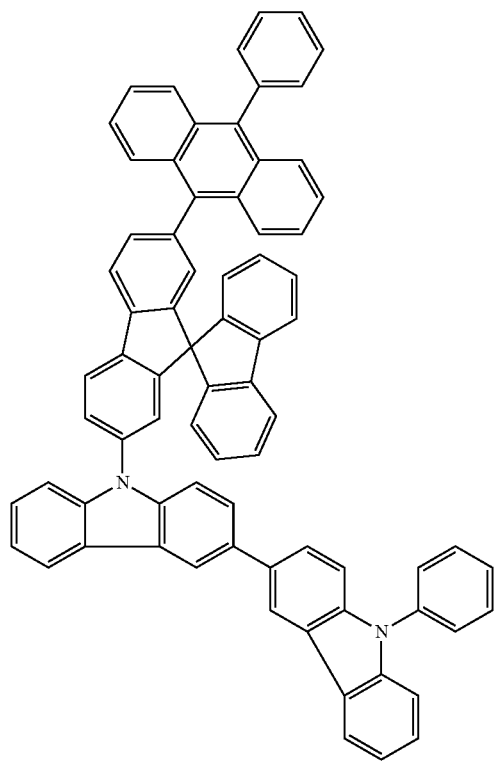
(118)
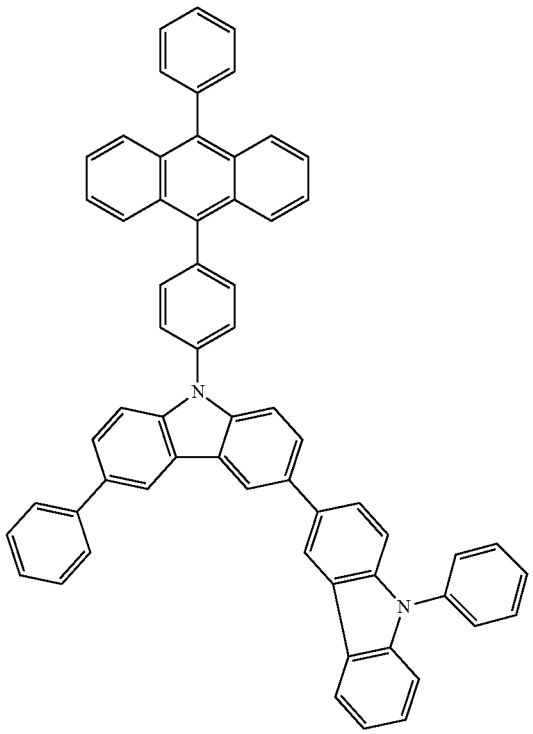

(119)
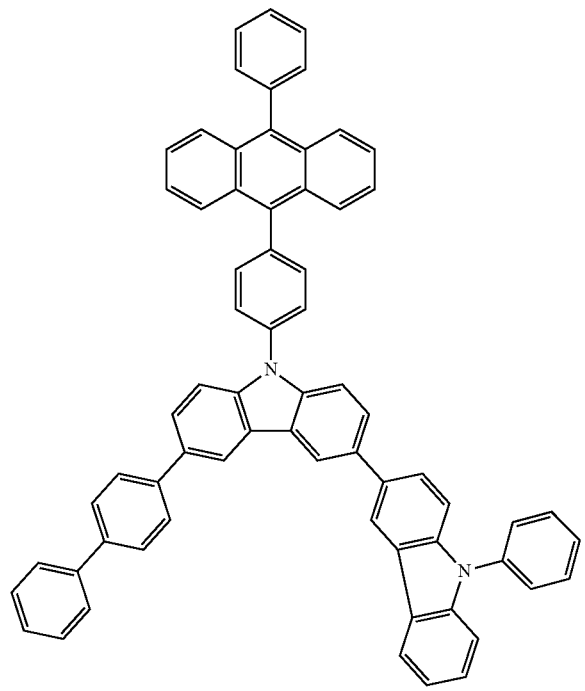
(120)
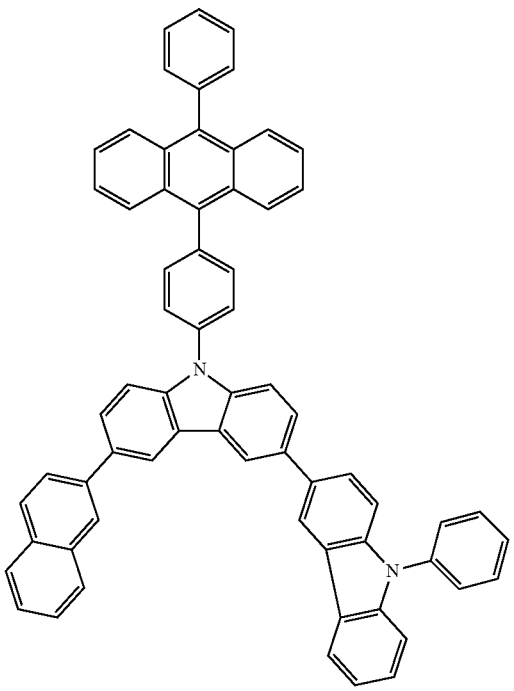
(121)
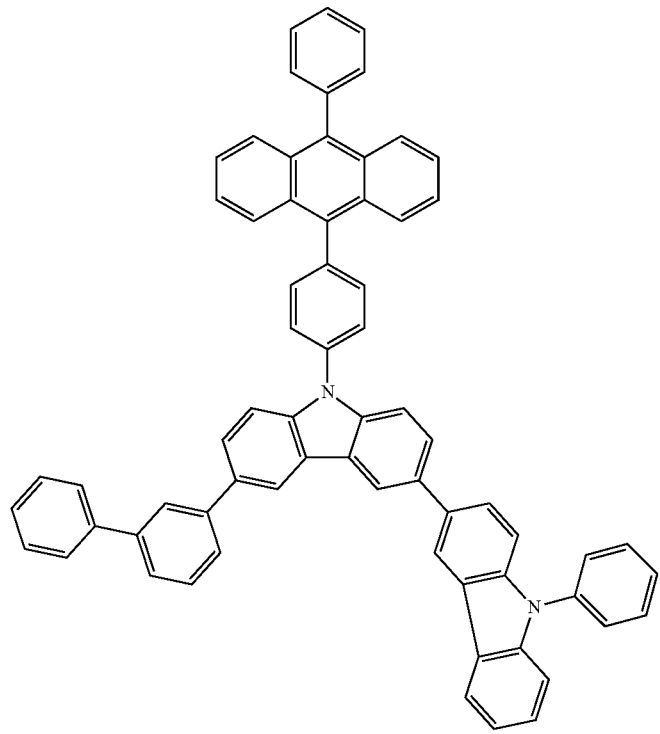

-continued
(122)
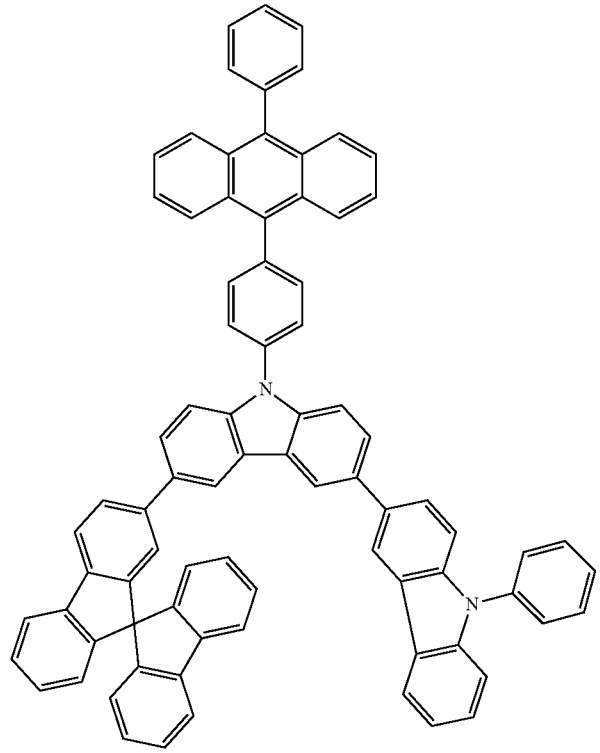
(123)
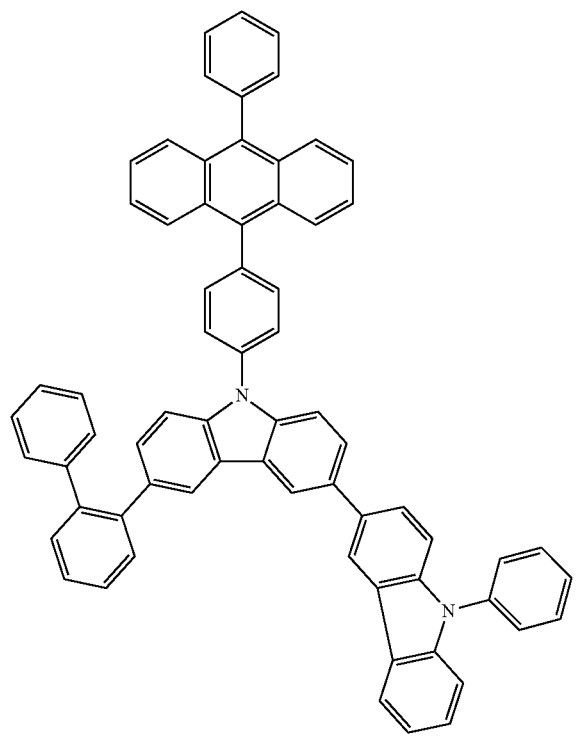
(124)
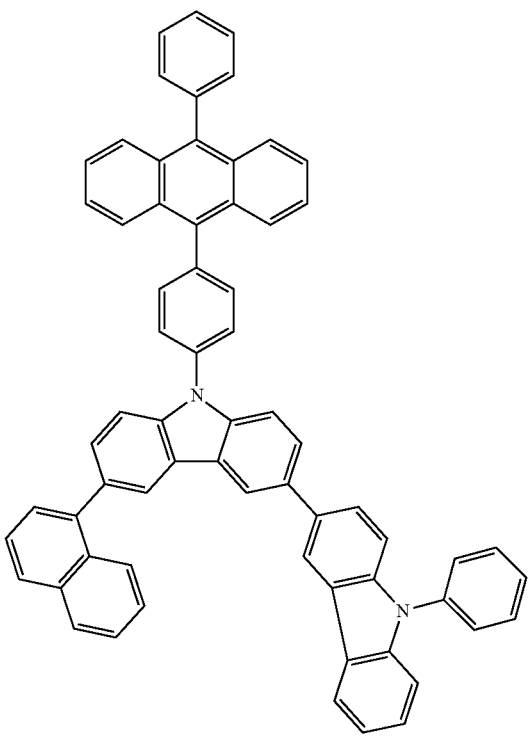

-continued
(125)
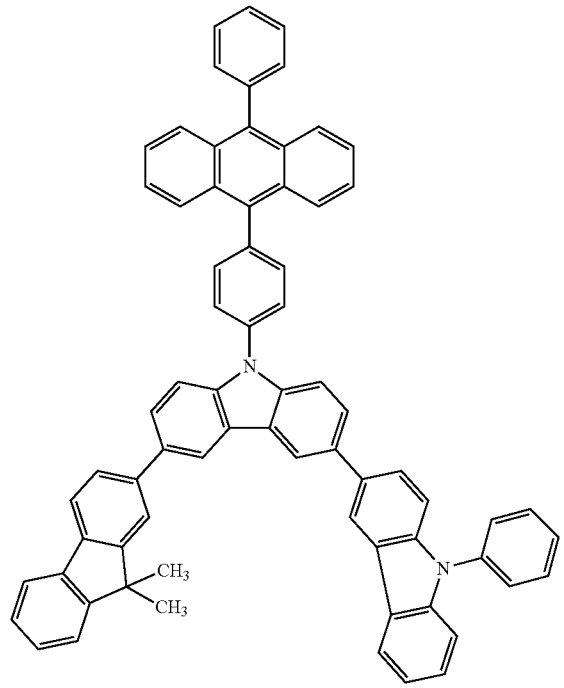
(126)
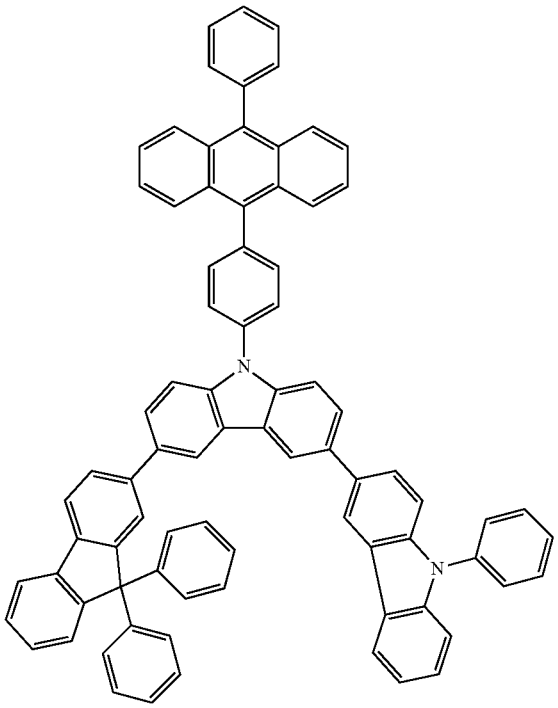
(127)
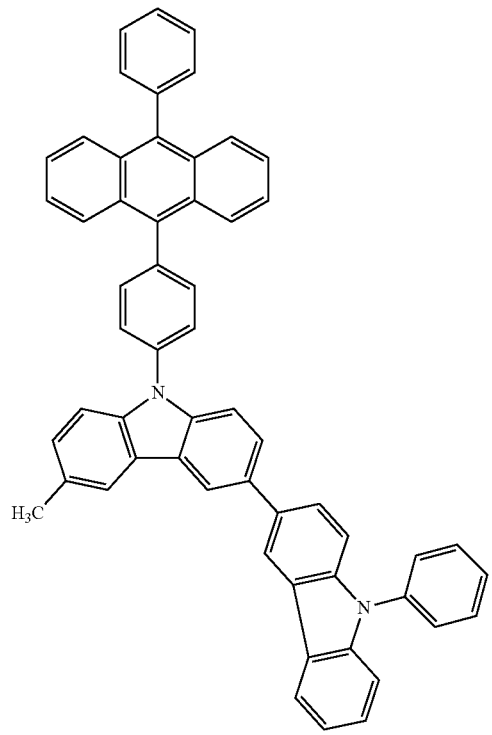
(128)
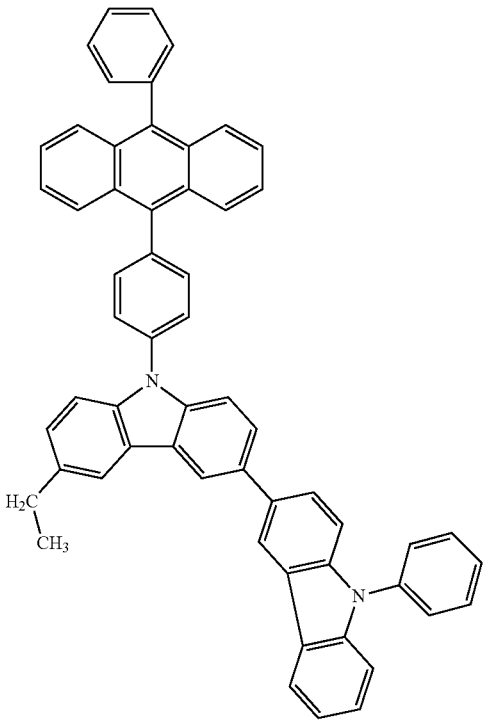

(129)
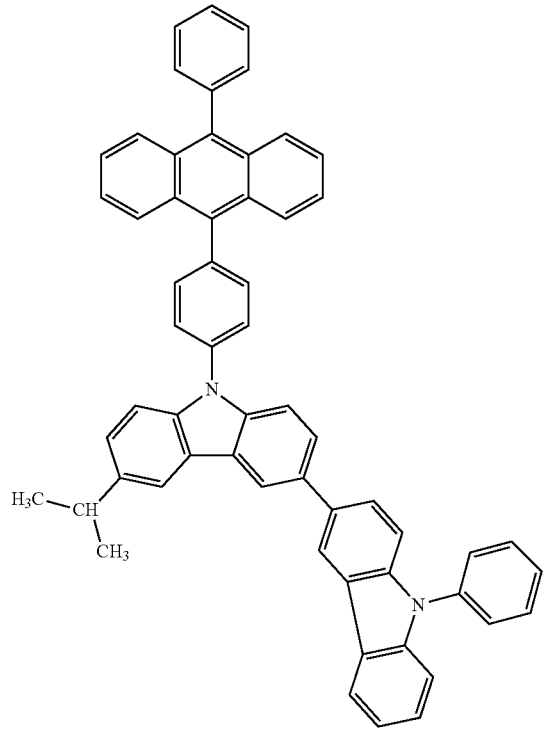
(130)
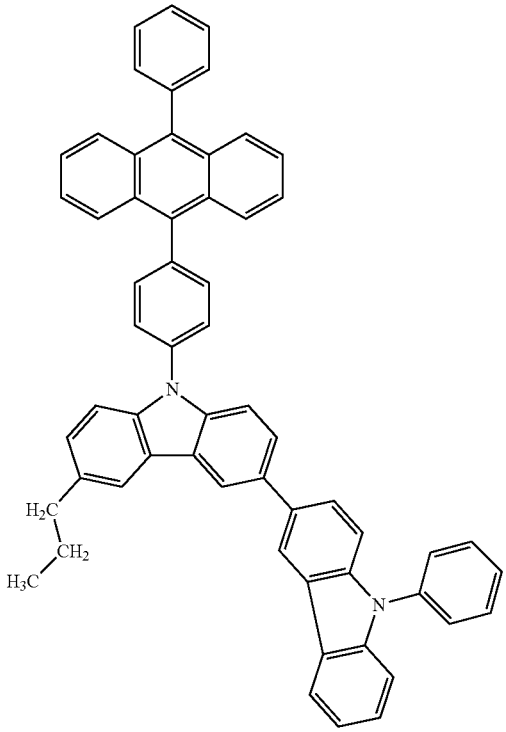
(131)
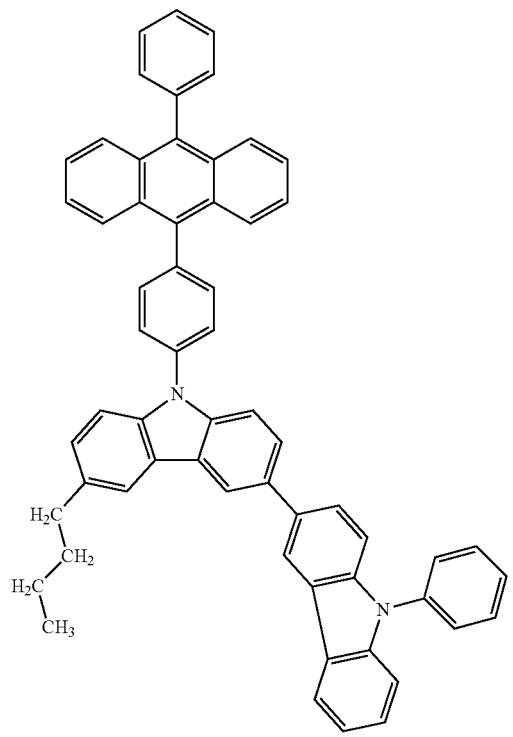
(132)
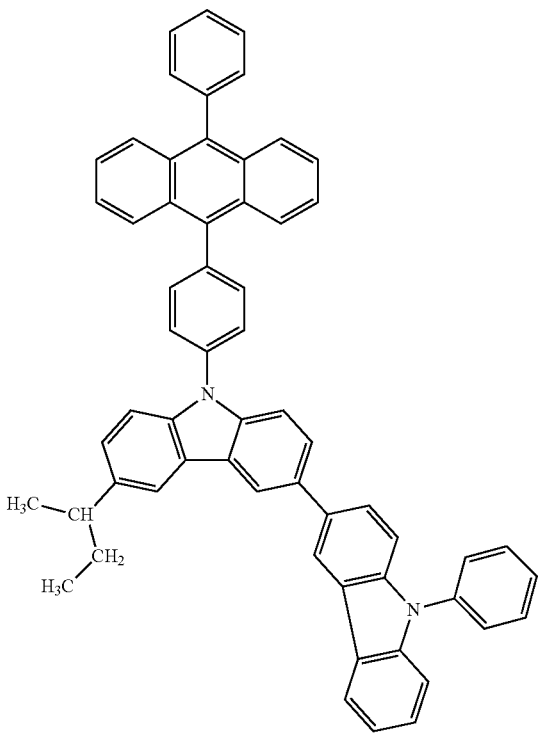

(133)
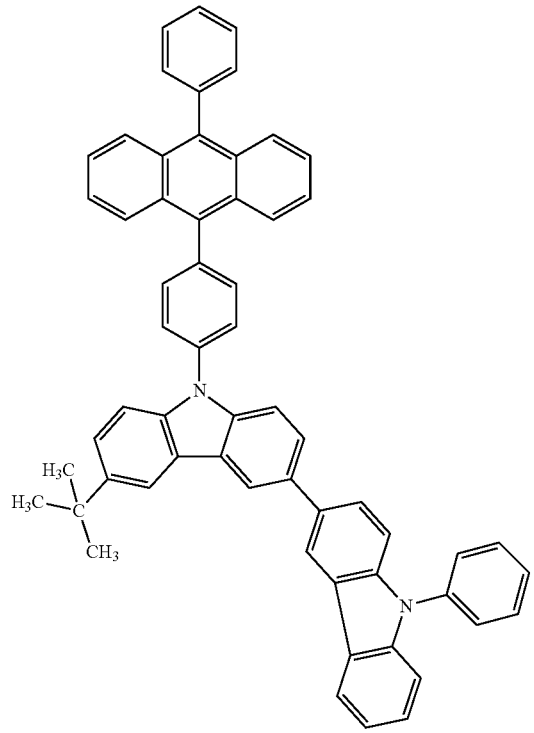
(134)
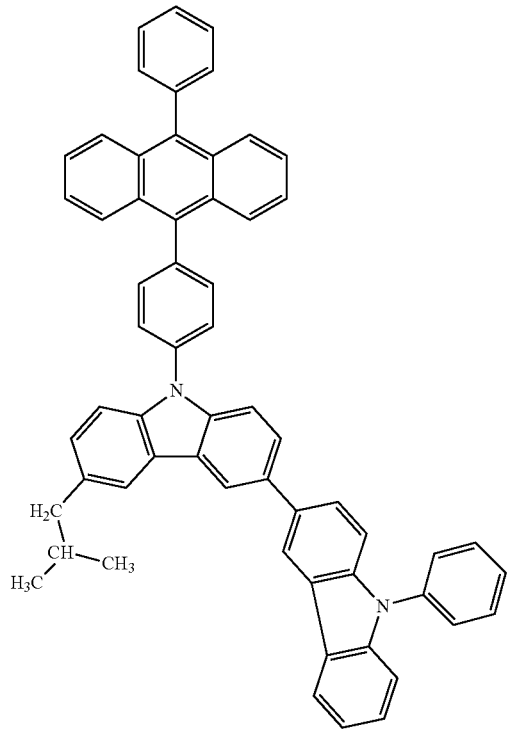
(135)
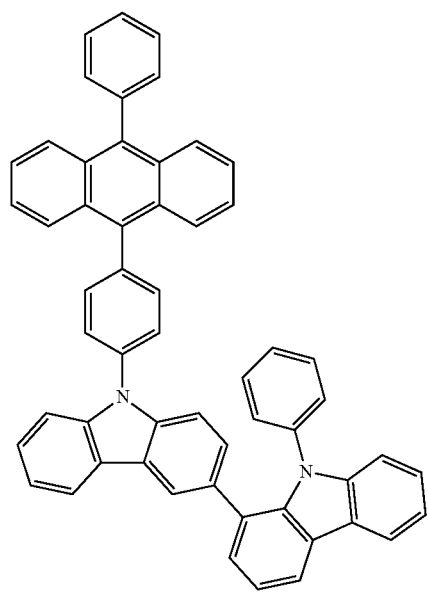
(136)
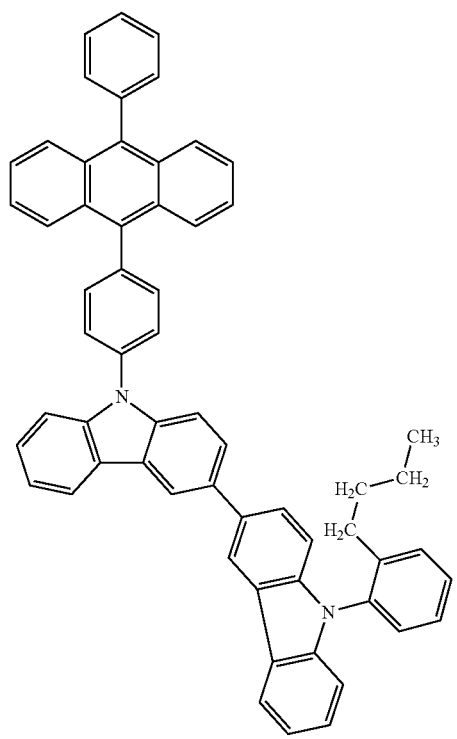

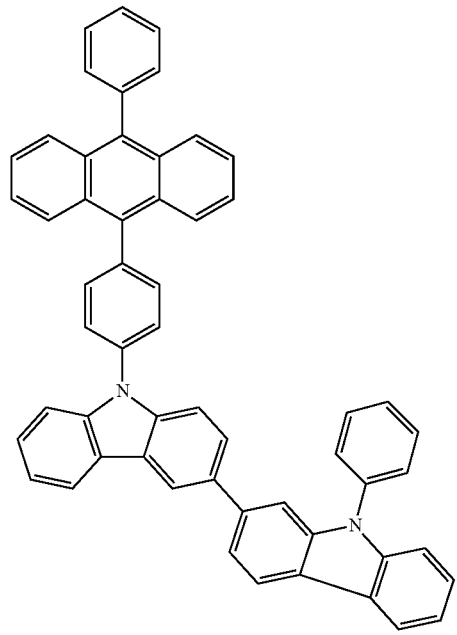
(137)
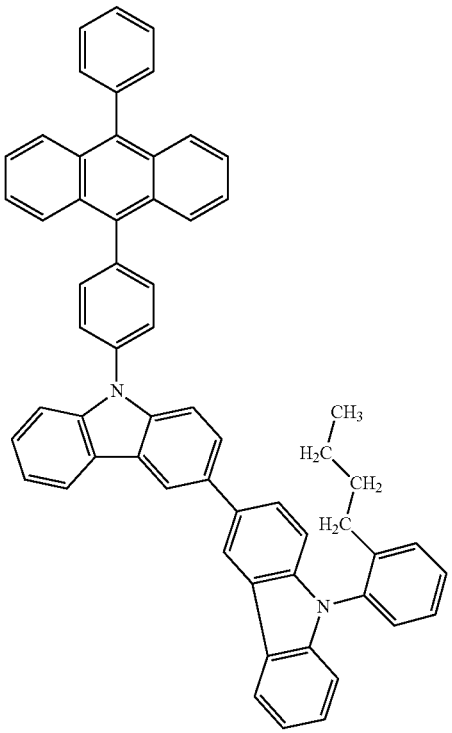
(138)
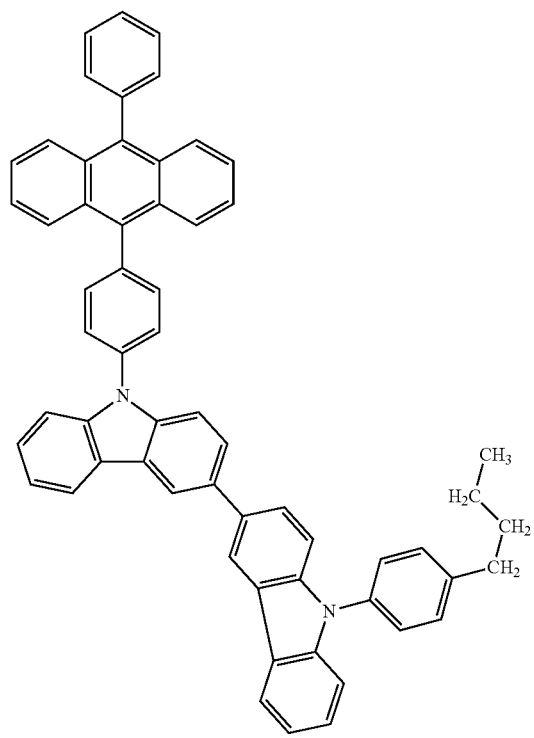
(139)

(140)
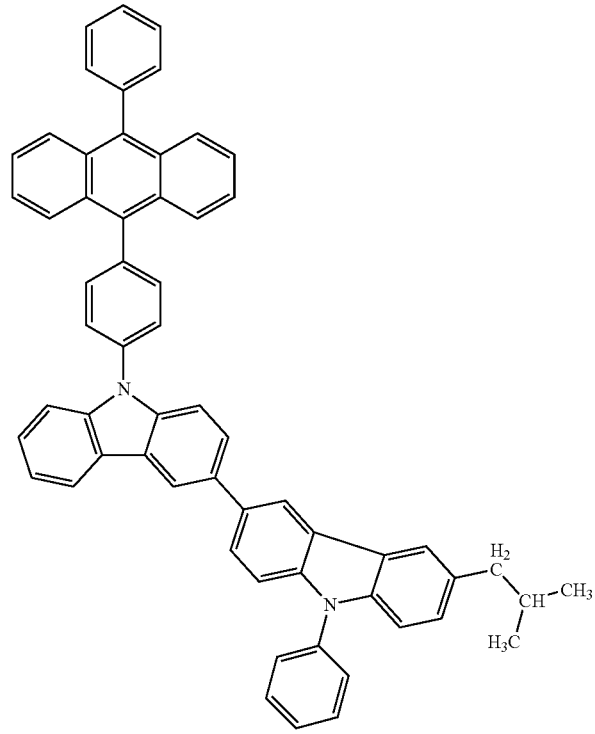
(141)
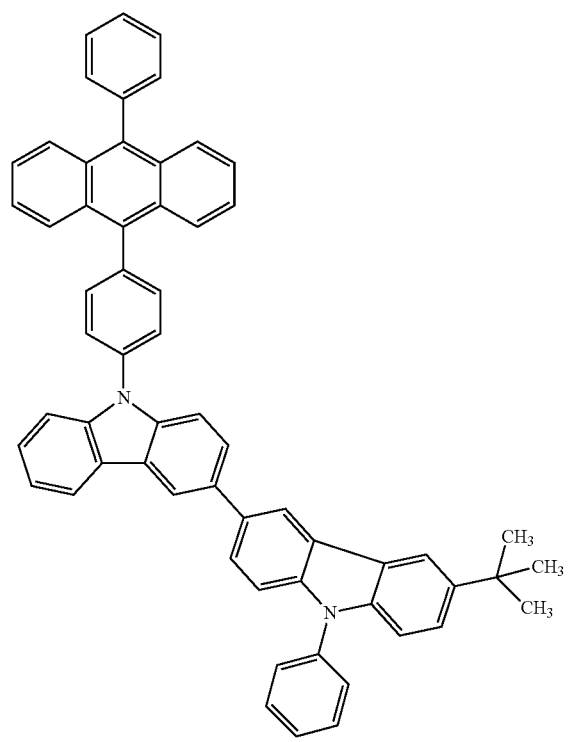
(142)
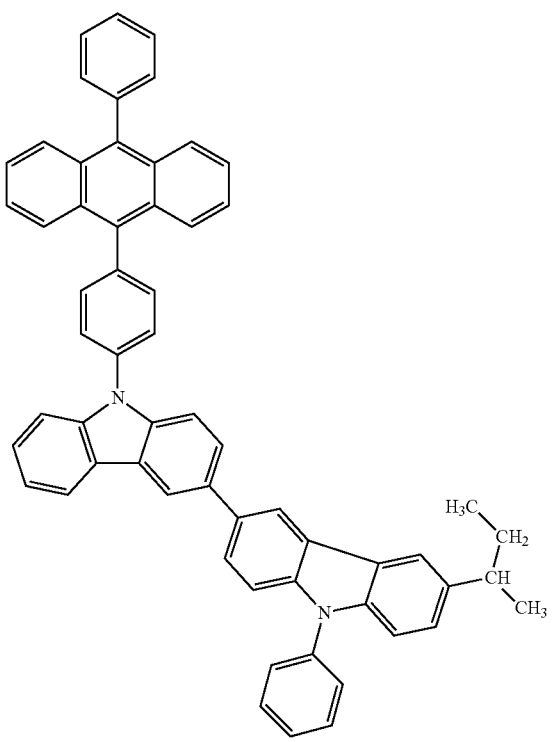

(143) 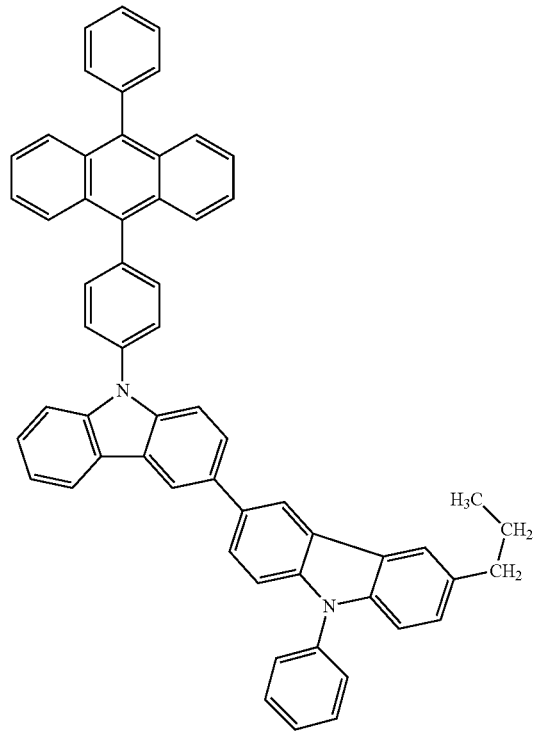
(144) 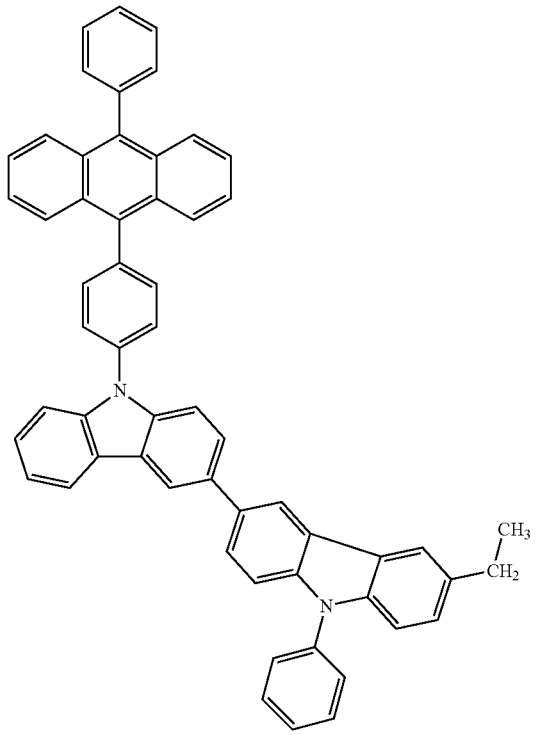
(145) 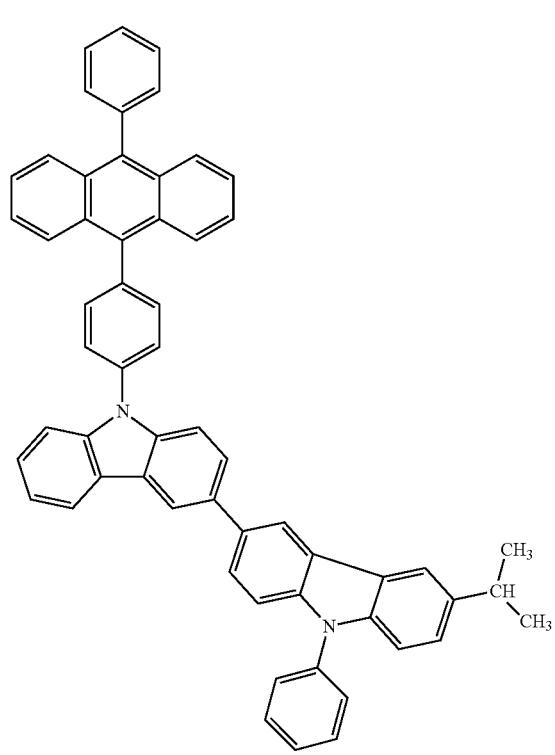
(146) 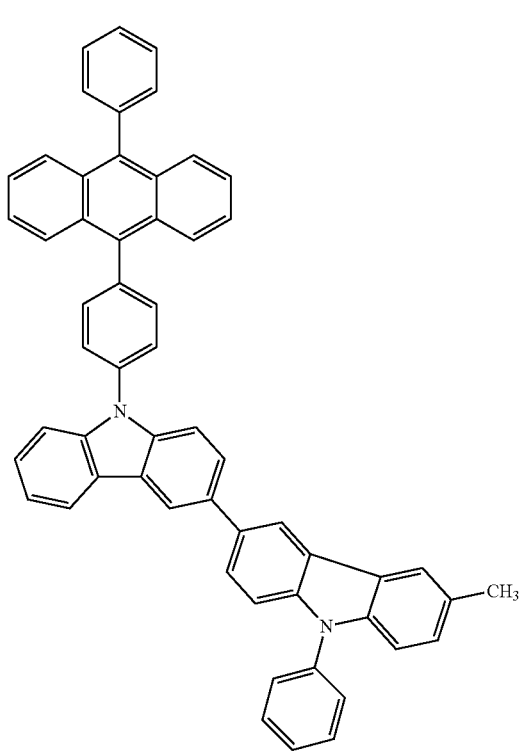

(147)
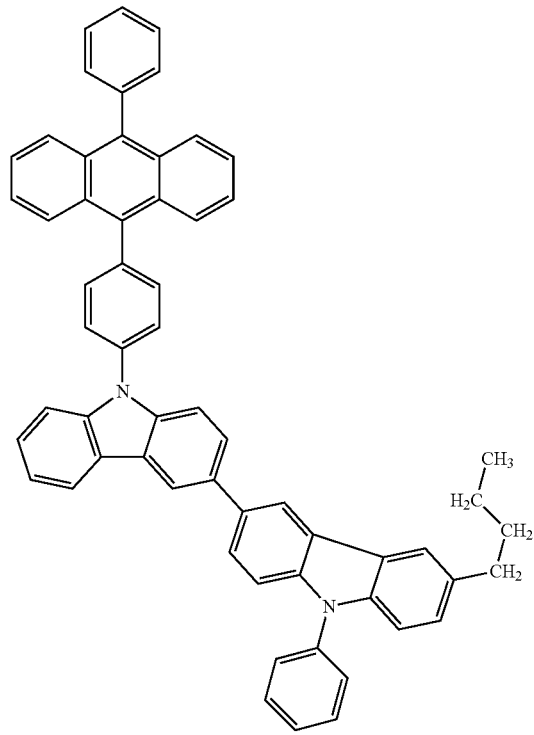
(148)
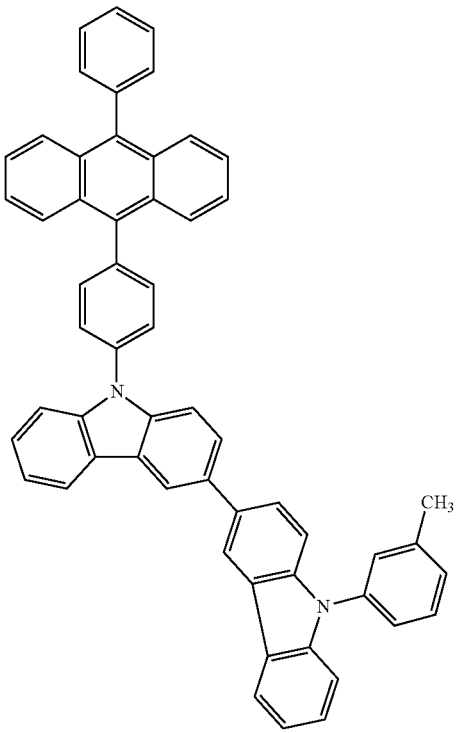
(149)
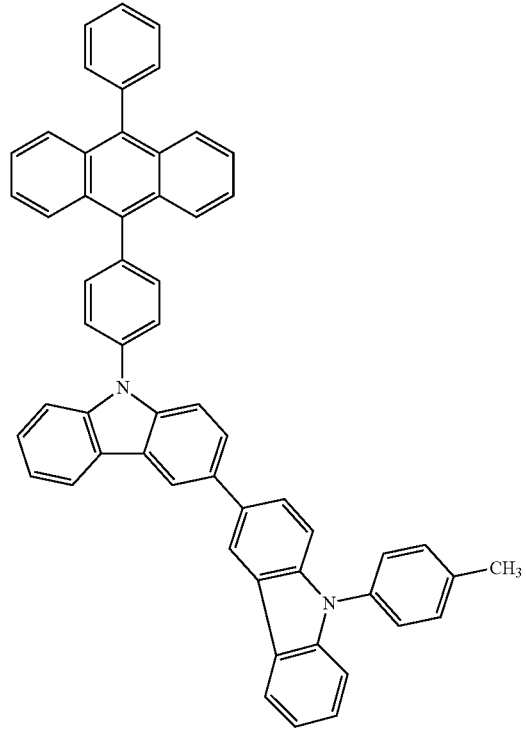
(150)
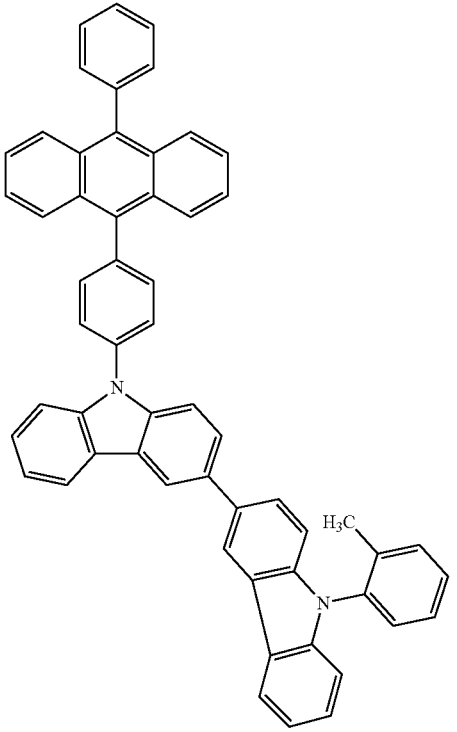

-continued
(151)
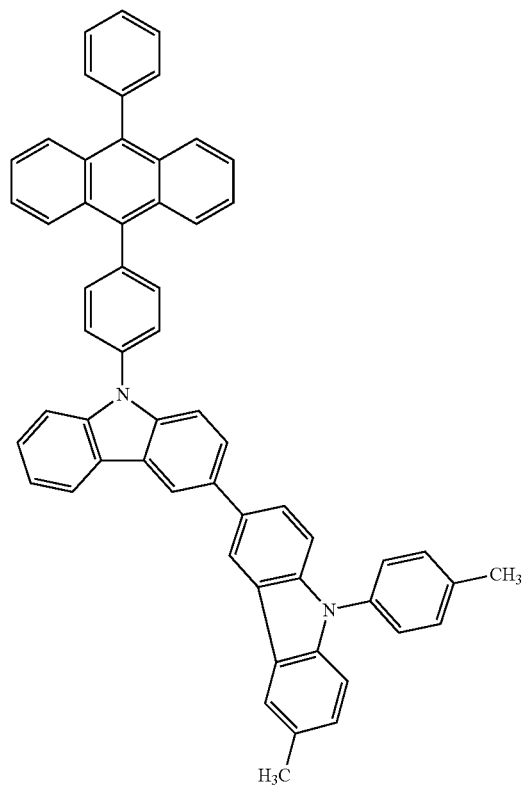
(152)
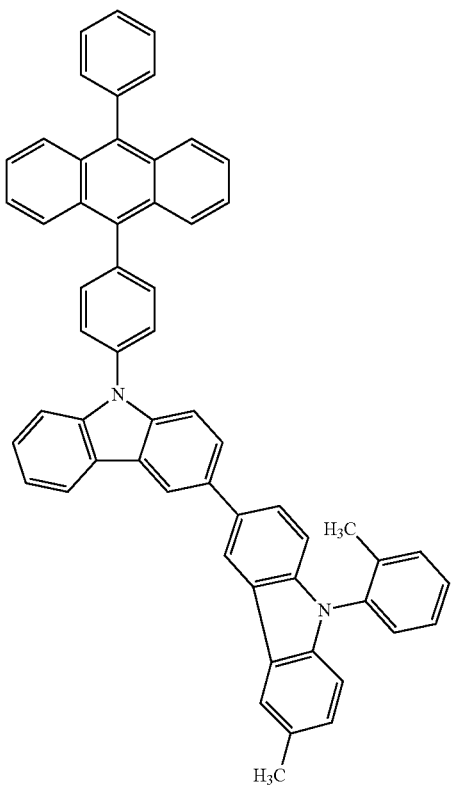
(153)
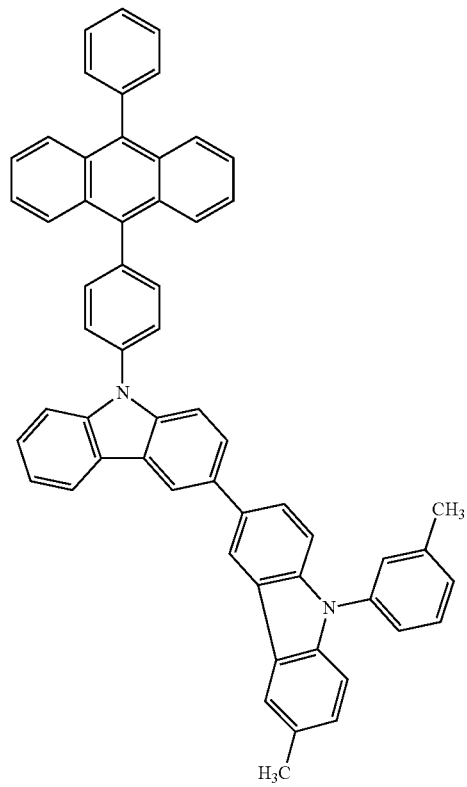
(154)
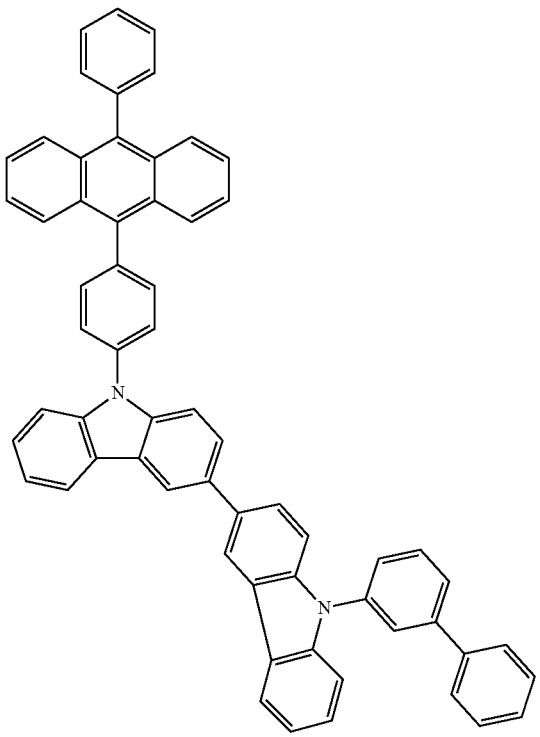

(155)
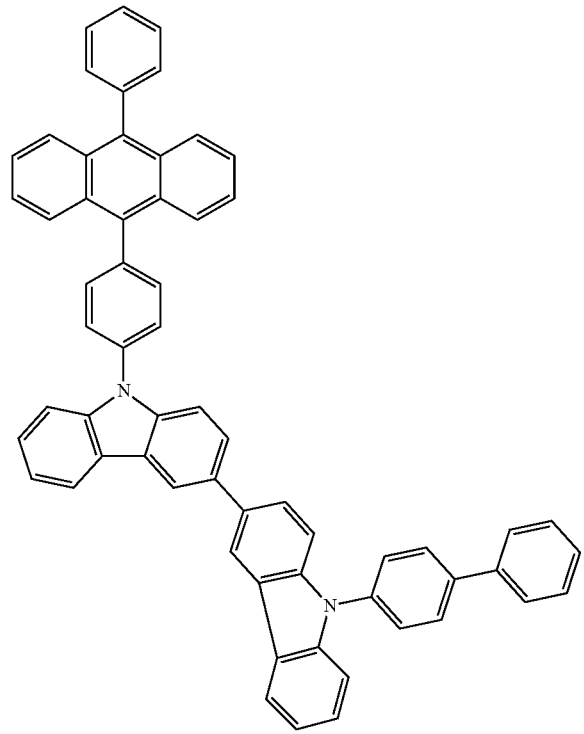
(156)
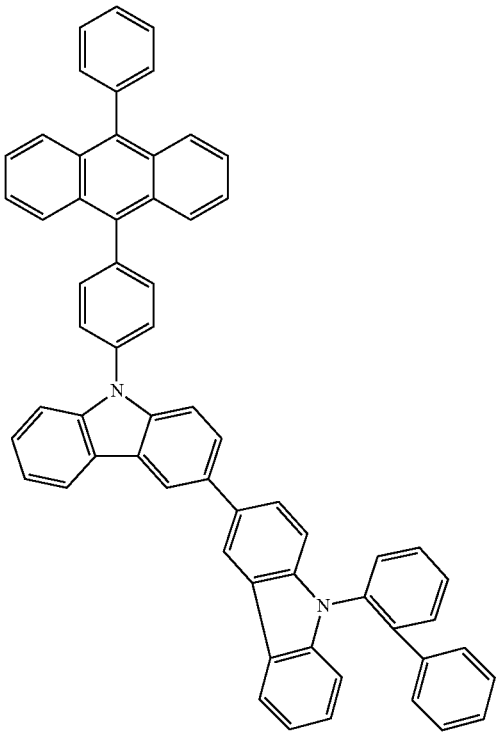
(157)
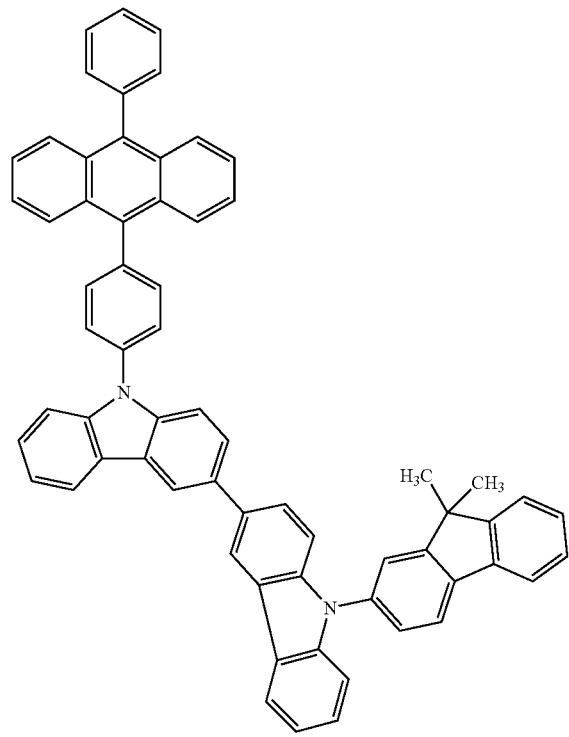
(158)
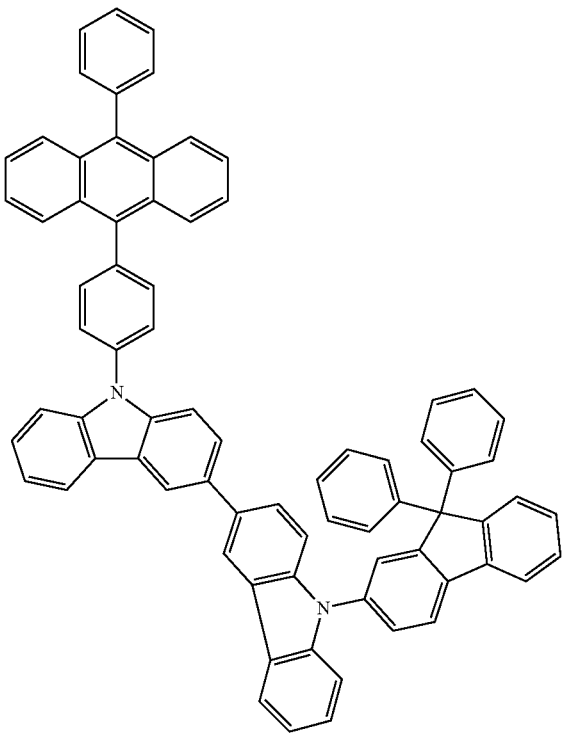

(159)
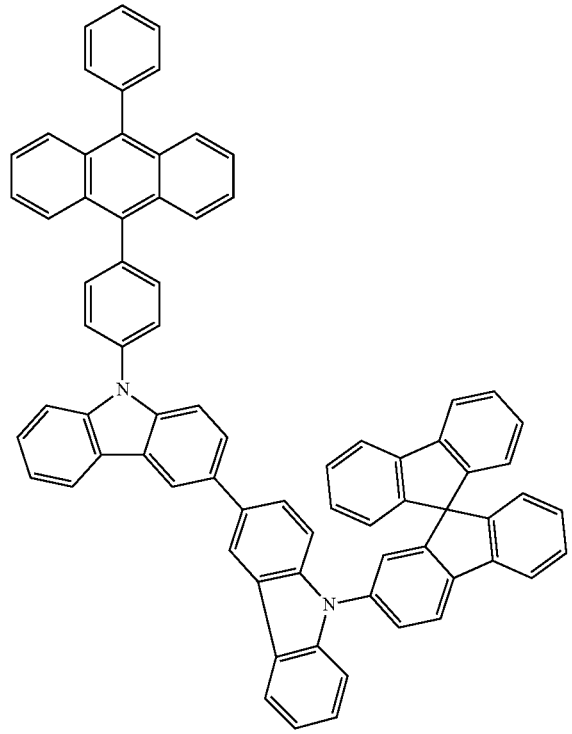
(160)
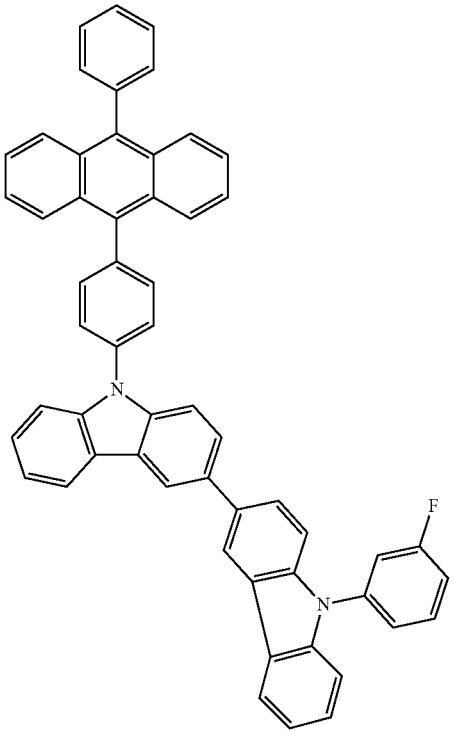
(161)
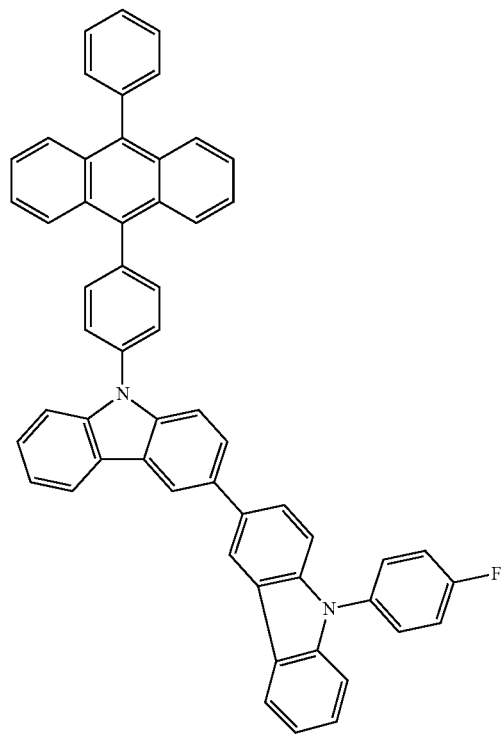
(162)
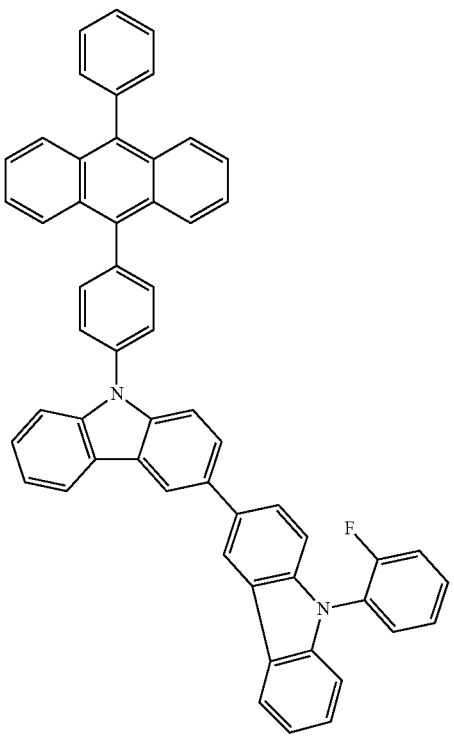

(163)
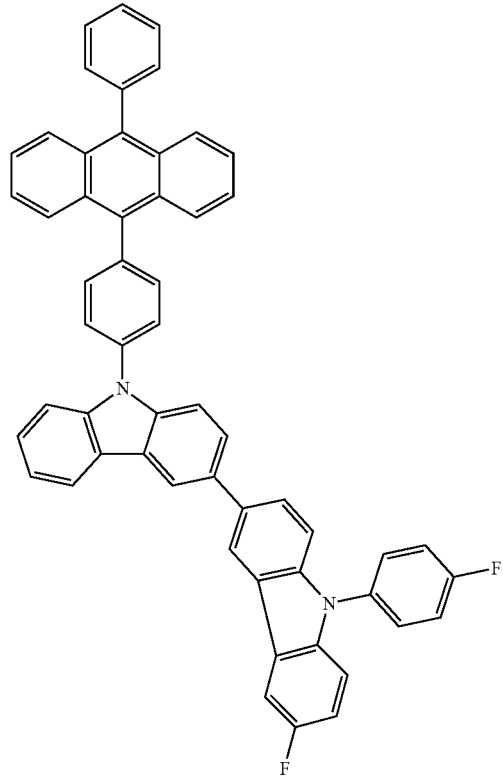
(164)
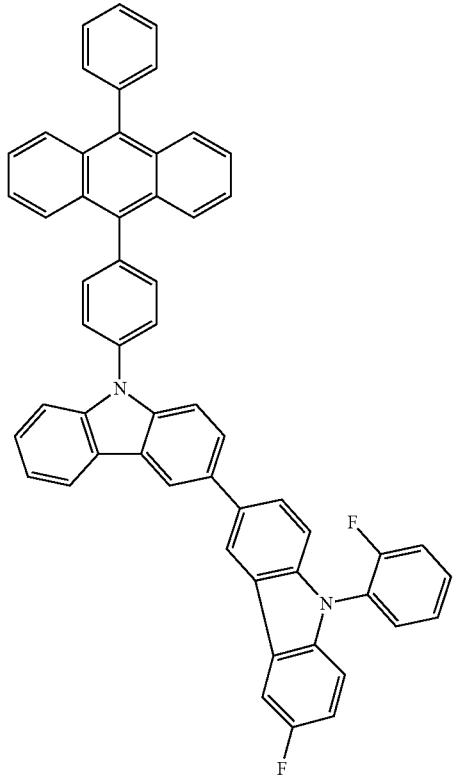
(165)
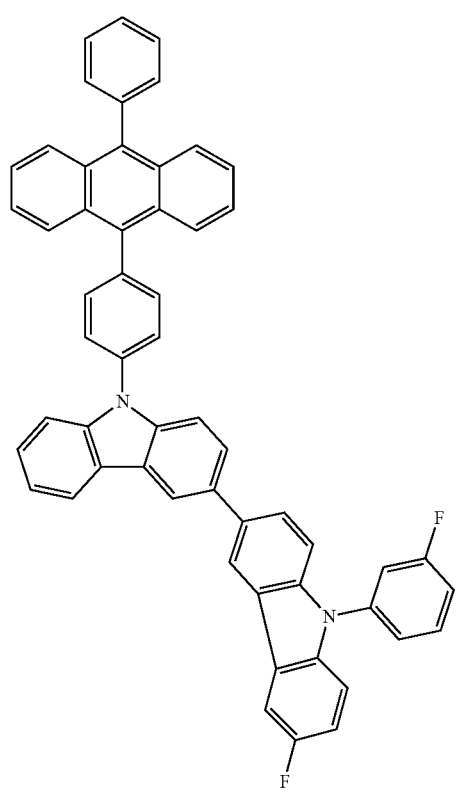
(166)
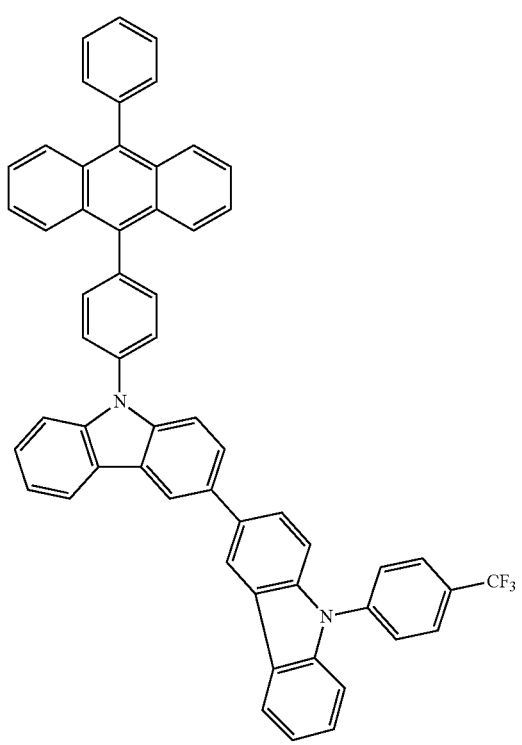

-continued
(167)
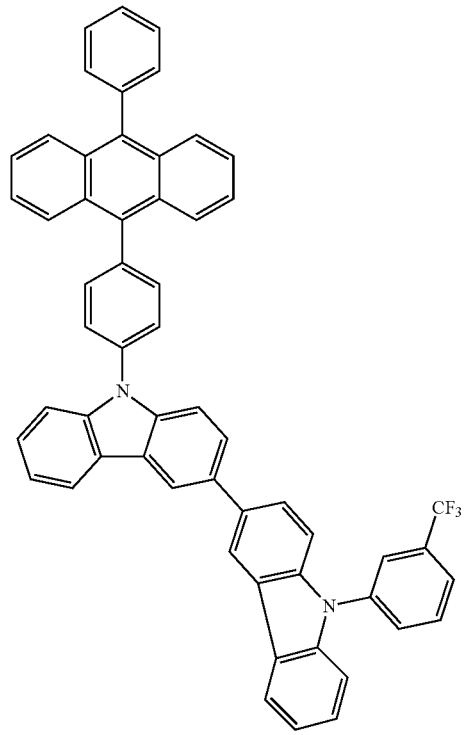
(168)
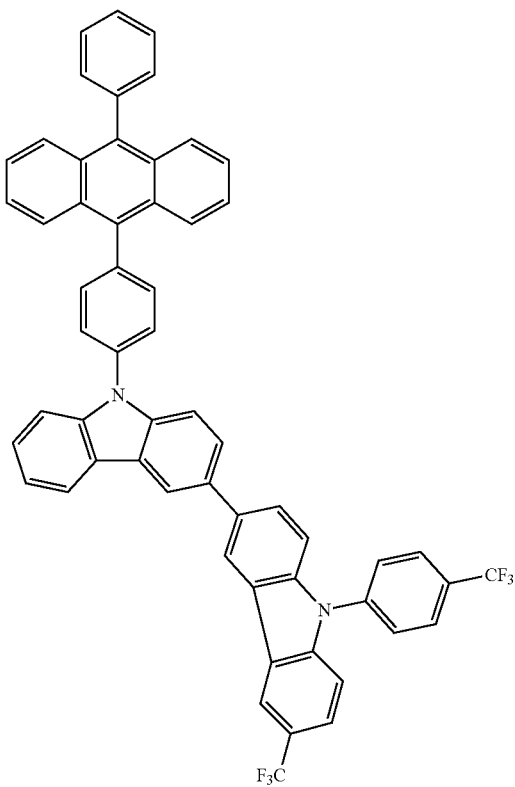
(169)
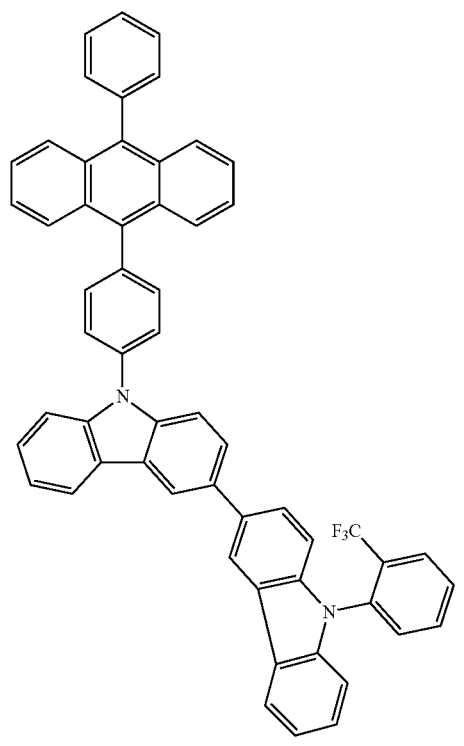
(170)
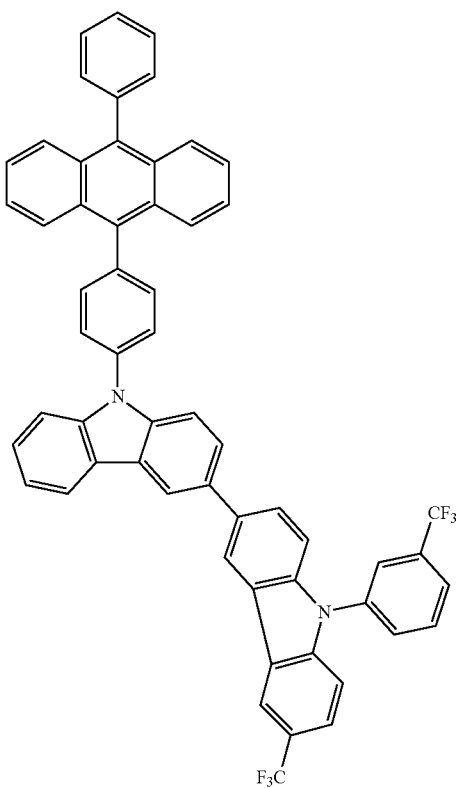

(171)
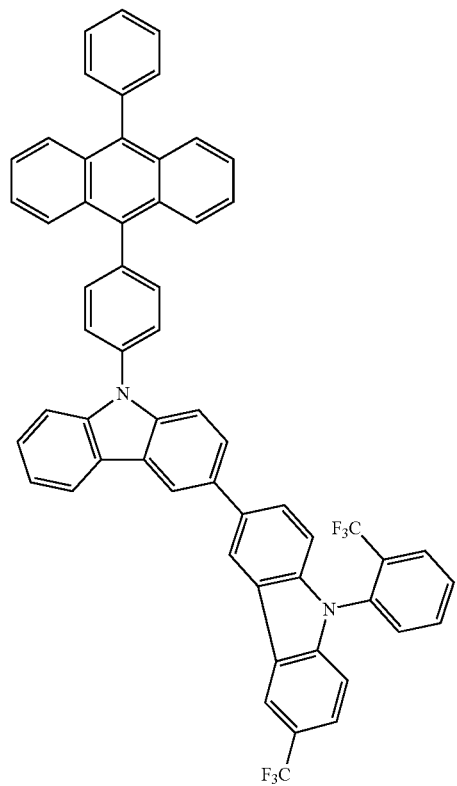
(172)
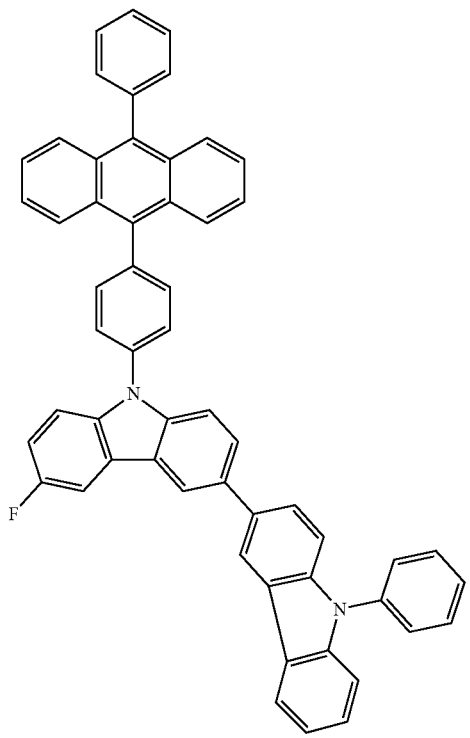
(173)
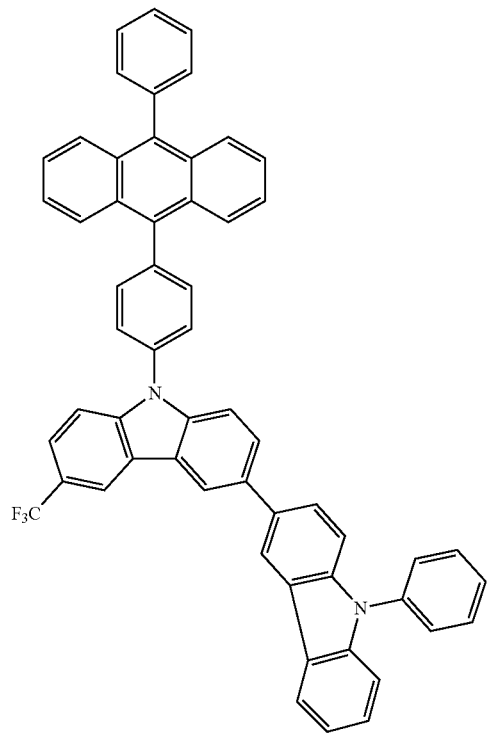
(174)
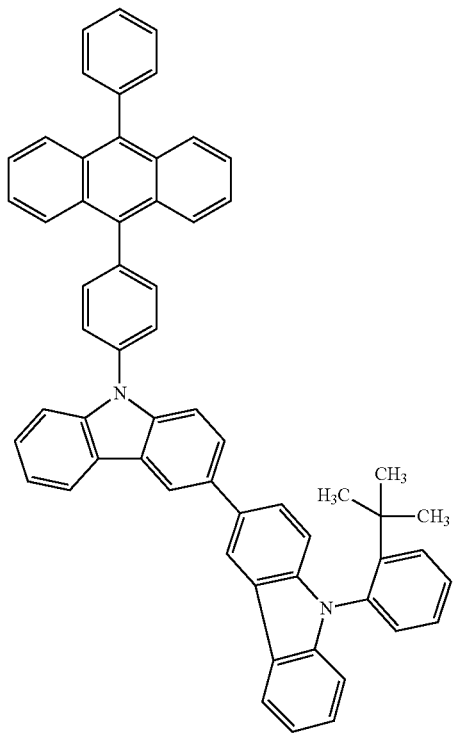

(175) 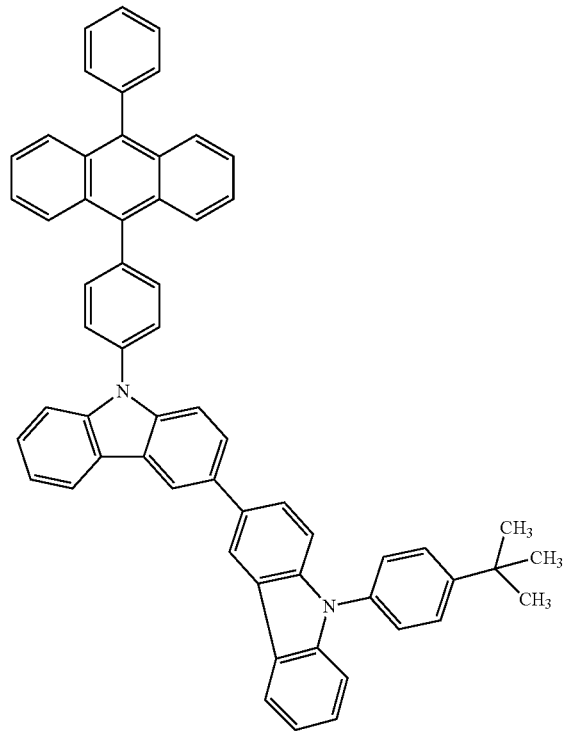
(176) 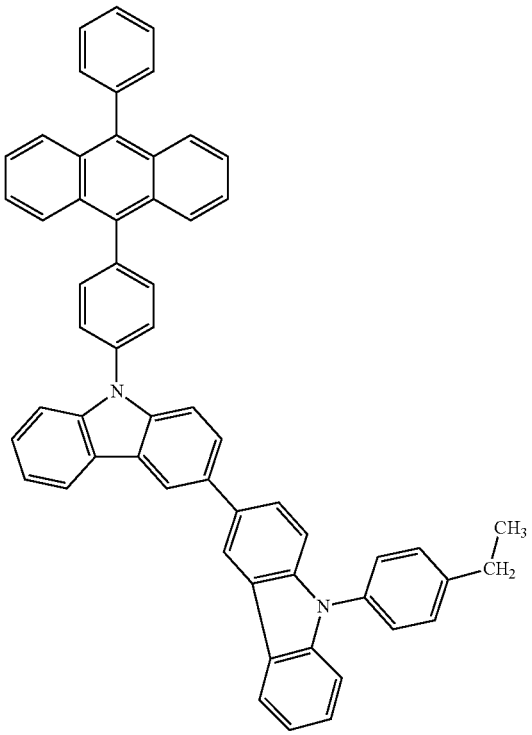
(177) 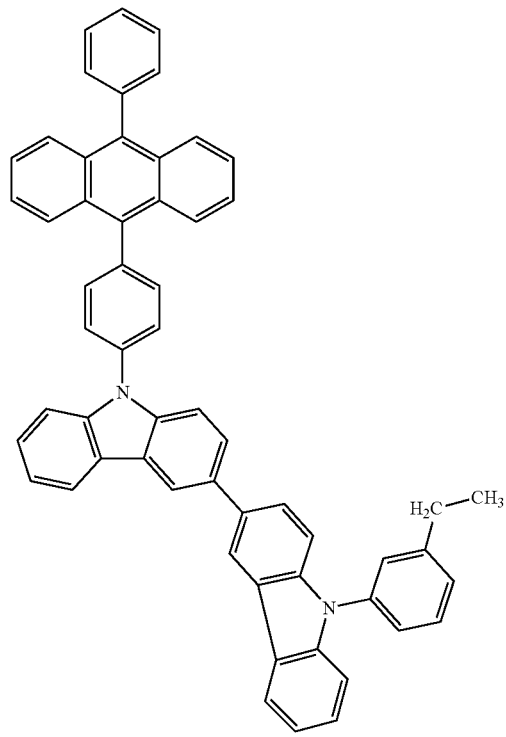
(178) 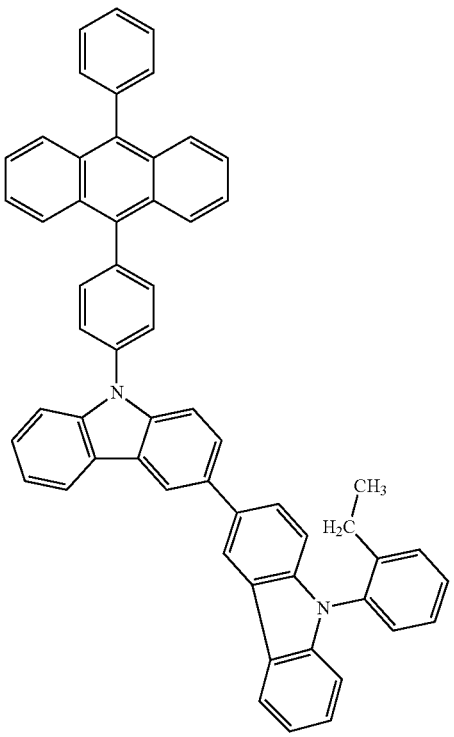

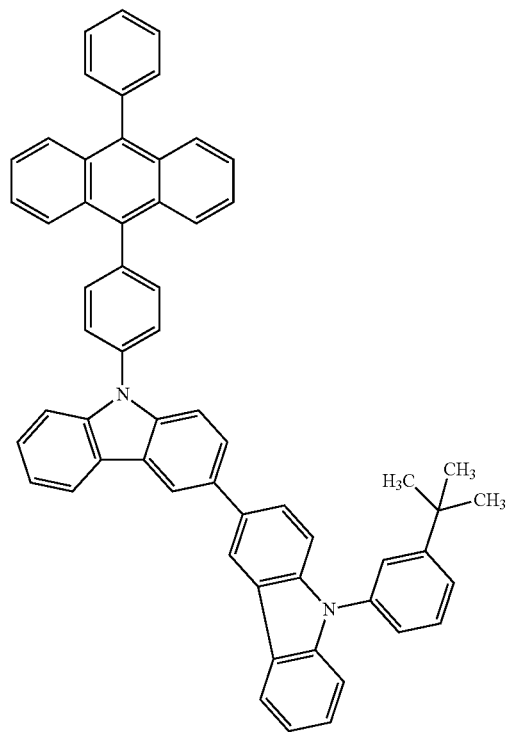
(179)
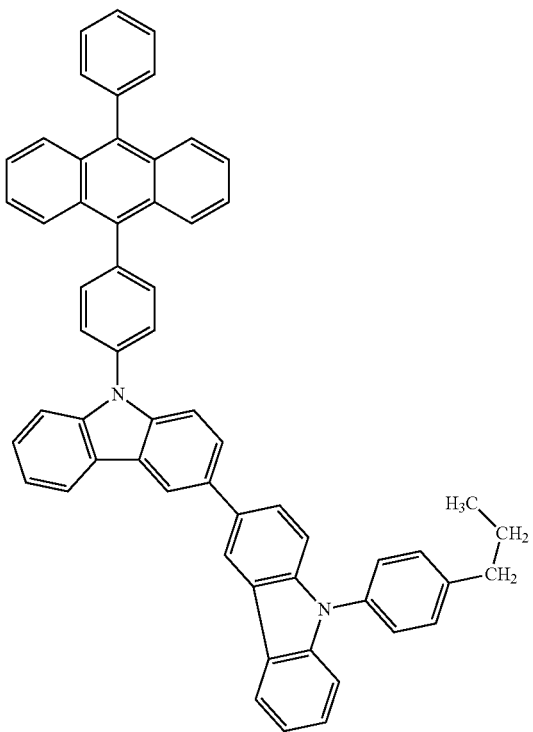
(180)
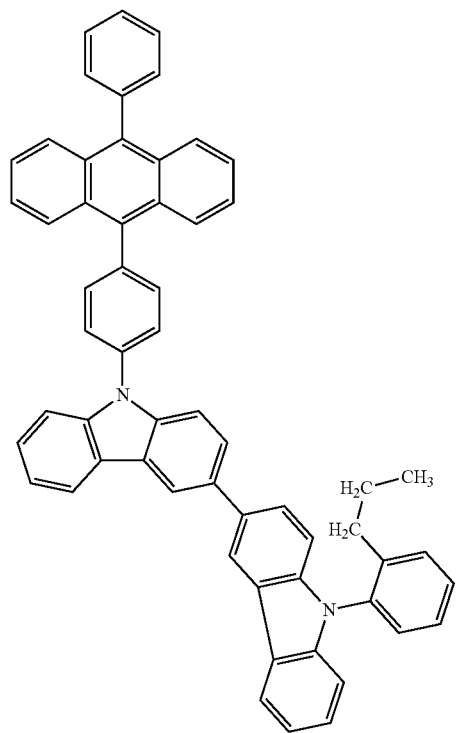
(181)
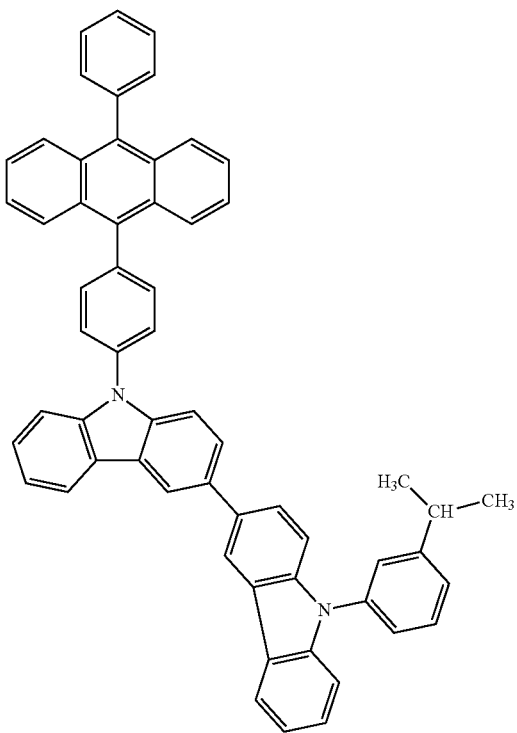
(182)

(183)
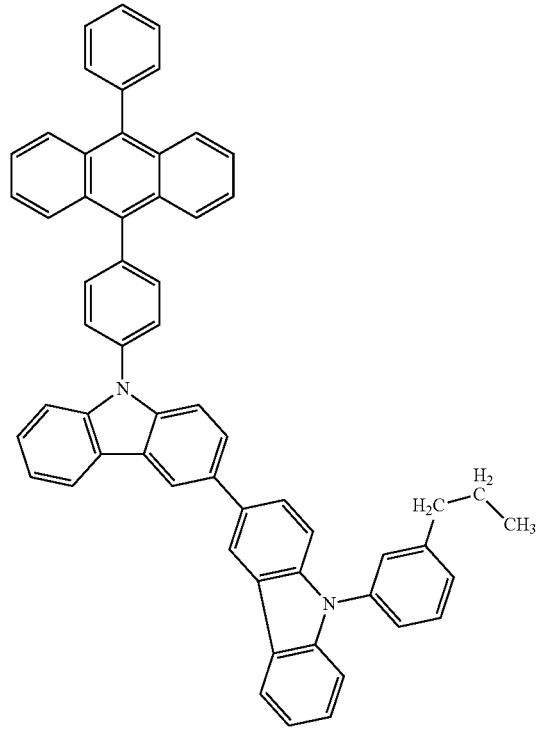
(184)
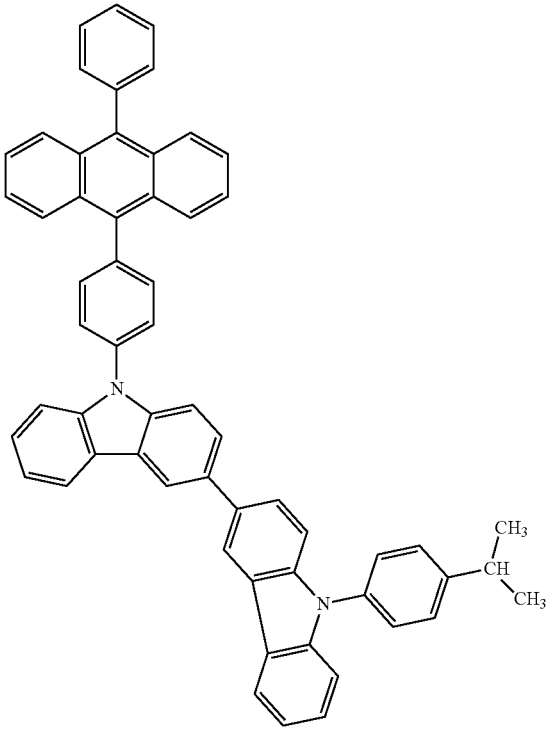
(185)
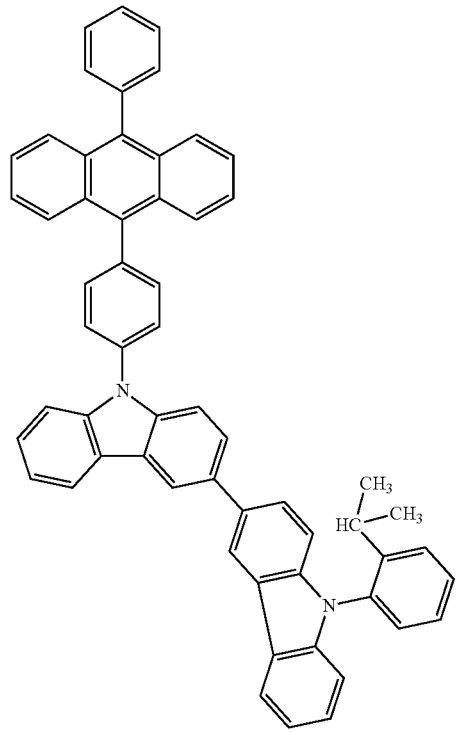
(186)
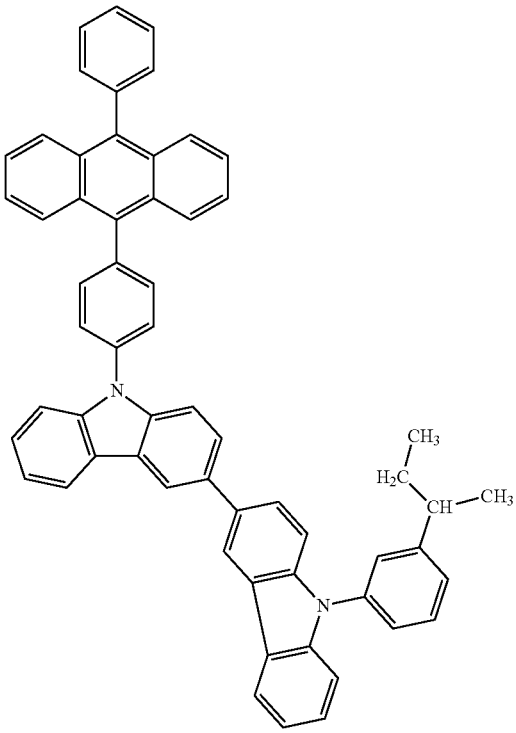

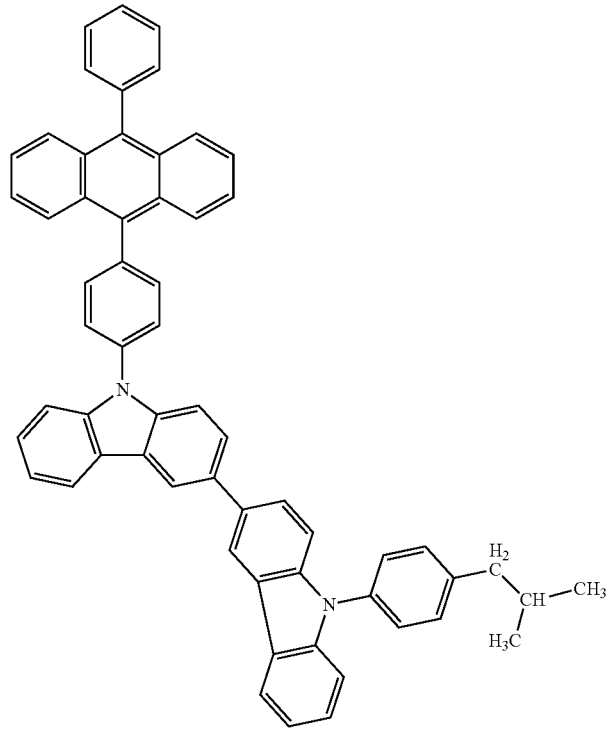
(187)
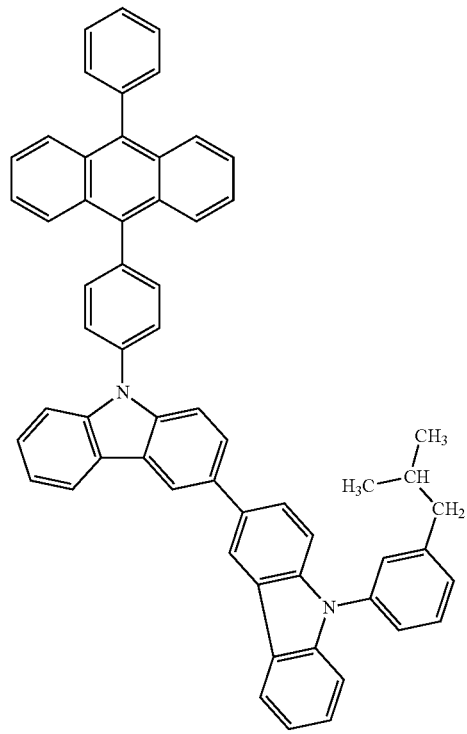
(188)
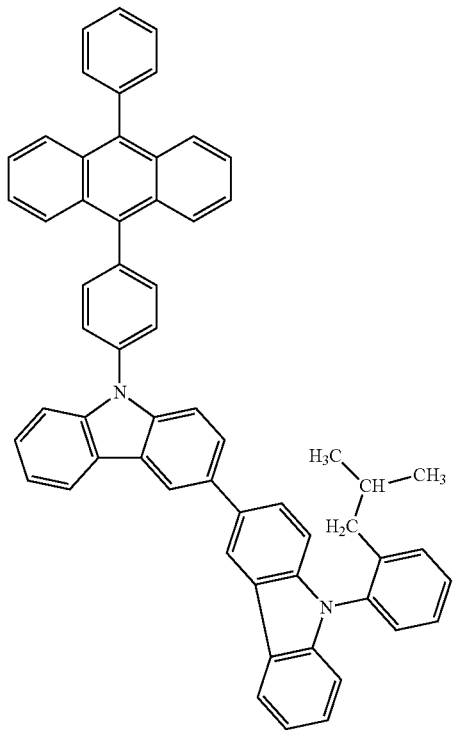
(189)

(190)
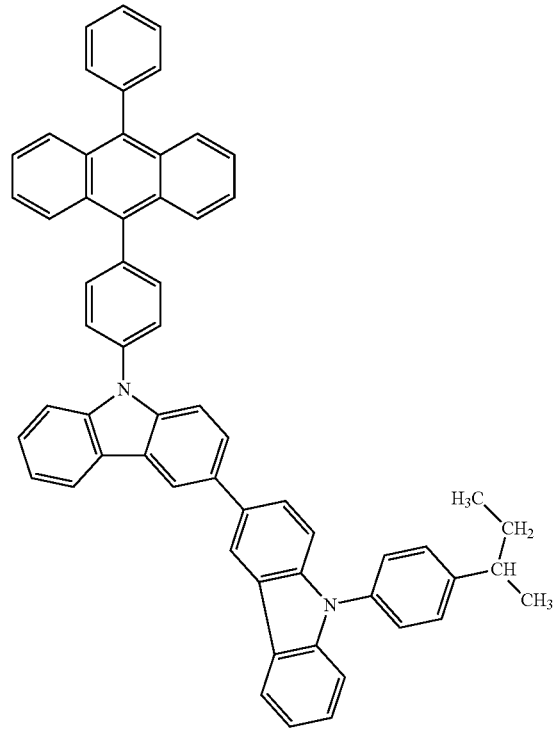
(191)
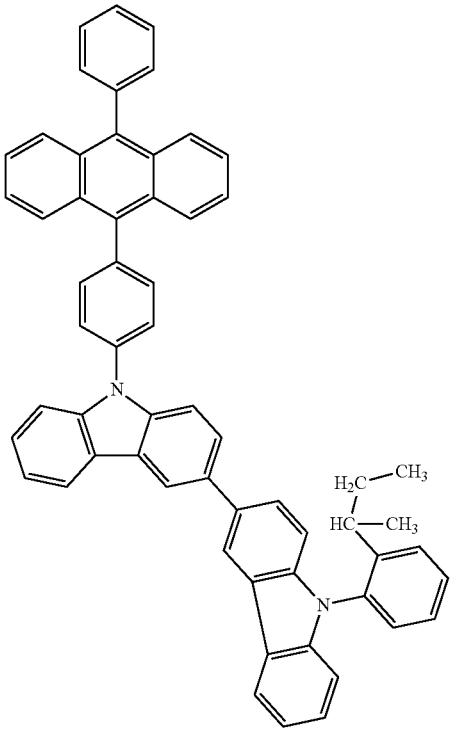
(192)
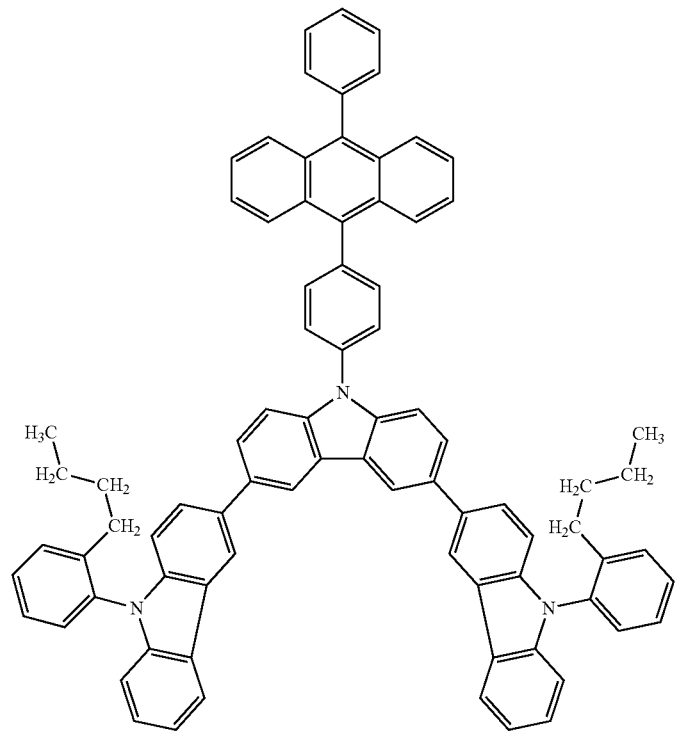

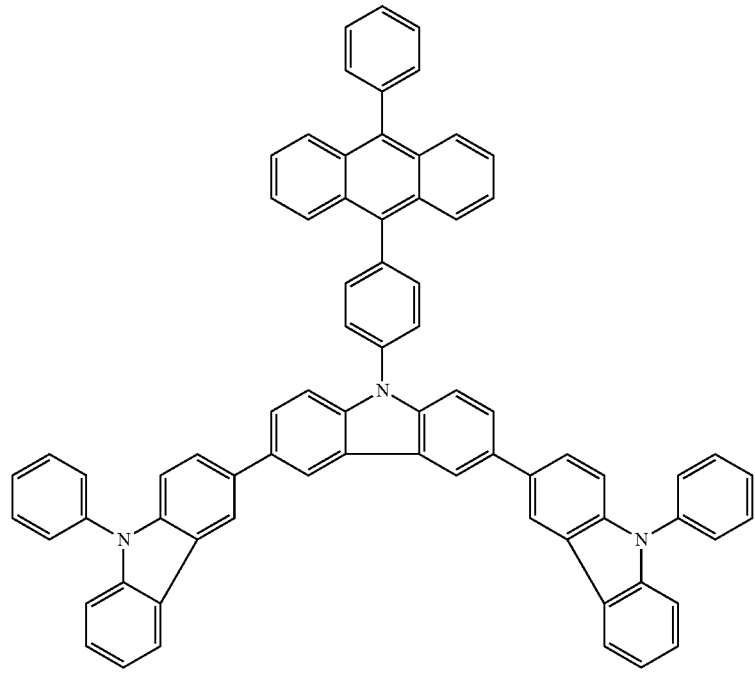
(193)
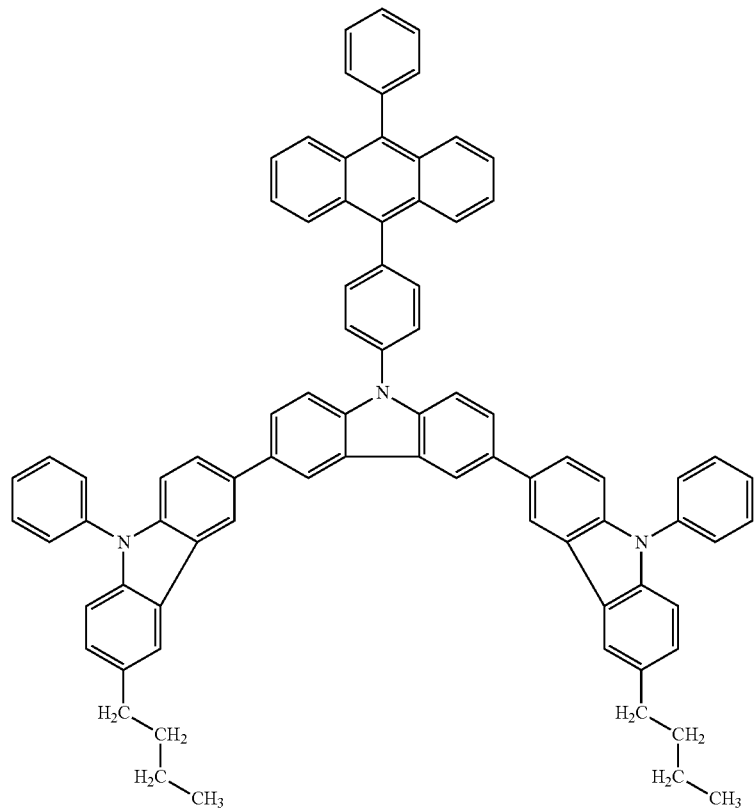
(194)

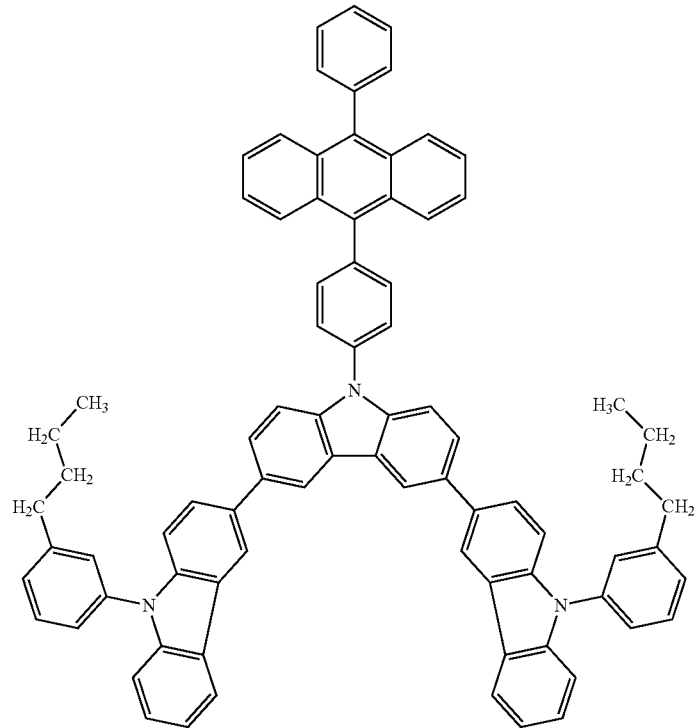
(195)
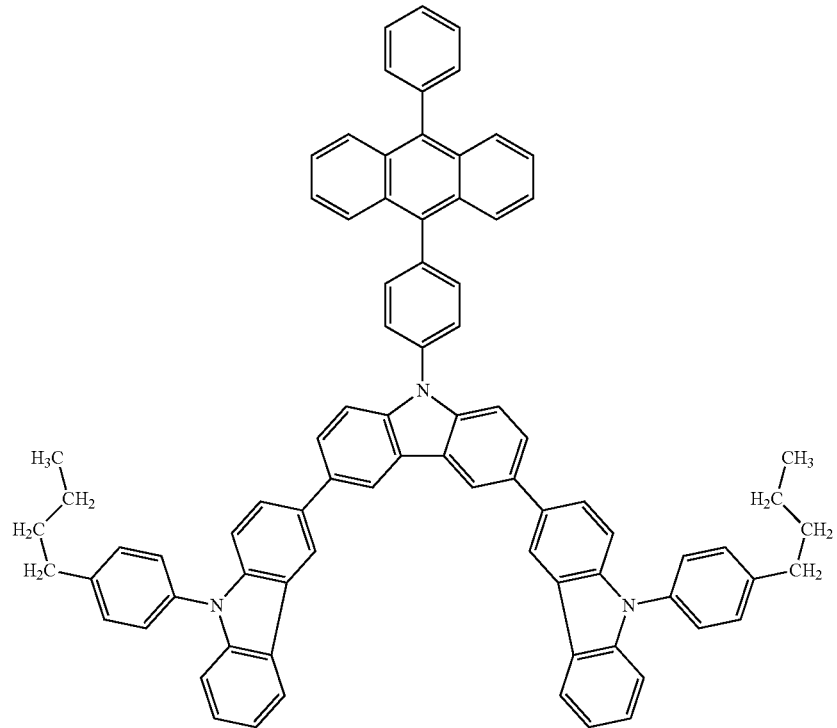
(196)

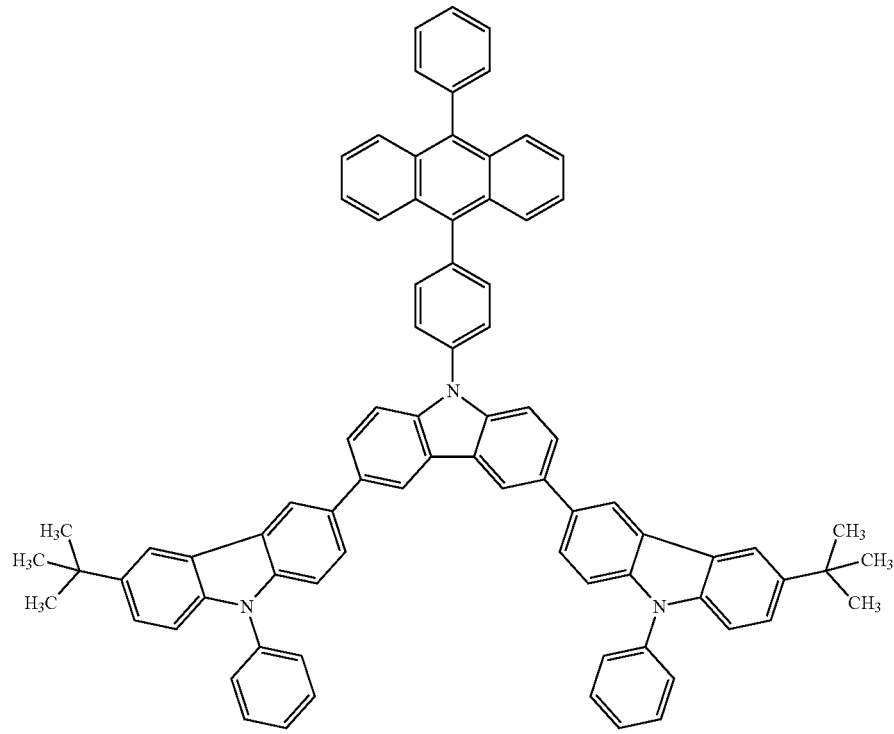
(197)
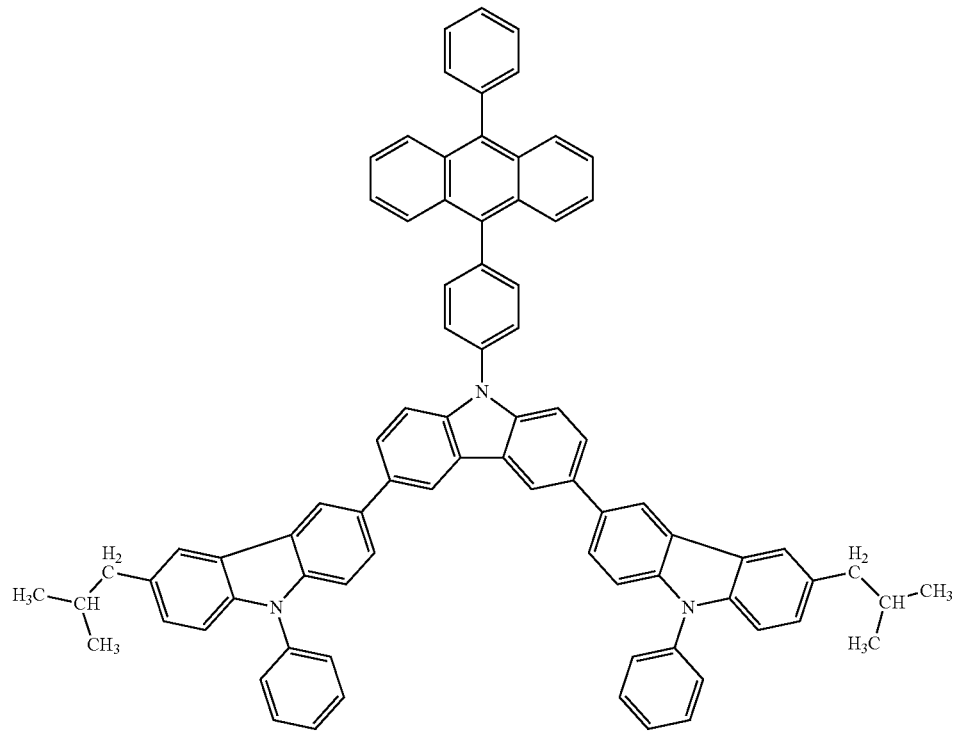
(198)

(199)
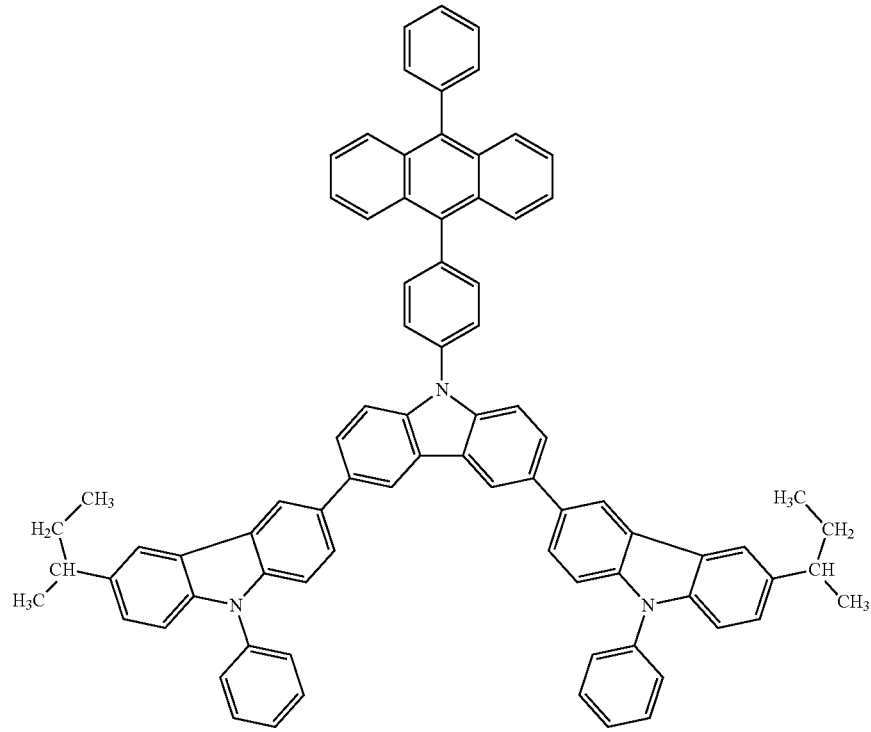
(200)
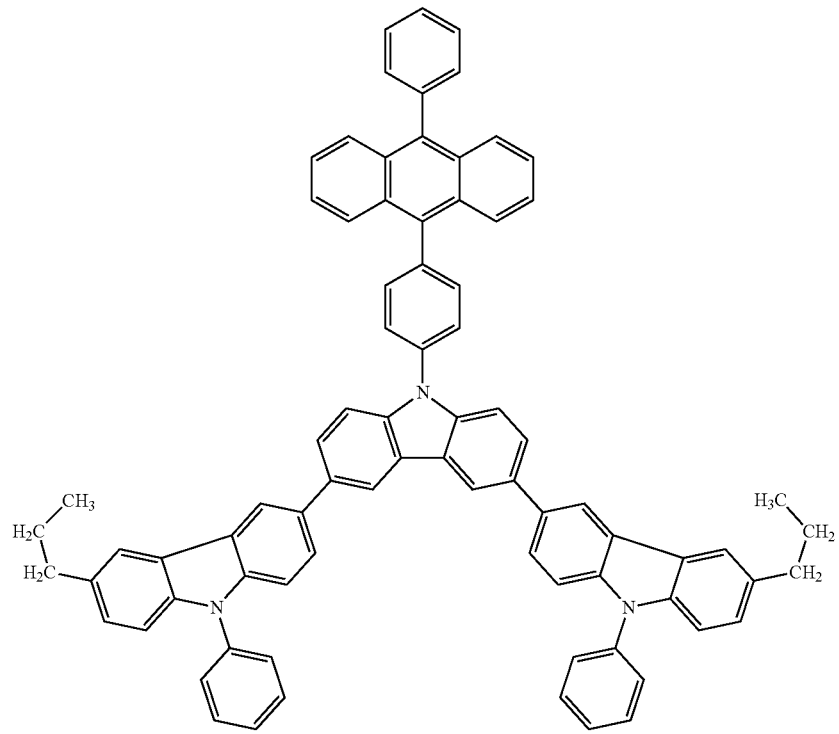

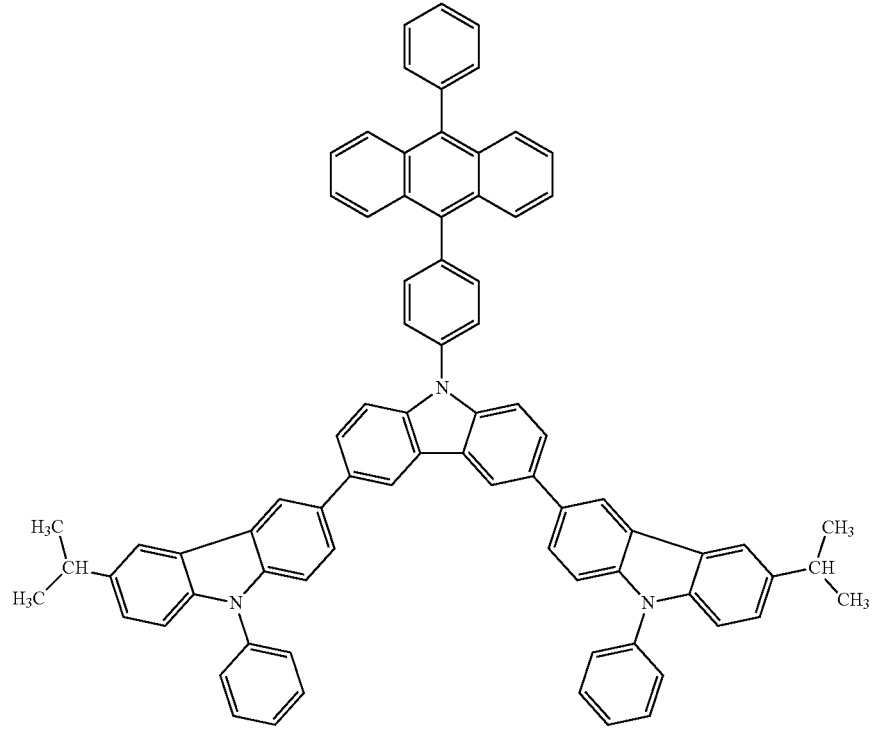
(201)
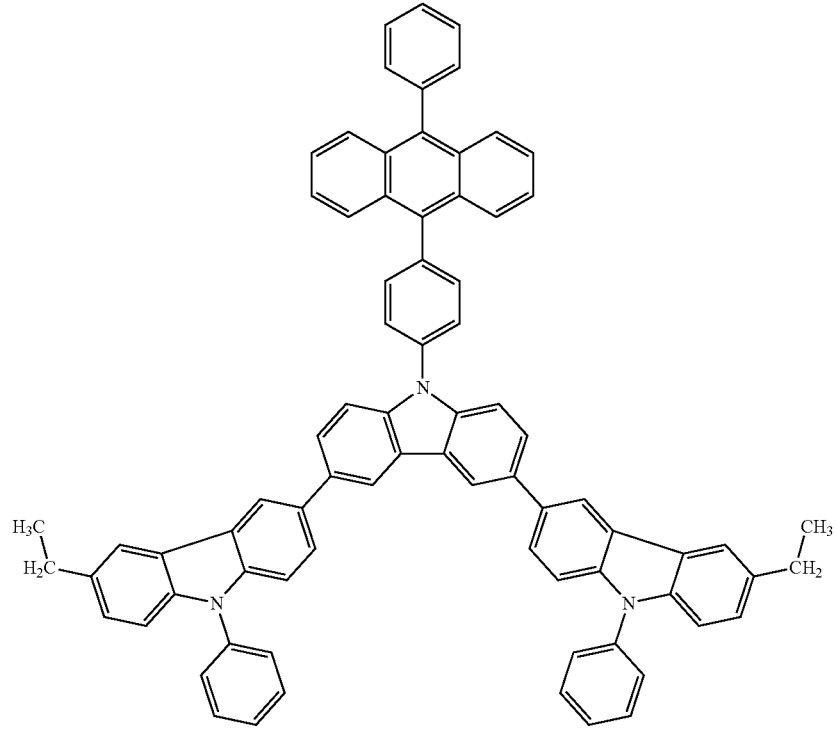
(202)

(203)
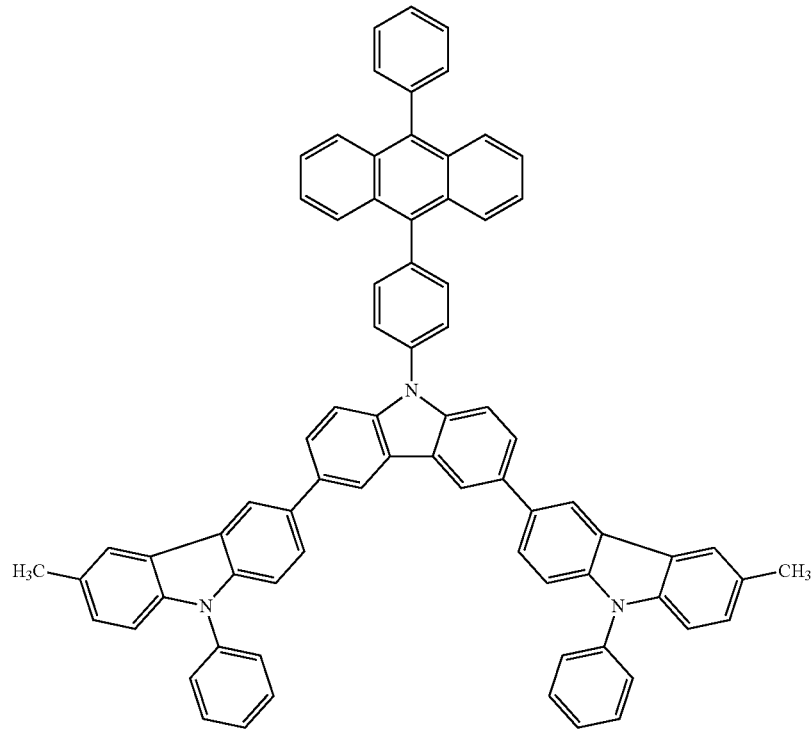
(204)
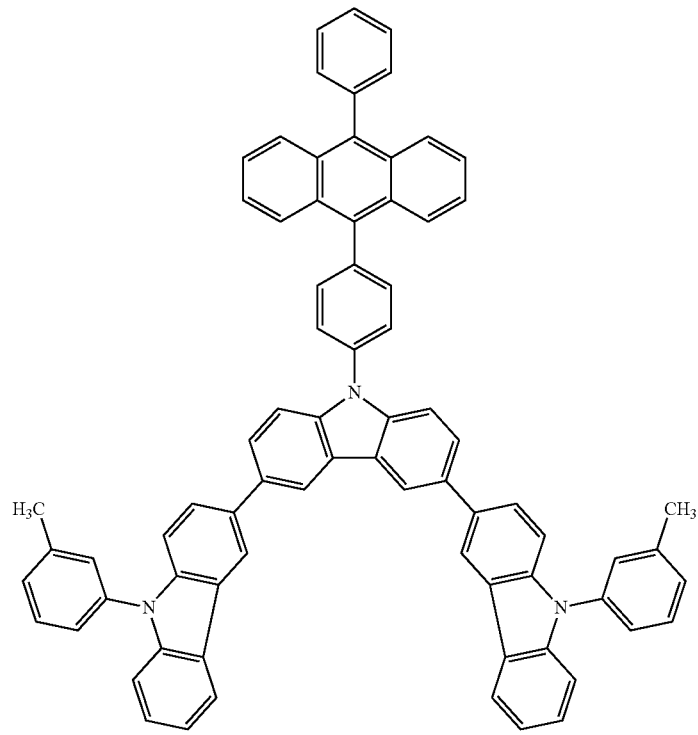

(205)
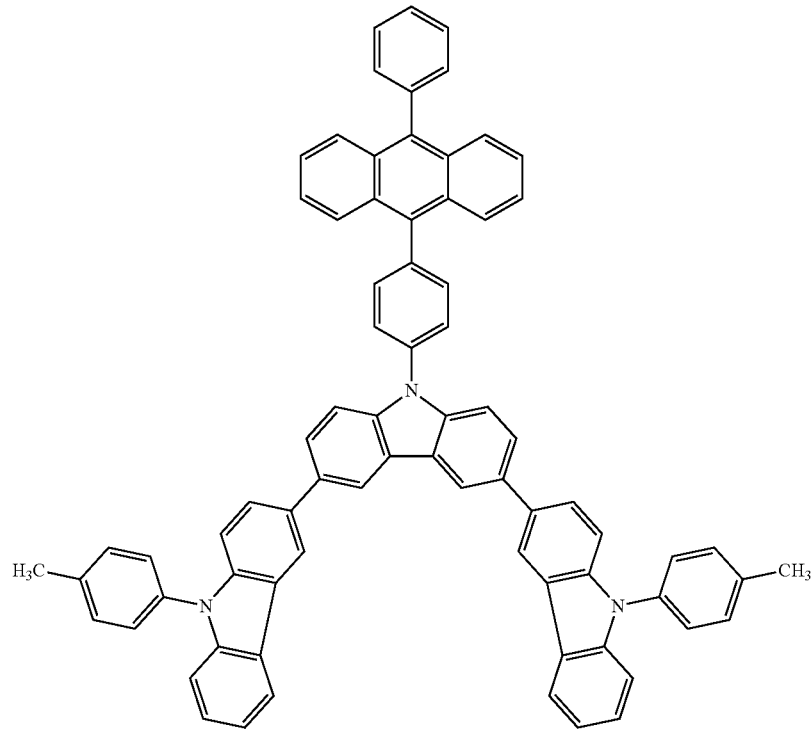
(206)
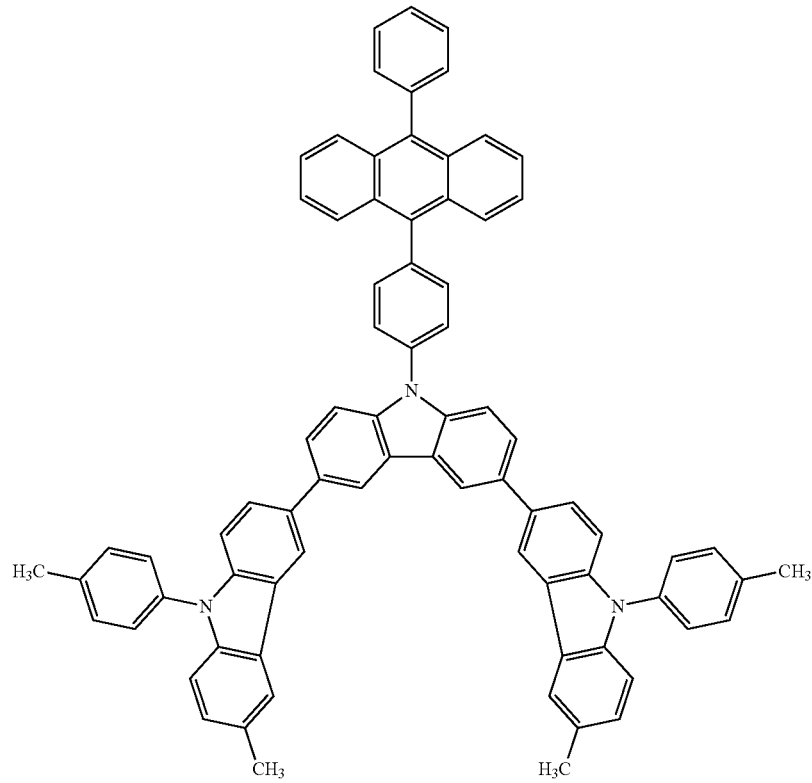

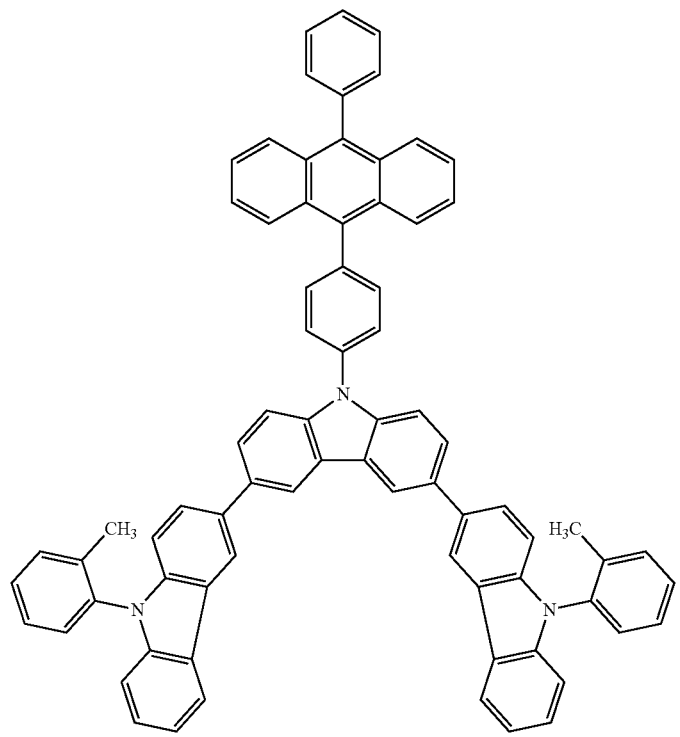
(207)
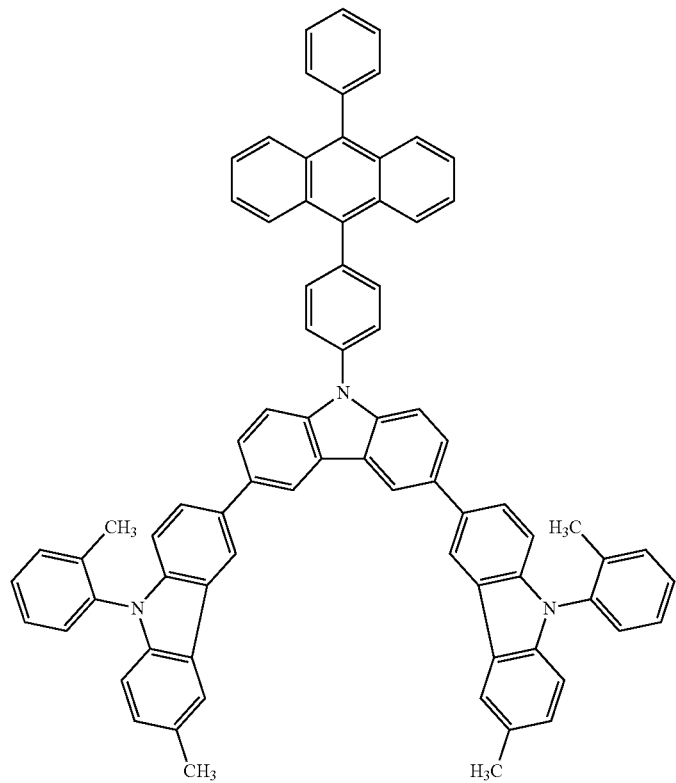
(208)

(209)
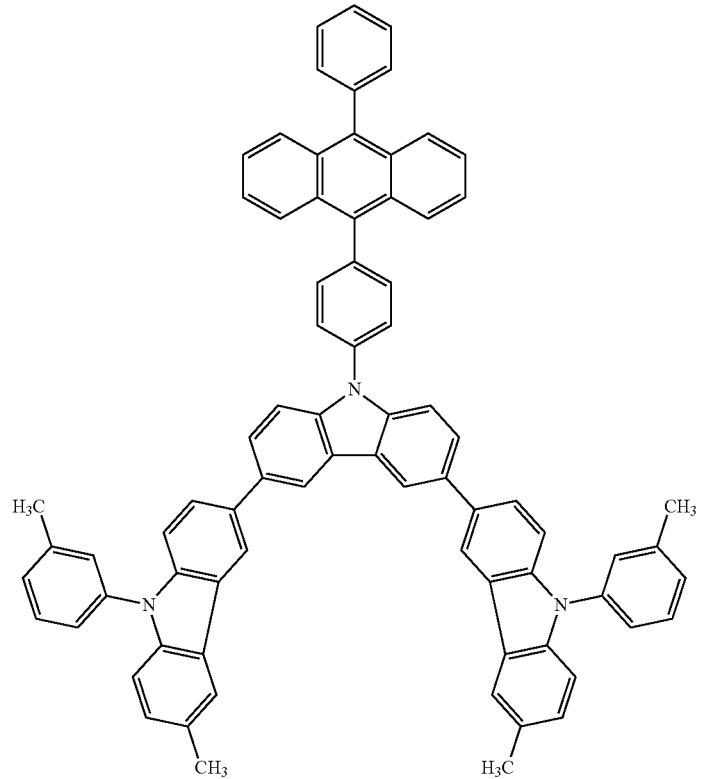
(210)
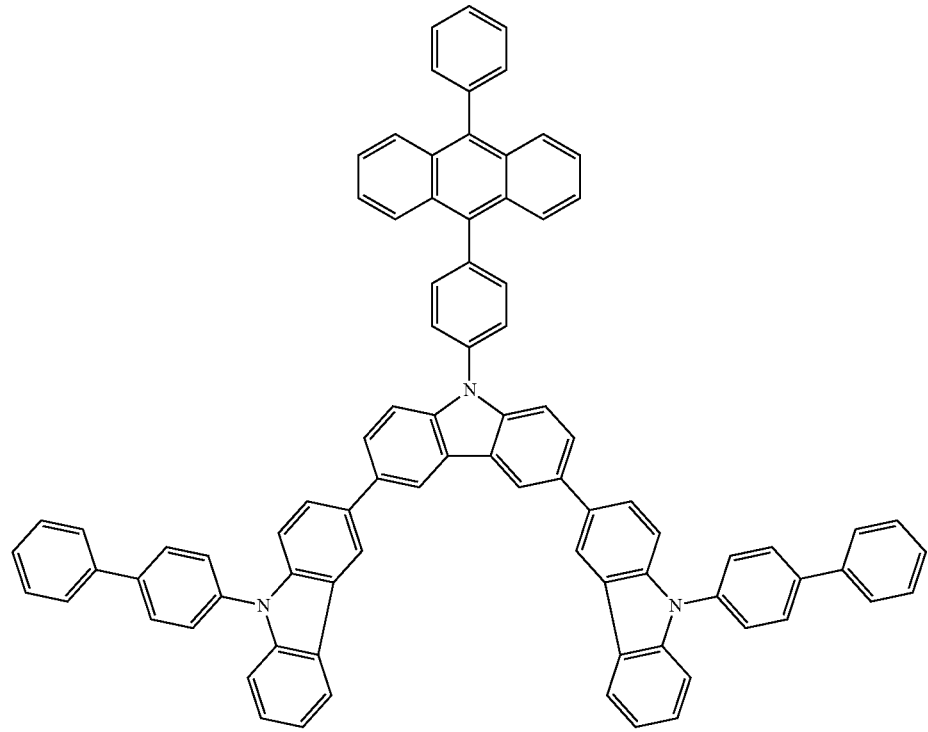

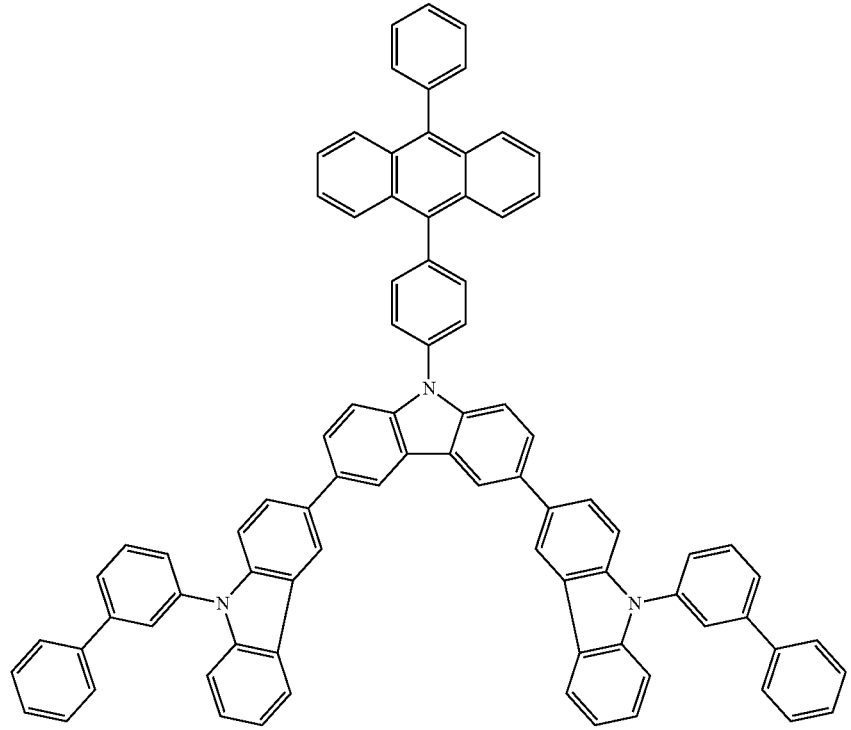
(211)
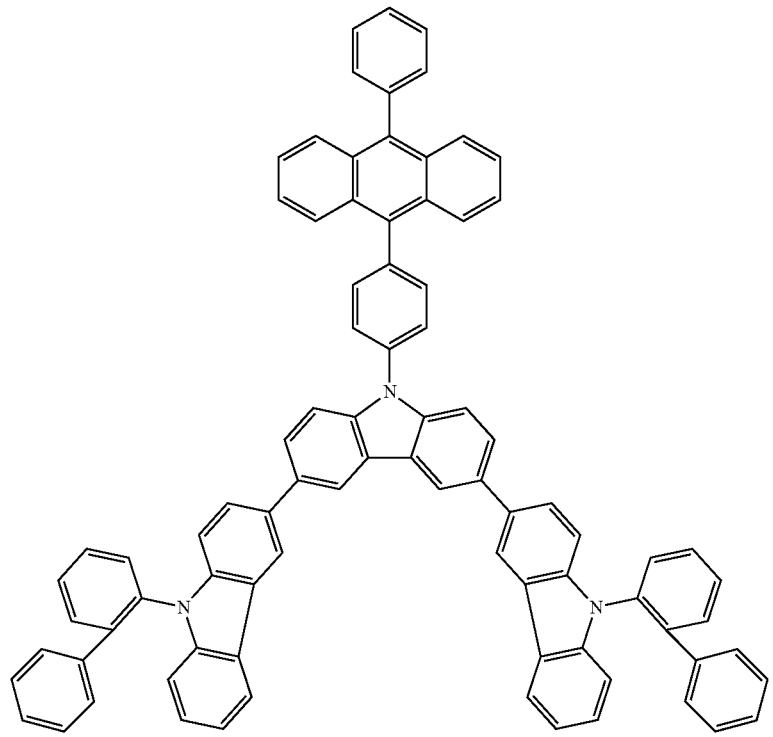
(212)

(213)
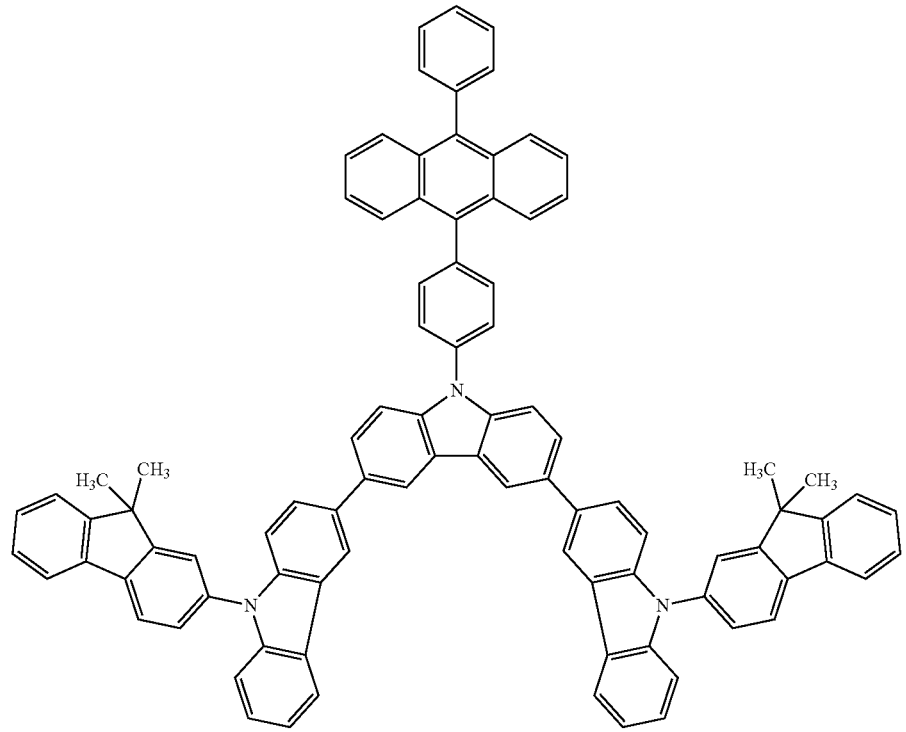
(214)
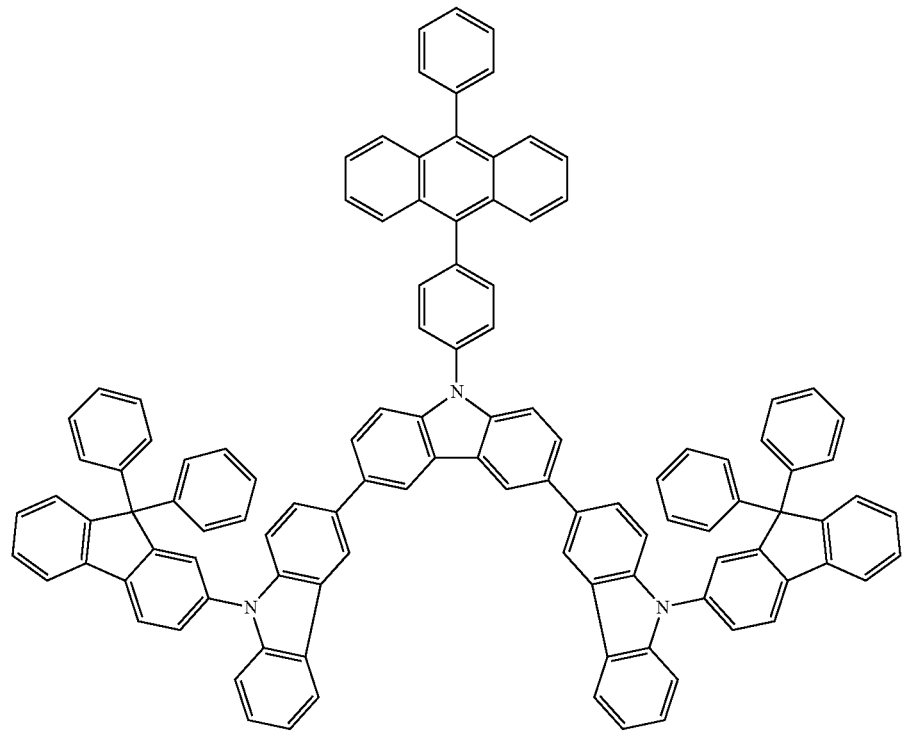

(215)
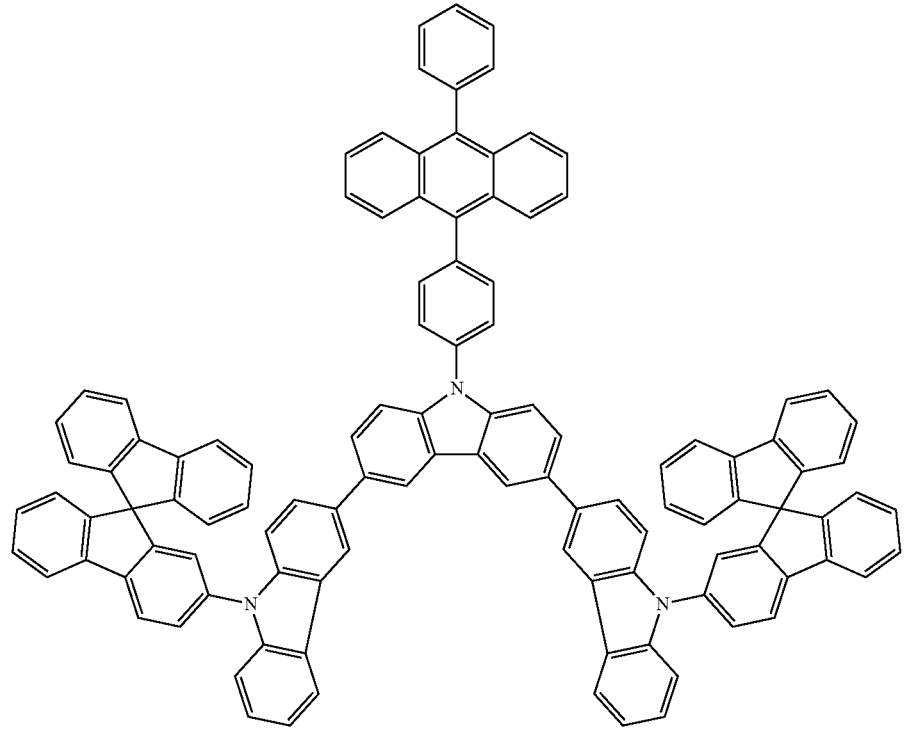
(216)
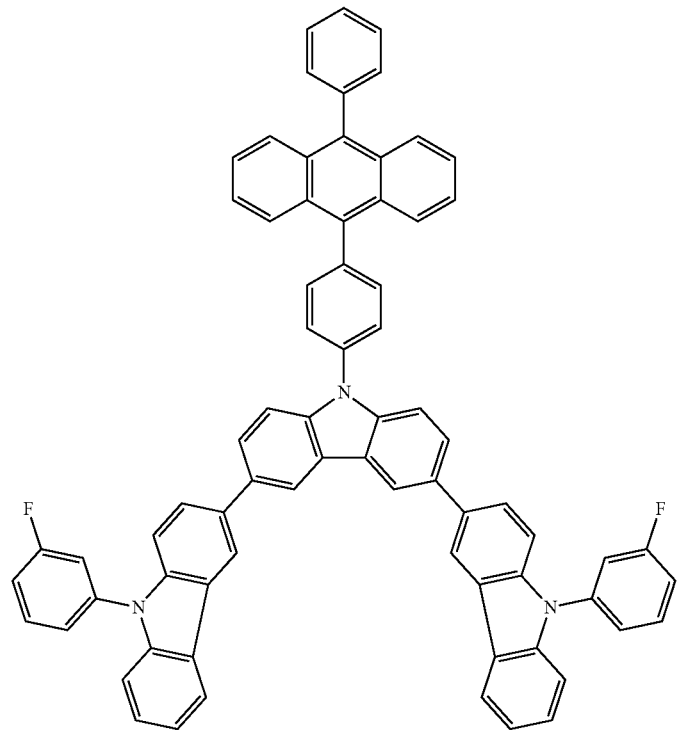

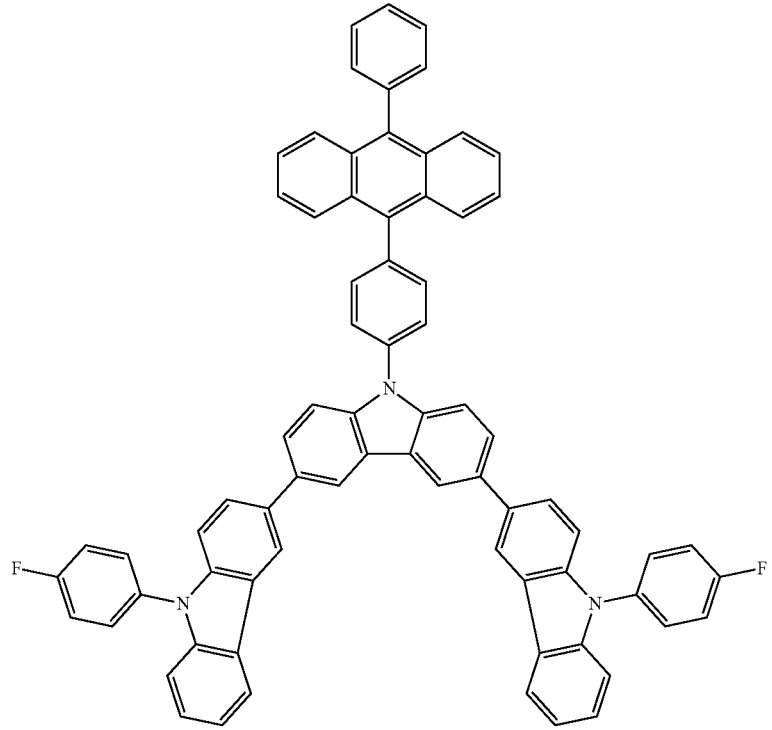
(217)
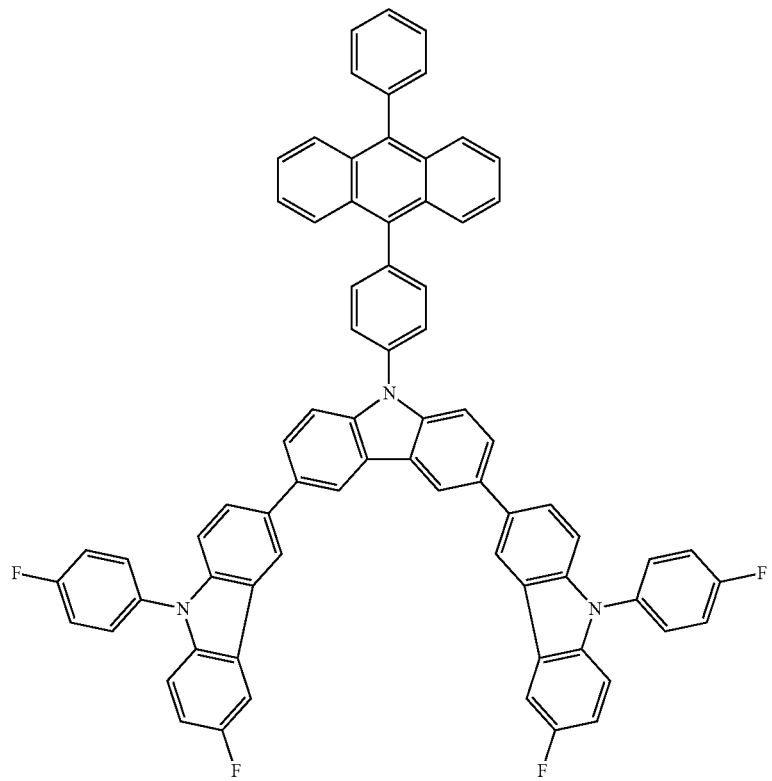
(218)

(219)
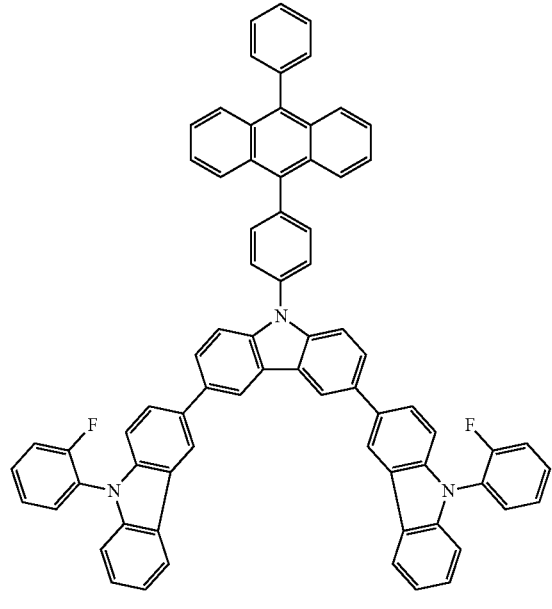
(220)
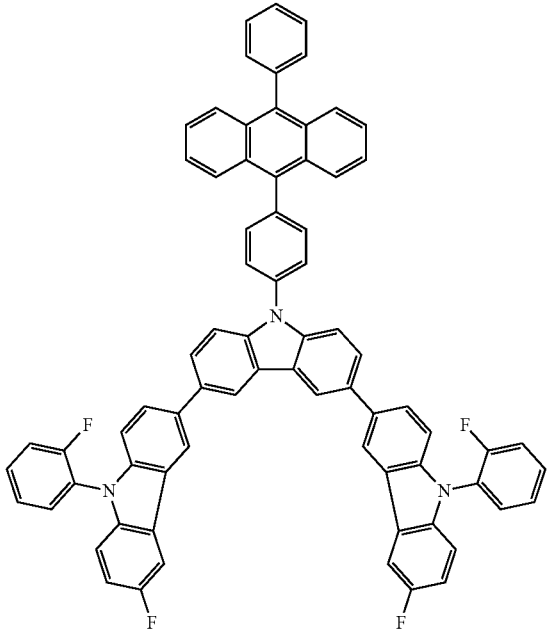
(221)
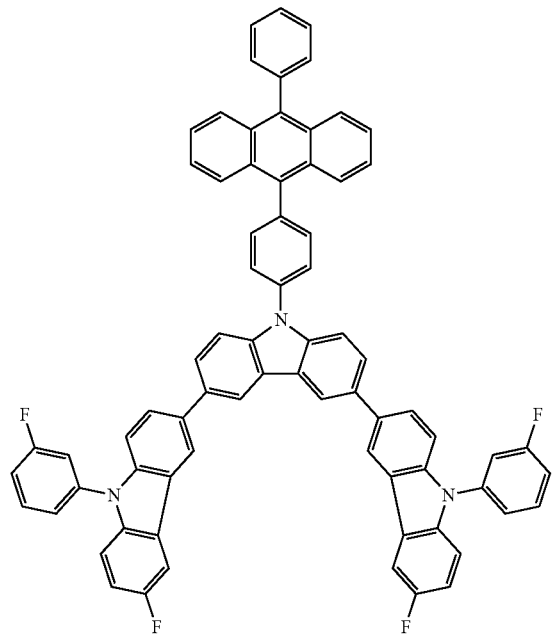
(222)
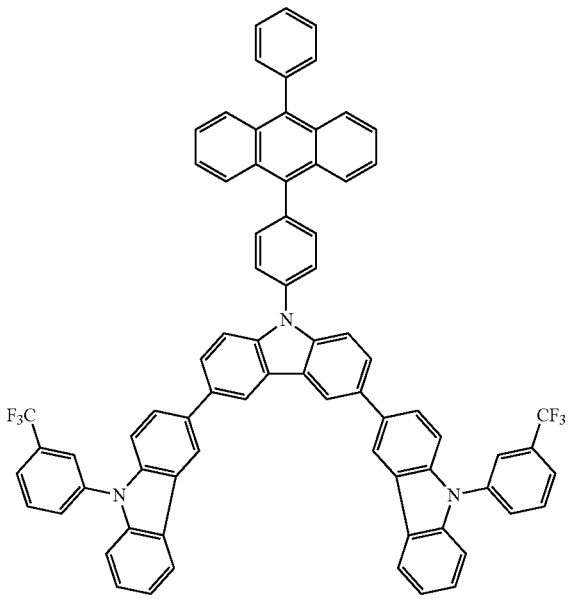

(223)
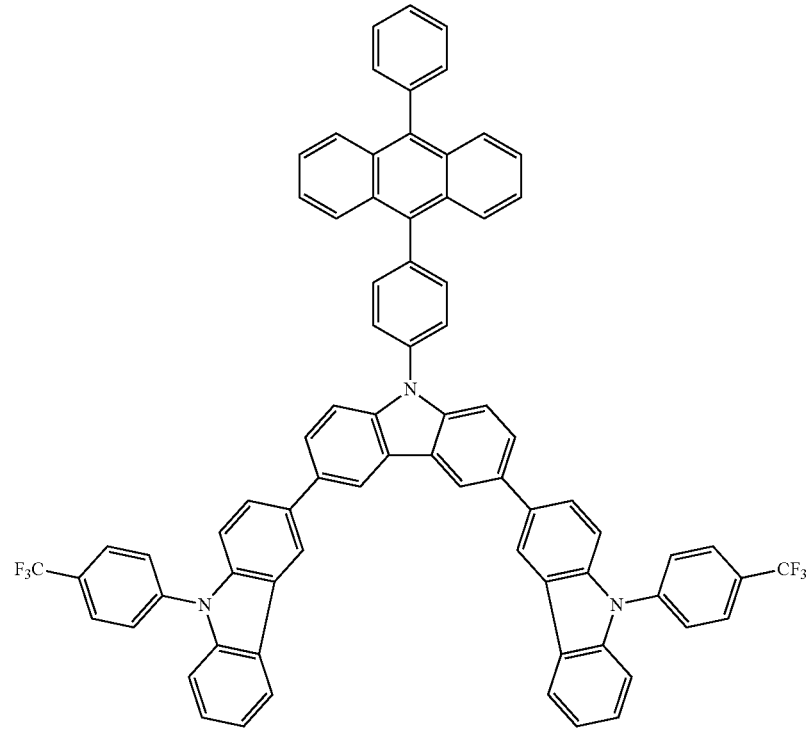
(224)
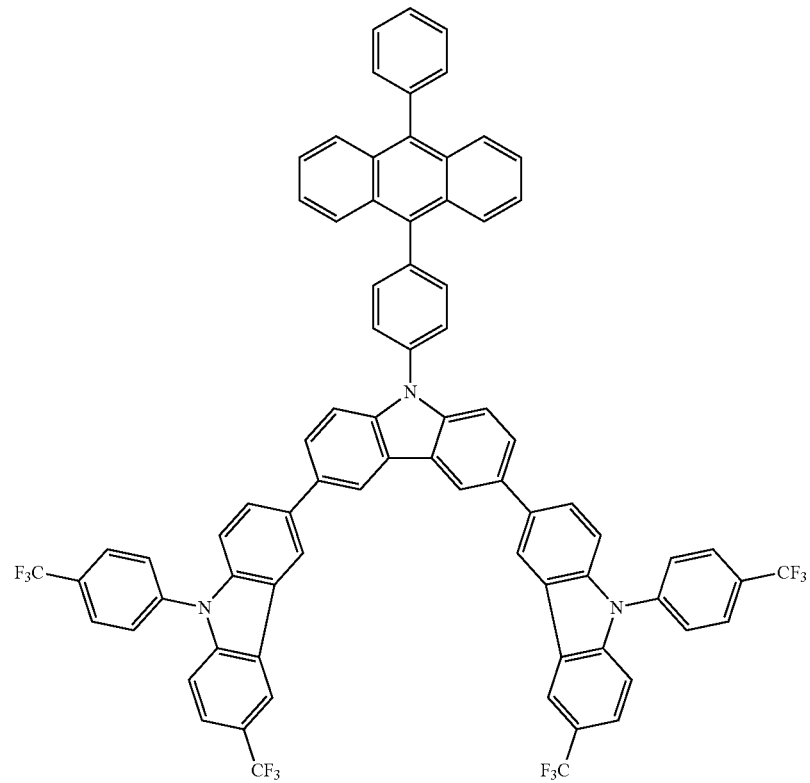

(225)
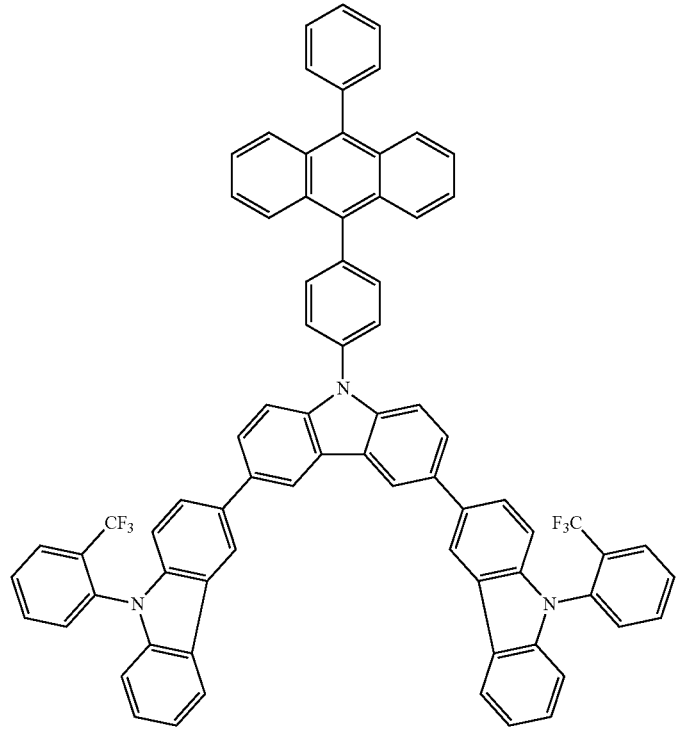
(226)
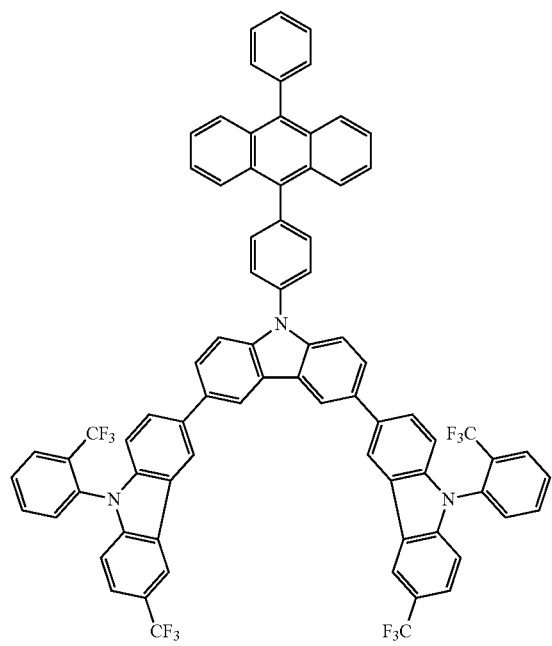
(227)
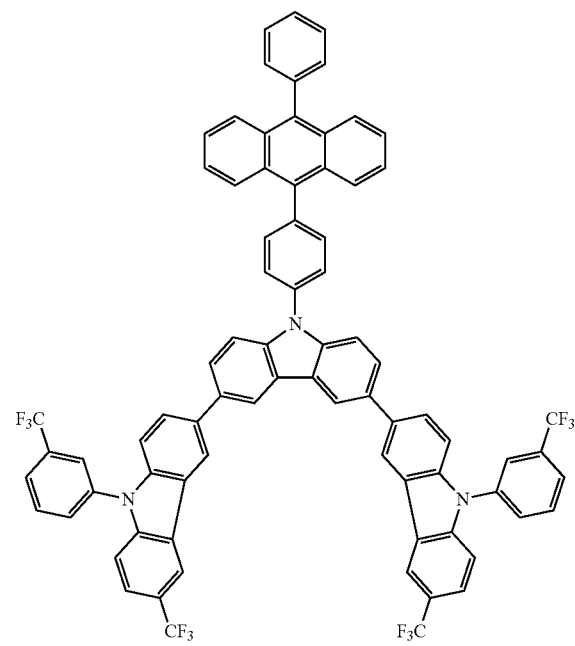

(228)
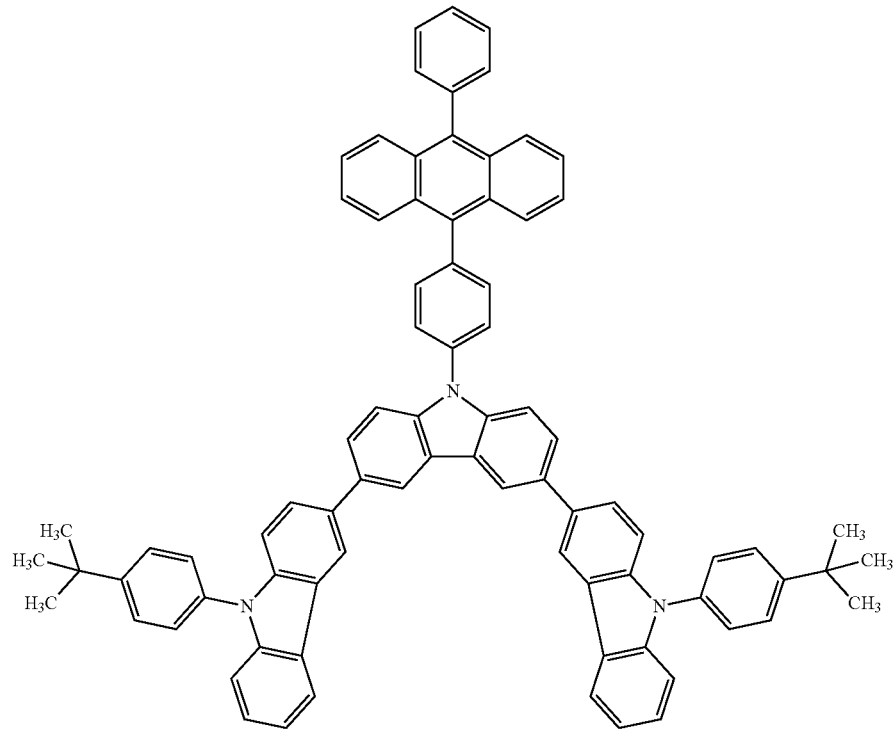
(229)
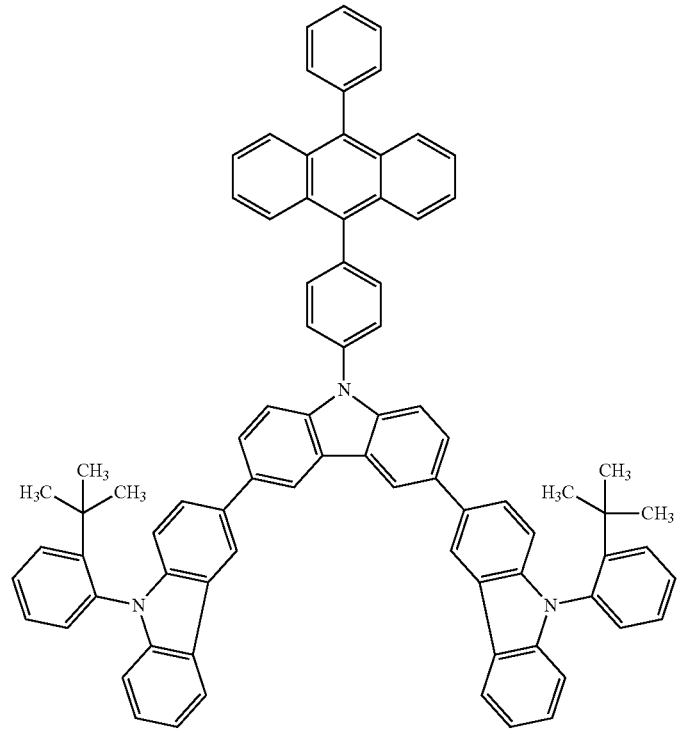

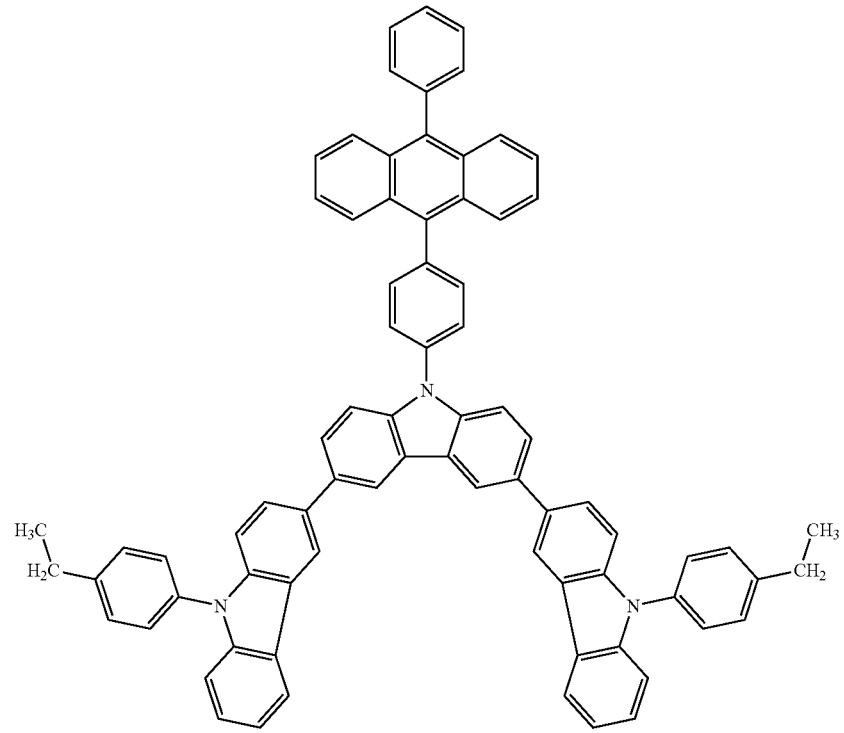
(230)
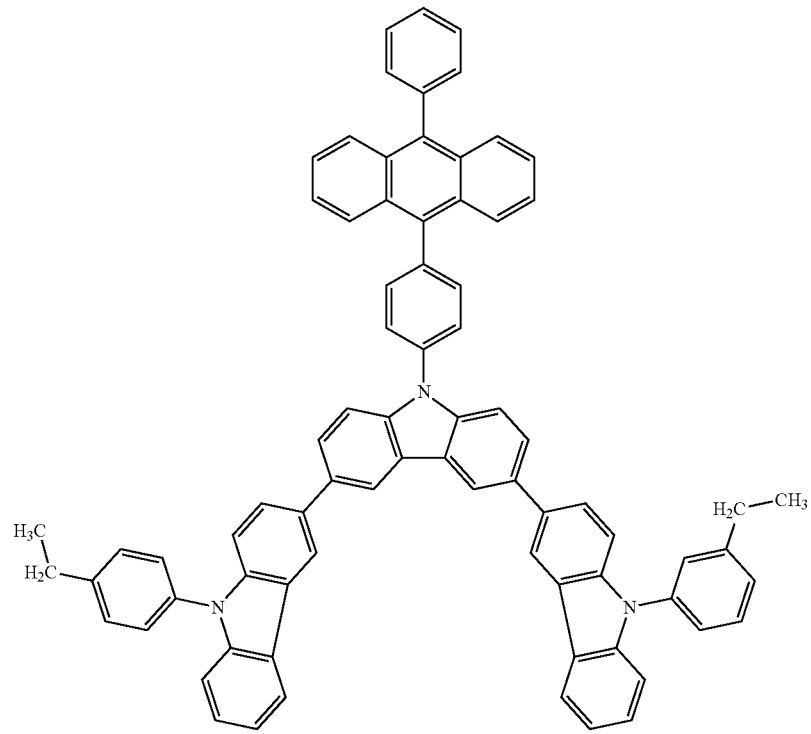
(231)

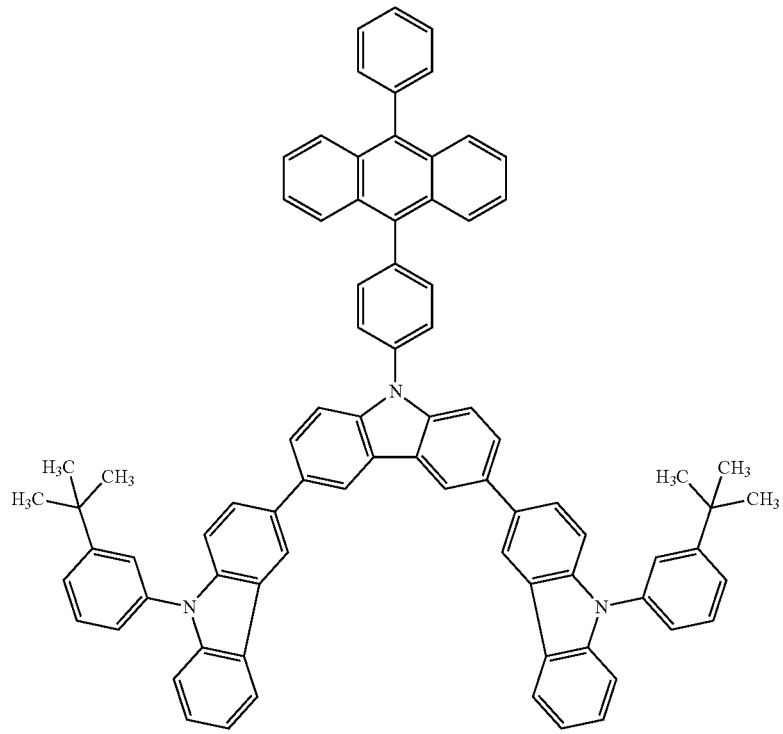
(232)
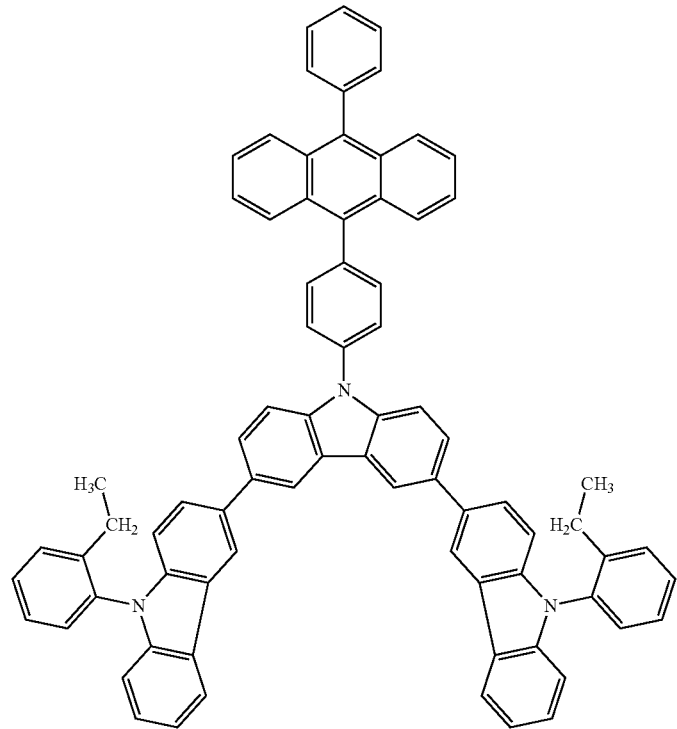
(233)

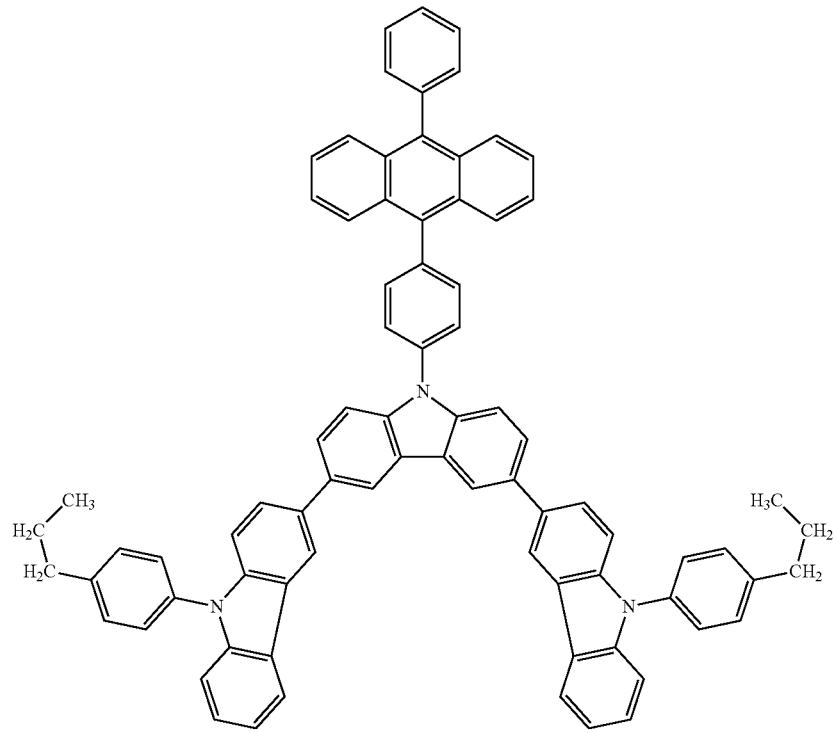
(234)
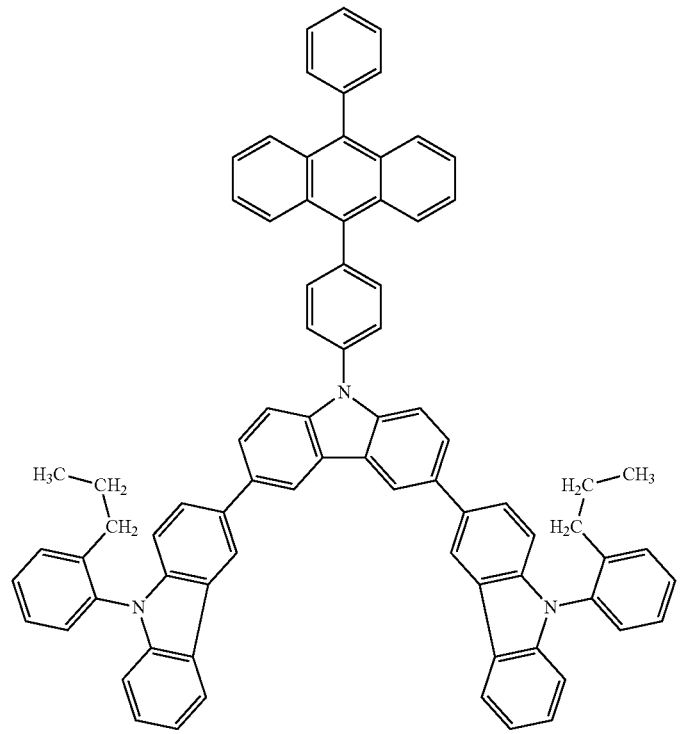
(235)

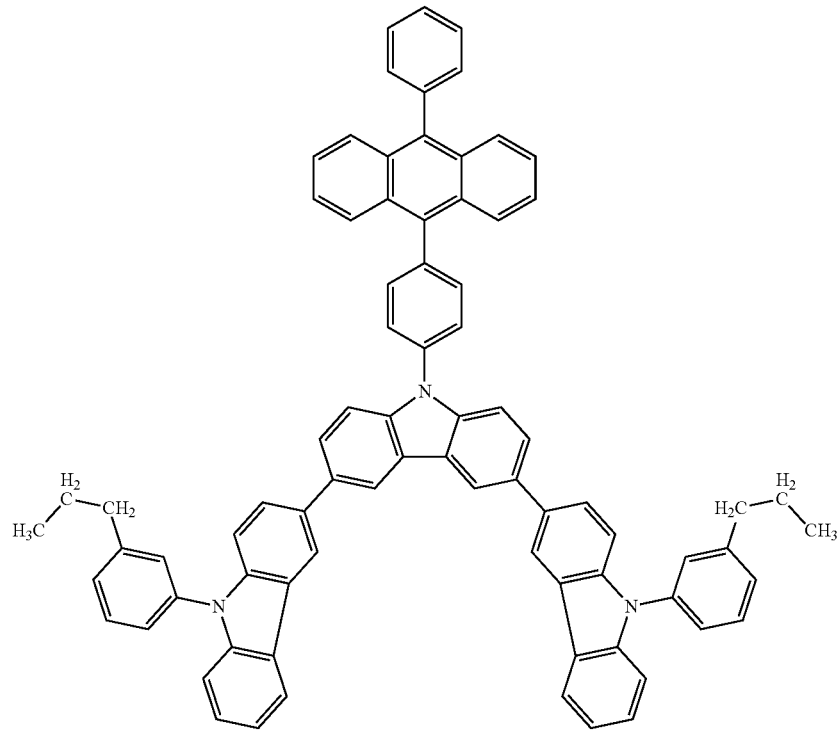
(236)
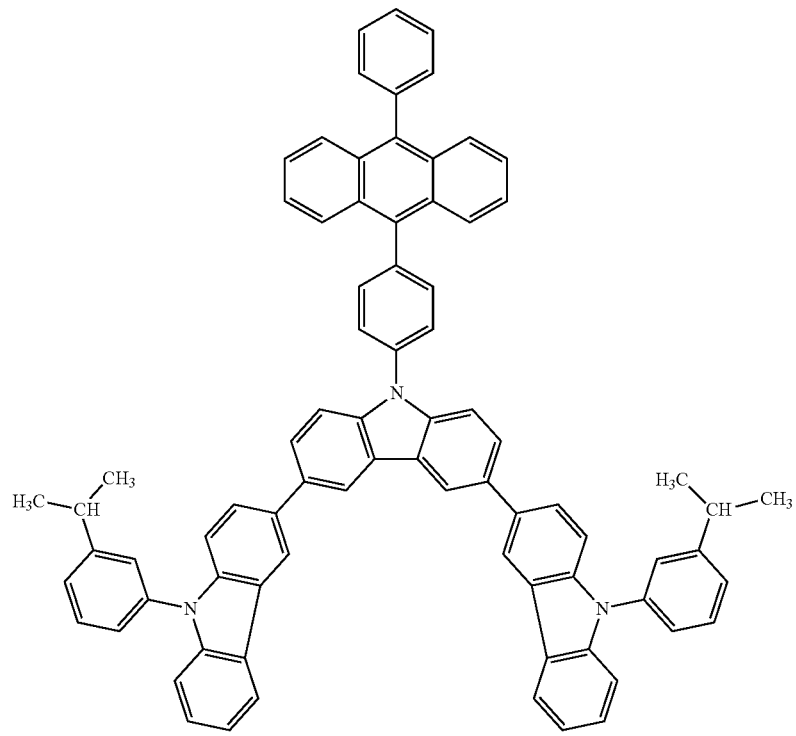
(237)

-continued
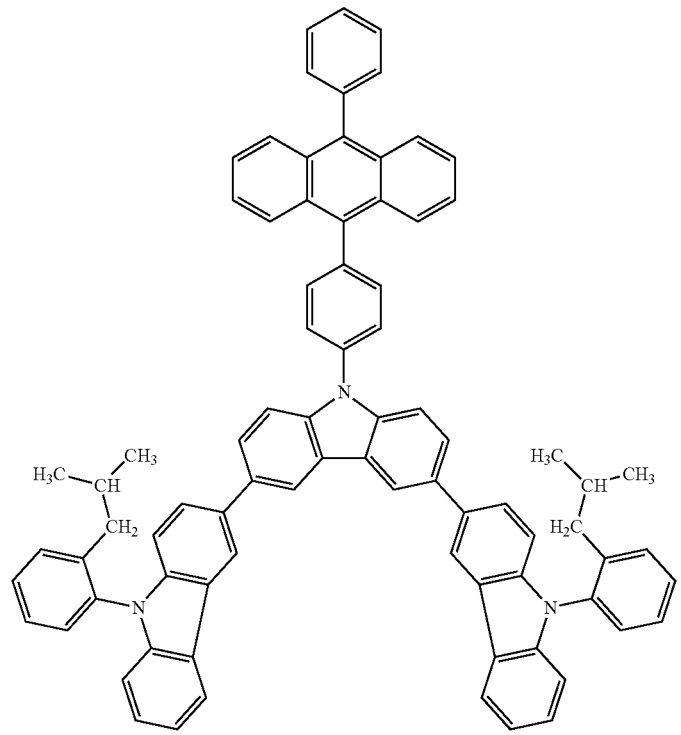
(238)
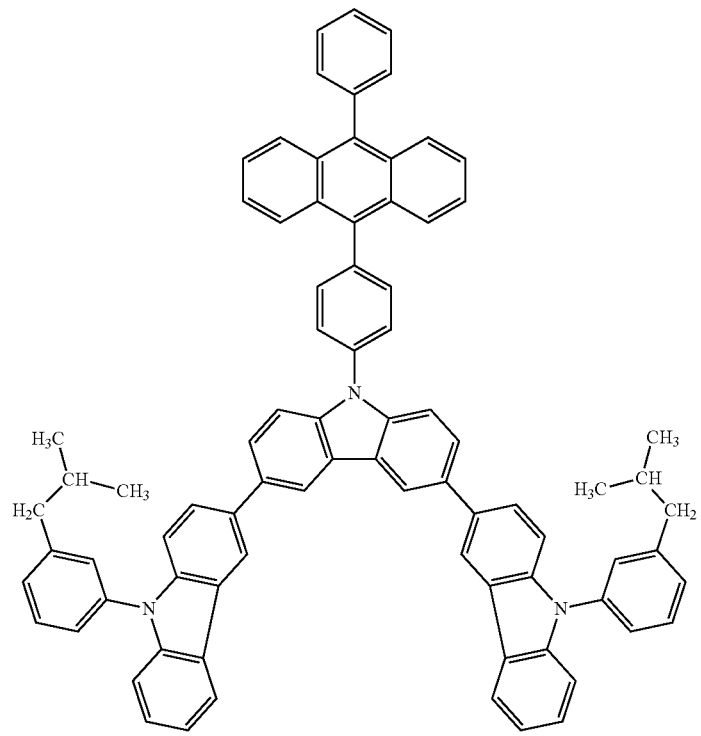
(239)

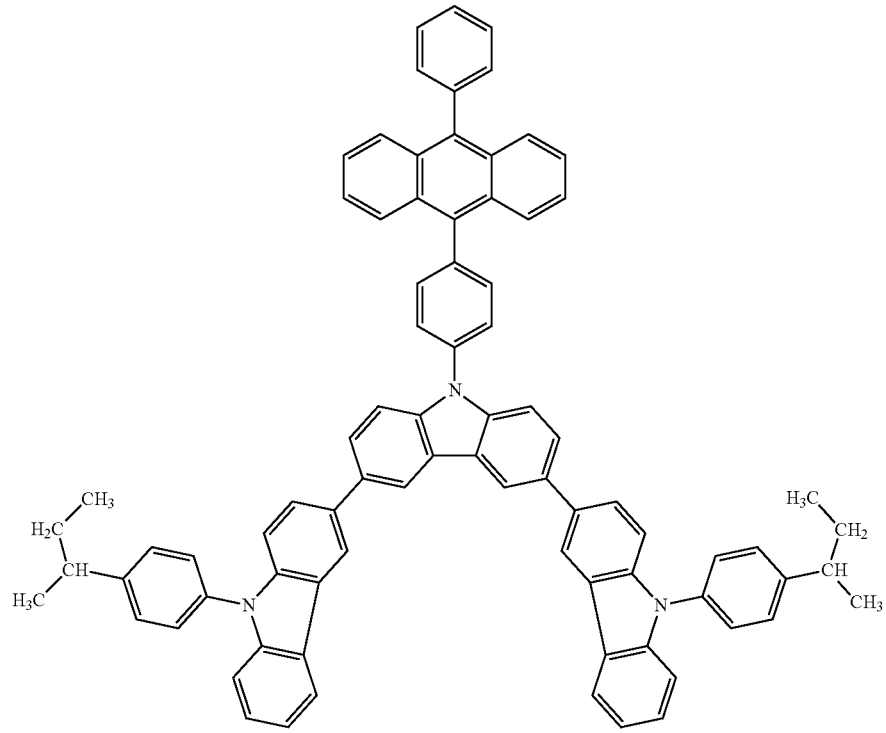
(240)
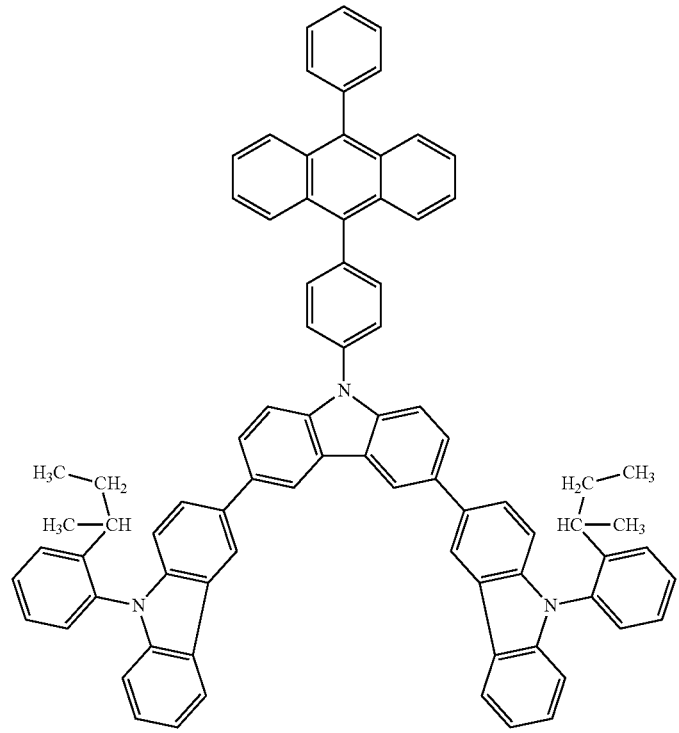
(241)

-continued
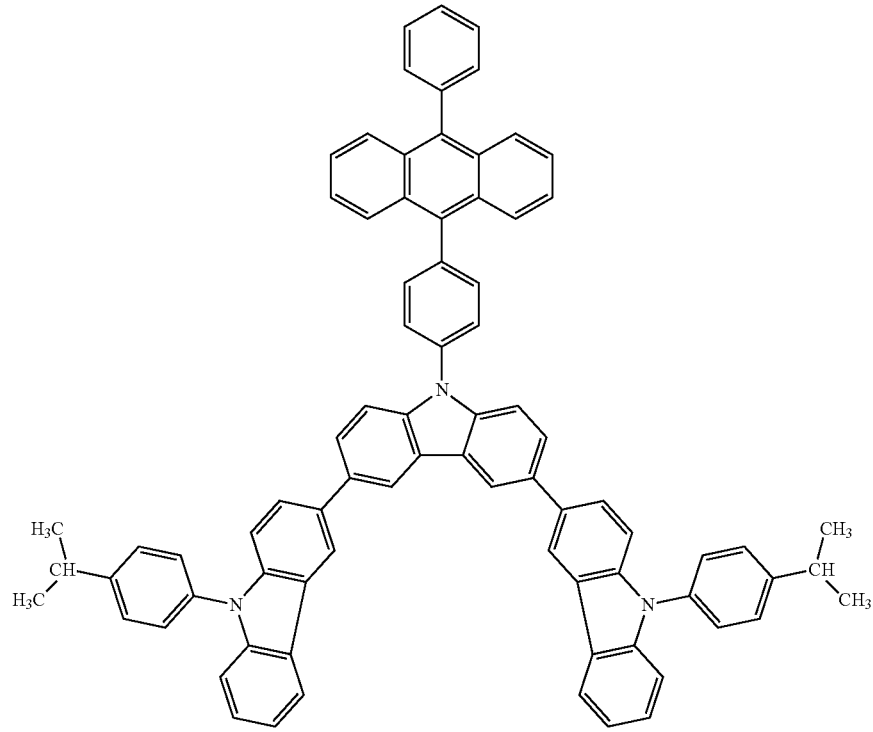
(242)
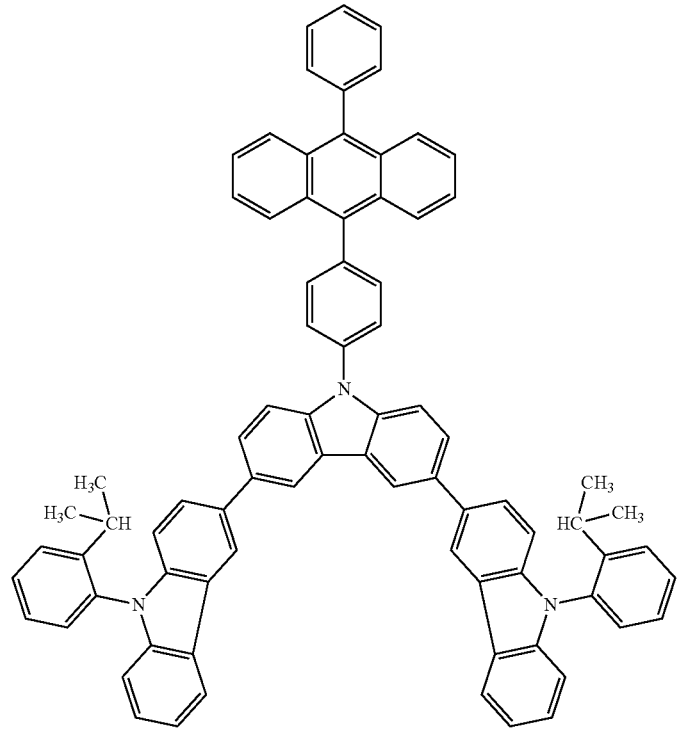
(243)

-continued
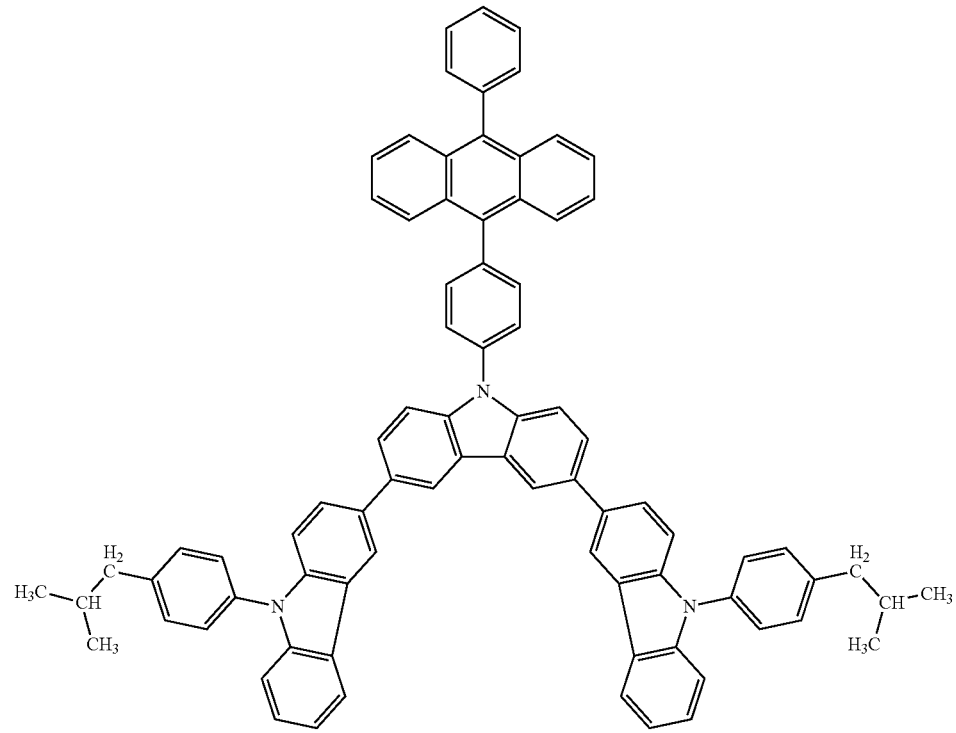
(244)
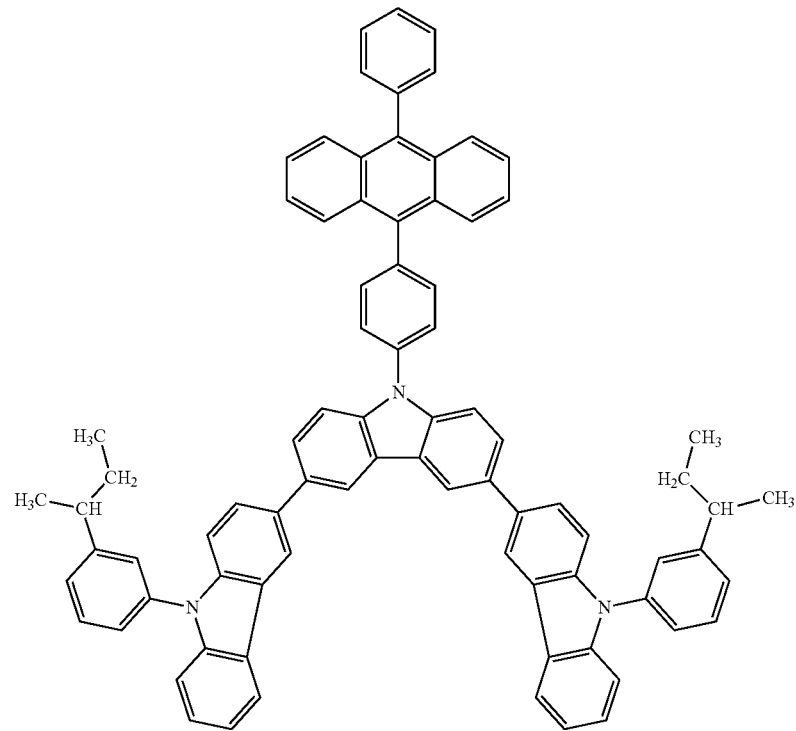
(245)

(246) 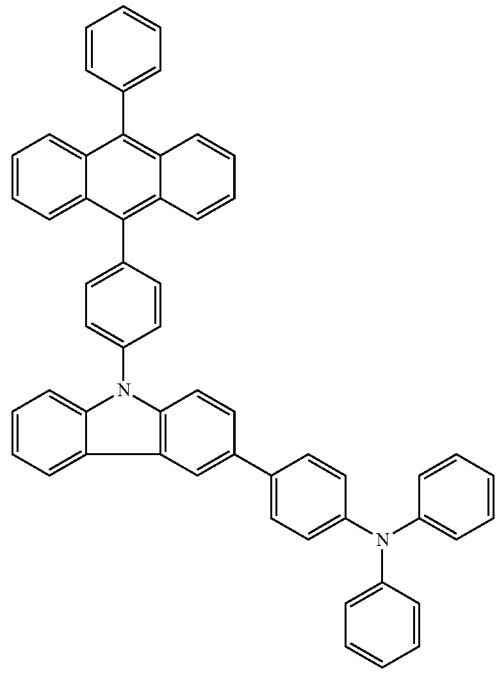
(247) 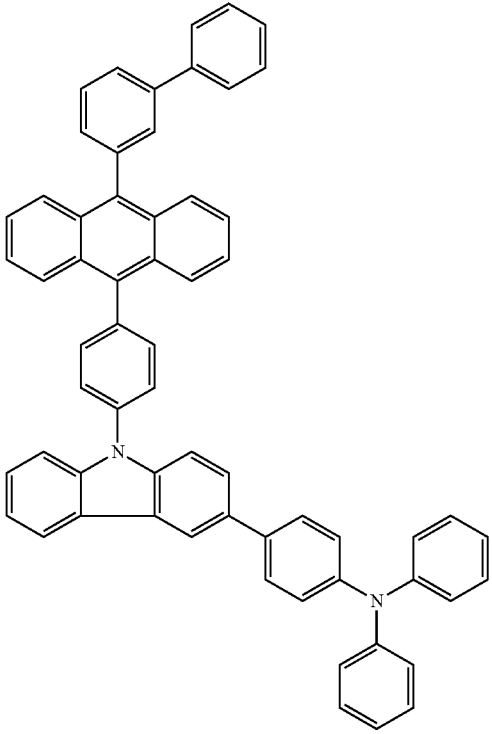
(248) 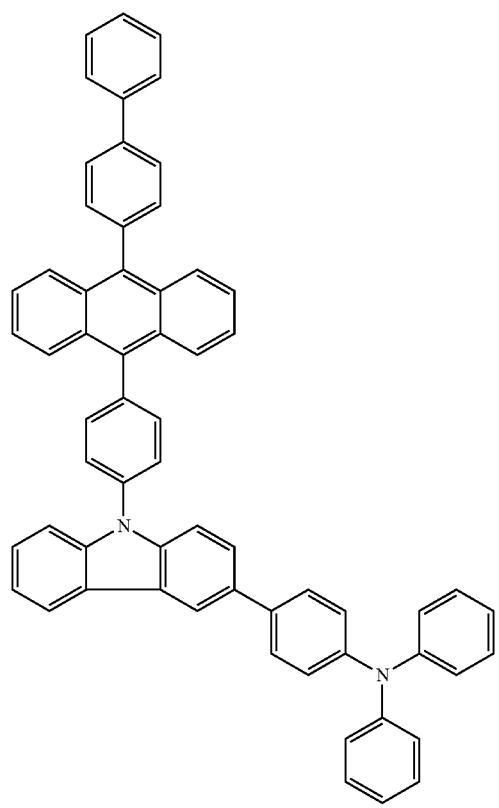
(249) 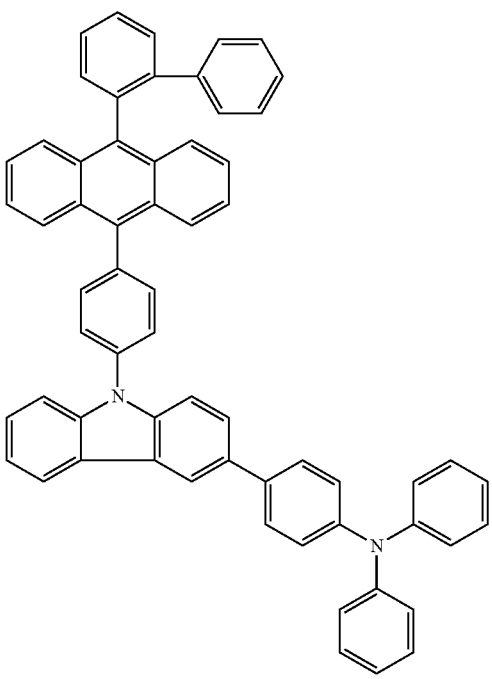

(250)
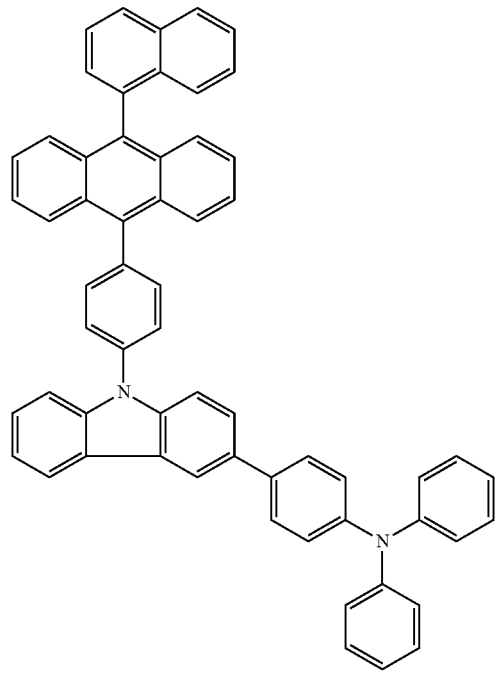
(251)
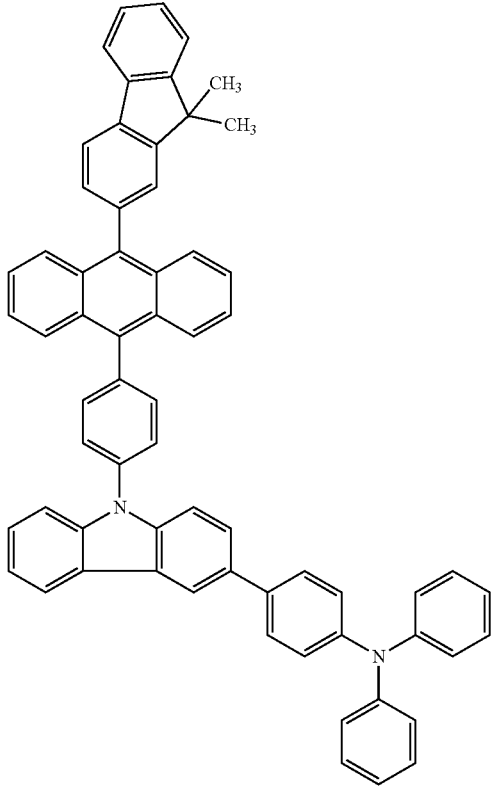
(252)
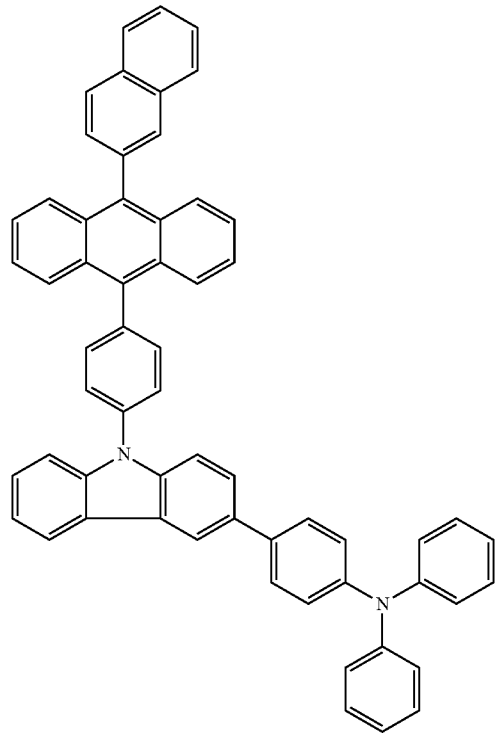
(253)
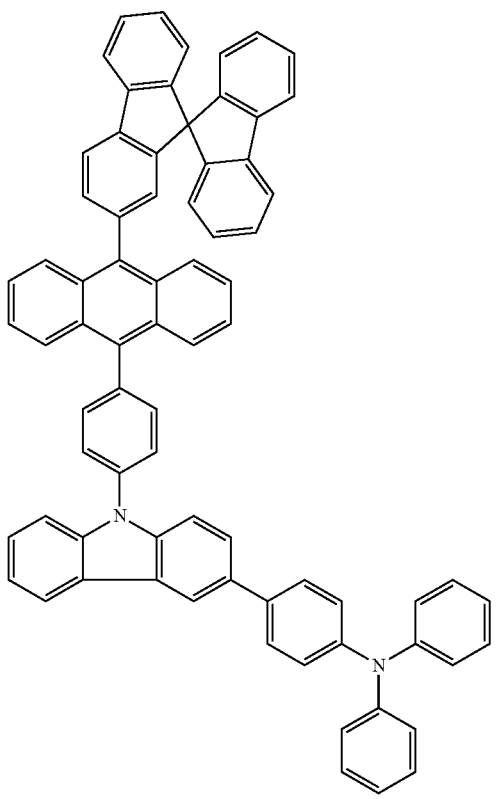

-continued
(254)
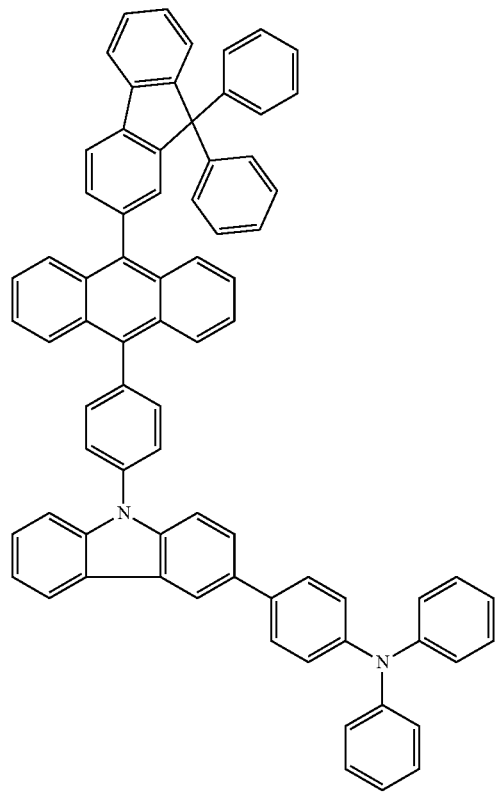
(255)
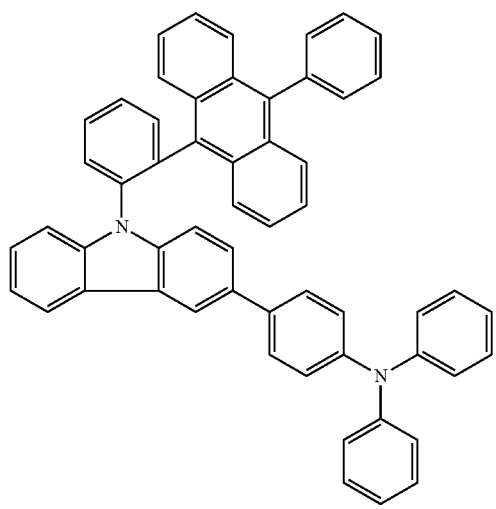
(256)
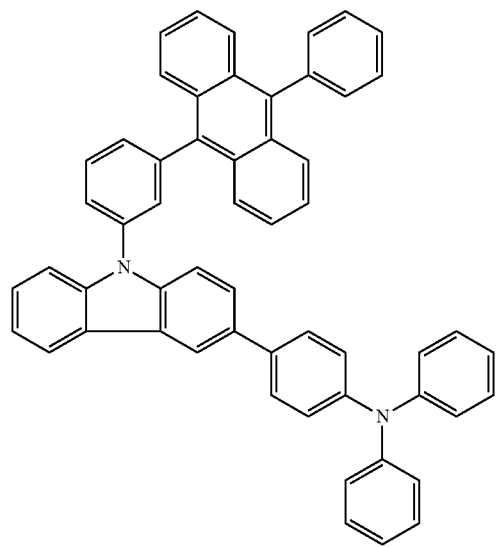
(257)
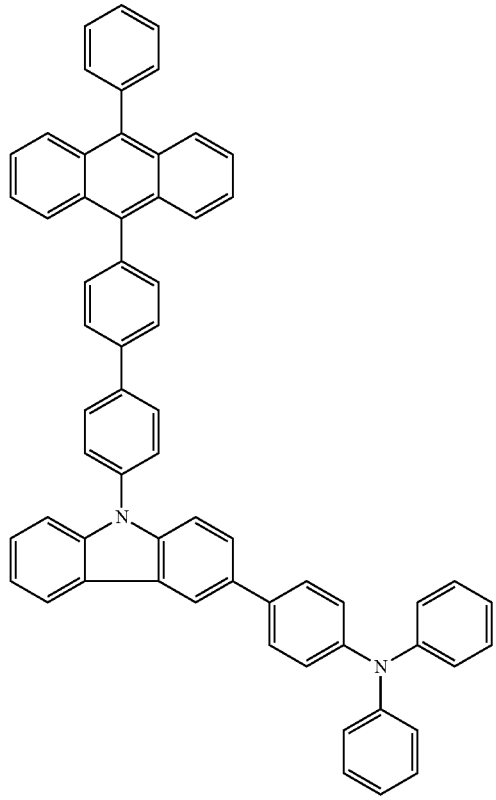

(258)
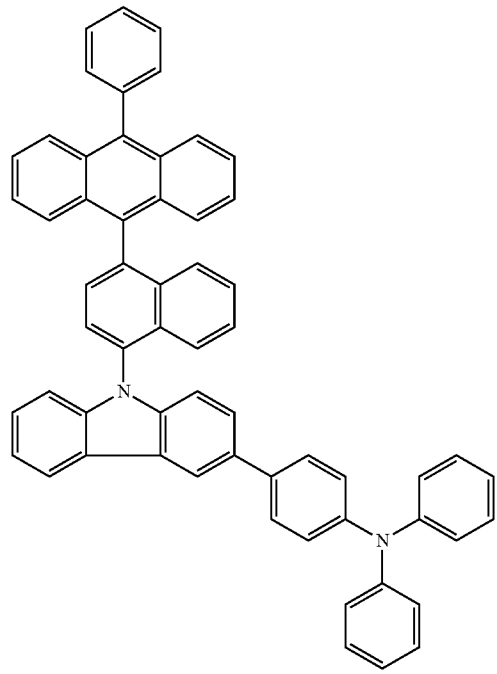
(259)
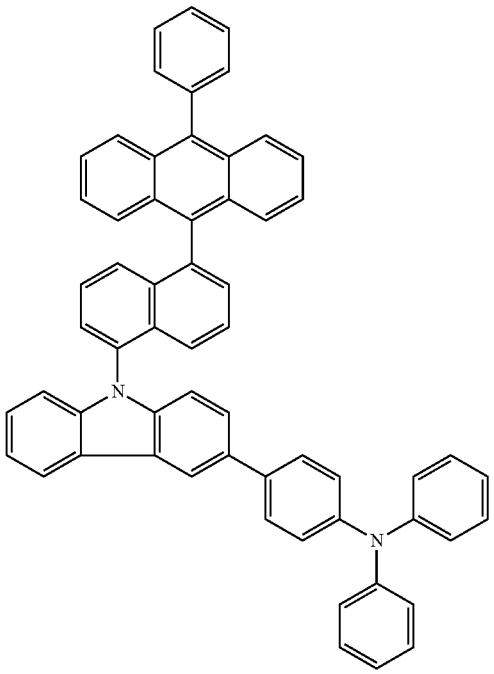
(260)
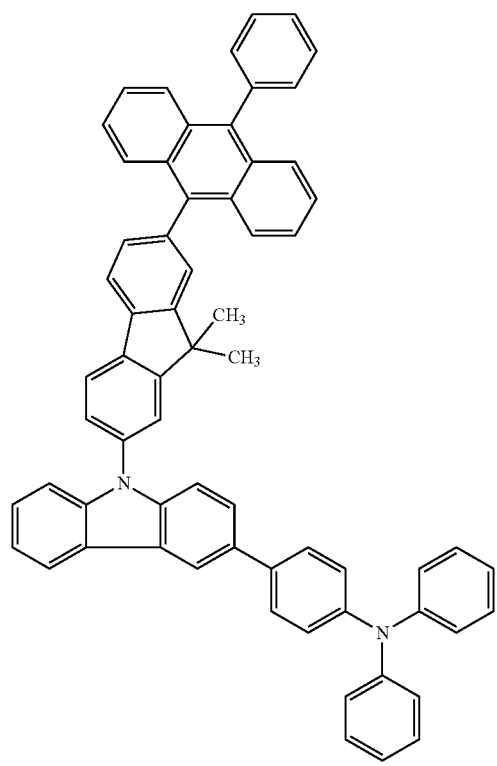
(261)
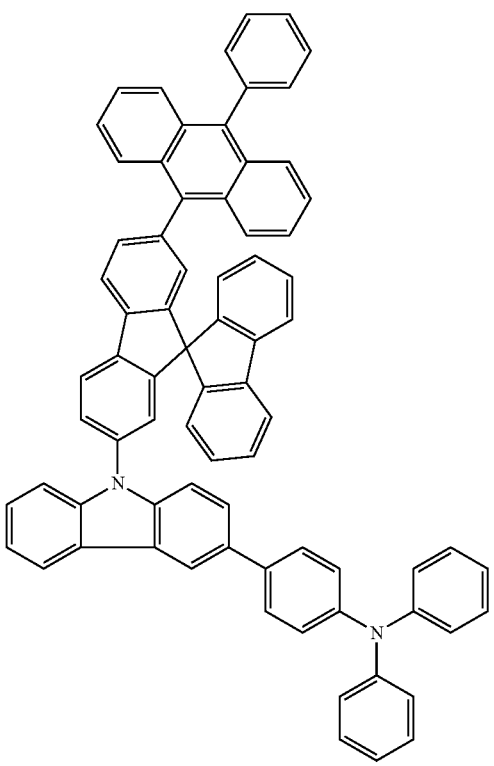

-continued
(262)
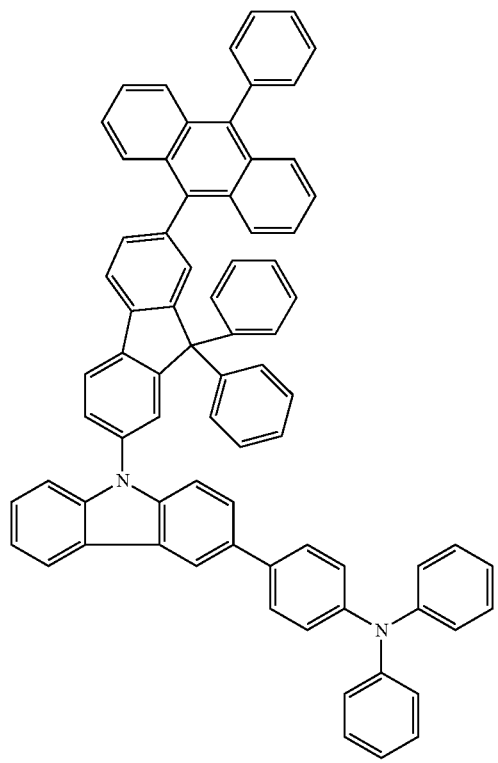
(263)
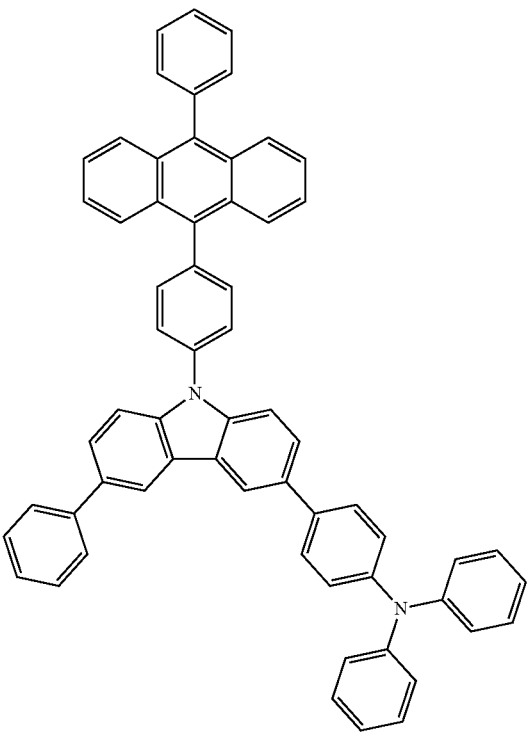
(264)
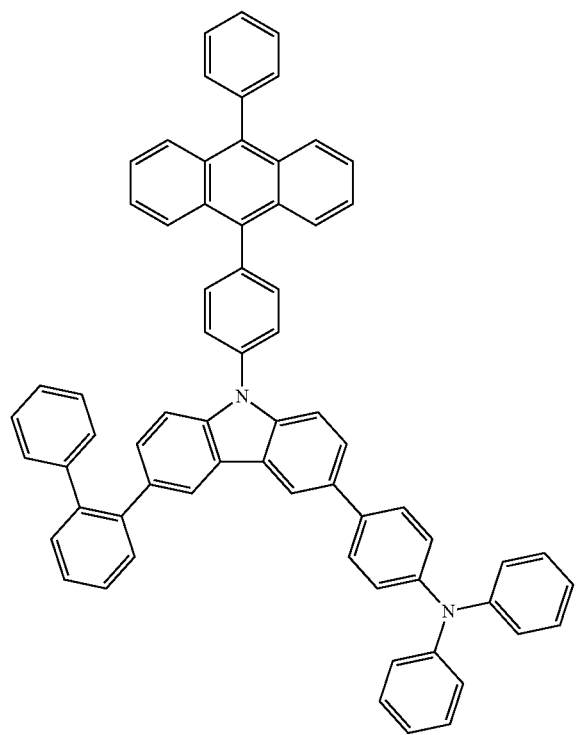

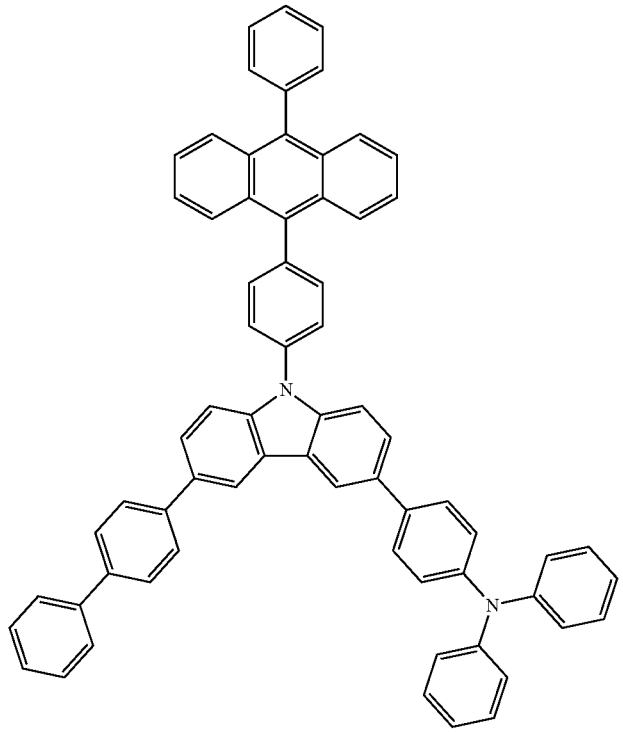
(265)
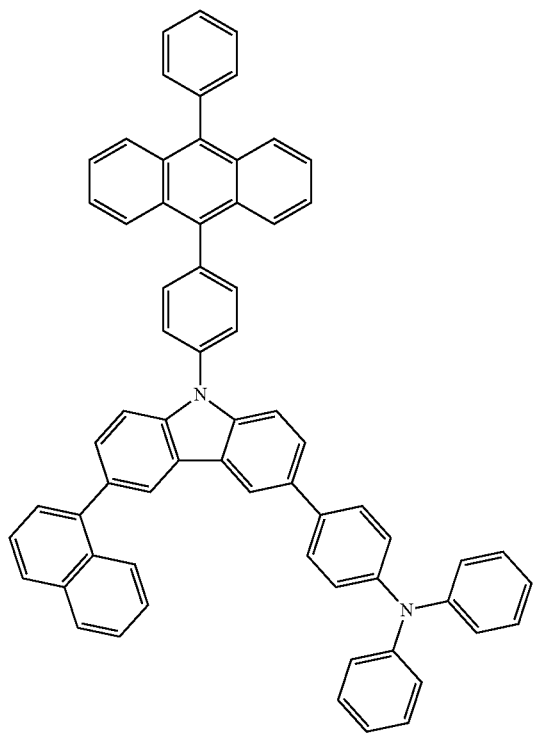
(266)

-continued
(267)
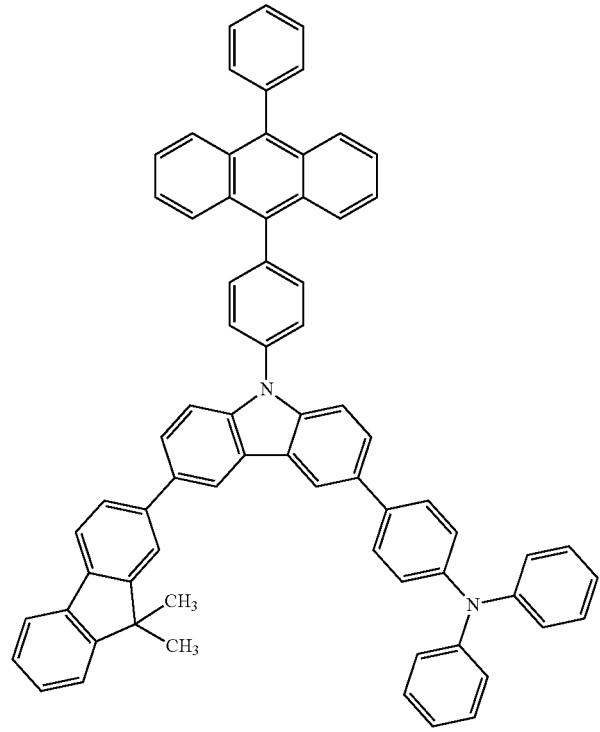
(268)
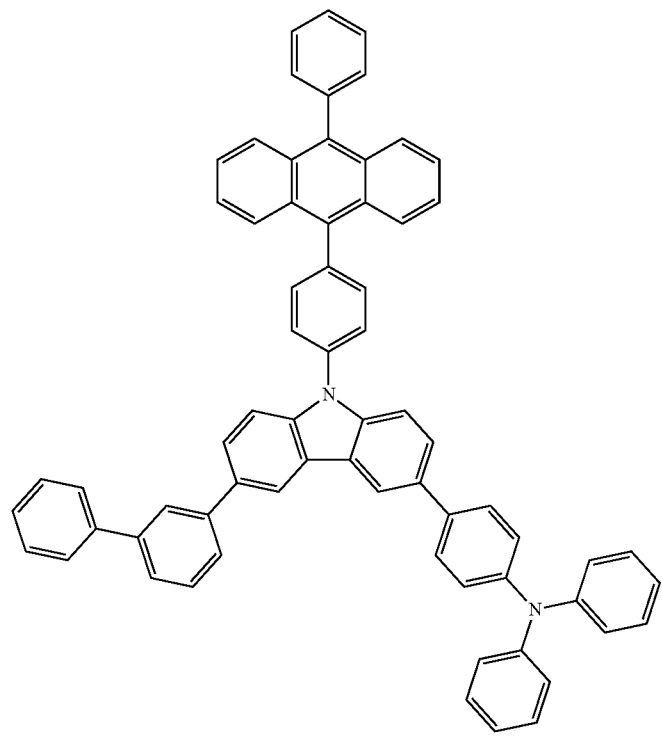

(269)
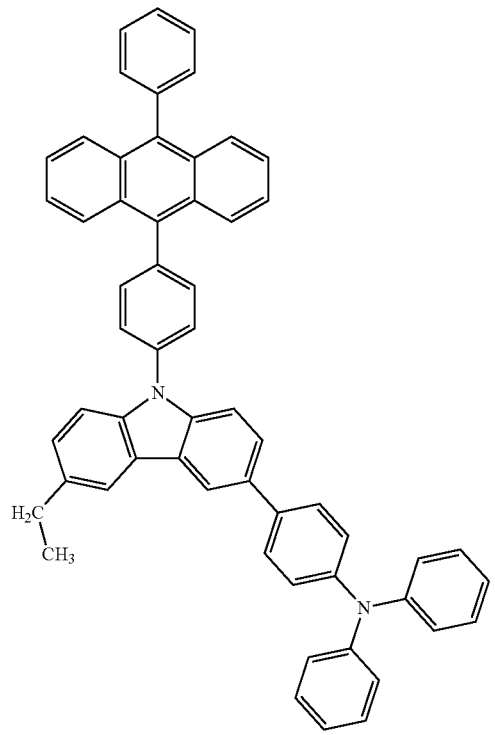
(270)
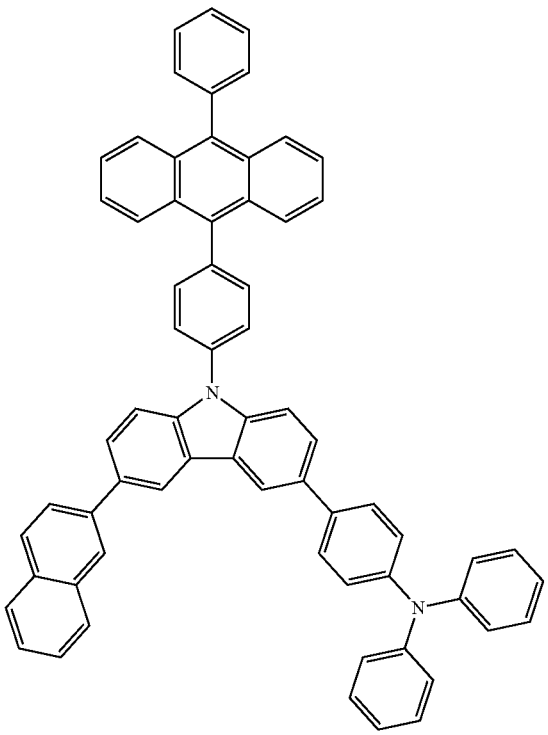
(271)
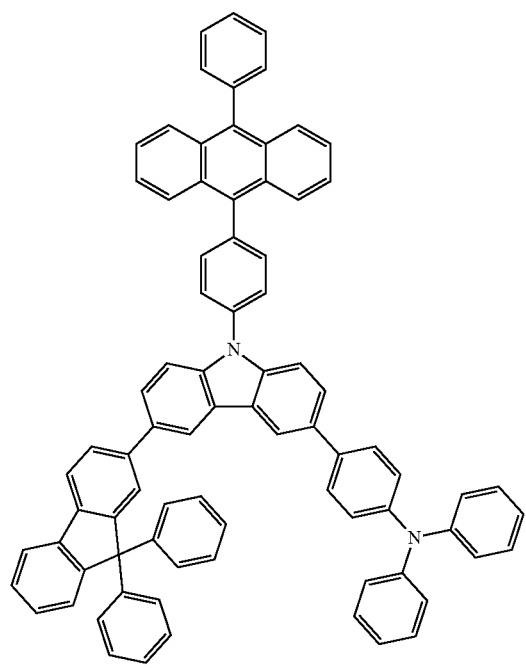
(272)
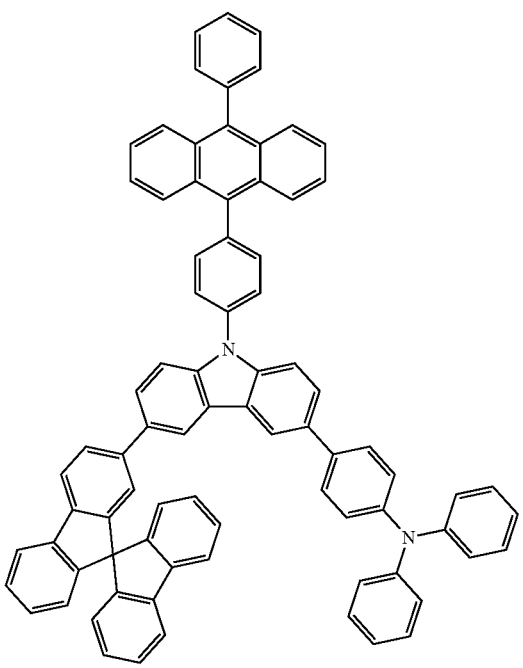

(273)
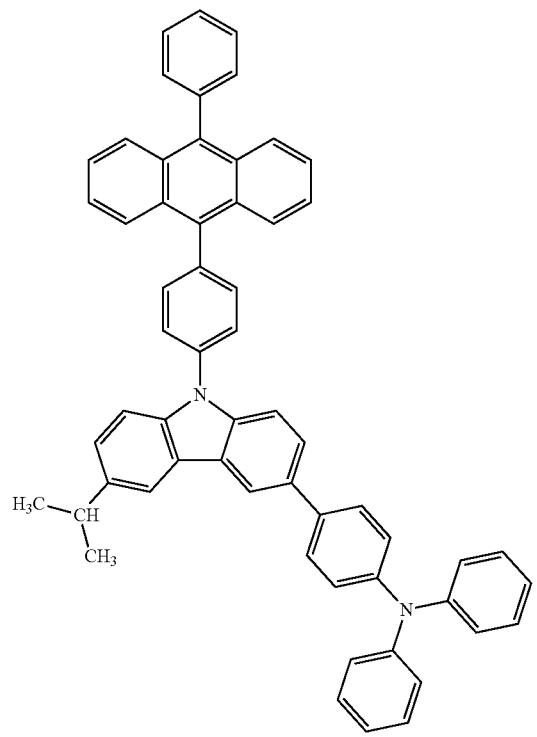
(274)
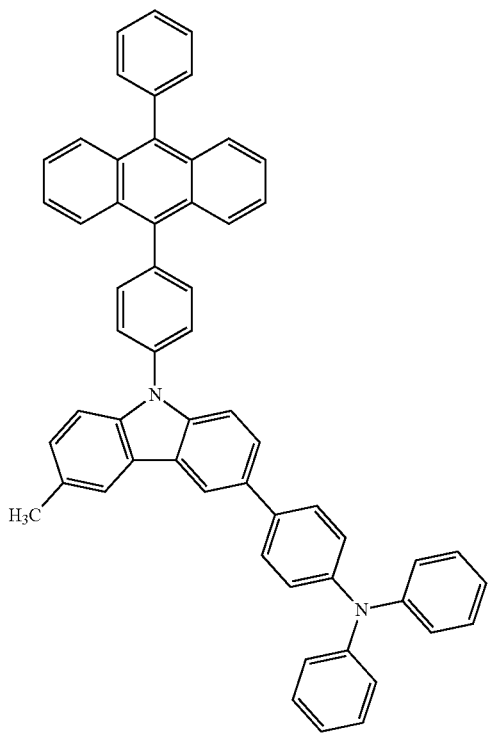
(275)
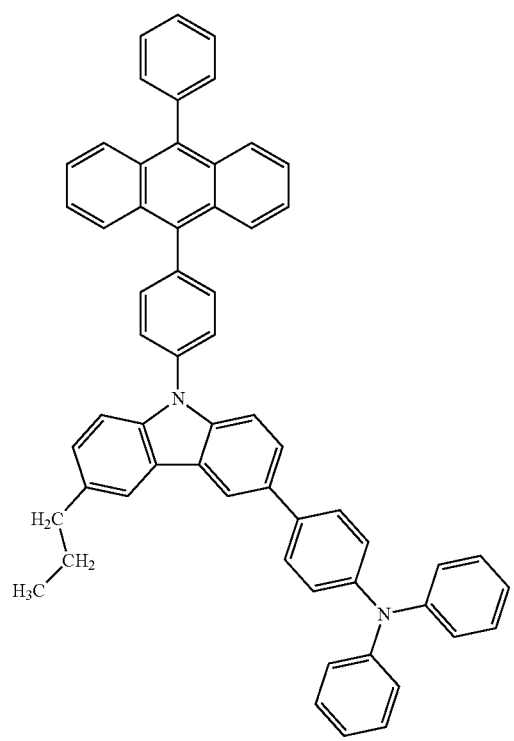
(276)
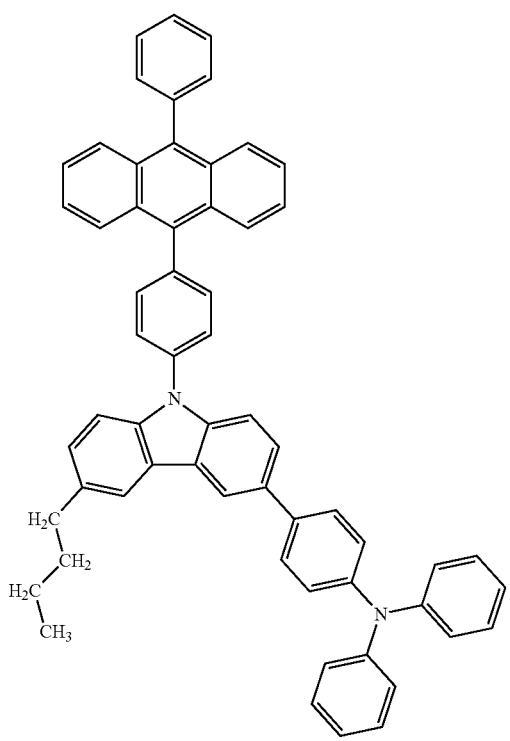

-continued
(277)
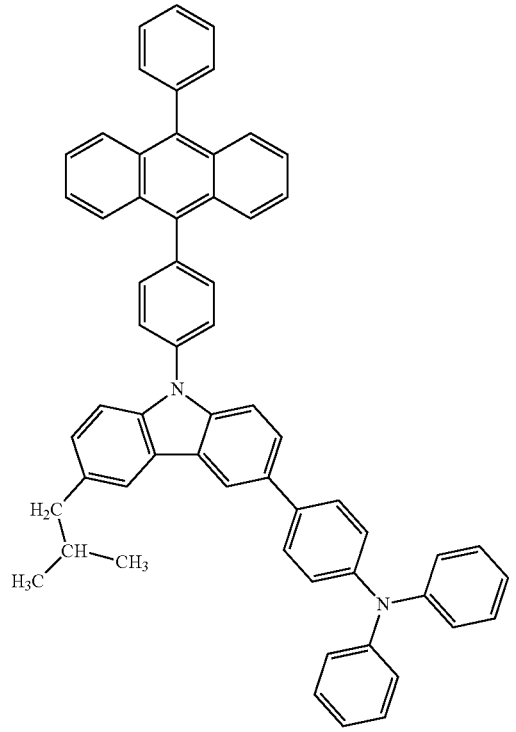
(278)
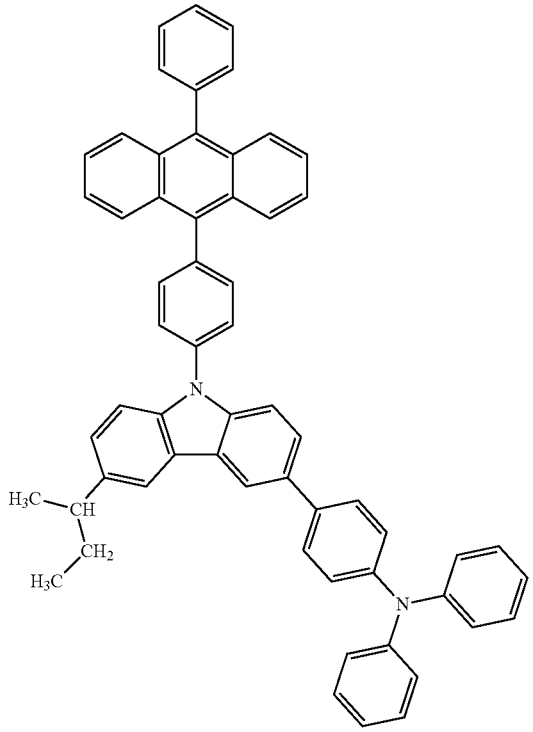
(279)
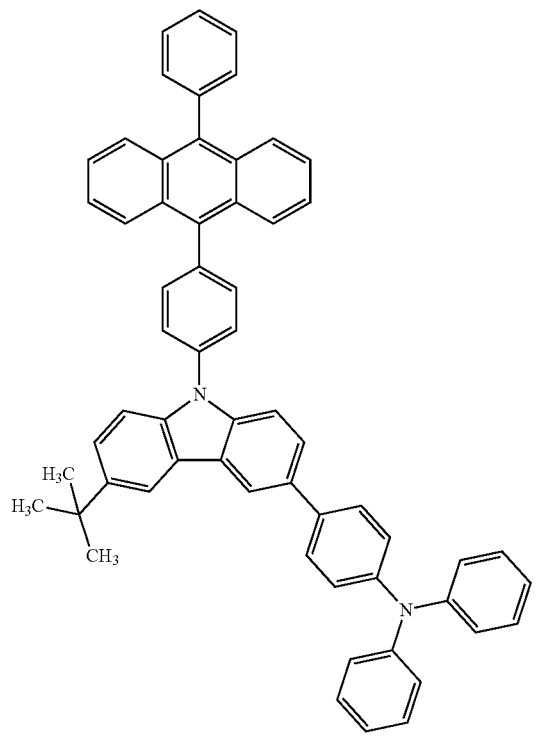
(280)
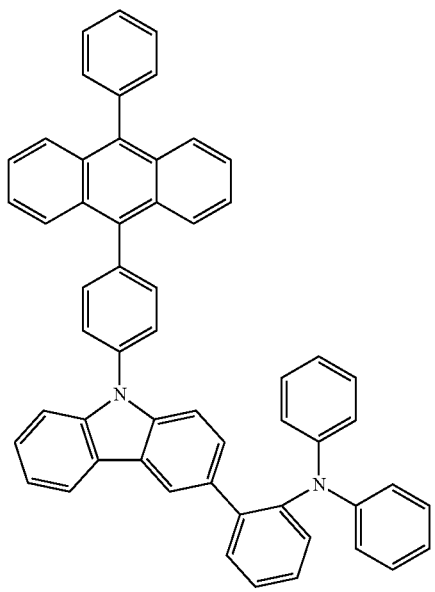

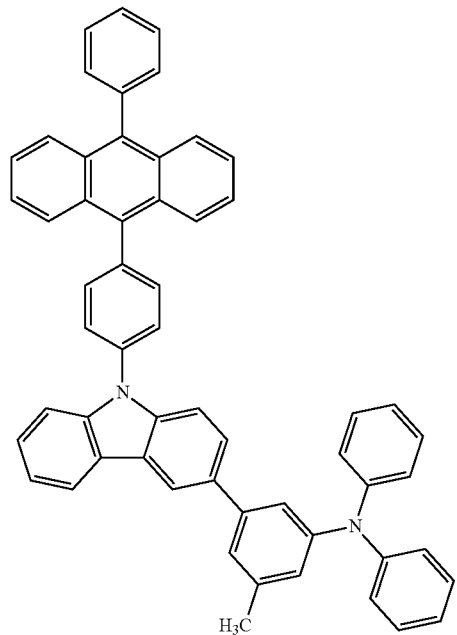
(281)
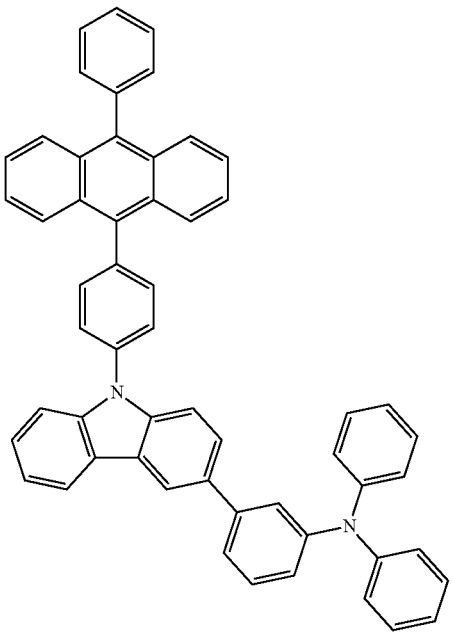
(282)
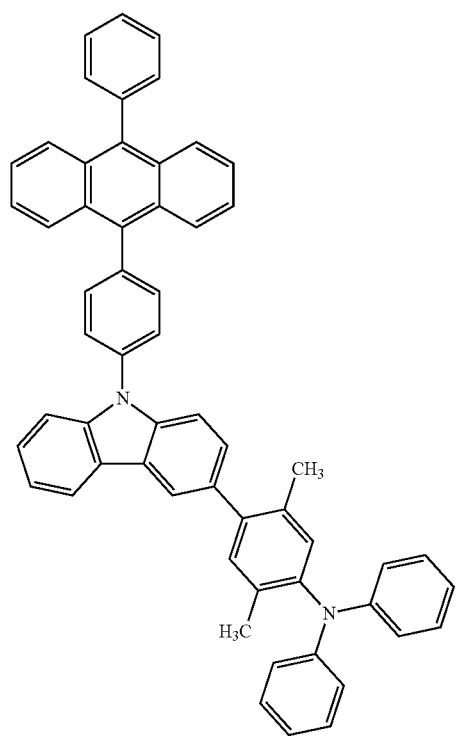
(283)

(284)
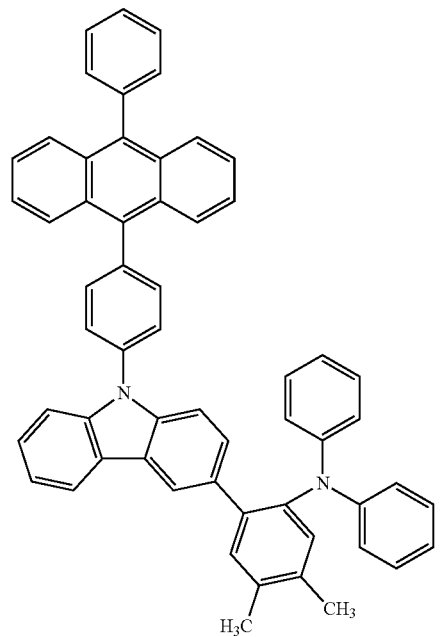
(285)
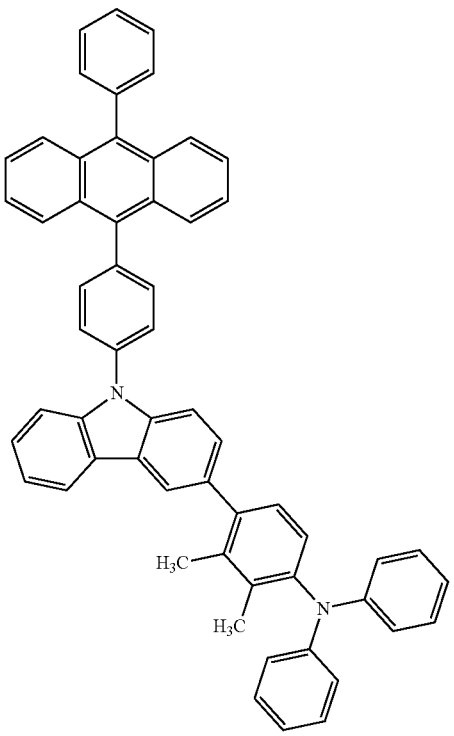
(286)
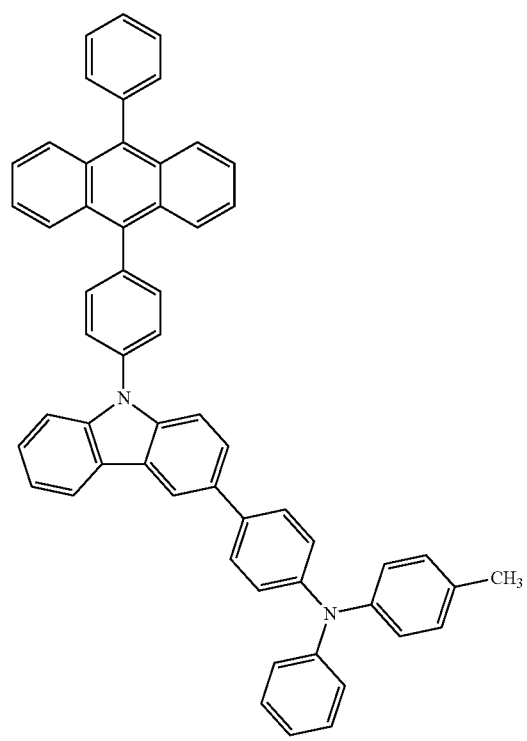
(287)
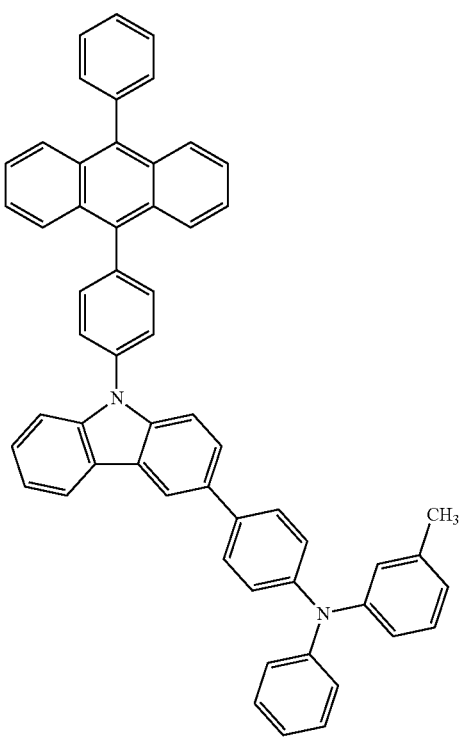

-continued
(288)
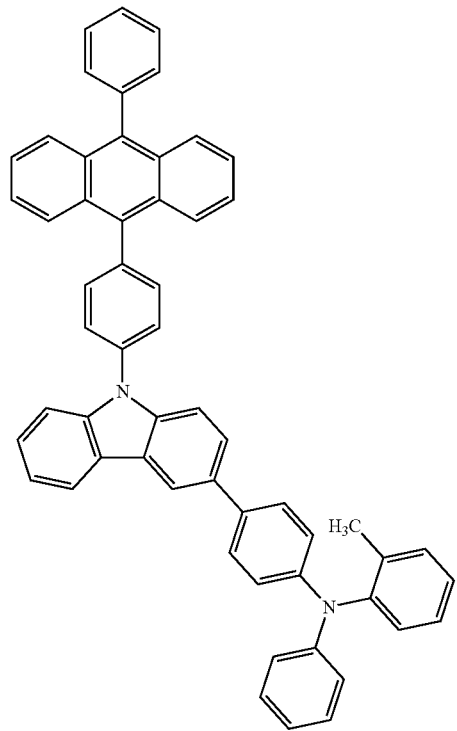
(289)
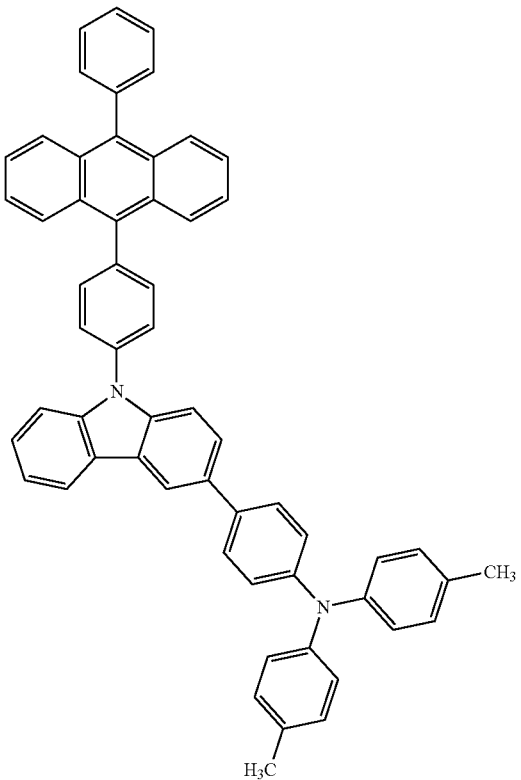
(290)
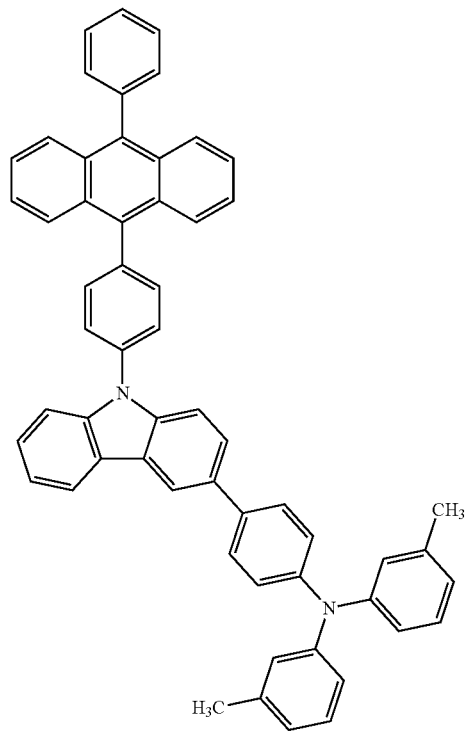
(291)
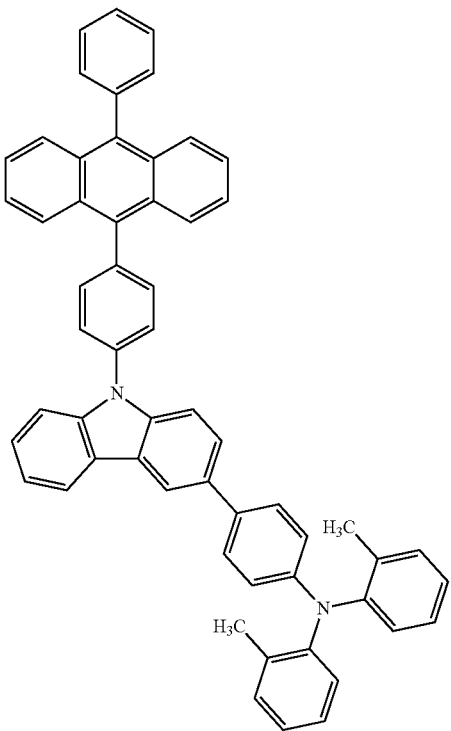

(292)
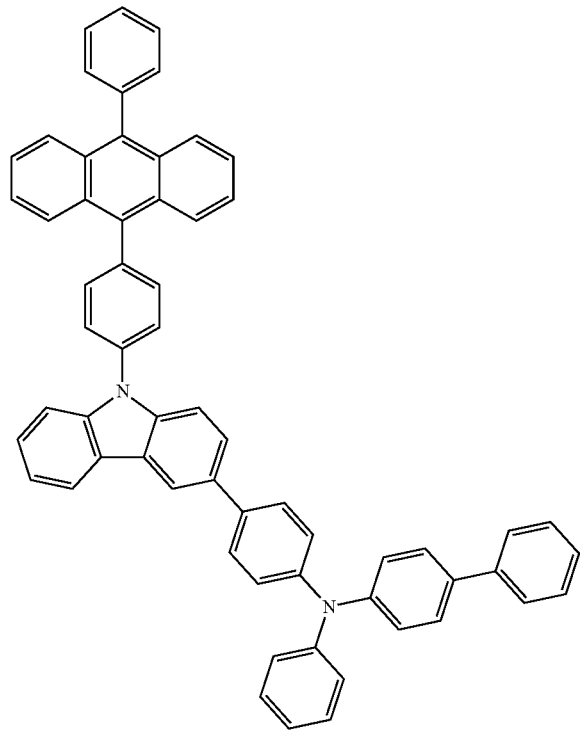
(293)
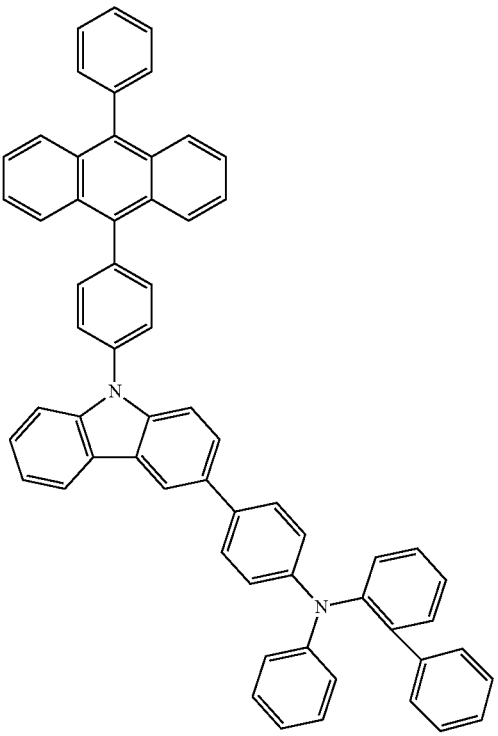
(294)
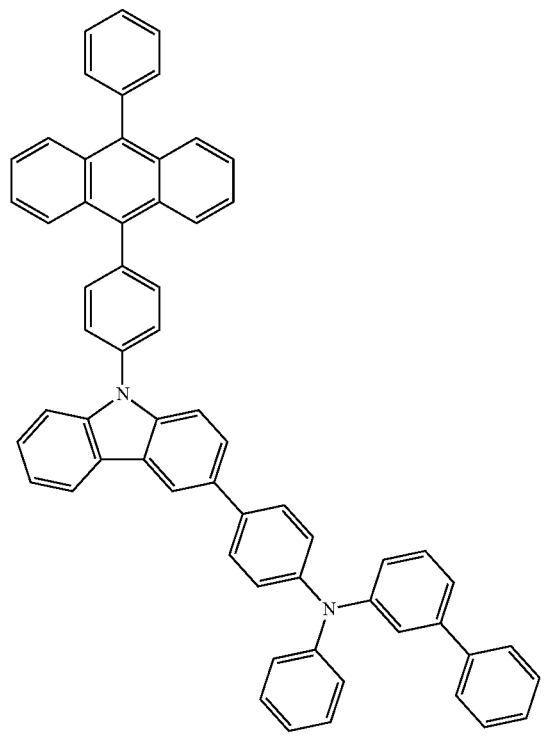
(295)
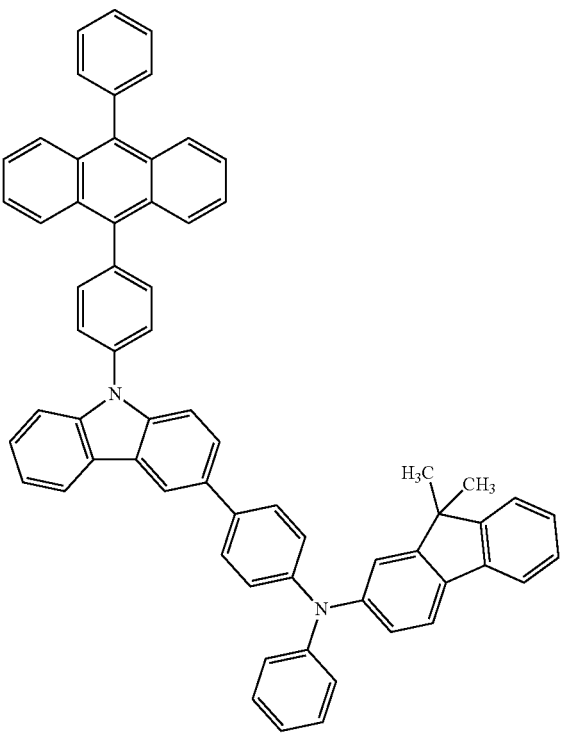

-continued
(296)
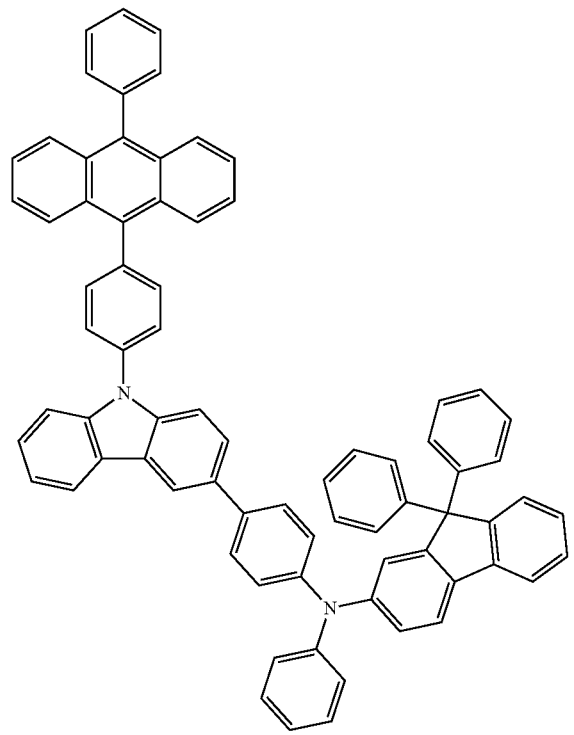
(297)
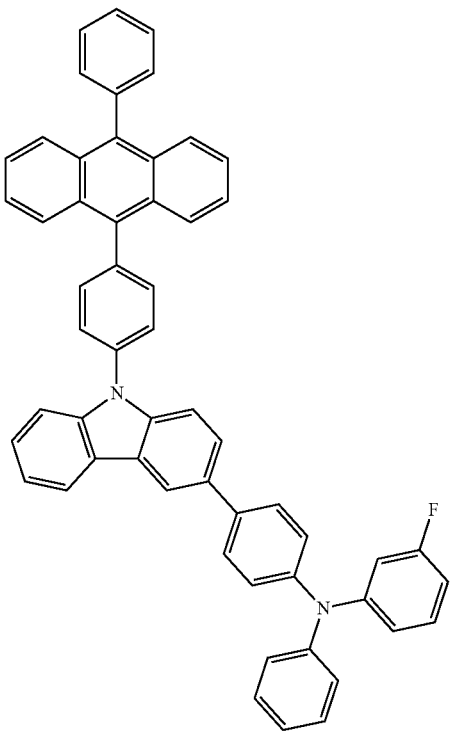
(298)
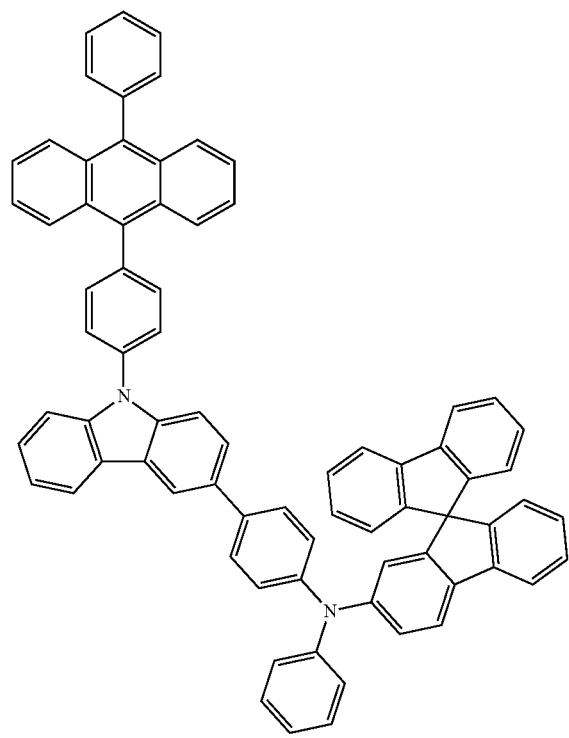
(299)
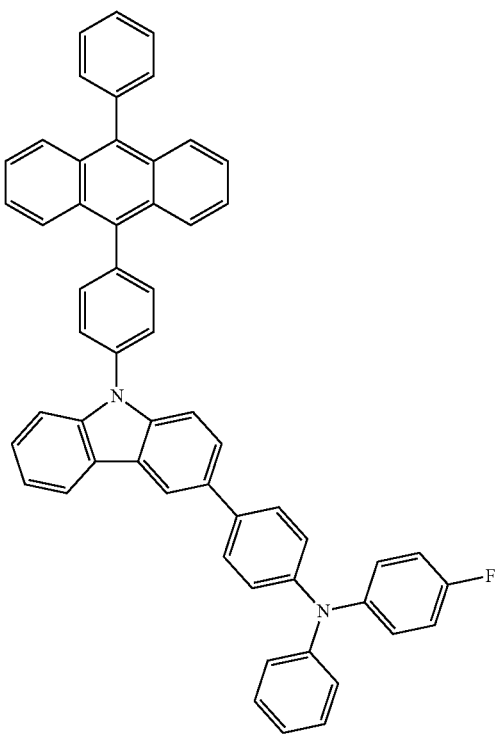

-continued
(300)
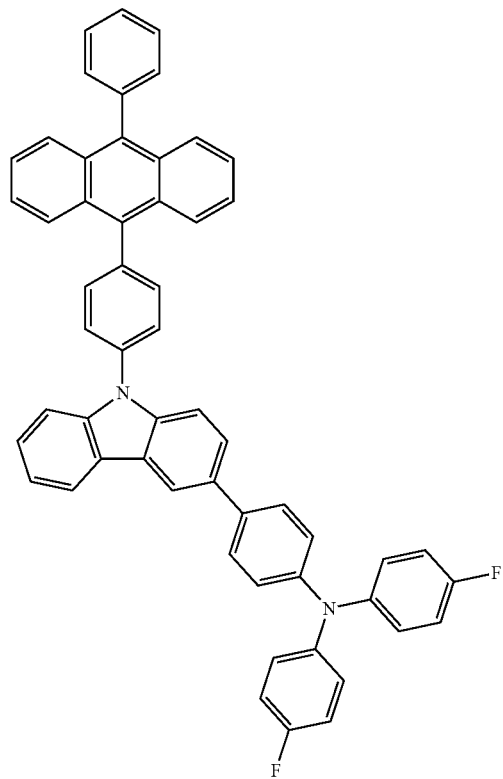
(301)
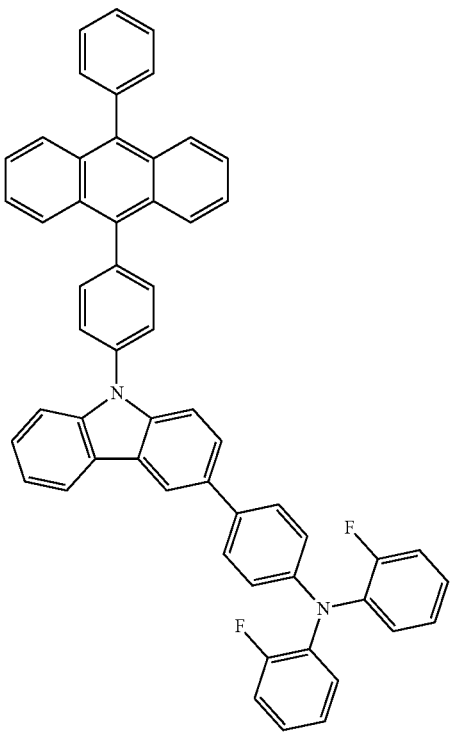
(302)
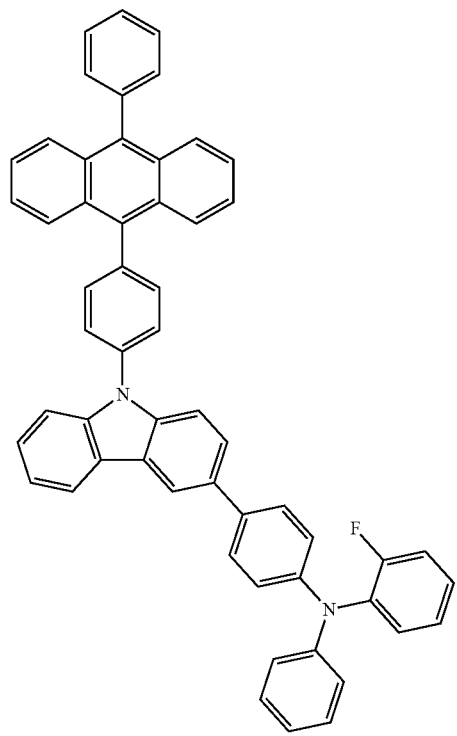
(303)
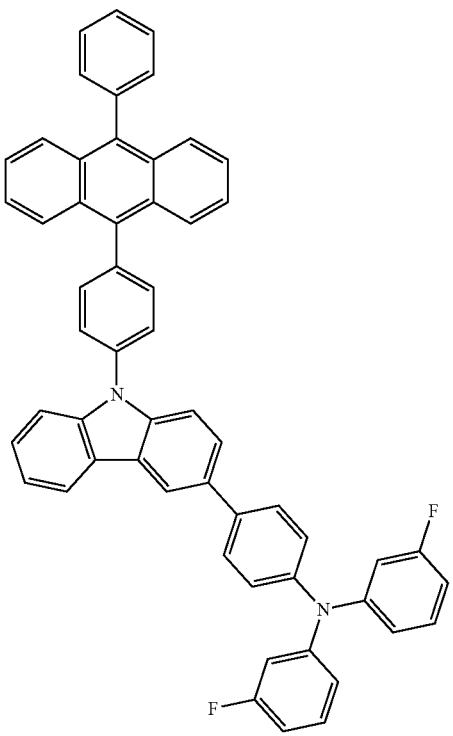

(304)
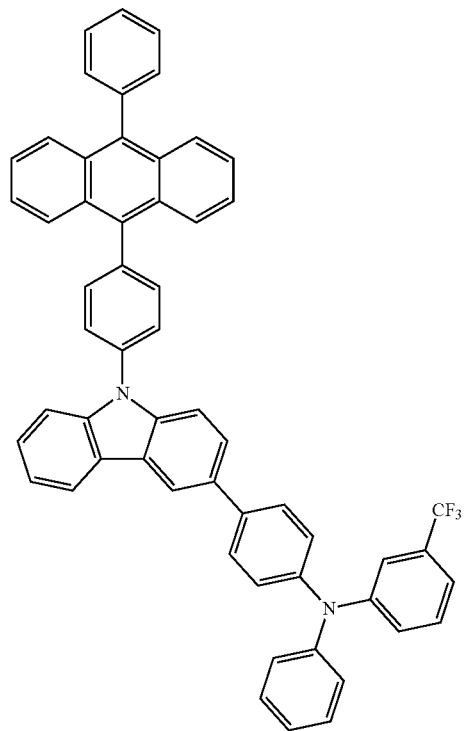
(305)
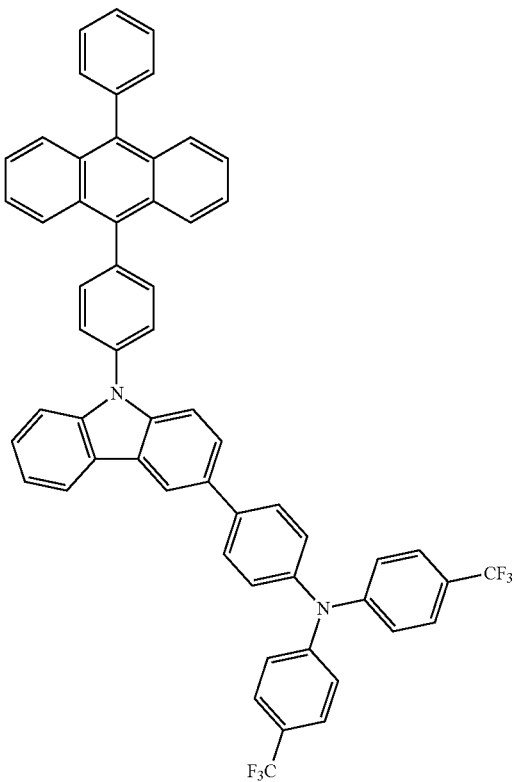
(306)
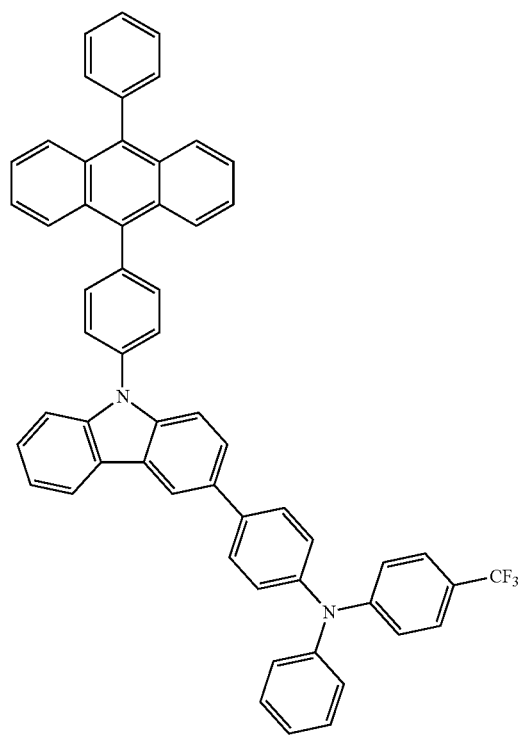
(307)
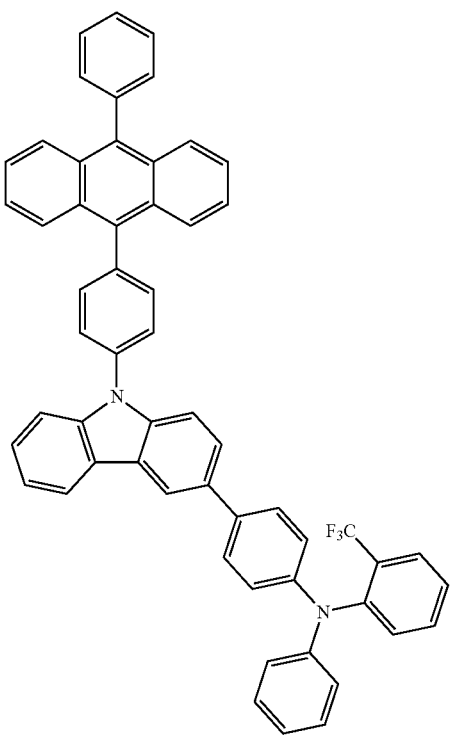

-continued
(308)
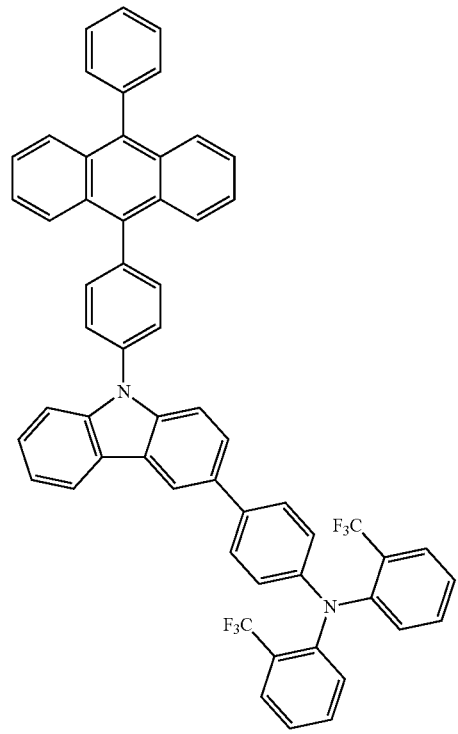
(309)
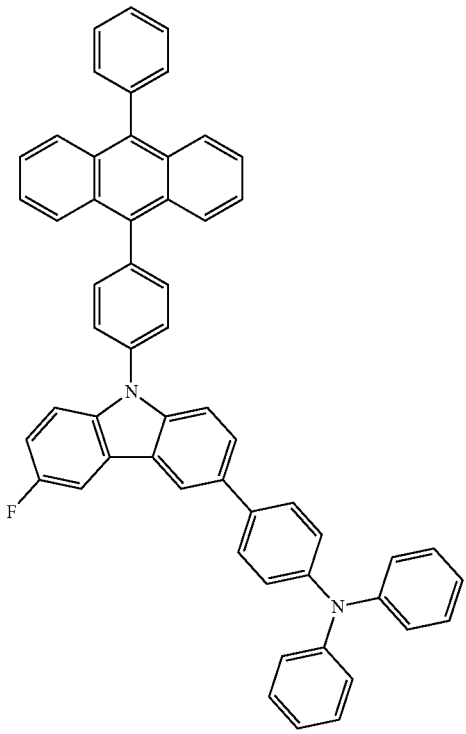
(310)
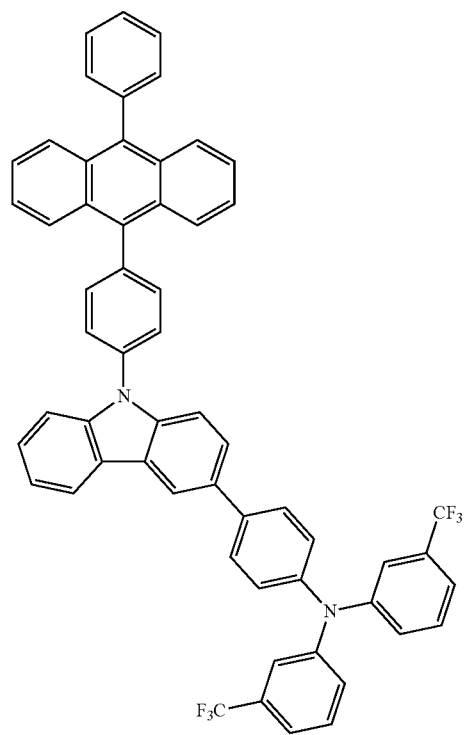
(311)
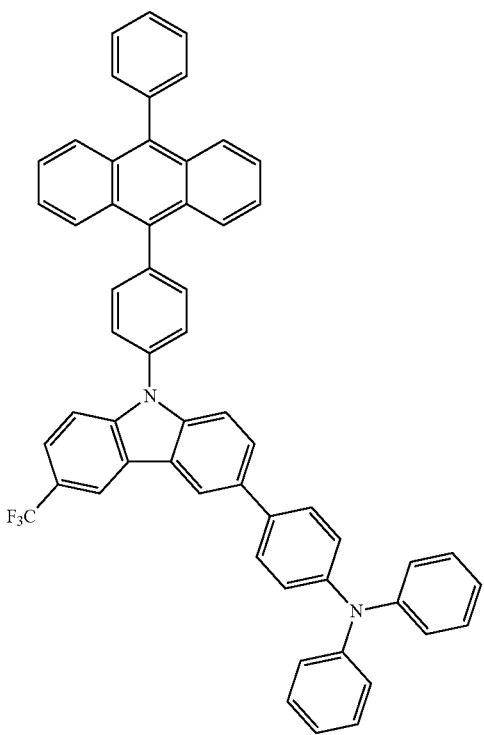

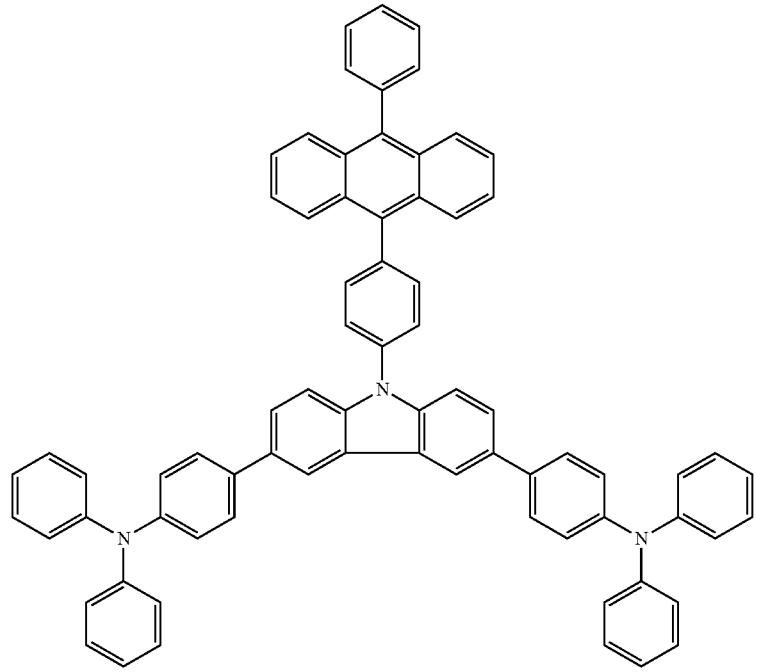
(312)
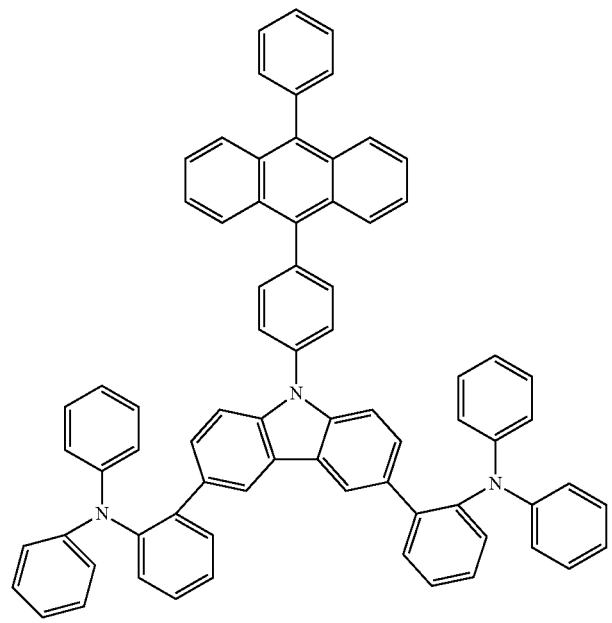
(313)

(314)
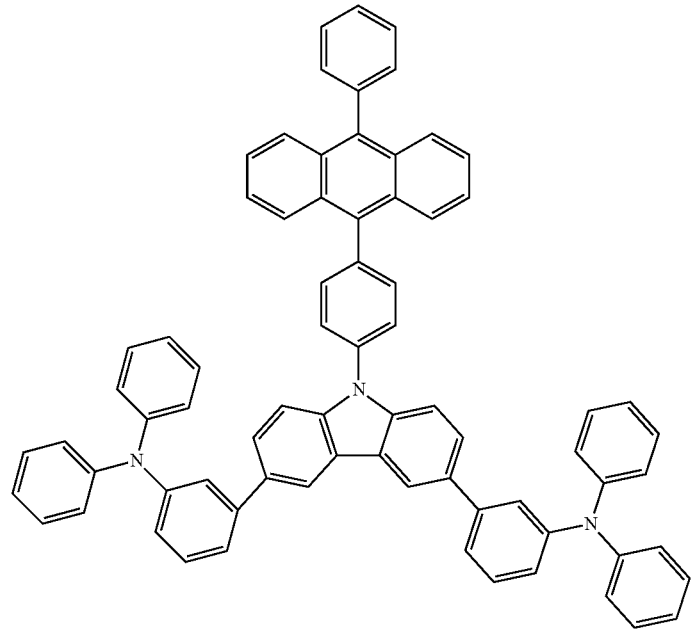
(315)
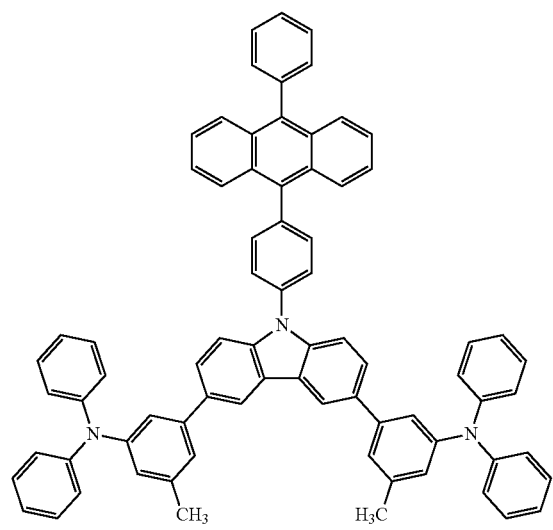
(316)
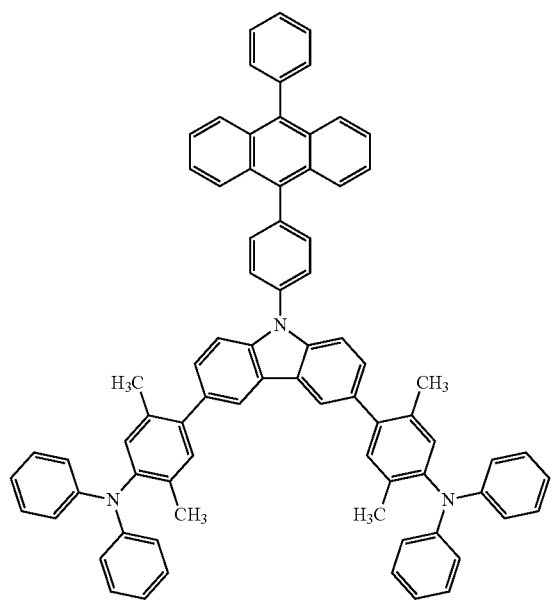

-continued
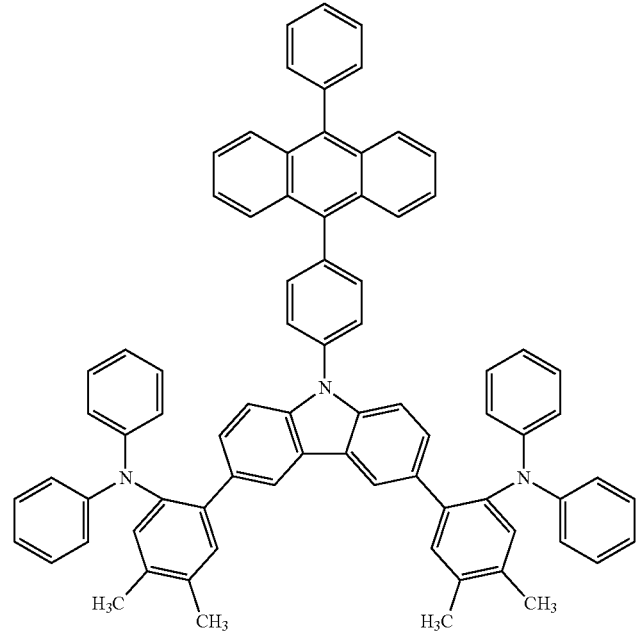
(317)
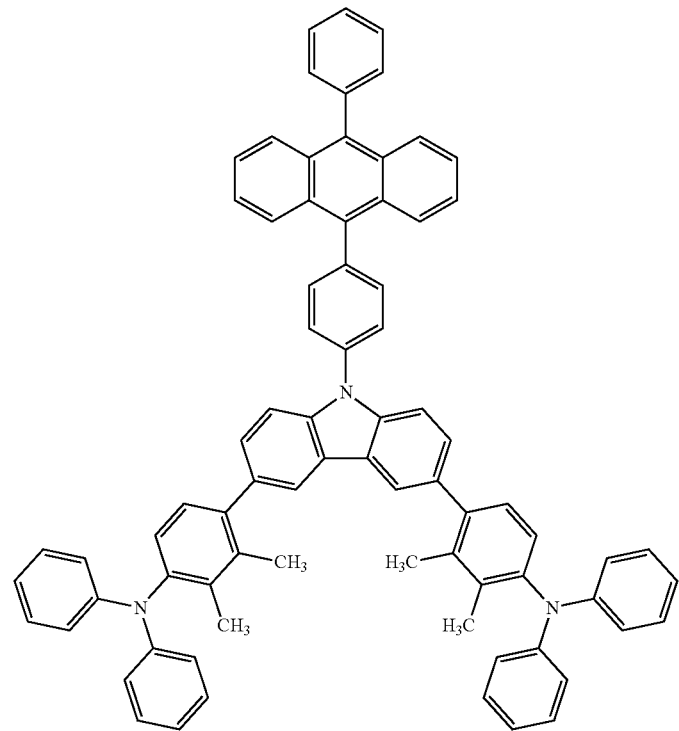
(318)

-continued
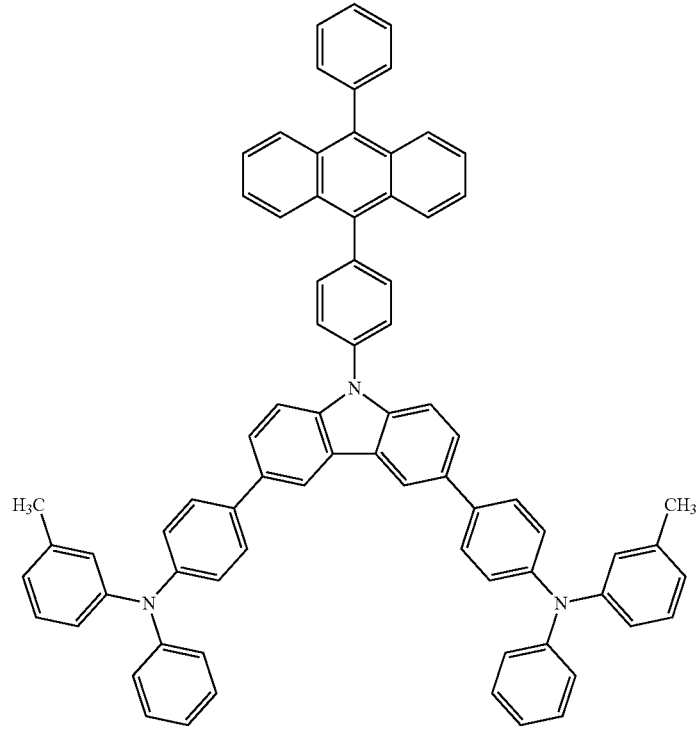
(319)
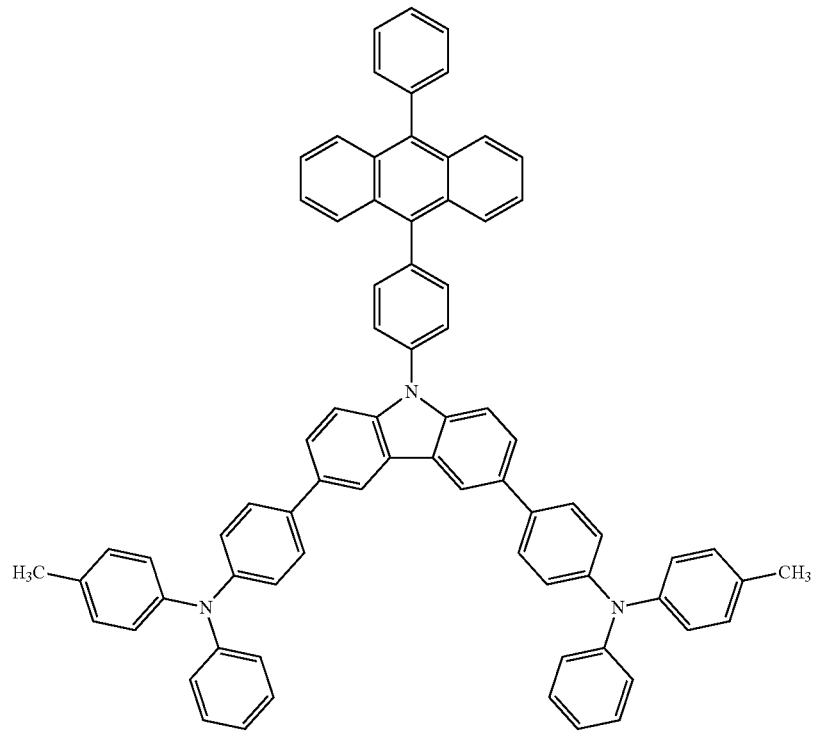
(320)

(321)
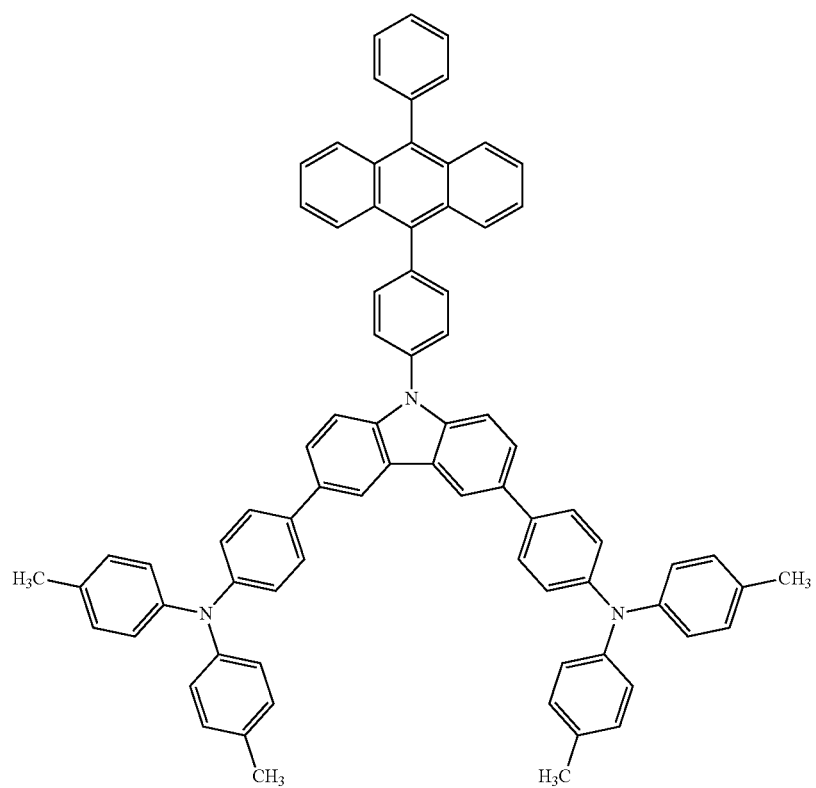
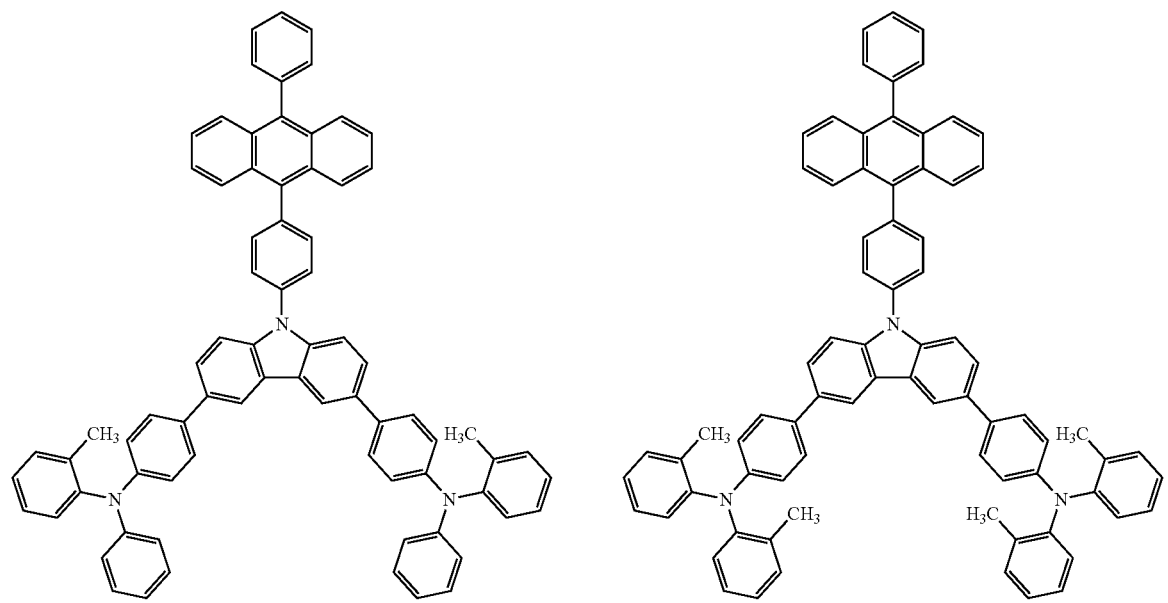

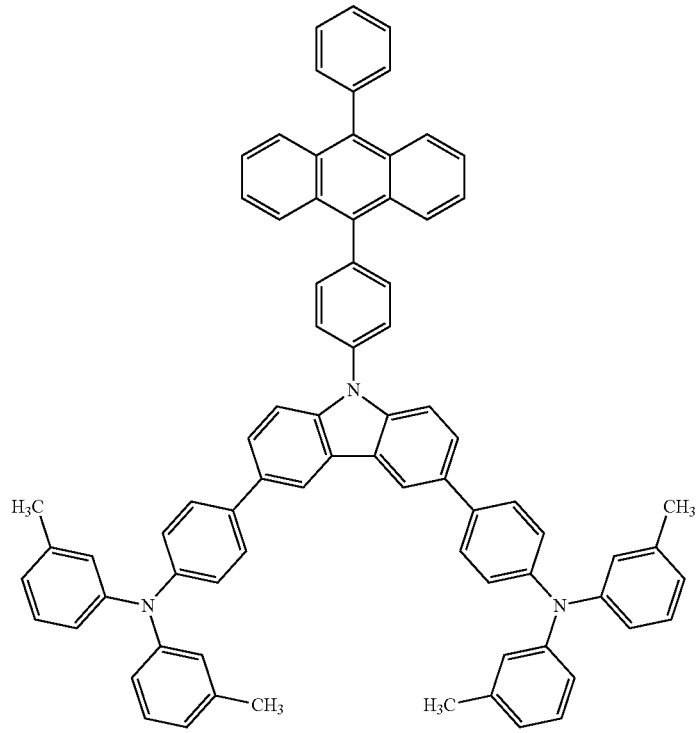
(324)
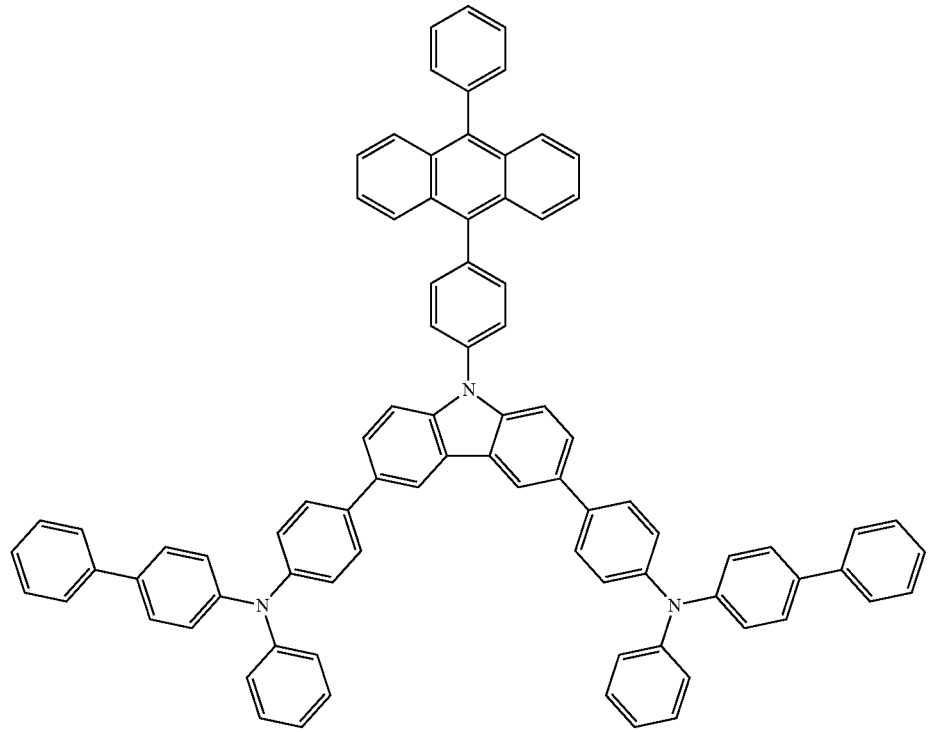
(325)

(326)
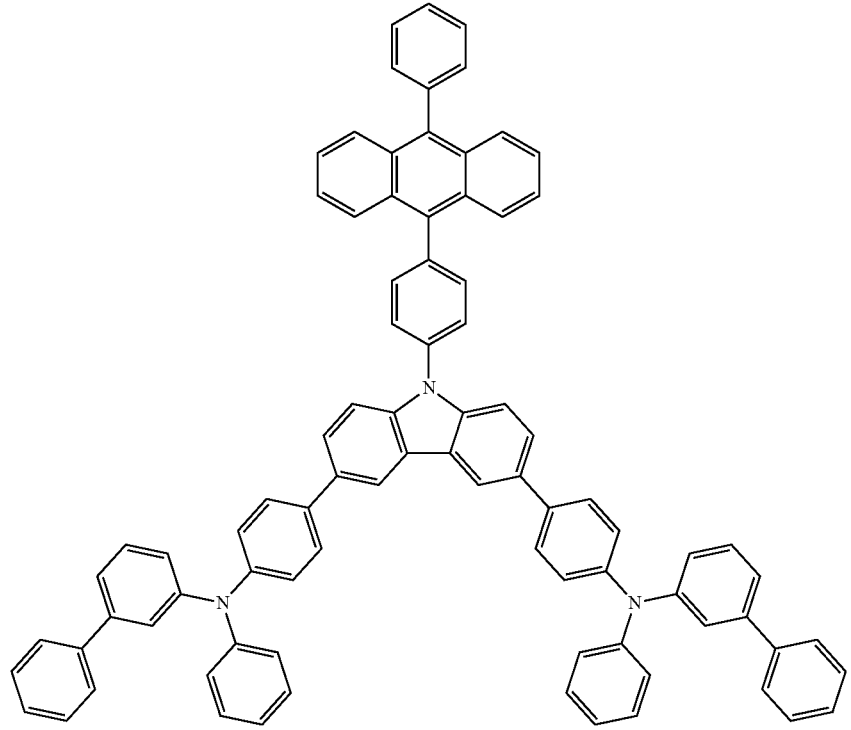
(327)
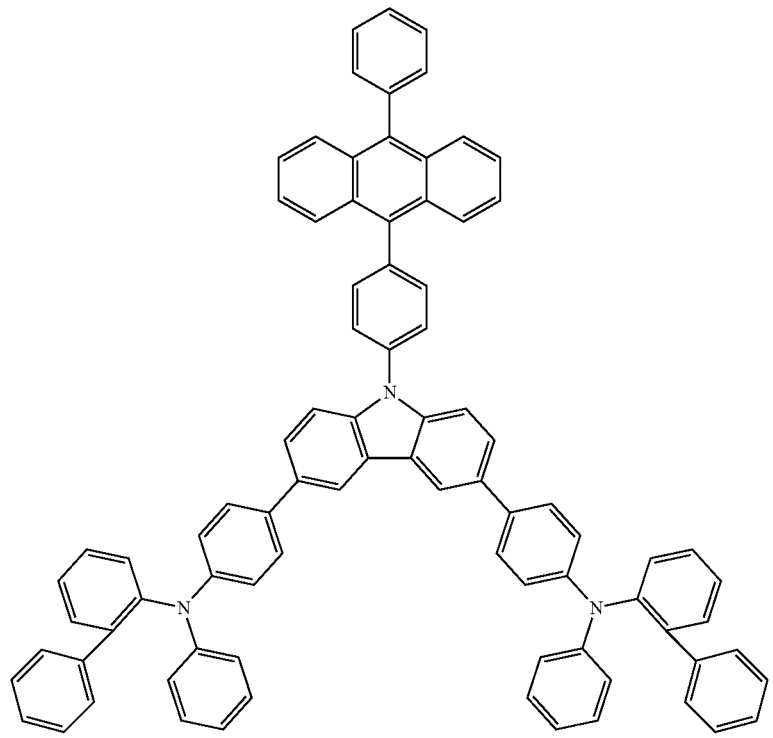

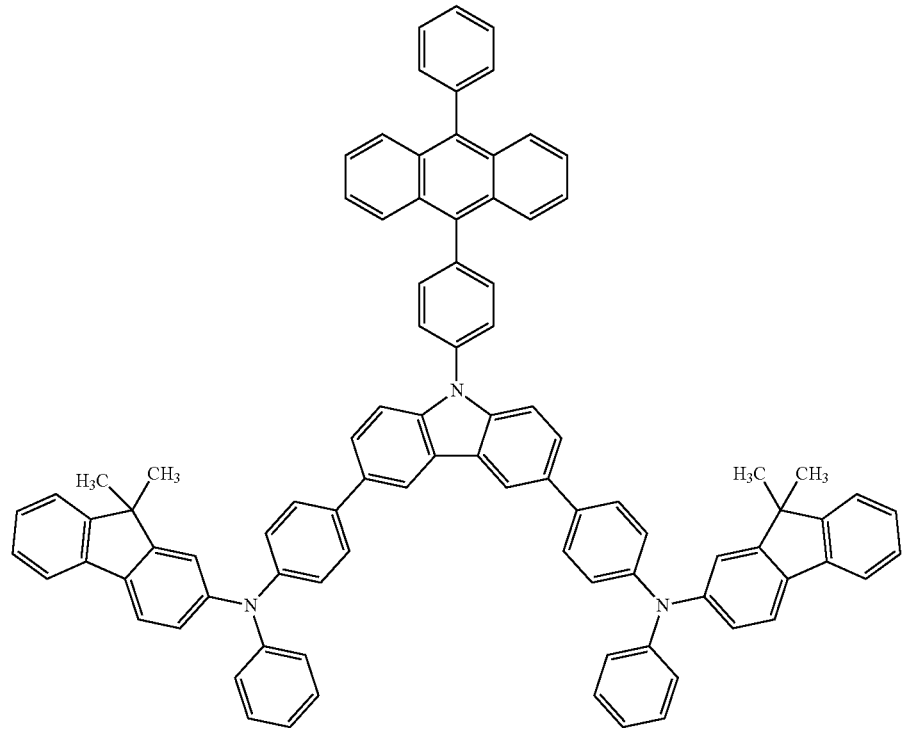
(328)
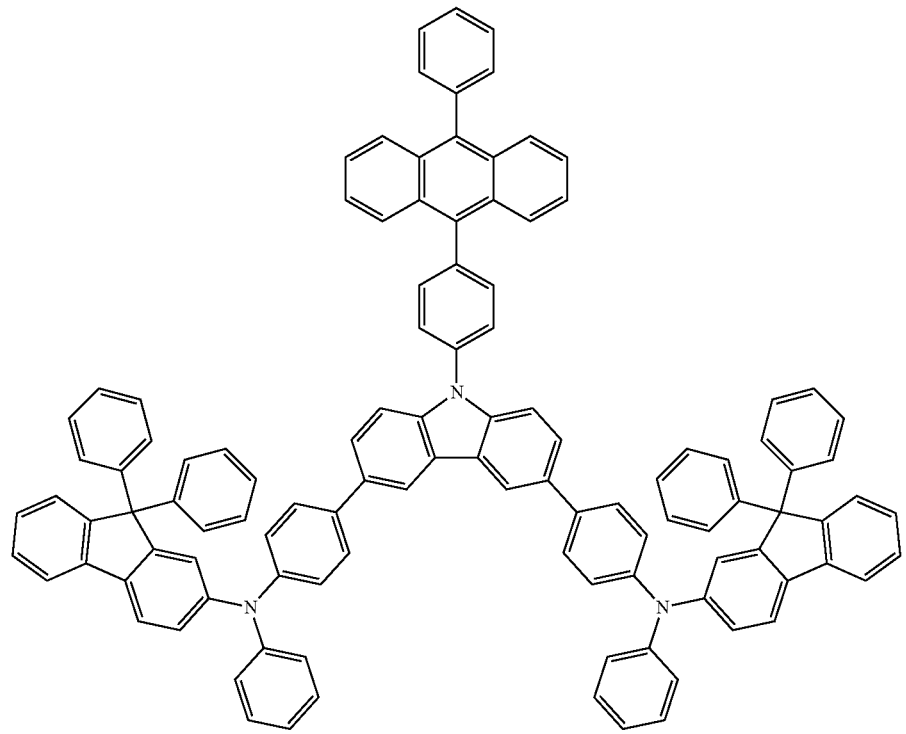
(329)

-continued
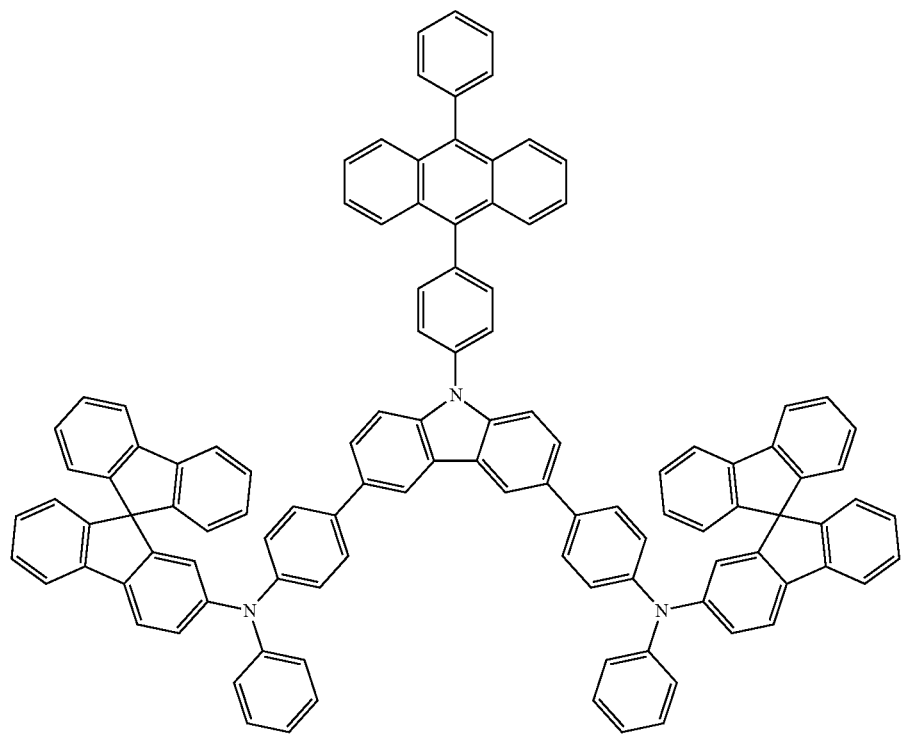
(330)
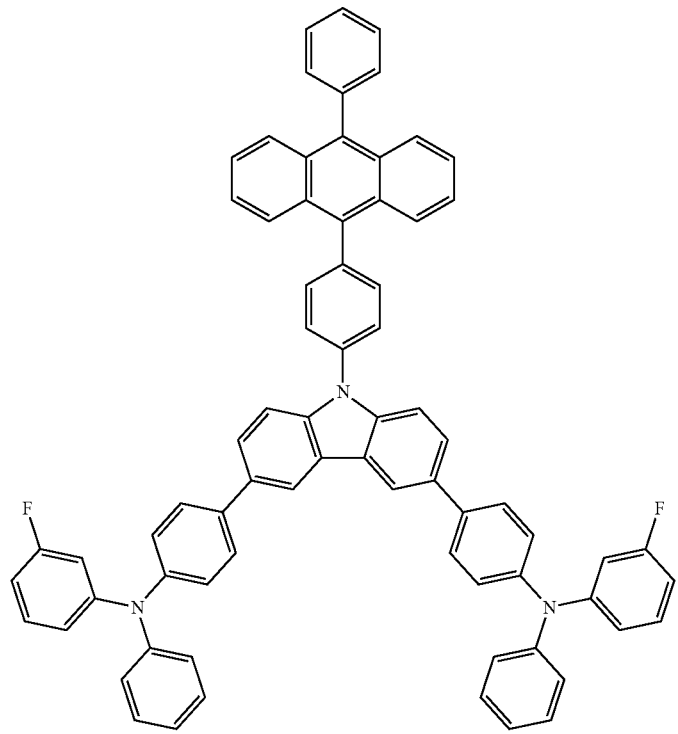
(331)

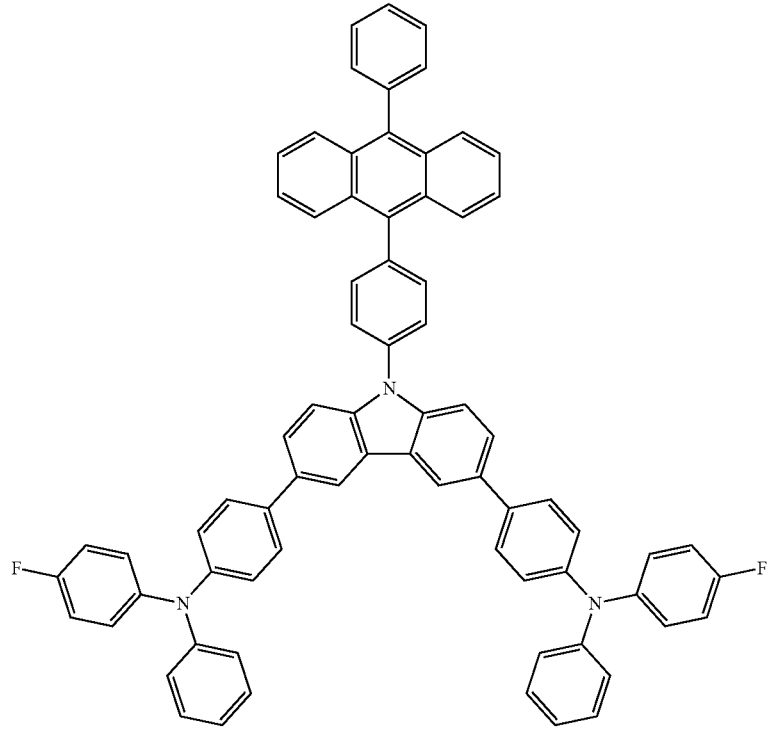
(332)
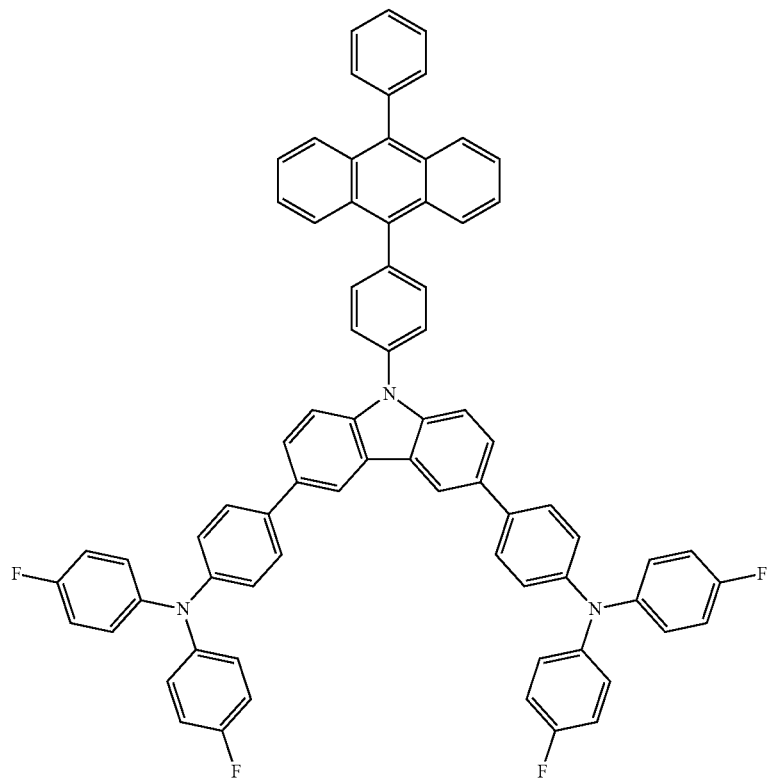
(333)

(334)
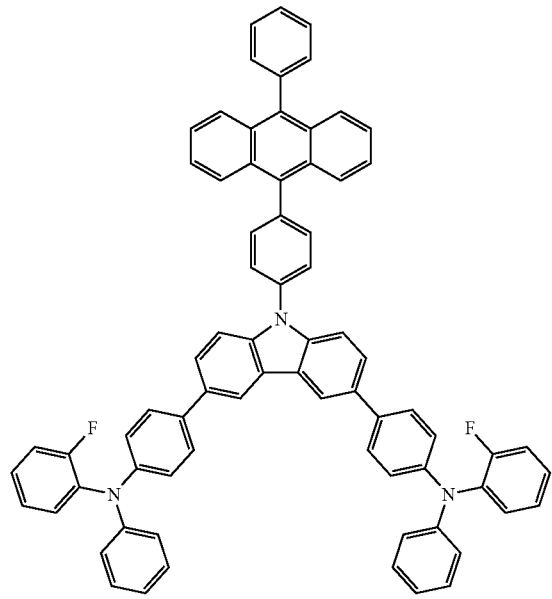
(335)
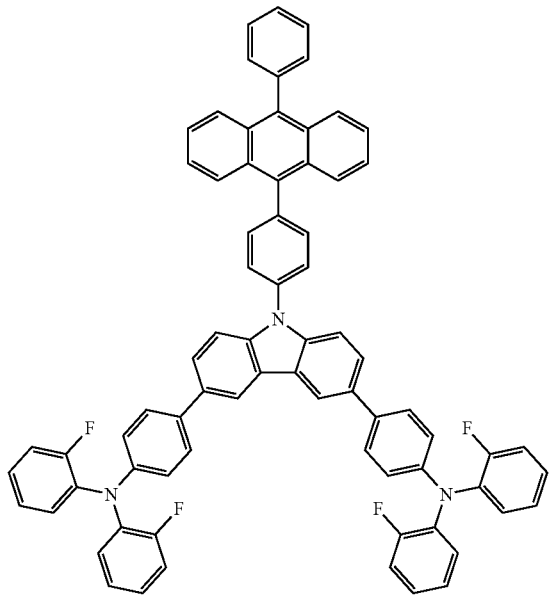
(336)
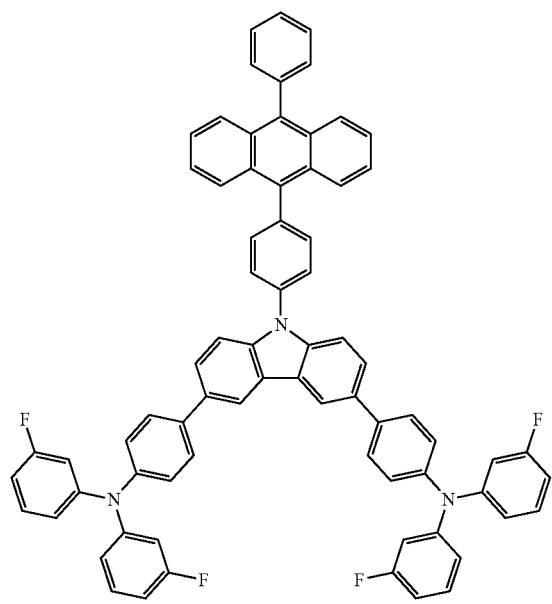
(337)
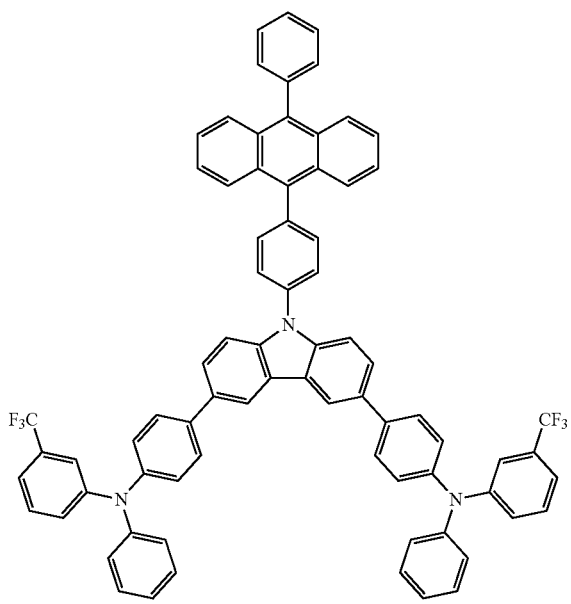

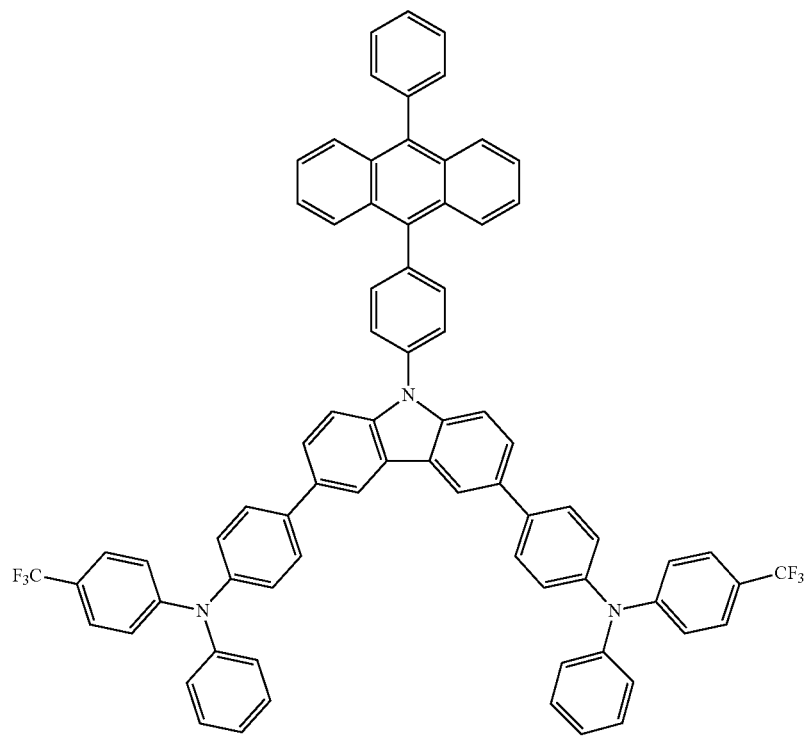
(338)
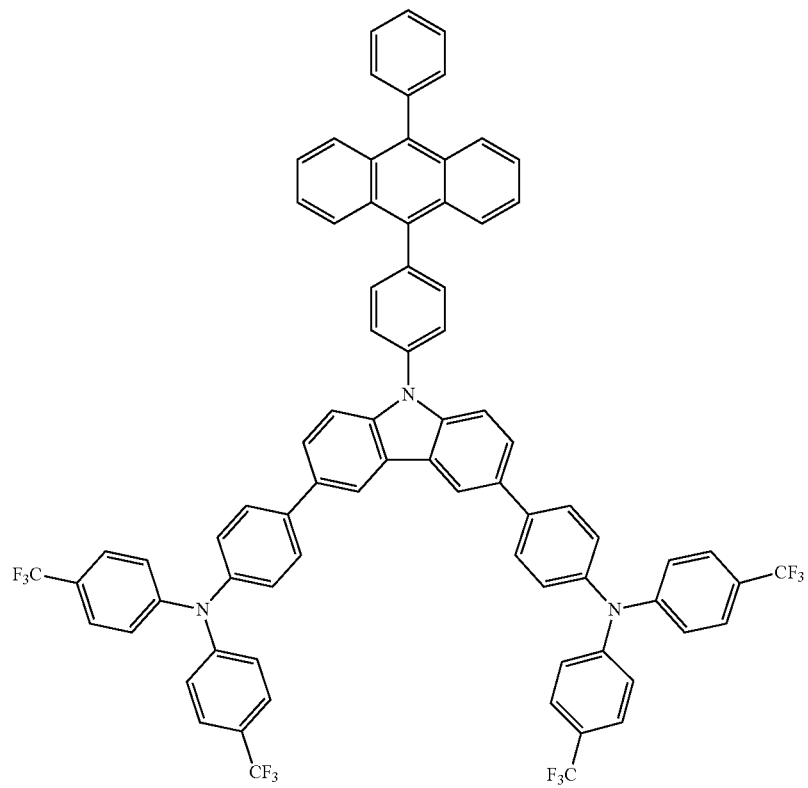
(339)

(340)
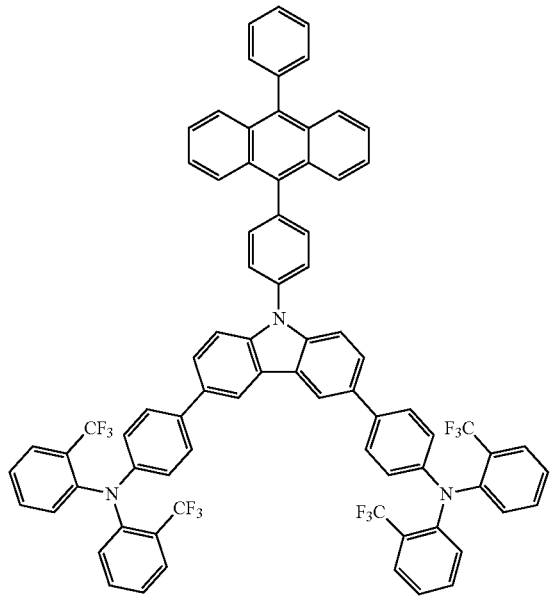
(341)
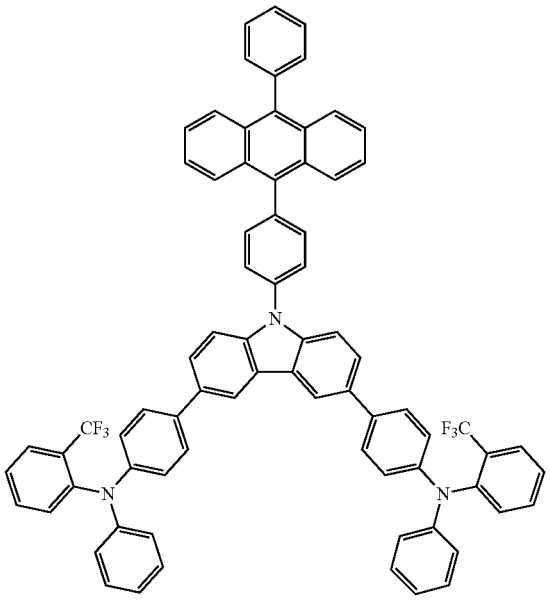
(342)
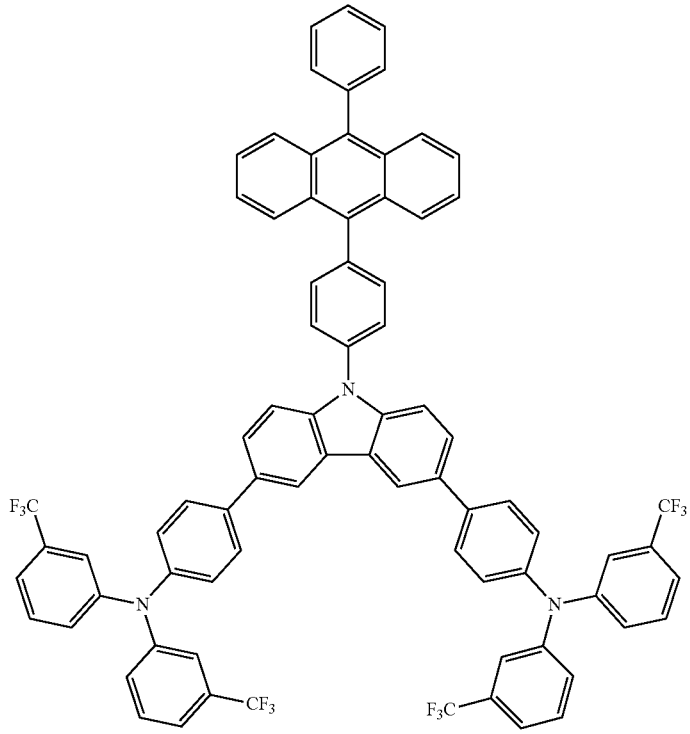

-continued
(343)
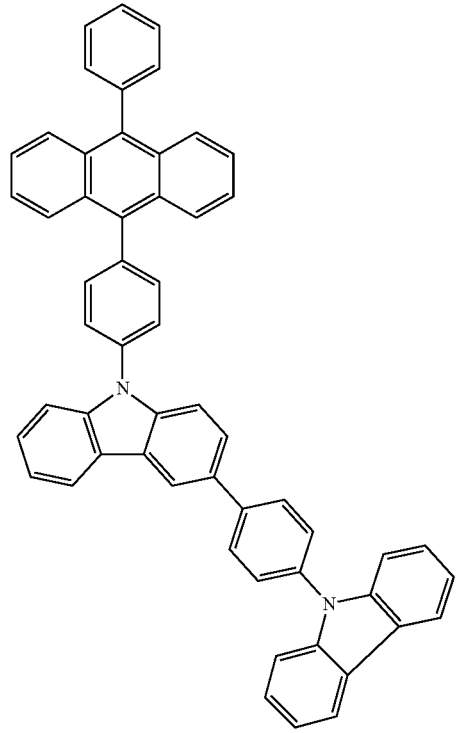
(344)
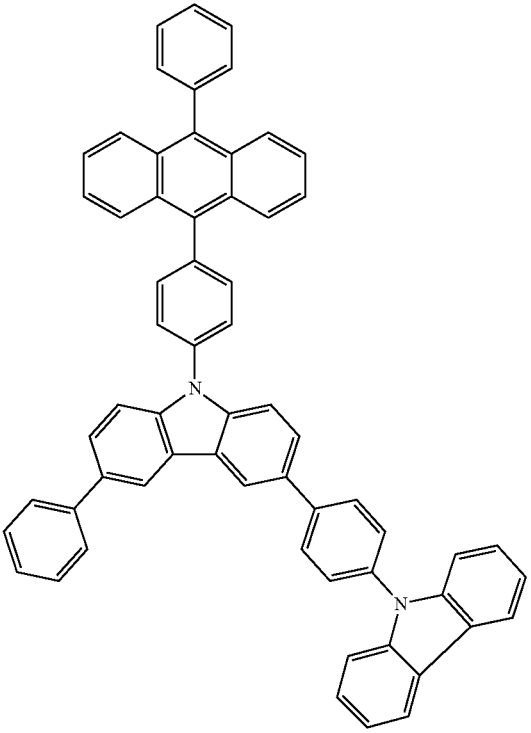
(345)
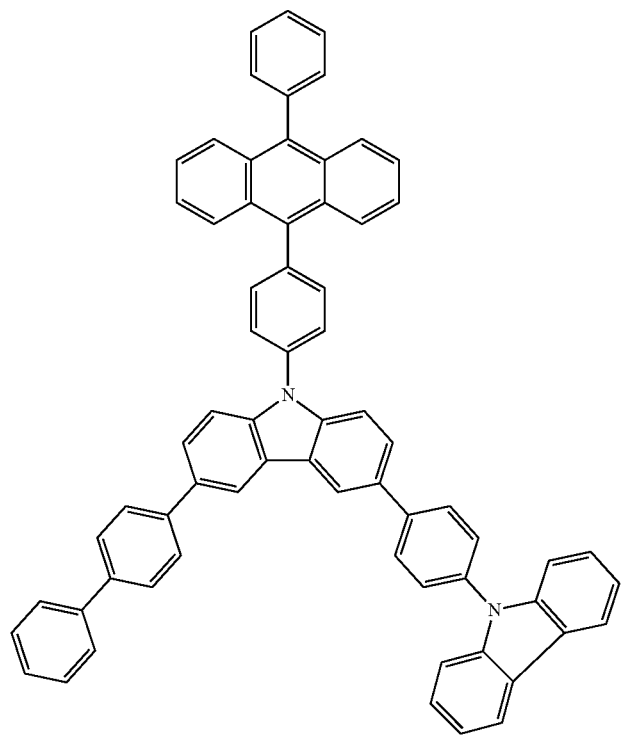

(346)
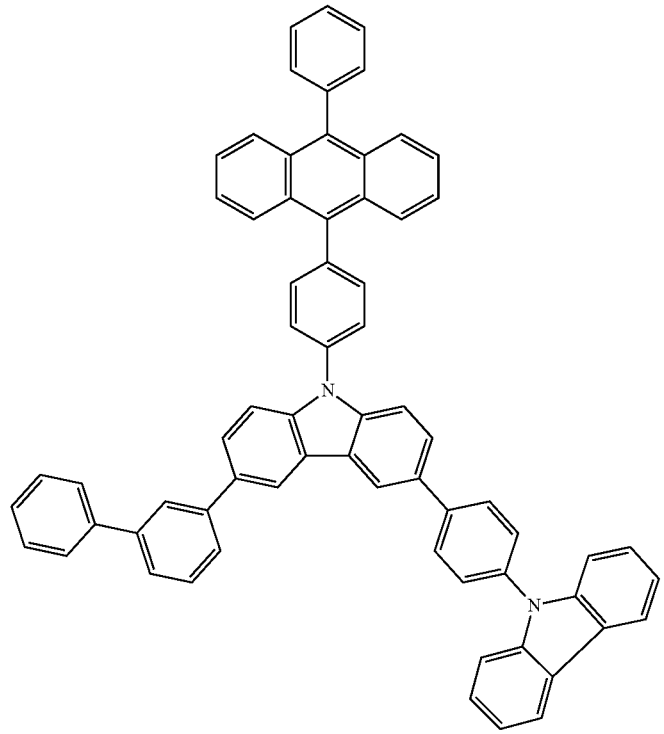
(347)
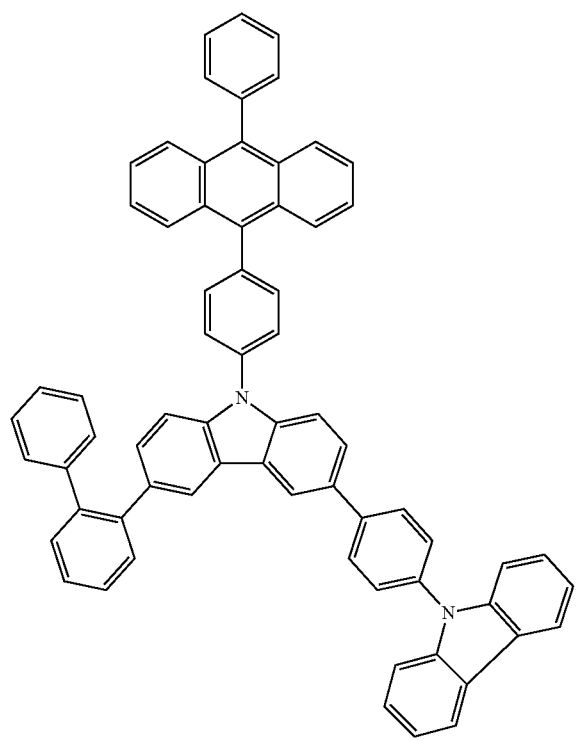
(348)
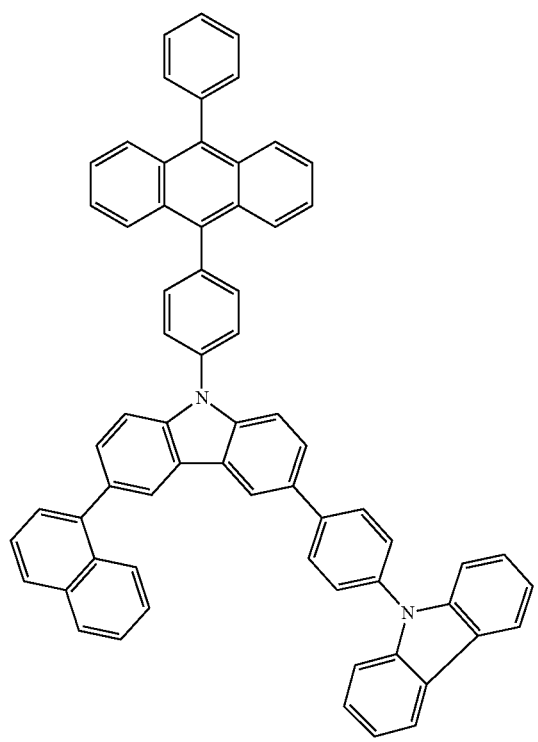

(349)
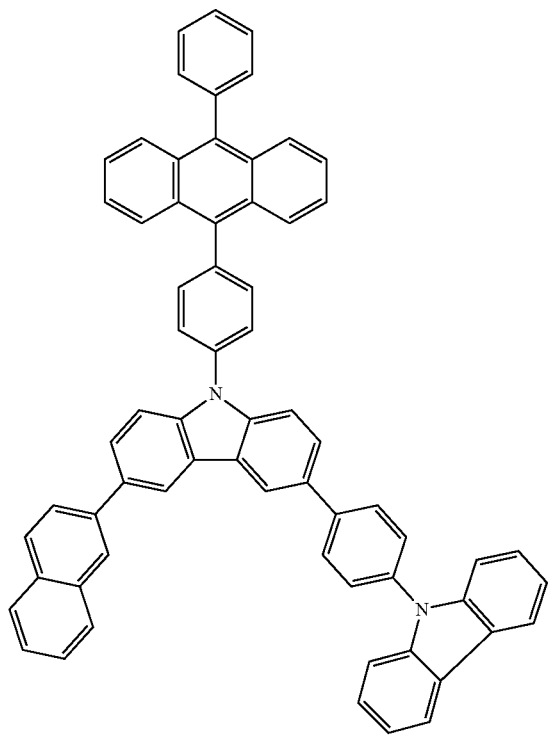
(350)
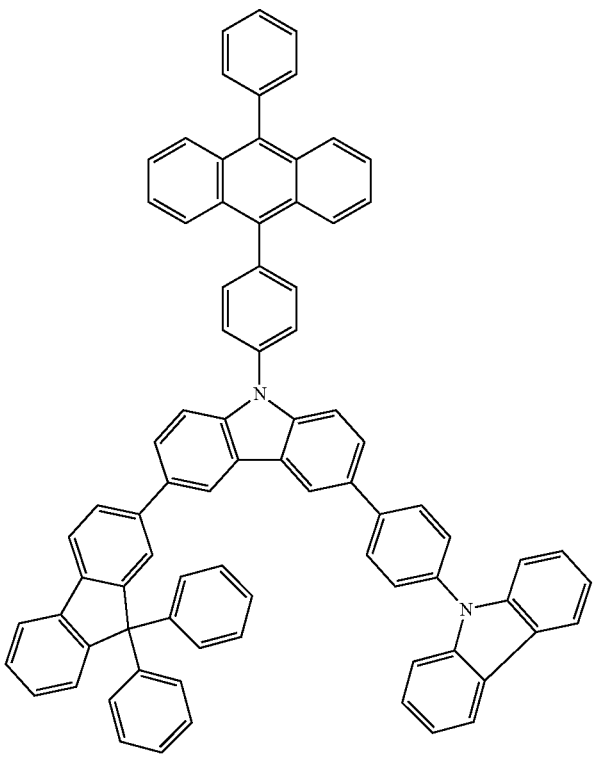
(351)
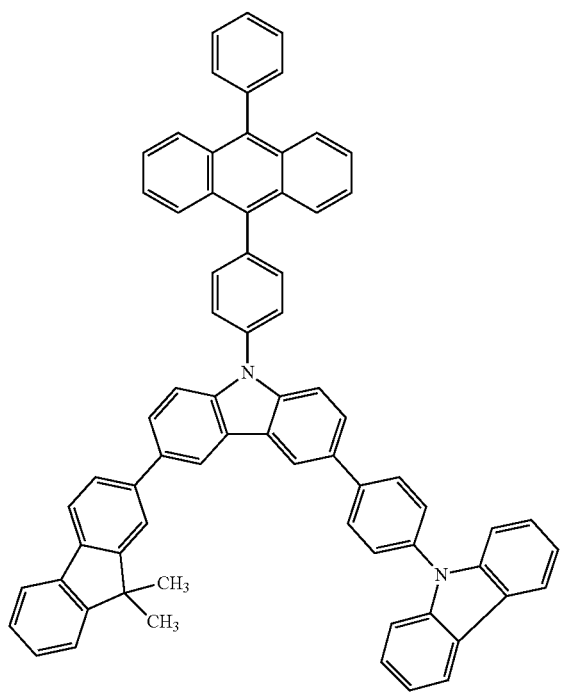
(352)
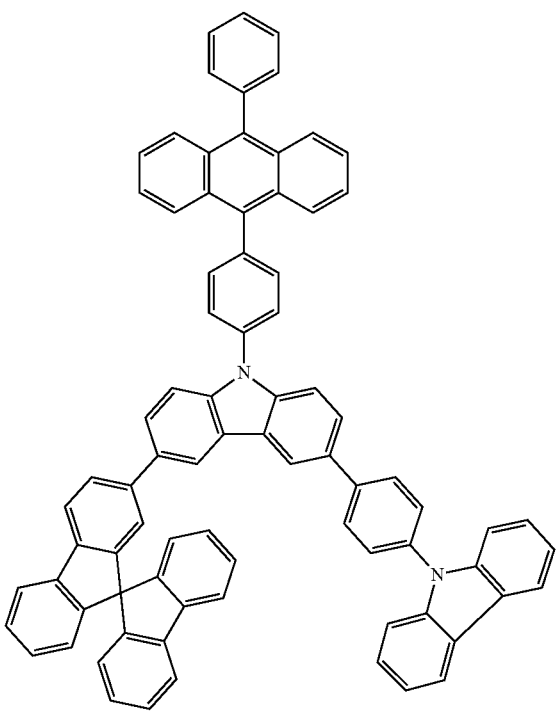

(353)
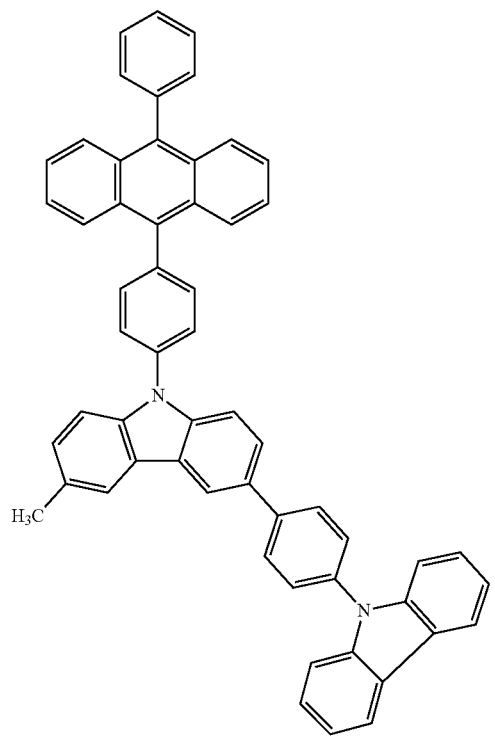
(354)
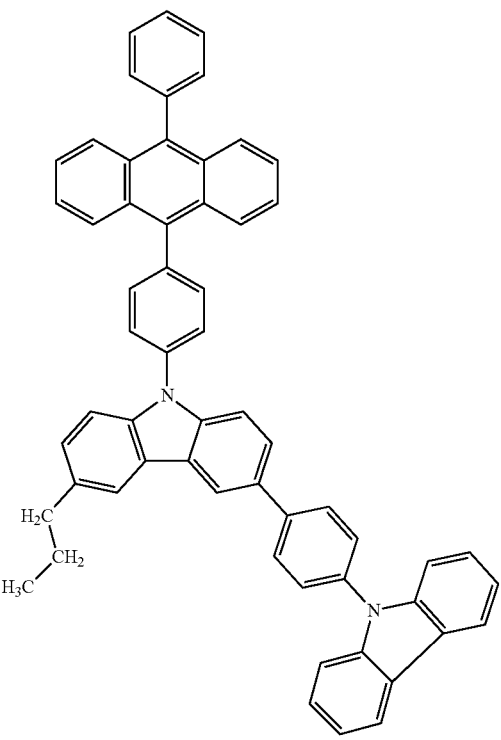
(355)
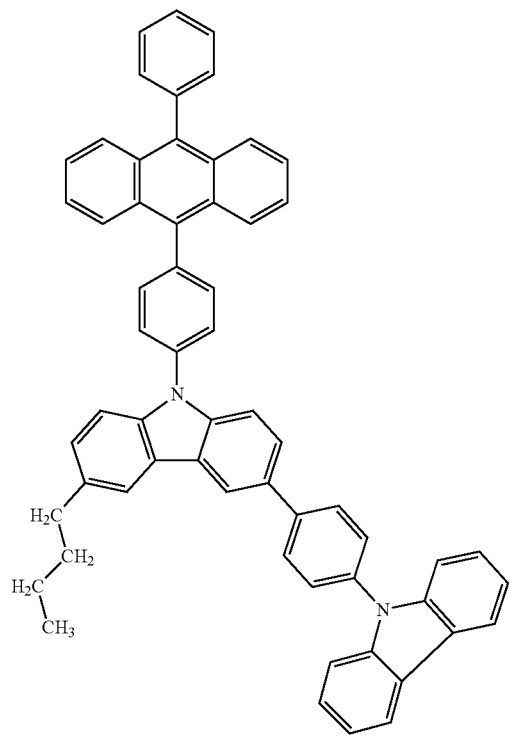
(356)
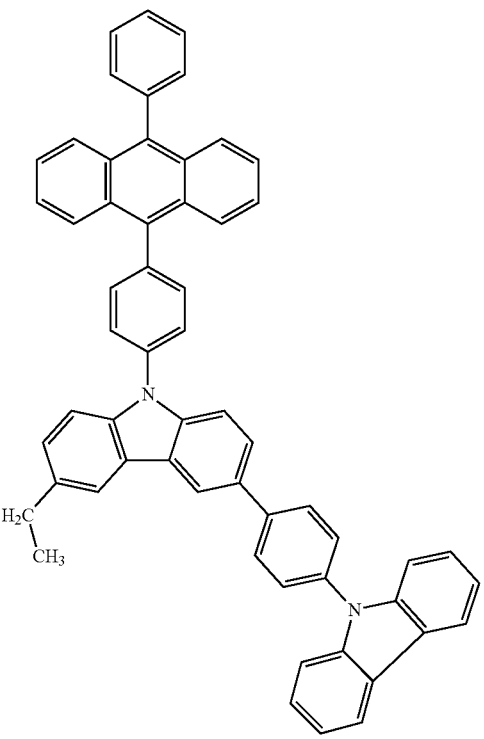

(357)
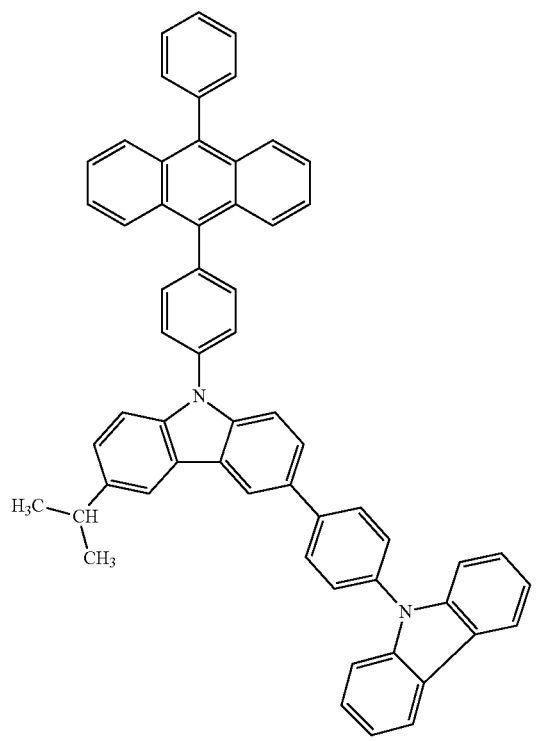
(358)
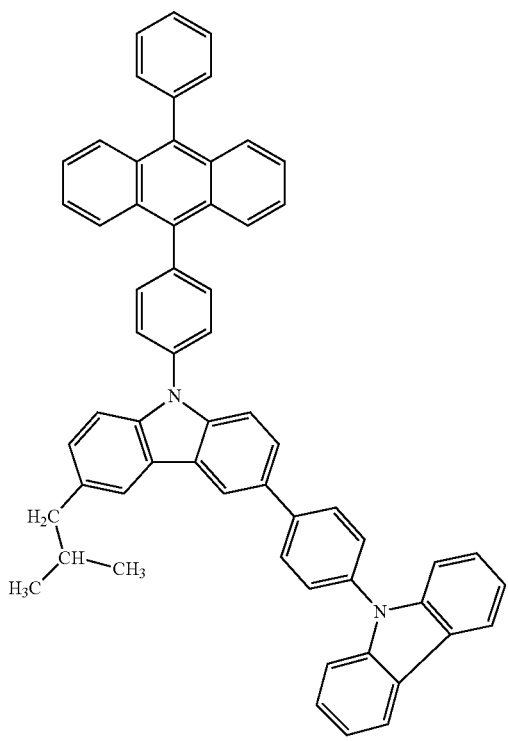
(359)
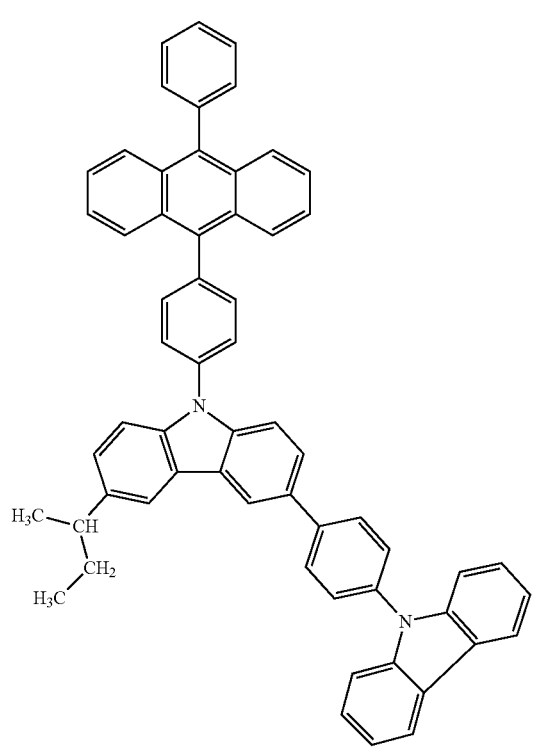
(360)
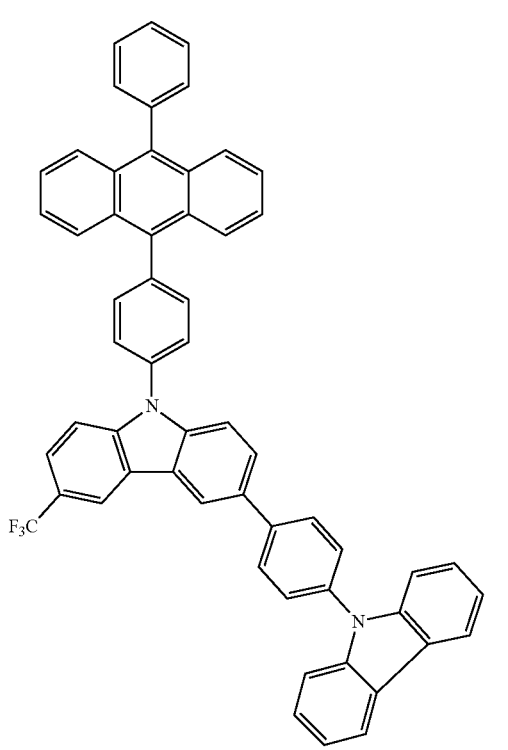

(361)
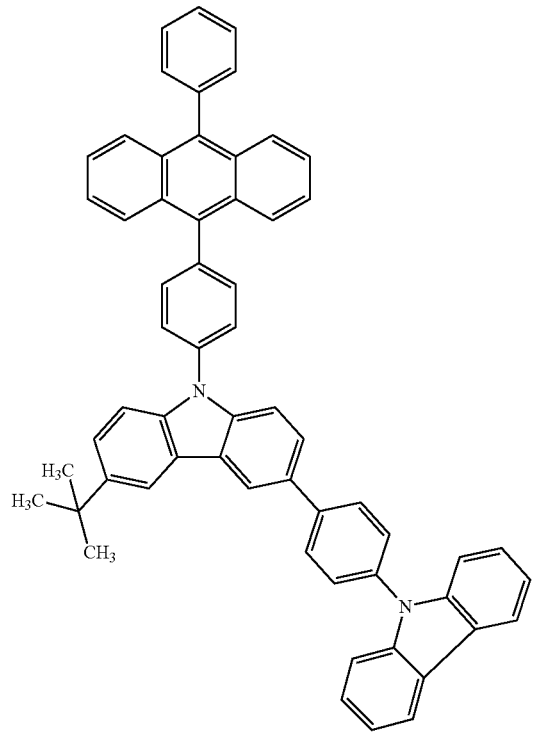
(362)
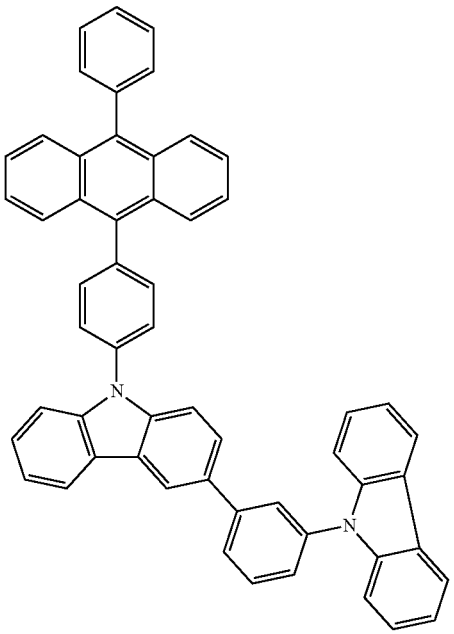
(363)
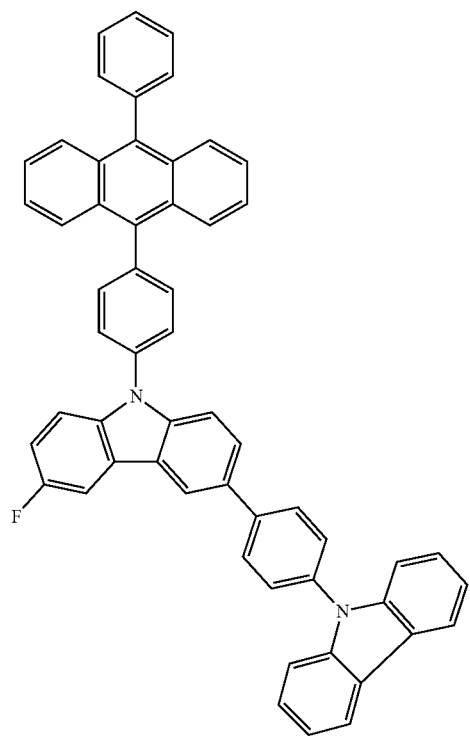
(364)
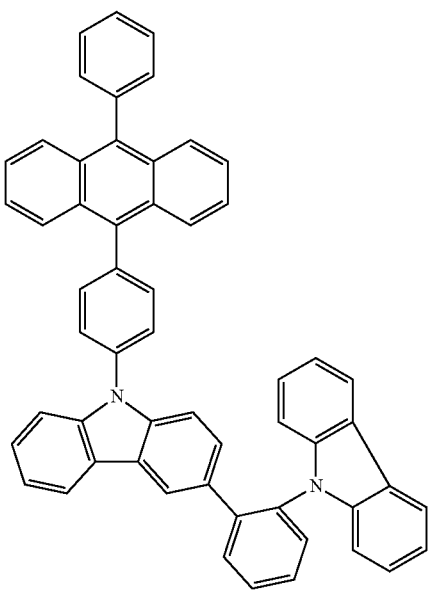

(365)
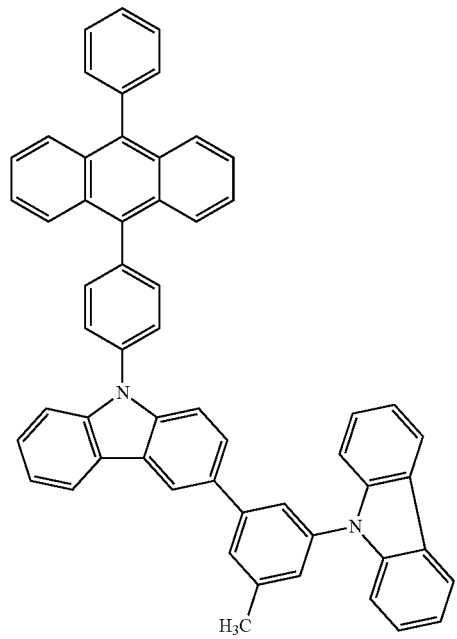
(366)
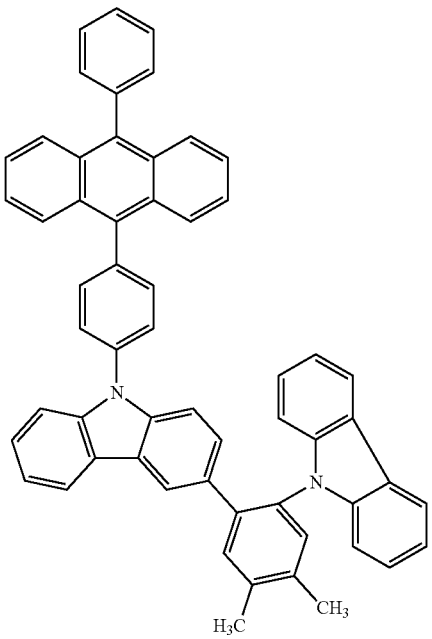
(367)
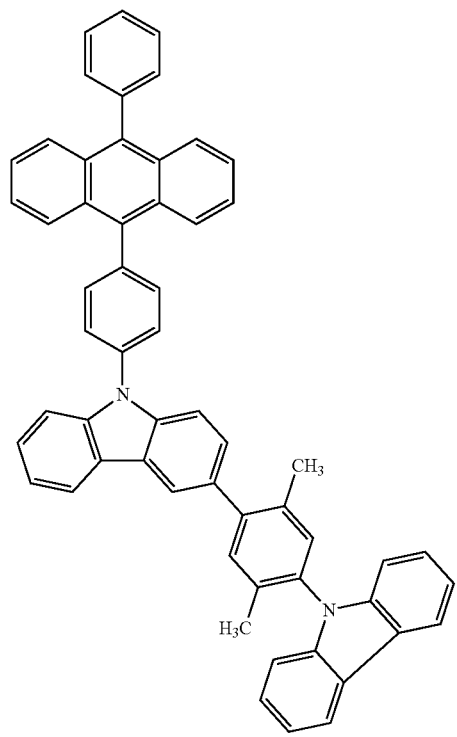
(368)
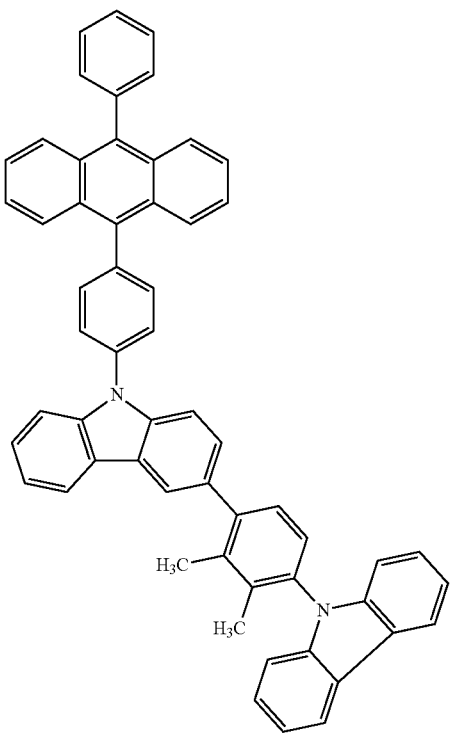

-continued
(369)
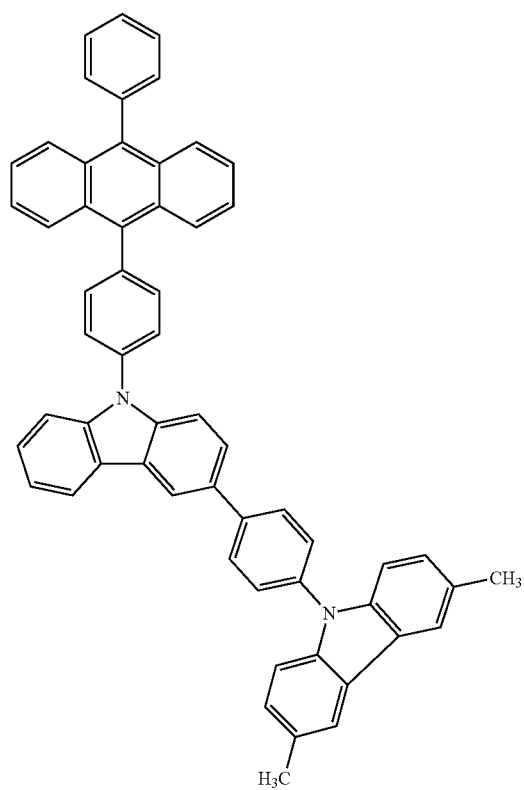
(370)
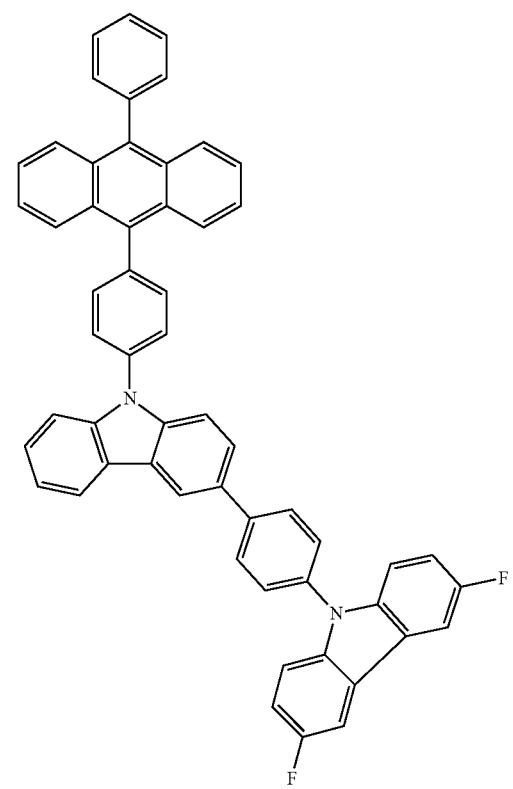
(371)
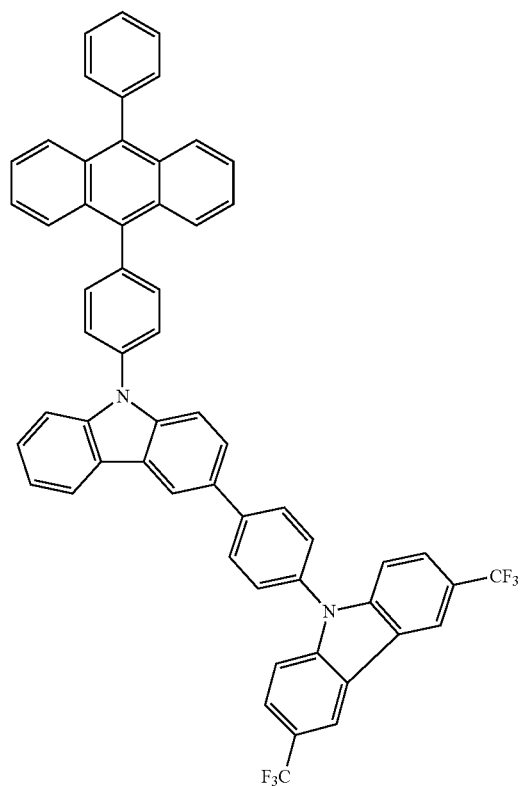
(372)
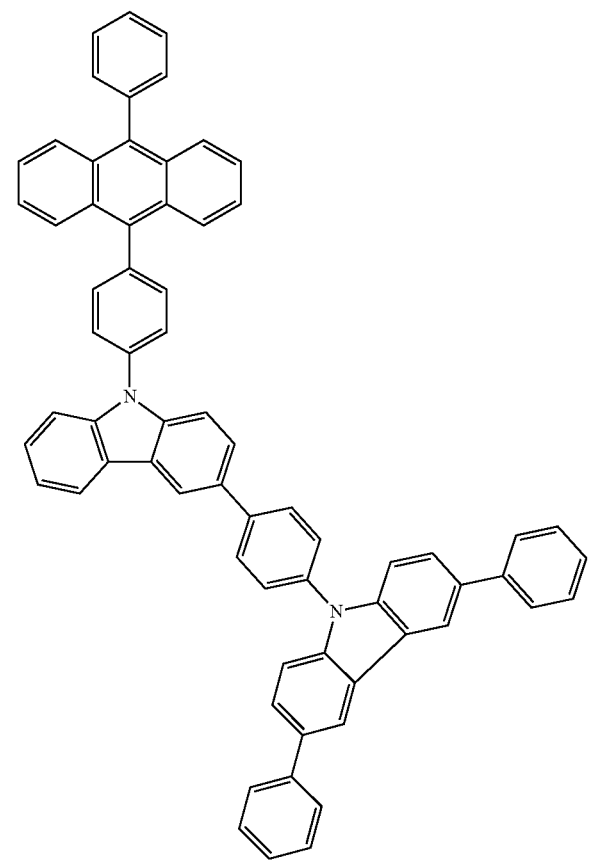

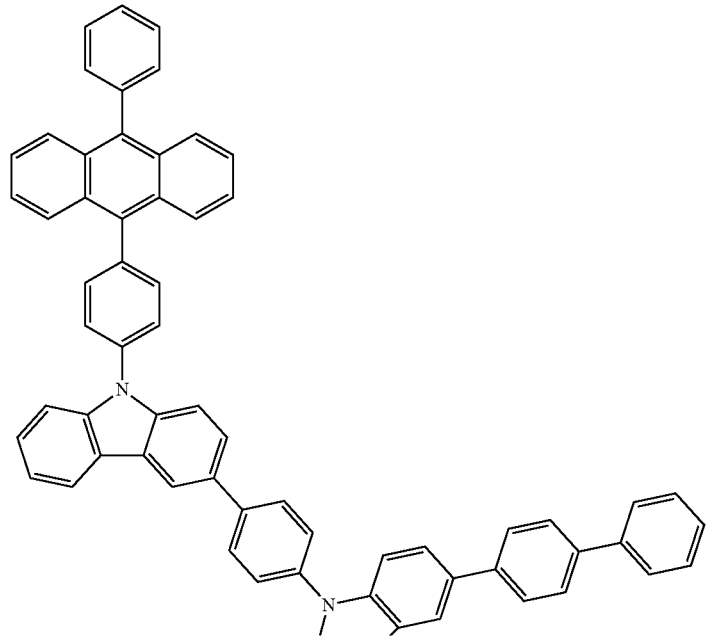
(373)
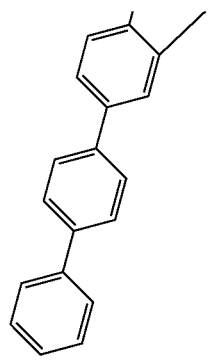

-continued
(374)
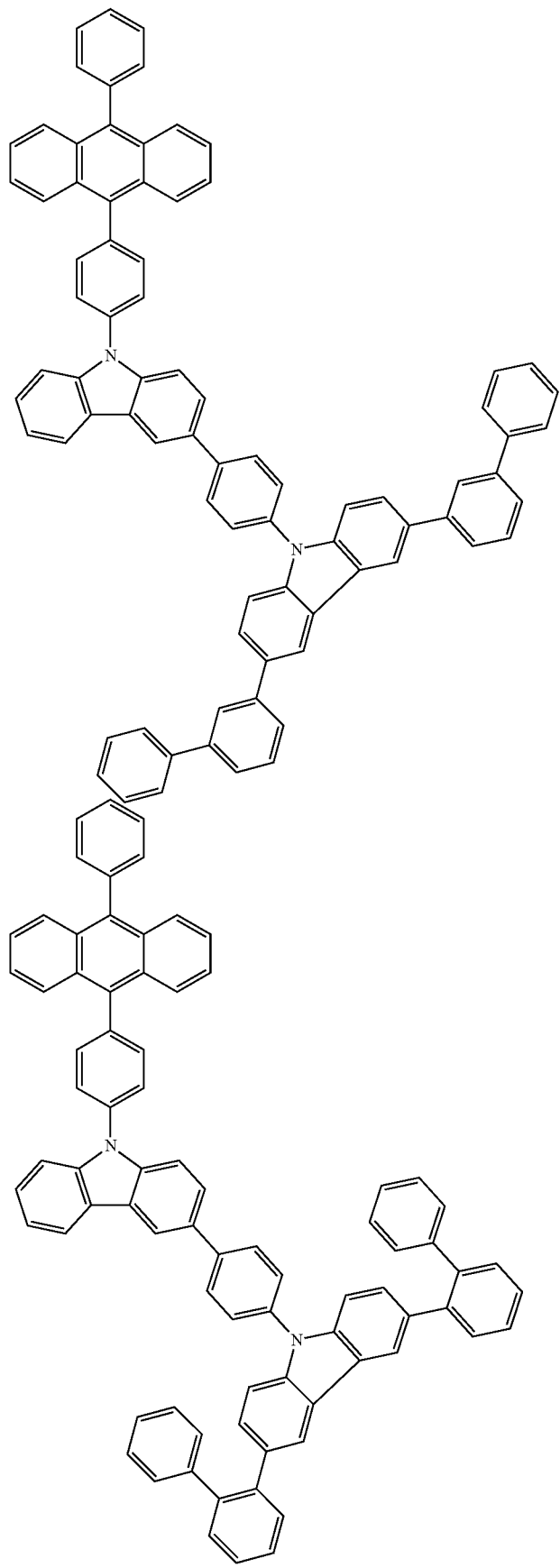
(375)

-continued
(375)
(376)
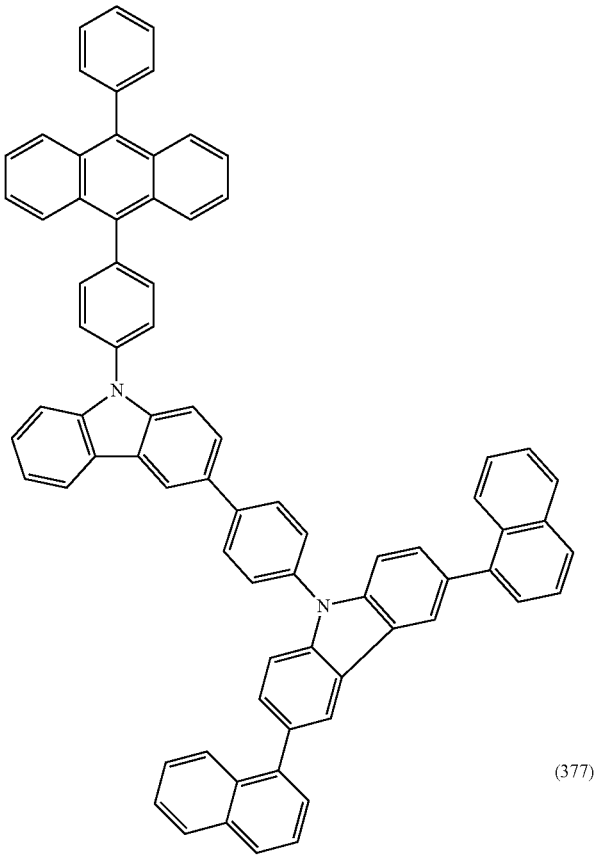
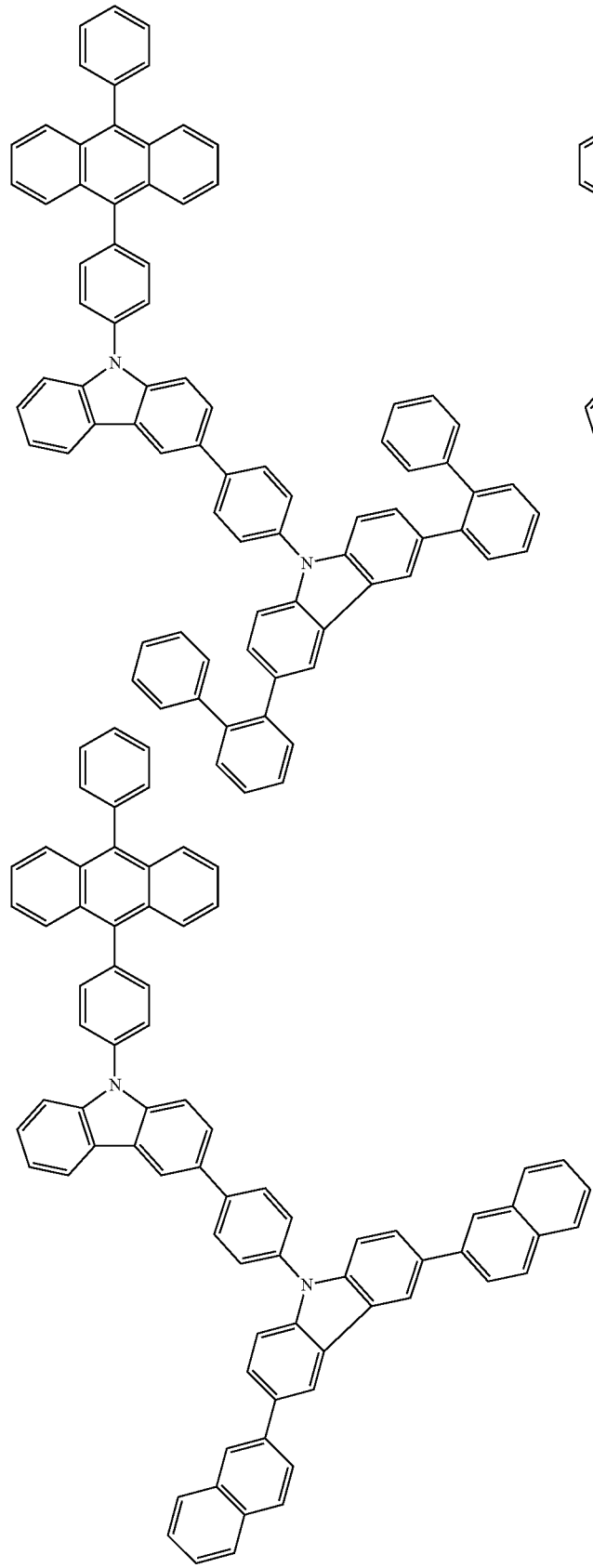
(377)

(378)
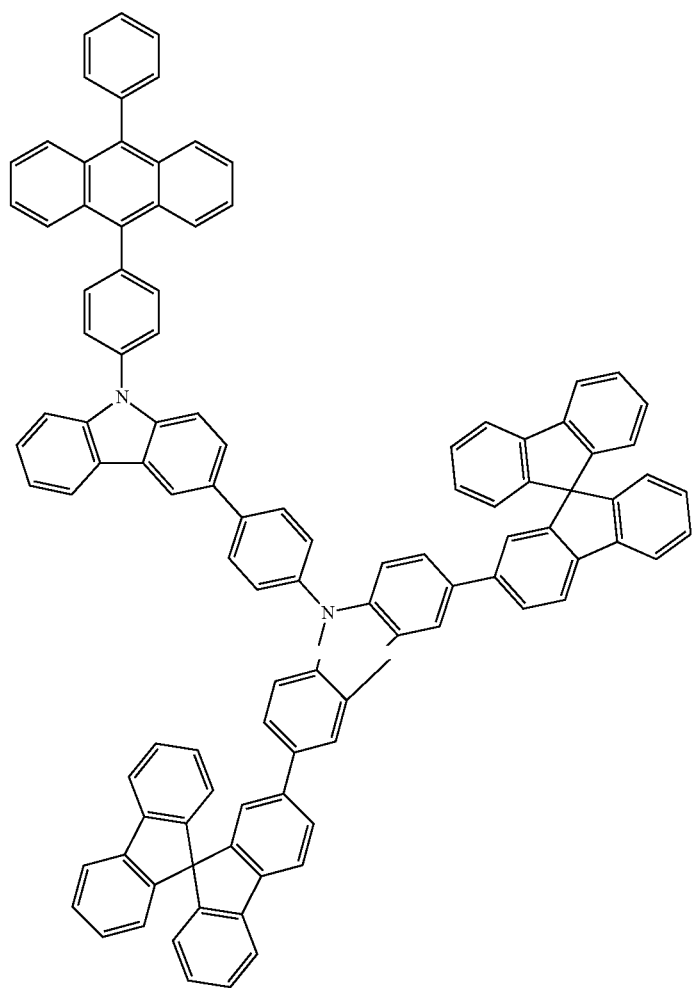
(379)
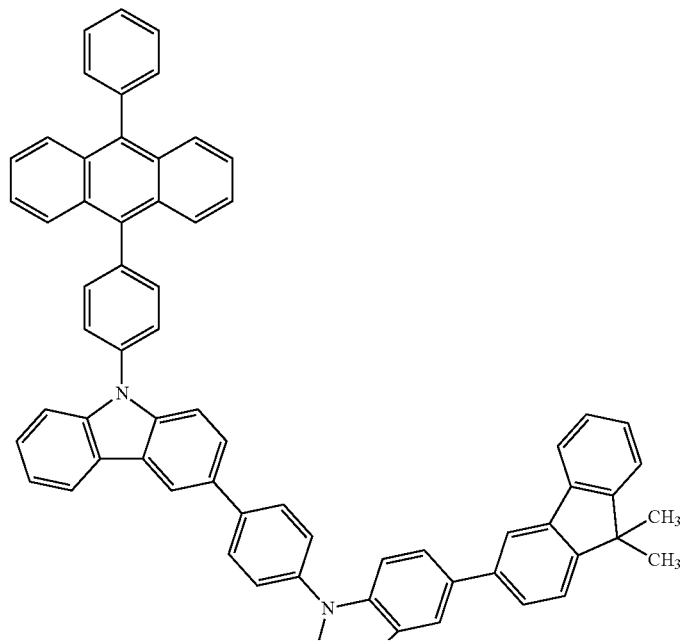

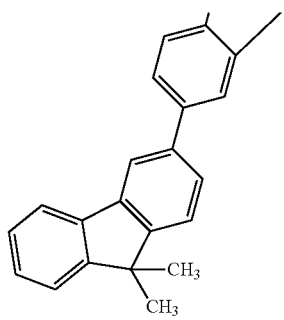
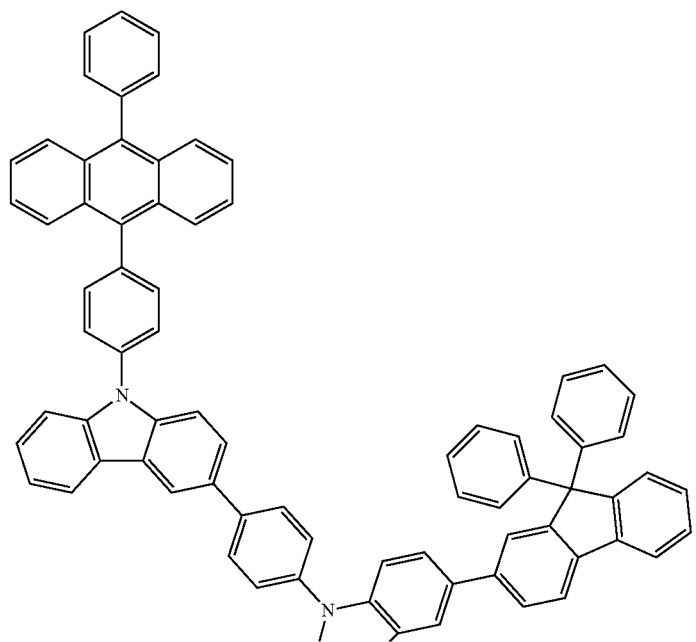
(380)
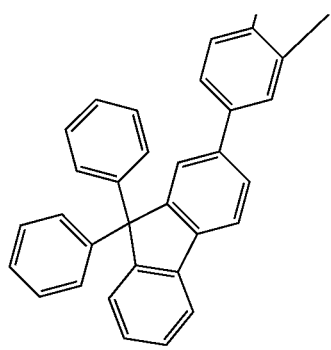

-continued
(381)
(382)
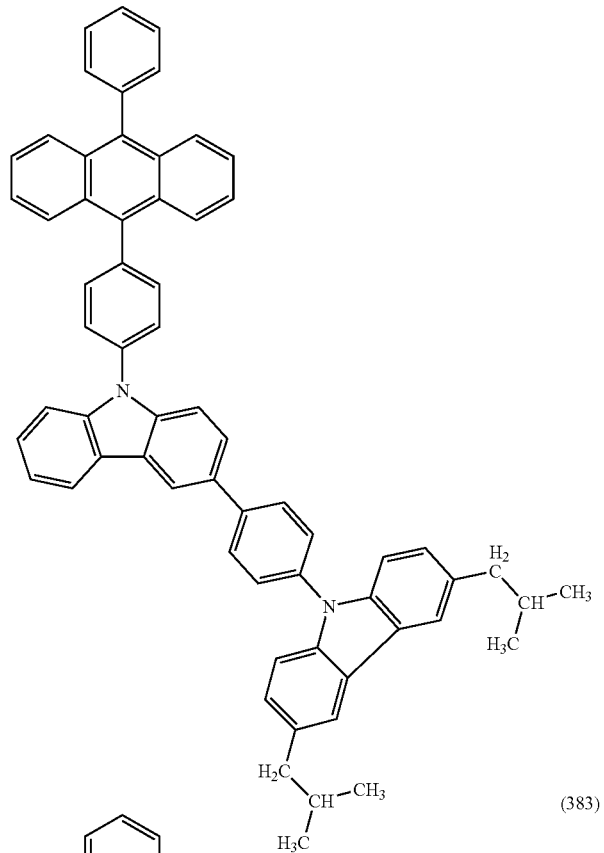
(383)
(384)
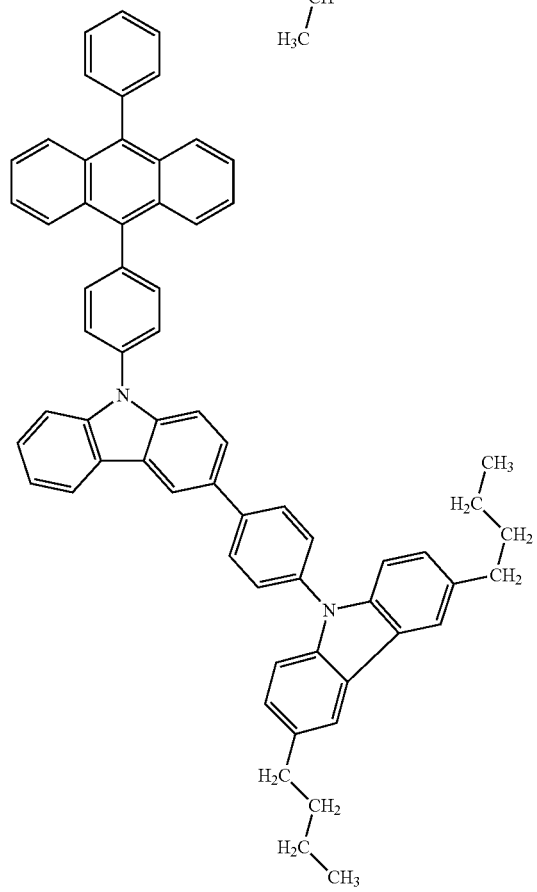

-continued
(385)
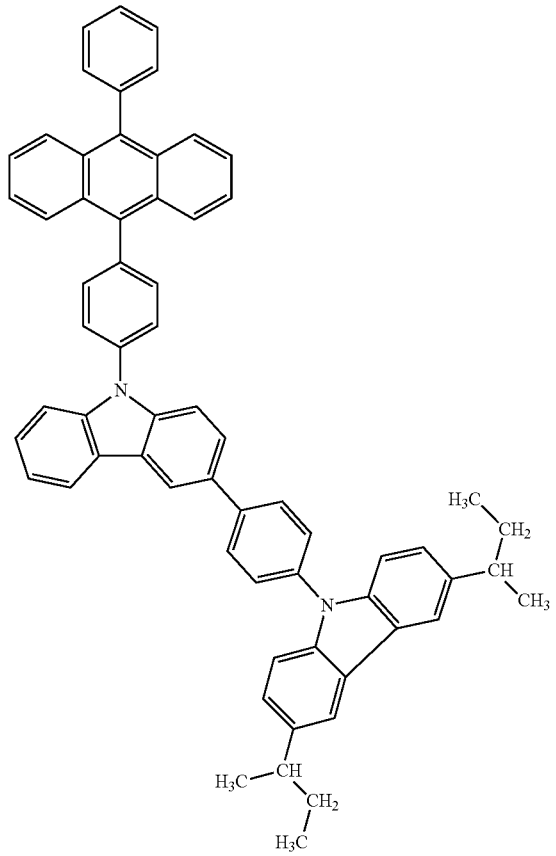
(386)
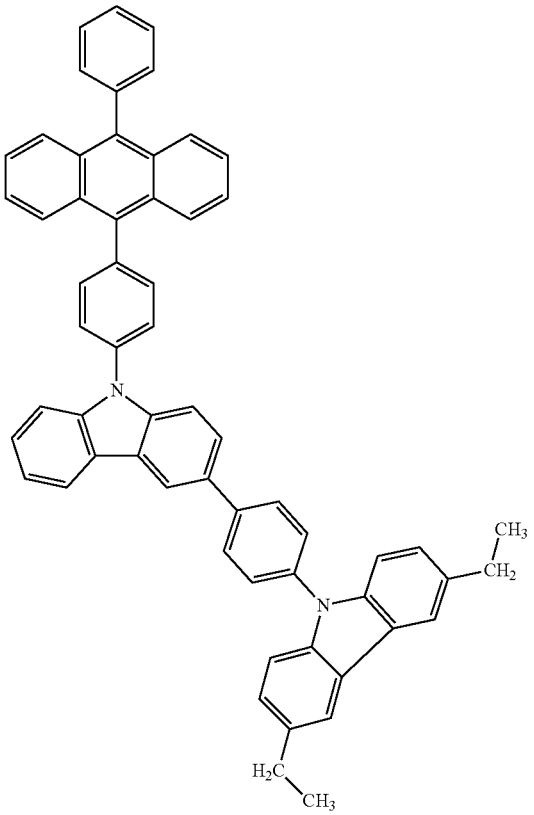
(387)
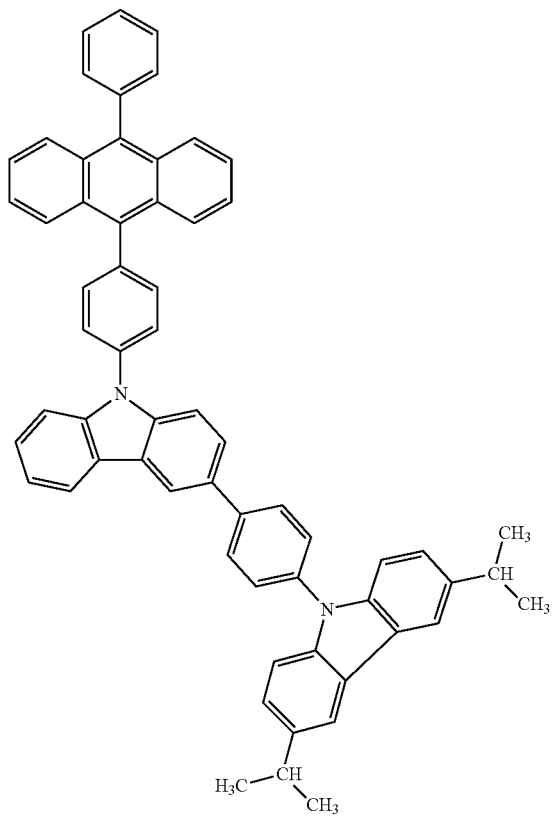

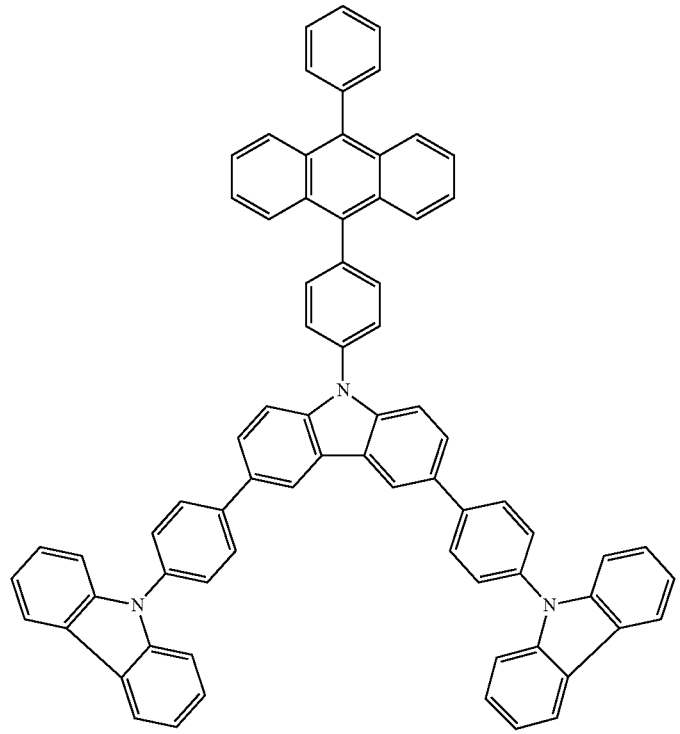
(388)
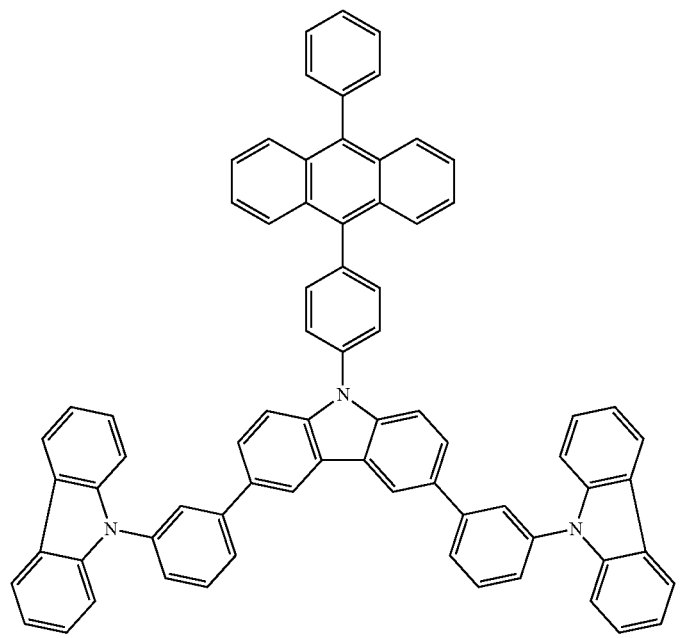
(389)

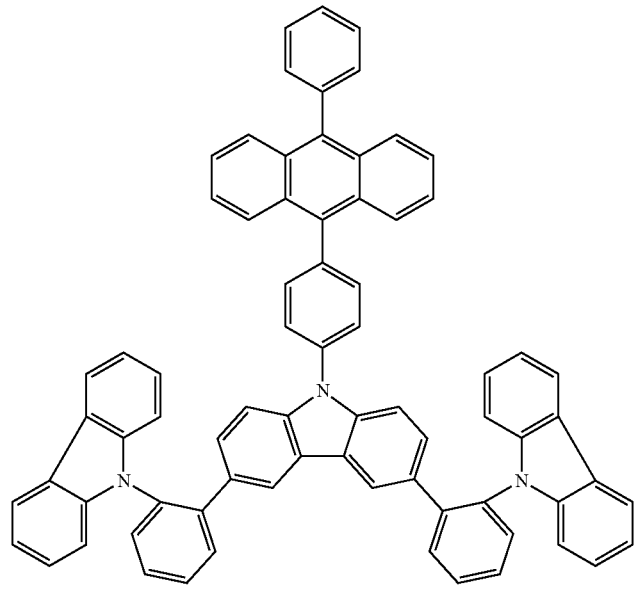
(390)
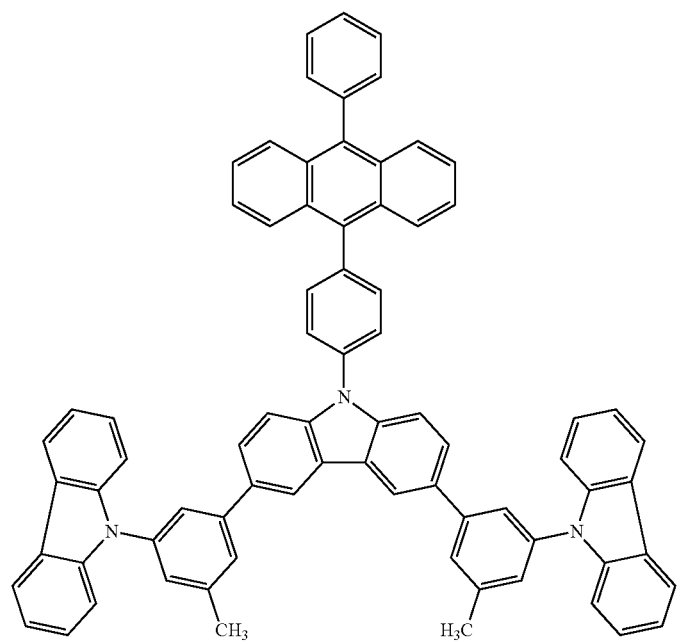
(391)

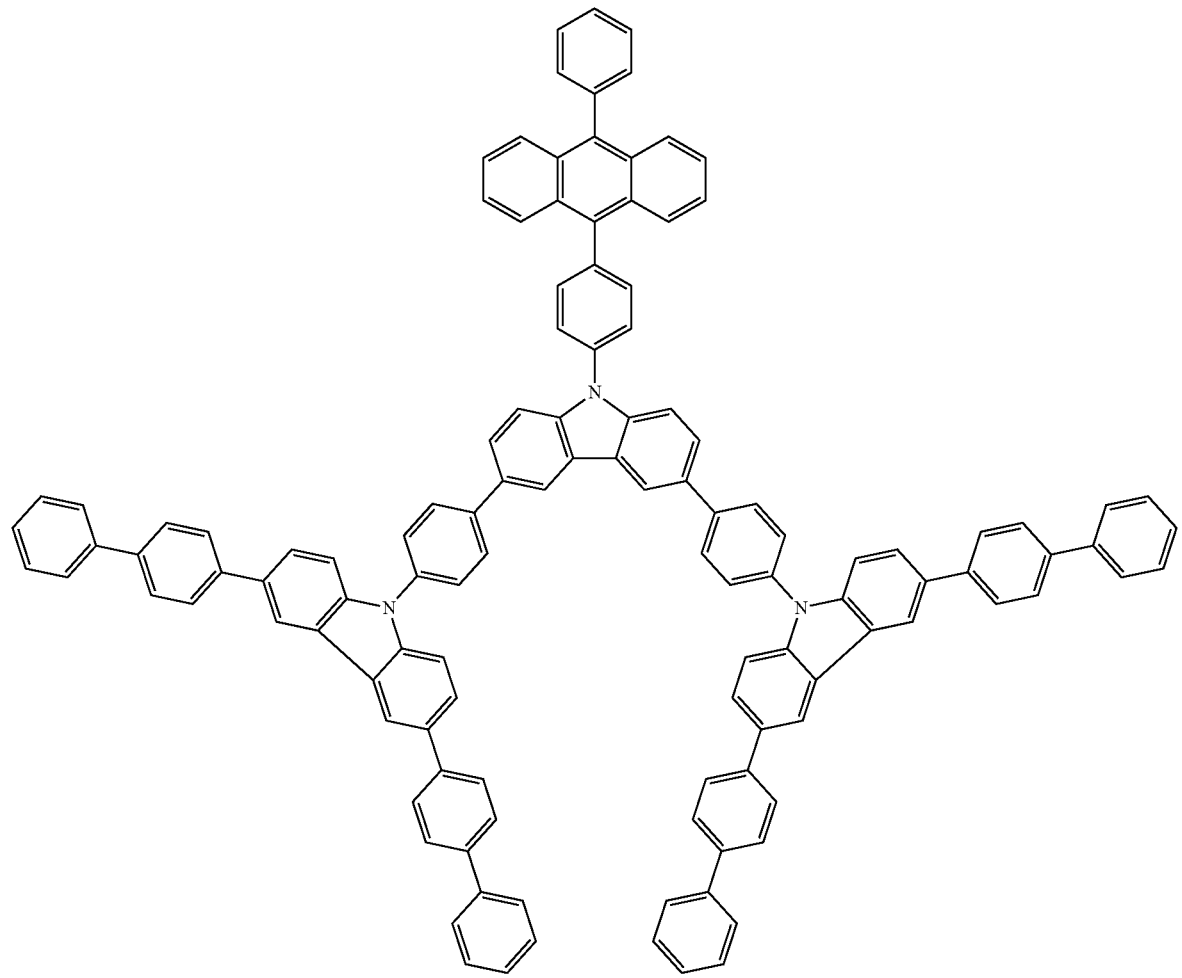
(392)

(393)
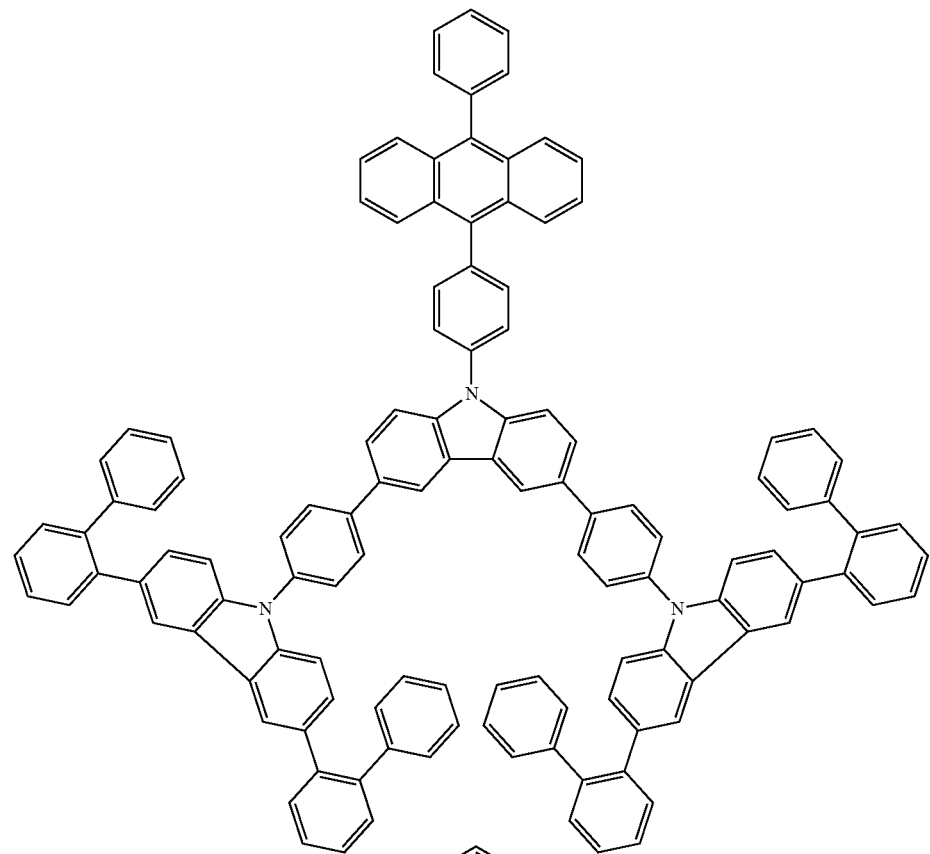
(394)
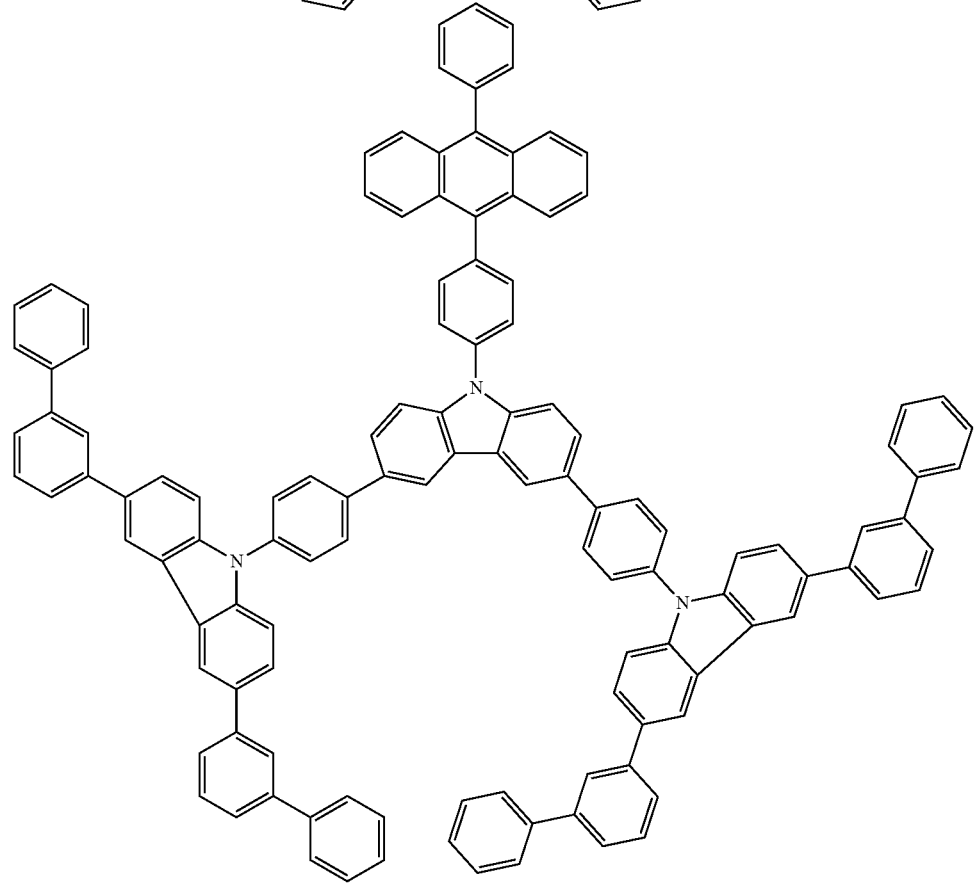

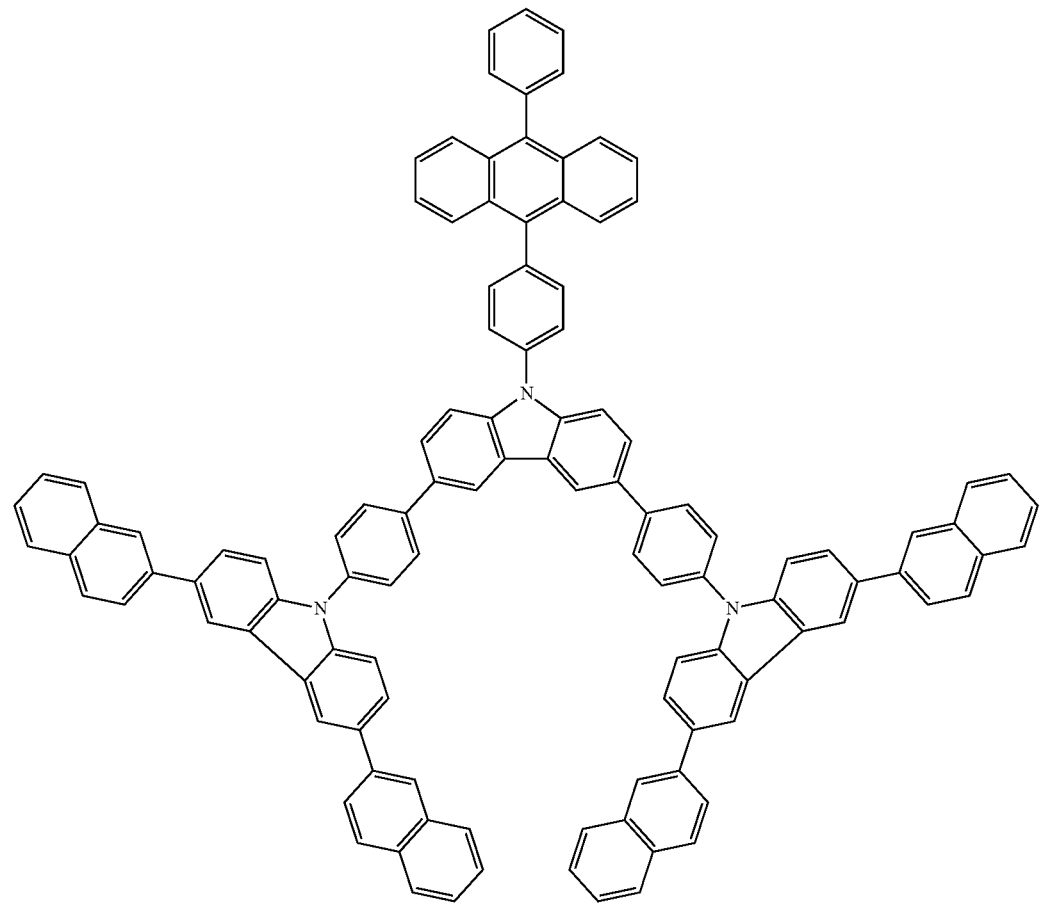
(395)

(396)
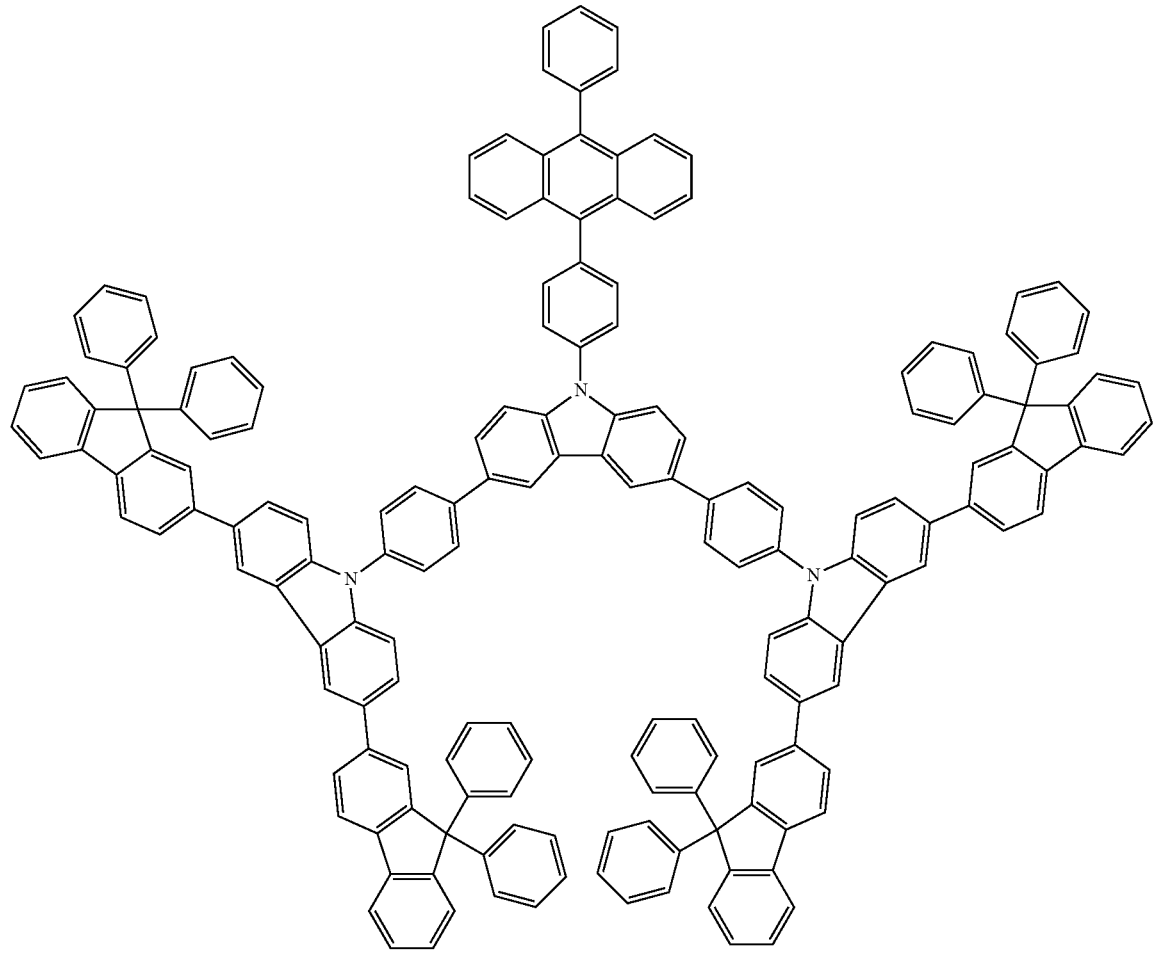
(397)
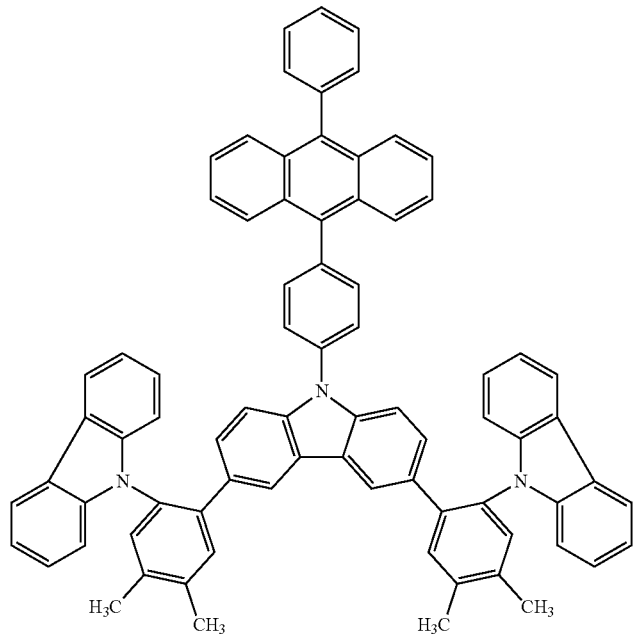

-continued
(398)
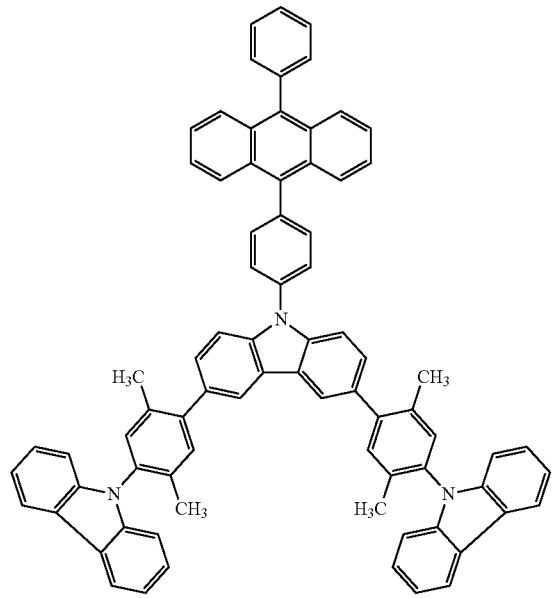
(399)
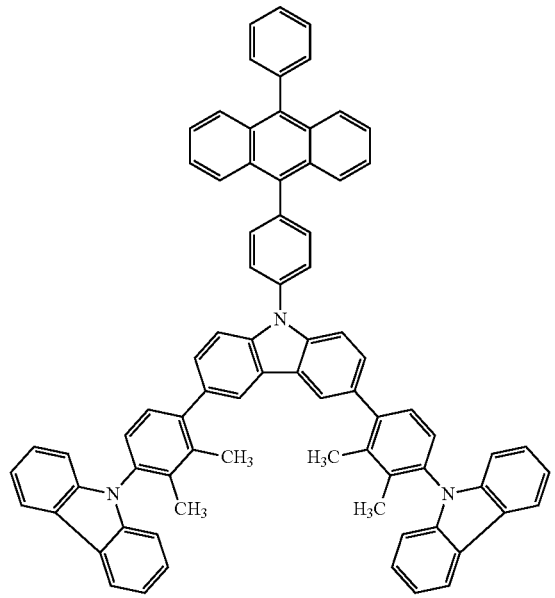
(400)
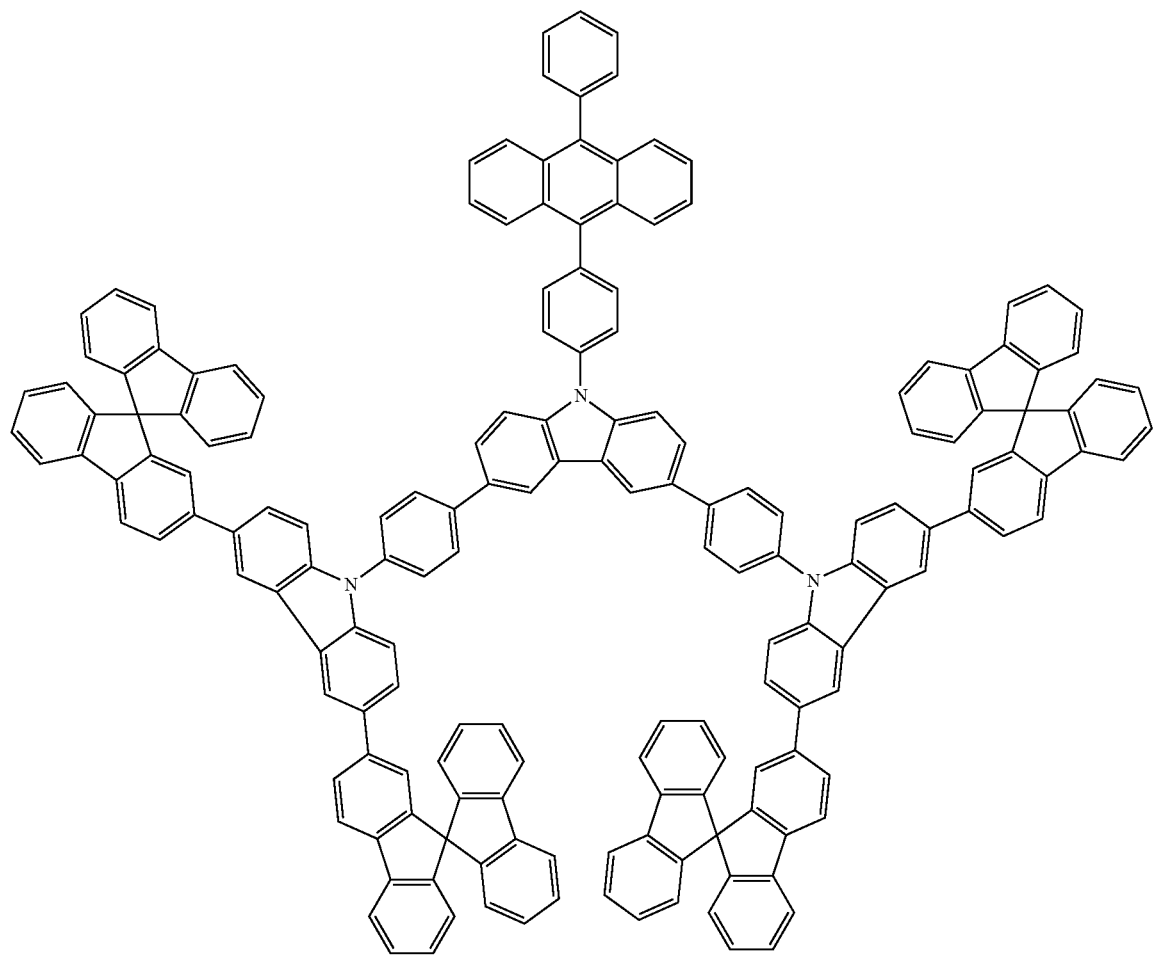

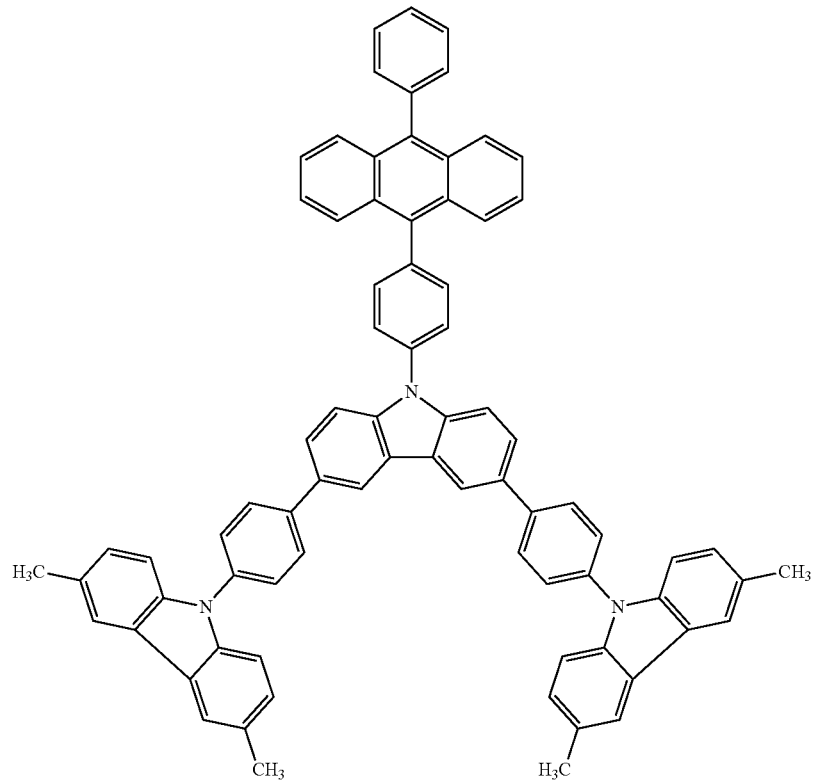
(401)
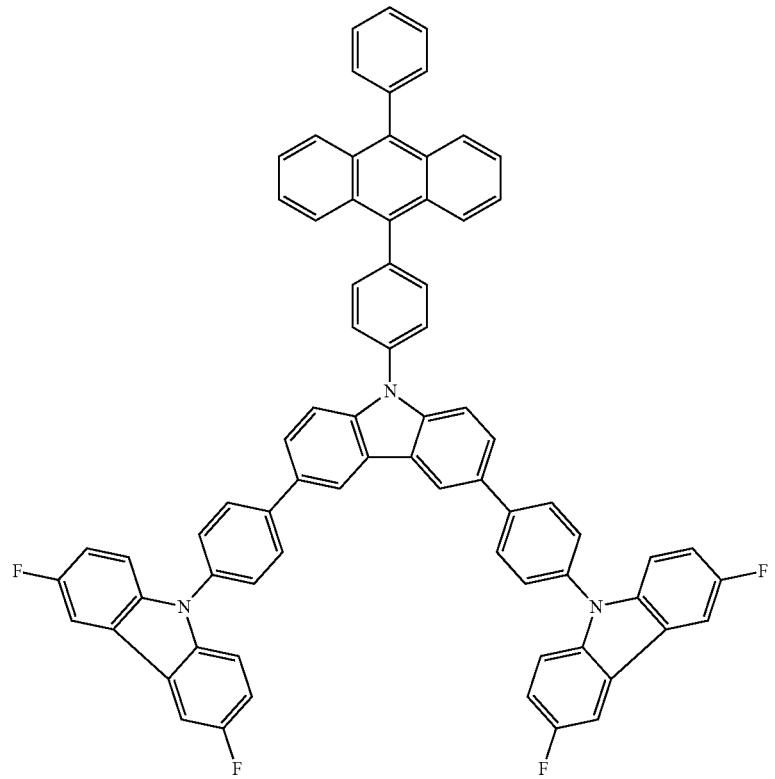
(402)

(403)
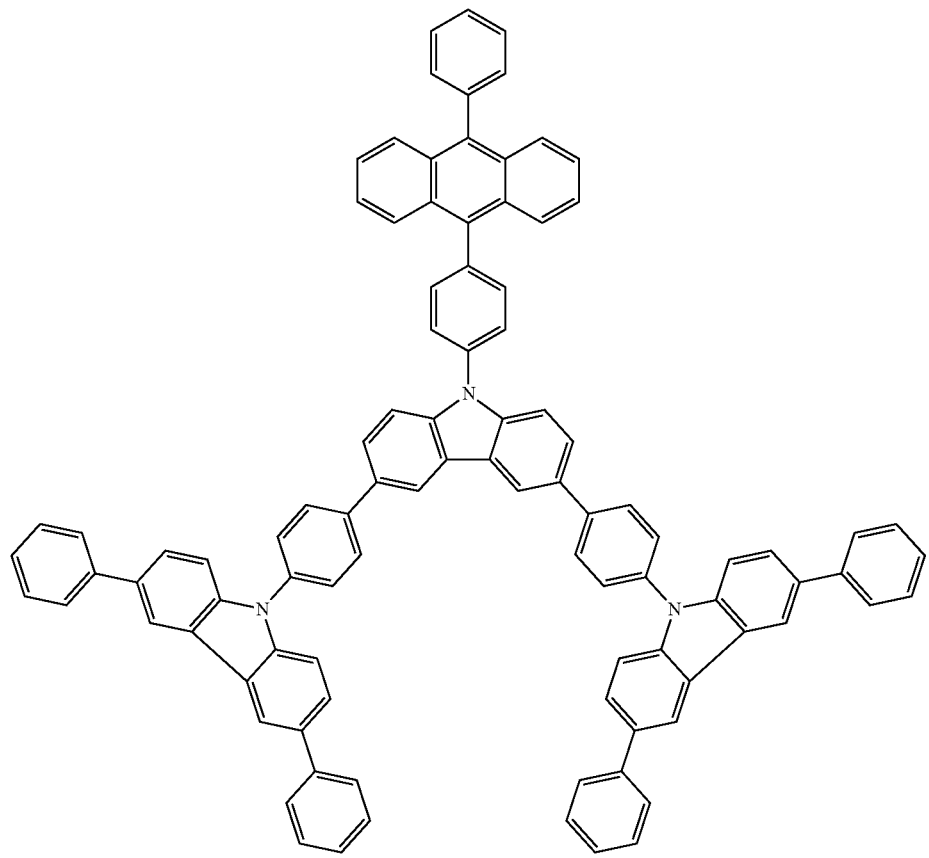
(404)
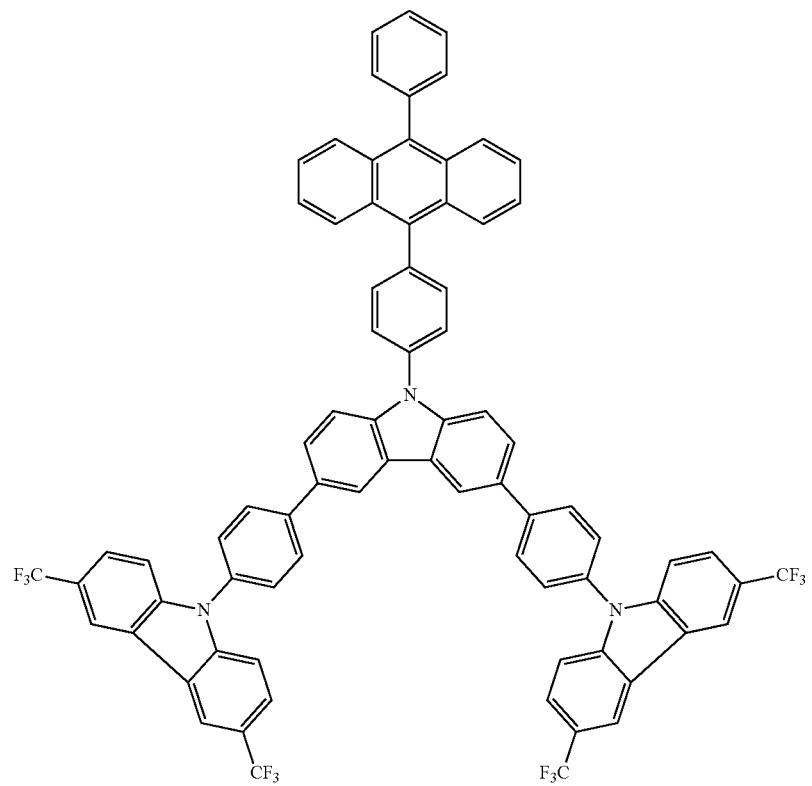

(405)
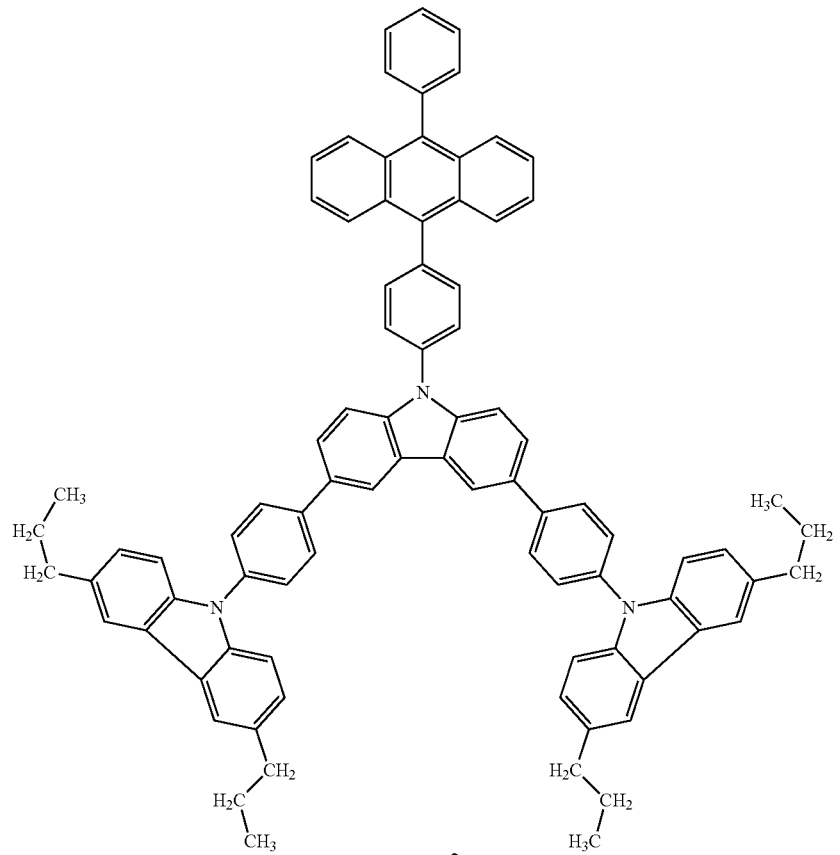
(406)
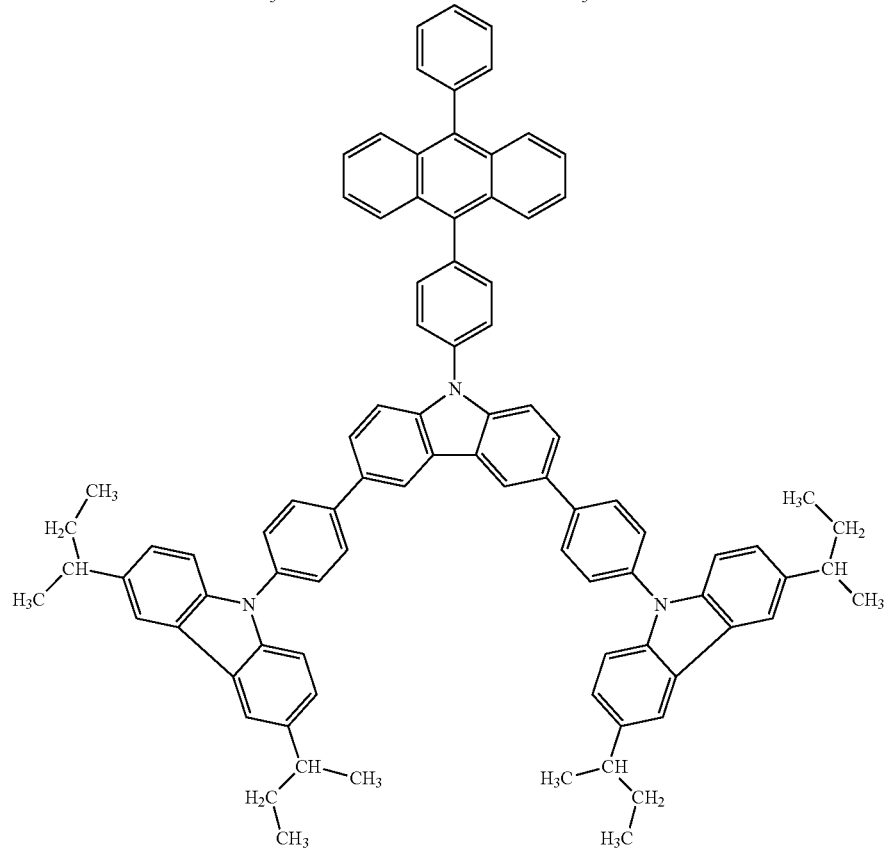

(407)
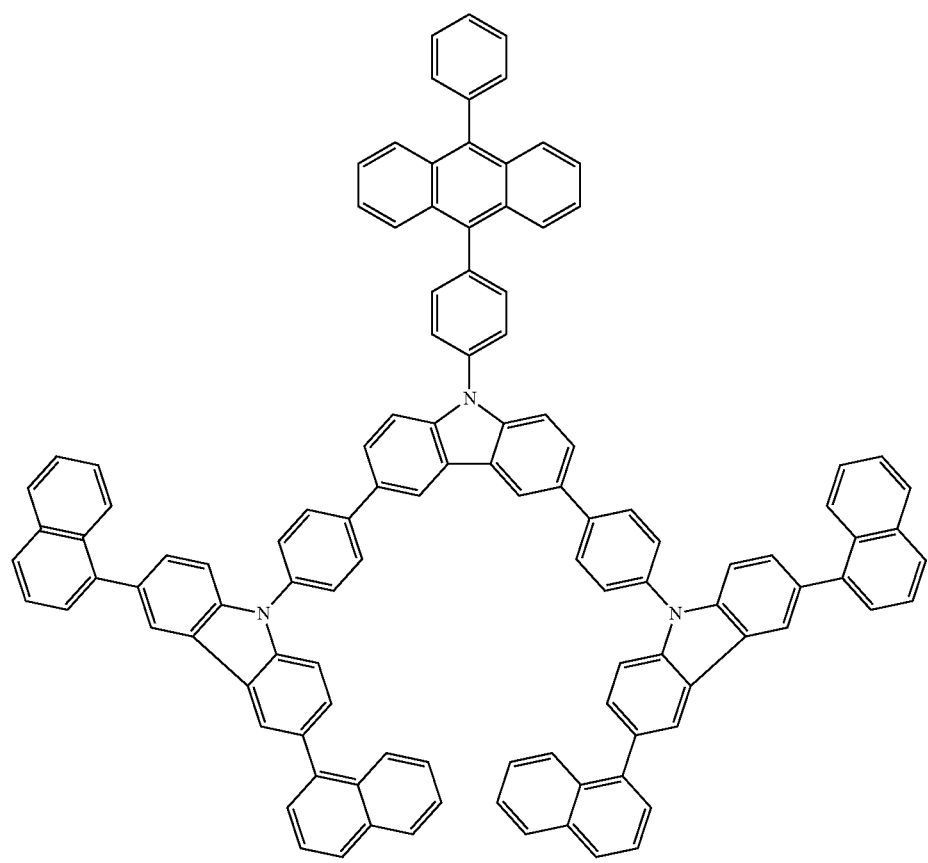
(408)
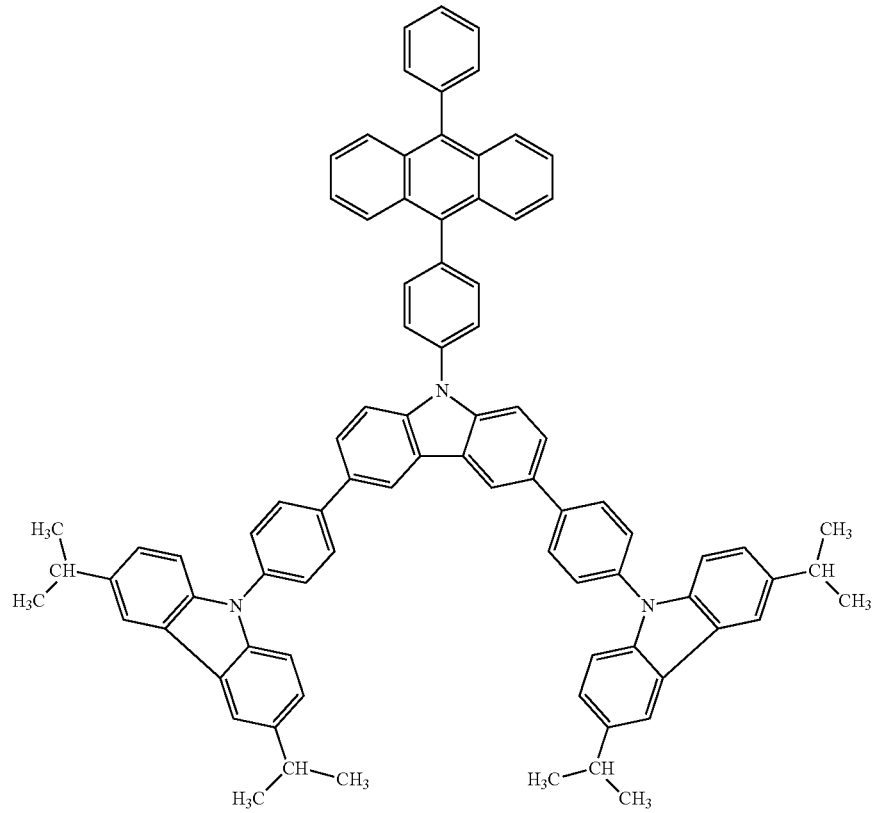

(409)
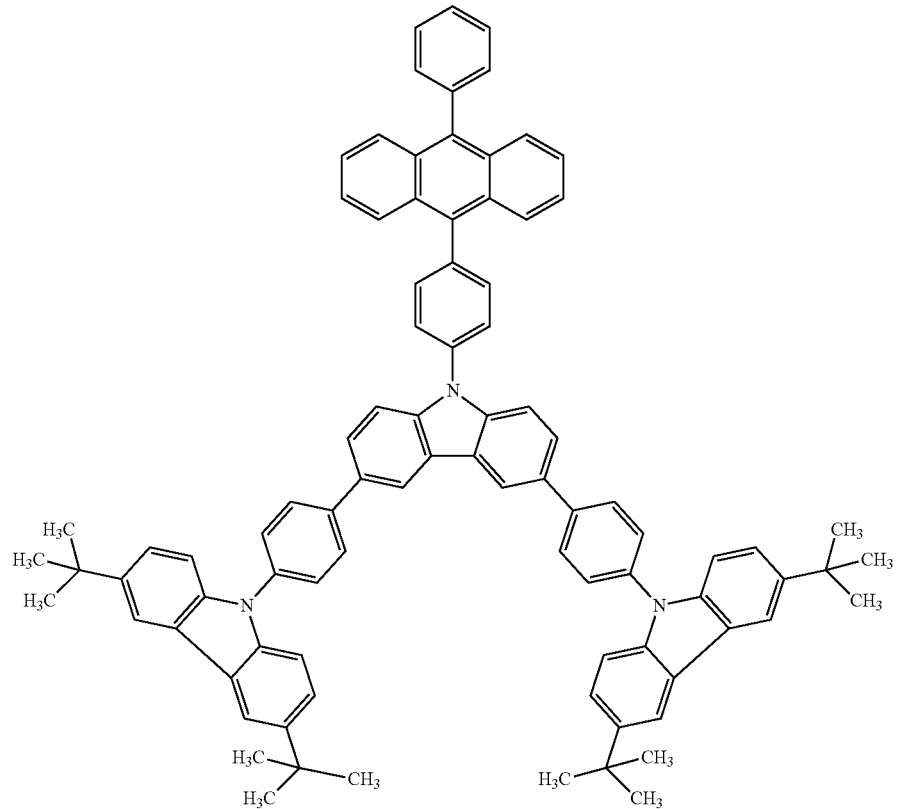
(410)
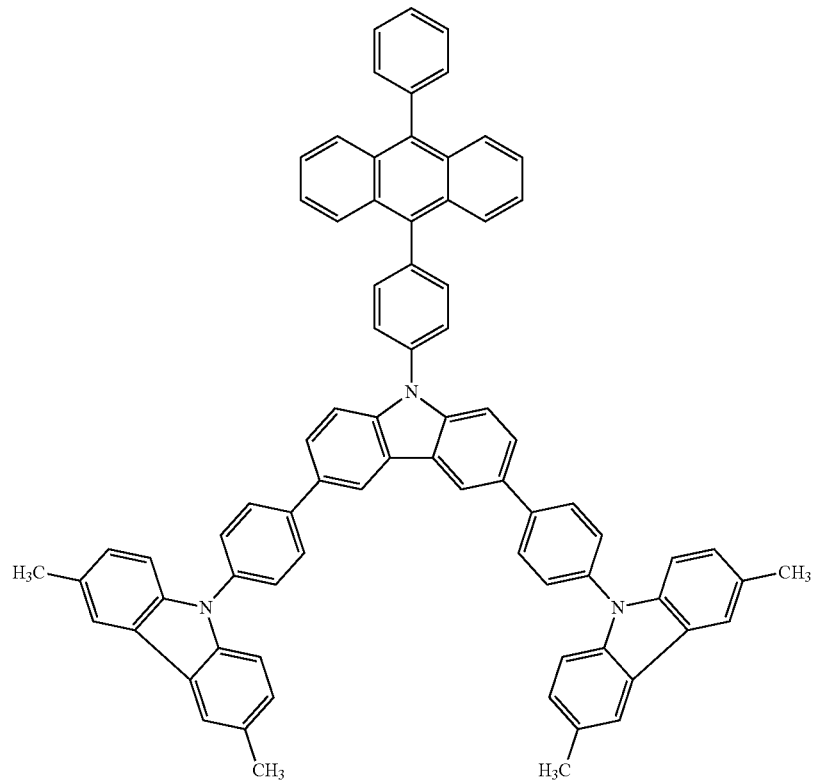

-continued
(411)
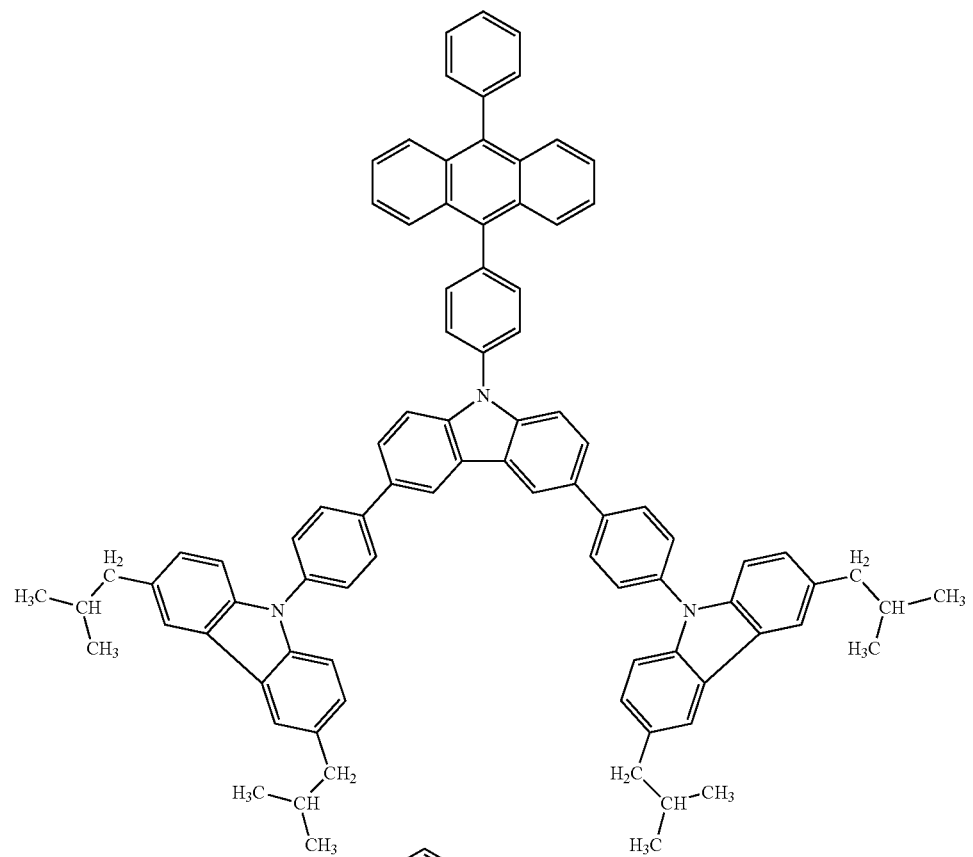
(412)
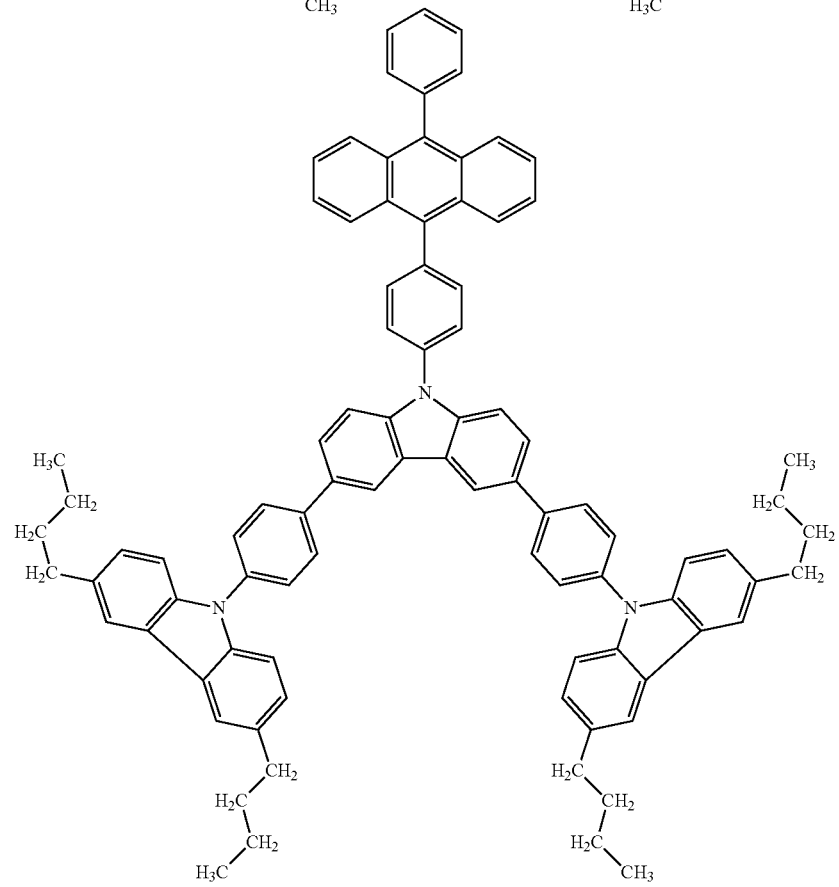

(413)
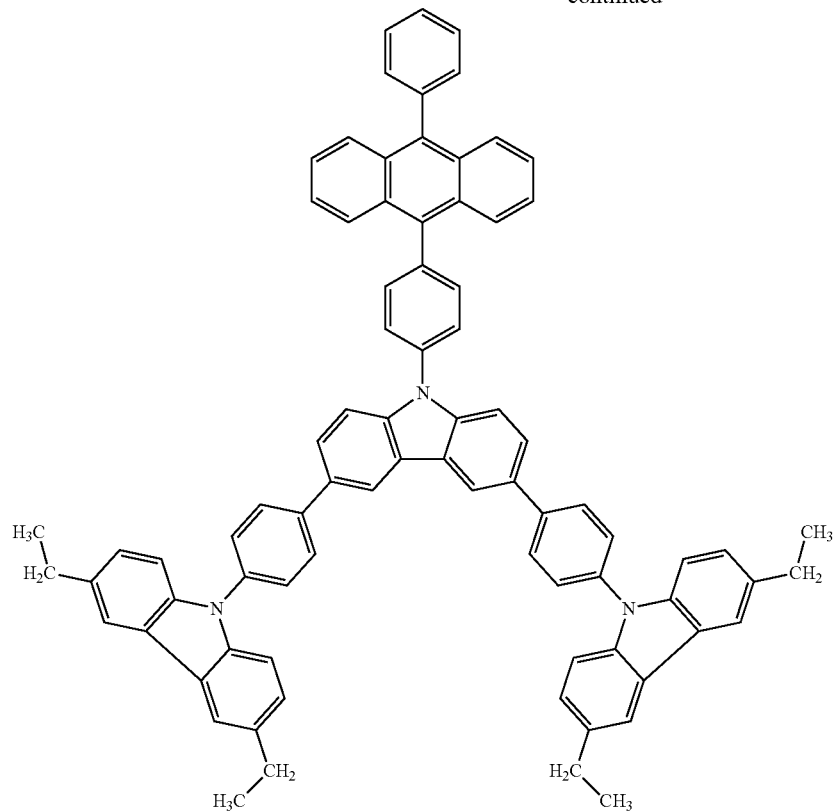
(414)
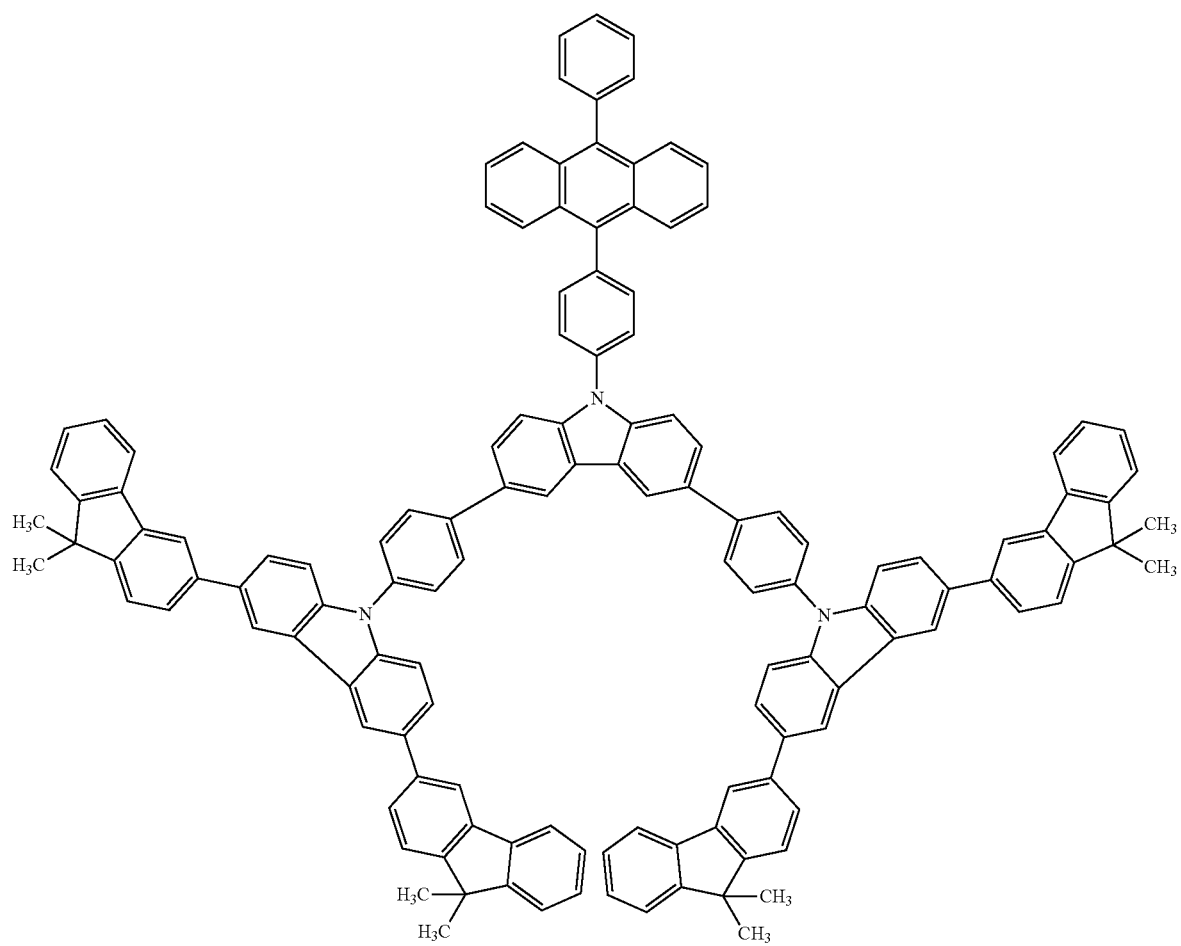

The anthracene derivatives of the present invention can be synthesized by any of a variety of methods. For example, the synthesis can be performed by the use of any of the synthesis methods shown in synthesis schemes (a-1) to (a-3) given below.

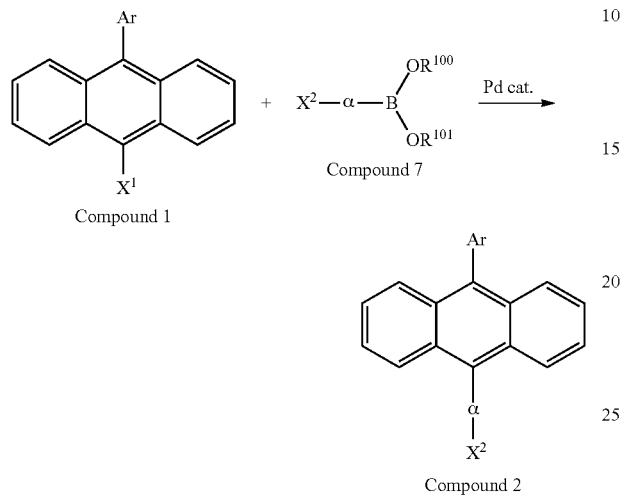

(a-1)

Compound 1 + Compound 7 → Compound 2 (Pd cat.)

First, 9-halid-10-arylanthracene (compound 1) and boronic acid which is an aryl halide or an organic boron compound which is an aryl halide (compound 7) are coupled by Suzuki-Miyaura Coupling using a palladium catalyst, and thus 9-(aryl halide)-10-arylanthracene (compound 2) can be obtained. In the reaction formula, $X^1$ represents halogen or a triflate group, and $X^2$ represents halogen. When $X^1$ is halogen, $X^1$ and $X^2$ may be the same or different from one another. Use of iodine and bromine are preferable for the halogen. It is more preferable that $X^1$ be iodine and $X^2$ be bromine. Further, $R^{100}$ and $R^{101}$ each represent hydrogen or an alkyl group having 1 to 6 carbon atoms, may be the same or different from one another, and may be combined with each other to form a ring. Ar represents an aryl group having 6 to 25 carbon atoms. In addition, a represents an arylene group having 6 to 25 carbon atoms. Examples of the palladium catalyst that can be used in the synthesis scheme (a-1) include, but are not limited to, palladium(II) acetate and tetrakis(triphenylphosphine)palladium(0). Examples of a ligand in the palladium catalyst, which can be used in the synthesis scheme (a-1), include, but are not limited to, tri(ortho-tolyl)phosphine, triphenylphosphine, and tricyclohexylphosphine. Examples of a base that can be used in the synthesis scheme (a-1) include, but are not limited to, an organic base such as sodium tert-butoxide and an inorganic base such as potassium carbonate. Examples of a solvent that can be used in the synthesis scheme (a-1) include, but are not limited to, a mixed solvent of toluene and water; a mixed solvent of toluene, an alcohol such as ethanol, and water; a mixed solvent of xylene and water; a mixed solvent of xylene, an alcohol such as ethanol, and water; a mixed solvent of benzene and water; a mixed solvent of benzene, an alcohol such as ethanol, and water; and a mixed solvent of ether such as ethyleneglycoldimethylether and water. Use of a mixed solvent of toluene and water or a mixed solvent of toluene, ethanol, and water is more preferable.

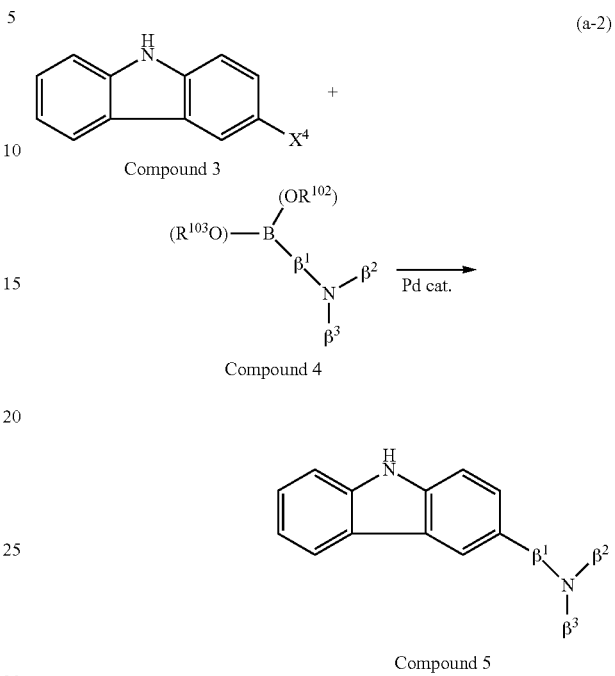

(a-2)

Compound 3 + Compound 4 → Compound 5 (Pd cat.)

3-carbazole halide (compound 3) and boronic acid which is a triarylamine or an organic boron compound which is a triarylamine (compound 4) are coupled by Suzuki-Miyaura Coupling using a palladium catalyst, and thus a carbazole compound in which the 3-position is substituted with triarylamine (compound 5) can be obtained. In the formula, $X^4$ represents a halogen or a triflate group, and iodine or bromine can be used as the halogen. Further, $R^{102}$ and $R^{103}$ each represent hydrogen or an alkyl group having 1 to 6 carbon atoms, may be the same or different from one another, and combined with each other to form a ring. $\beta^1$ to $\beta^3$ each represent a substituted or unsubstituted benzene ring. Examples of the palladium catalyst that can be used in the synthesis scheme (a-2) include, but are not limited to, palladium(II) acetate and tetrakis(triphenylphosphine)palladium(0). Examples of a ligand of the palladium catalyst, which can be used in the synthesis scheme (a-2), include, but are not limited to, tri(ortho-tolyl)phosphine, triphenylphosphine, and tricyclohexylphosphine. Examples of a base that can be used in the synthesis scheme (a-2) include, but are not limited to, an organic base such as sodium tert-butoxide and an inorganic base such as potassium carbonate. Examples of a solvent that can be used in the synthesis scheme (a-2) include, but are not limited to, a mixed solvent of toluene and water; a mixed solvent of toluene, an alcohol such as ethanol, and water; a mixed solvent of xylene and water; a mixed solvent of xylene, an alcohol such as ethanol, and water; a mixed solvent of benzene and water; a mixed solvent of benzene, an alcohol such as ethanol, and water; and a mixed solvent of ether such as ethyleneglycoldimethylether and water. Use of a mixed solvent of toluene and water or a mixed solvent of toluene, ethanol and water is more preferable.

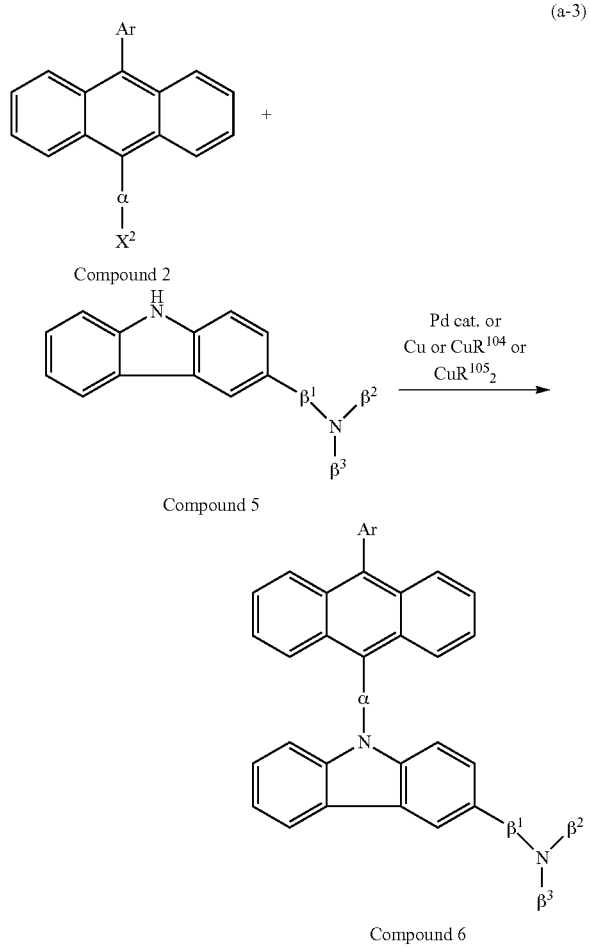

Then, 9-(aryl halide)-10-arylanthracene (compound 2), which is obtained by the synthesis scheme (a-1), and a carbazole (compound 5) compound in which the 3-position is substituted with triarylamine are coupled by a Buchwald-Hartwig reaction using a palladium catalyst or an Ullmann reaction using copper or a copper compound; thus, compound 6 which is one of the anthracene derivatives of the present invention can be obtained. In the case where a Buchwald-Hartwig reaction is performed in a synthesis scheme (a-3), examples of the palladium catalyst that can be used in the synthesis scheme (a-3) include, but are not limited to, bis(dibenzylideneacetone)palladium(0) and palladium(II) acetate. Examples of a ligand in the palladium catalyst, which can be used in the synthesis scheme (a-3), include, but are not limited to, tri(tert-butyl)phosphine, tri(n-hexyl)phosphine, and tricyclohexylphosphine. Examples of a base that can be used in the synthesis scheme (a-3) include, but are not limited to, an organic base such as sodium tert-butoxide and an inorganic base such as potassium carbonate. Examples of a solvent that can be used in the synthesis scheme (a-3) include, but are not limited to, toluene, xylene, benzene, tetrahydrofuran. The case in which an Ullmann reaction is performed in a synthesis scheme (a-3) is described. In the synthesis scheme (a-3), $R^{104}$ and $R^{105}$ each represent a halogen, an acetyl group, or the like, and chlorine, bromine, or iodine can be used as the halogen. It is preferred that $R^{104}$ be iodine to form copper(I) iodide or that $R^{105}$ be an acetyl group to form a copper(II) acetate. The copper compound used for the reaction is not limited to these, and copper can be used instead of the copper compound. Examples of a base that can be used in the synthesis scheme (a-3) include, but are not limited to, an inorganic base such as potassium carbonate. Examples of a solvent that can be used in the synthesis scheme (a-3) include, but are not limited to, 1,3-dimethyl-3,4,5,6-tetrahydro-2(1H) pyrimidinone (DMPU), toluene, xylene, and benzene. Use of DMPU or xylene which has a high boiling point is preferable because, by an Ullmann reaction, an object can be obtained in a shorter time and at a higher yield when the reaction temperature is greater than or equal to 100° C. Since it is further preferable that the reaction temperature be a temperature greater than or equal to 150° C., DMPU is more preferably used. In the formula, Ar represents an aryl group having 6 to 25 carbon atoms; α represents an arylene group having 6 to 25 carbon atoms; $X^2$ represents a halogen; and $β^1$ to $β^3$ each represent a substituted or unsubstituted benzene ring. It is to be noted that the "compound 6" is a compound formed under conditions in which, in the above-described general formula (31), A is represented by a general formula (32-1) and B is hydrogen.

Each of the anthracene derivatives of the present invention have a high quantum yield, and emit blue to blue green light. Therefore, each of the anthracene derivatives of the present invention is suitable for use in a light-emitting element. Also, since the anthracene derivatives of the present invention are stable with respect to repetitive redox reactions, a light-emitting element that use any of the anthracene derivatives of the present invention can be made to have a long life.

(Embodiment Mode 2)

In this embodiment mode, organic compounds that are materials used for the synthesis of the anthracene derivatives of the present invention are described. These organic compounds are novel materials and are thus included as one aspect of the present invention.

The above organic compounds are any of the organic compounds represented by general formulae (149-1), (150-1), and (151-1).

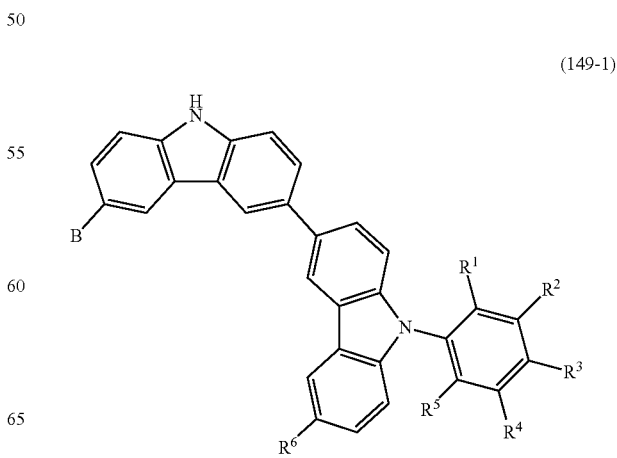

(149-2)

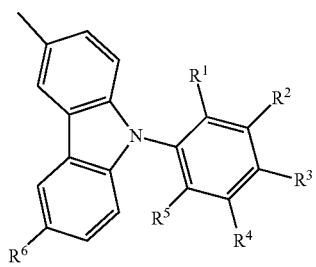

(150-1)

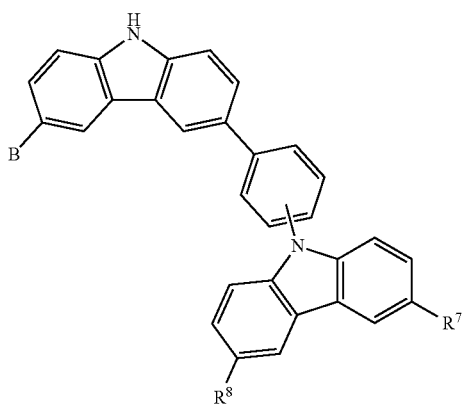

(150-2)

(151-1)

(151-2)

In the above general formula (149-1), $R^1$ to $R^6$ each represent any of hydrogen, an alkyl group having 1 to 4 carbon atoms, a halogen group, a haloalkyl group, and an aryl group having 6 to 25 carbon atoms and may be the same or different from one another; and B represents any of hydrogen, an alkyl group having 1 to 4 carbon atoms, an aryl group having 6 to 25 carbon atoms, a halogen group, and a halo alkyl group or is represented by the above structural formula (149-2). In the structural formula (149-2), $R^1$ to $R^6$ each represent any of hydrogen, an alkyl group having 1 to 4 carbon atoms, a halogen group, a haloalkyl group, and an aryl group having 6 to 25 carbon atoms and may be the same or different from one another.

In the general formula (150-1), $R^7$ and $R^8$ each represent any of hydrogen, an alkyl group having 1 to 4 carbon atoms, a halogen group, a haloalkyl group, and an aryl group having 6 to 25 carbon atoms and may be the same or different from one another; and B represents any of hydrogen, an alkyl group having 1 to 4 carbon atoms, an aryl group having 6 to 25 carbon atoms, a halogen group, and a haloalkyl group or is represented by the above structural formula (150-2). In the above structural formula (150-2), $R^7$ and $R^8$ each represent any of hydrogen, an alkyl group having 1 to 4 carbon atoms, a halogen group, a haloalkyl group, and an aryl group having 6 to 25 carbon atoms and may be the same or different from one another.

In the general formula (151-1), $R^{30}$ to $R^{39}$ each represent any of hydrogen, an alkyl group having 1 to 4 carbon atoms, a halogen group, a haloalkyl group, and an aryl group having 6 to 25 carbon atoms and may be the same or different from one another; and B represents any of hydrogen, an alkyl group having 1 to 4 carbon atoms, an aryl group having 6 to 25 carbon atoms, a halogen group, and a haloalkyl group or is represented by the above structural formula (151-2). In the structural formula (151-2), $R^{30}$ to $R^{39}$ each represent any of hydrogen, an alkyl group having 1 to 4 carbon atoms, a halogen group, a haloalkyl group, and an aryl group having 6 to 25 carbon atoms and may be the same or different from one another.

Specific examples of the above organic compounds include organic compounds represented by structural formulae (501) to (802). However, it is to be noted that the present invention is not limited to these.

(501)
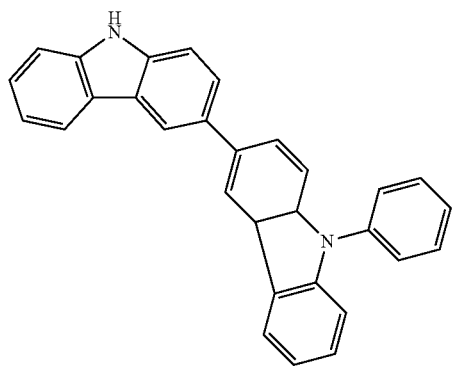
(502)
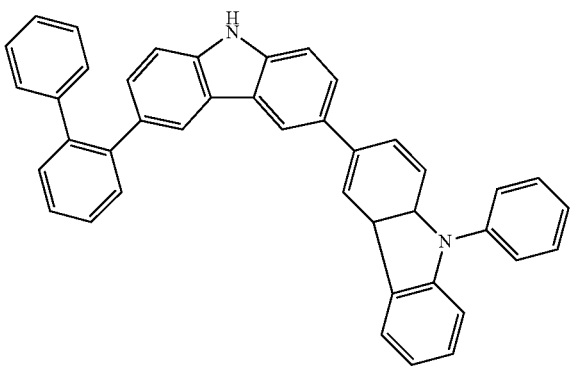
(503)
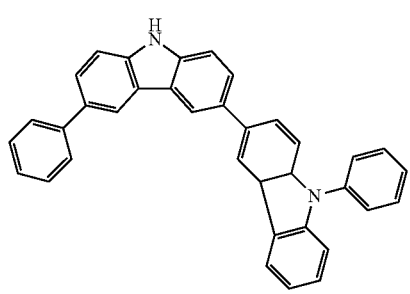
(504)
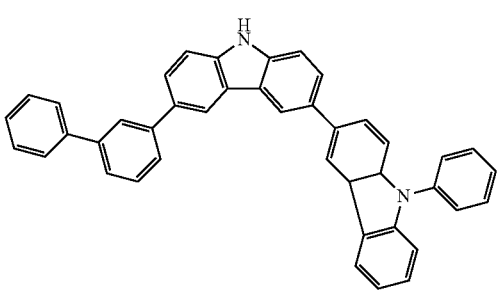
(505)
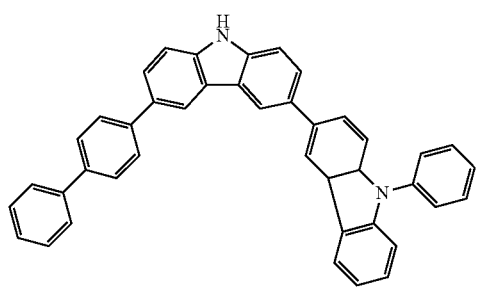
(506)
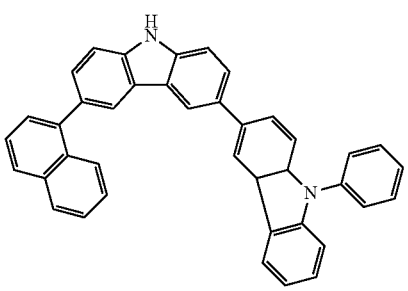
(507)
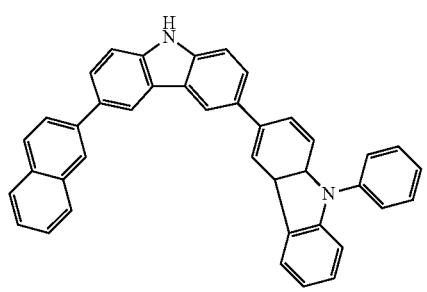
(508)
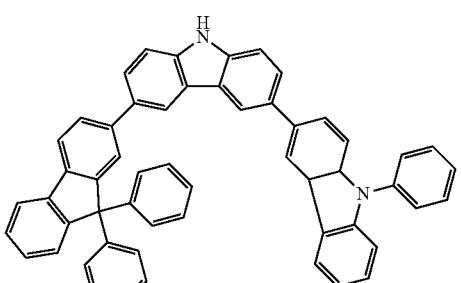
(509)
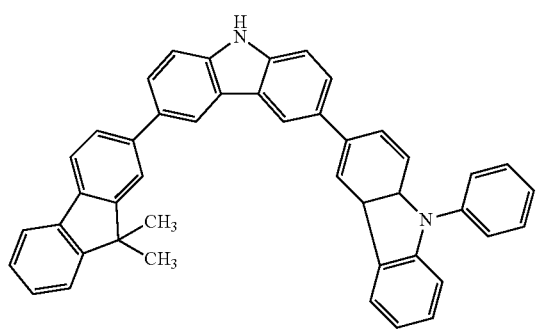
(510)
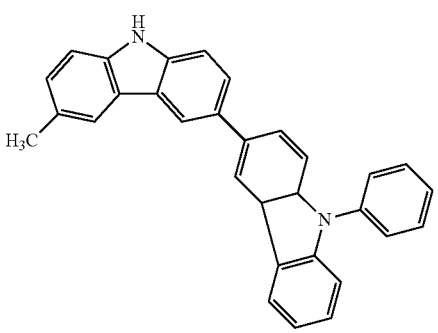

-continued
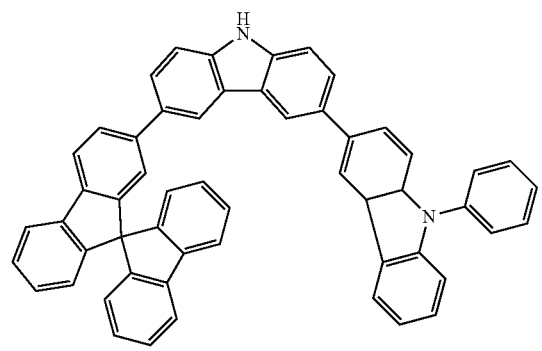
(511)
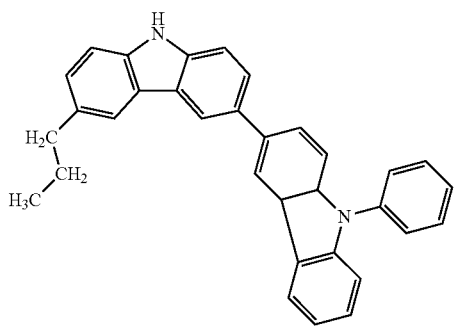
(512)
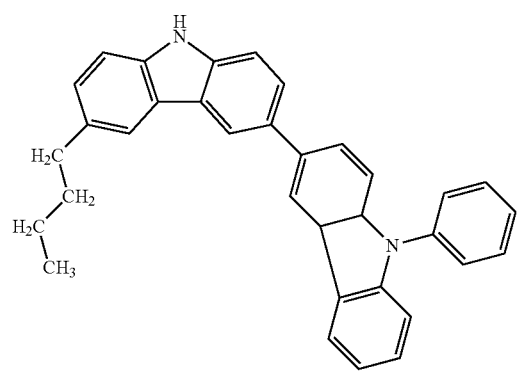
(513)
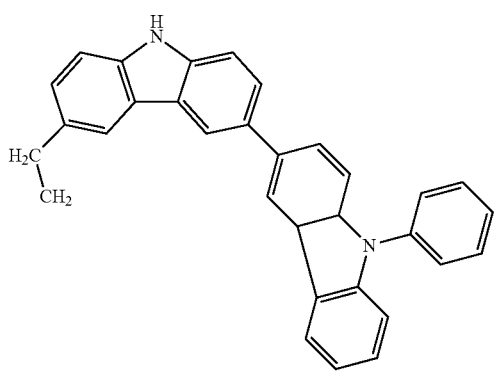
(514)
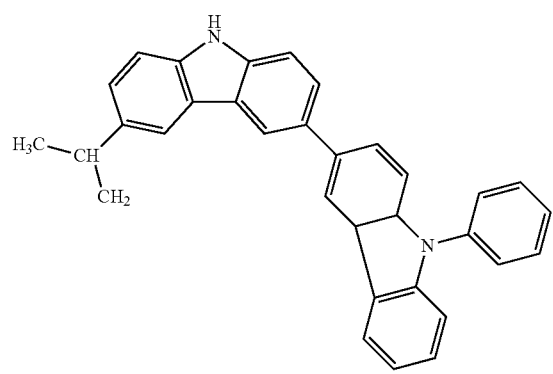
(515)
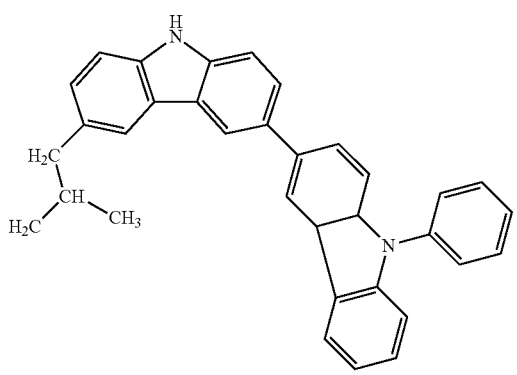
(516)
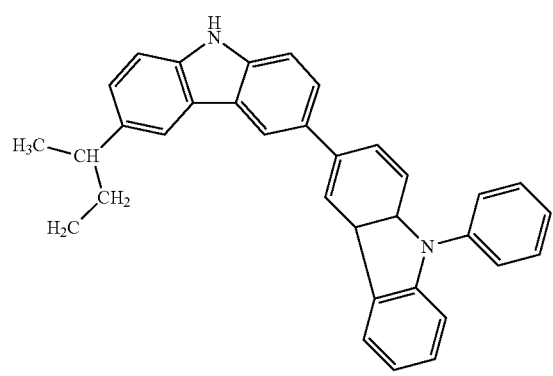
(517)
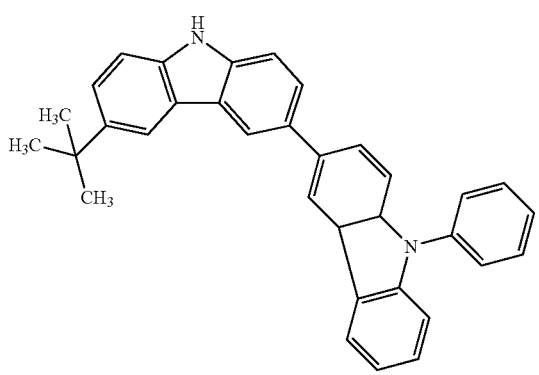
(518)

(519)
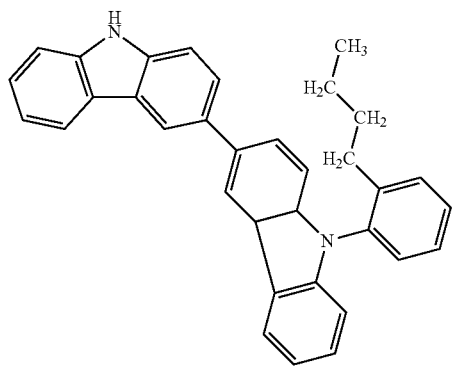
(520)
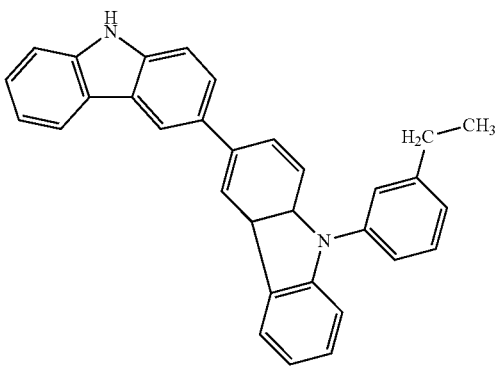
(521)
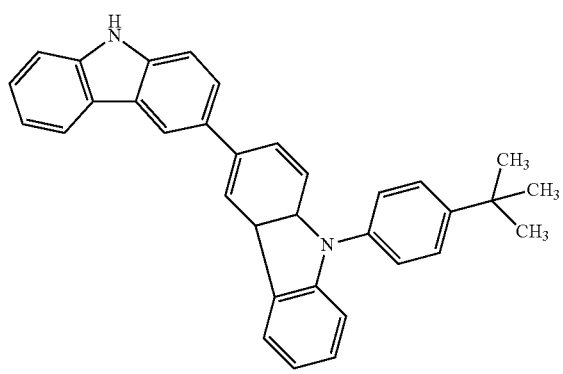
(522)
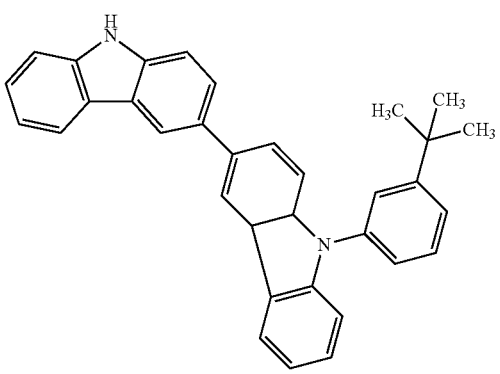
(523)
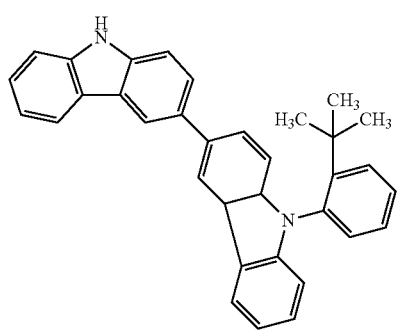
(524)
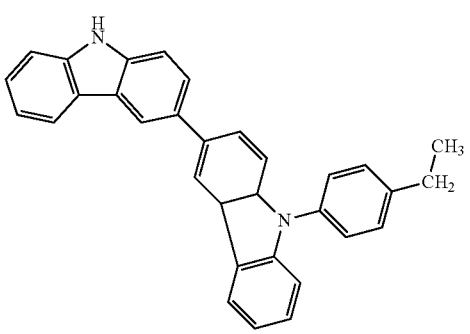
(525)
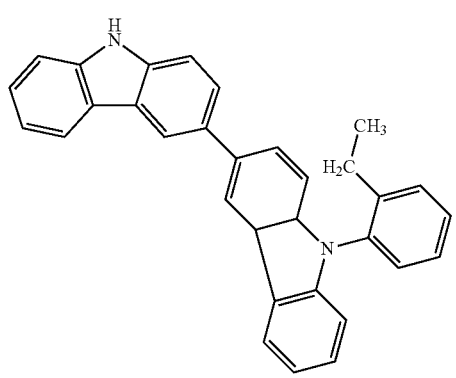
(526)
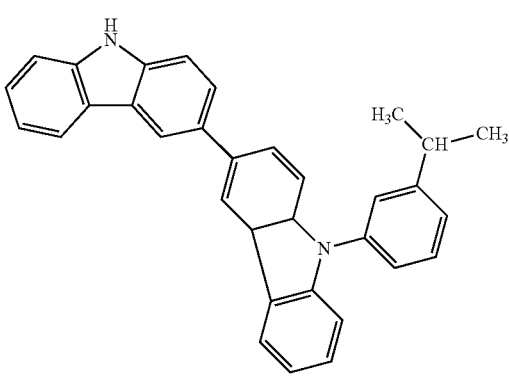

-continued
(527)
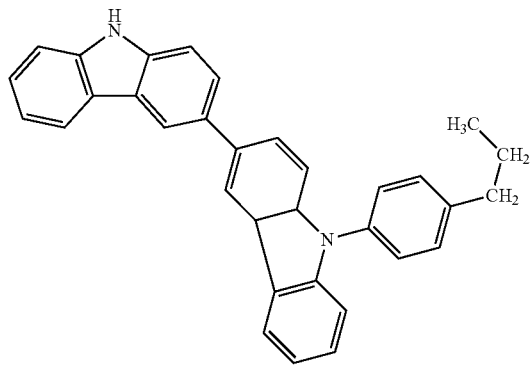
(528)
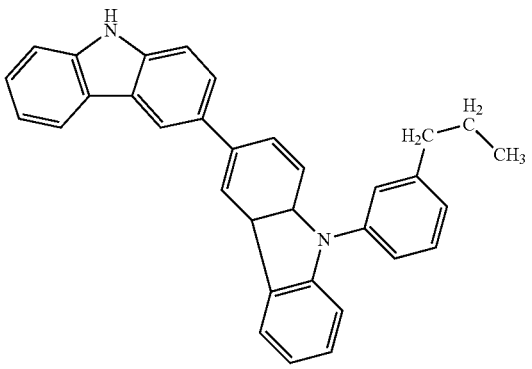
(529)
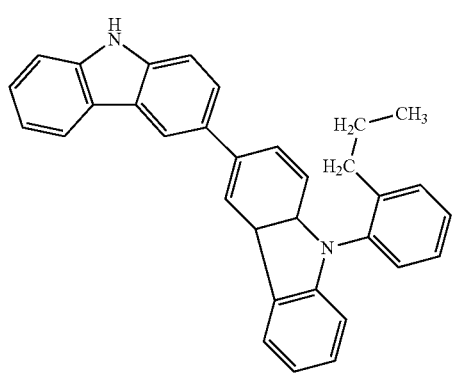
(530)
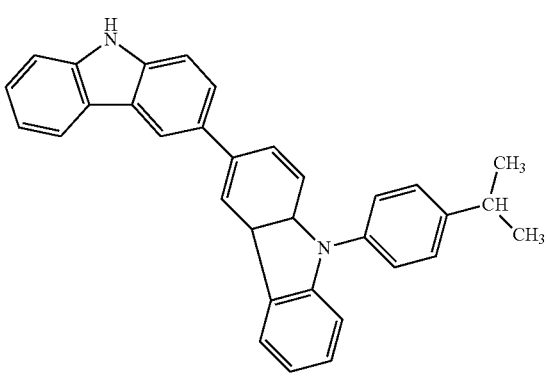
(531)
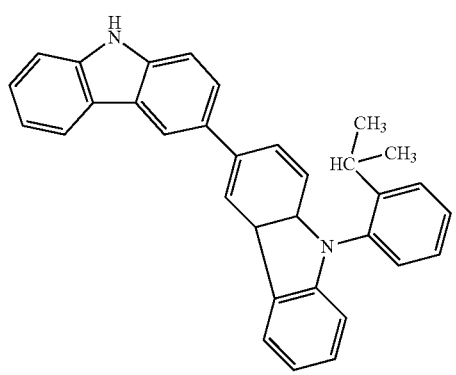
(532)
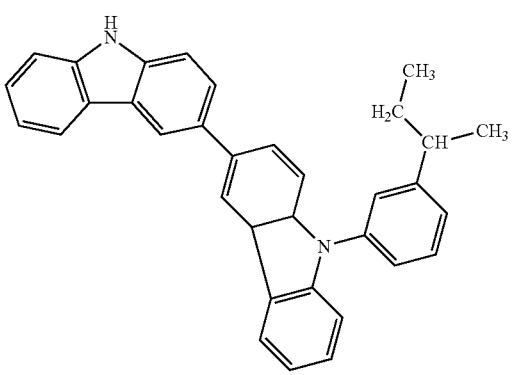
(533)
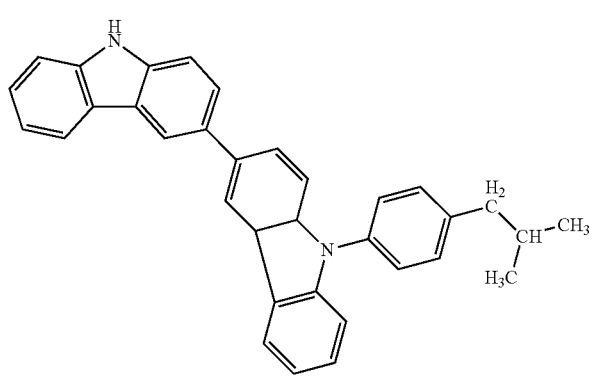
(534)
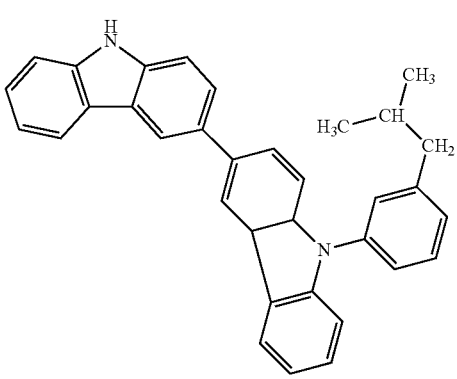

-continued
(535) 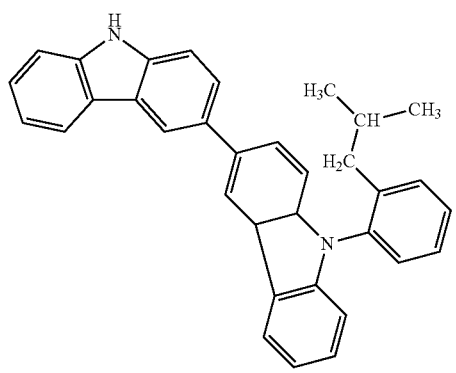
(536) 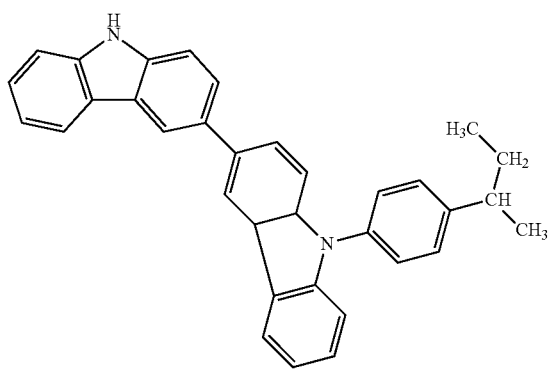
(537) 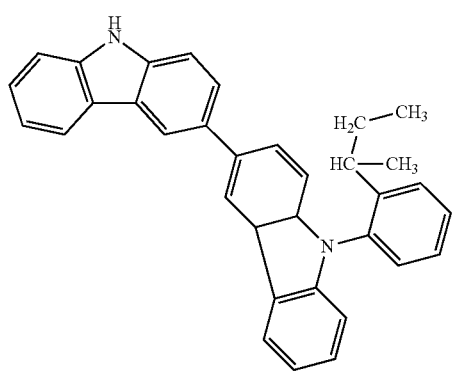
(538) 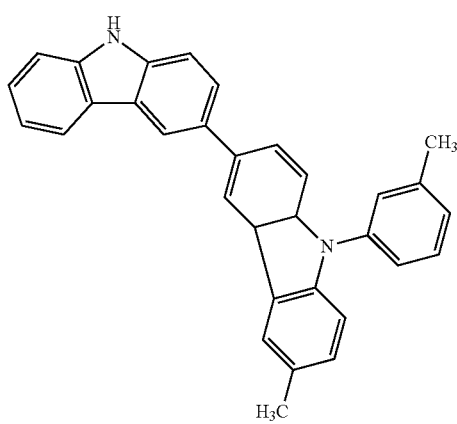
(539) 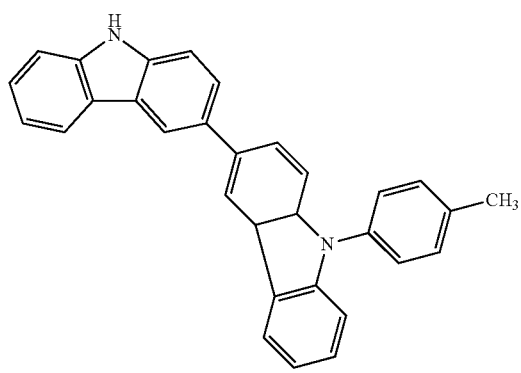
(540) 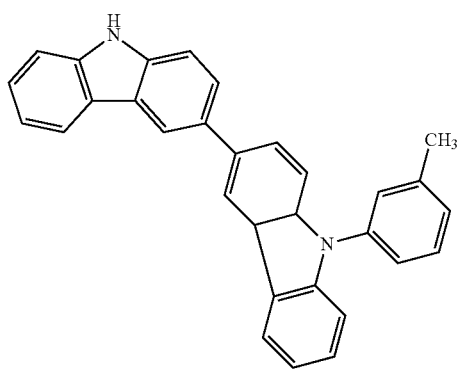
(541) 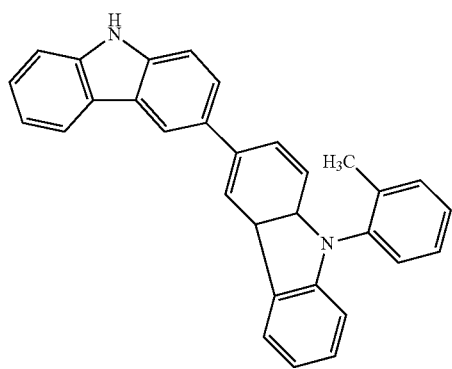
(542) 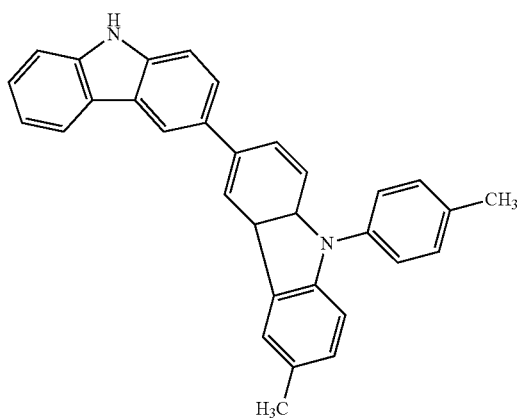

-continued
(543)
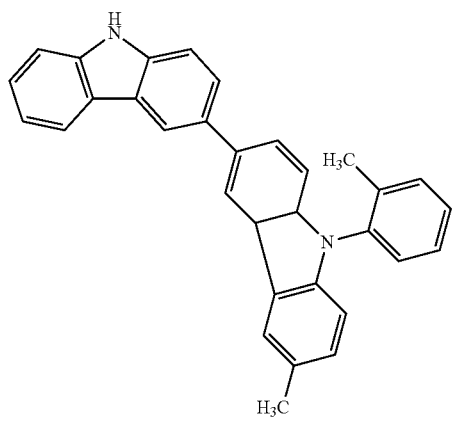
(544)
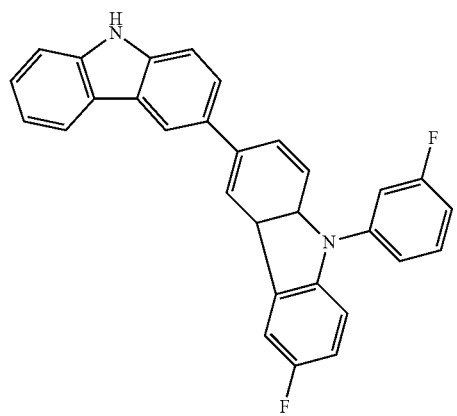
(545)
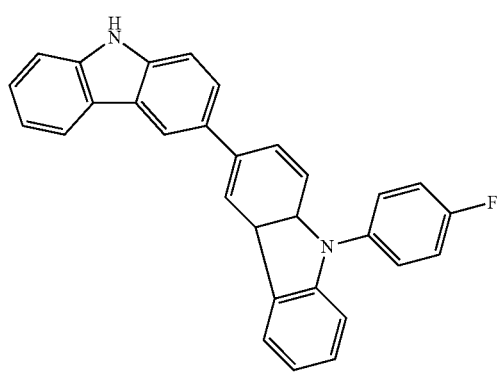
(546)
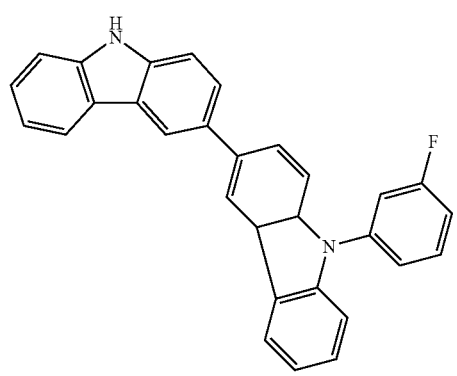
(547)
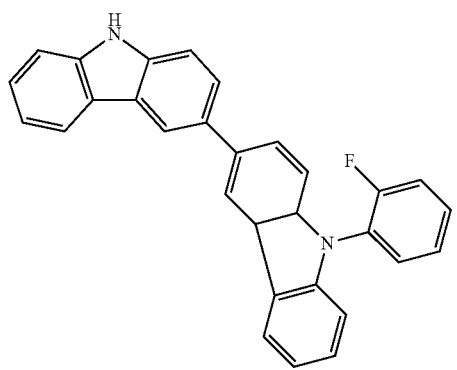
(548)
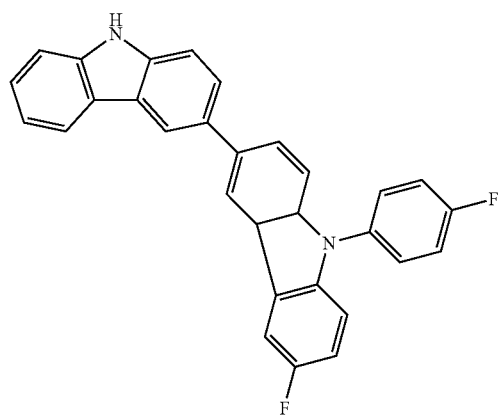
(549)
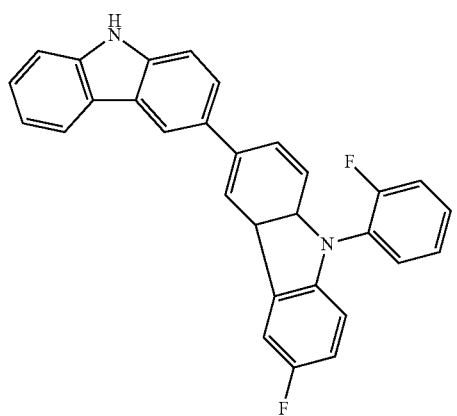
(550)
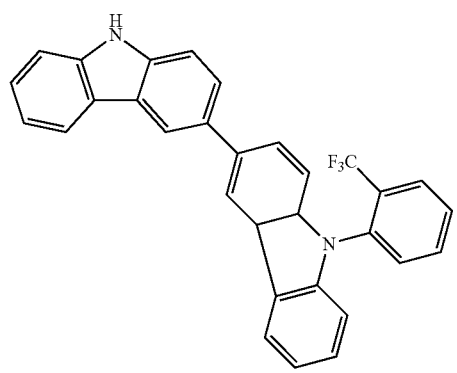

-continued
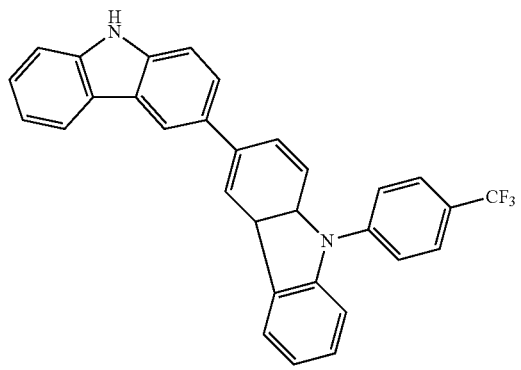
(551)
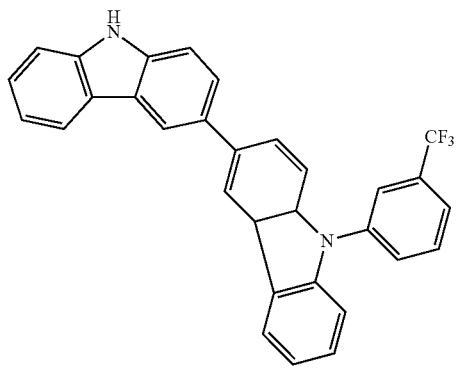
(552)
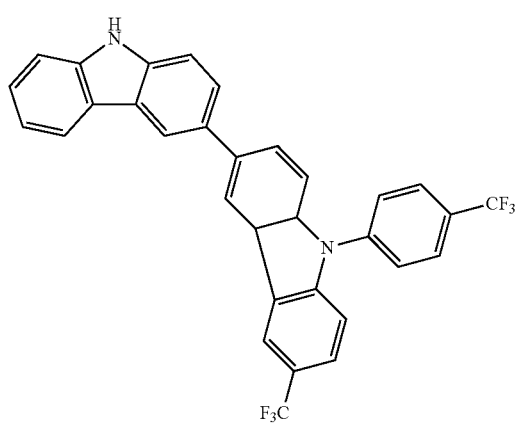
(553)
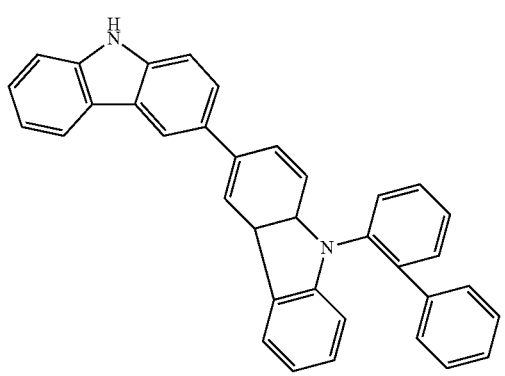
(554)
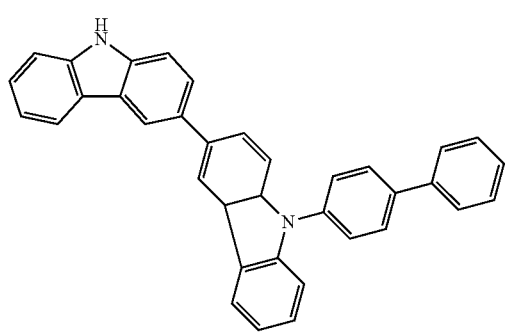
(555)
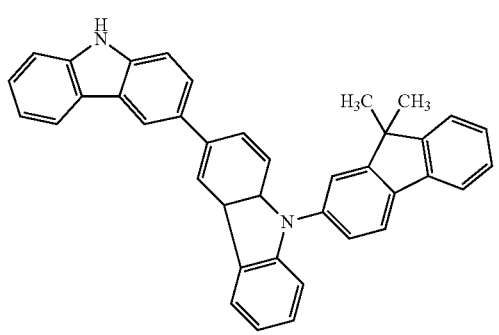
(556)
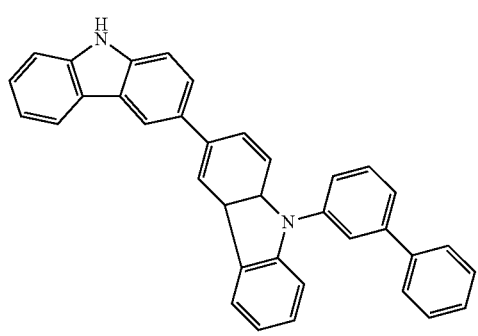
(557)
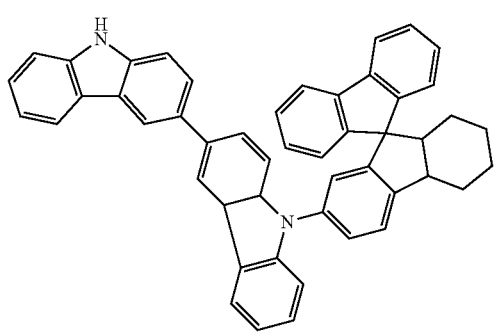
(558)

-continued
(559)
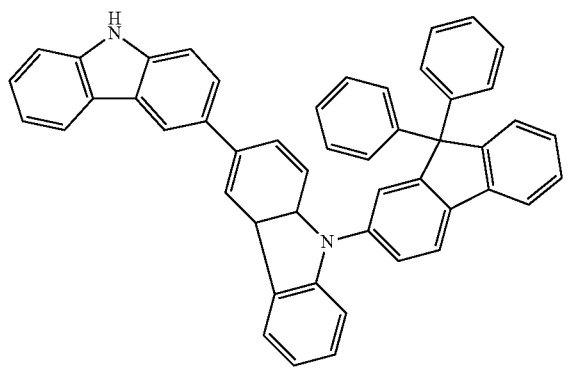
(560)
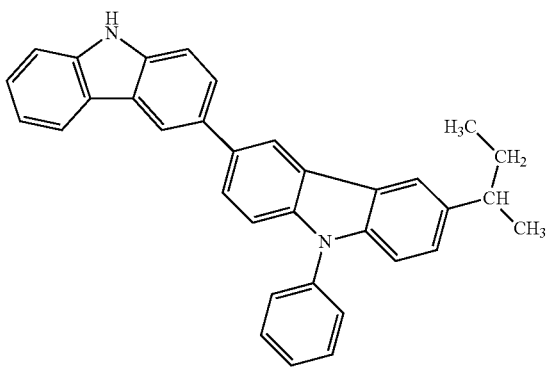
(561)
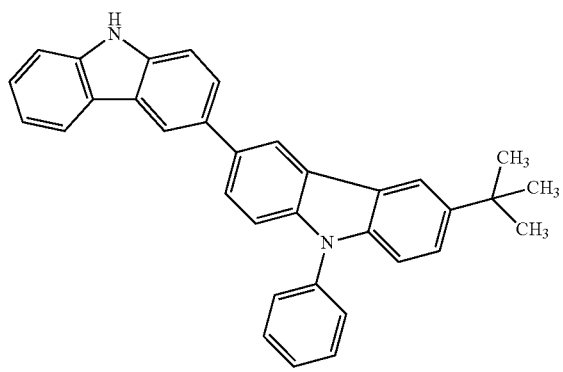
(562)
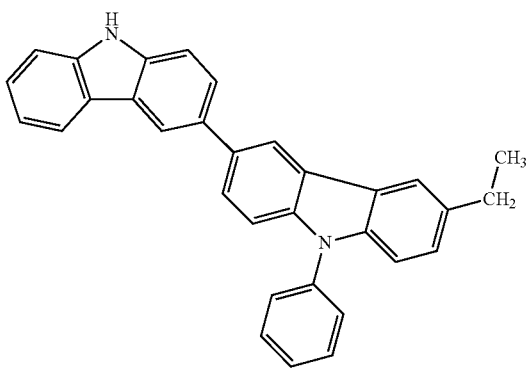
(563)
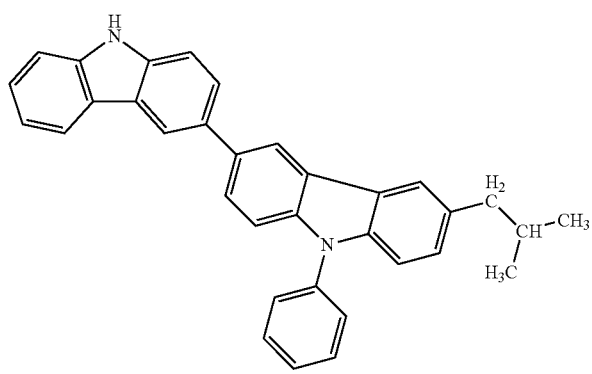
(564)
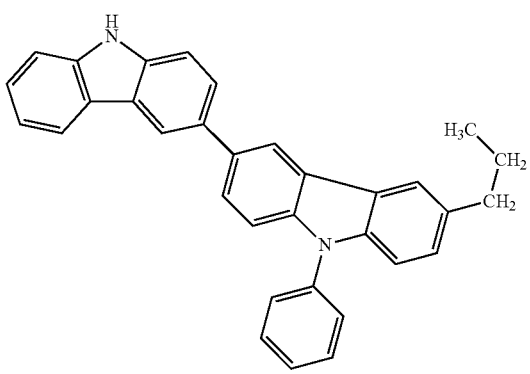
(565)
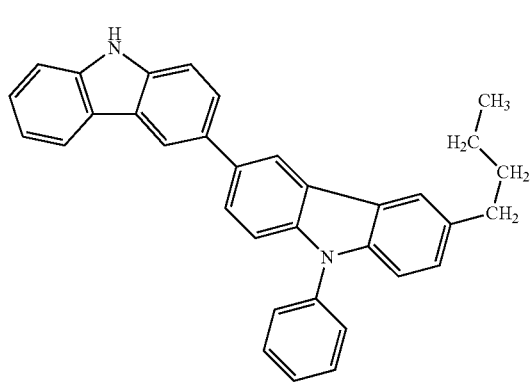
(566)
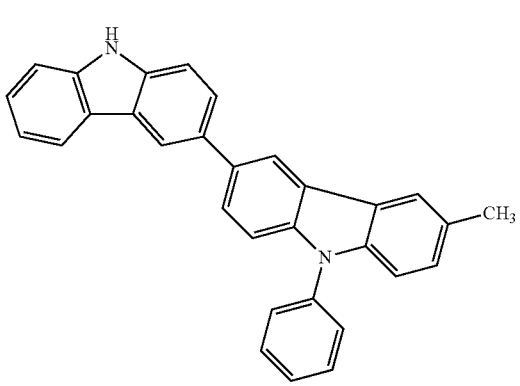

-continued
(567)
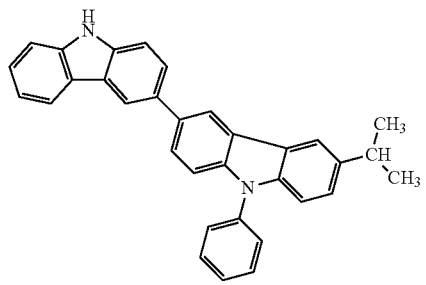
(568)
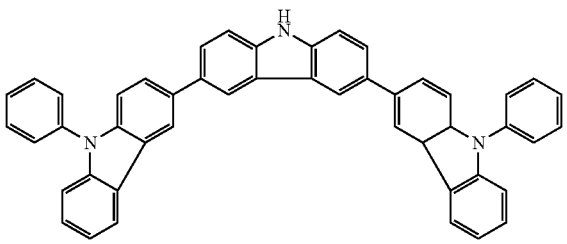
(569)
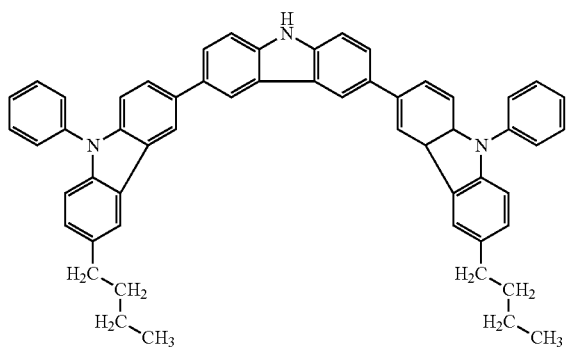
(570)
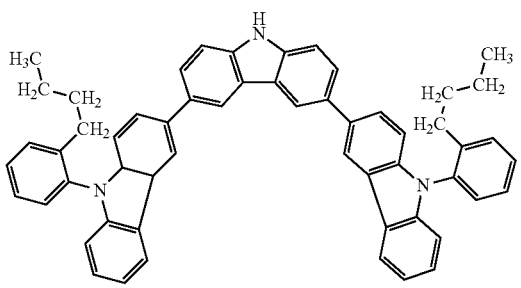
(571)
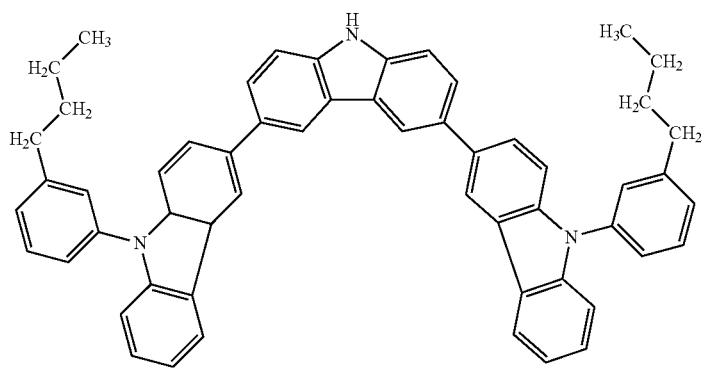
(572)
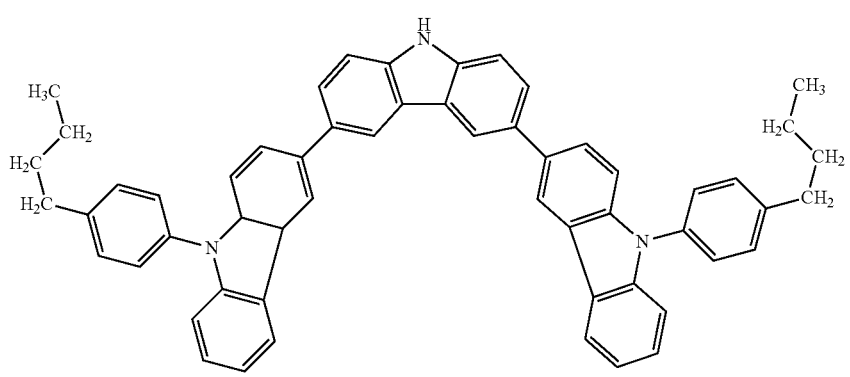

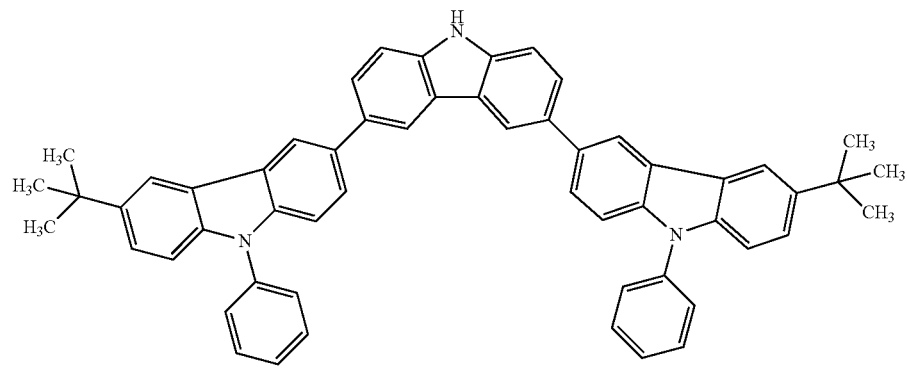
(573)
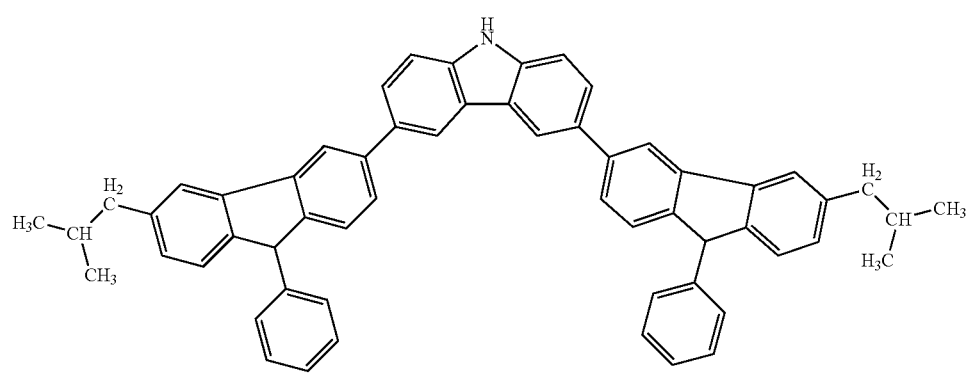
(574)
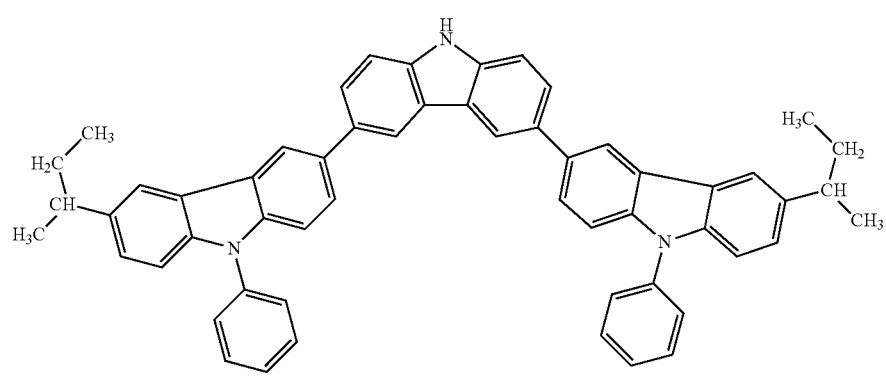
(575)
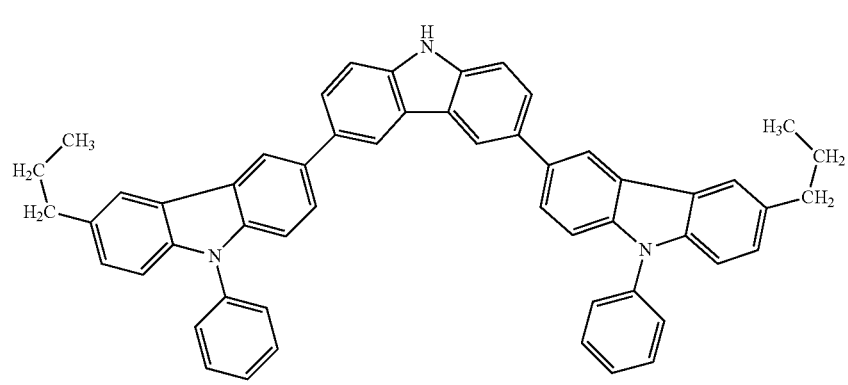
(576)

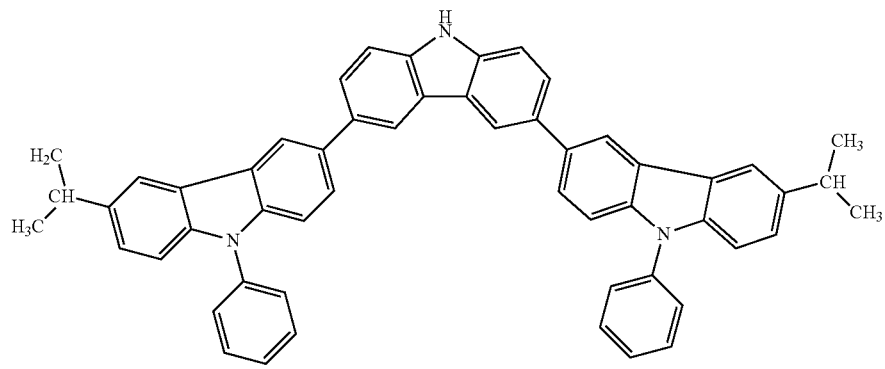
(577)
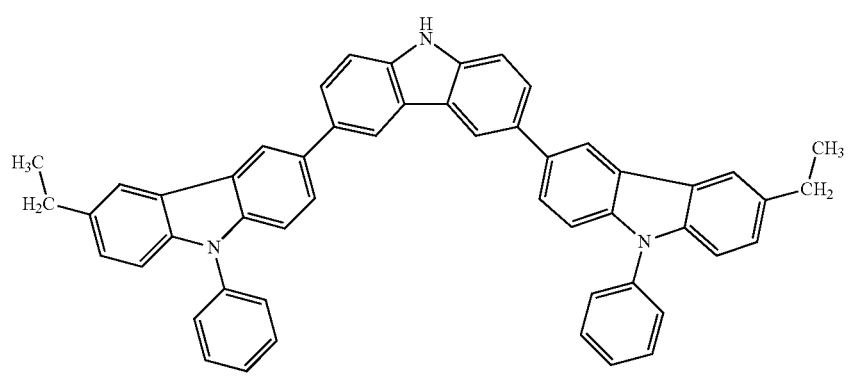
(578)
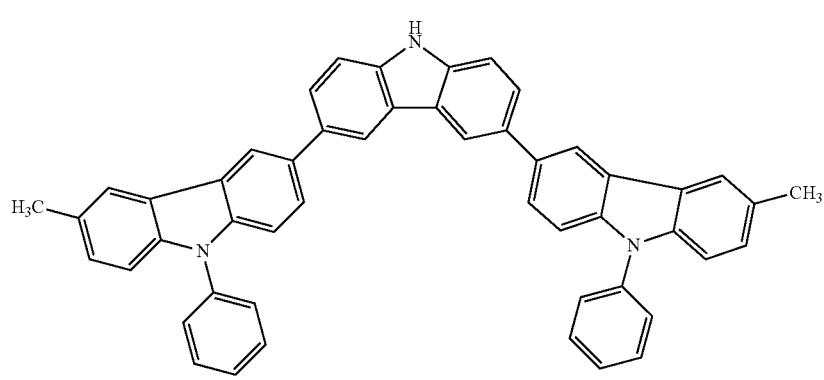
(579)
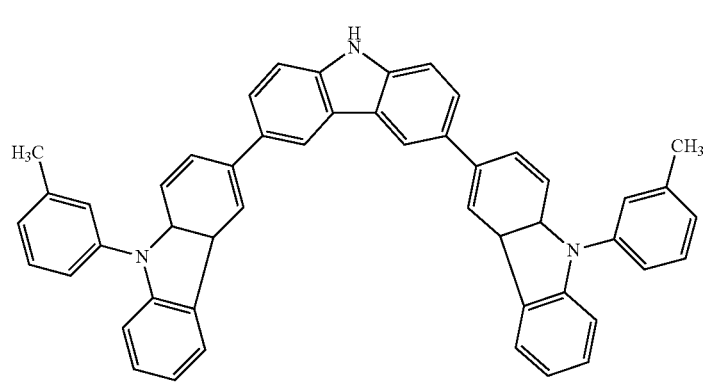
(580)

-continued
(581)
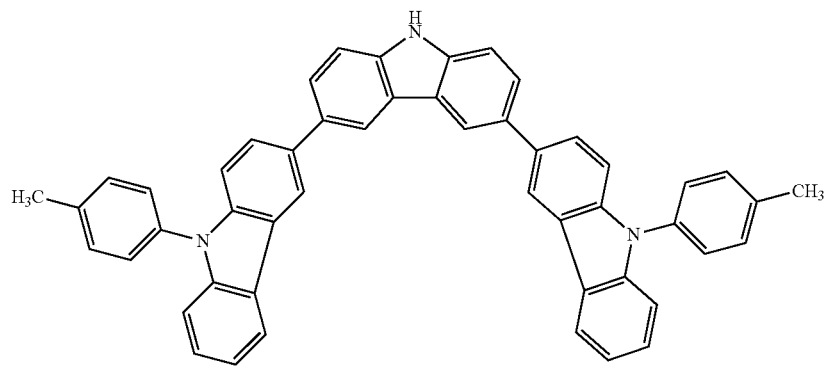
(582)
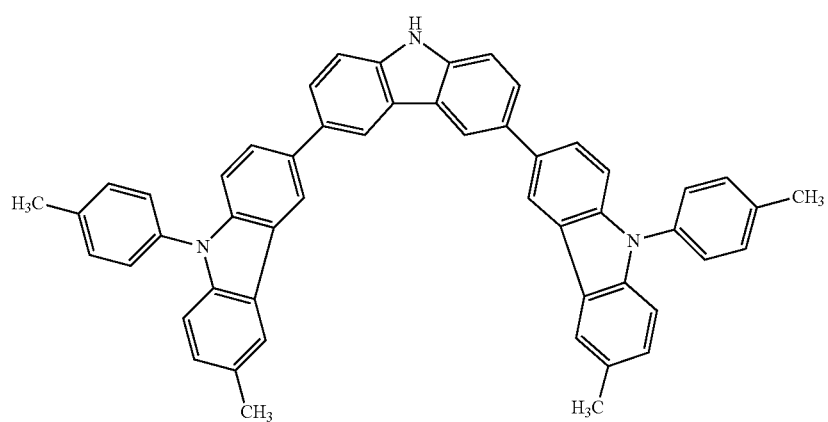
(583)
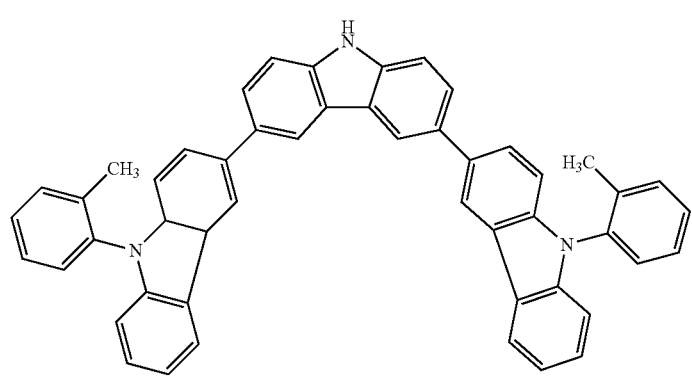
(584)
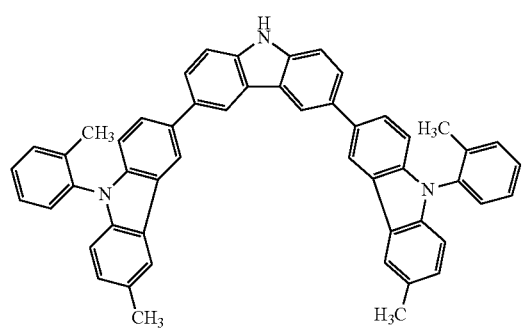
(585)
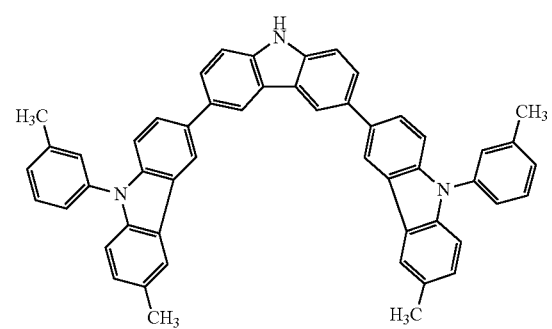

(586)
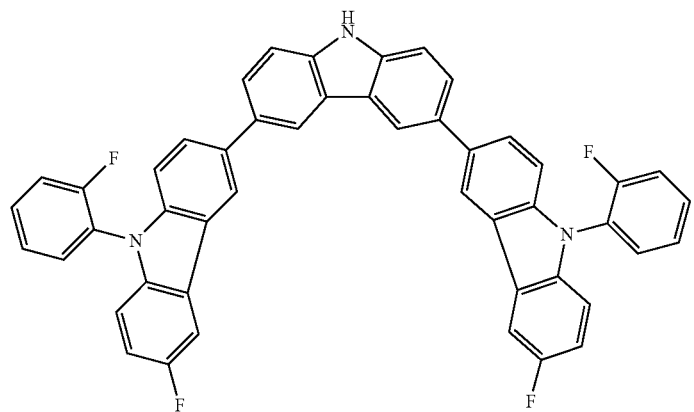
(587)
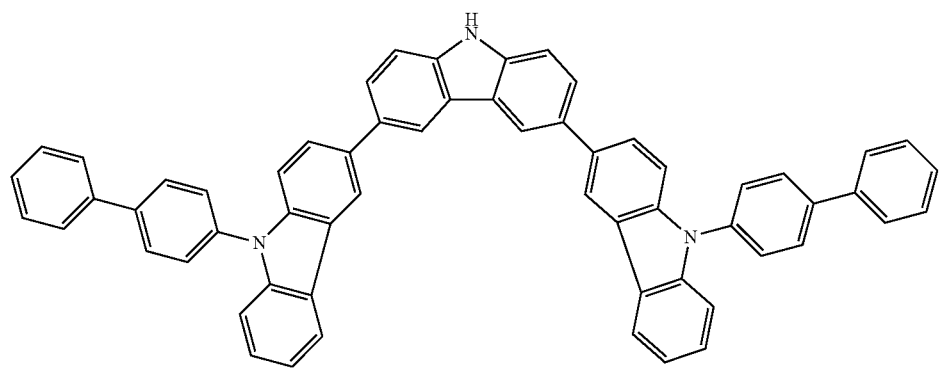
(588)
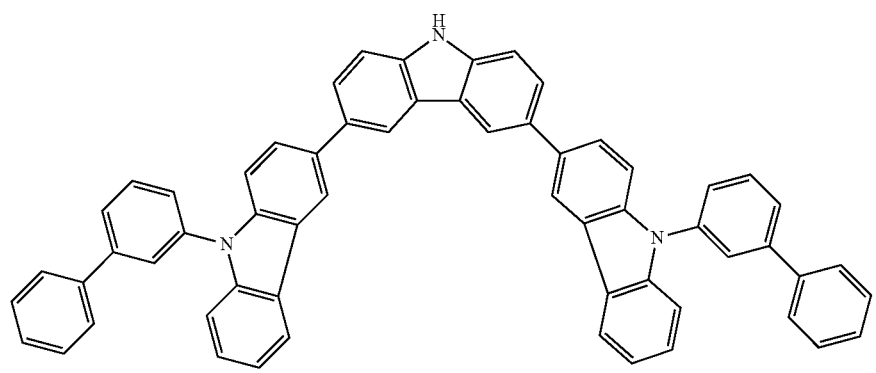
(589)
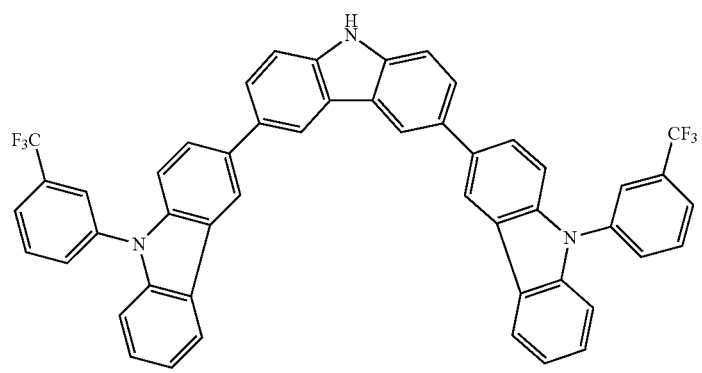

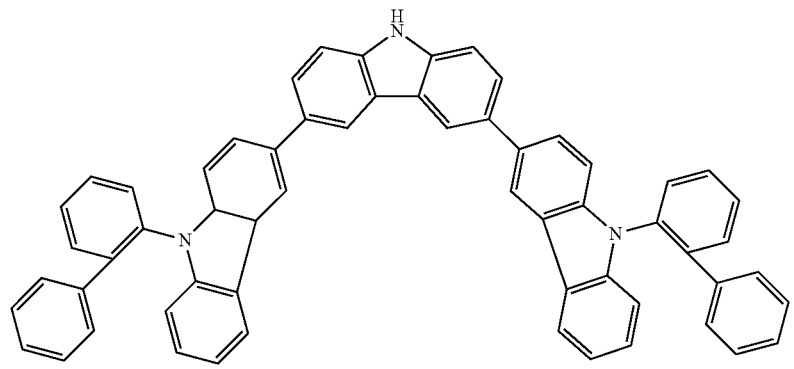
(590)
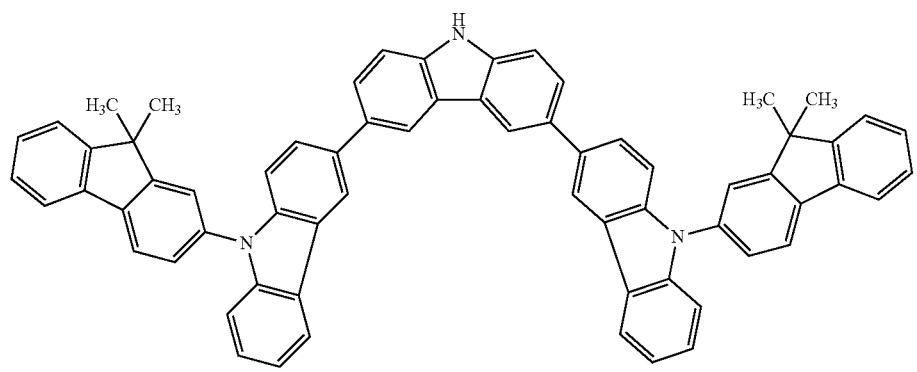
(591)
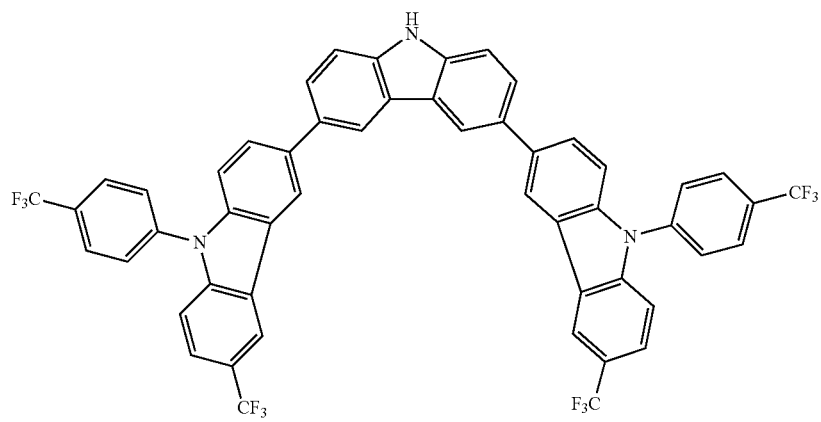
(592)
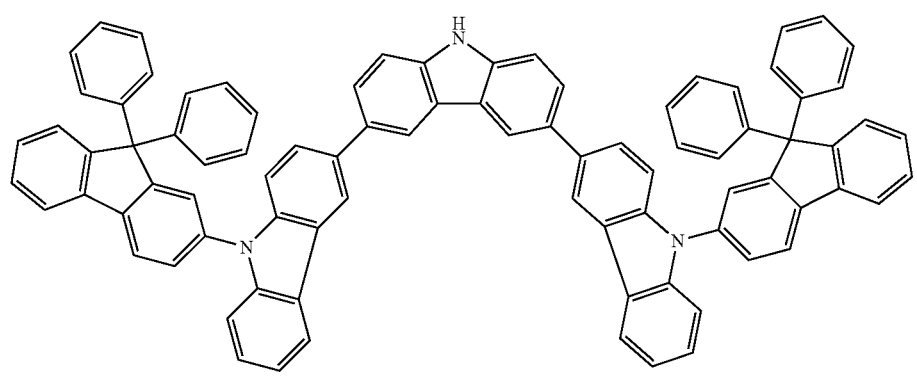
(593)

-continued
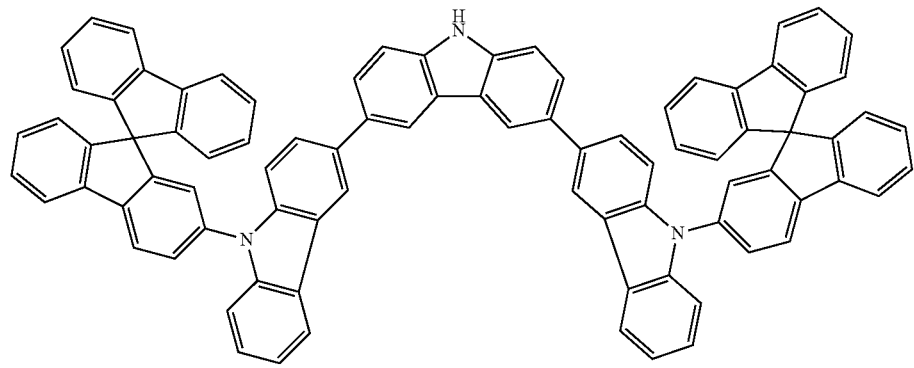
(594)
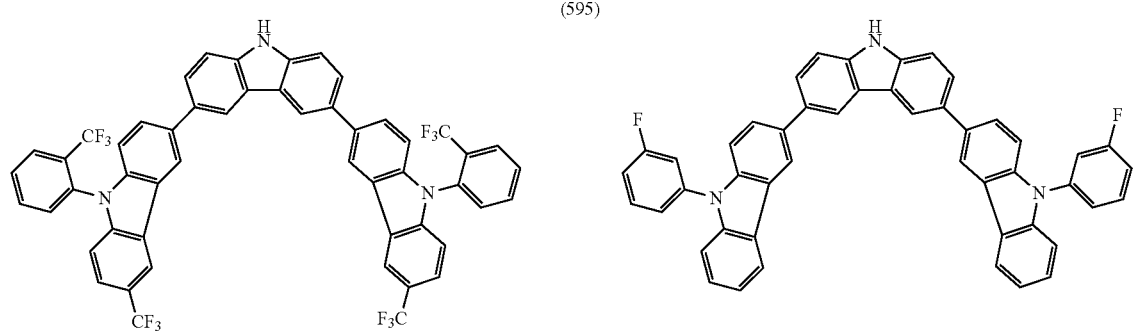
(595) (596)
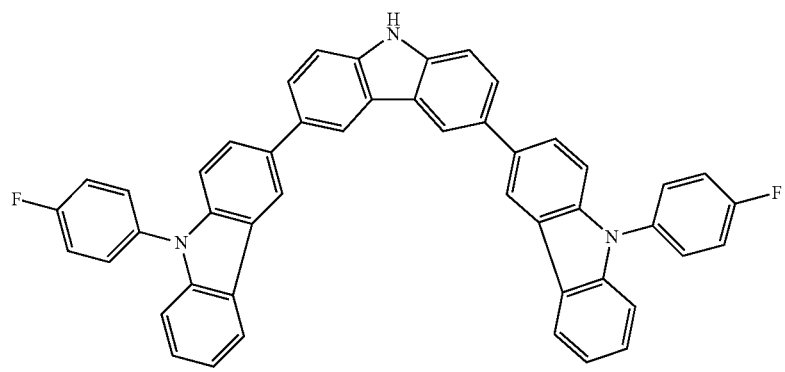
(597)
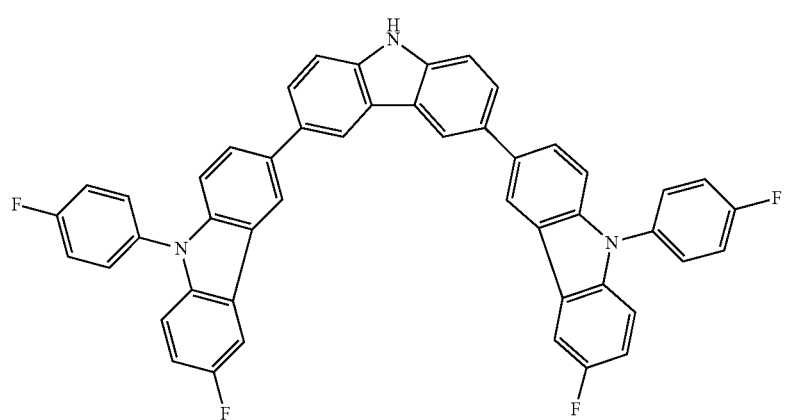
(598)

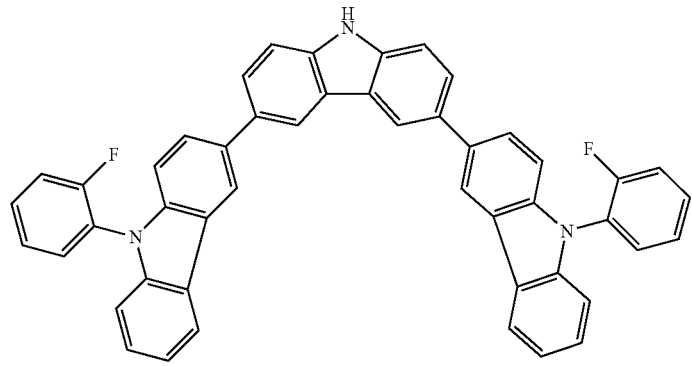
(599)
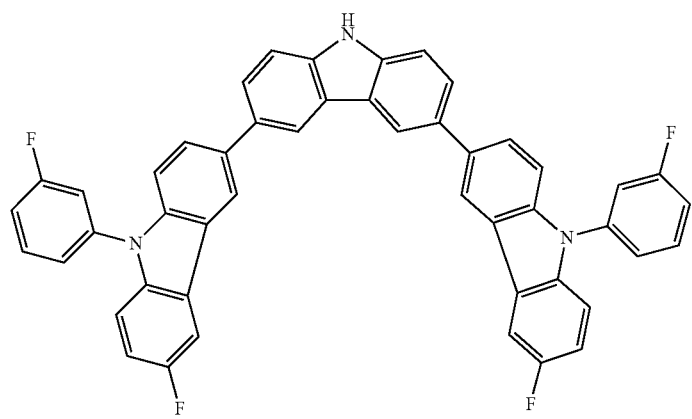
(600)
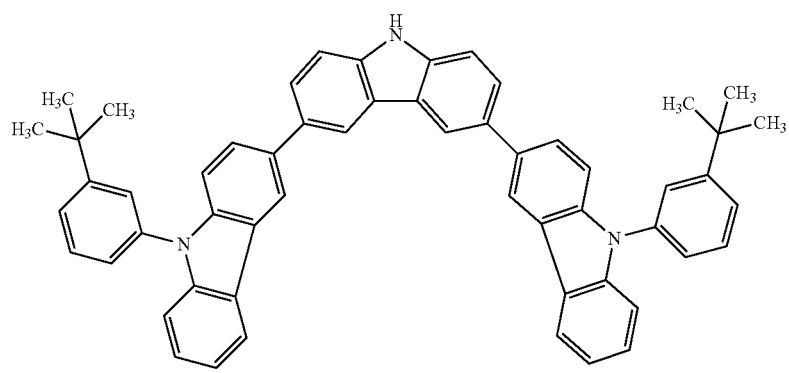
(601)
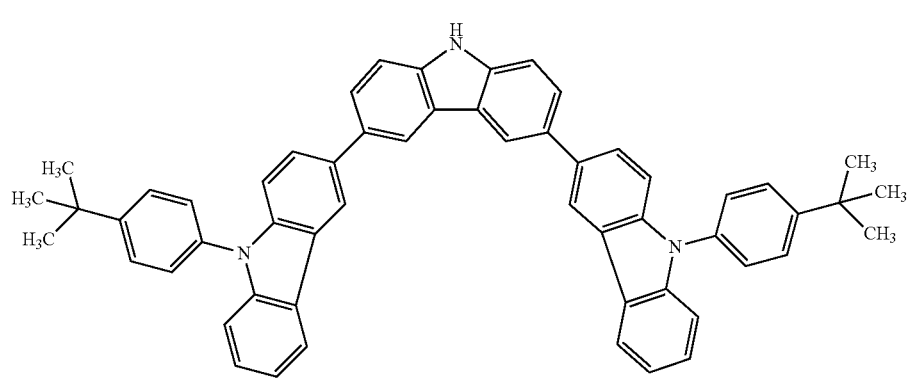
(602)

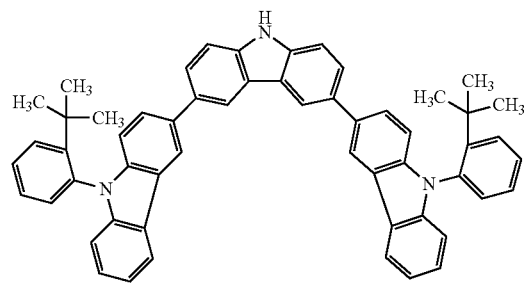 (603)
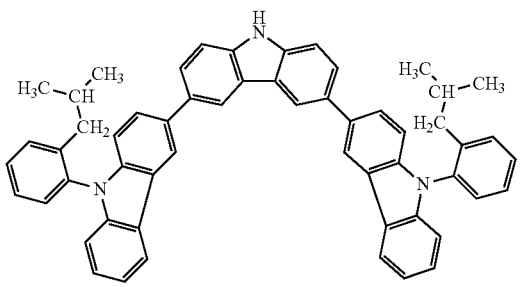 (604)
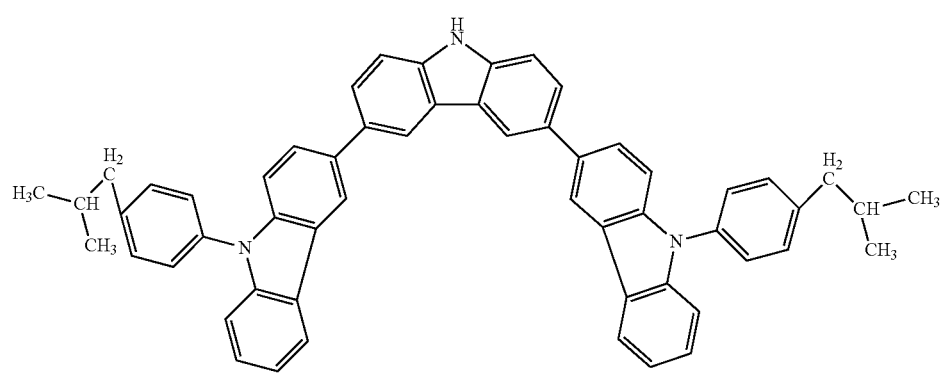 (605)
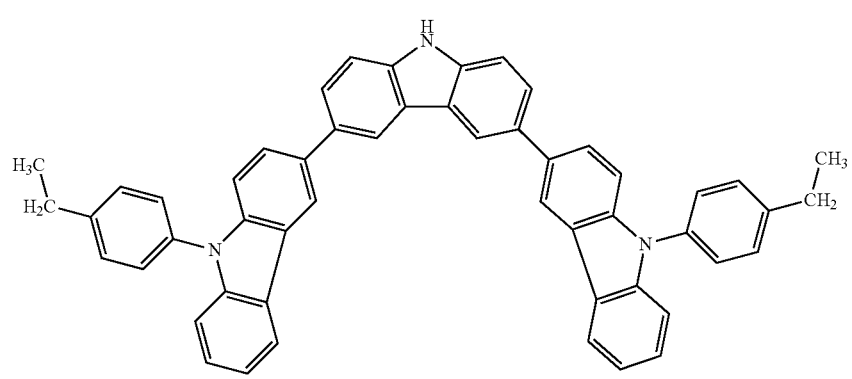 (606)
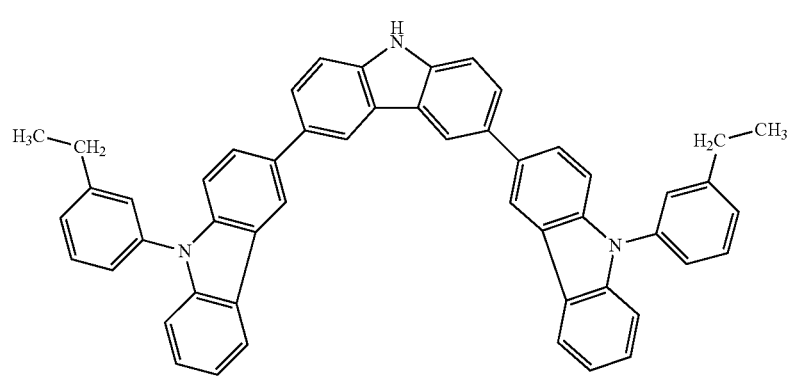 (607)

(608)
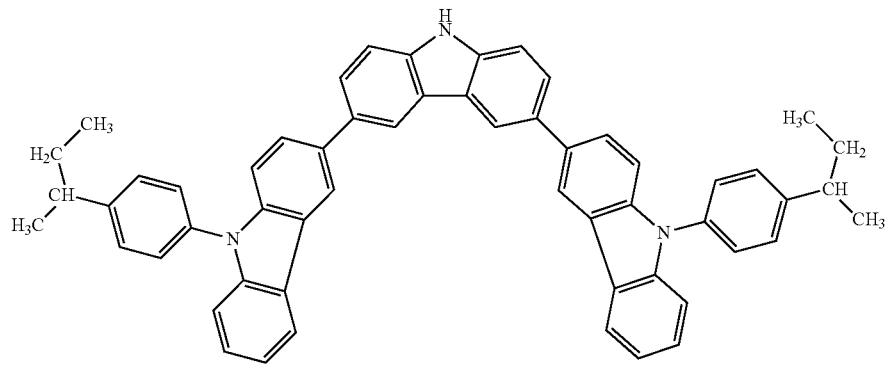
(609)
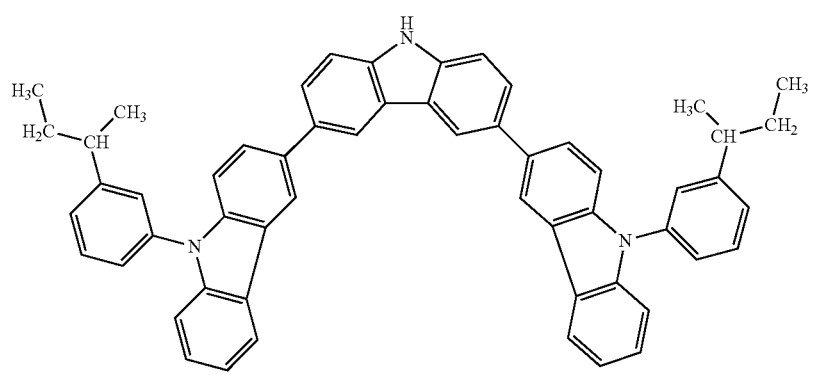
(610)
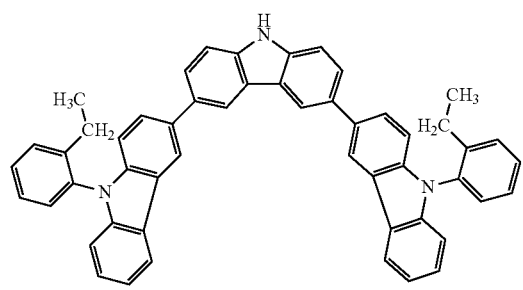
(611)
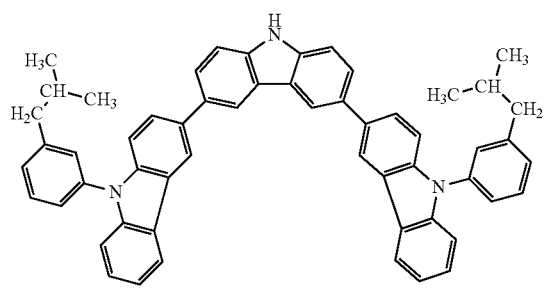
(613)
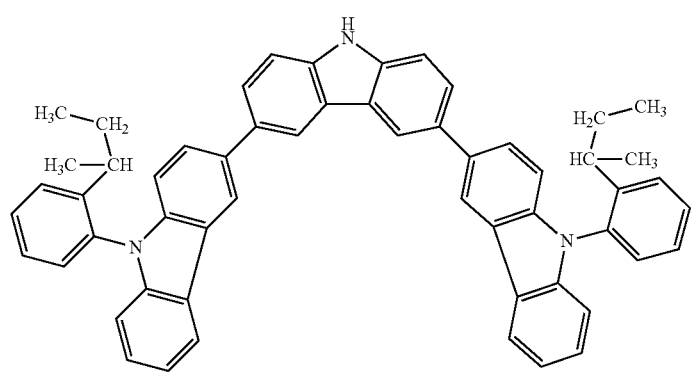

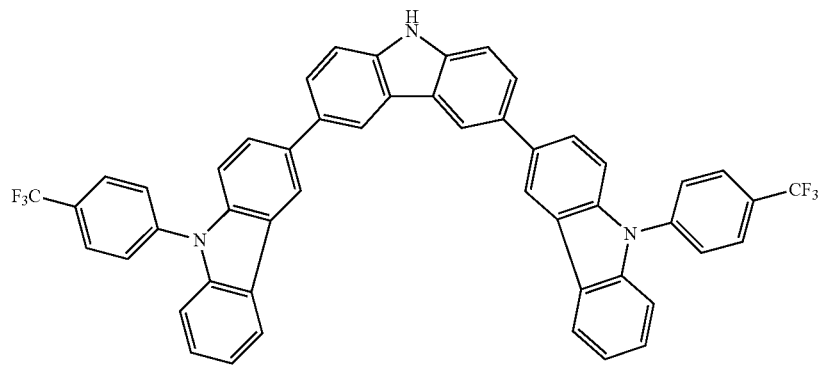
(614)
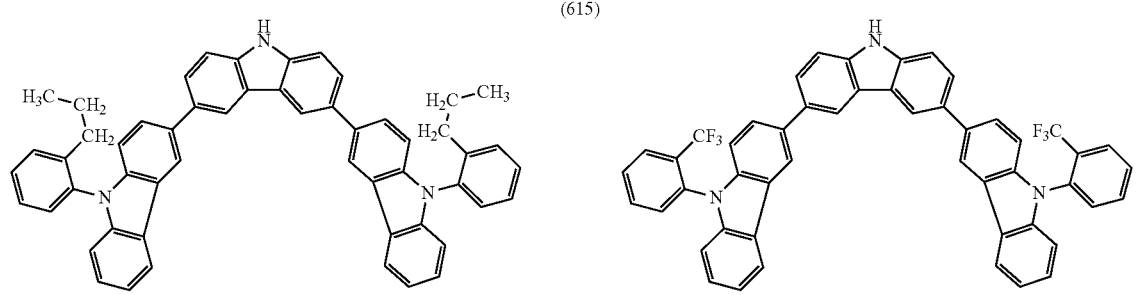
(615) (616)
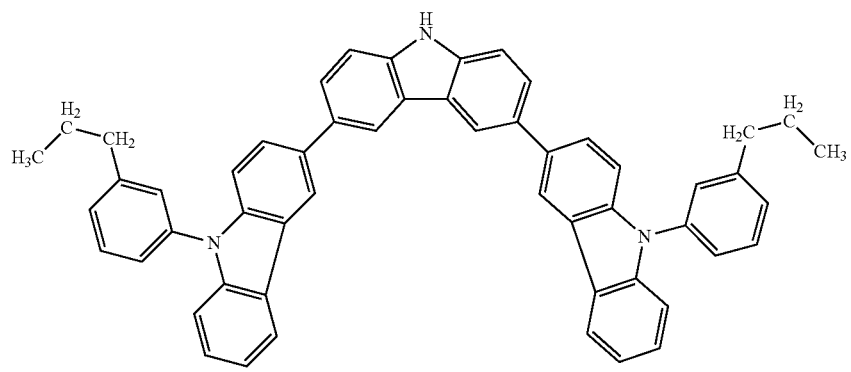
(617)
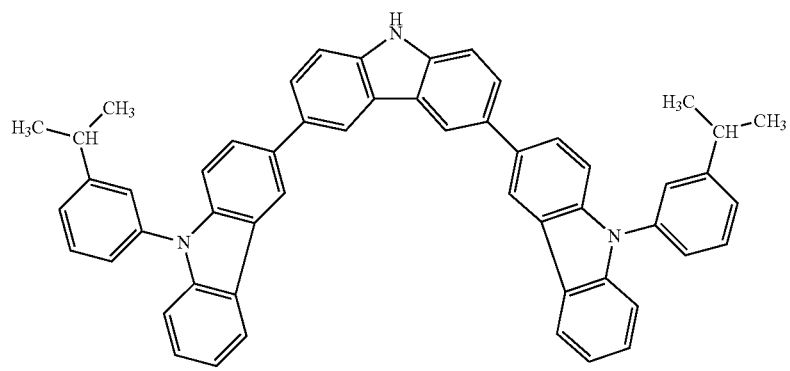
(618)

(619)
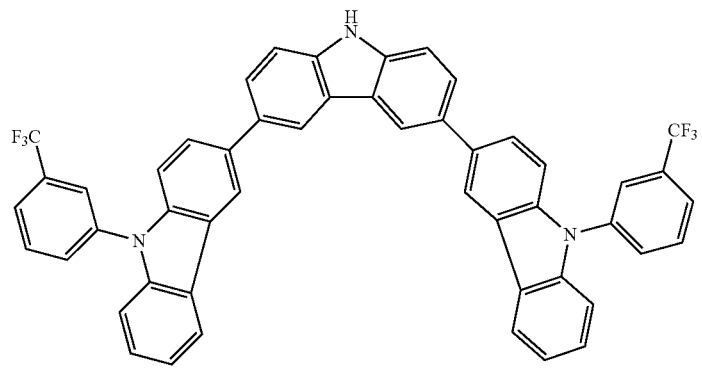
(620)
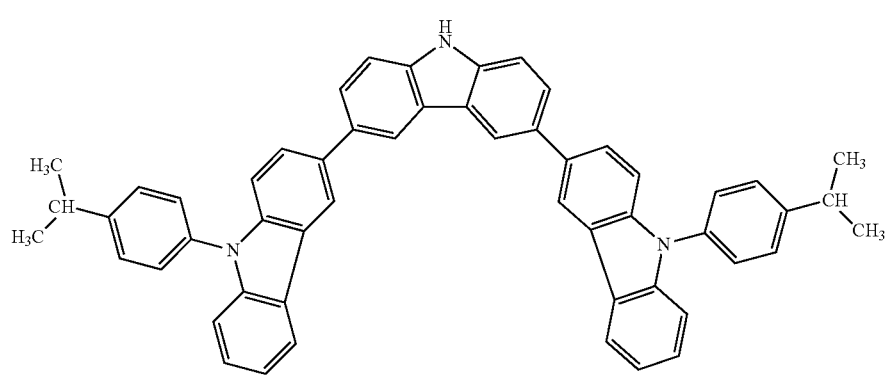
(621)
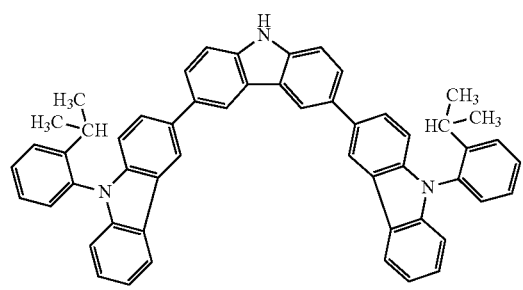
(622)
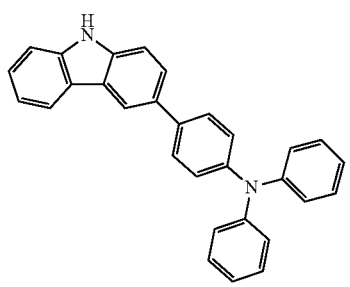
(623)
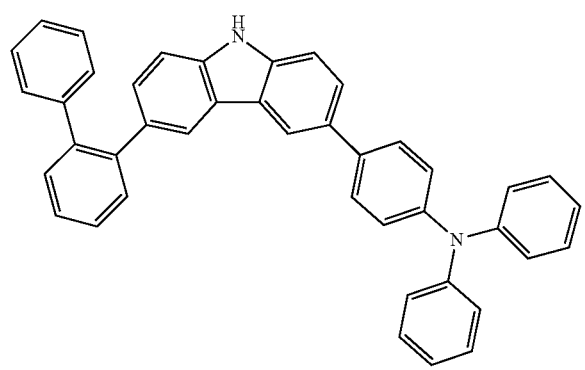
(624)
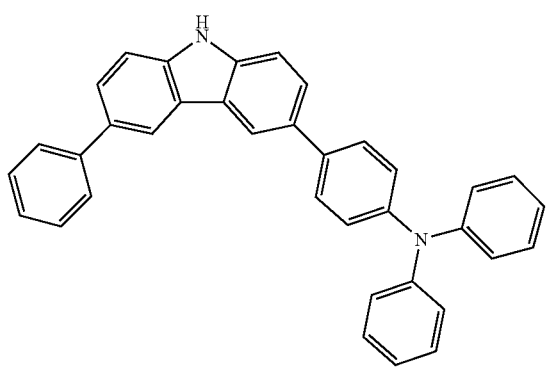

-continued
(625)
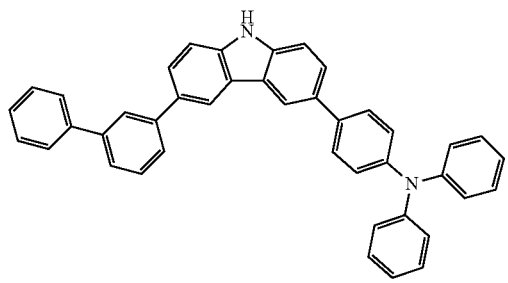
(626)
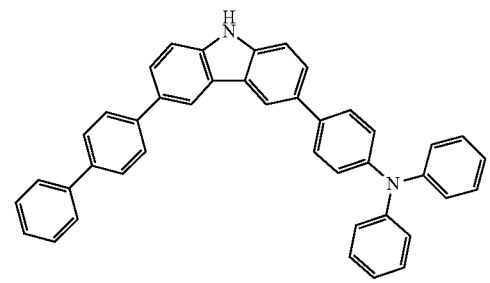
(627)
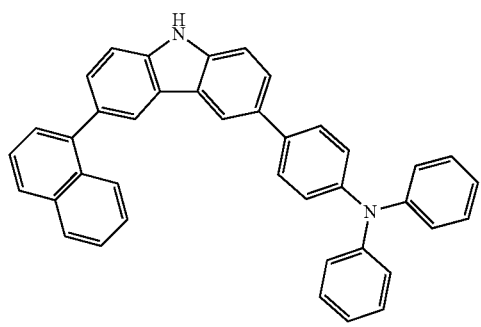
(628)
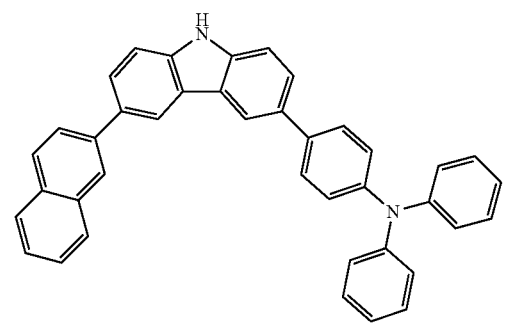
(629)
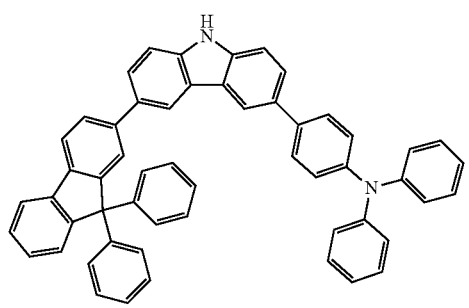
(630)
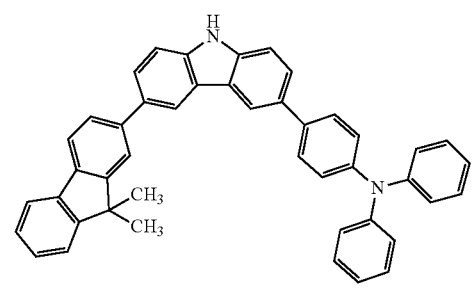
(631)
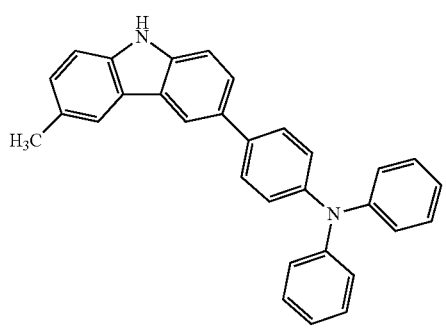
(632)
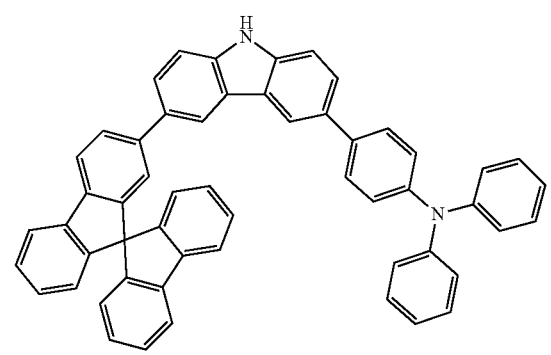
(633)
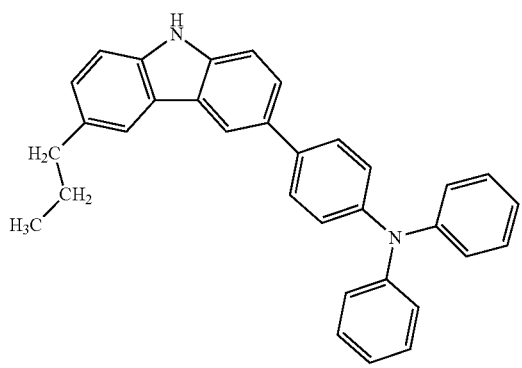
(634)
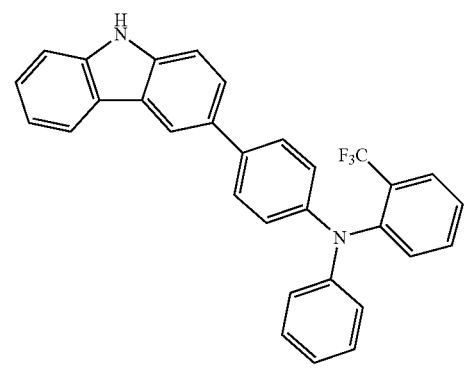

(635) 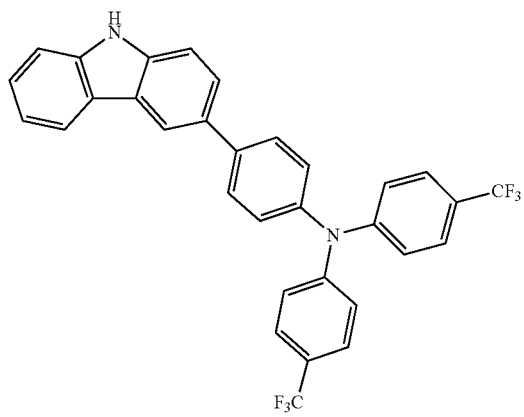
(636) 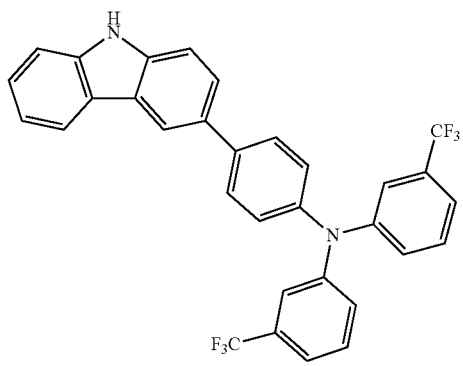
(637) 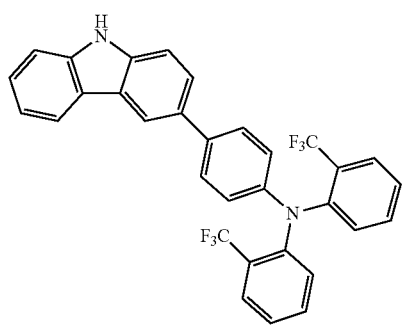
(638) 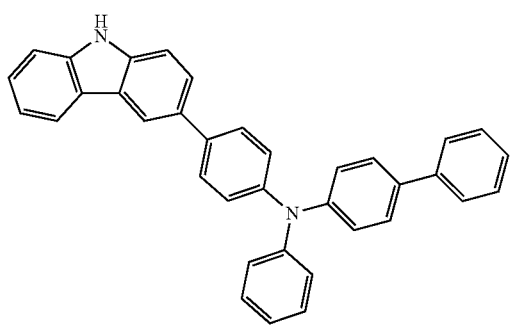
(639) 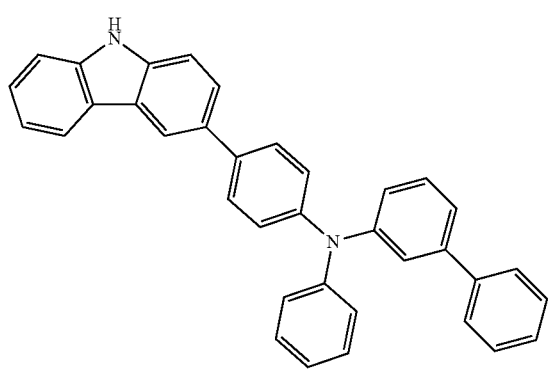
(640) 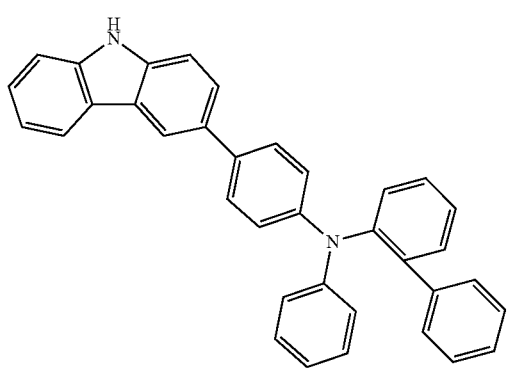
(641) 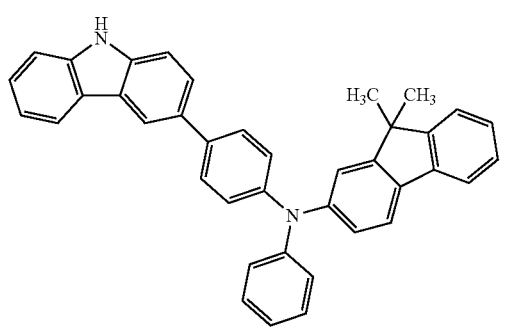
(642) 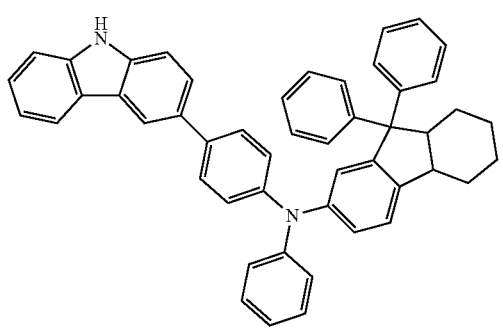

-continued
(643)
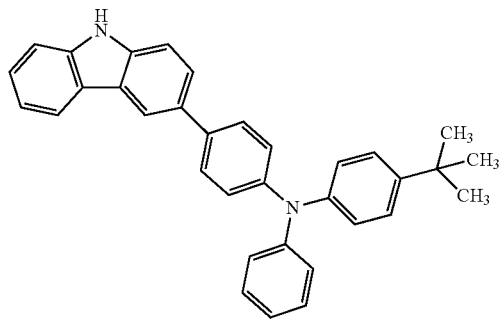
(644)
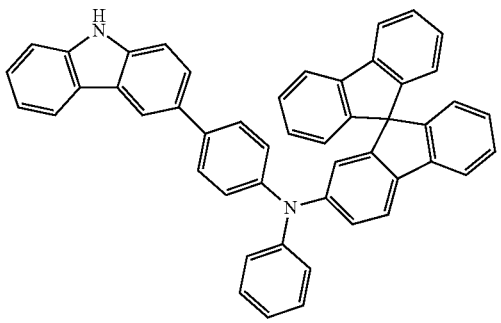
(645)
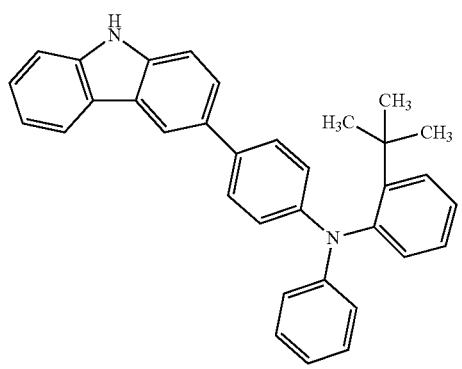
(646)
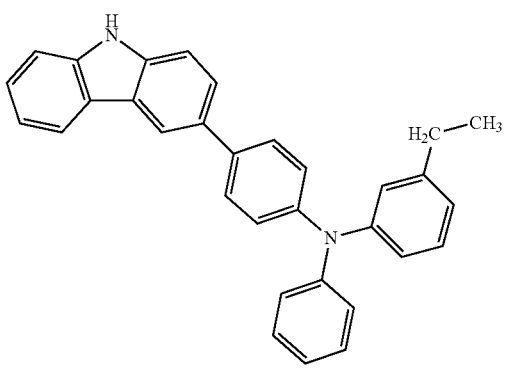
(647)
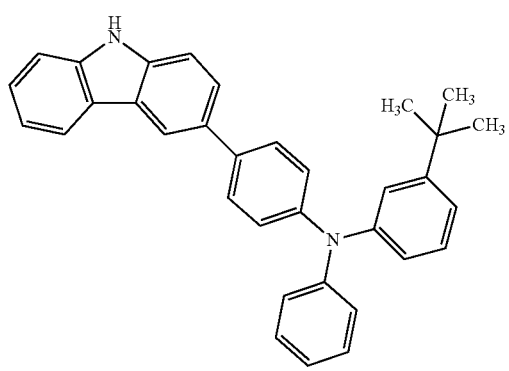
(648)
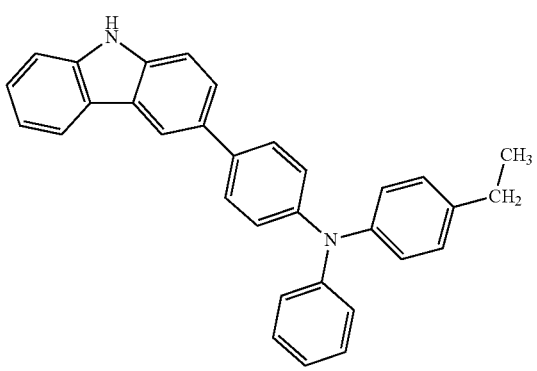
(649)
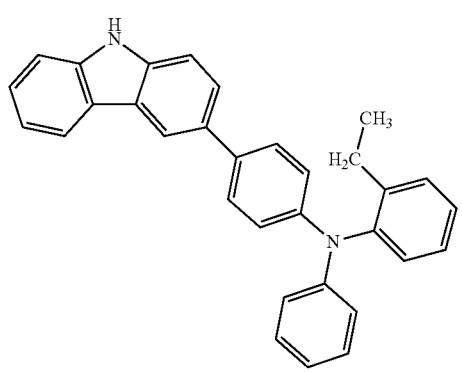
(650)
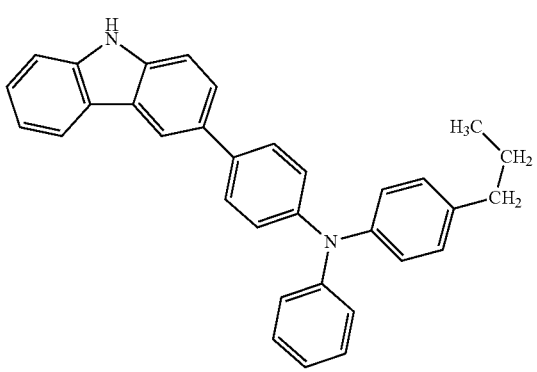

-continued
(651)
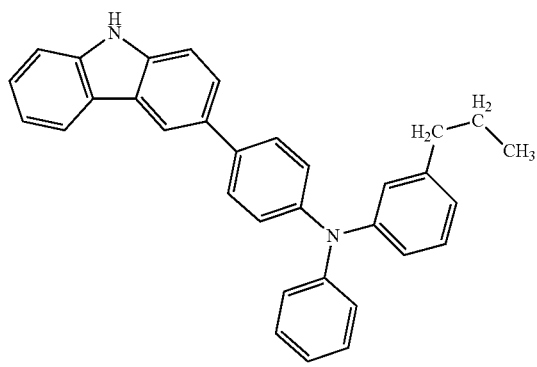
(652)
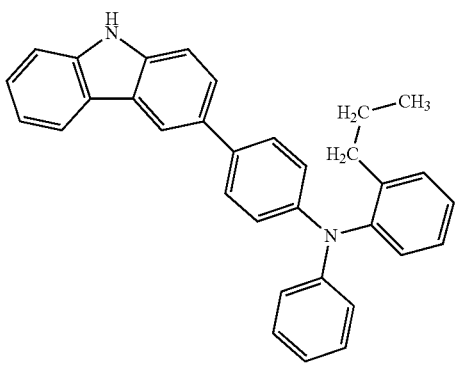
(653)
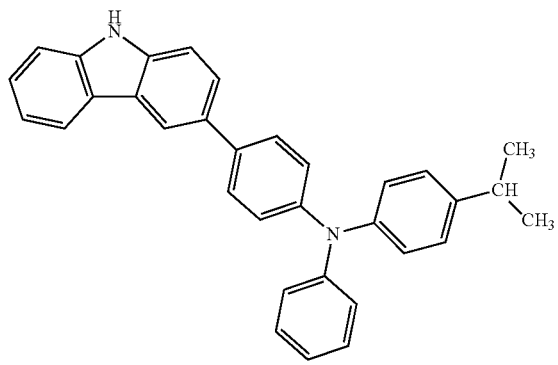
(654)
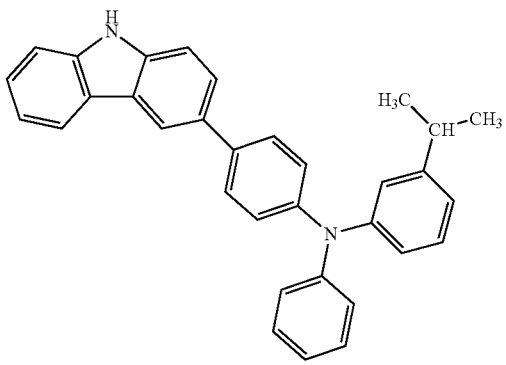
(655)
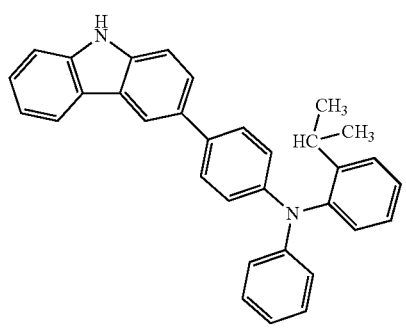
(656)
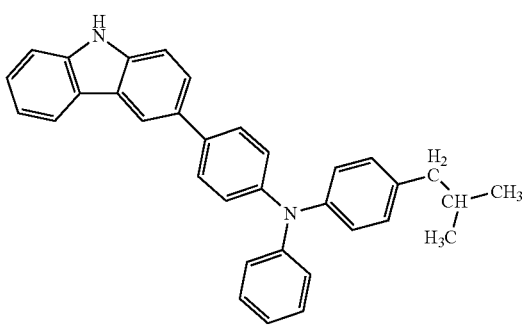
(657)
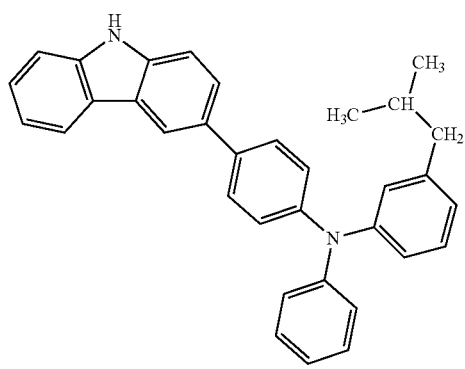
(658)
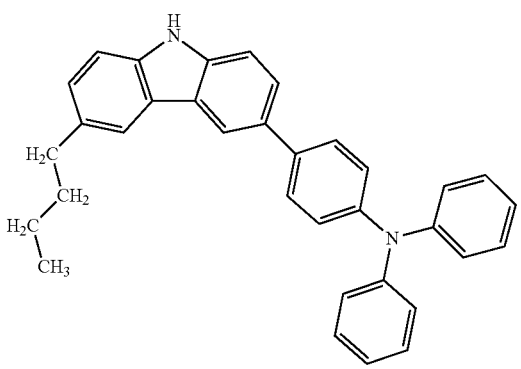

-continued
(659)
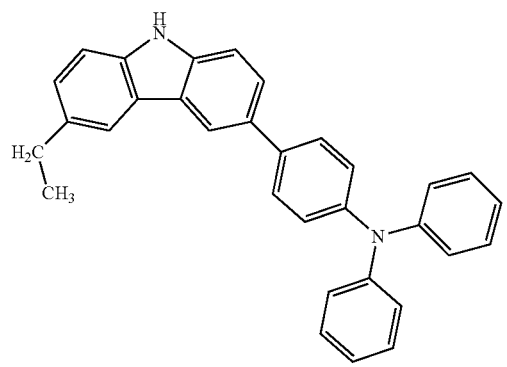
(660)
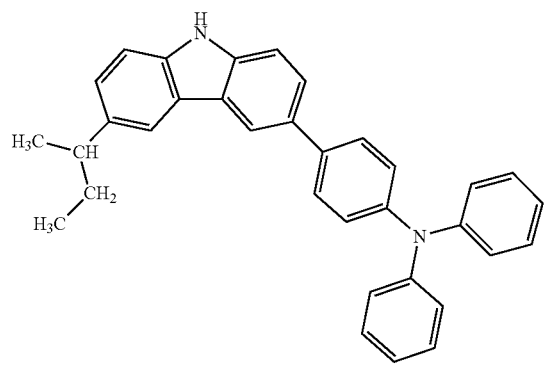
(661)
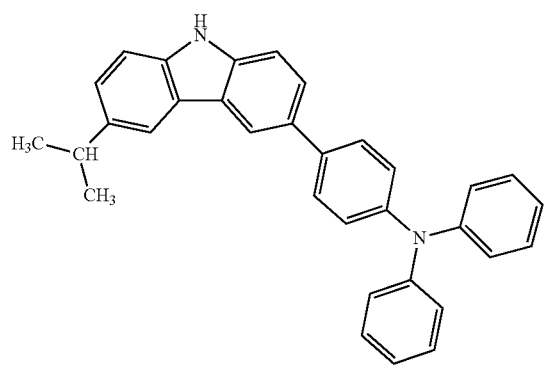
(662)
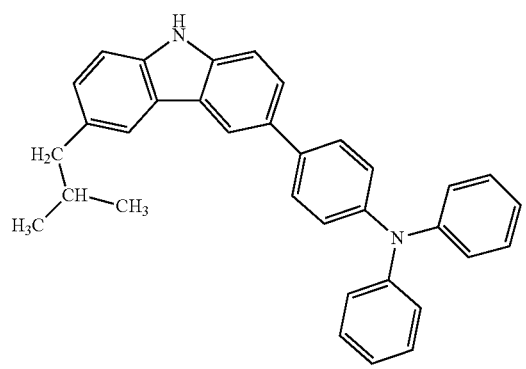
(663)
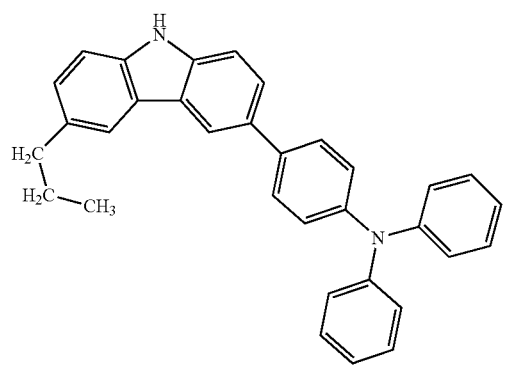
(664)
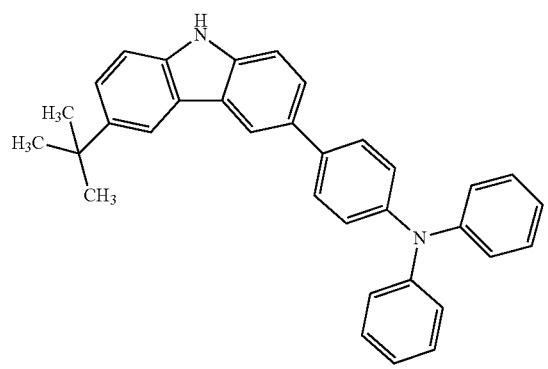
(665)
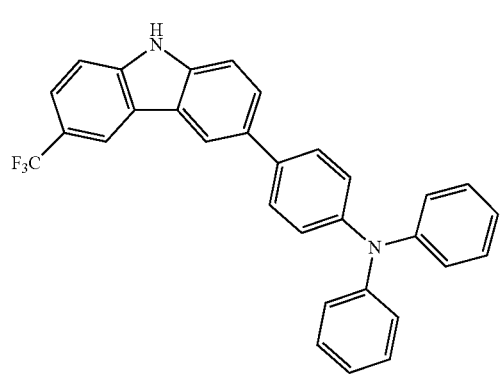
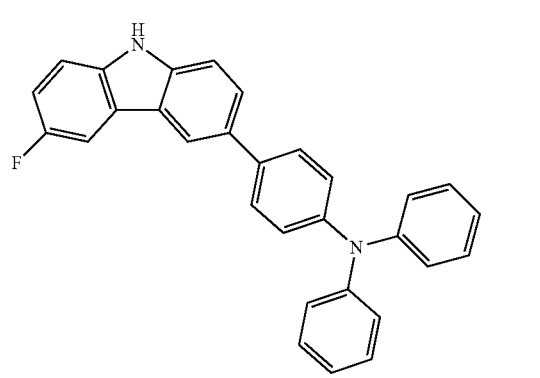

-continued
(666)
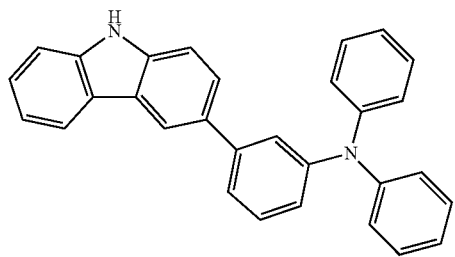
(667)
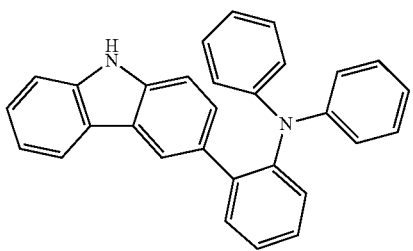
(668)
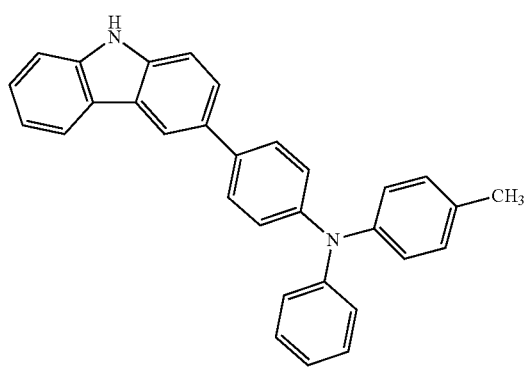
(669)
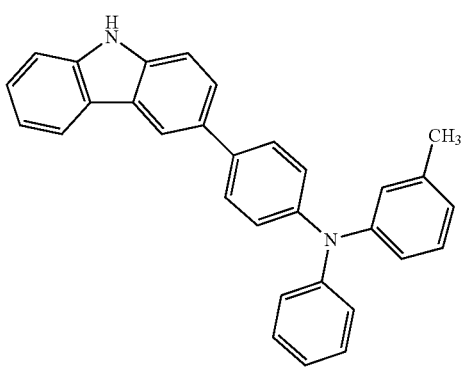
(670)
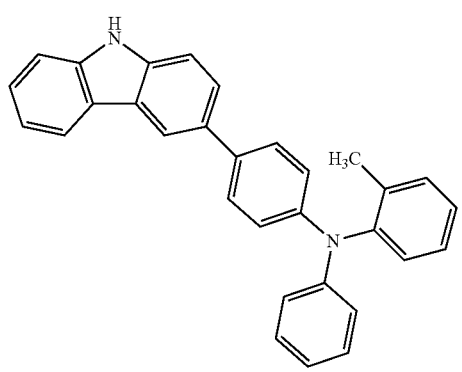
(671)
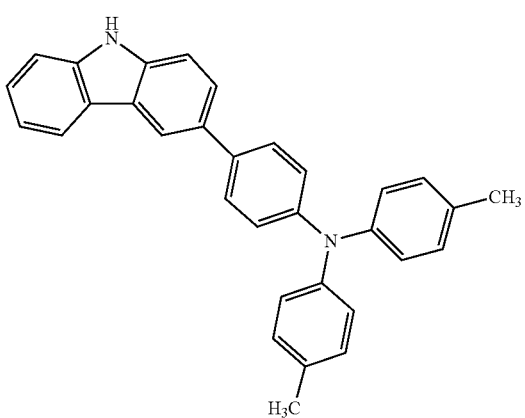
(672)
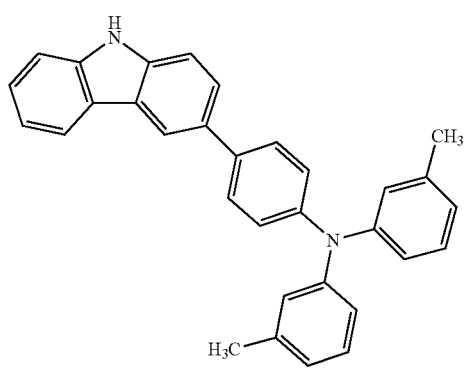
(673)
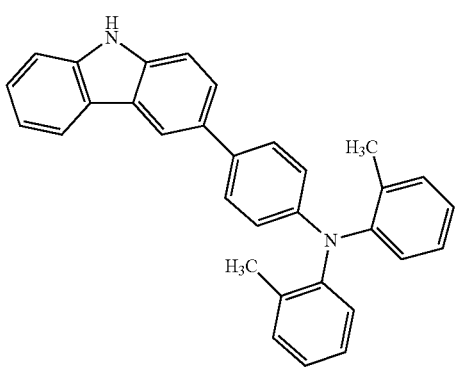

-continued
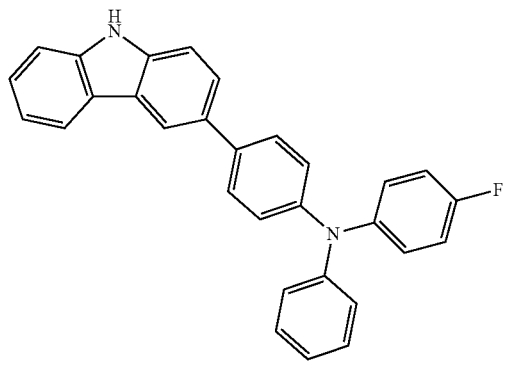 (674)
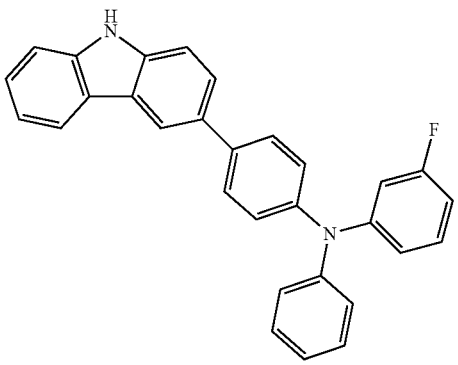 (675)
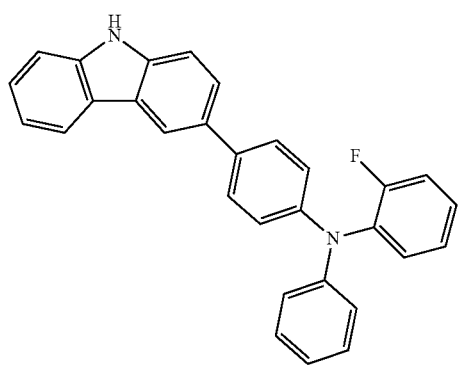 (676)
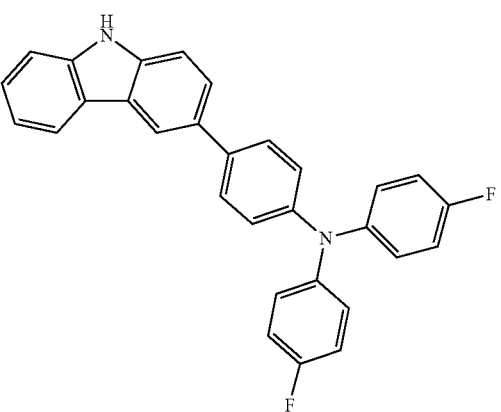 (677)
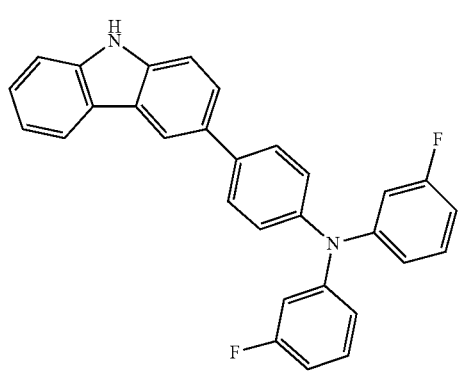 (678)
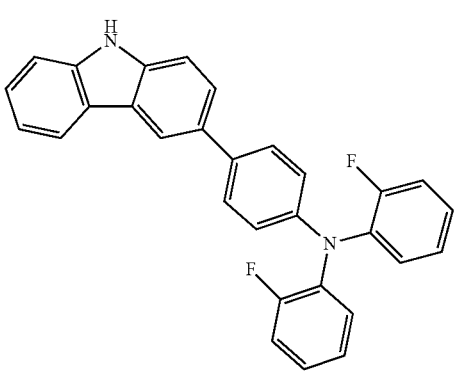 (679)
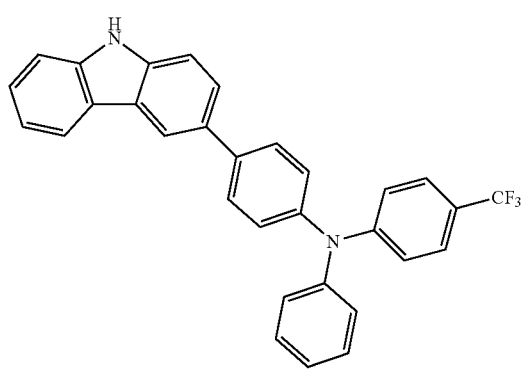 (680)
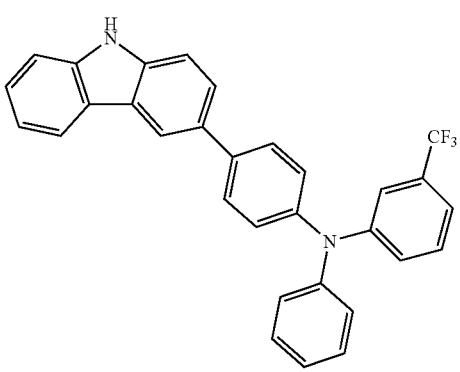 (681)

(682)
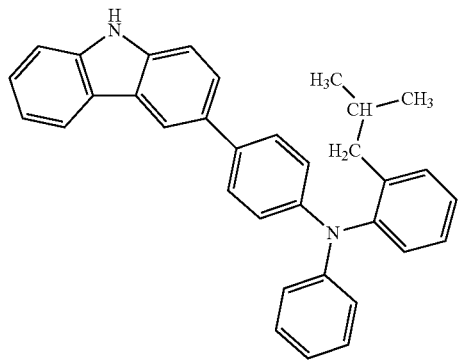
(683)
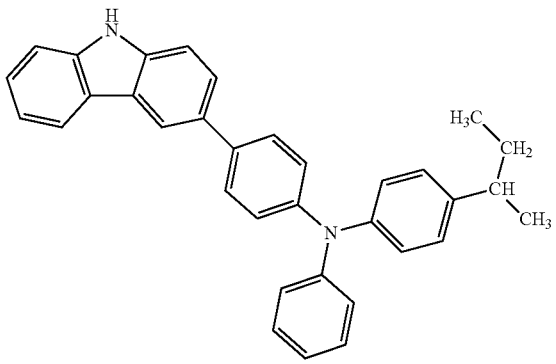
(684)
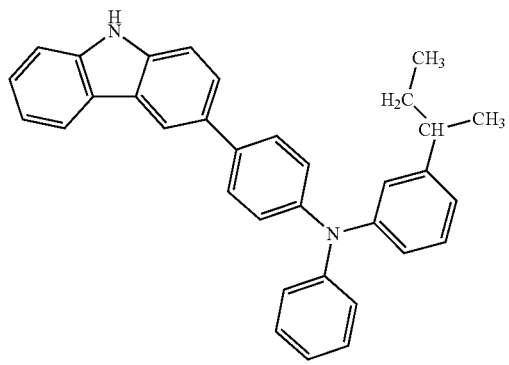
(685)
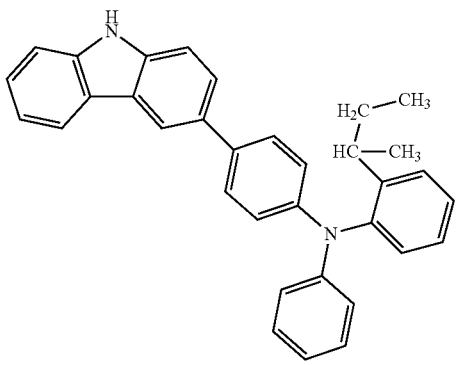
(686)
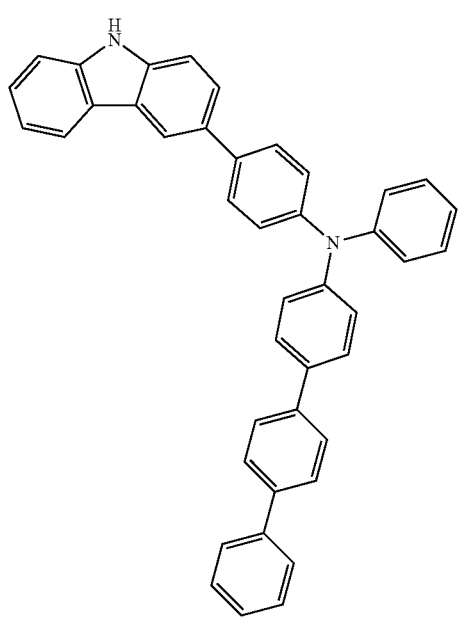
(687)
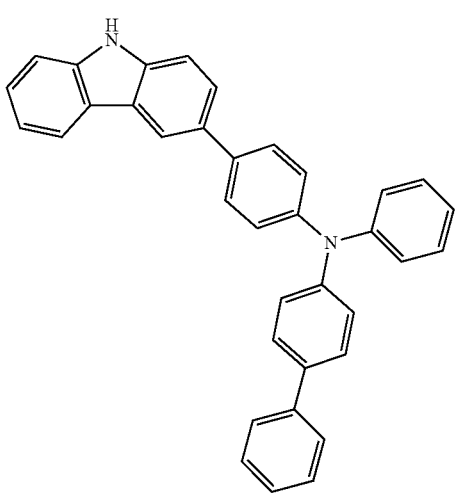

-continued
(688)
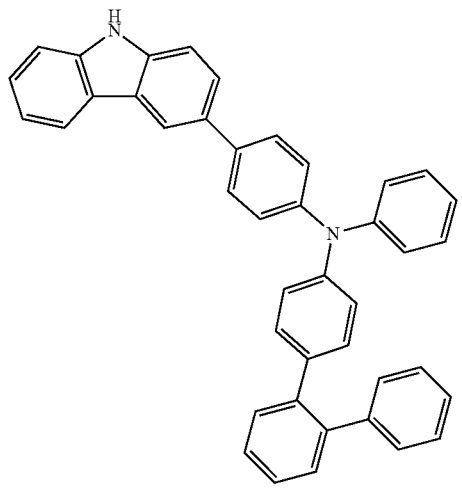
(689)
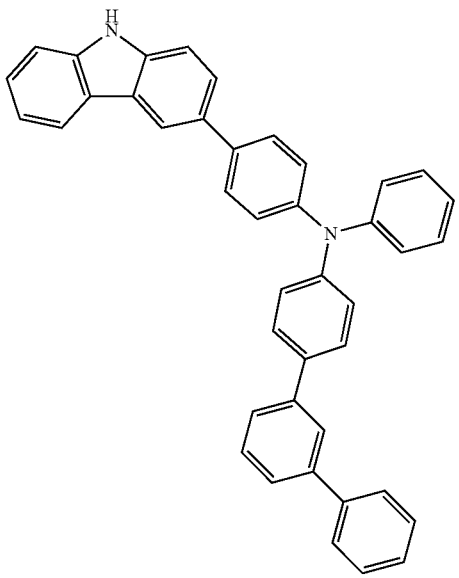
(690)
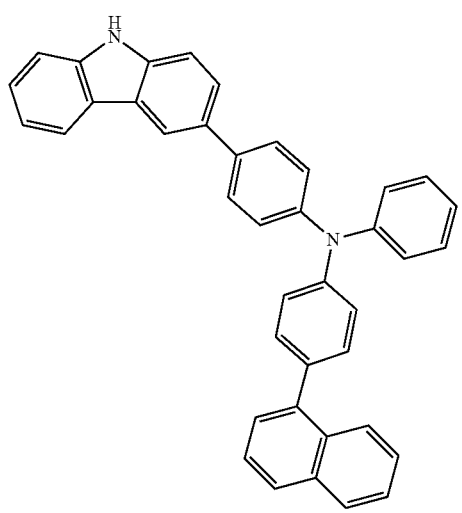
(681)
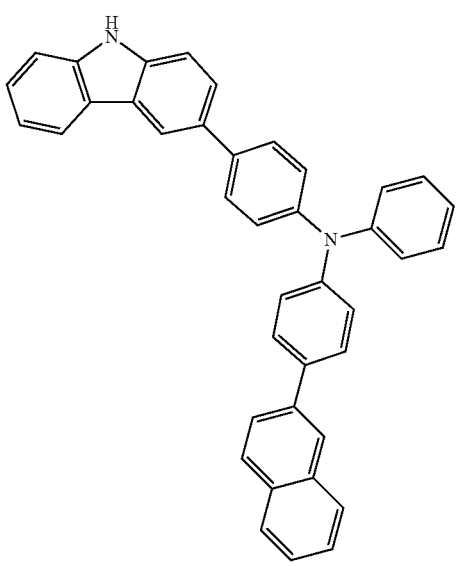
(692)
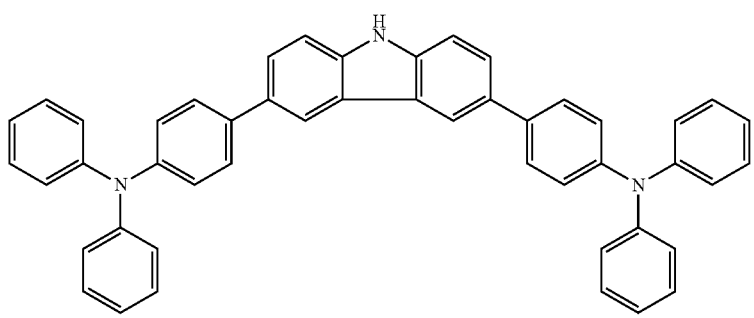

-continued
(693)
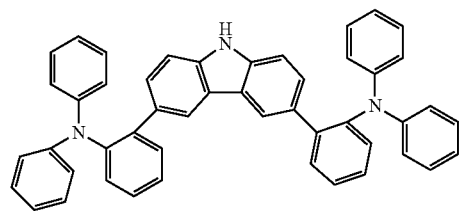
(694)
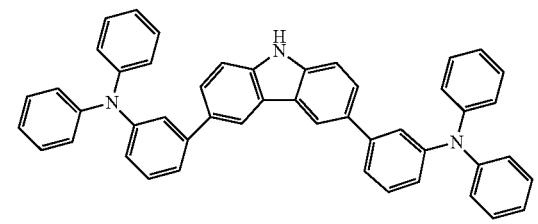
(695)
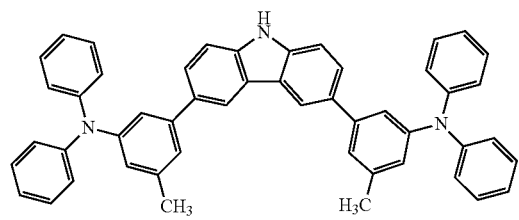
(696)
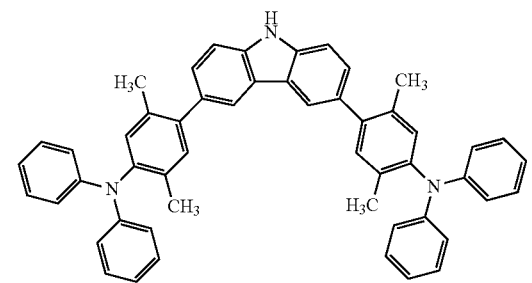
(697)
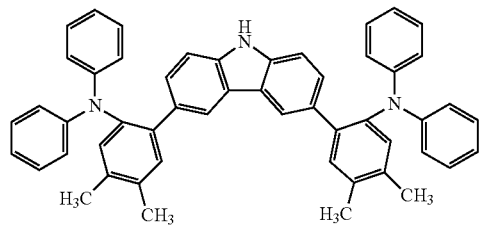
(698)
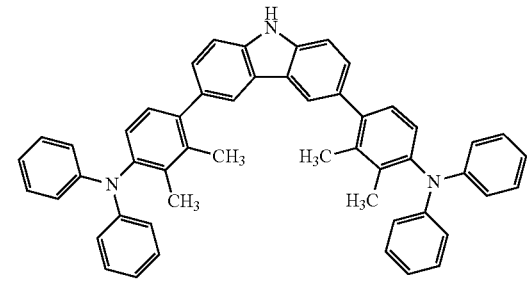
(699)
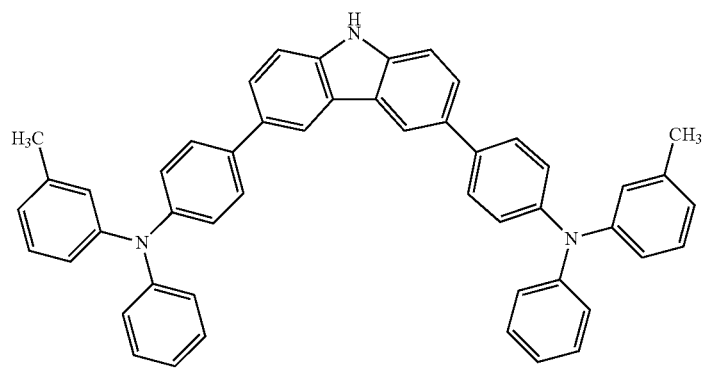
(700)
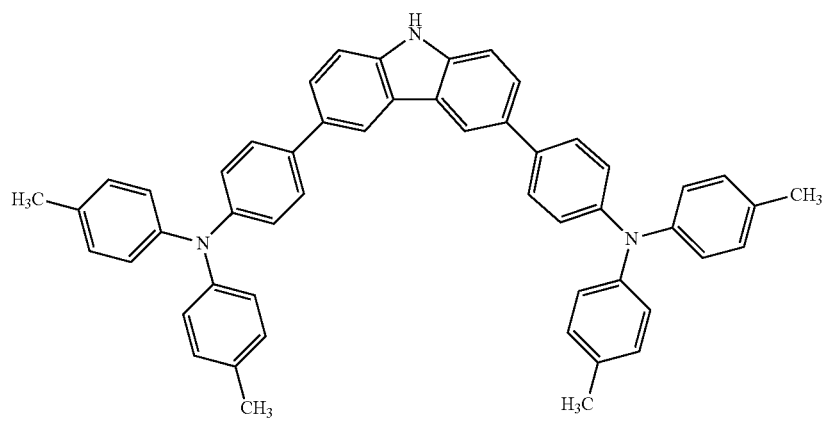

-continued
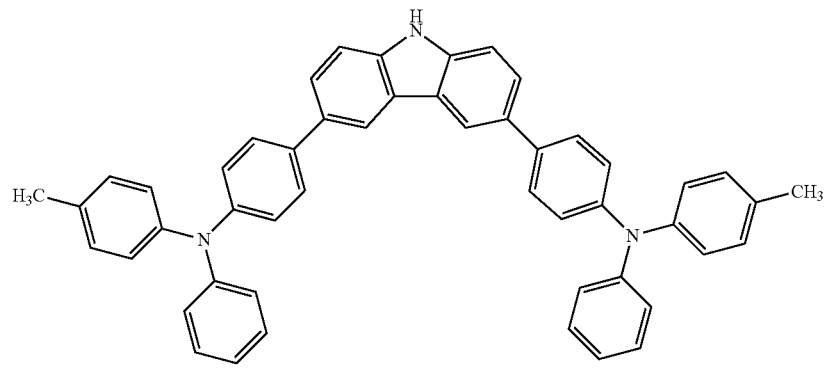
(701)
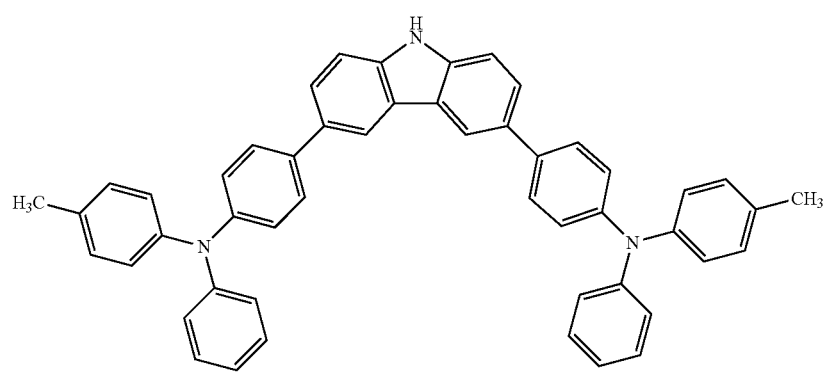
(702)
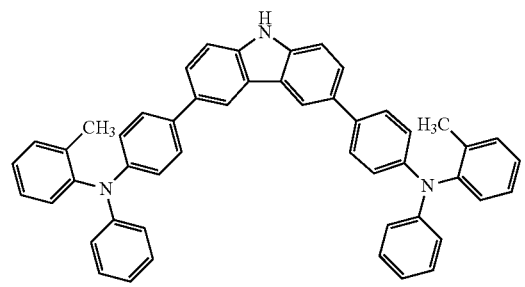
(703)
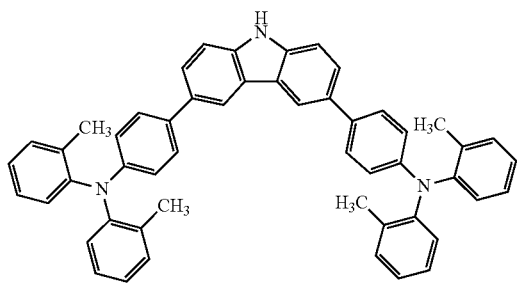
(704)
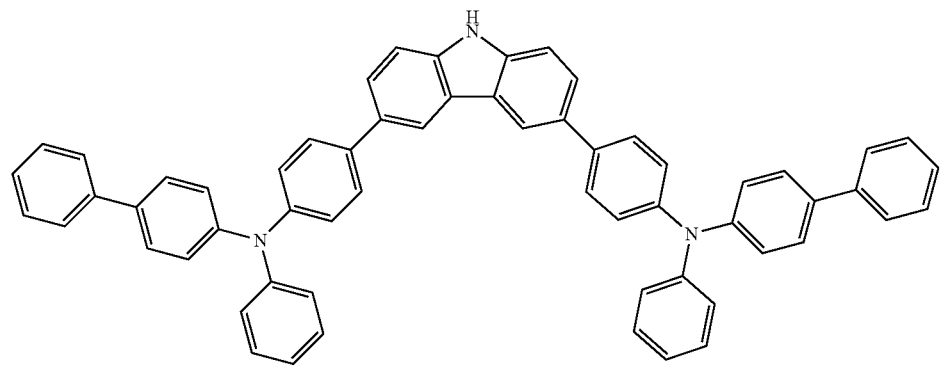
(705)

(706)
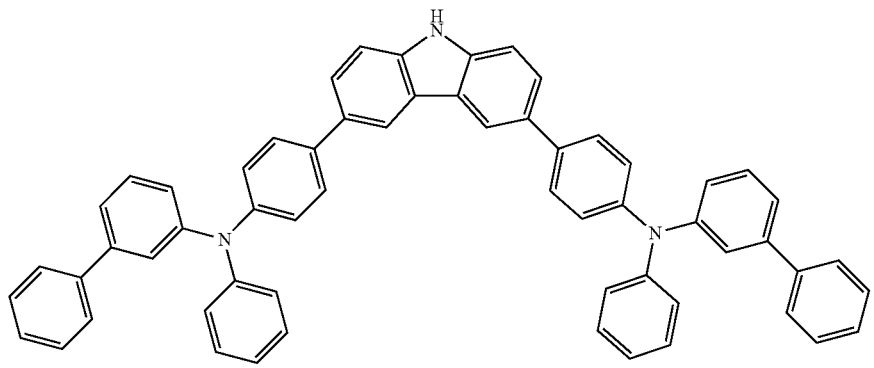
(707)
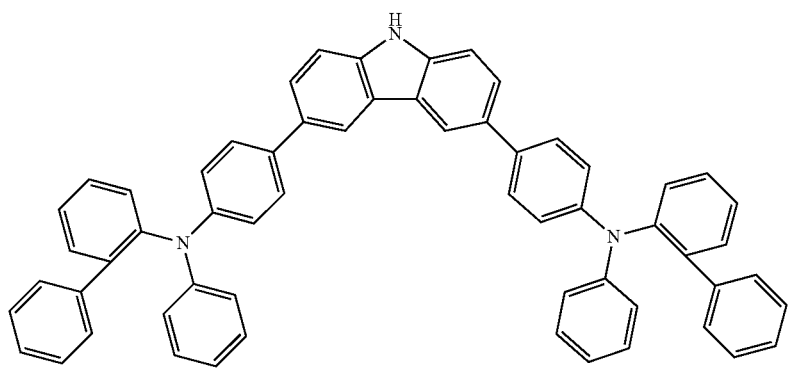
(708)
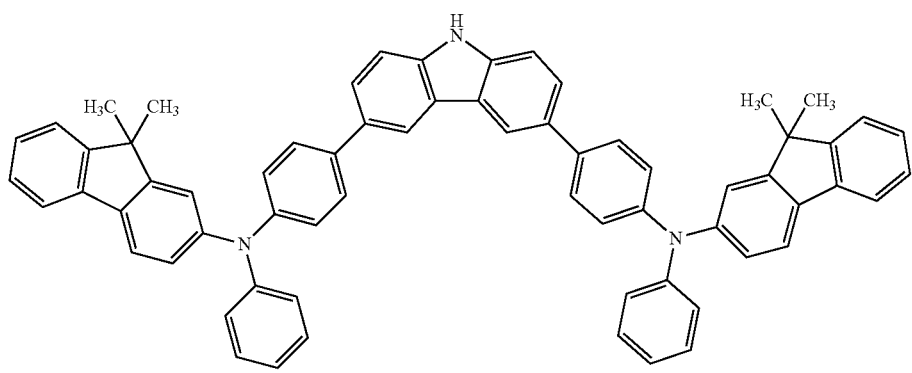
(709)
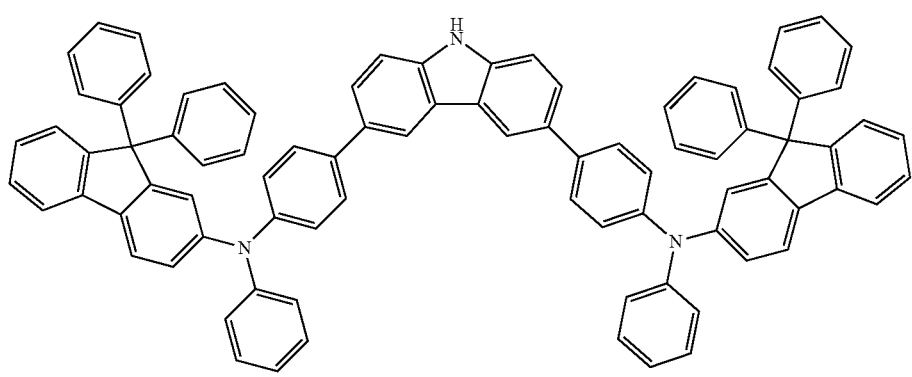

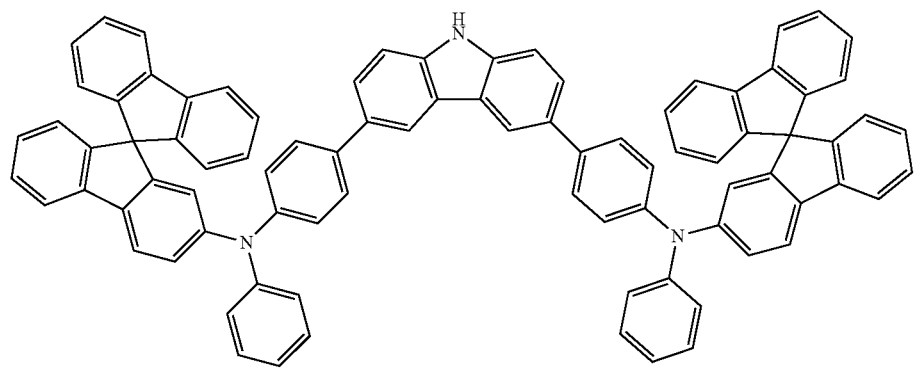
(710)
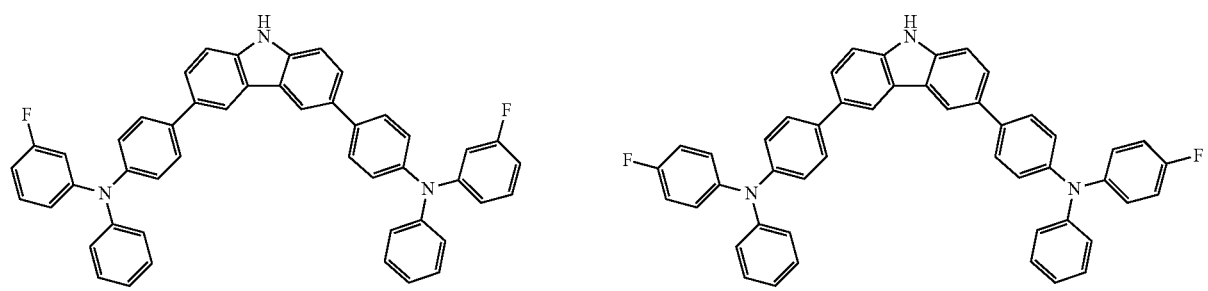
(711) (712)
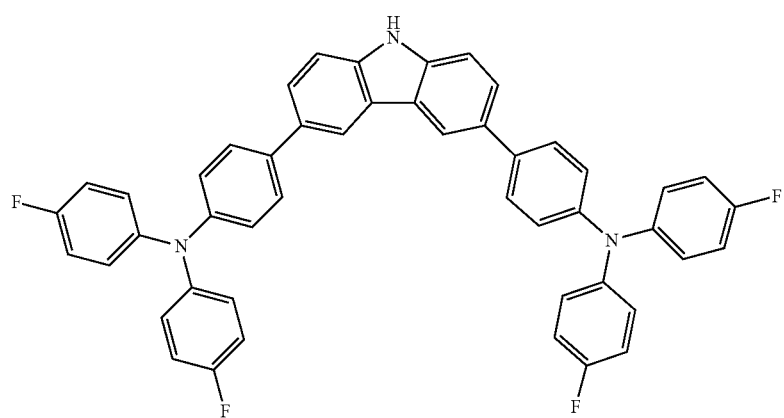
(713)
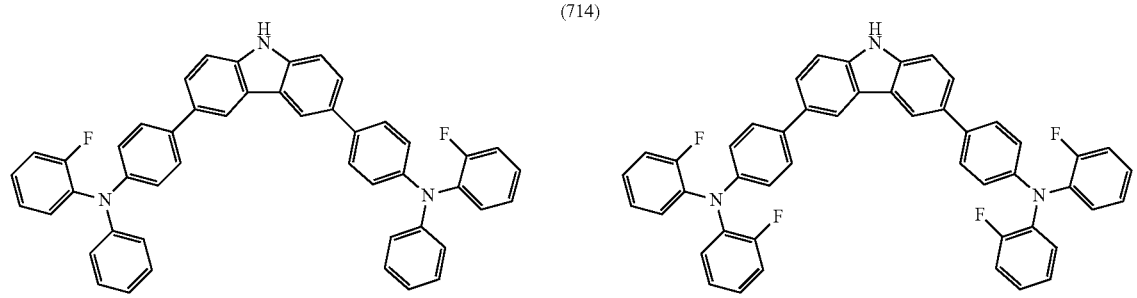
(714) (715)

-continued
(716)
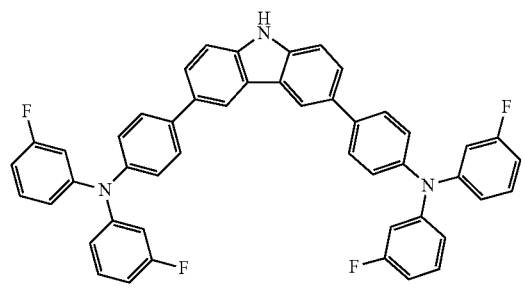
(717)
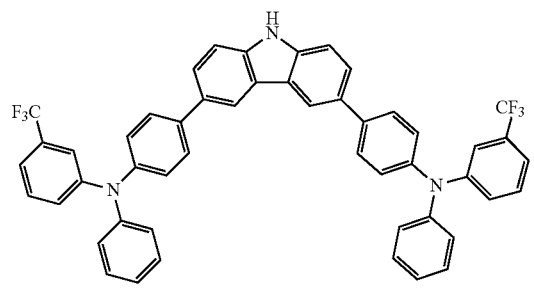
(718)
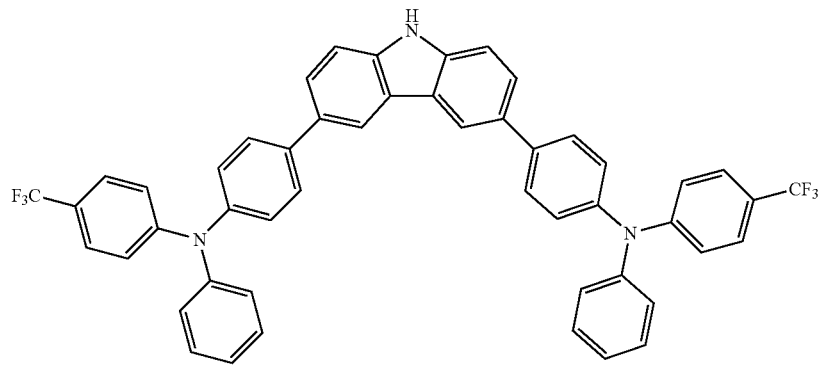
(719)
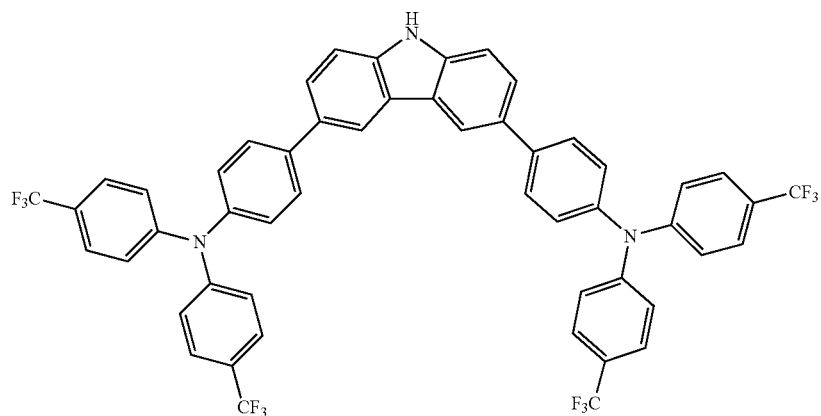
(720)
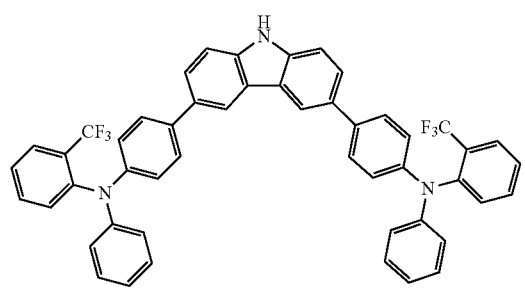
(721)
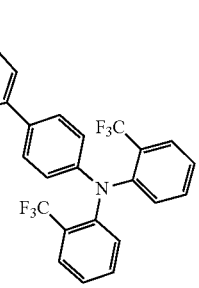
(722)
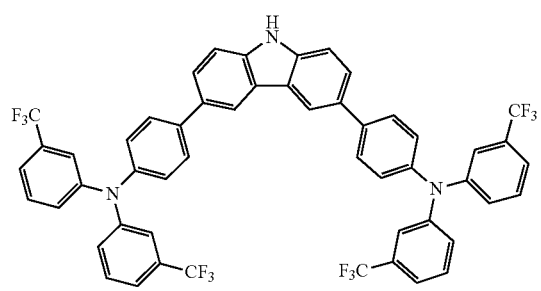
(723)
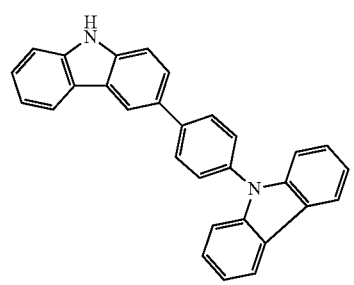

-continued
(724) 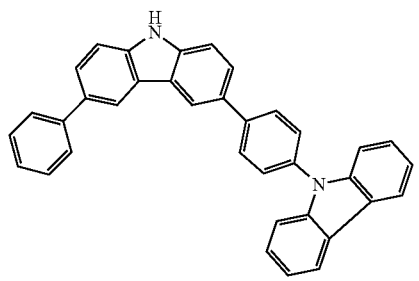
(725) 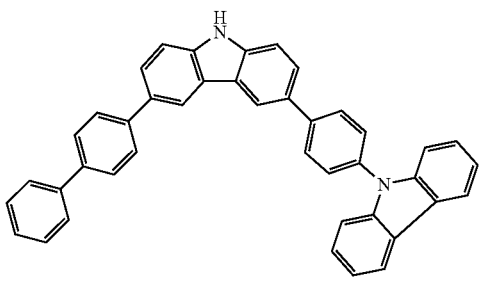
(726) 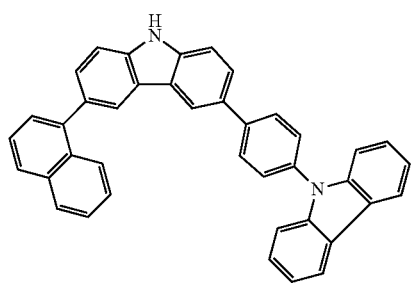
(727) 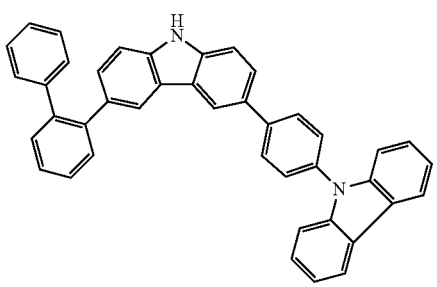
(728) 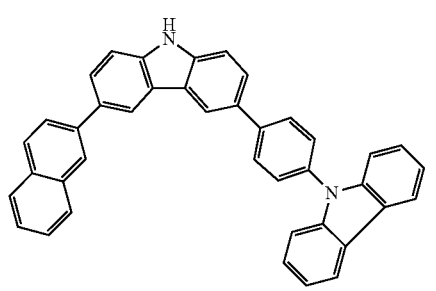
(729) 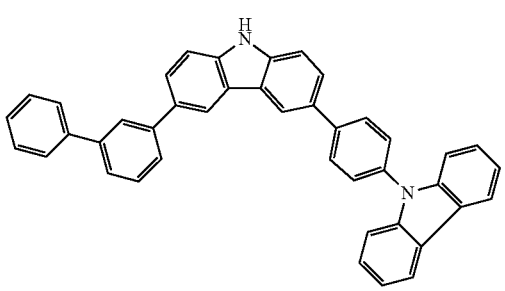
(730) 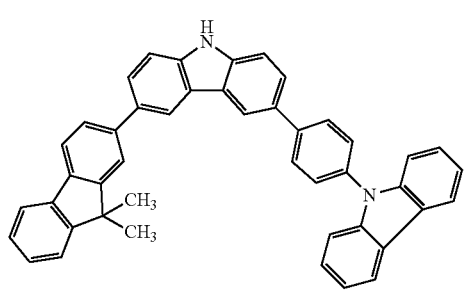
(731) 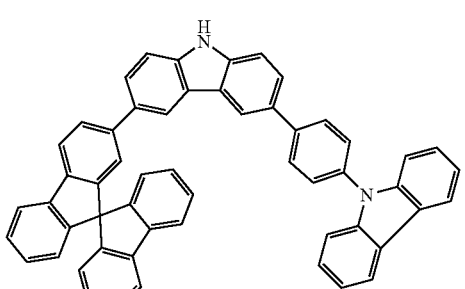
(732) 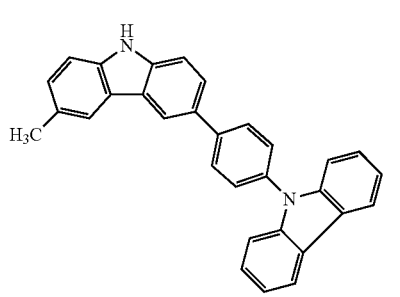
(733) 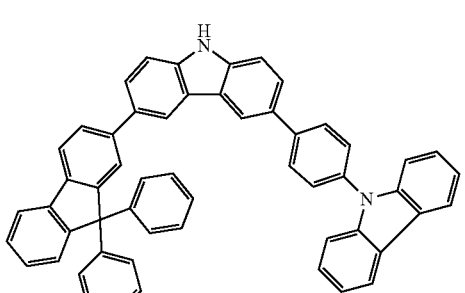

-continued
(734)
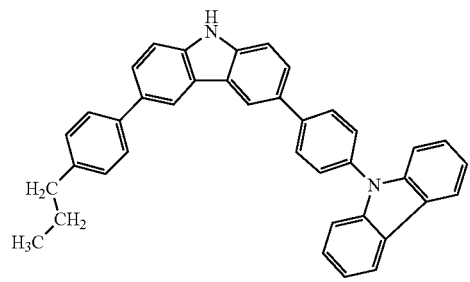
(735)
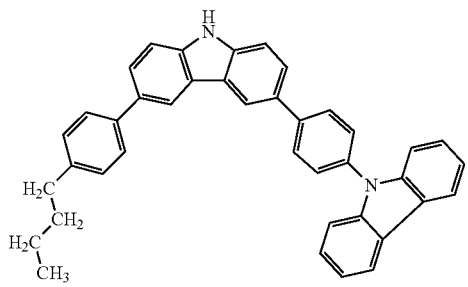
(736)
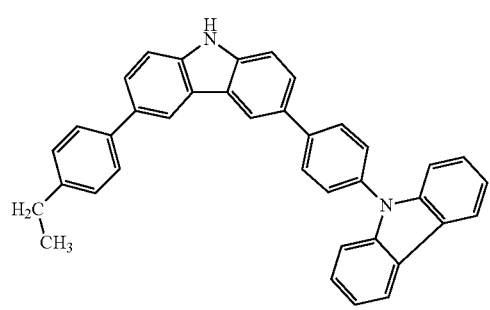
(737)
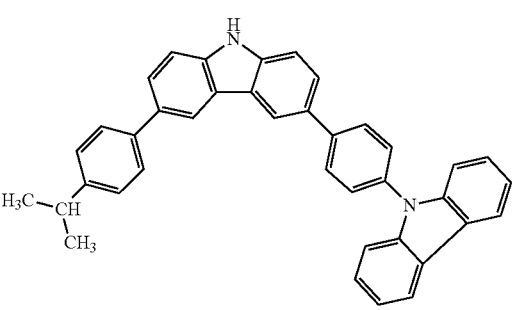
(738)
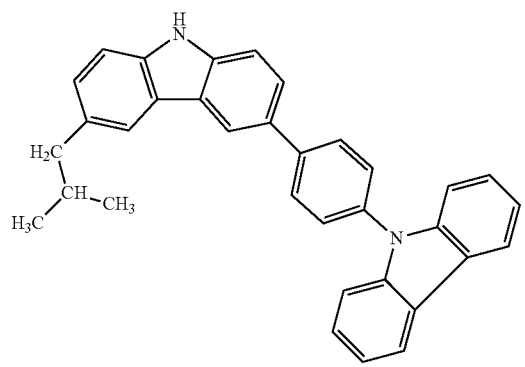
(739)
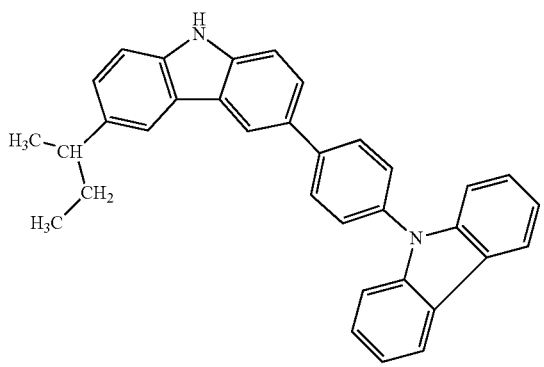
(740)
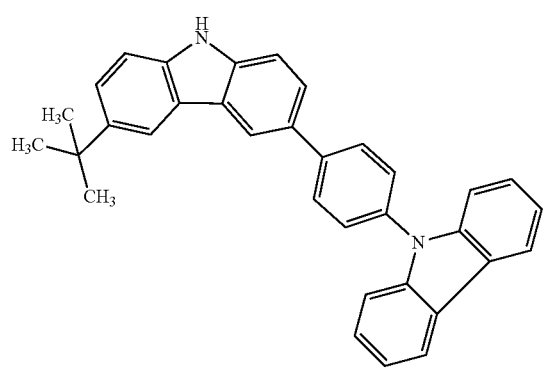
(741)
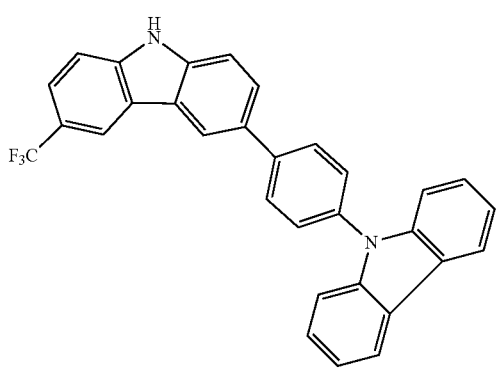
(742)
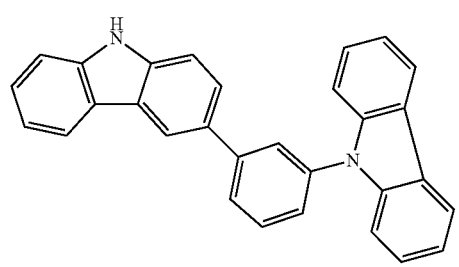
(743)
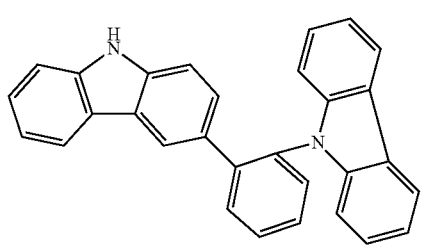

-continued
(744)
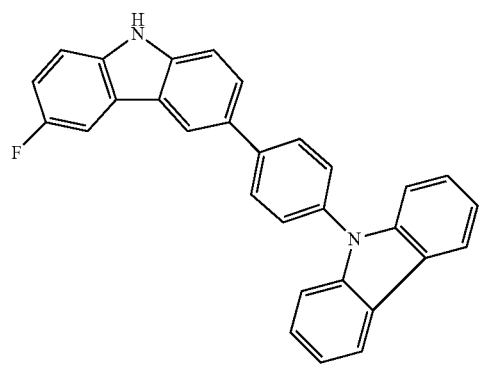
(745)
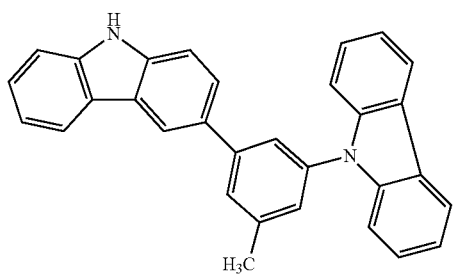
(746)
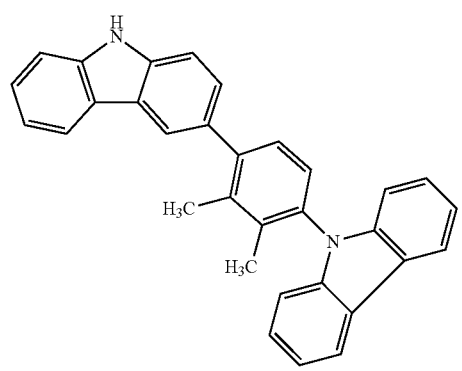
(747)
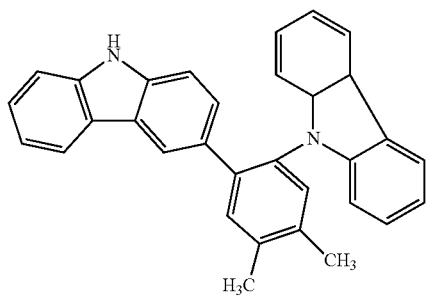
(748)
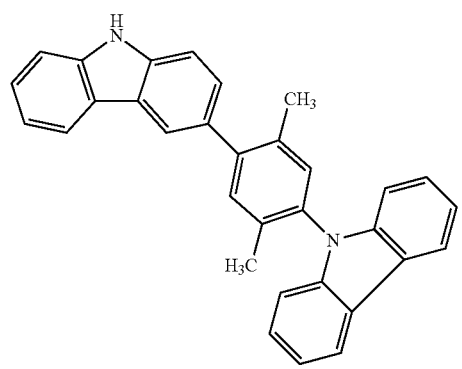
(749)
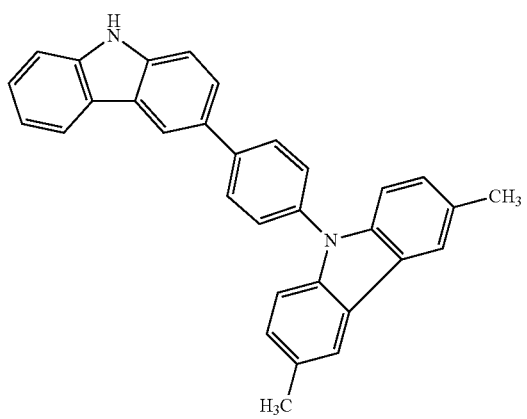
(750)
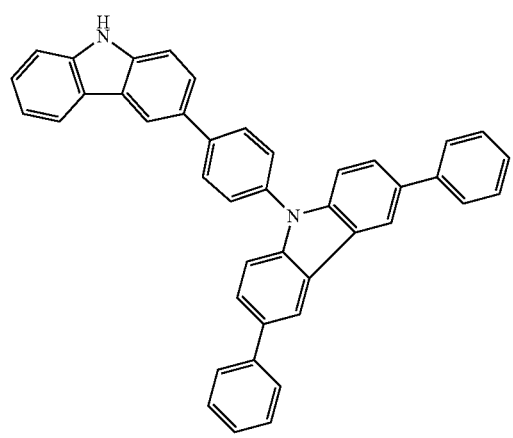
(751)
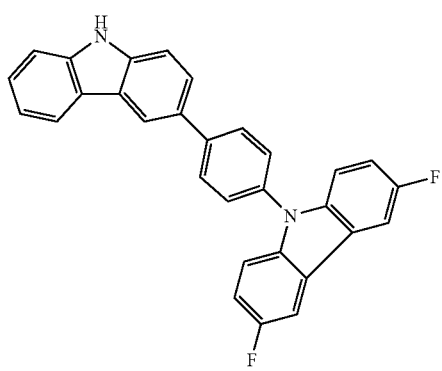

-continued
(752)
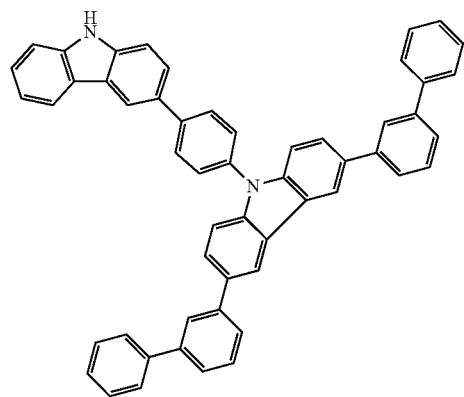
(753)
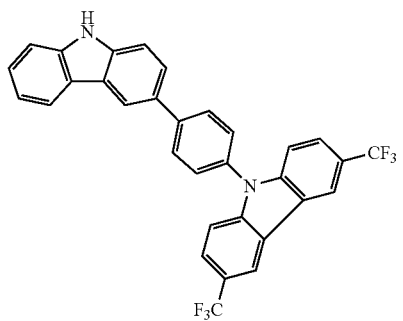
(754)
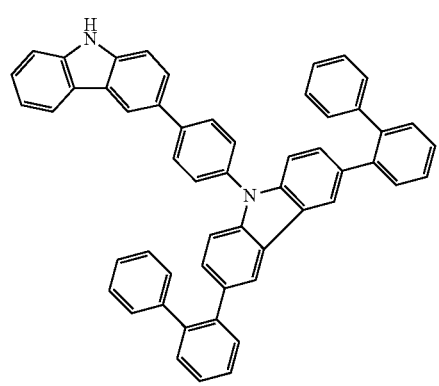
(755)
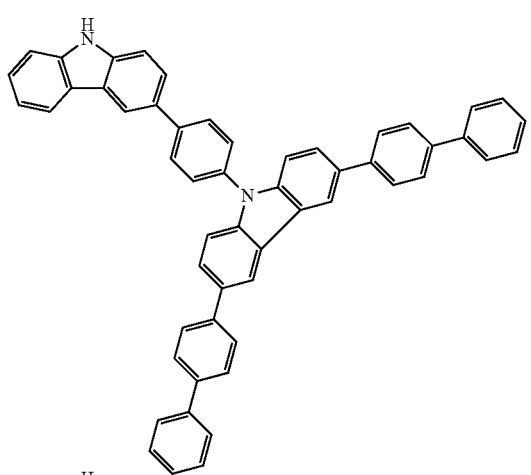
(756)
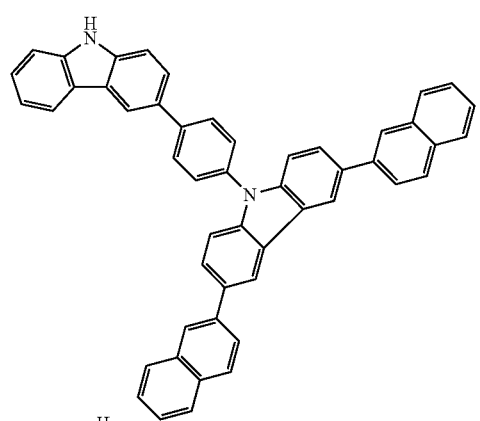
(757)
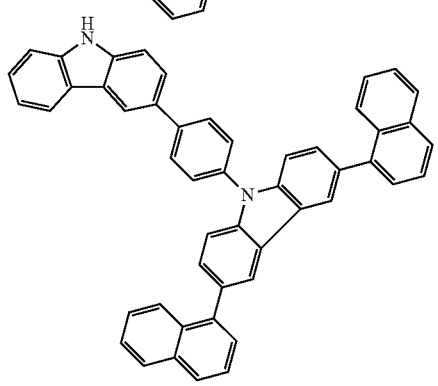
(758)
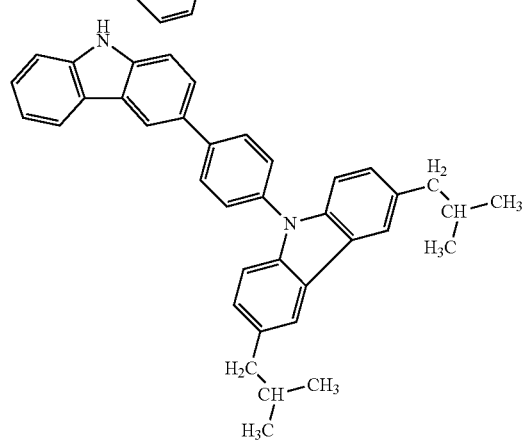
(759)
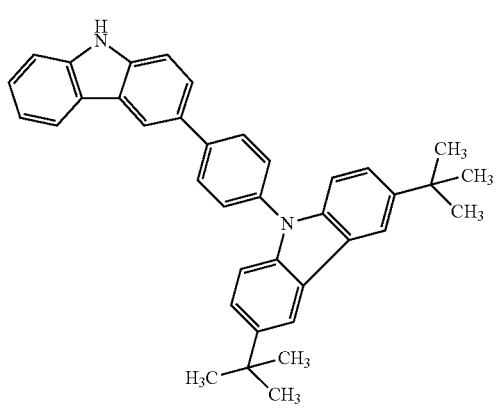

-continued
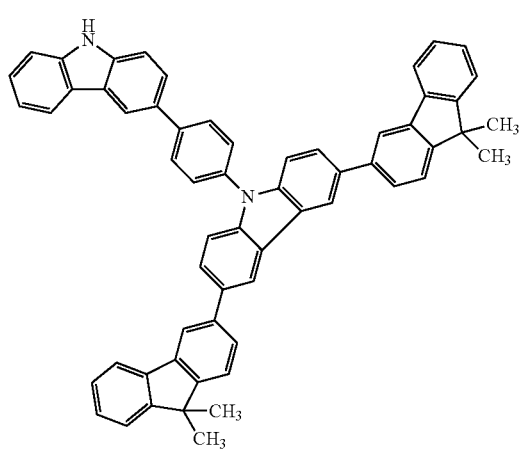
(760)
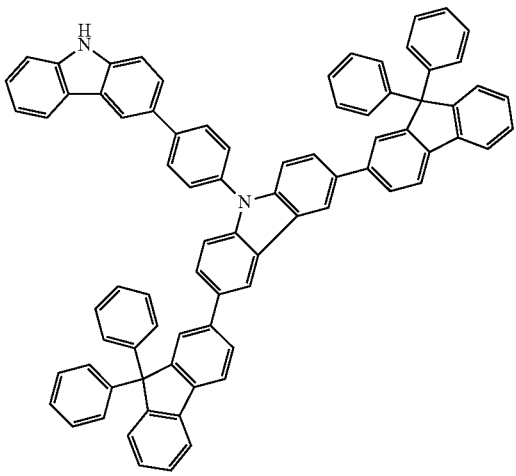
(761)
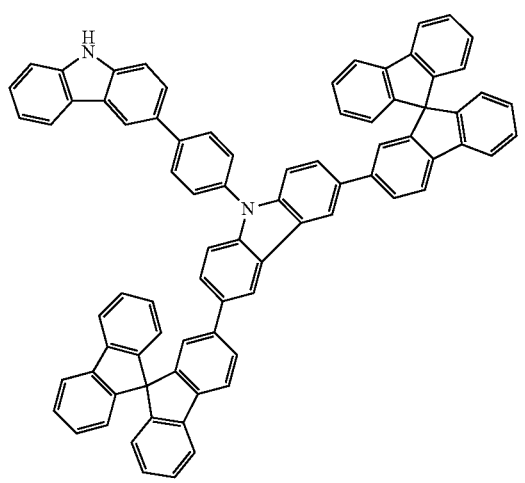
(762)
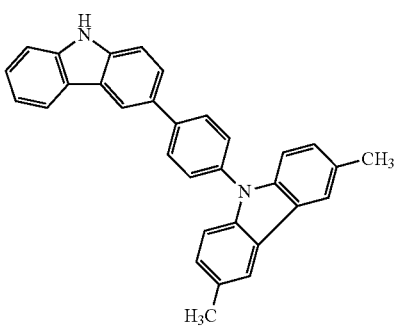
(763)
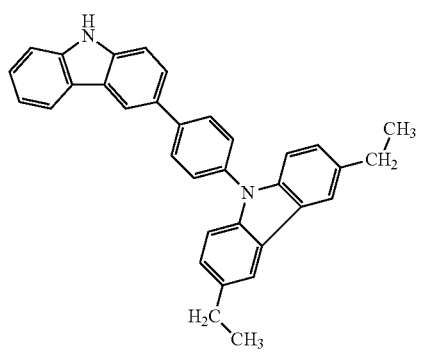
(764)
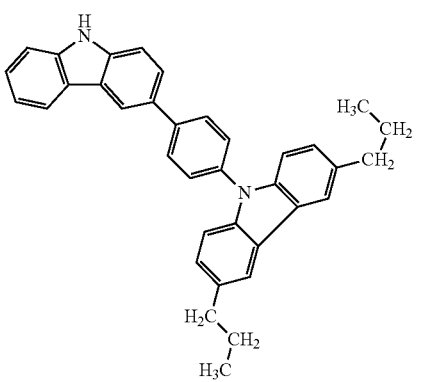
(765)

-continued
(766)
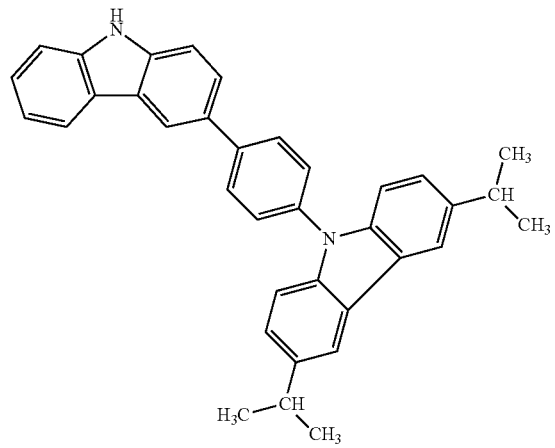
(767)
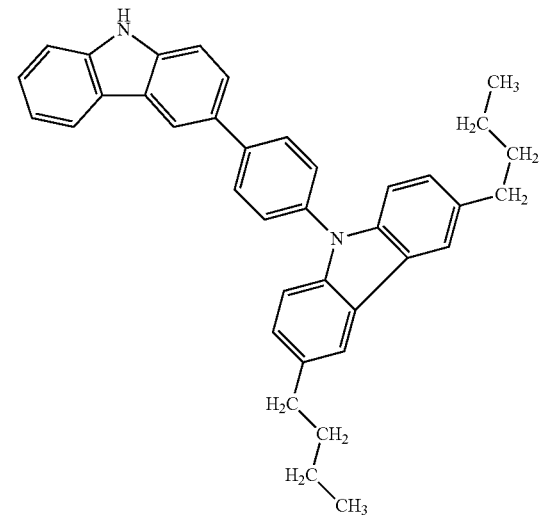
(768)
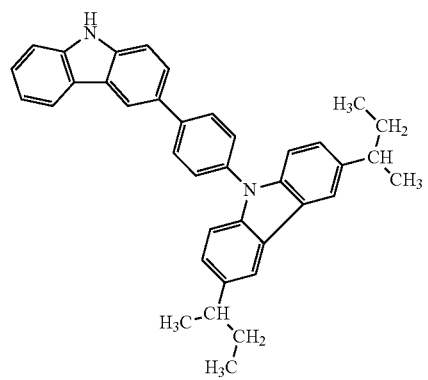
(769)
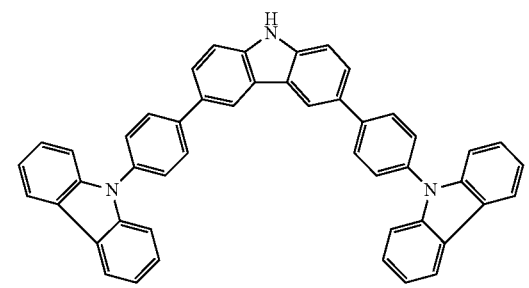
(770)
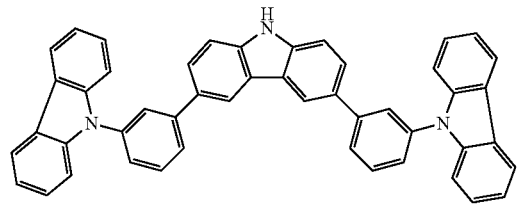
(771)
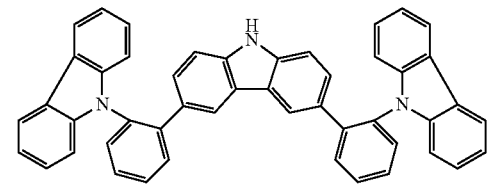
(772)
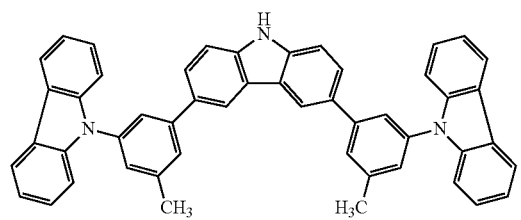
(773)
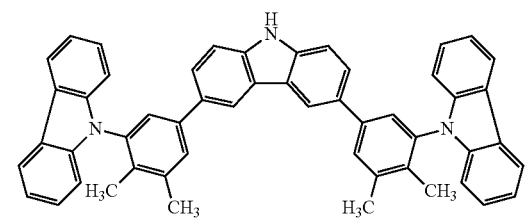
(774)
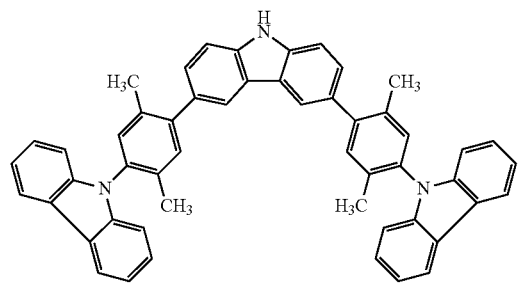
(775)
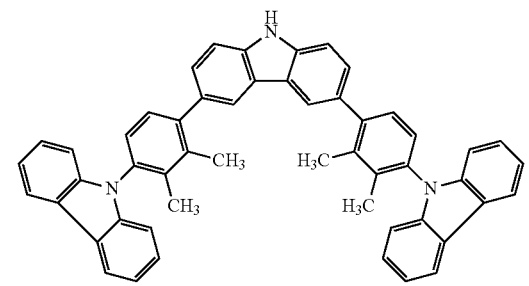

-continued
(776)
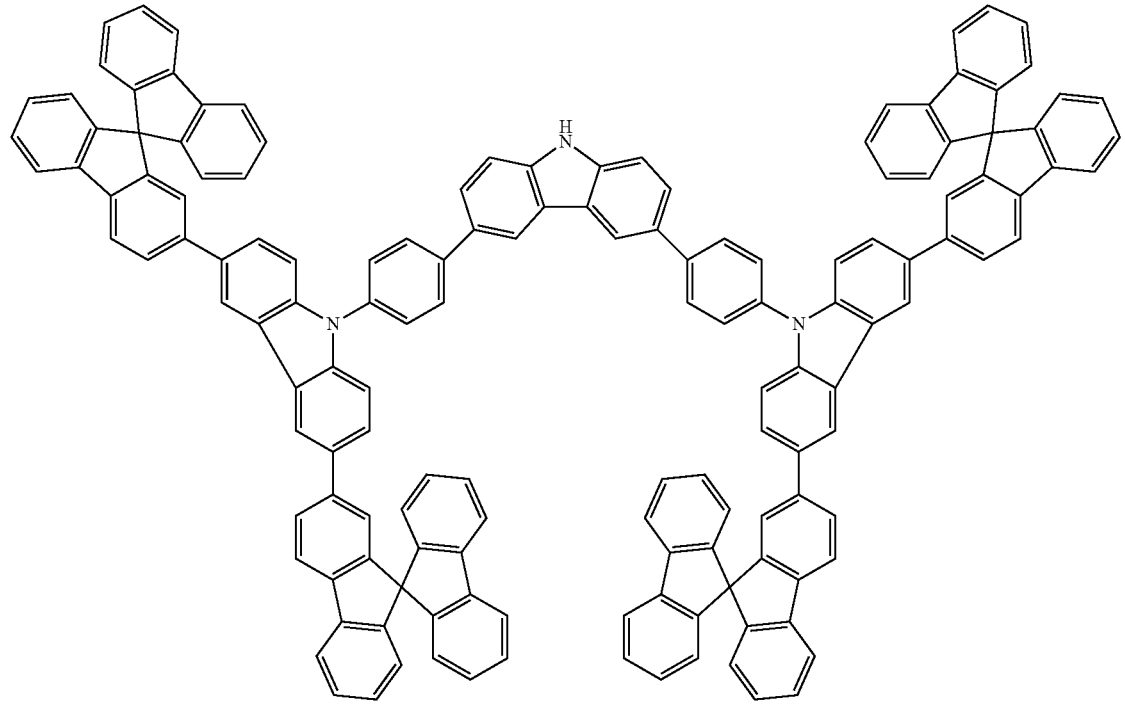
(777)
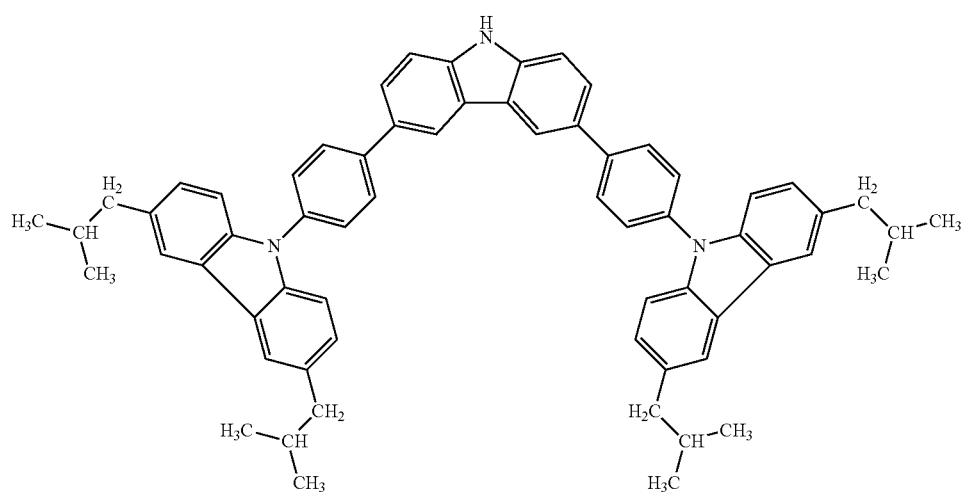
(778)
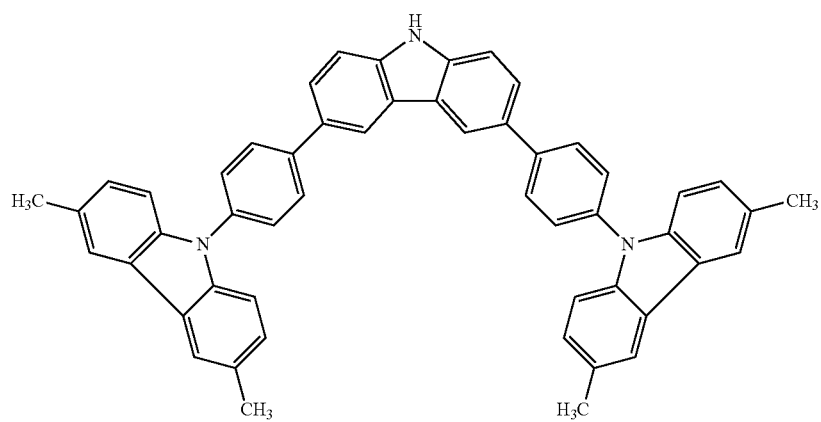

(779)
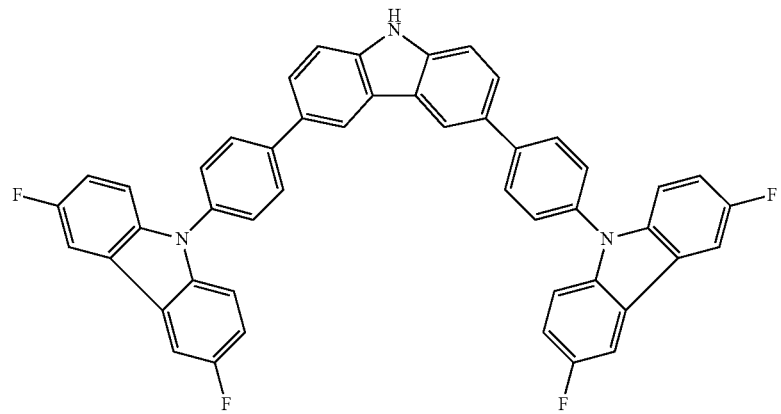
(780)
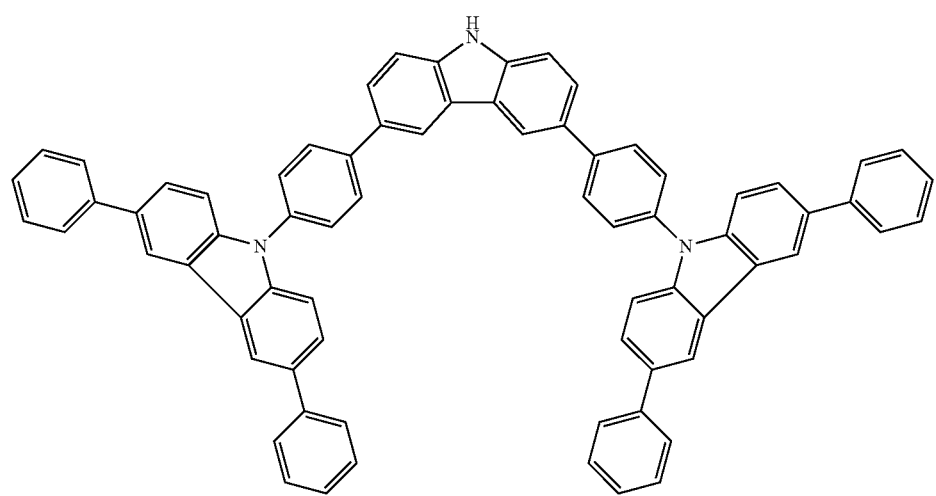
(781)
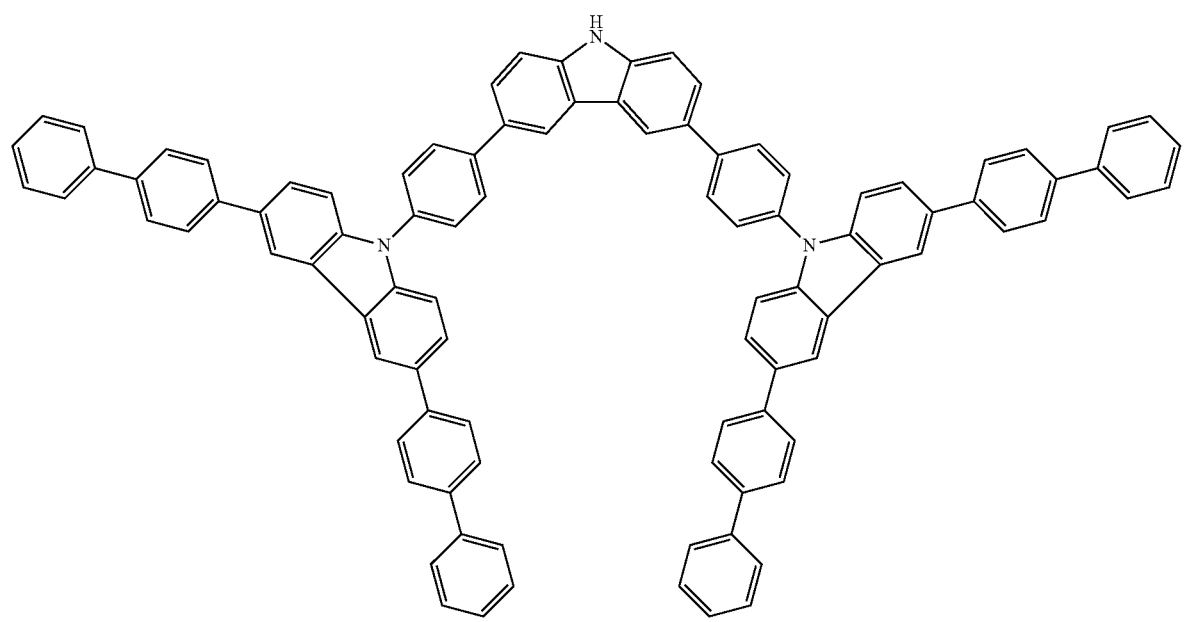

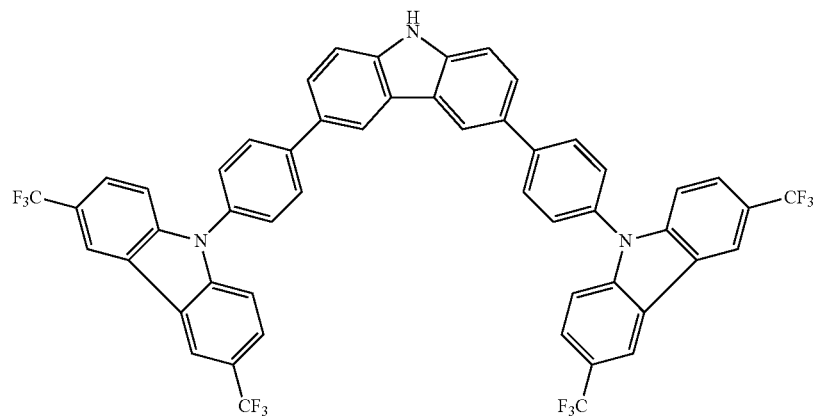
(782)
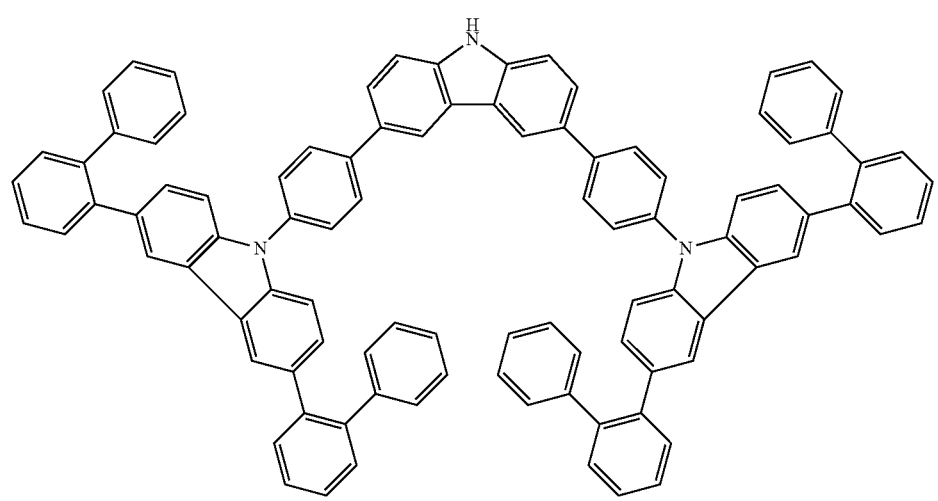
(783)
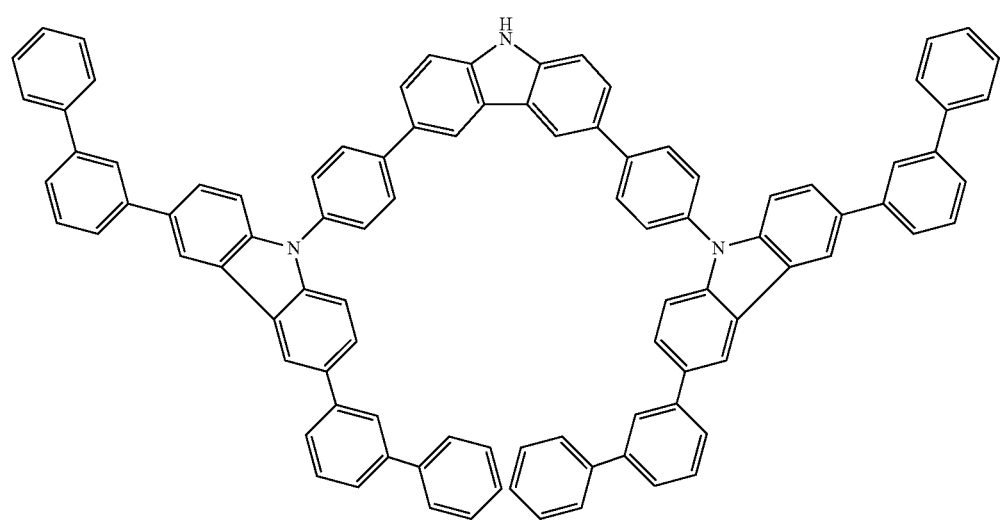
(784)

-continued
(785)
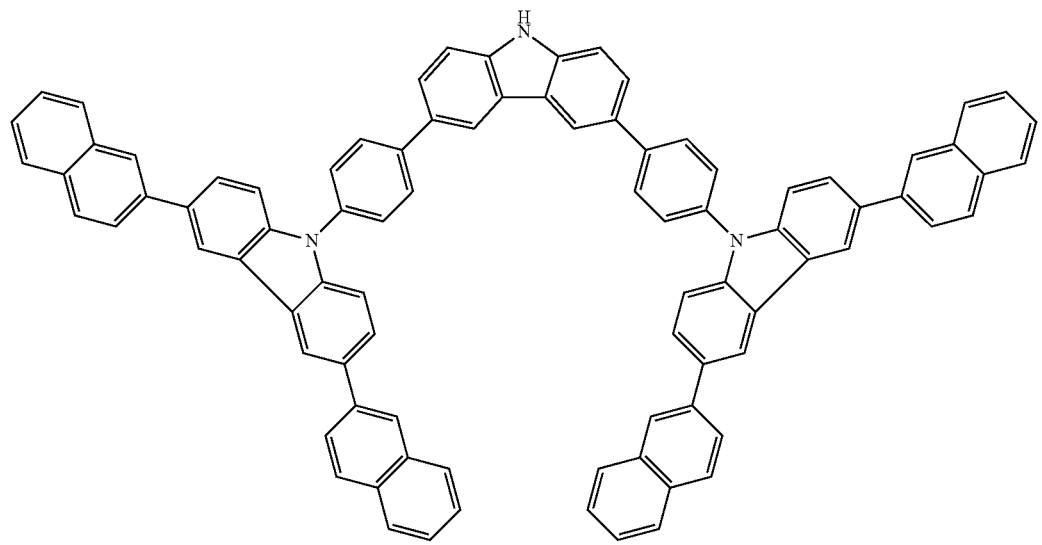
(786)
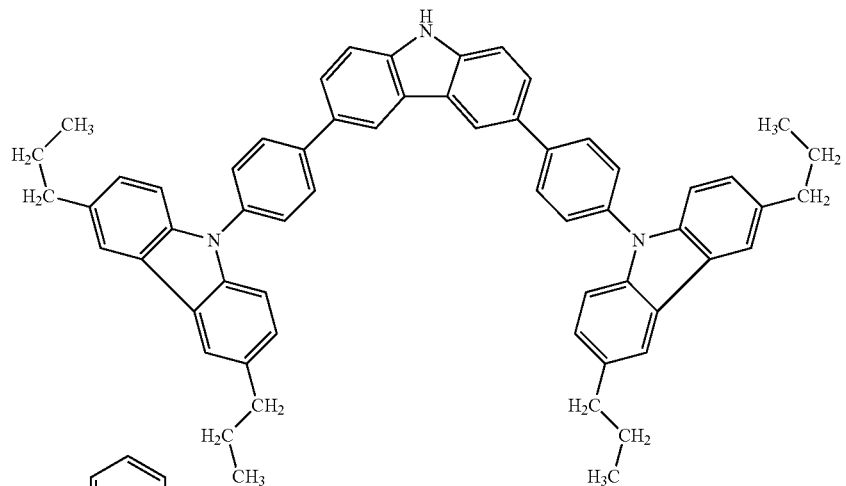
(787)
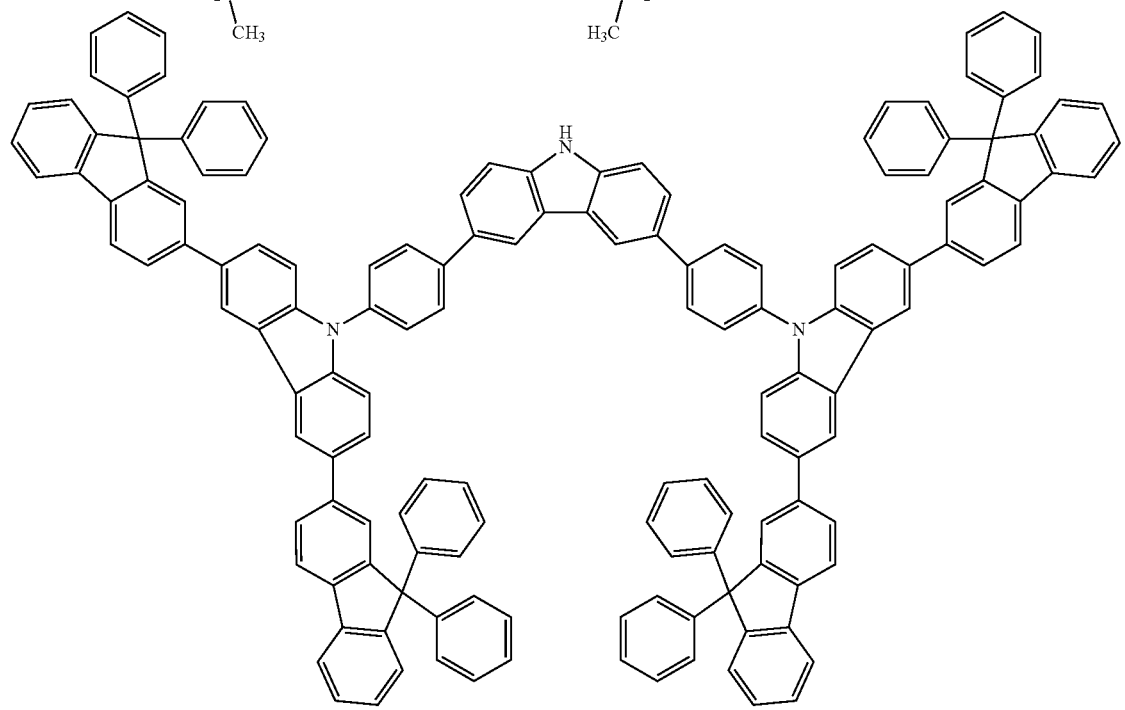

-continued
(788)
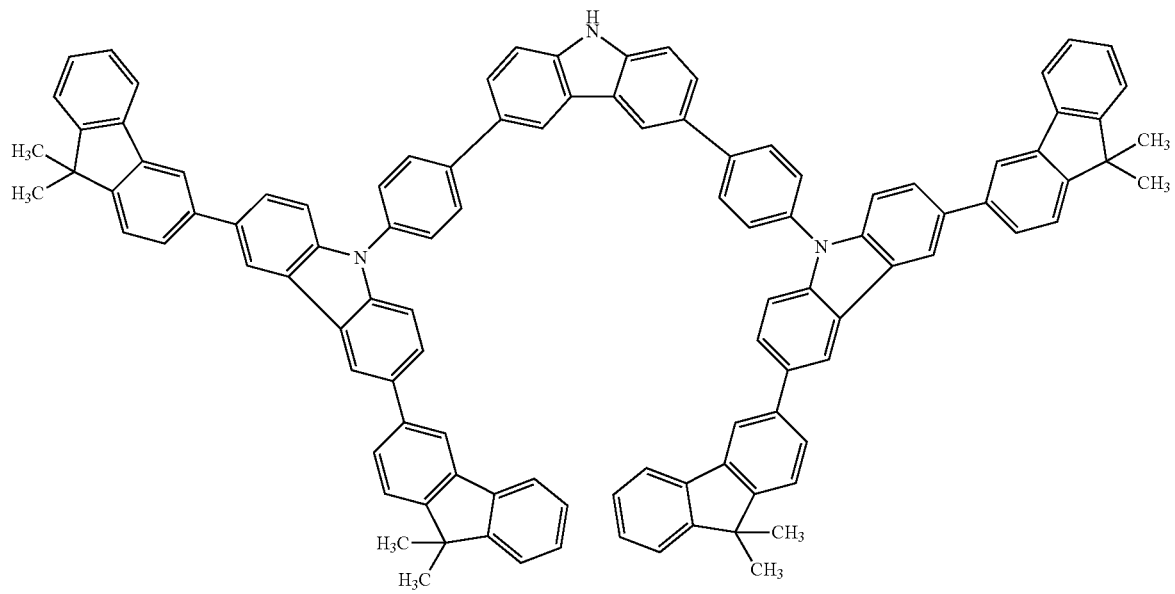
(789)
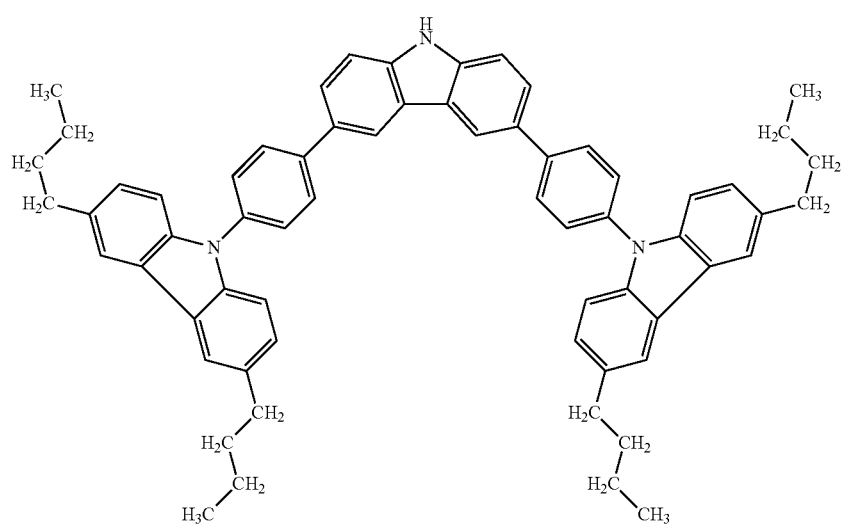
(790)
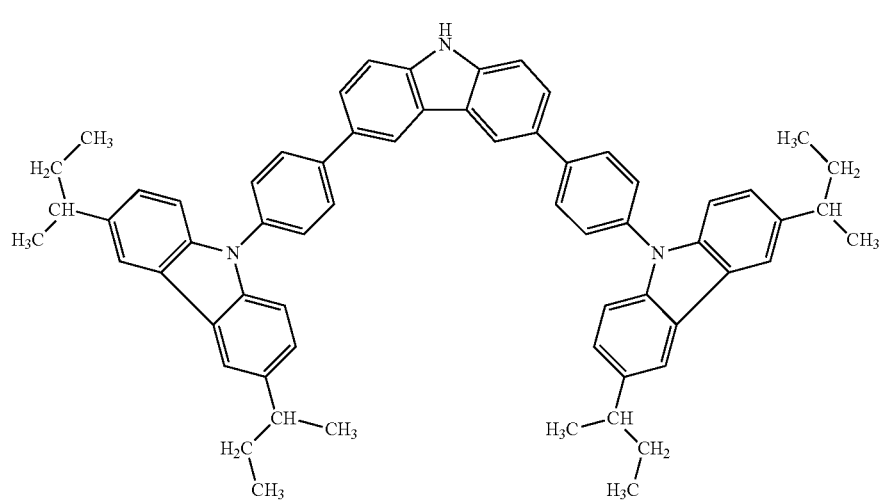

(791)
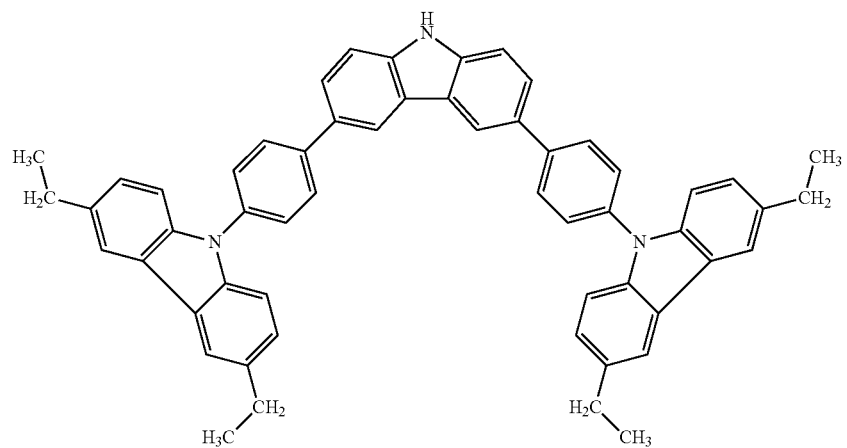
(792)
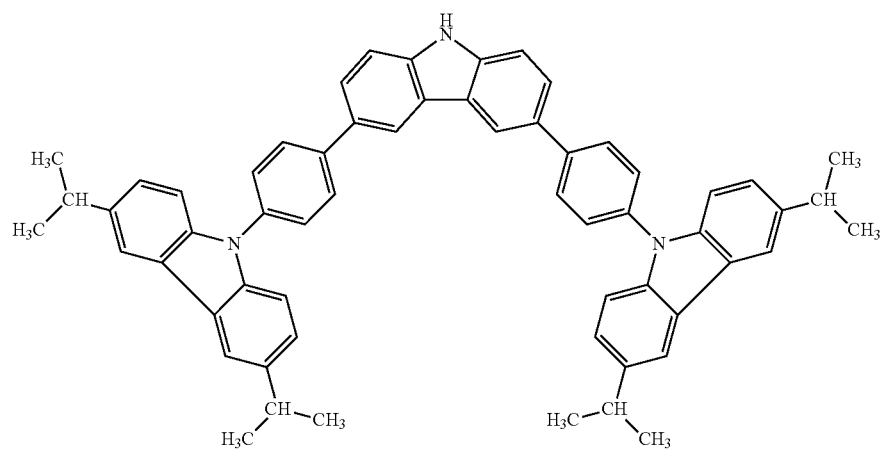
(793)
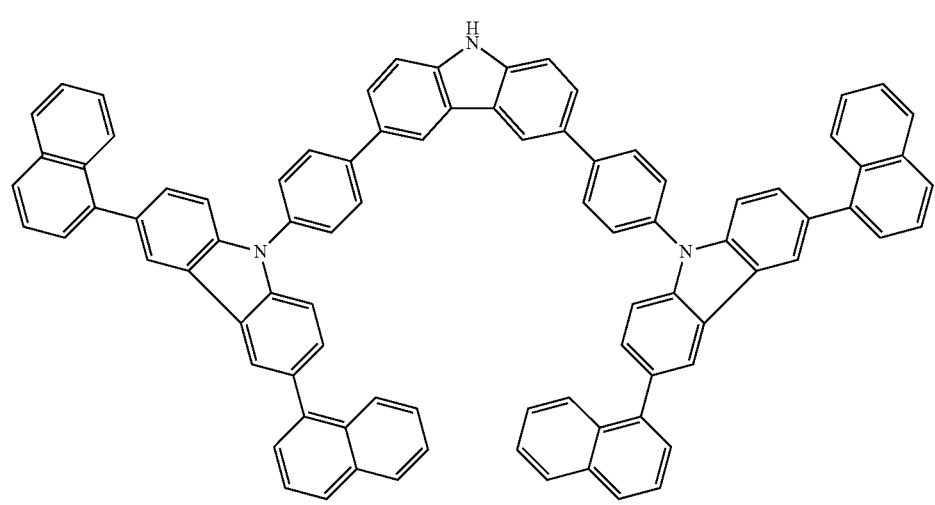

-continued
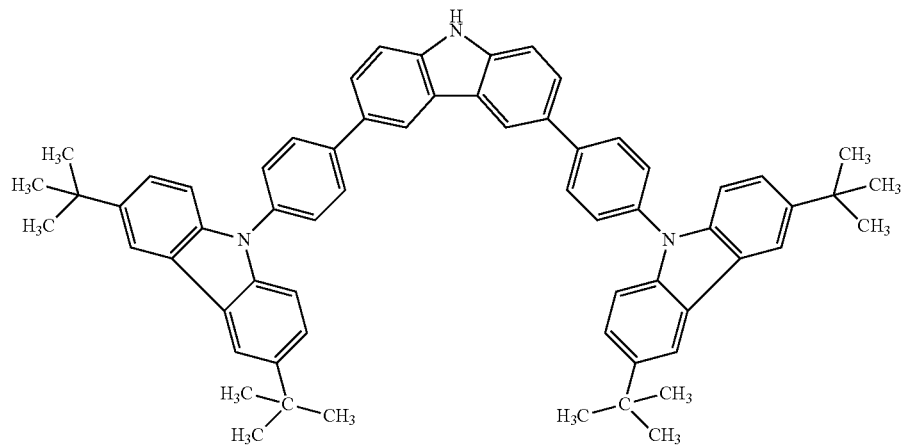
(794)
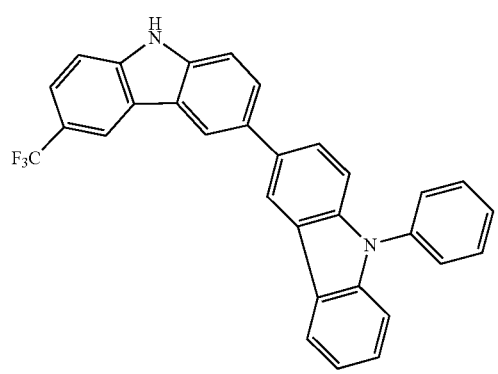
(795)
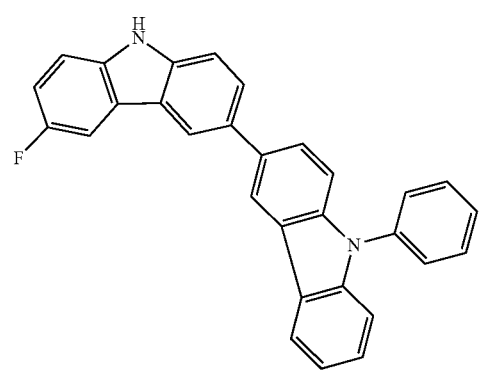
(796)
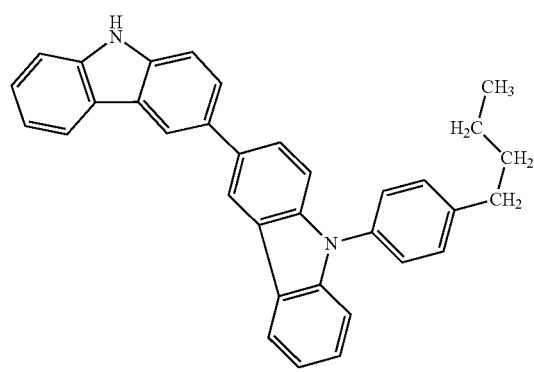
(797)
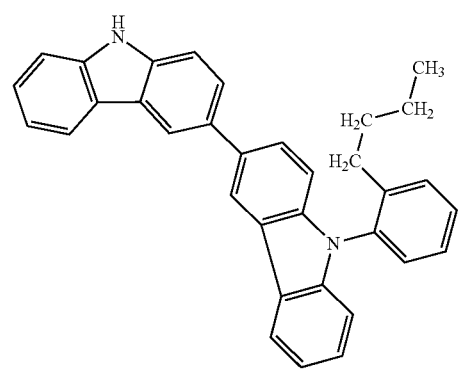
(798)
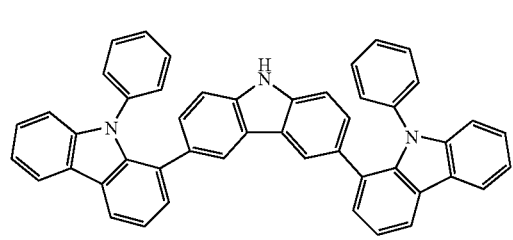
(799)
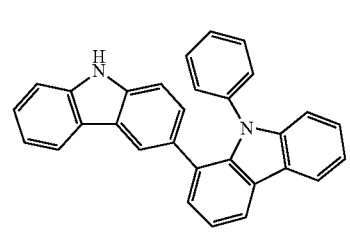
(800)

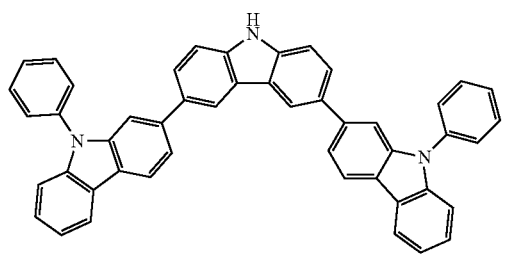
(801)

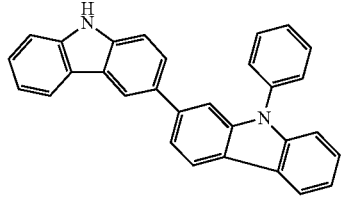
(802)

The above organic compounds can be synthesized by any of a variety of methods. For example, the synthesis can be performed by a similar synthesis method to the one of the compound 5, which is described in Embodiment Mode 1 (the synthesis scheme (a-2)).

(Embodiment Mode 3)

Hereinafter, one mode of a light-emitting element that uses any of the anthracene derivatives of the present invention is described using FIG. 1.

The light-emitting element of the present invention includes a plurality of layers between a pair of electrodes. For the plurality of layers, a combination of layers each including a substance having a high carrier-injecting property or a substance having a high carrier-transporting property is stacked so that a light-emitting region is formed apart from the electrodes, in other words, carriers are recombined in a portion apart from the electrodes.

In this embodiment mode, the light-emitting element includes a first electrode 101, a second electrode 103, and a layer 102 including an organic compound formed between the first electrode 101 and the second electrode 103 is described. In addition, in this embodiment mode, it is assumed that the first electrode 101 serves as an anode and the second electrode 103 serves as a cathode. In other words, in the description below, it is assumed that light emission can be obtained when a voltage is applied to the first electrode 101 and the second electrode 103 so that the potential of the first electrode 101 is higher than that of the second electrode 103.

A substrate 100 is used as a support of the light-emitting element. For the substrate 100, glass, plastic, or the like can be used, for example. It is to be noted that materials other than glass and plastic can be used as long as they can function as a support in a manufacturing process of a light-emitting element.

It is preferred that the first electrode 101 be formed using any of metal, alloy, and an electrically conductive compound each having a high work function (4.0 eV or higher), a mixture thereof, or the like. Specifically, indium tin oxide (ITO), indium tin oxide containing silicon or silicon oxide, indium zinc oxide (IZO), indium oxide containing tungsten oxide and zinc oxide (IWZO), or the like can be used. Films of such electrically conductive metal oxide are typically formed by sputtering, but may also be formed by applying a sol-gel method or the like. For example, indium zinc oxide (IZO) can be formed by a sputtering method using a target in which 1 to 20 wt % of zinc oxide is added to indium oxide. Indium oxide containing tungsten oxide and zinc oxide (IWZO) can be formed by a sputtering method using a target in which 0.5 to 5 wt % of tungsten oxide and 0.1 to 1 wt % of zinc oxide are added to indium oxide. Further, gold (Au), platinum (Pt), nickel (Ni), tungsten (W), chromium (Cr), molybdenum (Mo), iron (Fe), cobalt (Co), copper (Cu), palladium (Pd), nitride of a metal material (e.g., titanium nitride), or the like can be used as the material for the first electrode 101.

There is no particular limitation on a stacked structure of a layer 102 including an organic compound. It is acceptable as long as the layer 102 including an organic compound is formed by any combination of a light-emitting layer described in this embodiment mode, with layers each including a substance having a high electron-transporting property, a substance having a high electron-injecting property, a substance having a high hole-injecting property, a substance having a high hole-transporting property, a bipolar substance (a substance having high electron-transporting and a hole-transporting property), or the like. For example, any combination of a hole-injecting layer, a hole-transporting layer, a hole-blocking layer, a light-emitting layer, an electron-transporting layer, an electron-injecting layer, and the like can be employed. This embodiment mode describes a structure of the EL layer 103, in which a hole-injecting layer 111, a hole-transporting layer 112, a light-emitting layer 113, and an electron-transporting layer 114 are sequentially stacked over the first electrode 101.

The hole-injecting layer 111 is a layer that includes a substance having a high hole-injecting property. As a substance having a high hole-injecting property, molybdenum oxide, vanadium oxide, ruthenium oxide, tungsten oxide, manganese oxide, or the like can be used. Alternatively, the hole-injecting layer 111 can be formed using any one of the following materials: phthalocyanine based compounds such as phthalocyanine ($H_2PC$) and copper phthalocyanine (CuPc); aromatic amine compounds such as 4,4'-bis[N-(4-diphenylaminophenyl)-N-phenylamino]biphenyl (DPAB) and 4,4'-bis(N-{4-[N-(3-methylphenyl)-N-phenylamino]phenyl}-N-phenylamino)biphenyl (DNTPD); high molecular compounds such as poly(ethylenedioxythiophene)/poly(styrenesulfonic acid) (PEDOTTPSS); and the like.

Alternatively, the hole-injecting layer 111 can be formed using a composite material in which an acceptor substance is mixed into a substance having a high hole-transporting property. It is to be noted that a material for forming the electrode can be selected regardless of its work function by use of the composite material in which an acceptor substance is mixed into a substance having a high hole-transporting property. That is, not only a high-work function material, but also a low-work function material can be used for the first electrode 101. Examples of the acceptor substance include 7,7,8,8-tetracyano-2,3,5,6-tetrafluoroquinodimethane ($F_4$-TCNQ); chloranil; transition metal oxide; and oxide of metals that belong to Group 4 to Group 8 of the periodic table. Specifically, any of vanadium oxide, niobium oxide, tantalum oxide, chromium oxide, molybdenum oxide, tungsten oxide, manganese oxide, and rhenium oxide is preferably used because of their high electron accepting properties. In particular, use of molybdenum oxide is more preferable because of its stability in the atmosphere, a low hygroscopic property, and easiness of handling.

As the organic compound used for the composite material, any of a variety of compounds such as an aromatic amine compound, a carbazole derivative, aromatic hydrocarbon, and a high molecular compound (such as an oligomer, a dendrimer, or a polymer) can be used. It is preferable that the organic compound used for the composite material have a high hole-transporting property. Specifically, a substance having a hole mobility of greater than or equal to $10^{-6}$ cm$^2$/Vs is preferably used. It is to be noted that any substance other than the above substances may also be used as long as it is a substance in which the hole-transporting property is higher than the electron-transporting property. The organic compounds that can be used for the composite material are specifically shown below.

Examples of the aromatic amine compound include N,N'-di(p-tolyl)-N,N'-diphenyl-p-phenylenediamine (DTDPPA); 4,4'-bis[N-(4-diphenylaminophenyl)-N-phenylamino]biphenyl (DPAB); 4,4'-bis(N-{4-[N'-(3-methylphenyl)-N'-phenylamino]phenyl}-N-phenylamino)biphenyl (DNTPD), and 1,3,5-tris[N-(4-diphenylaminophenyl)-N-phenylamino]benzene (DPA3B).

Examples of the carbazole derivatives which can be used for the composite material include 3-[N-(9-phenylcarbazol-3-yl)-N-phenylamino]-9-phenylcarbazole (PCzPCA1); 3,6-bis[N-(9-phenylcarbazol-3-yl)-N-phenylamino]-9-phenylcarbazole (PCzPCA2), and 3-[N-(1-naphtyl)-N-(9-phenylcarbazol-3-yl)amino]-9-phenylcarbazole (PCzPCN1). Moreover, 4,4'-di(N-carbazolyl)biphenyl (CBP); 1,3,5-tris[4-(N-carbazolyl)phenyl]benzene (TCPB); 9-[4-(N-carbazolyl)]phenyl-10-phenylanthracene (CzPA); 1,4-bis[4-(N-carbazolyl)phenyl]-2,3,5,6-tetraphenylbenzene; or the like can also be used.

Examples of the aromatic hydrocarbon which can be used for the composite material include 2-tert-butyl-9,10-di(2-naphthyl)anthracene (t-BuDNA); 2-tert-butyl-9,10-di(1-naphthyl)anthracene; 9,10-bis(3,5-diphenylphenyl)anthracene (DPPA); 2-tert-butyl-9,10-bis(4-phenylphenyl)anthracene (t-BuDBA); 9,10-di(2-naphthyl)anthracene (DNA); 9,10-diphenylanthracene (DPAnth); 2-tert-butylanthracene (t-BuAnth); 9,10-bis(4-methyl-1-naphthyl)anthracene (DMNA); 2-tert-butyl-9,10-bis[2-(1-naphthyl)phenyl]anthracene; 9,10-bis[2-(1-naphthyl)phenyl]anthracene; 2,3,6,7-tetramethyl-9,10-di(1-naphthyl)anthracene; 2,3,6,7-tetramethyl-9,10-di(2-naphthyl)anthracene; 9,9'-bianthryl; 10,10'-diphenyl-9,9'-bianthryl; 10,10'-bis(2-phenylphenyl)-9,9'-bianthryl; 10,10'-bis[(2,3,4,5,6-pentaphenyl)phenyl]-9,9'-bianthryl; anthracene; tetracene; rubrene; perylene, and 2,5,8,11-tetra(tert-butyl)perylene. Besides these compounds, pentacene, coronene, or the like can also be used. In particular, use of an aromatic hydrocarbon which has a hole mobility of greater than or equal to $1\times10^{-6}$ cm$^2$/Vs and has 14 to 42 carbon atoms is more preferable.

It is to be noted that the aromatic hydrocarbon which can be used for the composite material may have a vinyl skeleton. Examples of the aromatic hydrocarbon having a vinyl skeleton include 4,4'-bis(2,2-diphenylvinyl)biphenyl (DPVBi) and 9,10-bis[4-(2,2-diphenylvinyl)phenyl]anthracene (DPVPA).

Examples of the substance used for the composite material further include high molecular compounds such as poly(N-vinylcarbazole) (PVK), poly(4-vinyltriphenylamine) (PVTPA), poly[N-(4-{N'-[4-(4-diphenylamino)phenyl]phenyl-N'-phenylamino}phenyl)methacrylamide] (PTPDMA); and poly[N,N'-bis(4-butylphenyl)-N,N'-bis(phenyl)benzidine] (Poly-TPD).

The hole-transporting layer 112 is a layer that includes a substance having a high hole-transporting property. Examples of the substance having a high hole-transporting property include aromatic amine compounds such as 4,4'-bis[N-(1-naphthyl)-N-phenylamino]biphenyl (NPB), N,N'-bis(3-methylphenyl)-N,N'-diphenyl-[1,1'-biphenyl]-4,4'-diamine (TPD), 4,4',4"-tris(N,N-diphenylamino)triphenylamine (TDATA), 4,4',4"-tris[N-(3-methylphenyl)-N-phenylamino]triphenylamine (m-MTDATA), and 4,4'-bis[N-(spiro-9,9'-bifluoren-2-yl)-N-phenylamino]-1,1'-biphenyl (BSPB). These substances described here mainly are substances each having a hole mobility of greater than or equal to $10^{-6}$ cm$^2$/Vs It is to be noted that any substance other than the above substances may also be used as long as it is a substance in which the hole-transporting property is higher than the electron-transporting property. The layer that includes a substance having a high hole-transporting property is not limited to a single layer, and may be a stack of two or more layers each including the aforementioned substance.

Alternatively, a high molecular compound such as poly(N-vinylcarbazole) (PVK) or poly(4-vinyltriphenylamine) (PVTPA) can also be used for the hole-transporting layer 112.

The light-emitting layer 113 is a layer that includes a substance having a high light-emitting property. In the light-emitting element of this embodiment mode, the light-emitting layer 113 includes any of the anthracene derivatives of the present invention that are described in Embodiment Mode 1. The anthracene derivatives of the present invention are suitable for application in a light-emitting element as a substance having a high light-emitting property since the anthracene derivatives of the present invention emit blue light.

The electron-transporting layer 114 is a layer that includes a substance having a high electron-transporting property. For example, it is possible to employ a layer made of a metal complex or the like having a quinoline or benzoquinoline skeleton, such as tris(8-quinolinolato)aluminum (Alq), tris(4-methyl-8-quinolinolato)aluminum (Almq$_3$), bis(10-hydroxybenzo[h]quinolinato)beryllium (BeBq$_2$), or bis(2-methyl-8-quinolinolato)(4-phenylphenolato)aluminum (BAlq). Alternatively, a metal complex or the like having an oxazole-based or thiazole-based ligand, such as bis[2-(2-hydroxyphenyl)benzoxazolato]zinc (Zn(BOX)$_2$) or bis[2-(2-hydroxyphenyl)-benzothiazolato]zinc (Zn(BTZ)$_2$) can be used. Instead of the metal complex, 2-(4-biphenylyl)-5-(4-tert-butylphenyl)-1,3,4-oxadiazole (PBD), 1,3-bis[5-(p-tert-butylphenyl)-1,3,4-oxadiazol-2-yl]benzene (OXD-7), 3-(4-biphenylyl)-4-phenyl-5-(4-tert-butylphenyl)-1,2,4-triazole (TAZ), bathophenanthroline (BPhen), bathocuproine (BCP), or the like can also be used. The substances described here mainly are substances each having an electron mobility of greater than or equal to $10^{-6}$ cm$^2$/Vs. It is to be noted that any substance other than the above substances may also be used as long it is a substance in which the electron-transporting property is higher than the hole-transporting property. Furthermore, the electron-transporting layer 114 is not limited to a single layer, and may be a stack of two or more layers each including the aforementioned substance.

For the electron-transporting layer 114, a high molecular compound can be used. For example, poly[(9,9-dihexylfluorene-2,7-diyl)-co-(pyridin-3,5-diyl)] (PF-Py), poly[(9,9-dioctylfluorene-2,7-diyl)-co-(2,2'-bipyridin-6,6'-diyl)] (PF-BPy), or the like can be used.

The second electrode 103 can be formed using any of metal, alloy, and an electrically conductive compound each having a low work function (3.8 eV or lower), a mixture of them, or the like. Specific examples of such cathode materials include elements belonging to Group 1 or 2 of the periodic table, i.e., alkali metals such as lithium (Li) and cesium (Cs) and alkaline earth metals such as magnesium (Mg), calcium (Ca), and strontium (Sr); alloys of them (e.g., MgAg and AlLi); rare earth metals such as europium (Eu) and ytterbium (Yb), and alloys of them. However, when the electron-injecting layer is provided between the second electrode 103 and the electron-transporting layer, any of a variety of conductive materials such as Al, Ag, ITO, and ITO containing silicon or silicon oxide can be used for the second electrode 103 regardless of its work function. Films of these electrically conductive materials can be formed by a sputtering method, an ink-jet method, a spin coating method, or the like.

As the layer having a function of promoting electron injection, an alkali metal, an alkaline earth metal, or a compound thereof, such as lithium fluoride (LiF), cesium fluoride (CsF), or calcium fluoride ($CaF_2$) can be used. Alternatively, a layer that includes a substance having an electron-transporting property and an alkali metal, an alkaline earth metal, or a compound thereof (Alq including magnesium (Mg) for example) can be used. The use of such a layer as an electron-injecting layer is advantageous because electron injection from the second electrode 103 proceeds efficiently.

Any of a variety of methods can be employed for forming the layer 102 including an organic compound regardless of whether it is a dry process or a wet process. For example, a vacuum evaporation method, an ink-jet method, a spin coating method, or the like can be used. Further, different deposition methods may be employed for each electrode or layer.

Similarly, the electrodes may be formed by a wet process such as a sol-gel process or by a wet process using a metal paste. Alternatively, the electrodes may be formed by a dry process such as a sputtering method or a vacuum evaporation method.

Hereinafter, a specific fabrication method of a light-emitting element is described. In the case where a light-emitting element of the present invention is applied to a display device and a light-emitting layer for each color is fanned separately, it is preferable to form the light-emitting layer by a wet process. By forming the light-emitting layers by a wet process such as an inkjet method, the formation of the light-emitting layers for the respective colors becomes easy even when a large substrate is used.

For example, in the structure described in this embodiment mode, the first electrode may be formed by a sputtering method, which is a dry process; the hole-injecting layer may be formed by an inkjet method or a spin coating method, which are wet processes; the hole-transporting layer may be formed by a vacuum evaporation method, which is a dry process; the light-emitting layer may be formed by an inkjet method, which is a wet process; the electron-injecting layer may be formed by a co-deposition method, which is a dry process; and the second electrode may be formed by an inkjet method or a spin coating method, which are wet processes. Alternatively, the first electrode may be formed by an inkjet method, which is a wet process; the hole-injecting layer may be formed by a vacuum evaporation method, which is a dry process; the hole-transporting layer may be formed by an inkjet method or a spin coating method, which are wet processes; the light-emitting layer may be formed by an inkjet method, which is a wet process; the electron-injecting layer may be formed by an inkjet method or a spin coating method, which are wet processes; and the second electrode may be formed by an inkjet method or a spin coating method, which are wet processes. It is to be noted that a wet process and a dry process can be combined as appropriate, without being limited to the above methods.

Further alternatively, for example, the first electrode can be formed by a sputtering method, which is a dry process; the hole-injecting layer and the hole-transporting layer can be formed by an inkjet method or a spin coating method, which are wet processes; the light-emitting layer can be formed by an inkjet method, which is a wet process; the electron-injecting layer can be formed by a vacuum evaporation method, which is a dry process; and the second electrode can be formed by a vacuum evaporation method, which is a dry process. In other words, on a substrate provided with the first electrode having a desired shape, a wet process can be employed for the formation of the hole-injecting layer to the light-emitting layer, and a dry process can be employed for the formation of the electron-injecting layer to the second electrode. In this method, the hole-injecting layer to the light-emitting layer can be formed at atmospheric pressure and the light-emitting layers for respective colors can be easily formed separately. In addition, from the electron-injecting layer to the second electrode can be formed in vacuum consistently. Therefore, the process can be simplified and productivity can be improved.

In the light-emitting element of the present invention having the structure as described above, the potential difference generated between the first electrode 101 and the second electrode 103 makes a current flow, whereby holes and electrons are recombined in the light-emitting layer 113 that is a layer including a high light-emitting property and thus light is emitted. That is, a light-emitting region is formed in the light-emitting layer 113.

It is to be noted that the structure of the layers provided between the first electrode 101 and the second electrode 103 is not limited to the above, and may be any structure as long as the light-emitting region for recombination of holes and electrons is positioned away from the first electrode 101 and the second electrode 103 so as to suppress quenching which would otherwise be caused by the proximity of the light-emitting region to metal.

That is, there is no particular limitation on the stacked structure of the layers. It is acceptable as long as the layer including any of the anthracene derivatives of the present invention is freely combined with the layers each including a substance having a high electron-transporting property, a substance having a high hole-transporting property, a substance having a high electron-injecting property, a substance having a high hole-injecting property, a bipolar substance (a substance having high electron-transporting and a hole-transporting property), or a hole-blocking material.

As shown in this embodiment mode, each of the anthracene derivatives of the present invention can be used for a light-emitting layer without any need for any other light-emitting substance, since the anthracene derivatives emit blue light.

Since each of the anthracene derivatives of the present invention have a high quantum yield, a light-emitting element that uses any of the anthracene derivatives of the present invention for a light-emitting element can be made to have high emission efficiency. Also, since the anthracene derivatives of the present invention are stable with respect to repetitive redox reactions, a light-emitting element that uses any of the anthracene derivatives can be made to have a long life.

Since the light-emitting element that uses any of the anthracene derivatives of the present invention can emit blue light at high efficiency, the light-emitting element is suitable for use in a full-color display. Further, since the light-emitting element can emit blue light with a long life, the light-emitting element is suitable for use in a full-color display. In particular, blue light-emitting elements are less developed in terms of life and efficiency than green light-emitting elements and red light-emitting elements; therefore, blue light-emitting elements having good characteristics are expected. The light-emitting element that uses any of the anthracene derivatives of the present invention can emit blue light at high efficiency and a long life, and thus is suitable for a full-color display.
(Embodiment Mode 4)

In Embodiment Mode 4, a light-emitting element having a different structure from that described in Embodiment Mode 3 is described.

In this embodiment mode, the light-emitting layer 113 shown in Embodiment Mode 2 has a structure in which any of the anthracene derivatives of the present invention is dispersed into another substance, whereby light emission can be obtained from the anthracene derivative of the present invention. Since the anthracene derivatives of the present invention emit blue light, a light-emitting element that emits blue light can be obtained.

Any of a variety of materials can be used as the substance in which one of the anthracene derivatives of the present invention is dispersed. In addition to the substance having a high hole-transporting property and the substance having a high electron-transporting property, which are described in Embodiment Mode 2, 4,4'-di(N-carbazolyl)-biphenyl (CBP), 2,2',2''-(1,3,5-benzenetriyl)-tris[1-phenyl-1H-benzimidazole] (TPBI), 9,10-di(2-naphthyl)anthracene (DNA), 2-tert-butyl-9,10-di(2-naphthyl)anthracene (t-BuDNA), or the like can be used. Further, as the substance in which one of the anthracene derivatives of the present invention is dispersed, a high molecular compound can be used. For example, poly(N-vinylcarbazole) (PVK); poly(4-vinyltriphenylamine) (PVTPA); poly[N-(4-{N'-[4-(4-diphenylamino)phenyl]phenyl-N'-phenylamino}phenyl)methacrylamide] (PTPDMA); poly[N,N'-bis(4-butylphenyl)-N,N'-bis(phenyl)benzidine] (Poly-TPD), poly[(9,9-dihexylfluorene-2,7-diyl)-co-(pyridine-3,5-diyl)] (PF-Py); poly[(9,9-dioctylfluorene-2,7-diyl)-co-(2,2'-bipyridine-6,6'-diyl)] (PF-BPy), or the like can be used.

Since the anthracene derivatives of the present invention have high emission efficiency, a light-emitting element with high emission efficiency can be obtained by use of any of the anthracene derivatives of the present invention in a light-emitting element. Also, by use of any of the anthracene derivatives of the present invention in a light-emitting element, a light-emitting element with a long life can be obtained.

Further, since a light-emitting element that uses any of the anthracene derivatives of the present invention can emit blue light at high efficiency, the light-emitting element can be suitable for use in a full-color display. In addition, since the light-emitting element that uses any of the anthracene derivatives of the present invention can emit blue light with a long life, the light-emitting element can be suitable for use in a full-color display.

It is to be noted that, regarding the layers other than the light-emitting layer 113, the structure shown in Embodiment Mode 3 can be as appropriate used.
(Embodiment Mode 5)

In Embodiment Mode 5, a light-emitting element with a structure different from the structures described in Embodiment Modes 3 and 4 is described.

The light-emitting layer 113 shown in Embodiment Mode 3 has a structure in which a light-emitting substance is dispersed into any of the anthracene derivatives of the present invention, whereby light emission from the light-emitting substance can be obtained.

When any of the anthracene derivatives of the present invention is used as a material in which another light-emitting substance is dispersed, a color generated by the light-emitting substance can be obtained. Further, a mixture of a color generated by the anthracene derivative of the present invention and a color generated by the light-emitting substance dispersed in the anthracene derivative can also be obtained.

In this case, any of a variety of materials can be used as the light-emitting substance dispersed in the anthracene derivative of the present invention. Specifically, examples of fluorescent substances that emit fluorescence include N,N'-diphenylquinacridon (DPQd), coumarin 6, coumarin 545T, 4-(dicyanomethylene)-2-methyl-6-(p-dimethylaminostyryl)-4H-pyran (DCM1), 4-(dicyanomethylene)-2-methyl-6-(julolidin-4-yl-vinyl)-4H-pyran (DCM2), N,N-dimethylquinacridone (DMQd), {2-(1,1-dimethylethyl)-6-[2-(2,3,6,7-tetrahydro-1,1,7,7-tetramethyl-1H,5H-benzo[ij]quinolizin-9-yl)ethenyl]-4H-pyran-4-ylidene}propanedinitrile (DCJTB), 5,12-diphenyltetracene (DPT), 4-(9H-carbazol-9-yl)-4'-(10-phenyl-9-anthryl)triphenylamine (YGAPA), 4,4'-(2-tert-butylanthracen-9,10-diyl)bis{N-[4-(9H-carbazol-9-yl)phenyl]-N-phenylaniline} (YGABPA), N,9-diphenyl-N-[4-(10-phenyl-9-anthryl)phenyl]-9H-carbazol-3-amine (PCAPA), N,N''-(2-tert-butylanthracene-9,10-diyldi-4,1-phenylene)bis[N,N',N'-triphenyl-1,4-phenylenediamine] (DPABPA), N,N'-bis[4-(9H-carbazol-9-yl)phenyl]-N,N'-diphenylstilbene-4,4'-diamine (YGA2S), N-[4-(9H-carbazol-9-yl)phenyl]-N-phenylstilben-4-amine (YGAS), N,N'-diphenyl-N,N'-bis(9-phenylcarbazol-3-yl)stilben-4,4'-diamine (PCA2S), 4,4'-bis(2,2-diphenylvinyl)biphenyl (DPVBi), 2,5,8,11-tetra(tert-butyl) perylene (TBP), perylene, rubrene, and 1,3,6,8-tetraphenylpyrene. Moreover, examples of phosphorescent substances that emit phosphorescence include (acetylacetonato)bis[2,3-bis(4-fluorophenyl)quinoxalinato]iridium(III) (Ir(Fdpq)$_2$(acac)), and (2,3,7,8,12,13,17,18-octaethyl-21H,23H-porphyrinato)platinum(II) (PtOEP).

It is to be noted that, regarding the layers other than the light-emitting layer 113, the structure shown in Embodiment Mode 3 can be appropriately used.
(Embodiment Mode 6)

In Embodiment Mode 6, a light-emitting element with a structure different from those of Embodiment Modes 3 to 5 is described.

Anthracene derivatives of the present invention each have a hole-transporting property. Therefore, a layer including any of the anthracene derivatives of the present invention can be used between an anode and a light-emitting layer. Specifically, the anthracene derivatives of the present invention can be used in the hole-injecting layer 111 and/or the hole-transporting layer 112 described in Embodiment Mode 2.

Also, in the case of applying any of the anthracene derivatives of the present invention as the hole-injecting layer 111, it is preferable to compose the anthracene derivative of the present invention and an inorganic compound having an electron accepting property with respect to the anthracene derivative of the present invention. By use of such a composite material, the carrier density increases, which contributes to improvement of the hole-injecting property and hole-transporting property. Also, in the case of using the composite material in the hole-injecting layer 111, the hole-injecting layer 111 can achieve an ohmic contact with the first electrode 101; therefore, a material of the first electrode 101 can be selected regardless of work function.

As the inorganic compound used for the composite material, an oxide of a transition metal is preferably used. Moreover, an oxide of metals belonging to Groups 4 to 8 in the periodic table can be used. Specifically, it is preferable to use vanadium oxide, niobium oxide, tantalum oxide, chromium oxide, molybdenum oxide, tungsten oxide, manganese oxide, or rhenium oxide, because of its high electron accepting property. Among them, use of molybdenum oxide is especially preferable since it is stable in the air, has a low hygroscopic property, and is easily treated.

It is to be noted that this embodiment mode can be combined with any other embodiment mode as appropriate.
(Embodiment Mode 7)

Figure 2:
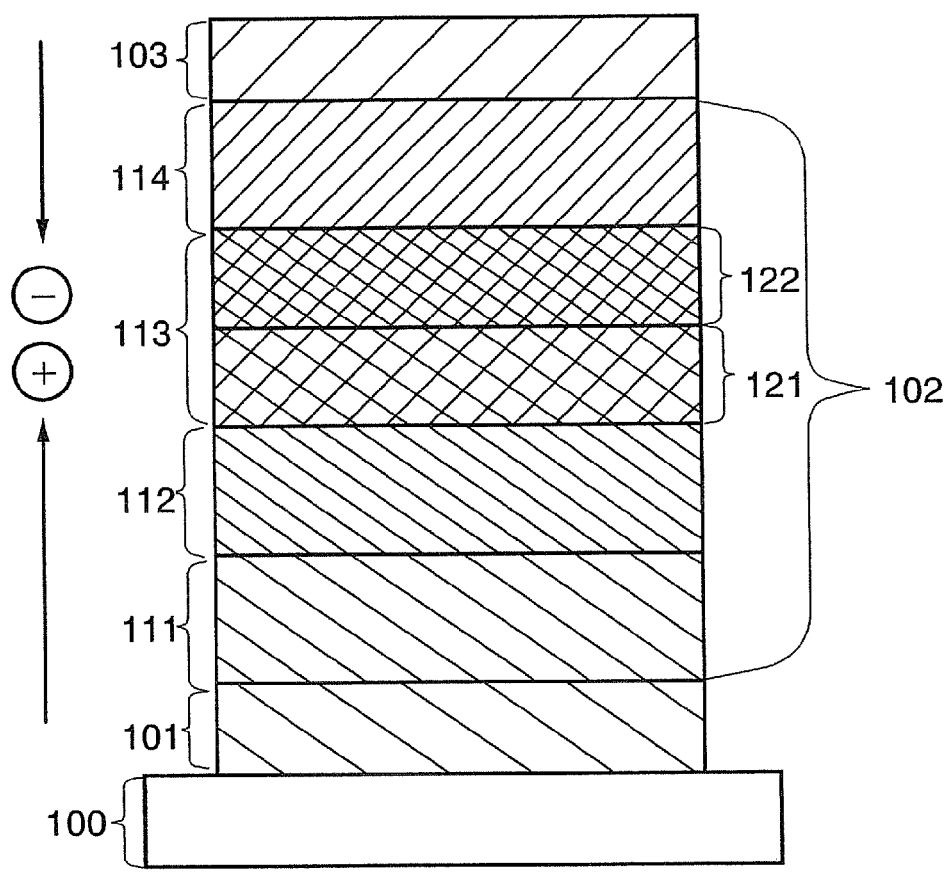
FIG. 2 illustrates a light-emitting element of the present invention.

In Embodiment Mode 7, a light-emitting element having a structure different from the structures described in Embodiment Modes 3 to 6 is described using FIG. 2.

In the light-emitting element described in this embodiment mode, a first layer 121 and a second layer 122 are provided in the light-emitting layer 113 of the light-emitting element described in Embodiment Mode 2.

The light-emitting layer 113 is a layer that includes a substance having a high light-emitting property. In the light-emitting element of the present invention, the light-emitting layer has the first layer 121 and the second layer 122. The first layer 121 includes a first organic compound and an organic compound having a hole-transporting property, and the second layer 122 includes a second organic compound and an electron-transporting organic compound. The first layer 121 is provided on the first electrode side of the second layer 122, in other words, on the anode side of the second layer 122.

Each of the first organic compound and the second organic compound is a substance having a high light-emitting property, for which any of a variety of materials can be used. Specifically, examples of fluorescent substances that emit fluorescence include N,N'-diphenylquinacridon (DPQd), coumarin 6, coumarin 545T, 4-(dicyanomethylene)-2-methyl-6-(p-dimethylaminostyryl)-4H-pyran (DCM1), 4-(dicyanomethylene)-2-methyl-6-(julolidin-4-yl-vinyl)-4H-pyran (DCM2), N,N-dimethylquinacridone (DMQd), {2-(1,1-dimethylethyl)-6-[2-(2,3,6,7-tetrahydro-1,1,7,7-tetramethyl-1H,5H-benzo[ij]quinolizin-9-yl)ethenyl]-4H-pyran-4-ylidene}propanedinitrile (DCJTB), 5,12-diphenyltetracene (DPT), 4-(9H-carbazol-9-yl)-4'-(10-phenyl-9-anthryl)triphenylamine (YGAPA), 4,4'-(2-tert-butylanthracen-9,10-diyl)bis{N-[4-(9H-carbazol-9-yl)phenyl]-N-phenylaniline} (YGABPA), N,9-diphenyl-N-[4-(10-phenyl-9-anthryl)phenyl]-9H-carbazole-3-amine (PCAPA), N,N"-(2-tert-butylanthracene-9,10-diyldi-4,1-phenylene)bis[N,N',N'-triphenyl-1,4-phenylenediamine] (DPABPA), N,N'-bis[4-(9H-carbazol-9-yl)phenyl]-N,N'-diphenylstilbene-4,4'-diamine (YGA2S), N-[4-(9H-carbazol-9-yl)phenyl]-N-phenylstilbene-4-amine (YGAS), N,N'-diphenyl-N,N'-bis(9-phenylcarbazol-3-yl)stilbene-4,4'-diamine (PCA2S), 4,4'-bis(2,2-diphenylvinyl)biphenyl (DPVBi), 2,5,8,11-tetra(tert-butyl)perylene (TBP), perylene, rubrene, and 1,3,6,8-tetraphenylpyrene. The first organic compound and the second organic compound may be the same or different from one another.

The organic compound having a hole-transporting property included in the first layer 121 is a substance in which the hole-transporting property is higher than the electron-transporting property, and any of the anthracene derivatives of the present invention can be preferably used as this organic compound. The organic compound having an electron-transporting property included in the second layer 122 is a substance in which the electron-transporting property is higher than the hole-transporting property.

A mechanism of the light-emitting element of the present invention having the above-described structure is described below using FIG. 2.

In FIG. 2, holes injected from the first electrode 101 are injected into the first layer 121. The holes injected into the first layer 121 are transported through the first layer 121 and further injected into the second layer 122. At this time, the organic compound having an electron-transporting property included in the second layer 122 is a substance in which having the electron-transporting property is higher than the hole-transporting property, and thus, the holes injected into the second layer 122 become difficult to move. Consequently, a large number of holes are present near the interface between the first layer 121 and the second layer 122. In addition, occurrence of a phenomenon in which holes reach the electron-transporting layer 114 without recombining with electrons can be suppressed.

On the other hand, electrons injected from the second electrode 103 are injected into the second layer 122. The electrons injected into the second layer 122 are transported through the second layer 122 and further injected into the first layer 121. At this time, the organic compound having a hole-transporting property included in the first layer 121 is a substance in which having the hole-transporting property is higher than the electron-transporting property, and thus, the electrons injected into the first layer 121 become difficult to move. Consequently, a large number of electrons are present near the interface between the first layer 121 and the second layer 122. In addition, occurrence of a phenomenon in which electrons reach the hole-transporting layer 112 without recombining with holes can be suppressed.

As described above, a large number of holes and electrons are present in a region in the vicinity of the interface between the first layer 121 and the second layer 122, so that recombination probability in the region in the vicinity of the interface can be increased. In other words, the light-emitting region is formed in the vicinity of the center of the light-emitting layer 113. As a result, occurrence of a phenomenon in which holes reach the electron-transporting layer 114 without recombining with electrons or electrons reach the hole-transporting layer 112 without recombining with holes can be suppressed, so that reduction in recombination probability can be prevented. Thus, reduction of carrier balance over time can be prevented, which leads to improvement of reliability.

In order that holes and electrons are injected into the first layer 121, the organic compound having a hole-transporting property can be oxidized and reduced, and it is preferred that it have the highest occupied molecular orbital level (HOMO level) of greater than or equal to −6.0 eV and less than or equal to −5.0 eV as well as the lowest unoccupied molecular orbital level (LUMO level) of greater than or equal to −3.0 eV and less than or equal to −2.0 eV. Accordingly, use of the anthracene derivatives of the present invention is preferable.

Similarly, in order that holes and electrons are injected into the second layer 122, it is necessary that the organic compound having a hole-transporting property is an organic compound which can be oxidized and reduced, and it is preferred that it have the HOMO level of greater than or equal to −6.0 eV and less than or equal to −5.0 eV as well as the LUMO level of greater than or equal to −3.0 eV and less than or equal to −2.0 eV.

As such an organic compound which can be oxidized or reduced, a tricyclic polyacene derivative, a tetracyclic polyacene derivative, a pentacyclic polyacene derivative, or a hexacyclic polyacene derivative is used. Specifically, an anthracene derivative, a phenanthrene derivative, a pyrene derivative, a chrysene derivative, a dibenzo[g,p]chrysene derivative, or the like is used. For example, as an compound having an electron-transporting property, which can be used for the second layer, 9-[4-(N-carbazolyl)]phenyl-10-phenylanthracene (CzPA), 3,6-diphenyl-9-[4-(10-phenyl-9-anthryl)phenyl]-9H-carbazole (DPCzPA), 9,10-bis(3,5-diphenylphenyl)anthracene (DPPA), 9,10-di(2-naphthyl)anthracene (DNA), 2-tert-butyl-9,10-di(2-naphthyl)anthracene (t-BuDNA), 9,9'-bianthryl (BANT), 9,9'-(stilben-3,3'-diyl)diphenanthrene (DPNS), 9,9'-(stilben-4,4'-diyl)diphenanthrene (DPNS2), 3,3',3"-(benzene-1,3,5-triyl)tripyrene (TPB3) and the like can be given.

As described above using FIG. 2, the light-emitting element of the present invention is structured so that holes are injected into the second layer 122 from the first layer 121. Thus, it is preferable that the difference in HOMO level between the anthracene derivative used for the organic compound having a hole-transporting property and the organic compound having an electron-transporting property is small. Further, since the light-emitting element of the present invention is structured so that electrons are injected into the first layer 121 from the second layer 122, it is preferable that the difference in LUMO level between the anthracene derivative used for the organic compound having a hole-transporting property and the organic compound having an electron-transporting property is small. If the difference in HOMO level between the organic compound having a hole-transporting property and the organic compound having an electron-transporting property is large, the light-emitting region is localized on the first layer side or the second layer side. Similarly, if the difference in LUMO level between the organic compound having a hole-transporting property and the organic compound having an electron-transporting property is large, the light-emitting region is localized on the first layer side or the second layer side. Accordingly, the difference between the HOMO level of the anthracene derivative used for the organic compound having a hole-transporting property and the HOMO level of the organic compound having an electron-transporting property is preferably 0.3 eV or less, and more preferably 0.1 eV or less. The LUMO level of the anthracene derivative used for the organic compound having a hole-transporting property and the LUMO level of the organic compound having an electron-transporting property is preferably 0.3 eV or less, and more preferably 0.1 eV or less.

Since light is emitted from the light-emitting element by recombination of electrons and holes, it is preferable that the organic compound used for the light-emitting layer 113 be stable with respect to repetitive redox reactions. In other words, it is preferable that the organic compound be able to be reversibly oxidized and reduced. It is preferable that, in particular, the organic compound having a hole-transporting property and the organic compound having an electron-transporting property be stable with respect to repetitive redox reactions. Accordingly, any of the anthracene derivatives of the present invention is suitable for use as the organic compound having a hole-transporting property. Whether the organic compounds are stable with respect to repetitive redox reactions or not can be confirmed by cyclic voltammetry (CV) measurement.

Specifically, whether the organic compounds are stable with respect to repetitive redox reactions or not can be confirmed by measurement of changes in an oxidation peak potential ($E_{pa}$) of an oxidation reaction of the organic compound or a reduction peak potential ($E_{pc}$) of an reduction reaction, changes in the peak shape, and the like. In the organic compound having a hole-transporting property and the organic compound having an electron-transporting property used for the light-emitting layer 113, the amount of change in the intensity of the oxidation peak potential or the intensity of the reduction peak potential is preferably less than 50%, and more preferably less than 30%. In other words, for example, a peak intensity of 50% or higher, more preferably, a peak intensity of 70% is kept, even if the oxidation peak potential decreases. In addition, the amount of change of the values of the oxidation peak potential or the reduction peak potential is preferably 0.05 V or lower, more preferably, 0.02 V or lower.

When the substance having a high light-emitting property included in the first layer and the substance having a high light-emitting property included in the second layer are the same, light can be emitted in the vicinity of the center of the light-emitting layer. In contrast, when the substance having a high light-emitting property included in the first layer and the substance having a high light-emitting property included in the second layer are different, there is a possibility that light is emitted from only one of the first layer and the second layer. Therefore, it is preferred that the substance having a light-emitting property included in the first layer and the substance having a light-emitting property included in the second layer be the same.

In the light-emitting element described in this embodiment mode, a light-emitting region is formed in the vicinity of the center of the light-emitting layer, not at the interface between the light-emitting layer and the hole-transporting layer or at the interface between the light-emitting layer and the electron-transporting layer. Accordingly, the light-emitting element is not affected by deterioration due to proximity of the light-emitting region to the hole-transporting layer or the electron-transporting layer. Therefore, the light-emitting element with a small amount of deterioration and a long life can be obtained. Furthermore, since the light-emitting layer in the light-emitting element of the present invention includes the compound that is stable with respect to repetitive redox reactions, there is little deterioration of the light-emitting layer after light emission by recombination of holes and electrons are repeated. Therefore, a light-emitting element that has a longer life can be obtained.

Further, since the anthracene derivatives of the present invention are suitable for excitation of a substance having a high light-emitting element property that exhibits blue to blue green light, the element structure shown in this embodiment mode is particularly effective for a light-emitting element for bluish color and a light-emitting element for blue-greenish color. Blue color is needed for fabrication of a full-color display, and a problem of the deterioration can be solved by applying the present invention. It is natural that the anthracene derivatives of the present invention may be used for a light-emitting element of a green or red color. This embodiment mode can be combined with any other embodiment mode as appropriate.

(Embodiment Mode 8)

In Embodiment Mode 7, a light-emitting element in which a plurality of light-emitting units according to the present invention is stacked (hereinafter, referred to as a stacked type element) is described using FIG. 3. This light-emitting element is a stacked type light-emitting element that has a plurality of light-emitting units between a first electrode and a second electrode. Each light-emitting unit can have a structure similar to that of the layer 102 including an organic compound described in Embodiment Modes 2 to 6 can be used for. In other words, the light-emitting elements described in Embodiment Modes 2 to 6 are each a light-emitting element having one light-emitting unit. In this embodiment mode, a light-emitting element having a plurality of light-emitting units is described.

Figure 3:
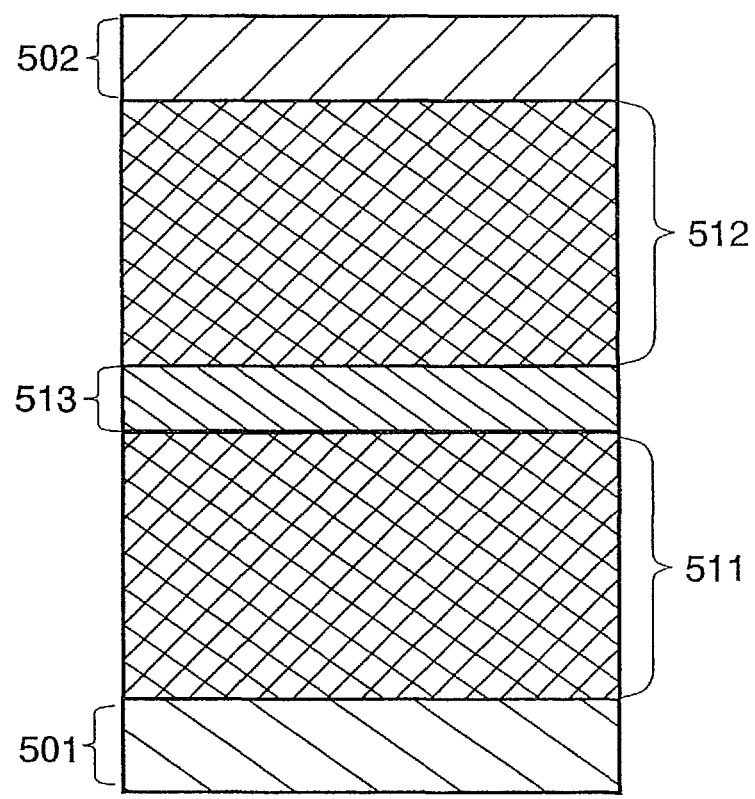
FIG. 3 illustrates a light-emitting element of the present invention.

In FIG. 3, a first light-emitting unit 511 and a second light-emitting unit 512 are stacked between a first electrode 501 and a second electrode 502, a charge generation layer 513 is provided between the first light-emitting unit 511 and the second light-emitting unit 512. Electrodes similar to those described in Embodiment Mode 2 can be applied to the first electrode 501 and the second electrode 502. The first light-emitting unit 511 and the second light-emitting unit 512 may have the same structure or different structures, and a structure similar to those described in Embodiment Modes 2 to 6 can be applied.

The charge generation layer 513 includes a composite material of an organic compound and metal oxide. The composite material of an organic compound and metal oxide is described in Embodiment Mode 2 or 5, and includes an organic compound and metal oxide such as vanadium oxide, molybdenum oxide, or tungsten oxide. As the organic compound, a variety of compounds such as an aromatic amine compound, a carbazole derivative, aromatic hydrocarbon, and a high molecular compound (oligomer, dendrimer, polymer, or the like) can be used. An organic compound having a hole mobility of greater than or equal to $1 \times 10^{-6}$ cm$^2$/Vs is preferably applied as the organic compound. However, other substances than these compounds may also be used as long as it is a substance in which the hole-transporting property thereof is higher than the electron-transporting property. The composite material of an organic compound and metal oxide is superior in carrier-injecting property and carrier-transporting property; accordingly, low-voltage driving and low-current driving can be realized.

It is to be noted that the charge generation layer 513 may be formed by a combination of a composite material of an organic compound and metal oxide with another material. For example, the charge generation layer 513 may be formed with a combination of a layer including the composite material of an organic compound and metal oxide with a layer including one compound selected among electron donating substances and a compound having a high electron-transporting property. Further, the charge generation layer 513 may be formed with a combination of a layer including the composite material of an organic compound and metal oxide with a transparent conductive film.

In any case, the charge generation layer 513 interposed between the first light-emitting unit 511 and the second light-emitting unit 512 is acceptable, as long as electrons are injected to one light-emitting unit and holes are injected to the other light-emitting unit when a voltage is applied between the first electrode 501 and the second electrode 502.

In this embodiment mode, the light-emitting element having two light-emitting units is described; however, the present invention can be applied to a light-emitting element in which three or more light-emitting units are stacked, similarly. By arranging a plurality of light-emitting units between a pair of electrodes in such a manner that the plurality of light-emitting units is partitioned with a charge generation layer, high luminance emission can be realized at a low current density, which contributes to enhancement of the life of the light-emitting element. For example, when the light-emitting element is applied to a lighting device, voltage drop due to resistance of an electrode material can be suppressed, which leads to uniform emission in a large area. In other words, a light-emitting device capable of low-voltage driving and low-power consuming can be realized.

This embodiment mode can be combined with any other embodiment mode as appropriate.

(Embodiment Mode 9)

In Embodiment Mode 9, a light-emitting device manufactured using any of the anthracene derivatives of the present invention is described.

In this embodiment mode, a light-emitting device manufactured using any of the anthracene derivatives of the present invention is described using FIGS. 4A and 4B. FIG. 4A is a top view illustrating a light-emitting device, and FIG. 4B is a cross-sectional view of FIG. 4A taken along lines A-A' and B-B'. The light-emitting device have a driver circuit portion (source side driver circuit) 401, a pixel portion 402, and a driver circuit portion (gate side driver circuit) 403 which are indicated by dotted lines. Reference numerals 404 and 405 denote a sealing substrate and a sealing material, respectively. A portion surrounded by the sealing material 405 corresponds to a space 407.

A leading wiring 408 is a wiring for transmitting signals to be inputted to the source side driver circuit 401 and the gate side driver circuit 403, and this wiring 408 receives a video signal, a clock signal, a start signal, a reset signal, and the like from a flexible printed circuit (FPC) 409 which is an external input terminal. It is to be noted that only the FPC is illustrated in this case; however, the FPC may be provided with a printed wiring board (PWB). The category of the light-emitting device in this specification includes not only a light-emitting device itself but also a light-emitting device attached with an FPC or a PWB.

Next, a cross-sectional structure is described using FIG. 4B. The driver circuit portion and the pixel portion are formed over an element substrate 410. In this case, one pixel in the pixel portion 402 and the source side driver circuit 401 which is the driver circuit portion are illustrated.

A CMOS circuit, which is a combination of an n-channel TFT 423 with a p-channel TFT 424, is formed as the source side driver circuit 401. Each driver circuit portion may be any of a variety of circuits such as a CMOS circuit, PMOS circuit, and an NMOS circuit. Although a driver-integration type device, in which a driver circuit is formed over the substrate provided with the pixel portion, is described in this embodiment mode, a driver circuit is not necessarily formed over the same substrate as the pixel portion, but can be formed outside a substrate.

The pixel portion 402 has a plurality of pixels, each of which includes a switching TFT 411, a current control TFT 412, and a first electrode 413 which is electrically connected to a drain of the current control TFT 412. It is to be noted that an insulator 414 is formed so as to cover end portions of the first electrode 413. In this case, the insulator 414 is faulted using a positive photosensitive acrylic resin film.

The insulator 414 is formed so as to have a curved surface having curvature at an upper end portion or lower end portion thereof in order to make the coverage favorable. For example, in the case of using positive photosensitive acrylic as a material for the insulator 414, it is preferable that the insulator 414 be formed so as to have a curved surface with a curvature radius (0.2 µm to 3 µm) only at the upper end portion thereof. The insulator 414 can be formed using either a negative type which becomes insoluble in an etchant by light irradiation or a positive type which becomes soluble in an etchant by light irradiation.

A layer 416 including an organic compound and a second electrode 417 are formed over the first electrode 413. In this case, it is preferred that the first electrode 413 serving as an anode be formed using a high-work function material. For example, the first electrode 413 can be formed using a single-layer film of an ITO film, an indium tin oxide film containing silicon, an indium oxide film containing 2 to 20 wt % of zinc oxide, a titanium nitride film, a chromium film, a tungsten film, a Zn film, a Pt film, or the like; a stack of a titanium nitride film and a film containing aluminum as its main component; a three-layer structure of a titanium nitride film, a film containing aluminum as its main component, and another titanium nitride film; or the like. When the first electrode 413 has a stacked structure, it can have low resistance as a wiring, form a favorable ohmic contact, and further function as an anode.

The layer 406 including an organic compound is formed by any of a variety of methods such as an evaporation method using an evaporation mask, an ink-jet method, and a spin coating method. The layer 406 including an organic compound includes any of the anthracene derivatives of the present invention that are described in Embodiment Mode 1. Further, the layer 406 including an organic compound may be formed using another material such as a low molecular weight compound or a high molecular compound (the category of the high molecular compound includes an oligomer and a dendrimer).

As a material used for the second electrode 417 which is formed over the layer 406 including an organic compound and serves as a cathode, it is preferable that a low-work function material (e.g., Al, Mg, Li, Ca, or an alloy or compound thereof such as MgAg, Mg—In, Al—Li, LiF, or $CaF_2$) be used. In the case where light generated in the layer 406 including an organic compound is transmitted through the second electrode 417, the second electrode 417 may be formed of a stack of a metal thin film having a reduced thickness and a transparent conductive film (e.g., ITO, indium oxide containing 2 to 20 wt % of zinc oxide, indium tin oxide containing silicon or silicon oxide, or zinc oxide (ZnO)).

The sealing substrate 404 is attached to the element substrate 410 with the sealing material 405; thus, a light-emitting element 418 is provided in the space 407 surrounded by the element substrate 410, the sealing substrate 404, and the sealing material 405. It is to be noted that the space 407 is filled with a filler such as an inert gas (e.g., nitrogen or argon) or the sealing material 405.

It is preferable that the sealing material 405 be formed of any of epoxy-based resins and such materials permeate little moisture and oxygen as much as possible. The sealing substrate 404 can be formed of a glass substrate; a quartz substrate; or a plastic substrate including fiberglass-reinforced plastics (FRP), polyvinyl fluoride (PVF), polyester, acrylic, or the like.

Accordingly, a light-emitting device manufactured using any of the anthracene derivatives of the present invention can be obtained.

Since any of the anthracene derivatives described in Embodiment Mode 1 is used for the light-emitting device of the present invention, a light-emitting device having high performance can be obtained. Specifically, a light-emitting device having a long life can be obtained.

Also, since the anthracene derivatives of the present invention have high emission efficiency, a light-emitting device with low power consumption can be provided.

Further, since that the light-emitting element that uses any of the anthracene derivatives of the present invention can emit blue to green light at high efficiency, the anthracene derivatives are suitable for use in a full-color display. Further, since the light-emitting element that uses any of the anthracene derivatives of the present invention can emit blue light with a long life, the anthracene derivatives are suitable for use in full-color displays.

Figure 5A:
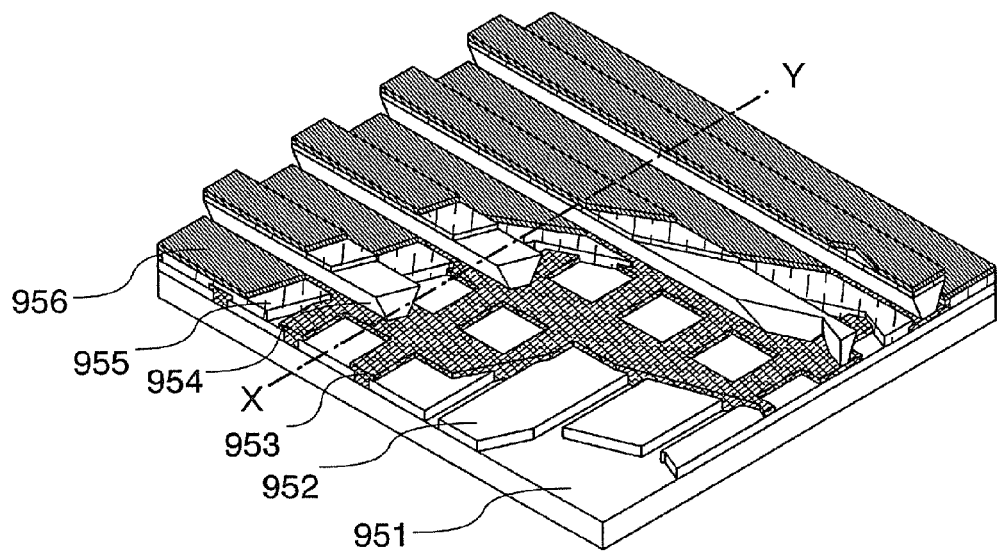
FIGS. 5A and 5B illustrate a light-emitting device of the present invention.
Figure 5B:
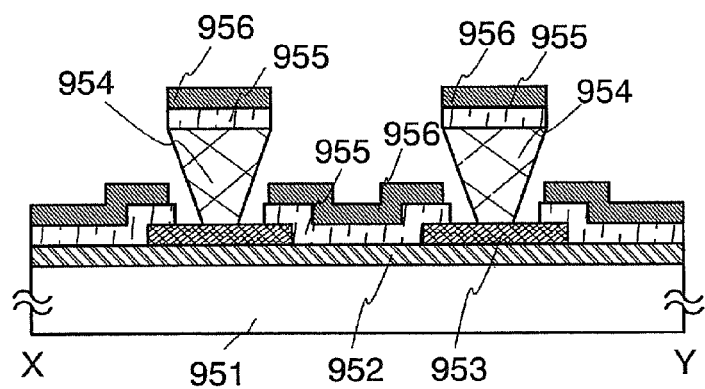

As described above, this embodiment mode describes an active matrix light-emitting device in which operation of a light-emitting element is controlled by transistors, which may be replaced with a passive matrix light-emitting device. FIGS. 5A and 5B show a passive matrix light-emitting device to which the present invention is applied. FIG. 5A is a perspective view of the light-emitting device, and FIG. 5B is a cross-sectional view taken along a line X-Y of FIG. 5A. In FIGS. 5A and 5B, a layer 955 including an organic compound is provided between an electrode 952 and an electrode 956 over a substrate 951. End portions of the electrode 952 are covered with an insulating layer 953. Then, a partition layer 954 is provided over the insulating layer 953. A side wall of the partition layer 954 slopes so that a distance between one side wall and the other side wall becomes narrow toward the substrate surface. In other words, a cross section taken in the direction of the short side of the partition layer 954 is trapezoidal, and the base of the cross-section (a side facing in the same direction as a plane direction of the insulating layer 953 and in contact with the insulating layer 953) is shorter than the upper side thereof (a side facing in the same direction as the plane direction of the insulating layer 953 and not in contact with the insulating layer 953). The partition layer 954 provided in this manner can prevent the light-emitting element from being defective due to static electricity or the like. In the case of a passive matrix light-emitting device, when the light-emitting device includes the light-emitting element of the present invention, a light-emitting device with a long life and also a light-emitting device with low power consumption can be obtained.

(Embodiment Mode 10)

In Embodiment Mode 10, electronic devices of the present invention including the light-emitting device described in Embodiment Mode 9 are described. The electronic devices of the present invention include the anthracene derivatives described in Embodiment Mode 1, and have display portions with a long life. Further, the display portions included in the electronic devices of the present invention consume lower power.

As electronic devices including light-emitting elements fabricated using the anthracene derivative of the present invention, cameras such as video cameras or digital cameras, goggle type displays, navigation systems, audio reproducing devices (car audio component stereo, audio component stereo, or the like), computers, game machines, portable information terminals (mobile computers, mobile phones, portable game machines, electronic books, or the like), and image reproducing devices provided with a recording medium (specifically, a device capable of reproducing content of a recording medium such as a Digital Versatile Disc (DVD) and provided with a display device that can display the image), and the like are given. Specific examples of these electronic devices are shown in FIGS. 6A to 6D.

Figure 6A:
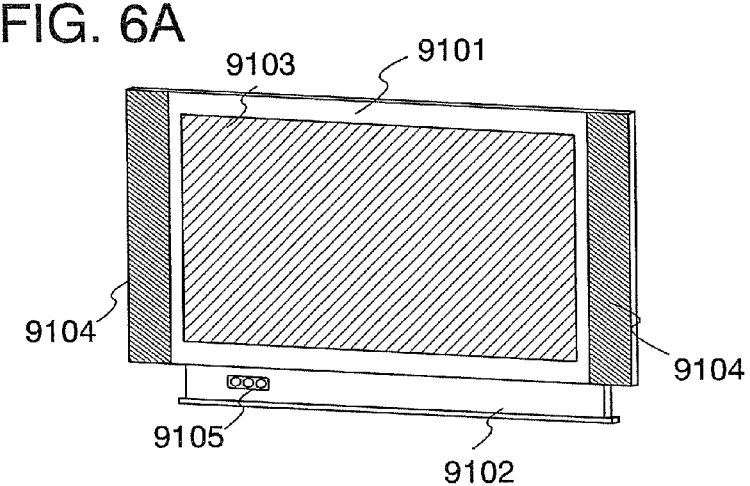
FIGS. 6A to 6D illustrate electronic devices of the present invention.

FIG. 6A shows a television device according to the present invention, which includes a housing 9101, a supporting base 9102, a display portion 9103, a speaker portion 9104, a video input terminal 9105, and the like. In the television device, the display portion 9103 has light-emitting elements similar to those described in Embodiment Modes 2 to 7, and the light-emitting elements are arranged in matrix. The light-emitting element is characterized by the high emission efficiency and a long life. The display portion 9103 including the light-emitting elements has similar characteristics. Accordingly, in the television device, image quality does not deteriorate much and low power consumption is achieved. Thus, deterioration compensation function circuits and power supply circuits can be significantly reduced or downsized in the television device, which enables reduction of the size and weight of the housing 9101 and supporting base 9102. In the television device according to the present invention, low power consumption, high image quality, and small size and lightweight are achieved; therefore, products suitable for living environment can be provided. Also, since the anthracene derivatives described in Embodiment Mode 1 can emit blue to green light, full-color display is possible, and television devices having a display portion with a long life can be provided.

Figure 6B:
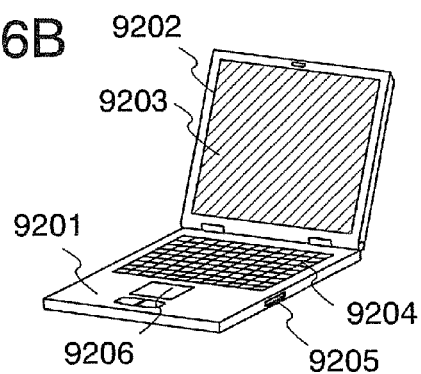

FIG. 6B shows a computer according to the present invention, which includes a main body 9201, a housing 9202, a display portion 9203, a keyboard 9204, an external connection port 9205, a pointing device 9206, and the like. In the computer, the display portion 9203 has light-emitting elements similar to those described in Embodiment Modes 2 to 7, and the light-emitting elements are arranged in matrix. The light-emitting element is characterized by the high emission efficiency and a long life. The display portion 9203 including the light-emitting elements has similar characteristics. Accordingly, in the computer, image quality does not deteriorate much and lower power consumption is achieved. Owing to these characteristics, deterioration compensation function circuits and power supply circuits can be significantly reduced or downsized in the computer; thus, small sized and lightweight main body 9201 and housing 9202 can be achieved. In the computer according to the present invention, low power consumption, high image quality, and small size and lightweight are achieved; therefore, products suitable for an environment can be supplied. Further, since the anthracene derivatives described in Embodiment Mode 1 can emit blue to green light, full-color display is possible, and computers having a display portion with a long life can be provided.

Figure 6C:
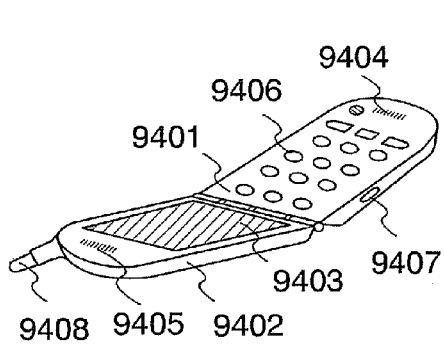

FIG. 6C shows a mobile phone according to the present invention, which includes a main body 9401, a housing 9402, a display portion 9403, an audio input portion 9404, an audio output portion 9405, an operation key 9406, an external connection port 9407, an antenna 9408, and the like. In the mobile phone, the display portion 9403 has light-emitting elements similar to those described in Embodiment Modes 2 to 7, and the light-emitting elements are arranged in matrix. The light-emitting element is characterized by high emission efficiency and a long life. The display portion 9403 including the light-emitting elements has similar characteristics. Accordingly, in the mobile phone, image quality does not deteriorate much and lower power consumption is achieved. Owing to these characteristics, deterioration compensation function circuits and power supply circuits can be significantly reduced or downsized in the mobile phone; thus, small sized and lightweight main body 9401 and housing 9402 can be supplied. In the mobile phone according to the present invention, low power consumption, high image quality, and a small size and lightweight are achieved; therefore, products suitable for carrying can be provided. Since the anthracene derivatives described in Embodiment Mode 1 can emit blue to green light, full-color display is possible, and mobile phones having a display portion with a long life can be provided.

Figure 6D:
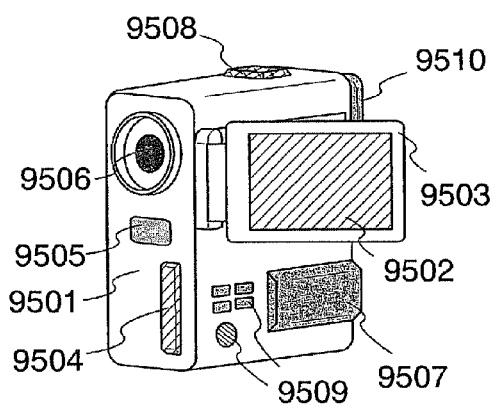

FIG. 6D shows a camera according to the present invention, which includes a main body 9501, a display portion 9502, a housing 9503, an external connection port 9504, a remote control receiving portion 9505, an image receiving portion 9506, a battery 9507, an audio input portion 9508, operation keys 9509, an eye piece portion 9510, and the like. In the camera, the display portion 9502 has light-emitting elements similar to those described in Embodiment Modes 2 to 7, and the light-emitting elements are arranged in matrix. Some features of the light-emitting element are its high emission efficiency and a long life. The display portion 9502 including the light-emitting elements has similar characteristics. Accordingly, in the camera, image quality does not deteriorate much and lower power consumption can be achieved. Such features contribute to significant reduction and downsizing of the deterioration compensation function circuits and power supply circuits in the camera; thus, a small sized and lightweight main body 9501 can be supplied. In the camera according to the present invention, low power consumption, high image quality, and small size and lightweight are achieved; therefore, products suitable for carrying can be provided. Since the anthracene derivatives described in Embodiment Mode 1 can emit blue to green light, full-color display is possible, and cameras having a display portion with a long life can be provided.

As described above, the applicable range of the light-emitting devices of the present invention is so wide that the light-emitting devices can be applied to electronic devices in a variety of fields. By use of the anthracene derivatives of the present invention, electronic devices which have display portions with a long life can be obtained.

Such light-emitting devices of the present invention can also be used for a lighting device. One mode using the light-emitting device of the present invention as the lighting device is described using FIG. 7.

Figure 7:
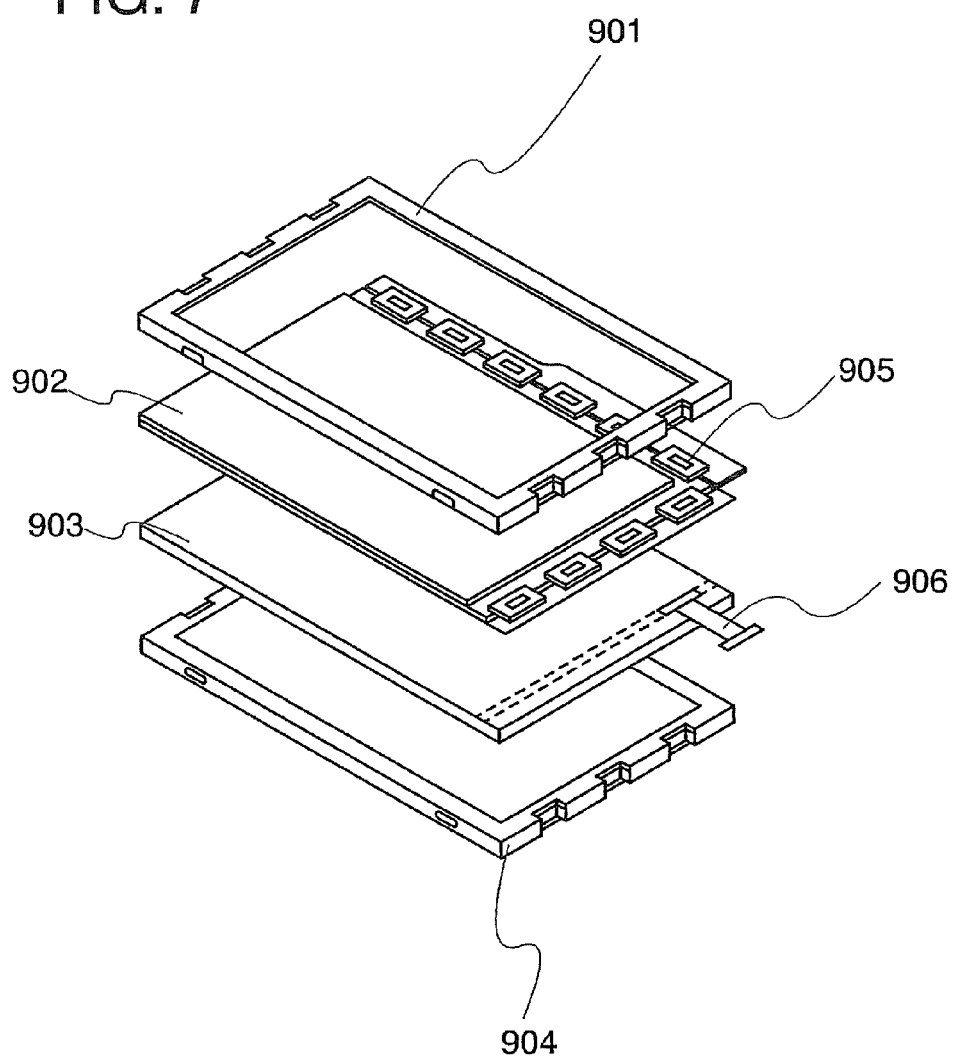
FIG. 7 illustrates a lighting device of the present invention.

FIG. 7 shows an example of a liquid crystal display that uses the light-emitting device of the present invention as a backlight. The liquid crystal display device shown in FIG. 7 includes a housing 901, a liquid crystal layer 902, a backlight 903, and a housing 904, and the liquid crystal layer 902 is connected to a driver IC 905. The light-emitting device of the present invention is used for the backlight 903, and current is supplied through a terminal 906.

By use of the light-emitting device of the present invention as the backlight of the liquid crystal display device, a backlight with reduced power consumption and high emission efficiency can be provided. The light-emitting device of the present invention is a lighting device with plane light emission, and can have a large area. Therefore, the backlight can have a large area, and a liquid crystal display device having a large area can be obtained. Furthermore, the light-emitting device of the present invention has a thin shape and has low power consumption; thus, a thin shape and low power consumption of a display device can also be achieved. Since the light-emitting device of the present invention has a long life, a liquid crystal display device that uses the light-emitting device of the present invention also has a long life.

Figure 8:
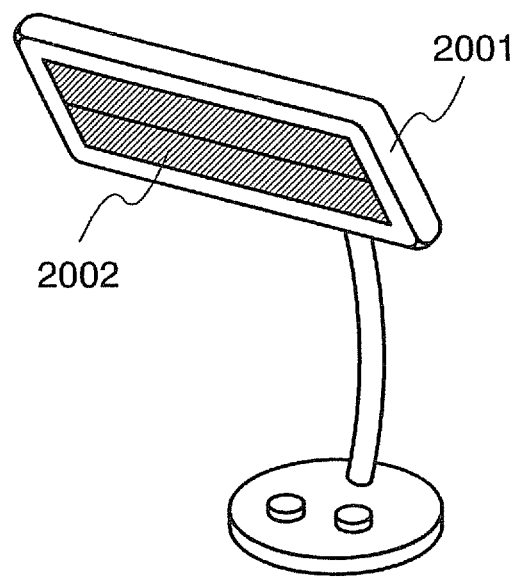
FIG. 8 illustrates a lighting device of the present invention.

FIG. 8 shows an example of using the light-emitting device to which the present invention is applied, as a table lamp which is an example of a lighting device. The table lamp shown in FIG. 8 has a housing 2001 and a light source 2002, and the light-emitting device of the present invention is used as the light source 2002. The light-emitting device of the present invention has high emission efficiency and has a long life; accordingly, the table lamp also has high emission efficiency and a long life.

Figure 9:
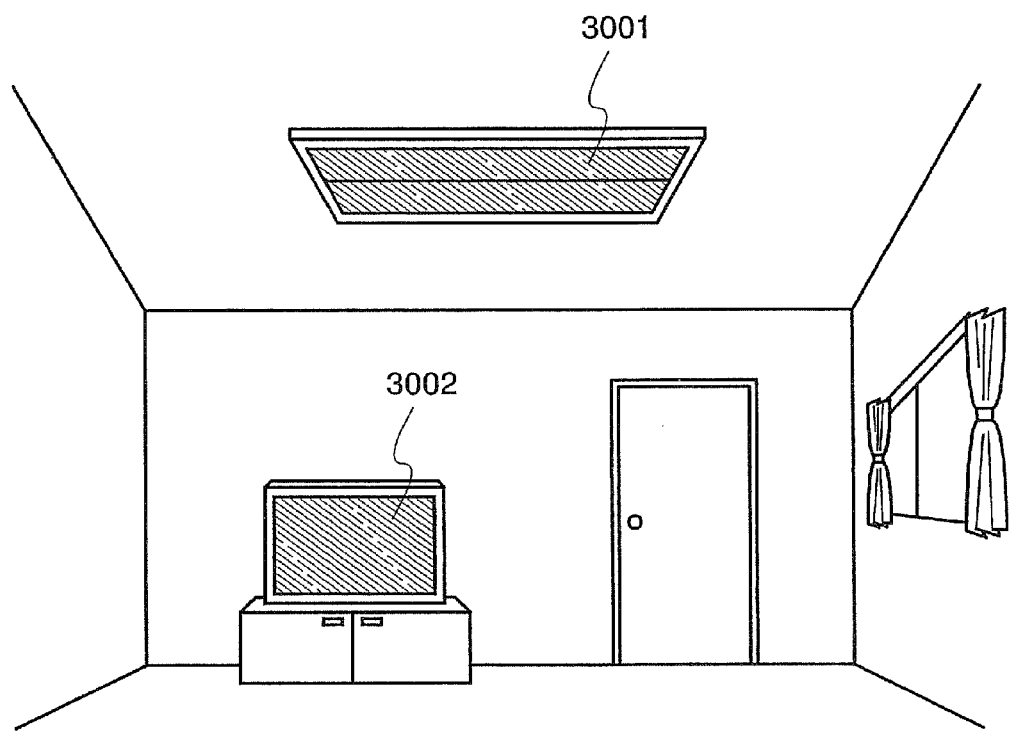
FIG. 9 illustrates a lighting device of the present invention.

FIG. 9 shows an example of using a light-emitting device to which the present invention is applied, as an indoor lighting device 3001. Since the light-emitting device of the present invention can also have a large area, the light-emitting device of the present invention can be used as a lighting device having a large emission area. Further, the light-emitting device of the present invention has a thin shape and consumes low power; accordingly, the light-emitting device of the present invention can be used as a lighting device having a thin shape and low-power consumption. A television device 3002 according to the present invention as described in FIG. 6A is placed in a room in which the light-emitting device fabricated by the present invention is used as the indoor lighting device 3001, and public broadcasting and movies can be watched. In such a case, since both of the devices consume low power, a powerful image can be watched in a bright room without concern about electricity charges.

Example 1

Synthesis Example 1

In Synthesis Example 1, a synthesis method of an anthracene derivative 9-phenyl-9'-[4-10-phenyl-9-anthryl)phenyl]-3,3'-bi(9H-carbazole) (PCCPA) of the present invention represented by a structural formula (101) is specifically described.

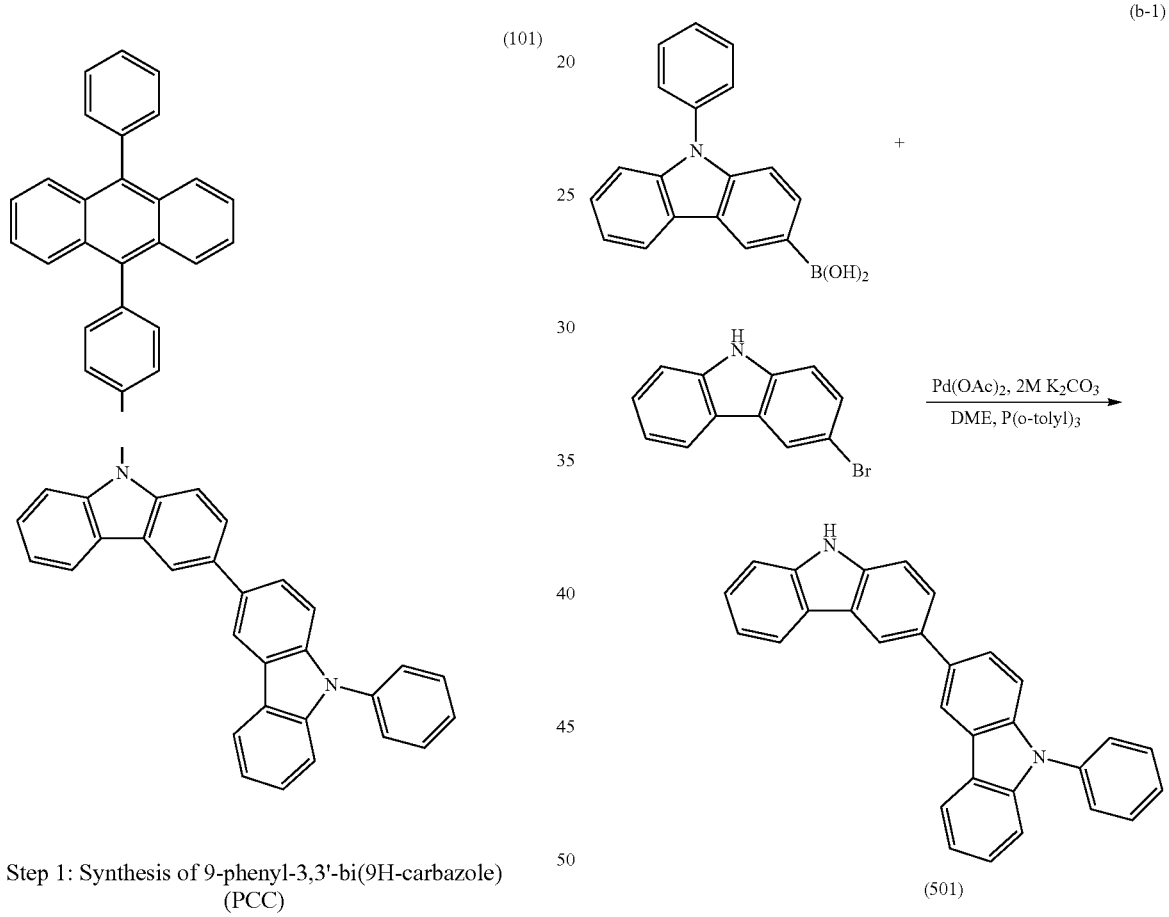

Step 1: Synthesis of 9-phenyl-3,3'-bi(9H-carbazole) (PCC)

2.5 g of (10 mmol) 3-bromo-9H-carbazole, 2.9 g of (10 mmol) N-phenylcarbazol-3-boronic acid, and 152 mg of (0.50 mmol) tri(ortho-tolyl)phosphine were put into a 200 mL three-neck flask. The air in the flask was replaced with nitrogen. To the mixture were added 50 mL of dimethoxyethanol and 10 mL of an aqueous solution of potassium carbonate (2 mol/L). This mixture was stirred to be degassed while the pressure was reduced. After the degassing, 50 mg (0.2 mmol) of palladium acetate was added to the mixture. This mixture was stirred at 80° C. for 3 hours under a stream of nitrogen. After the stirring, about 50 mL of toluene was added to this mixture. The mixture was stirred for about 30 minutes and then washed with water and a saturated saline solution in this order. After the washing, an organic layer was dried with magnesium sulfate. This mixture was subjected to gravity filtration. The obtained filtrate was condensed to give an oily substance. The obtained oily substance was dissolved in toluene. This solution was subjected to suction filtration through Florisil (produced by Wako Pure Chemical Industries, Ltd., Catalog No. 540-00135), alumina, and celite (produced by Wako Pure Chemical Industries, Ltd., Catalog No. 531-16855). The obtained filtrate was concentrated to give 3.3 g of a white solid, which was the object of the synthesis, at a yield of 80%. A synthesis scheme of Step 1 is shown in (b-1) given below.

Figure 10:
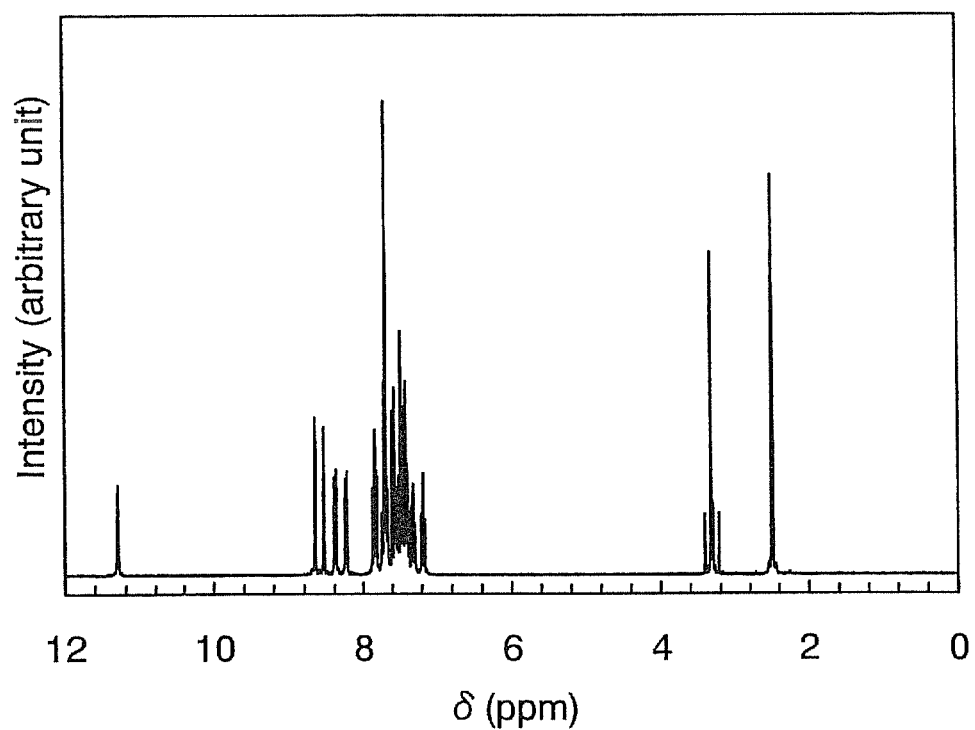
FIG. 10 is a $^1$H-NMR chart of PCC.

The solid obtained in the above Step 1 was analyzed by nuclear magnetic resonance measurement ($^1$H NMR). The measurement result is described below, and the $^1$H NMR chart is shown in FIG. 10. They show that the organic compound PCC of the present invention represented by the structural formula (501), which is used in any of the anthracene derivatives of the present invention, was obtained in this synthesis example.

$^1$H NMR (DMSO-$d_6$, 300 MHz): δ=7.16-7.21 (m, 1H), 7.29-7.60 (m, 8H), 7.67-7.74 (m, 4H), 7.81-7.87 (m, 2H), 8.24 (d, J=7.8 Hz, 1H), 8.83 (d, J=7.8 Hz, 1H), 8.54 (d, J=1.5 Hz, 1H), 8.65 (d, J=1.5 Hz, 1H), 11.30 (s, 1H).

Step 2: Synthesis of PCCPA 1.2 g of (3.0 mmol)9-phenyl-10-(4-bromophenyl)anthracene, 1.2 g (3.0 mmol) of PCC, and 1.0 g (10 mmol) of sodium tert-butoxide were put into a 100 mL three-neck flask. The air in the flask was replaced with nitrogen. To the mixture were added 20 mL of toluene and 0.1 mL of tri(tert-butyl) phosphine (a 10 wt % hexane solution). This mixture was stirred to be degassed while the pressure was reduced. After the degassing, 96 mg (0.17 mmol) of bis(dibenzylideneacetone)palladium(0) was added to the mixture. This mixture was refluxed at 110° C. for 8 hours under a stream of nitrogen. After the reflux, about 50 mL of toluene was added to this mixture. The mixture was stirred for about 30 minutes and then washed with water and a saturated saline solution in this order. After the washing, the organic layer was dried with magnesium sulfate. This mixture was subjected to gravity filtration. The obtained filtrate was condensed to give an oily substance. The obtained oily substance was purified by silica gel column chromatography (a developing solvent was a mixed solvent of hexane:toluene=1:1). The obtained light yellow solid was recrystallized with chloroform/hexane to give 1.2 g of a light yellow powdered solid PCCPA, which was the object of the synthesis, at a yield of 54%. 2.4 g of the obtained light yellow powdered solid was sublimed for purification by train sublimation. PCCPA was heated under a pressure of 8.7 Pa, with a flow rate of argon of 3.0 mL/min, at 350° C. for 15 hours to give 2.2 g of a light yellow solid PCCPA, which was the object of the synthesis, at a yield of 94%. A synthesis scheme of Step 2 is shown in (b-2) given below.

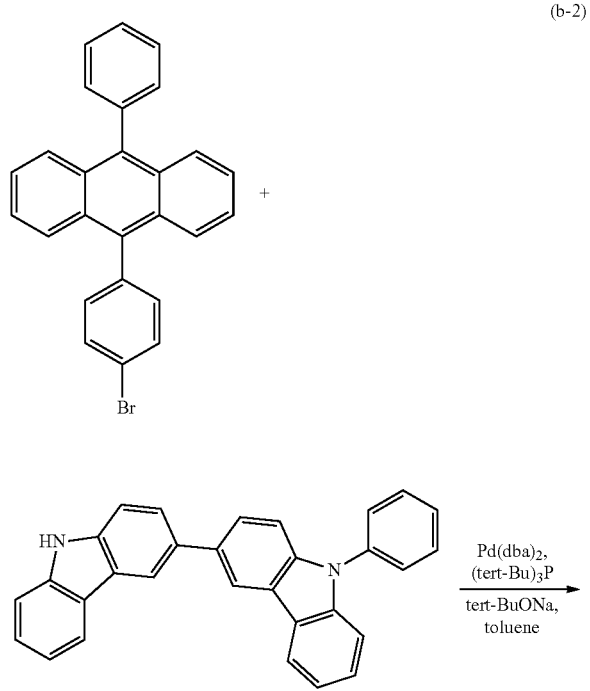

(b-2)

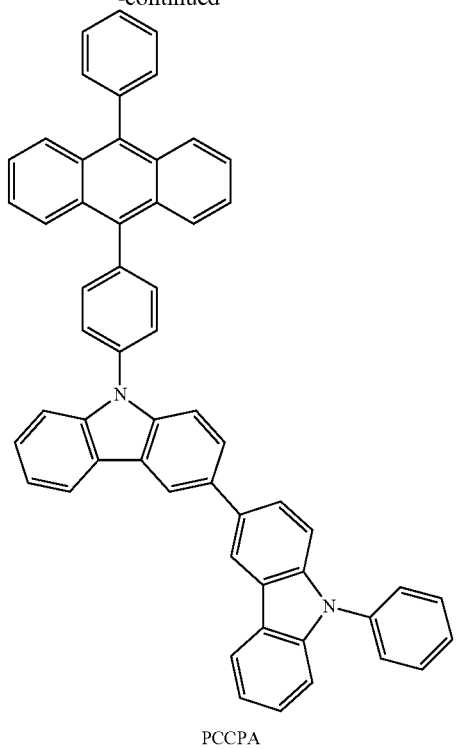

PCCPA

Figure 11:
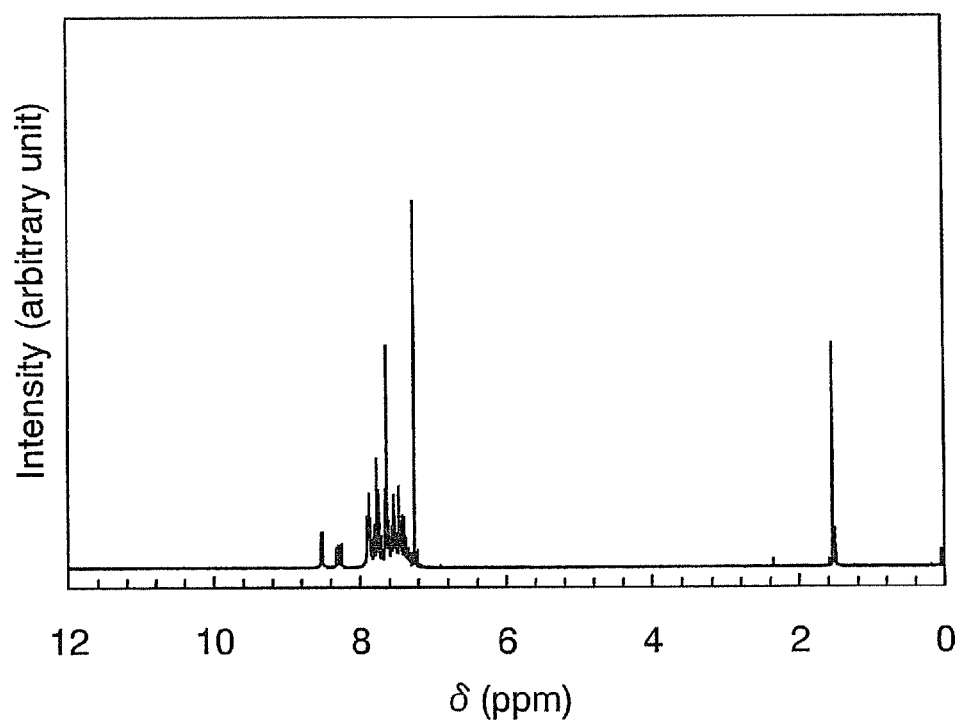
FIG. 11 is a $^1$H-NMR chart of PCCPA.

The solid obtained in the above Step 2 was analyzed by $^1$H NMR. The measurement result is described below, and the $^1$H NMR chart is shown in FIG. 11. They show that the anthracene derivative PCCPA of the present invention, represented by the structural formula (220), was obtained in this synthesis example.

$^1$H NMR (CDCl$_3$, 300 MHz): δ=7.34-7.91 (m, 32H), 8.27 (d, J=7.2 Hz, 1H), 8.31 (d, J=7.5 Hz, 1H), 8.52 (dd, J$_1$=1.5 Hz, J$_2$=5.4 Hz, 2H).

Figure 12:
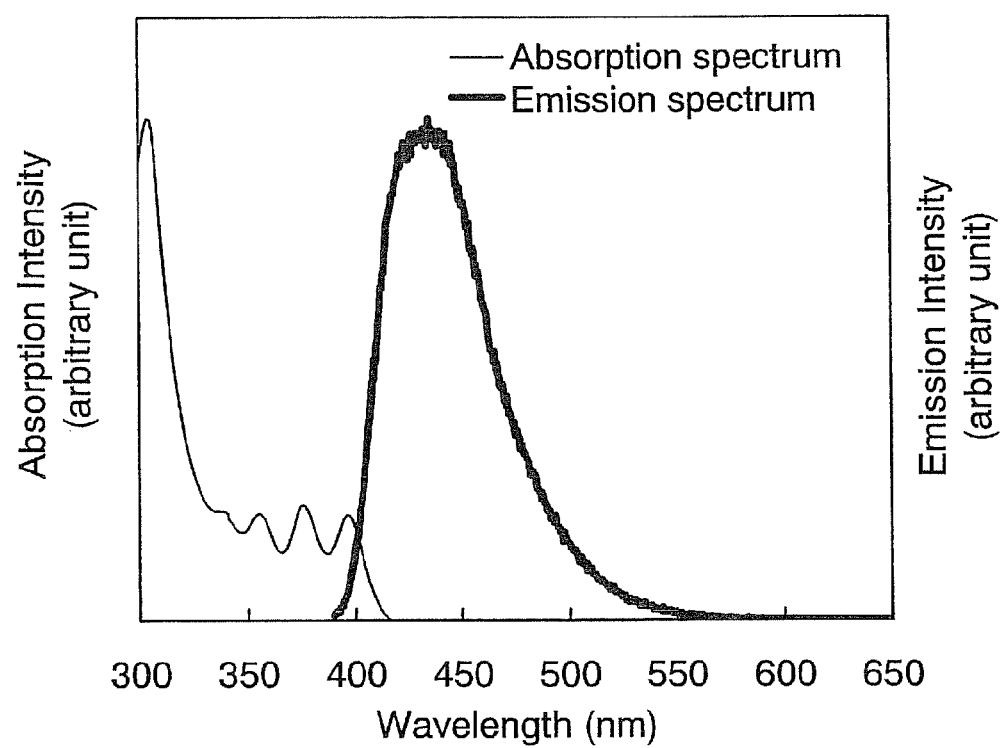
FIG. 12 illustrates an absorption spectrum and an emission spectrum of a toluene solution of PCCPA.
Figure 13:
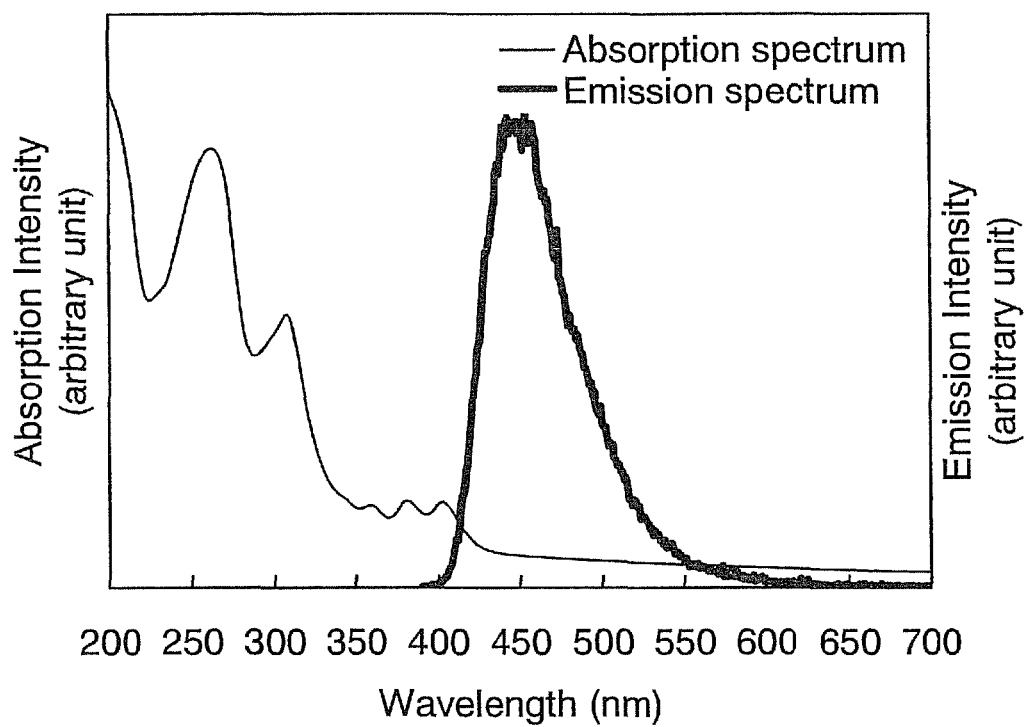
FIG. 13 illustrates an absorption spectrum and an emission spectrum of a thin film of PCCPA.

Next, an absorption spectrum of PCCPA was measured at room temperature using an ultraviolet-visible spectrophotometer (V-550, manufactured by JASCO Corporation) with the use of a toluene solution. An emission spectrum of PCCPA was measured at room temperature using a fluorescence spectrophotometer (FS920, manufactured by Hamamatsu Photonics Corporation) with the use of a toluene solution. The measurement results are shown in FIG. 12. Further, a thin film of PCCPA was similarly measured by film formation of PCCPA by an evaporation method. The measurement results are shown in FIG. 13. In each of FIG. 12 and FIG. 13, the horizontal axis indicates the wavelength (nm) and the vertical axis indicates the absorption intensity (arbitrary unit) and emission intensity (arbitrary unit).

According to FIG. 12, in the case of the toluene solution of PCCPA, absorption was observed at wavelengths of around 355 nm, around 375 nm, and around 395 nm. According to FIG. 13, in the case of the thin film of PCCPA, absorption was observed at wavelengths of around 357 nm, around 379 nm, and around 401 nm.

According to FIG. 12 and FIG. 13, the thin film of PCCPA has an emission peak at 454 nm (the excitation wavelength: 380 nm), and the toluene solution thereof has an emission peak at 436 nm (the excitation wavelength: 370 nm). Thus, it is found that PCCPA is suitable for use in a light-emitting element that emits blue light in particular.

The ionizing potential of the thin film of PCCPA was measured using a photoelectron spectrometer (AC-2, manufactured by Riken Keiki Co., Ltd) in the air and found to be 5.40 eV. As a result, the HOMO level was found to be −5.40 eV. Further, an absorption edge was obtained from a Tauc plot assuming direct transition by use of the data of the absorption spectrum of PCCPA in the thin film state, and the absorption edge was regarded as an optical energy gap. The energy gap was 2.90 eV. A LUMO level of −2.50 eV was obtained from the obtained values of the energy gap and the HOMO level.

Figure 14:
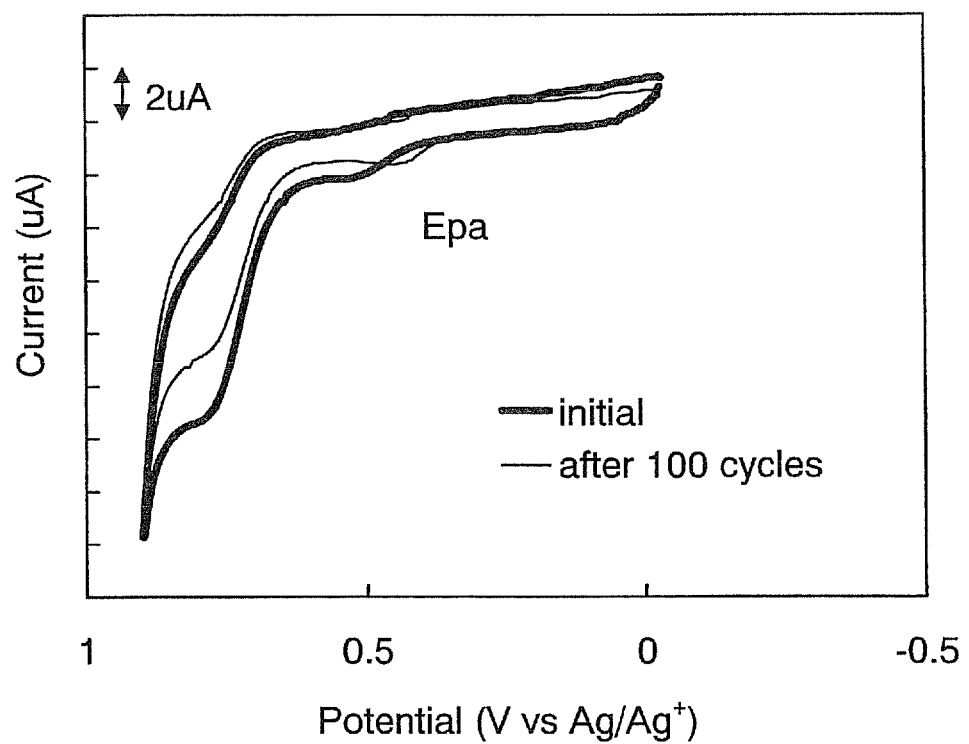
FIG. 14 illustrates a cyclic voltammogram (oxidation) of PCCPA.
Figure 15:
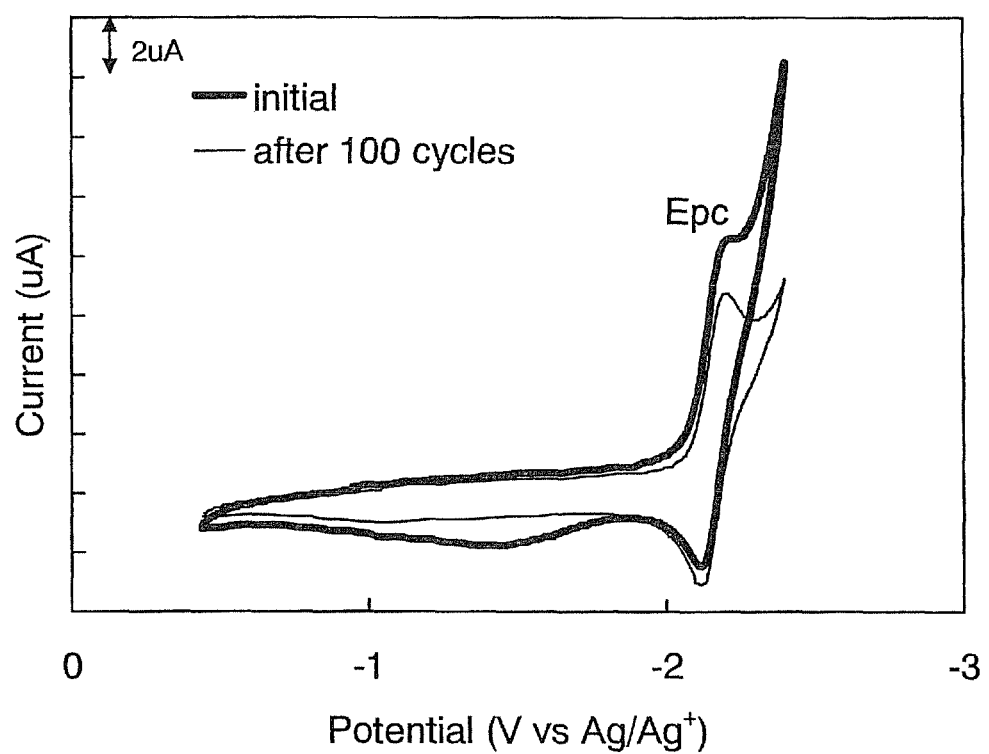
FIG. 15 illustrates a cyclic voltammogram (reduction) of PCCPA.

The oxidation-reduction characteristics of PCCPA were measured by cyclic voltammetry (CV). An electrochemical analyzer (ALS model 600a, manufactured by BAS Inc.) was used for the measurement. Further, dimethylformamide (DMF) and tetra-n-butylammonium perchlorate (n-Bu$_4$NClO$_4$) were used as a solvent and a supporting electrolyte, respectively, and the amount thereof adjusted to yield a concentration of 10 mmol per L of DMF. Furthermore, the amount of PCCPA was adjusted to yield a concentration of 1 mmol per L of the electrolysis solution. A platinum electrode (PTE platinum electrode, produced by BAS Inc.), a platinum electrode (Pt counter electrode (5 cm) for VC-3, produced by BAS Inc.), and an Ag/Ag$^+$ electrode (RE5 non-aqueous solvent reference electrode, produced by BAS Inc.) were used as a working electrode, an auxiliary electrode, and a reference electrode, respectively. The measurement was performed at a scan rate of 0.1 V/s for 100 cycles. FIG. 14 shows the measurement result on the oxidation side. FIG. 15 shows the measurement result on the reduction side. In each of FIG. 14 and FIG. 15, the horizontal axis indicates a potential (V) of the working electrode with respect to the reference electrode, and the vertical axis indicates a current value (μA) that flowed between the working electrode and the counter electrode.

FIG. 14 shows that the oxidation potential of PCCPA was 0.47 V (with respect to Ag/Ag$^+$). FIG. 15 shows that the reduction potential of PCCPA was −2.19 V (with respect to Ag/Ag$^+$). Through the measurement for 100 cycles of scanning, distinct oxidation peaks and reduction peaks were observed in the CV curves. Therefore, it is found that the anthracene derivative of the present invention is a substance in which the reversibility of oxidation-reduction reactions is excellent.

Synthesis Example 2

In Synthesis Example 2, a synthesis method of an anthracene derivative 4-{9-[4-(10-phenyl-9-anthryl)phenyl]-9H-carbazol-3-yl}triphenylamine (TPCPA) of the present invention represented by a structural formula (246) is specifically described.

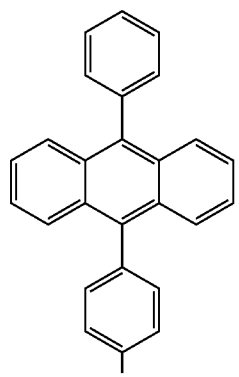

(246)

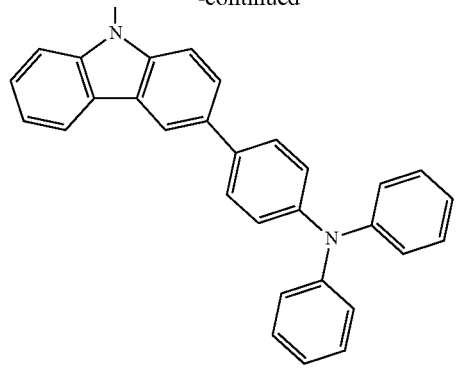

-continued

Step 1: Synthesis of 3-bromo-9H-carbazole 32 g (0.19 mmol) of 9H-carbazole was put into a 2 L Erlenmeyer flask, and then ether acetate (1.2 L) was added thereto so that the 9H-carbazole was dissolved in the ether acetate. To this solution was added 34 g (0.19 mol) of N-bromosuccinimide (NBS), and the mixture was stirred for about 15 hours in the air at room temperature. After the stirring, water was added to the mixture so that the precipitate was dissolved in the mixture. The organic layer of this mixture was washed with water three times and then with a saturated saline solution once. Magnesium sulfate was added so that the organic layer was dried. After the drying, the mixture was subjected to gravity filtration. The obtained filtrate was condensed to give a white solid. The obtained solid was recrystallized with ether acetate/hexane to give 36 g of a white powdered solid, which was the object of the synthesis, at a yield of 67%. A synthesis scheme of Step 1 is shown in (c-1) given below.

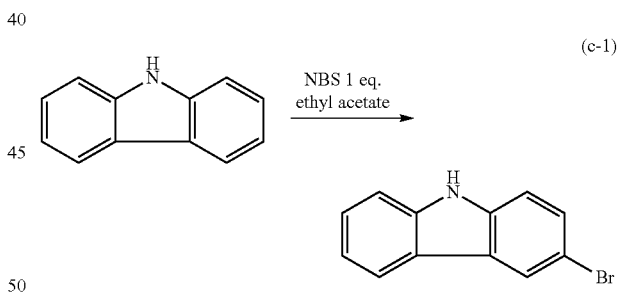

(c-1)

Step 2: Synthesis of N,N-diphenylanilin-4-boronic acid 10 g (30 mmol) of 4-bromotriphenylamine was put into a 500 mL three-neck flask. The air in the flask was replaced with nitrogen. To the mixture were added 20 mL of tetrahydrofuran (THF), and then the mixture was stirred at −80° C. Into this solution, 20 mL (32 mmol) of n-butyllithium (a 1.6 mol/L hexane solution) was dropped by a syringe. After the dropping, this solution was stirred at the same temperature for 1 hour. After the stirring, 40 mL (60 mmol) of trimethyl borate was added to the solution, and the solution was stirred for 1 hour while the temperature of the solution was being increased to room temperature. To the solution was added 200 mL (1.0 mol/L) of hydrochloric acid, and then the solution was stirred for about 15 hours. The organic layer was washed with a saturated sodium hydrogen carbonate solution and then a saturated saline solution. Then, the organic layer was dried with magnesium sulfate. This mixture was subjected to gravity filtration. The obtained filtrate was condensed to give a white solid. The obtained solid was recrystallized with chloroform/hexane to give 5.2 g of a white powdered solid, which was the object of the synthesis, at a yield of 58%. A synthesis scheme of Step 2 is shown in (c-2) given below.

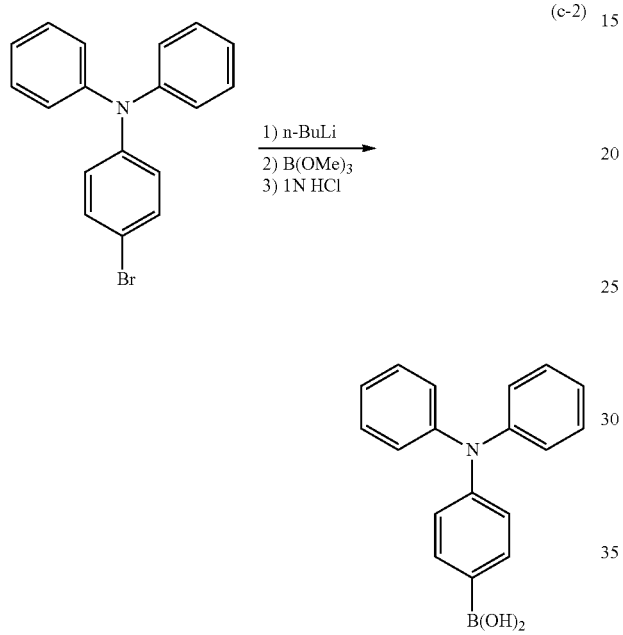

Step 3: Synthesis of 4-(9H-carbazol-3-yl)triphenylamine (TPC)

2.5 g (10 mmol) of 3-bromo-9H-carbazole, 2.9 g (10 mmol) of N,N-diphenylanilin-4-boronic acid, and 152 mg (0.50 mmol) of tri(ortho-tolyl)phosphine were put into a 200 mL three-neck flask. The air in the flask was replaced with nitrogen. To the mixture were added 50 mL of ethyleneglycoldimethylether and 10 mL (2.0 mol/L) of an aqueous solution of potassium carbonate. This mixture was stirred to be degassed while the pressure was reduced. After the degassing, 50 mg (0.20 mmol) of palladium(II) acetate was added to the mixture. This mixture was stirred at 80° C. for 3 hours. After the stirring, this mixture was washed with water and then a saturated saline solution. After the washing, magnesium sulfate was added to the organic layer so that the organic layer was dried. The mixture was subjected to gravity filtration. The obtained filtrate was condensed to give a solid. This solid was purified by silica gel column chromatography (a developing solvent was a mixed solvent of hexane:toluene=6:4) to give 3.4 g of a white solid TPC, which was the object of the synthesis, at a yield of 82%. A synthesis scheme of Step 3 is shown in (c-3) given below.

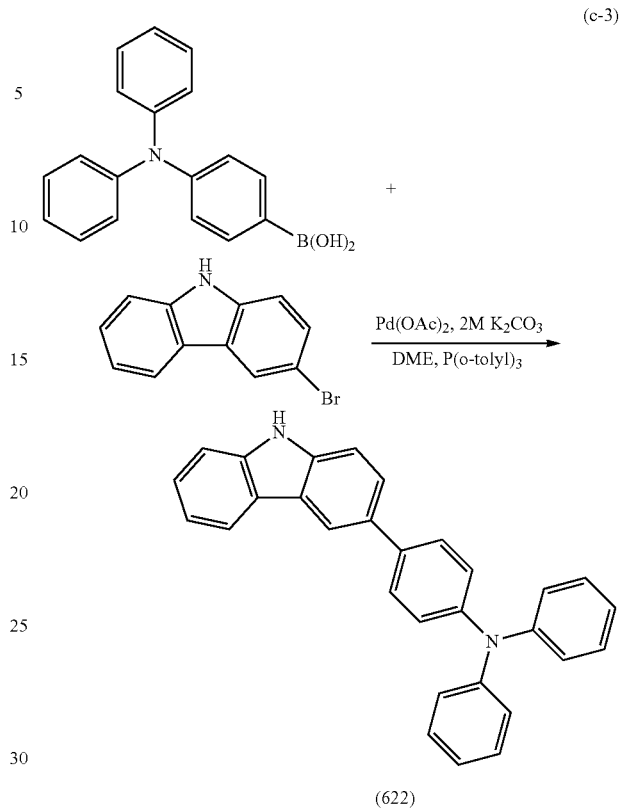

Figure 16:
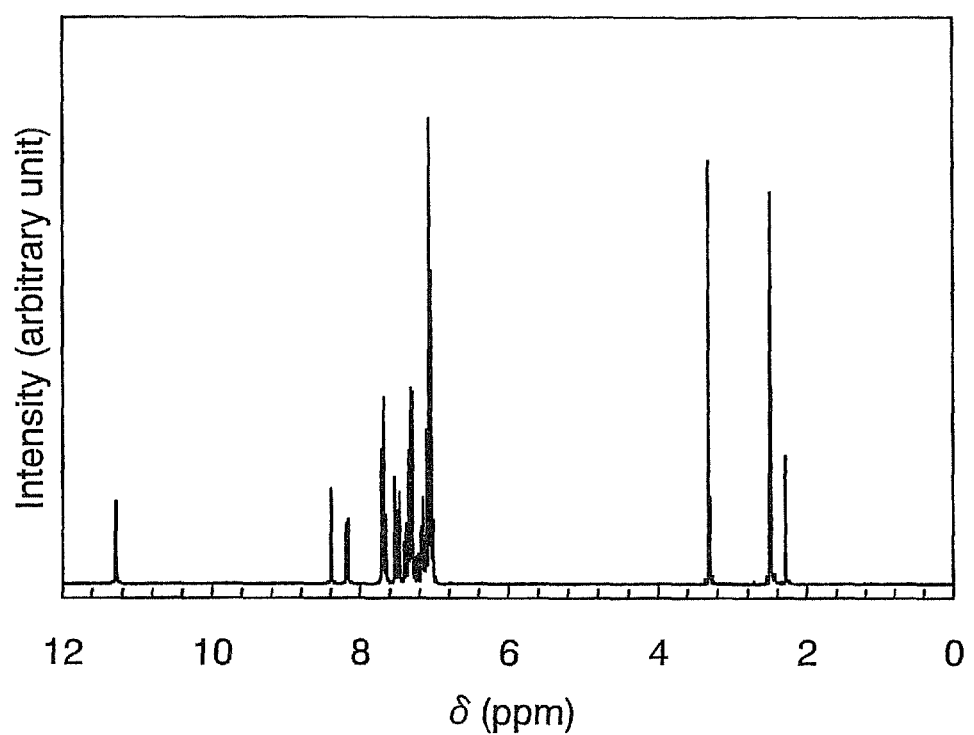
FIG. 16 is a $^1$H-NMR chart of TPC.

The solid obtained in the above Step 3 was analyzed by $^1$H NMR. The measurement result is described below, and the $^1$H NMR chart is shown in FIG. 16. They show that the organic compound TPC of the present invention represented by the structural formula (622), which is used in any of the anthracene derivatives of the present invention, was obtained in this synthesis example.

$^1$H NMR (DMSO-$d_6$, 300 MHz): δ=6.99-7.41 (m, 14H), 7.48 (d, J=8.1 Hz, 1H), 7.52 (d, J=8.7 Hz, 1H), 7.65-7.71 (m, 3H), 8.18 (d, J=7.8 Hz, 1H), 8.39 (d, J=1.5 Hz, 1H), 11.28 (s, 1H).

Step 4: Synthesis of TPCPA 1.2 g (3.0 mmol) of 9-phenyl-10-(4-bromophenyl)anthracene, 1.2 g (3.0 mmol) of TPC, and 1.0 g (10 mmol) of sodium tert-butoxide were put into a 100 mL three-neck flask. The air in the flask was replaced with nitrogen. To the mixture were added 20 mL of toluene and 0.1 mL of tri(tert-butyl)phosphine (a 10 wt % hexane solution). This mixture was stirred to be degassed while the pressure was reduced. After the degassing, 50 mg (0.090 mmol) of bis(dibenzylideneacetone)palladium(0) was added the mixture. This mixture was refluxed at 110° C. for 8 hours. After the reflux, about 50 mL of toluene was added to the mixture, and then the mixture was stirred for about 30 minutes. Then, this mixture was washed with water and a saturated saline solution in this order. After the washing, the organic layer was dried with magnesium sulfate. This mixture was subjected to gravity filtration. The obtained filtrate was condensed to give an oily substance. The obtained oily substance was purified by silica gel column chromatography (a developing solvent was a mixed solvent of hexane:toluene=1:1) to give a light yellow solid TPCPA. This solid was recrystallized with toluene/hexane to give 1.0 g of a light yellow powdered solid TPCPA, which was the object of the synthesis, at a yield of 41%. A synthesis scheme of Step 4 is shown in (c-4) given below.

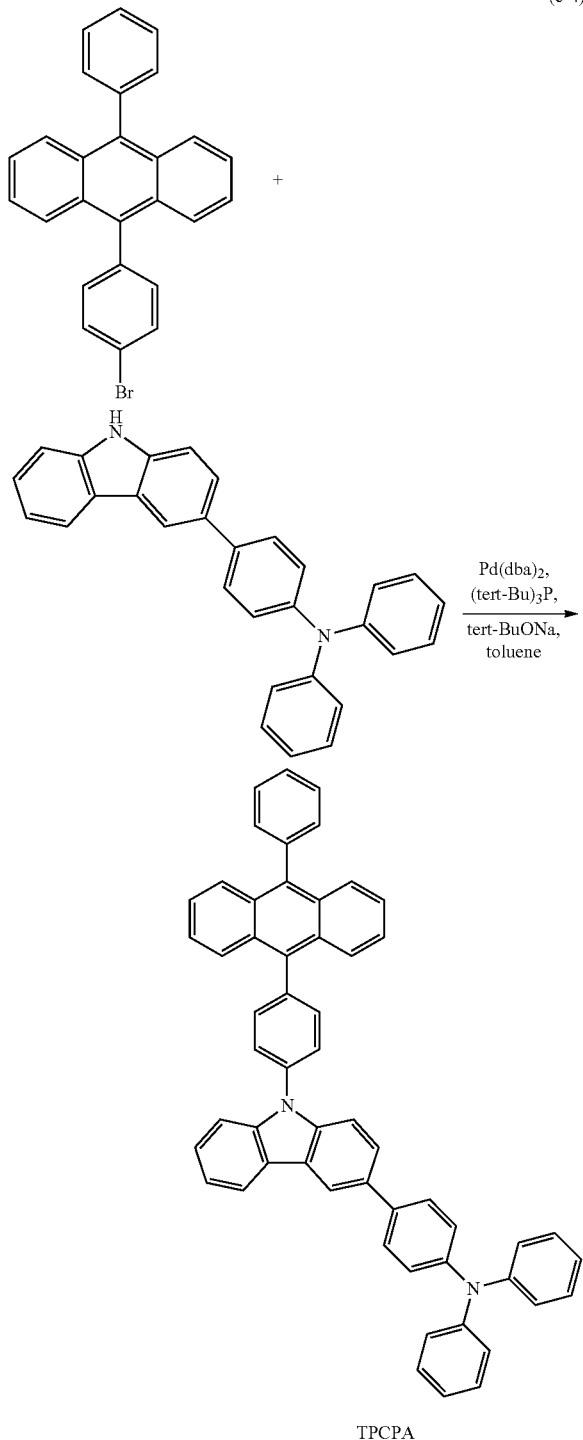

(c-4)

TPCPA

Figure 17:
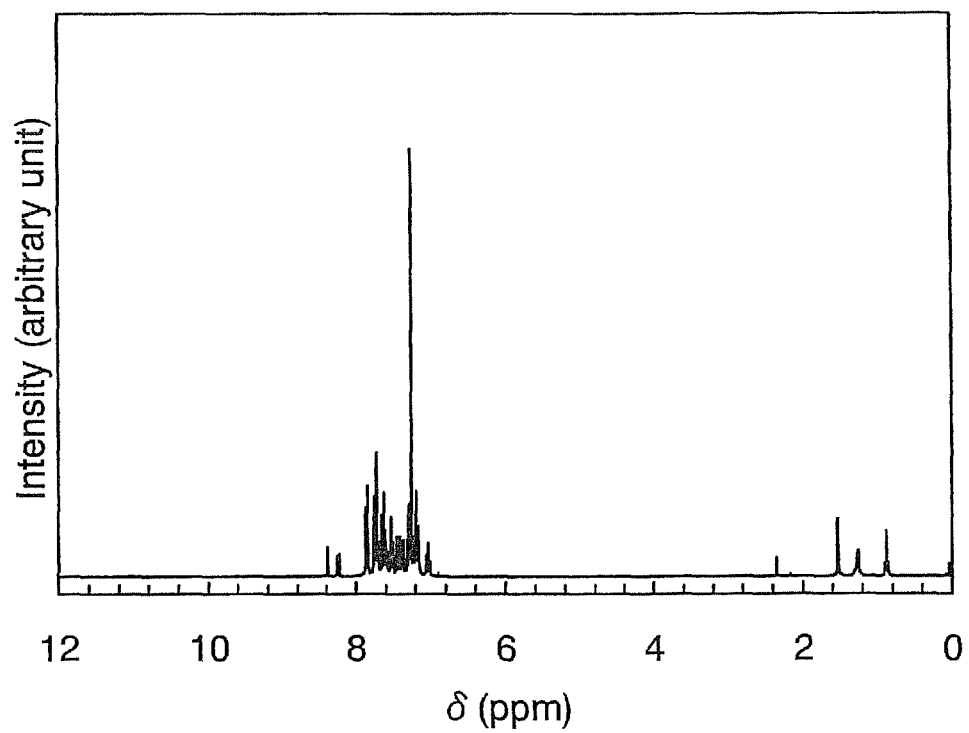
FIG. 17 is a $^1$H-NMR chart of TPCPA.

The solid obtained in the above Step 4 was analyzed by $^1$H NMR. The measurement result is described below, and the $^1$H NMR chart is shown in FIG. 17. They show that the anthracene derivative TPCPA of the present invention represented by the structural formula (223) was obtained in this synthesis example.

$^1$H NMR (CDCl$_3$, 300 MHz): δ=7.02-7.87 (m, 36H), 8.24 (d, J=7.8 Hz, 1H), 8.39 (s, 1H).

Further, the decomposition temperature of TPCPA which is the anthracene derivative of the present invention was measured using a high vacuum differential type differential thermal balance (TG-DTA2410SA, manufactured by Bruker AXS K.K.). When the temperature was increased at a rate of 10° C./min under a pressure of 10 Pa, 5% weight reduction was seen at 330° C., which is indicative of high thermal stability.

Figure 18:
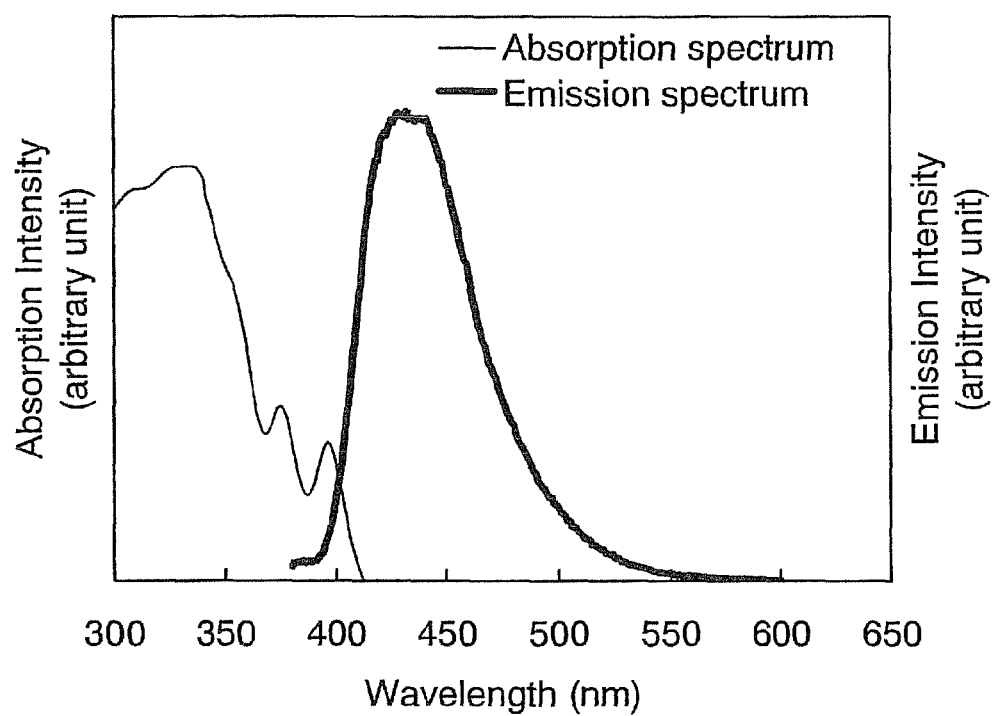
FIG. 18 illustrates an absorption spectrum and an emission spectrum of a toluene solution of TPCPA.
Figure 19:
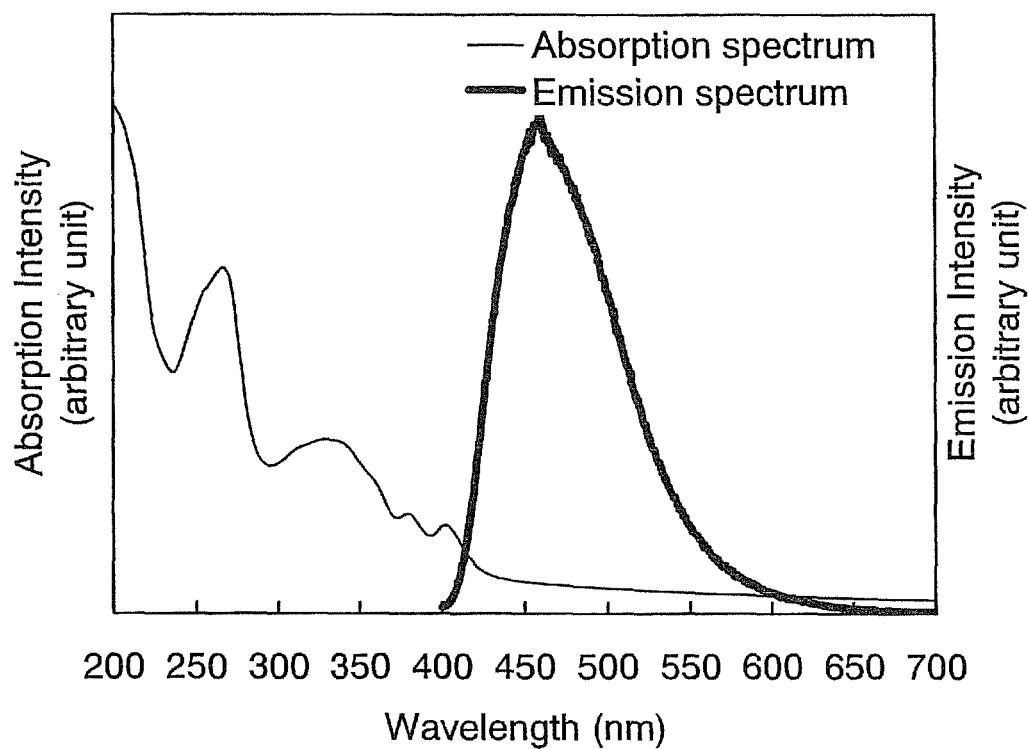
FIG. 19 illustrates an absorption spectrum and an emission spectrum of a thin film of TPCPA.

Next, an absorption spectrum of TPCPA was measured at room temperature using an ultraviolet-visible spectrophotometer (V-550, manufactured by JASCO Corporation) with the use of a toluene solution. An emission spectrum of TPCPA was measured at room temperature using a fluorescence spectrophotometer (FS920, manufactured by Hamamatsu Photonics Corporation) with the use of a toluene solution. The measurement results are shown in FIG. 18. Further, a thin film of TPCPA was similarly measured by film formation of TPCPA by an evaporation method. The measurement results are shown in FIG. 19. In each of FIG. 18 and FIG. 19, the horizontal axis indicates the wavelength (nm) and the vertical axis indicates the absorption intensity (arbitrary unit) and the emission intensity (arbitrary unit).

According to FIG. 18, in the case of the toluene solution of TPCPA, absorption was observed at wavelengths around 374 nm and around 394 nm. According to FIG. 19, in the case of the thin film of TPCPA, absorption was observed at wavelengths of around 376 nm and around 402 nm.

According to FIG. 18 and FIG. 19, the thin film of TPCPA has an emission peak at 460 nm (the excitation wavelength: 395 nm), and the toluene solution thereof has an emission peak at 432 nm (the excitation wavelength: 370 nm). Thus, it is found that TPCPA is suitable for use in a light-emitting element that emits blue light in particular.

The ionizing potential of the thin film of TPCPA was measured using a photoelectron spectrometer (AC-2, manufactured by Riken Keiki Co., Ltd) in the air and found to be 5.28 eV. As a result, the HOMO level was found to be −5.28 eV. Further, an absorption edge was obtained from a Tauc plot assuming direct transition by use of the data of the absorption spectrum of TPCPA in the thin film state, and the absorption edge was regarded as an optical energy gap. The energy gap was 2.93 eV. A LUMO level of −2.35 eV was obtained from the obtained values of the energy gap and the HOMO level.

Figure 20:
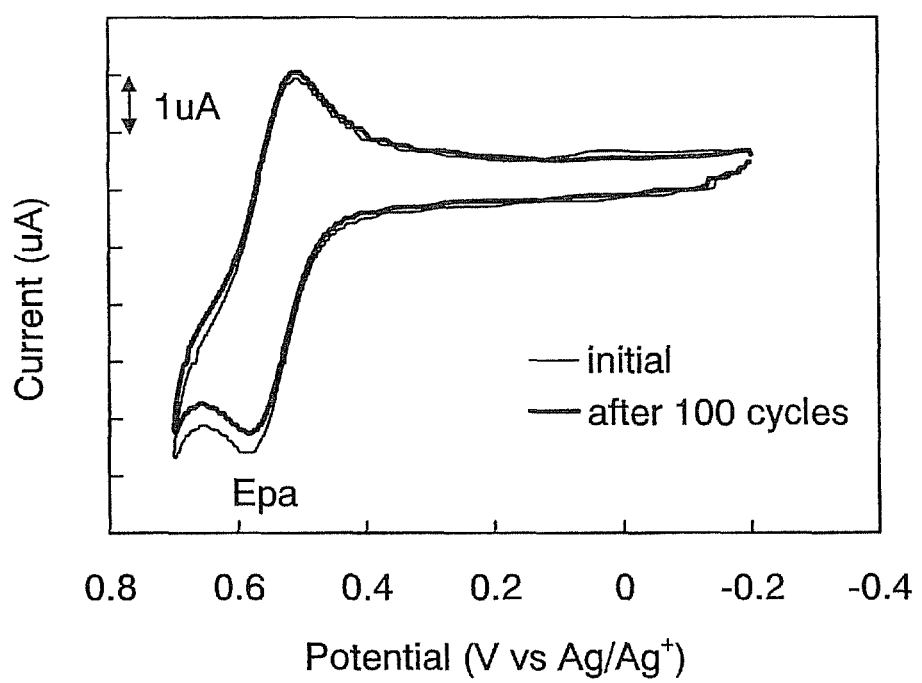
FIG. 20 illustrates a cyclic voltammogram (oxidation) of TPCPA.
Figure 21:
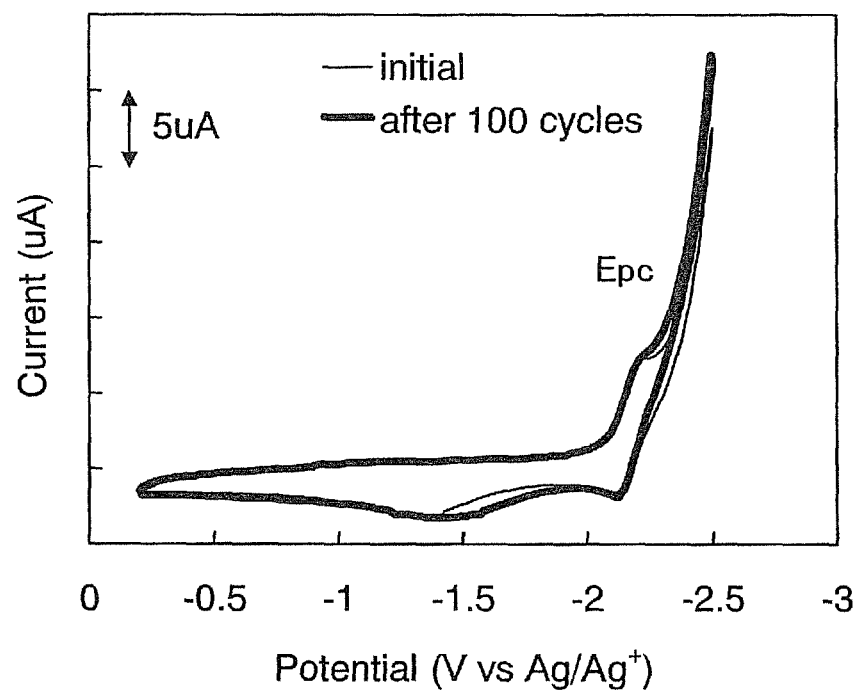
FIG. 21 illustrates a cyclic voltammogram (reduction) of TPCPA.

The oxidation-reduction characteristics of TPCPA were measured by cyclic voltammetry (CV). An electrochemical analyzer (ALS model 600a, manufactured by BAS Inc.) was used for the measurement. Further, dimethylformamide (DMF) and tetra-n-butylammonium perchlorate (n-Bu$_4$NClO$_4$) were used as a solvent and a supporting electrolyte, respectively, and the amount thereof adjusted to yield a concentration of 10 mmol per L of DMF. Furthermore, the amount of TPCPA was adjusted to yield a concentration of 1 mmol per L of the electrolysis solution. A platinum electrode (PIE platinum electrode, produced by BAS Inc.), a platinum electrode (Pt counter electrode (5 cm) for VC-3, produced by BAS Inc.), and an Ag/Ag$^+$ electrode (RE5 non-aqueous solvent reference electrode, produced by BAS Inc.) were used as a working electrode, an auxiliary electrode, and a reference electrode, respectively. The measurement was performed at a scan rate of 0.1 V/s for 100 cycles. FIG. 20 shows the measurement result on the oxidation side. FIG. 21 shows the measurement result on the reduction side. In each of FIG. 20 and FIG. 21, the horizontal axis indicates a potential (V) of the working electrode with respect to the reference electrode, and the vertical axis indicates a current value (μA) that flowed between the working electrode and the counter electrode.

FIG. 20 shows that the oxidation potential of TPCPA was 0.58 V (with respect to Ag/Ag$^+$). FIG. 21 shows that the reduction potential of TPCPA was −2.22 V (with respect to Ag/Ag+). Through the measurement for 100 cycles of scanning, distinct oxidation peaks and reduction peaks were observed in the CV curves. Therefore, it is found that the anthracene derivative of the present invention is a substance in which the reversibility of oxidation-reduction reactions is excellent.

Example 2

Figure 22:
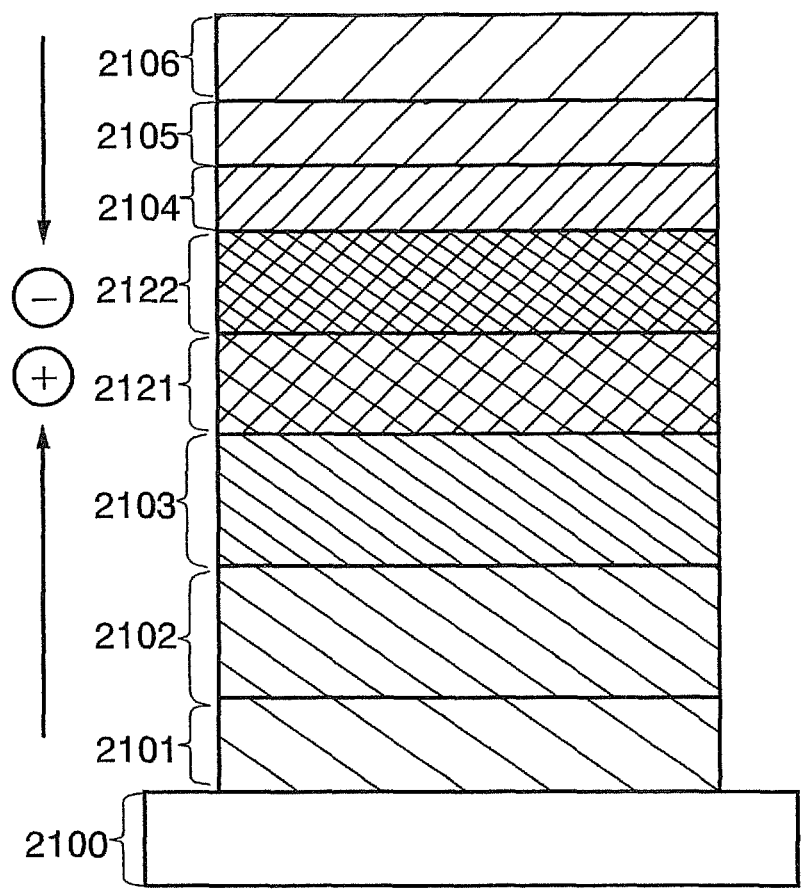
FIG. 22 illustrates a light-emitting element of Example 2.

In Example 2, a light-emitting element of the present invention is described using FIG. 22. Chemical formulae of materials used in this example are shown below.

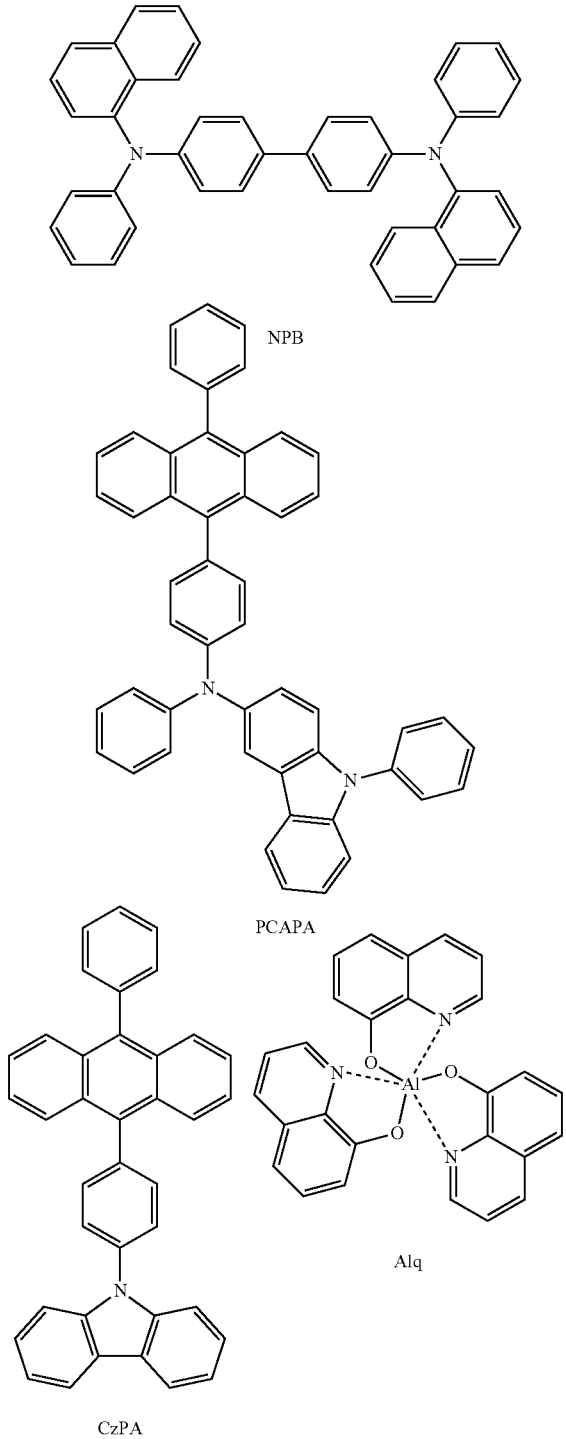

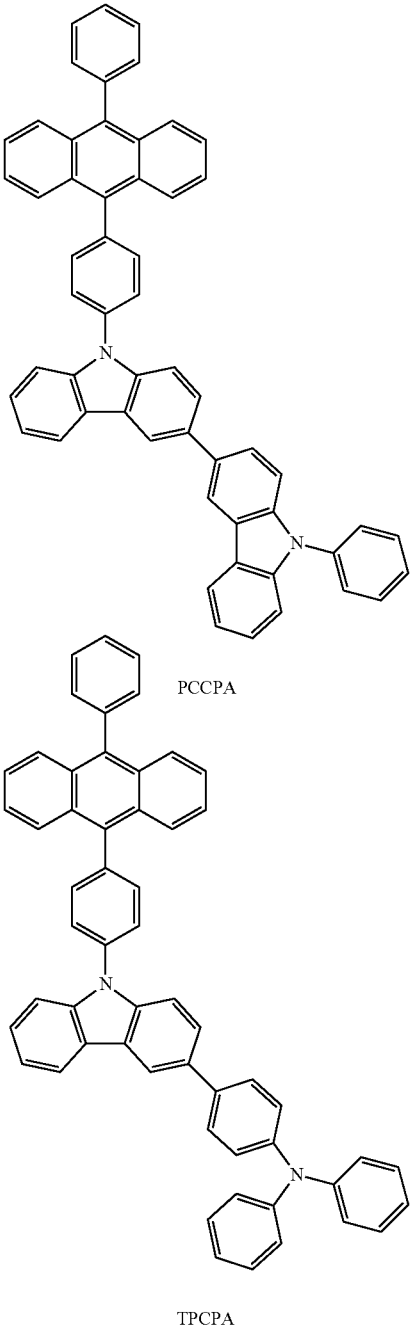

(Light-Emitting Element 1)

First, indium tin oxide containing silicon oxide (ITSO) was deposited by a sputtering method over a glass substrate 2100 to form a first electrode 2101. It is to be noted that the film thickness of the first electrode was 110 nm, and the area of the electrode was 2 mm×2 mm.

Next, the substrate over which the first electrode was formed was fixed to a substrate holder provided in a vacuum evaporation apparatus, so that a surface over which the first electrode was formed faced downward. Then, after the pressure of the vacuum evaporation apparatus was reduced to about $10^{-4}$ Pa, a layer 2102 including a composite material, which was formed of an organic compound and an inorganic compound, was formed over the first electrode 2101 by co-deposition of NPB and molybdenum(VI) oxide. The film thickness of the layer 2102 was to be 50 nm, and the ratio of NPB and molybdenum(VI) oxide was adjusted to be 4:1 (=NPB:molybdenum oxide) in weight ratio. It is to be noted that the co-deposition method is an evaporation method in which evaporation is carried out from a plurality of evaporation sources at the same time in one treatment chamber.

Subsequently, NPB was deposited to a thickness of 10 nm over the layer 2102 including a composite material by an evaporation method using the resistance heating system, thereby forming a hole-transporting layer 2103.

Further, by co-deposition of PCAPA and PCCPA which is the anthracene derivative of the present invention and was synthesized in Synthesis Example 1 of Example 1, a first layer 2121 was formed to a thickness of 30 nm over the hole-transporting layer 2103. The weight ratio of PCCPA and PCAPA was adjusted to 1:0.05 (=PCCPA:PCAPA).

Further, by co-deposition of CzPA and PCAPA, a second layer 2122 was formed to a thickness of 30 nm over the first layer 2121. The weight ratio of CzPA and PCAPA was adjusted to 1:0.05 (=CzPA:PCAPA).

Thereafter, tris(8-quinolinolato)aluminum (Alq) was deposited to a film thickness of 30 nm over the second layer 2122 by an evaporation method using the resistance heating system, thereby an electron-transporting layer 2104 was formed.

Furthermore, lithium fluoride was deposited to a thickness of 1 nm was formed over the electron-transporting layer 2104 to form an electron-injecting layer 2105.

Lastly, aluminum was deposited to a film thickness of 200 nm over the electron-injecting layer 2105 by the evaporation method using the resistance heating system, a second electrode 2106 was formed. Accordingly, a light-emitting element 1 was fabricated.

Figure 23:
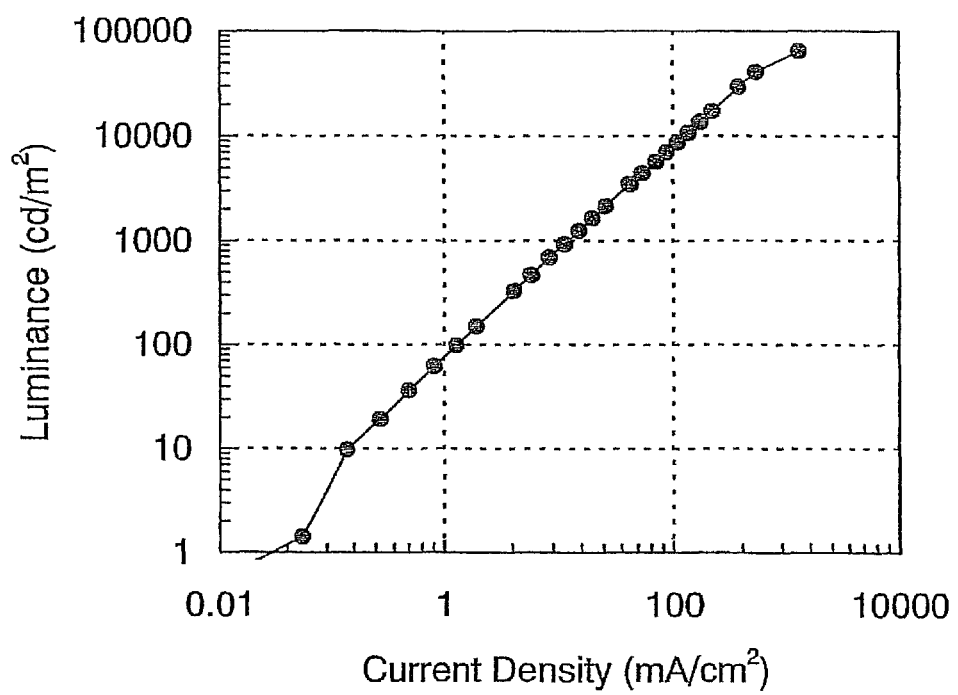
FIG. 23 illustrates current density-luminance characteristics of a light-emitting element manufactured in Example 2.
Figure 24:
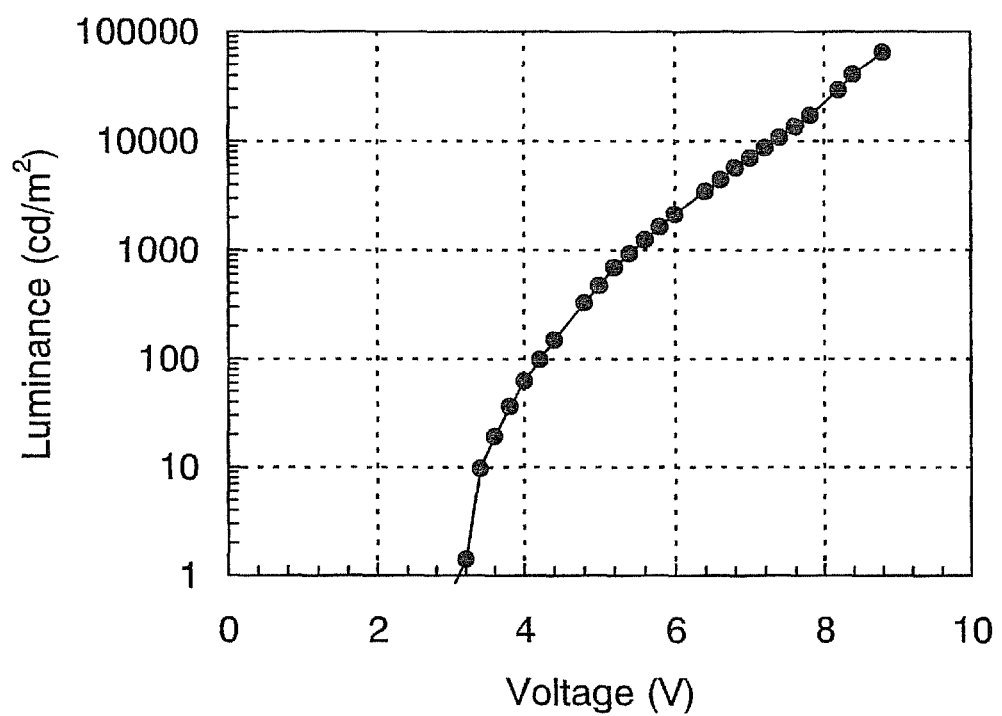
FIG. 24 illustrates voltage-luminance characteristics of a light-emitting element manufactured in Example 2.
Figure 25:
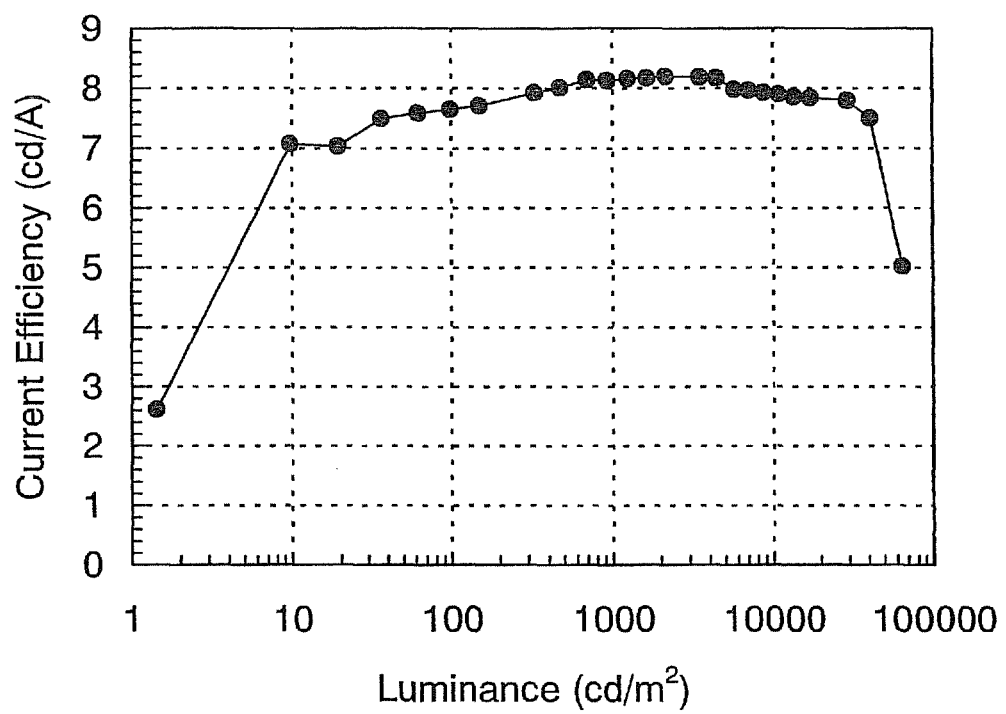
FIG. 25 illustrates luminance-current efficiency characteristics of a light-emitting element manufactured in Example 2.
Figure 26:
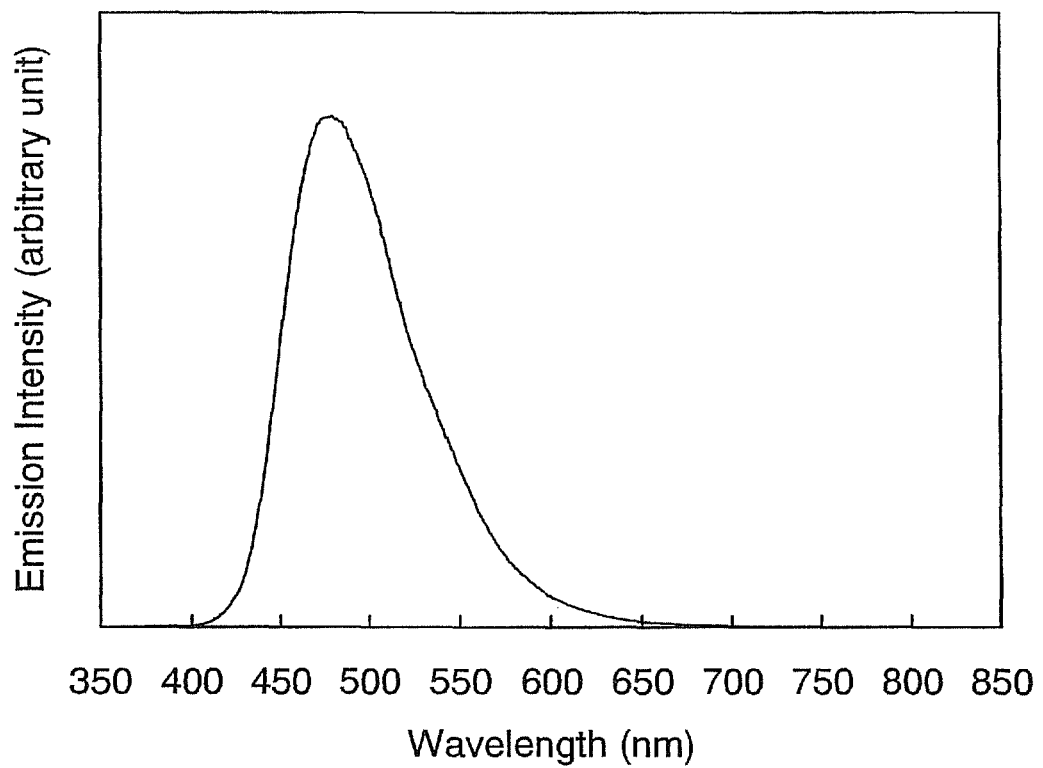
FIG. 26 illustrates an emission spectrum of a light-emitting element manufactured in Example 2.

Current density-luminance characteristics, voltage-luminance characteristics, and luminance-current efficiency characteristics of the light-emitting element 1 are shown in FIG. 23, FIG. 24, and FIG. 25, respectively. Also, the emission spectrum measured at a current of 1 mA is shown in FIG. 26. A CIE chromaticity coordinate of the light-emitting element 1 at luminance of 1000 cd/m$^2$ was (x=0.17, y=0.29), and light emission from the light-emitting element 1 was blue.

(Light-Emitting Element 2)

A light-emitting element 2 was fabricated in a similar manner to the light-emitting element 1 except that TPCPA which is the anthracene derivative of the present invention synthesized in Synthesis Example 2 of Example 1 was used instead of PCCPA. In other words, as illustrated in FIG. 22, PCAPA and TPCPA were co-deposited to form a first layer 2121 having a thickness of 30 nm over the hole-transporting layer 2103, and the other layers of the light-emitting element 2 were formed in a similar manner to the light-emitting element 1. The weight ratio of TPCPA and PCAPA was adjusted to 1:0.05 (=TPCPA:PCAPA).

Figure 27:
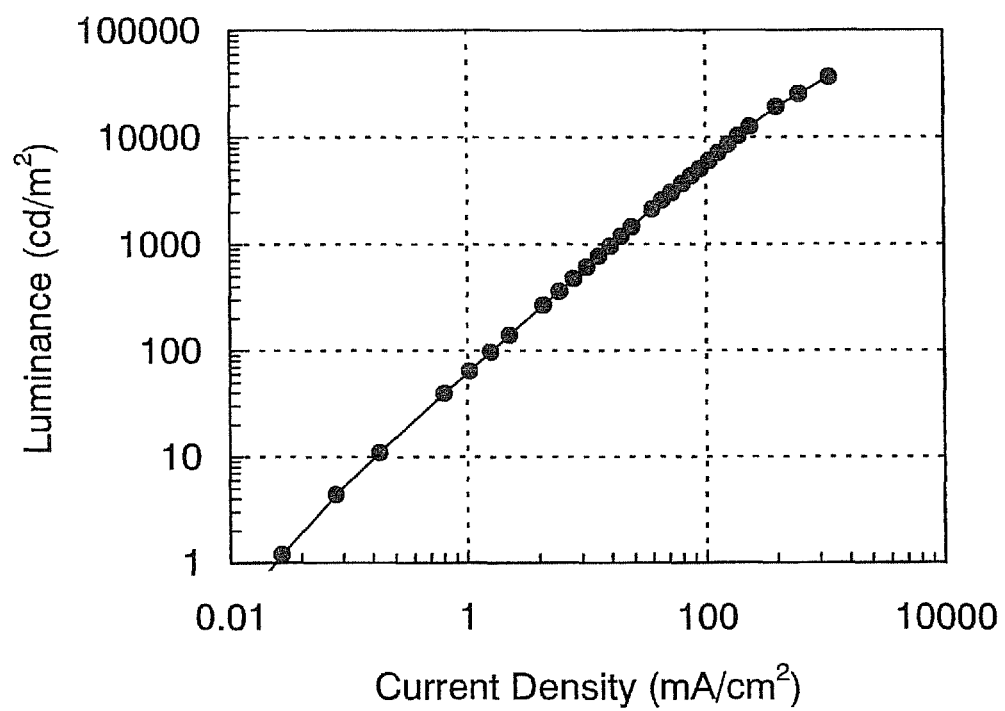
FIG. 27 illustrates current density-luminance characteristics of a light-emitting element manufactured in Example 2.
Figure 28:
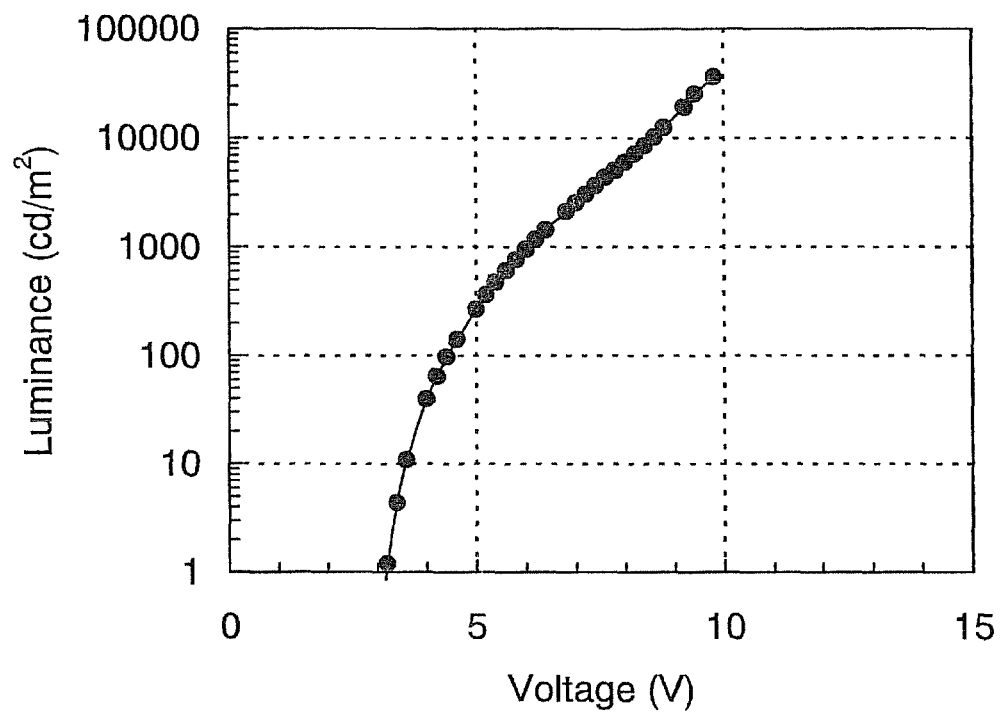
FIG. 28 illustrates voltage-luminance characteristics of a light-emitting element manufactured in Example 2.
Figure 29:
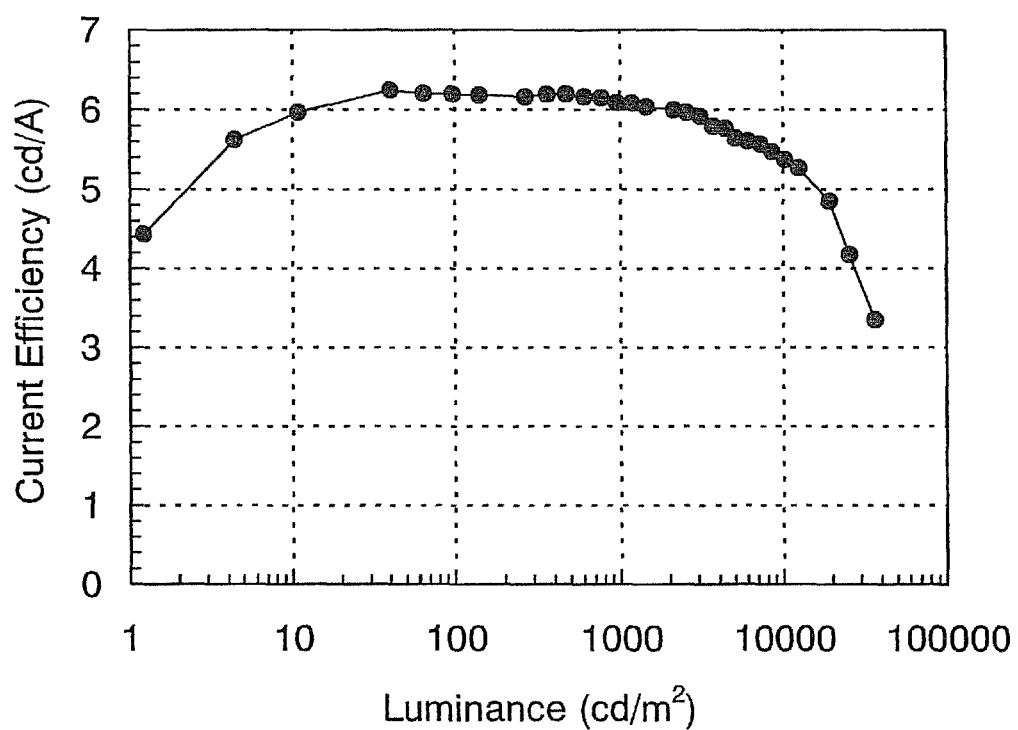
FIG. 29 illustrates luminance-current efficiency characteristics of a light-emitting element manufactured in Example 2.
Figure 30:
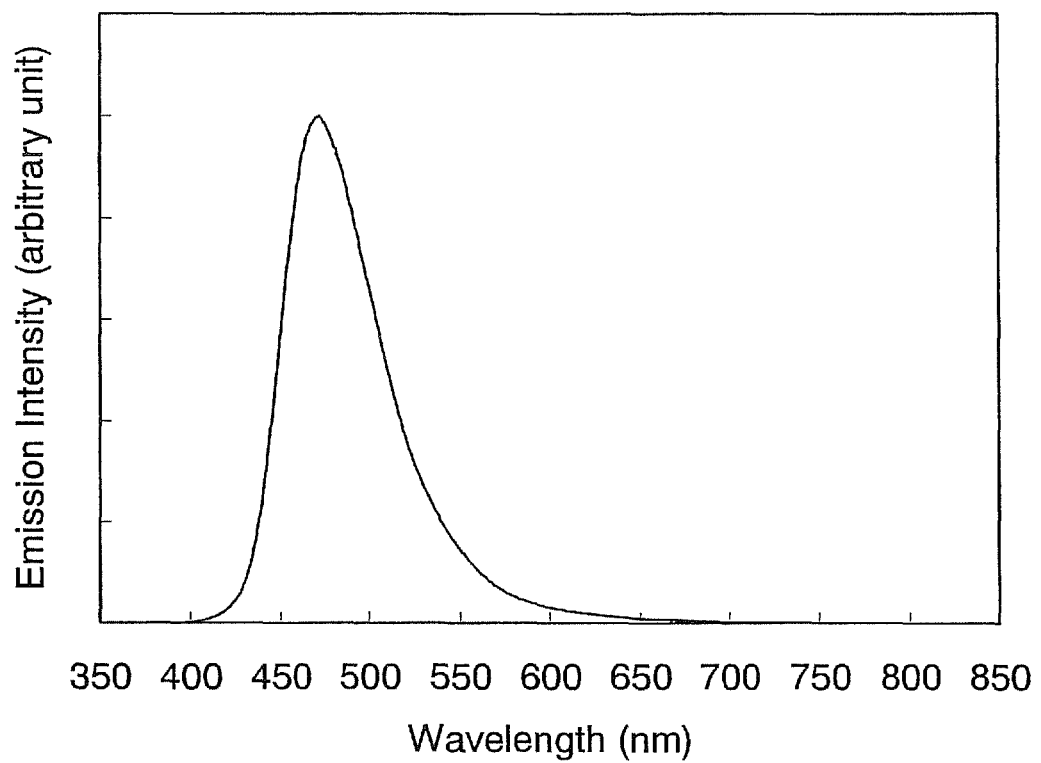
FIG. 30 illustrates an emission spectrum of a light-emitting element manufactured in Example 2.

Current density-luminance characteristics, voltage-luminance characteristics, and luminance-current efficiency characteristics of the light-emitting element 2 are shown in FIG. 27, FIG. 28, and FIG. 29, respectively. Also, the emission spectrum measured at a current of 1 mA is shown in FIG. 30. A CIE chromaticity coordinate of the light-emitting element 2 at luminance of about 1000 cd/m$^2$ was (x=0.15, y=0.22), and light emission from the light-emitting element 2 was blue.

Comparative Example 1

In Comparative Example 1, a comparative element 1 was fabricated in a similar manner to the light-emitting elements 1 and 2 except that the first layer 2121 in FIG. 22 was not formed.

Figure 31:
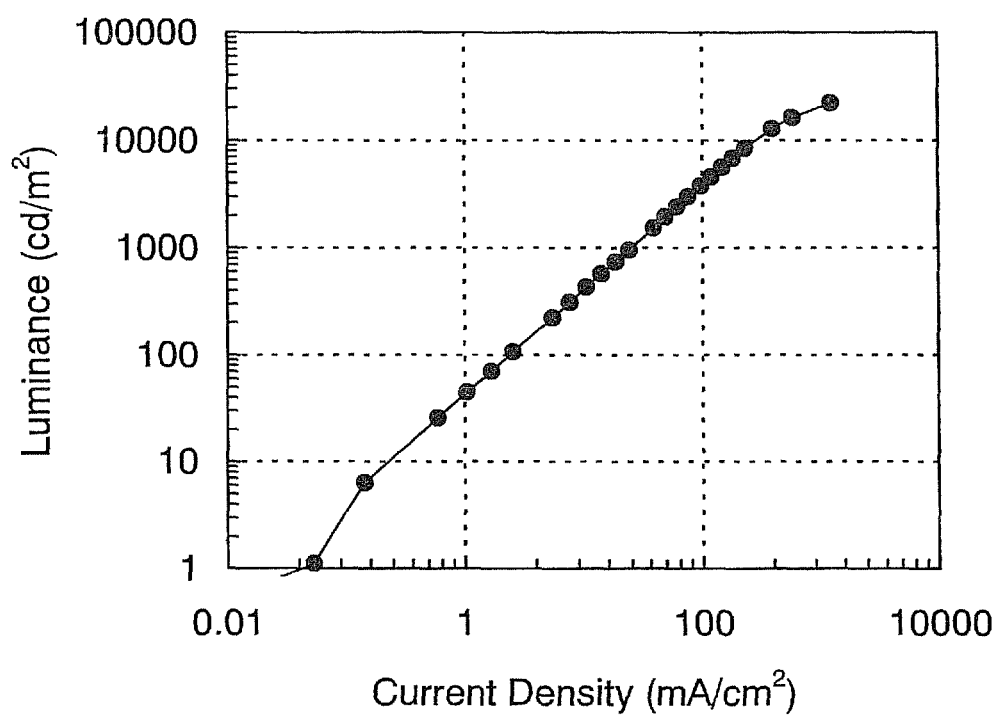
FIG. 31 illustrates current density-luminance characteristics of a light-emitting element manufactured in Comparative Example 1.
Figure 32:
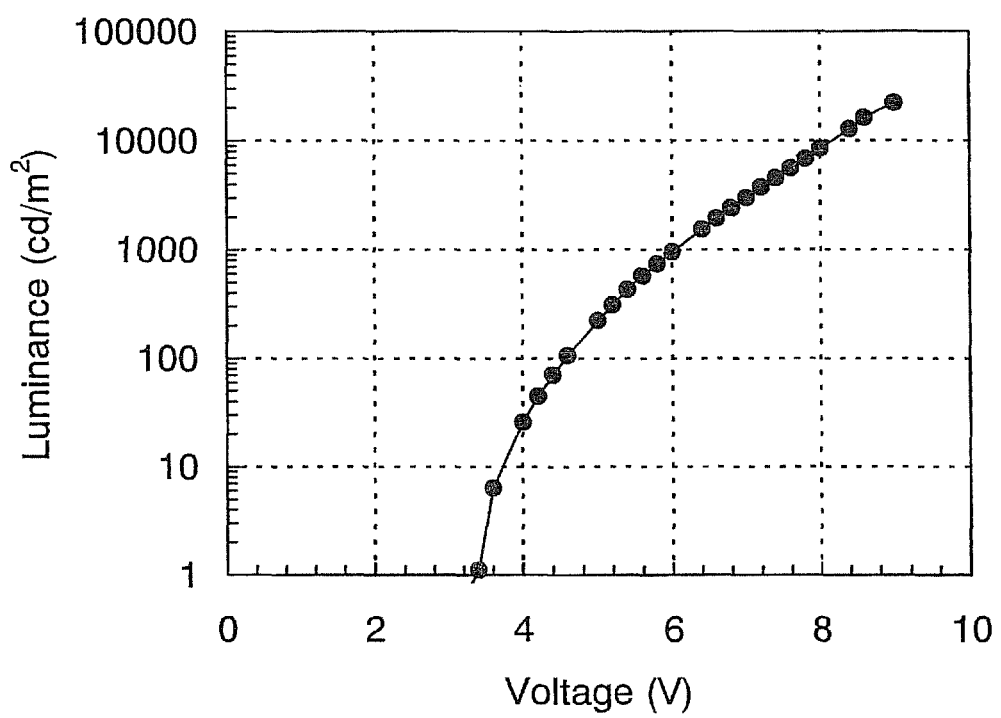
FIG. 32 illustrates voltage-luminance characteristics of a light-emitting element manufactured in Comparative Example 1.
Figure 33:
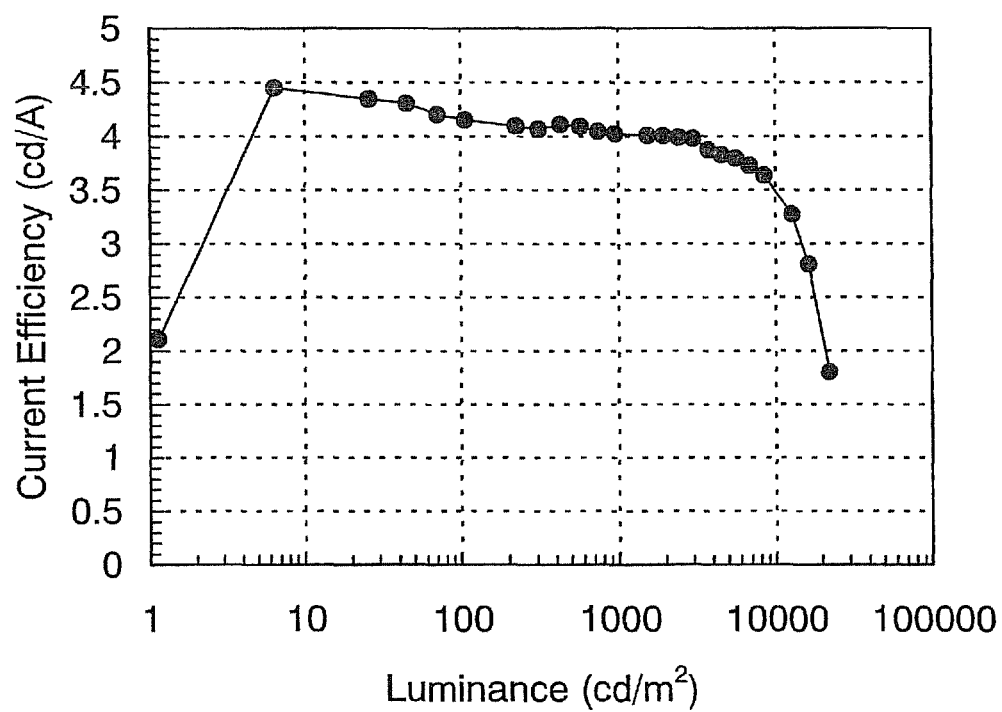
FIG. 33 illustrates luminance-current efficiency characteristics of a light-emitting element manufactured in Comparative Example 1.
Figure 34:
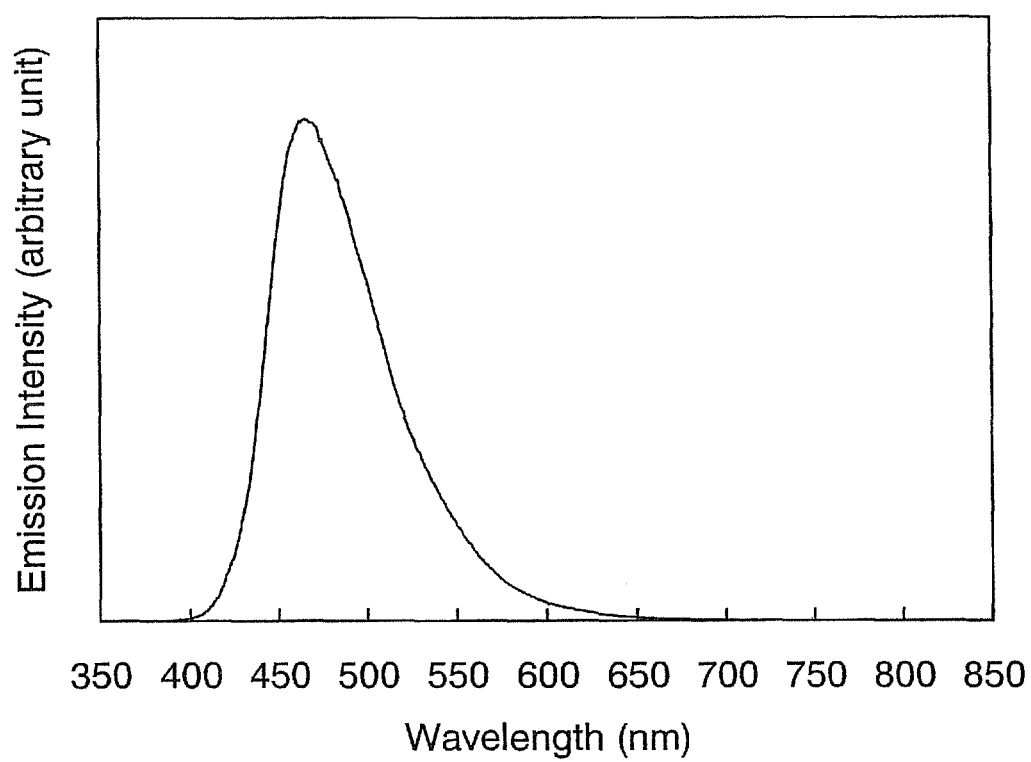
FIG. 34 illustrates an emission spectrum of a light-emitting element manufactured in Comparative Example 1.

Current density-luminance characteristics, voltage-luminance characteristics, and luminance-current efficiency characteristics of the comparative element 1 are shown in FIG. 31, FIG. 32, and FIG. 33, respectively. Also, the emission spectrum measured at a current of 1 mA is shown in FIG. 34. A CIE chromaticity coordinate of the comparative element 1 at luminance of 1000 cd/m$^2$ was (x=0.16, y=0.21), and light emission from the comparative element 1 was blue.

Figure 35:
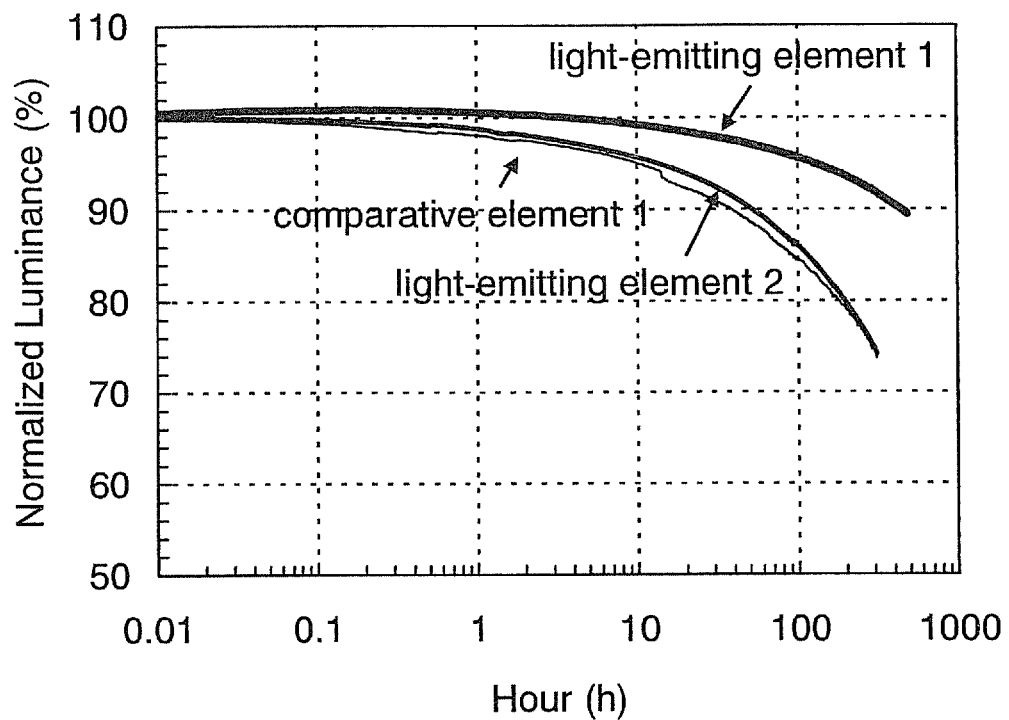
FIG. 35 illustrates a measurement result of reliability of light-emitting elements manufactured in Example 2.

FIG. 35 shows the results of luminances of the light-emitting element 1, the light-emitting element 2, and the comparative element 1, which were measured under the conditions that the initial luminance of each element was set 1000 cd/m$^2$ and each element was operated at a constant current density.

The current efficiency and life of each light-emitting element was compared using the above measurement results. The result is shown in Table 1 given below.

TABLE 1

|  | current efficiency (cd/A) | life (time) |
|---|---|---|
| light-emitting element 1 | 8.1 | 440 |
| light-emitting element 2 | 6.1 | 52 |
| comparative element 1 | 4.0 | 38 |

In Table 1, "current efficiency" refers to the current efficiency measured at luminance of 1000 cd/m$^2$ and "life" refers to time that is needed to reduce an initial luminance of 1000 cd/m$^2$ to 90 percent. The light-emitting element 1 drastically improved in the current efficiency and the life compared to the comparative element 1. Further, the light-emitting element 2 improved in the current efficiency and the life compared to the comparative element 1.

As described above, the light-emitting elements of the present invention exhibited extremely favorable characteristics. Since the anthracene derivative of the present invention is a substance in which the reversibility of oxidation-reduction reactions is excellent, the light-emitting element of the present shows little luminance decay over an emission time and has a long element life.

Example 3
In Example 3, a light-emitting element of the present invention is described using FIG. 22. Chemical formulae of materials used in this example are shown below.
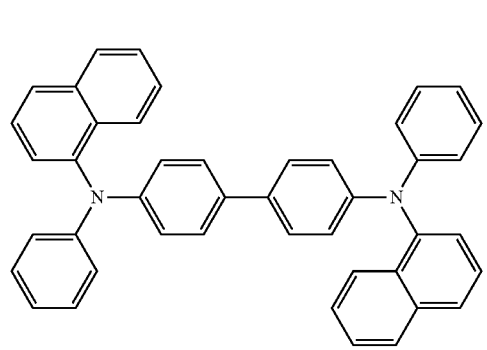
NPB
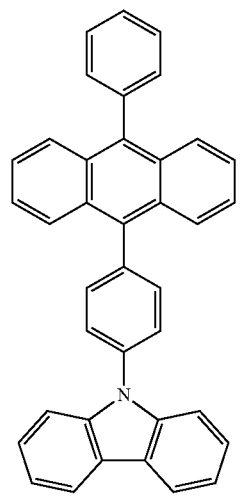
CzPA
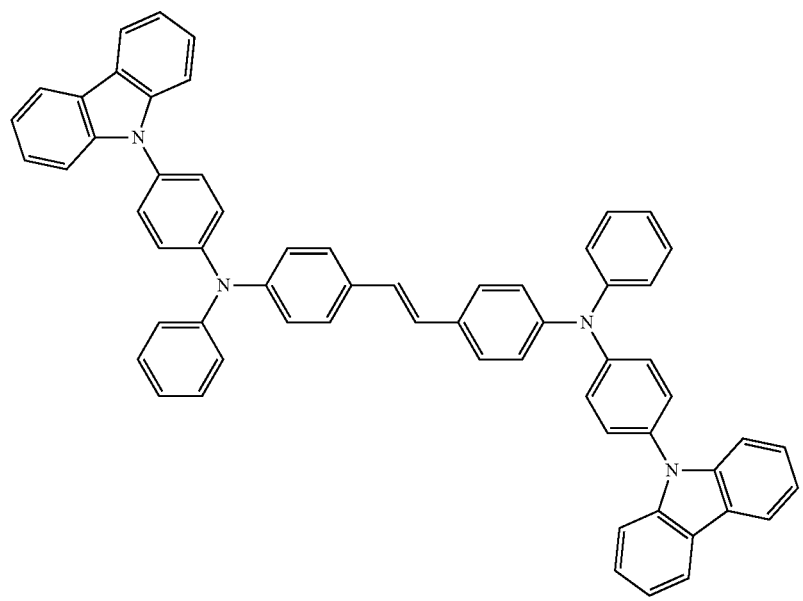
YGA2S

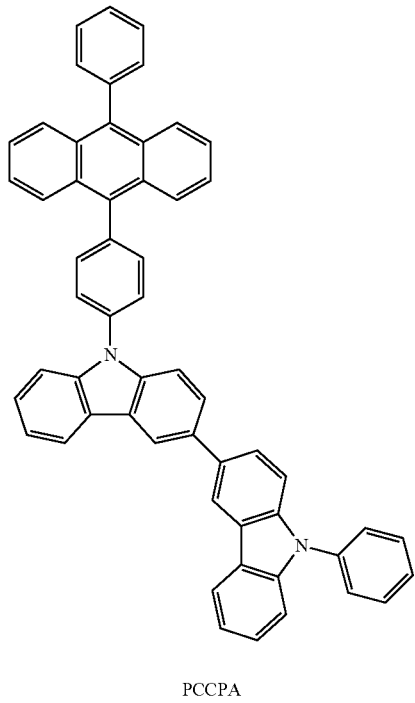

PCCPA

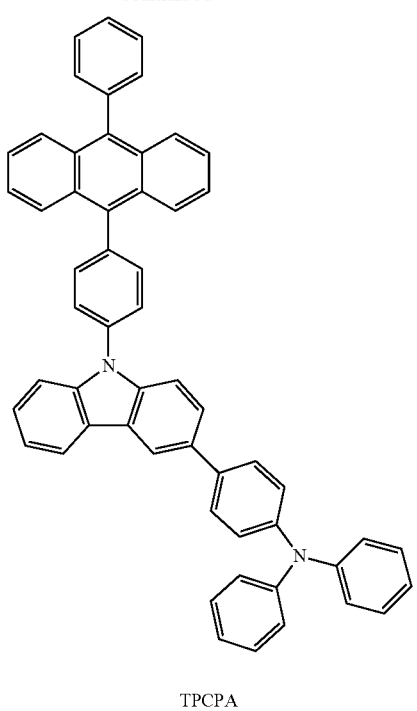

TPCPA

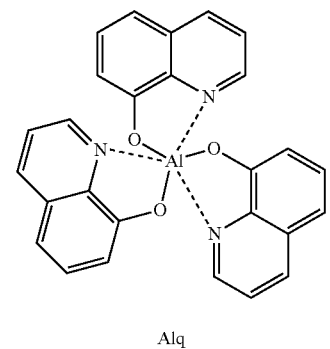

Alq (Light-Emitting Element 3)

A light-emitting element 3 in Example 3 was fabricated in a similar manner to the light-emitting element 1 of Example 2 except that YGA2S was used instead of PCAPA in the first layer and YGA2S was used instead of PCAPA in the second layer. In other words, as illustrated in FIG. 22, PCCPA and YGA2S were co-deposited to form a first layer 2121 having a thickness of 30 nm over the hole-transporting layer 2103, CzPA and YGA2S were co-deposited to form a second layer 2121 having a thickness of 30 nm over the first layer 2121, and the other layers of the light-emitting element 3 were formed in a similar manner to the light-emitting element 1. The weight ratio of PCCPA and YGA2S was adjusted to 1:0.05 (=PCCPA:YGA2S), and that of CzPA and YGA2S was adjusted to 1:0.05 (=CzPA:YGA2S).

Figure 36:
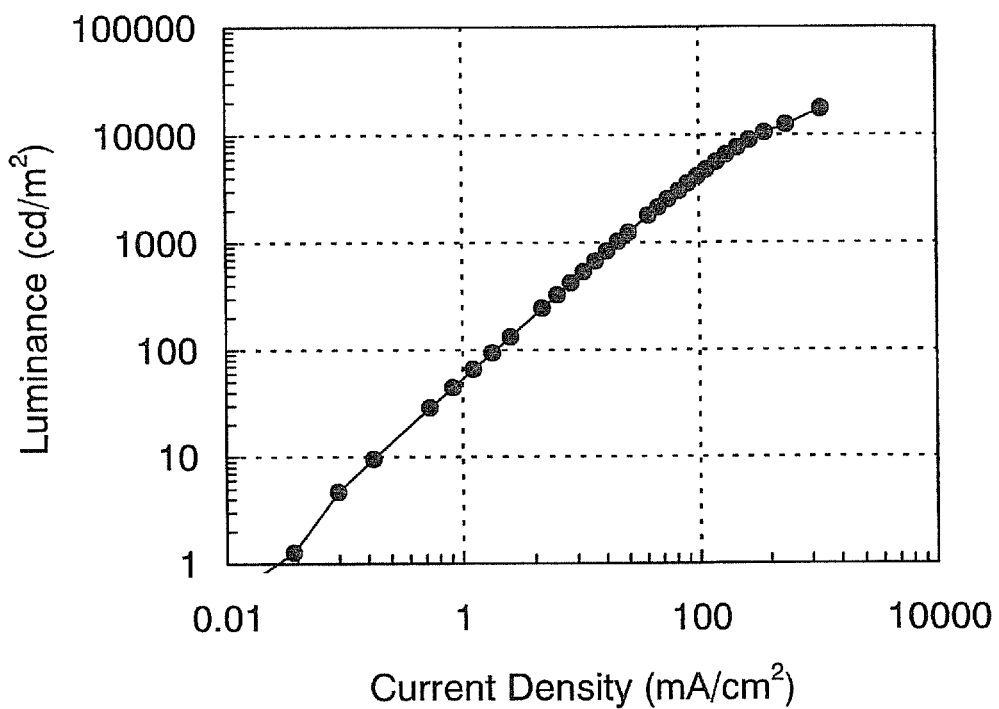
FIG. 36 illustrates current density-luminance characteristics of a light-emitting element manufactured in Example 3.
Figure 37:
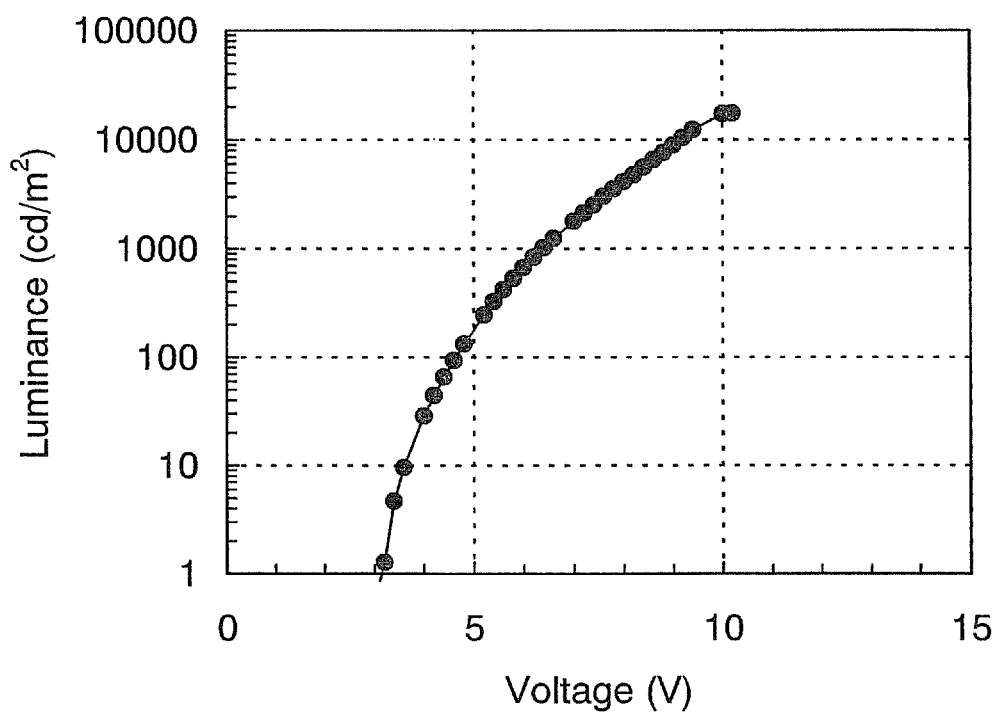
FIG. 37 illustrates voltage-luminance characteristics of a light-emitting element manufactured in Example 3.
Figure 38:
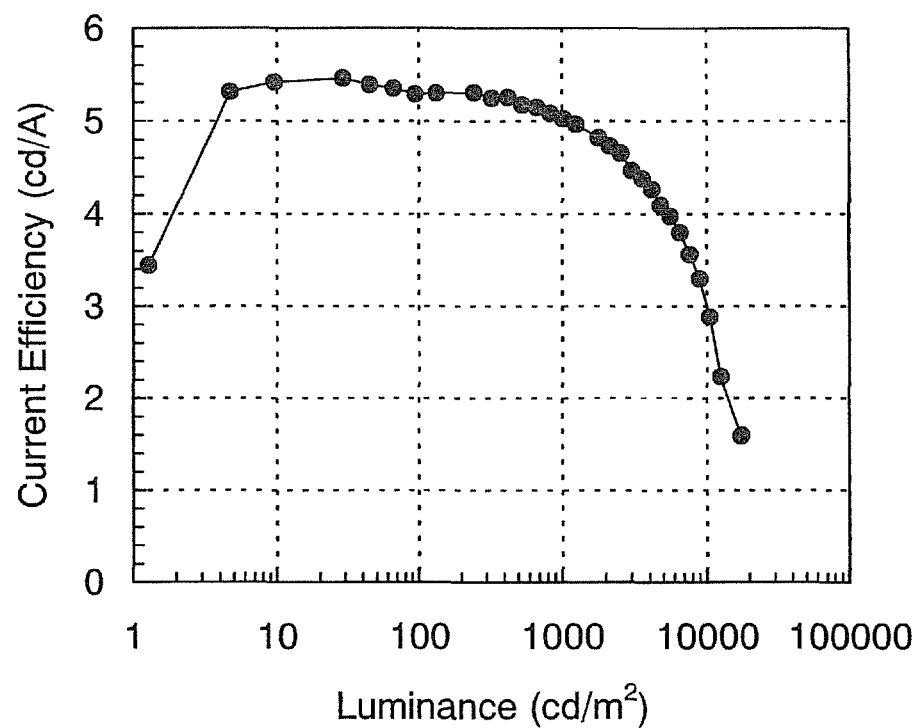
FIG. 38 illustrates luminance-current efficiency characteristics of a light-emitting element manufactured in Example 3.
Figure 39:
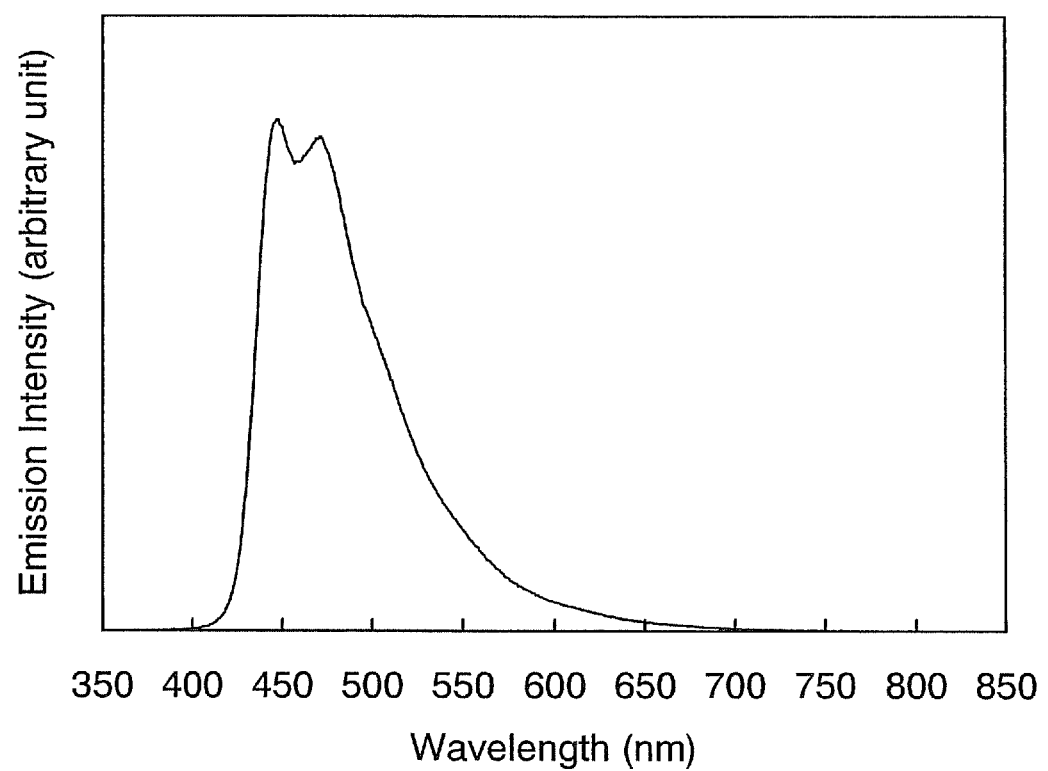
FIG. 39 illustrates an emission spectrum of a light-emitting element manufactured in Example 3.

Current density-luminance characteristics, voltage-luminance characteristics, and luminance-current efficiency characteristics of the light-emitting element 3 are shown in FIG. 36, FIG. 37, and FIG. 38, respectively. Also, the emission spectrum measured at a current of 1 mA is shown in FIG. 39. A CIE chromaticity coordinate of the light-emitting element 3 at luminance of about 1000 cd/m² was (x=0.17, y=0.19), and light emission from the light-emitting element 3 was blue.

A light-emitting element 4 fabricated in Example 3 is a light-emitting element that uses the anthracene derivative TPCPA of the present invention. The light-emitting element 4 is specifically described.

(Light-Emitting Element 4)

A light-emitting element 4 was fabricated in a similar manner to the light-emitting element 3 except that TPCPA was used instead of PCCPA. In other words, as illustrated in FIG. 22, YGA2S and TPCPA which is represented by a structural formula (223) were co-deposited to form a first layer 2121 having a thickness of 30 nm over the hole-transporting layer 2103, and the other layers of the light-emitting element 4 were formed in a similar manner to the light-emitting element 3. The weight ratio of TPCPA and YGA2S was adjusted to 1:0.05 (=TPCPA:YGA2S).

Figure 40:
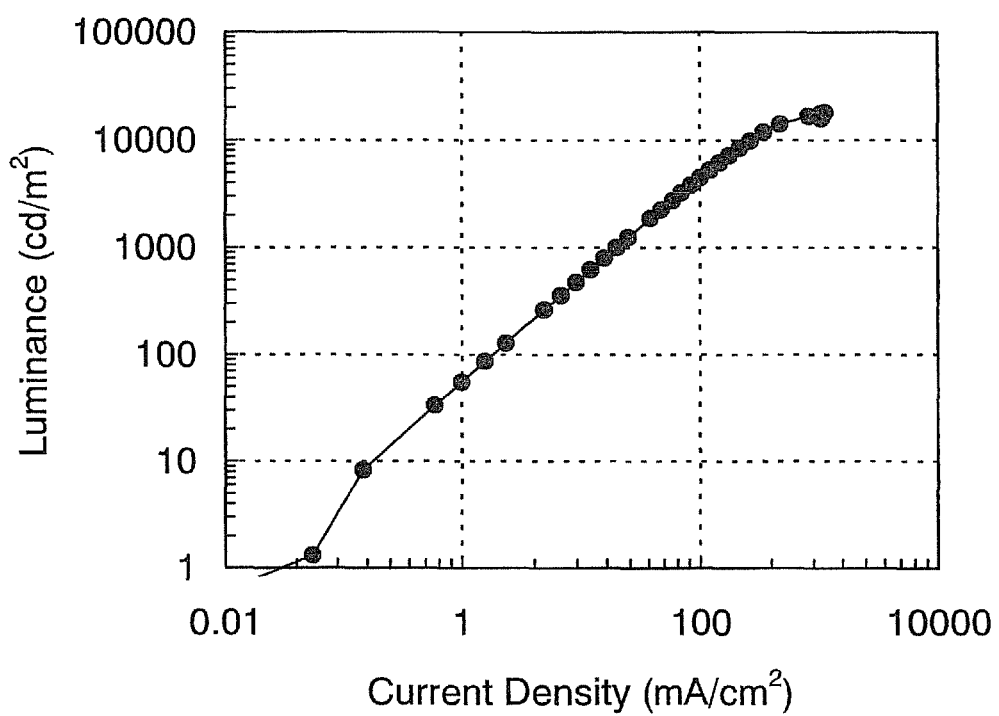
FIG. 40 illustrates current density-luminance characteristics of a light-emitting element manufactured in Example 3.
Figure 41:
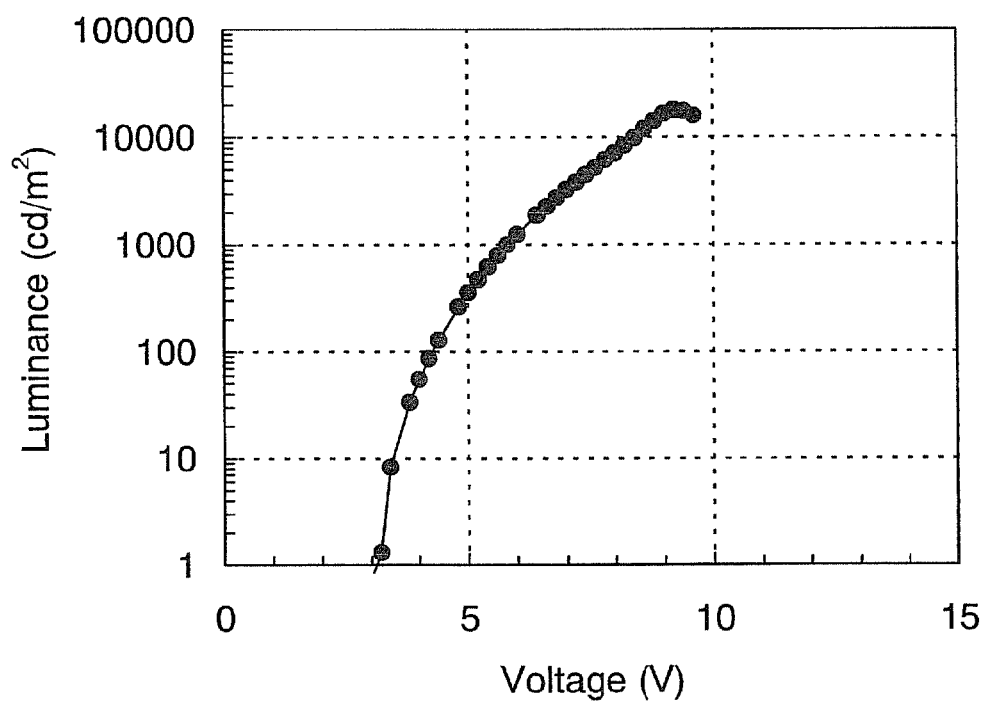
FIG. 41 illustrates voltage-luminance characteristics of a light-emitting element manufactured in Example 3.
Figure 42:
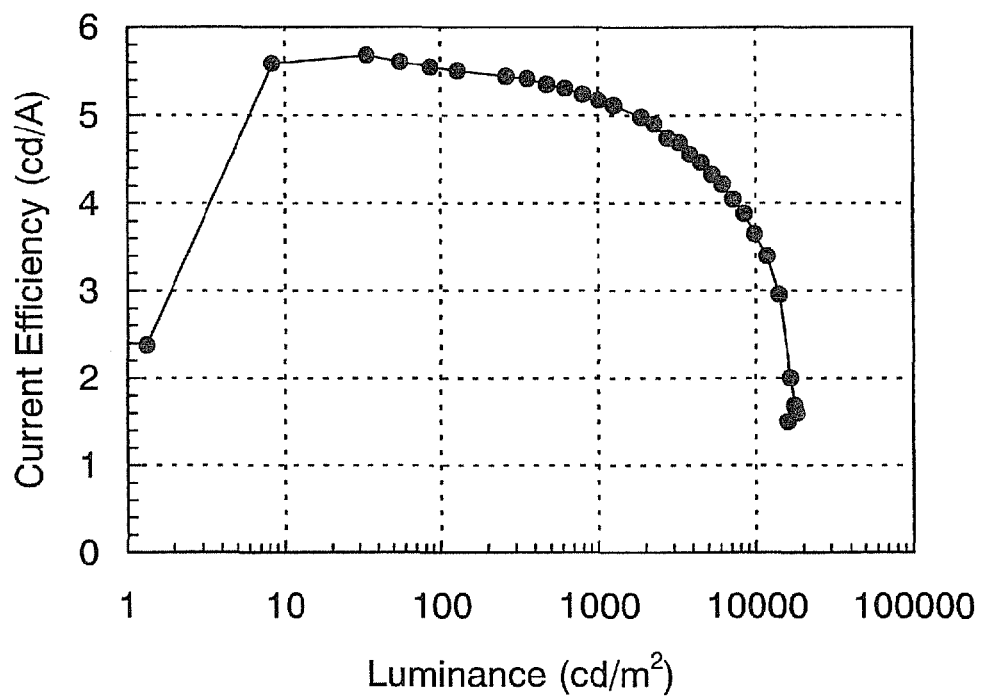
FIG. 42 illustrates luminance-current efficiency characteristics of a light-emitting element manufactured in Example 3.
Figure 43:
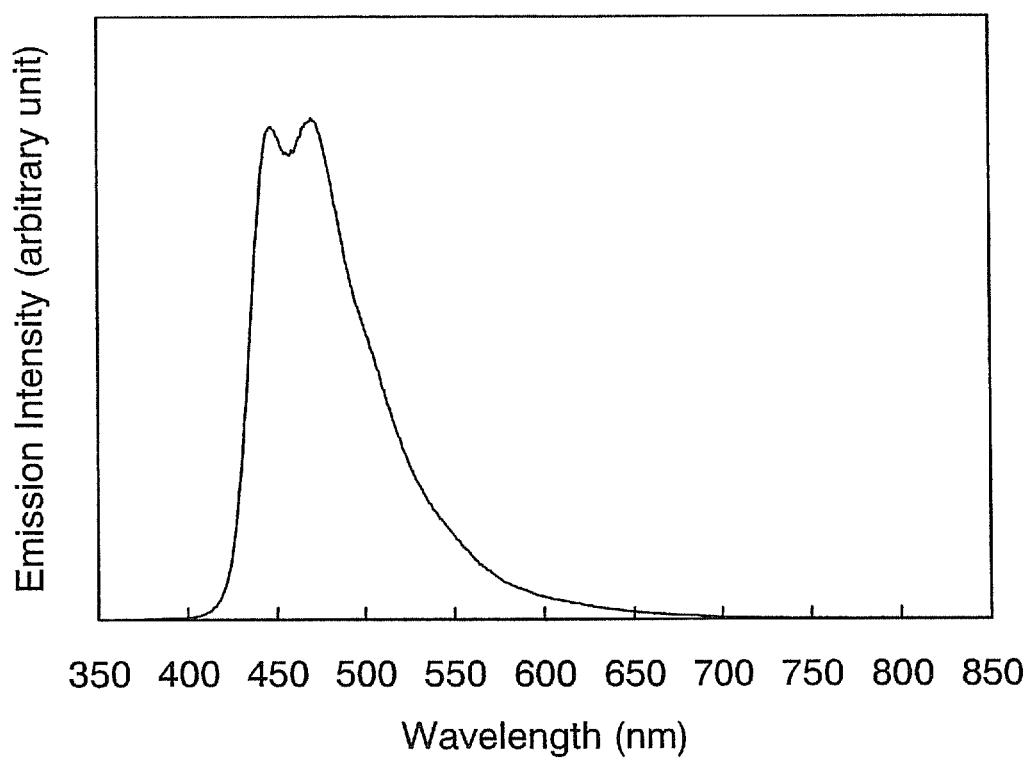
FIG. 43 illustrates an emission spectrum of a light-emitting element manufactured in Example 3.

Current density-luminance characteristics, voltage-luminance characteristics, and luminance-current efficiency characteristics of the light-emitting element 4 are shown in FIG. 40, FIG. 41, and FIG. 42, respectively. Also, the emission spectrum measured at a current of 1 mA is shown in FIG. 43. A CIE chromaticity coordinate of the light-emitting element 4 at luminance of 1000 cd/m² was (x=0.16, y=0.17), and light emission from the light-emitting element 4 was blue.

Comparative Example 2

In Comparative Example 2, a comparative element 2 was fabricated in a similar manner to the light-emitting elements 3 and 4 except that the first layer 2121 in FIG. 22 was not formed.

Figure 44:
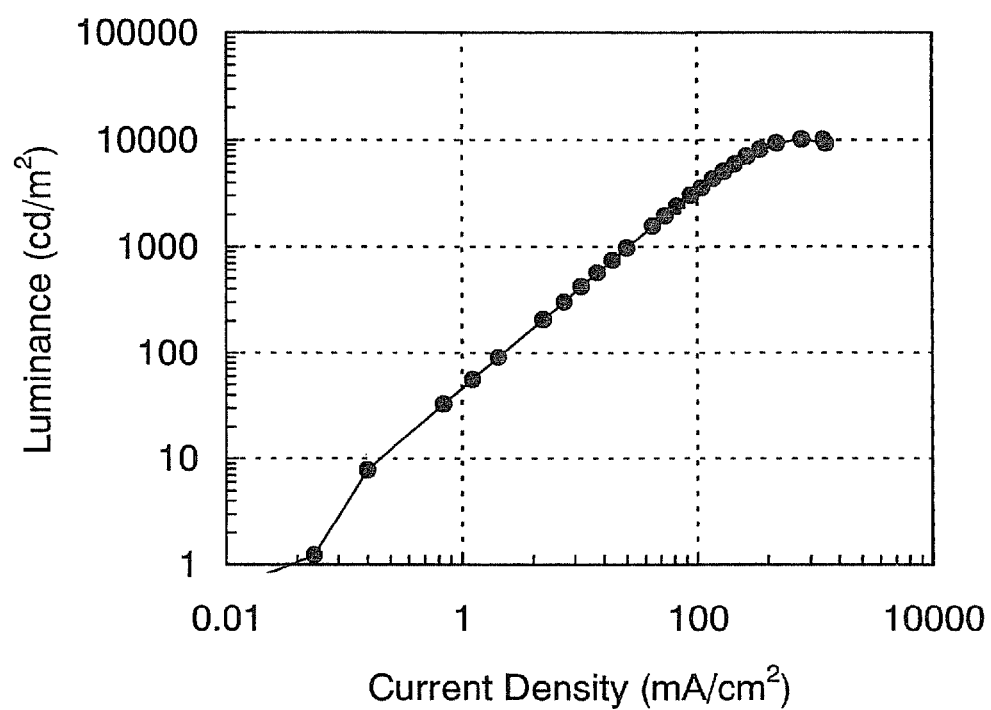
FIG. 44 illustrates current density-luminance characteristics of a light-emitting element manufactured in Comparative Example 2.
Figure 45:
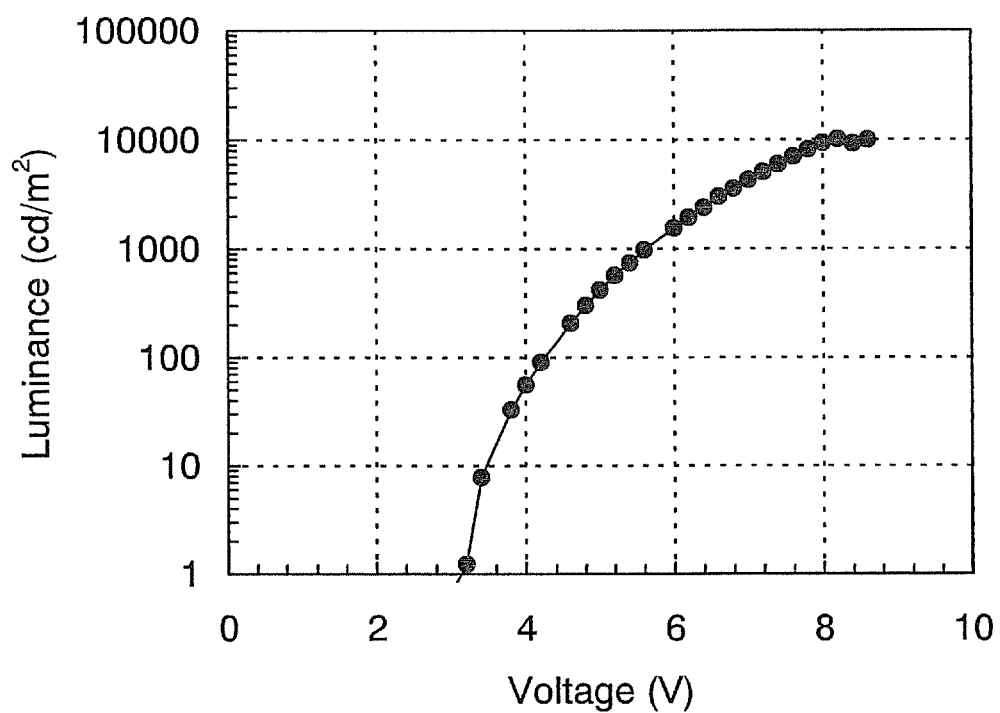
FIG. 45 illustrates voltage-luminance characteristics of a light-emitting element manufactured in Comparative Example 2.
Figure 46:
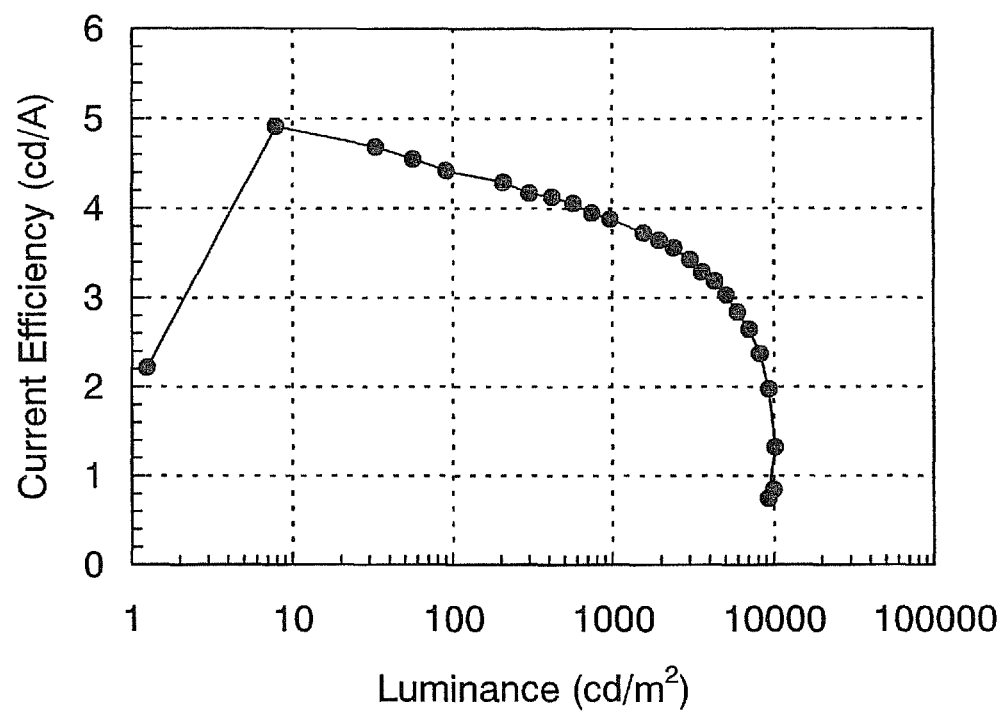
FIG. 46 illustrates luminance-current efficiency characteristics of a light-emitting element manufactured in Comparative Example 2.
Figure 47:
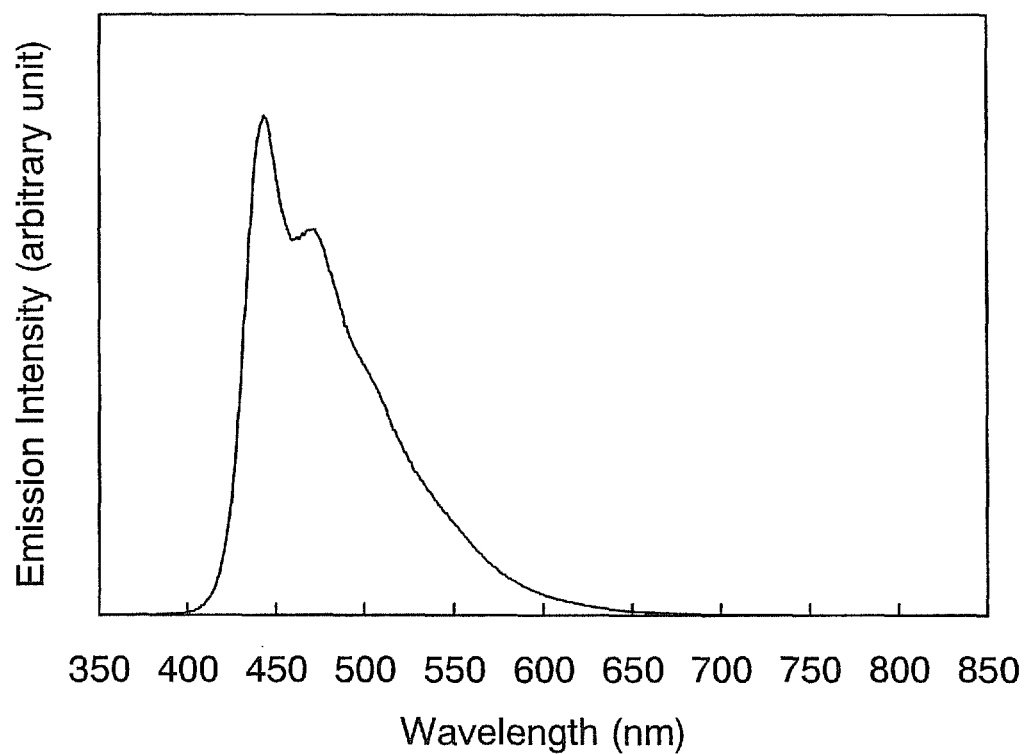
FIG. 47 illustrates an emission spectrum of a light-emitting element manufactured in Comparative Example 2.

Current density-luminance characteristics, voltage-luminance characteristics, and luminance-current efficiency characteristics of the comparative element 2 are shown in FIG. 44, FIG. 45, and FIG. 46, respectively. Also, the emission spectrum measured at a current of 1 mA is shown in FIG. 47. A CIE chromaticity coordinate of the comparative element 2 at luminance of 1000 cd/m² was (x=0.16, y=0.17), and light emission from the comparative element 2 was blue.

The current efficiencies at a luminance of 1000 cd/m² of the light-emitting element 3, the light-emitting element 4, and the comparative element 2 were compared. The current efficiencies of the light-emitting element 3, the light-emitting element 4, and the comparative element 2 were, respectively, 5.0 cd/A, 5.2 cd/A, and 3.9 cd/A. Thus, it is found that the light-emitting element having high emission efficiency can be realized according to the present invention.

Example 4

Synthesis Example 3

In Synthesis Example 3, a synthesis method of an anthracene derivative 9,9"-diphenyl-9'-[4-(10-phenyl-9-anthryl)phenyl]-3,3':6',3"-ter(9H-carbazole) (PC2CPA) of the present invention represented by a structural formula (193) is specifically described.

(193)

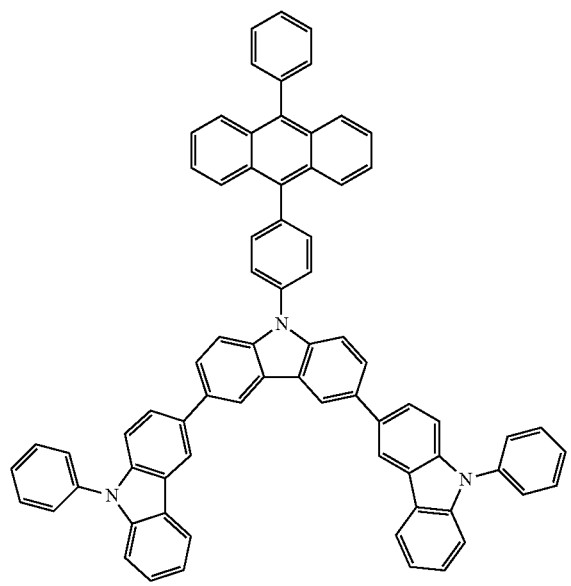

Step 1: Synthesis of 9-phenyl-9H-carbazol-3-boronic acid 10 g (32 mmol) of 3-bromo-9-phenyl-9H-carbazole was put into a 500 mL three-neck flask. The air in the flask was replaced with nitrogen. To the mixture were added 150 mL of tetrahydrofuran (THF), and then the solution was cooled to −80° C. Into this solution, 22 mL (36 mmol) of n-butyllithium (a 1.61 mol/L hexane solution) was dropped by a syringe. After the dropping was completed, this solution was stirred at the same temperature for 1 hour. After the stirring, 4.6 mL, (40 mmol) of trimethyl borate was added to the solution, and the solution was stirred for about 15 hours while the temperature of the solution was being increased to room temperature. Thereafter, to the solution was added about 50 mL (1.0 mol/L) of dilute hydrochloric acid, and then the solution was stirred for 1 hour. After the stirring, the aqueous layer of the mixture was extracted with ether acetate. The extract was combined with the organic layer and then washed with a saturated sodium hydrogen carbonate solution. The organic layer was dried with magnesium sulfate. After the drying, this mixture was subjected to gravity filtration. The obtained filtrate was condensed to give an oily light brown substance. The obtained oily substance was recrystallized with chloroform/hexane to give 6.2 g of a light brown powder, which was the object of the synthesis, at a yield of 68%. A synthesis scheme of Step 1 is shown in (d-1) given below.

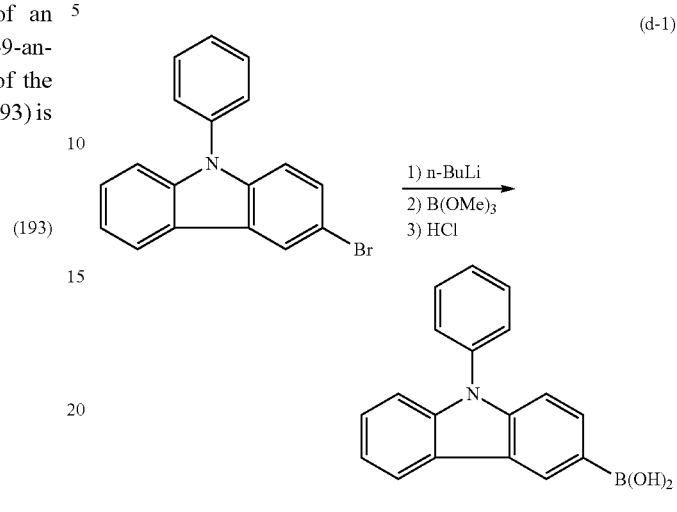

(d-1)

Step 2: Synthesis of 9,9"-diphenyl-3,3':6',3"-ter(9H-carbazole) (PC2C)

1.0 g (3.1 mmol) of 3,6-dibromocarbazole, 1.8 g (6.2 mmol) of N-phenyl-9H-carbazol-3-boronic acid, and 457 mg (1.5 mmol) of tris(ortho-tolyl)phosphine were put into a 300 mL three-neck flask. To the mixture were added 20 mL of ethanol, 50 mL of toluene, and 20 mL (2.0 mol/L) of an aqueous solution of potassium carbonate. This mixture was stirred to be degassed while the pressure was reduced. To this mixture was added 70 mg (0.30 mmol) of palladium(II) acetate. This mixture was refluxed at 110° C. for 5 hours. After a predetermined time passed, the aqueous layer was extracted with toluene. The extract was combined with the organic layer and then washed with water and further with a saturated saline solution. The organic layer was dried with magnesium sulfate. This mixture was subjected to gravity filtration. The obtained filtrate was condensed to give an oily brown substance. The obtained oily substance was purified by silica gel column chromatography (a developing solvent was a mixed solvent of hexane ether acetate=3:1) to give a white solid. This solid was recrystallized with chloroform/hexane to give 1.2 g of a white powder, which was the object of the synthesis, at a yield of 60%. A synthesis scheme of Step 2 is shown in (d-2) given below.

(d-2)

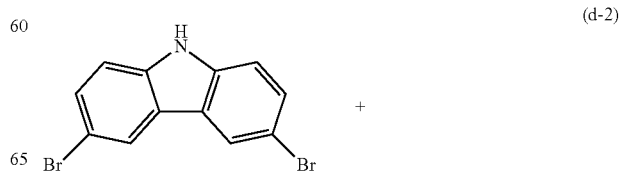

+

-continued

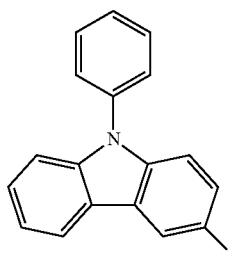

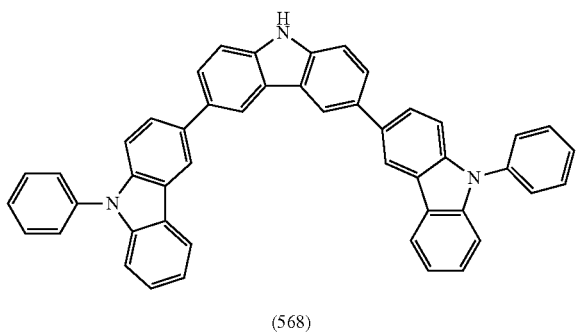

(568)

The obtained compound was analyzed by nuclear magnetic resonance (NMR) measurement, whereby it is confirmed that the compound is PC2C which is an organic compound of the present invention represented by a structural formula (568).

Figure 48A:
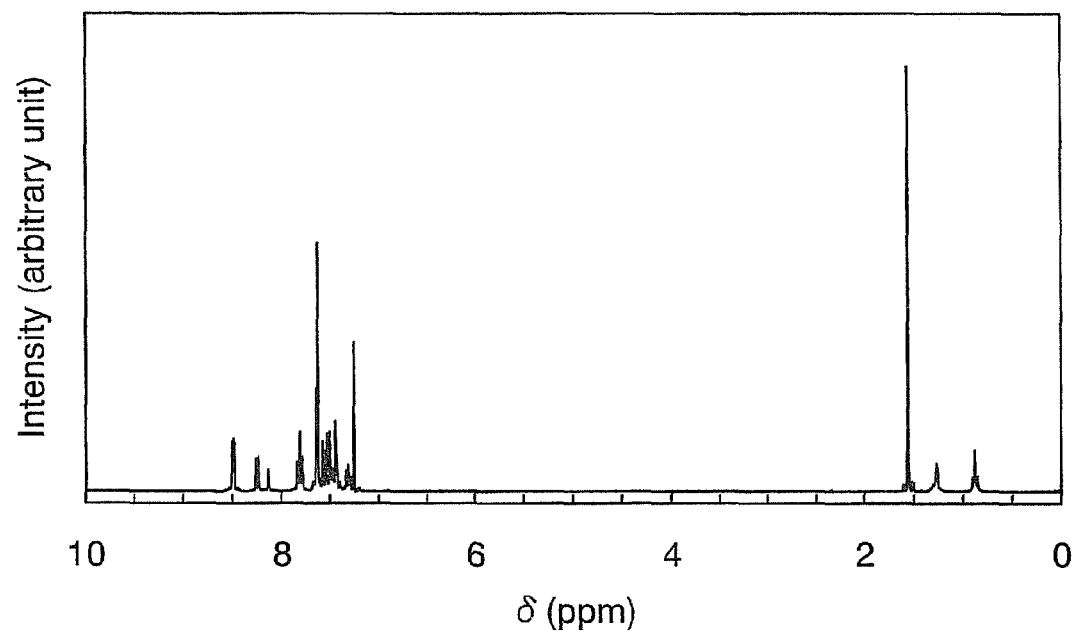
FIGS. 48A and 48B are $^1$H-NMR charts of PC2C.
Figure 48B:
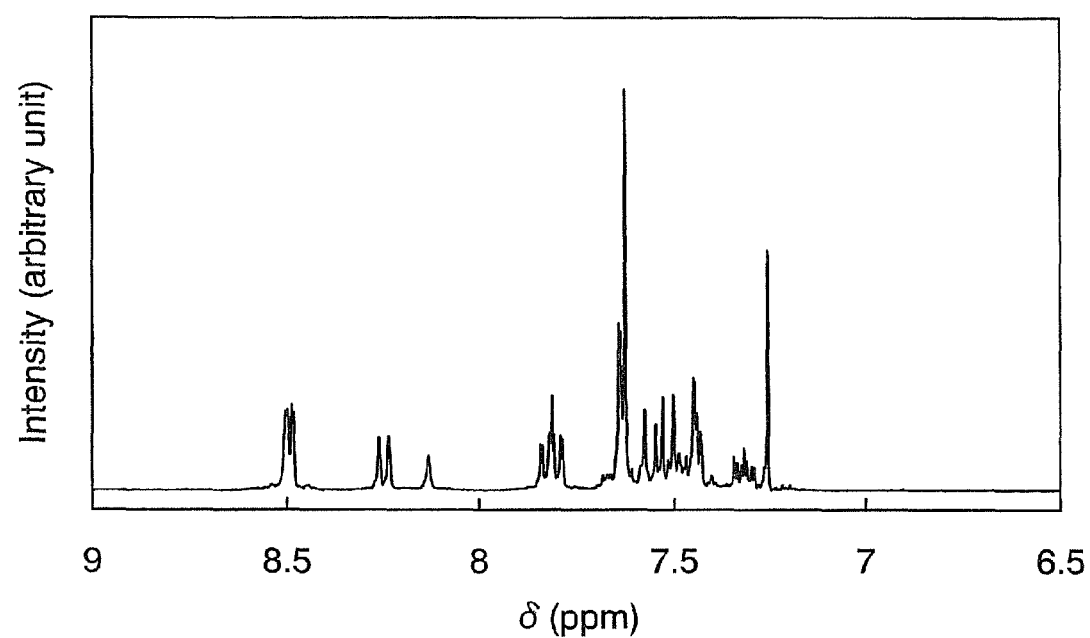

Hereinafter, the $^1$H NMR data is shown. $^1$H NMR (CDCl$_3$, 300 MHz): δ=7.43-7.62 (m, 20H), 7.78-7.83 (m, 4H), 8.11 (s, 1H), 8.24 (d, J=7.8 Hz, 2H), 8.49 (dd, J$_1$=1.5 Hz, J$_2$=4.8 Hz, 4H). The $^1$H NMR charts are shown in FIGS. 48A and 48B. The range of 6.5 ppm to 9.0 ppm in FIG. 48A is expanded and shown in FIG. 48B.

Step 3: Synthesis of 9,9''-diphenyl-9'-[4-(10-phenyl-9-anthryl)phenyl]-3,3':6',3''-ter(9H-carbazole) (PC2CPA)

0.63 g (1.5 mmol) of 9-(4-bromophenyl)-10-phenylanthracene, 1.0 g (1.5 mmol) of 9,9''-diphenyl-3,3':6',3''-ter(9H-carbazole) (PC2C), and 0.50 g (4.5 mmol) of sodium tert-butoxide were put into a 200 mL three-neck flask. The air in the flask was replaced with nitrogen. To the mixture were added 20 mL of toluene and 0.10 mL of tri(tert-butyl)phosphine (a 10 wt % hexane solution). This mixture was stirred to be degassed while the pressure was reduced. After the degassing, 43 mg of (0.075 mmol) bis(dibenzylideneacetone)palladium(0) of was added to the mixture. This mixture was stirred at 110° C. for 2 hours under a stream of nitrogen. After the stirring, the mixture was subjected to suction filtration through celite (produced by Wako Pure Chemical Industries, Ltd., Catalog No. 531-16855), alumina, and Florisil (produced by Wako Pure Chemical Industries, Ltd., Catalog No. 540-00135). The obtained filtrate was condensed to give a solid. The solid was purified by silica gel column chromatography (a developing solvent was a mixed solvent of hexane: toluene=3:1) to give a light yellow solid. This solid was recrystallized with toluene/hexane to give 0.69 g of a light yellow powder, which was the object of the synthesis, at a yield of 47%. A synthesis scheme of Step 3 is shown in (d-3) given below.

(d-3)

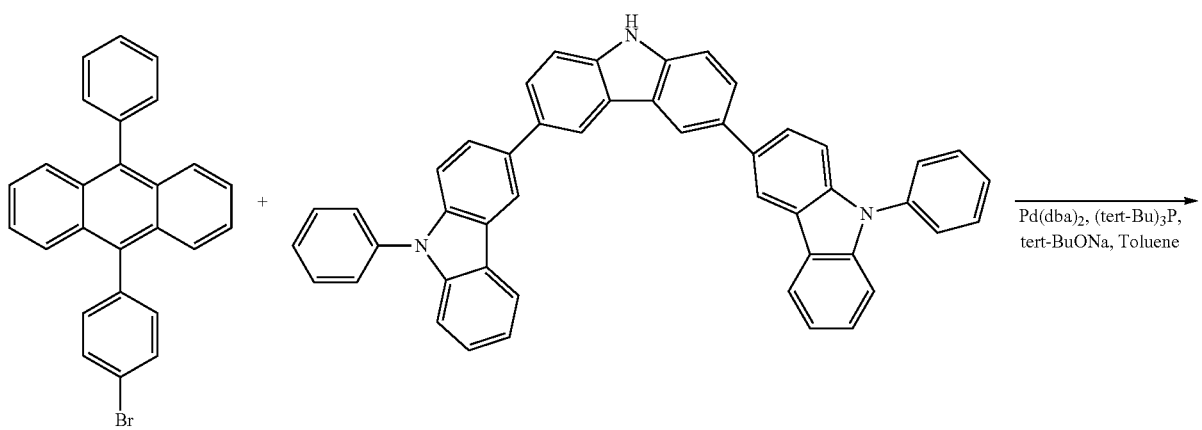

-continued

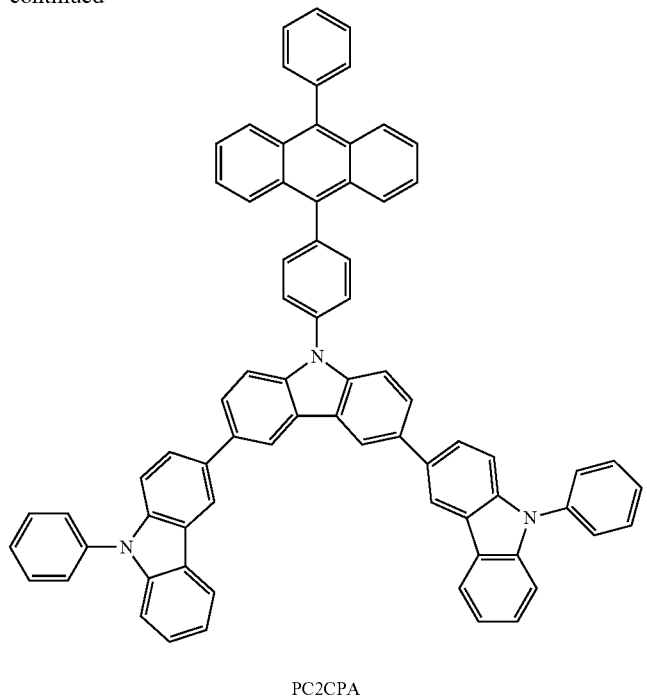

PC2CPA

The obtained compound was analyzed by nuclear magnetic resonance (NMR) measurement, whereby it is confirmed that the compound is 9,9''-diphenyl-9'-[4-(10-phenyl-9-anthryl)phenyl]-3,3':6',3''-ter(9H-carbazole) (PC2CPA).

Figure 49A:
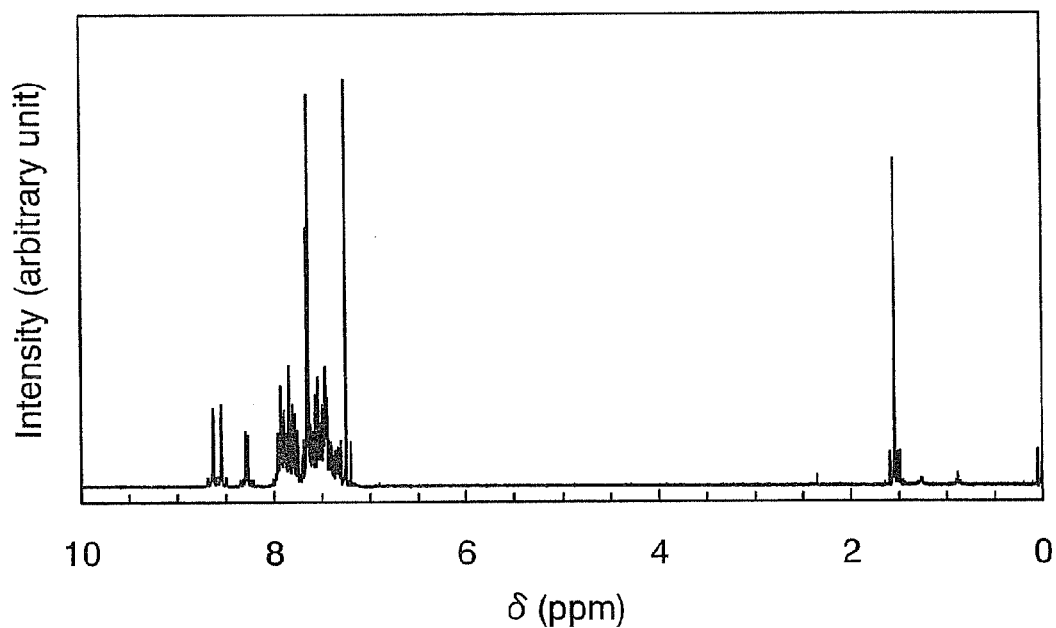
FIGS. 49A and 49B are $^1$H-NMR charts of PC2CPA.
Figure 49B:
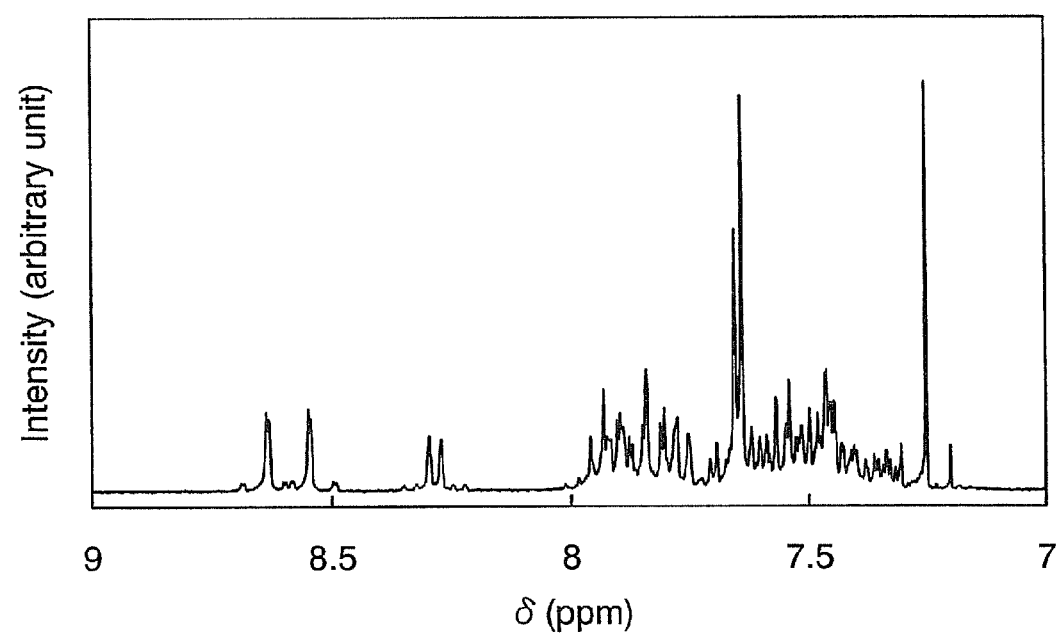

Hereinafter, the $^1$H NMR data is shown. $^1$H NMR (CDCl$_3$, 300 MHz): δ=7.30-7.70 (m, 27H), 7.75-7.96 (m, 14H), 8.28 (d, J=7.8 Hz, 2H), 8.54 (d, J=1.5 Hz, 2H), 8.63 (d, J=1.5 Hz, 2H). The $^1$H NMR charts are shown in FIGS. 49A and 49B. The range of 7.0 ppm to 9.0 ppm in FIG. 49A is expanded and shown in FIG. 49B.

Figure 50:
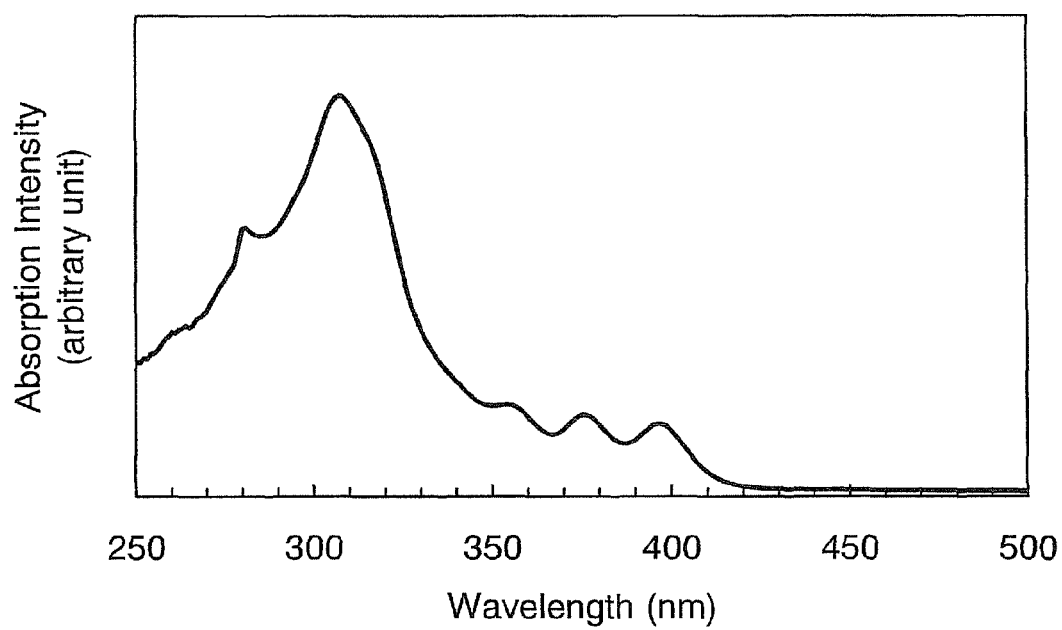
FIG. 50 illustrates an absorption spectrum of a toluene solution of PC2CPA.
Figure 51:
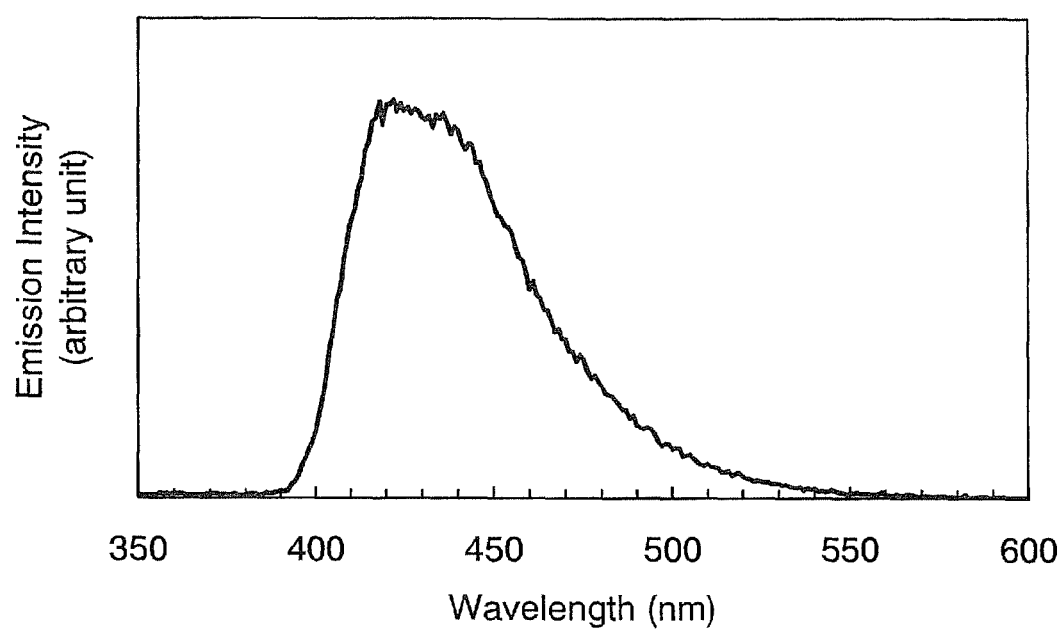
FIG. 51 illustrates an emission spectrum of a toluene solution of PC2CPA.

Next, an absorption spectrum of PC2CPA was measured at room temperature using an ultraviolet-visible spectrophotometer (V-550, manufactured by JASCO Corporation) with the use of a toluene solution. The measurement result is shown in FIG. 50. In FIG. 50, the horizontal axis indicates the wavelength (nm) and the vertical axis indicates the absorption intensity (arbitrary unit). An emission spectrum of PC2CPA was measured at room temperature using a fluorescence spectrophotometer (FS920, manufactured by Hamamatsu Photonics Corporation) with the use of a toluene solution. The measurement result is shown in FIG. 51. In FIG. 51, the horizontal axis indicates the wavelength (nm) and the vertical axis indicates the emission intensity (arbitrary unit).

Figure 52:
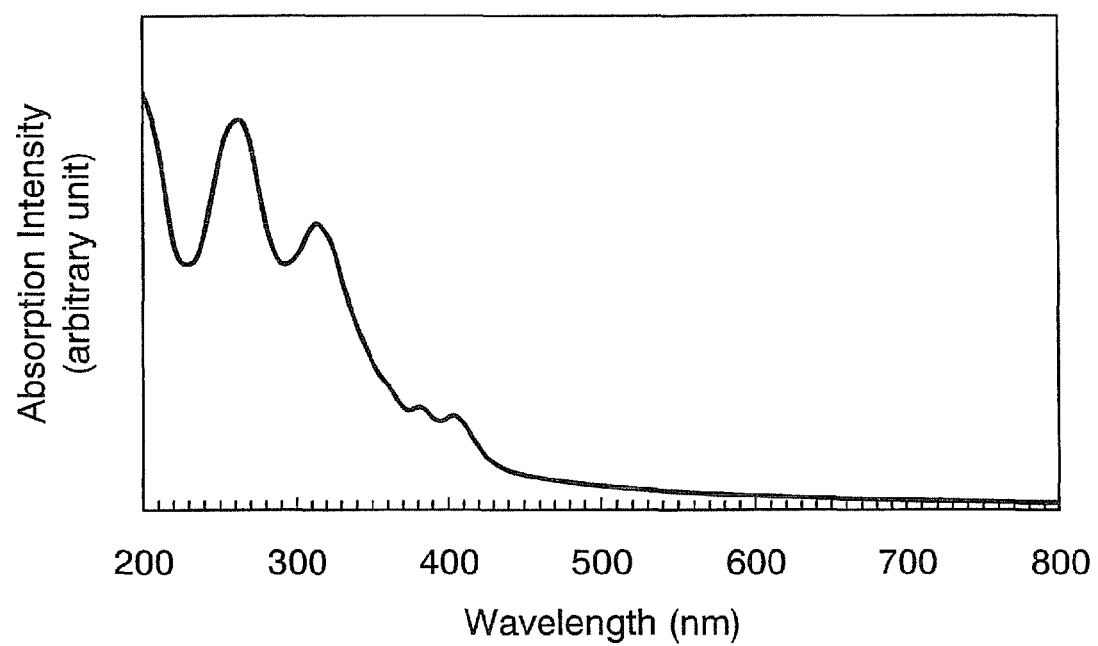
FIG. 52 illustrates an absorption spectrum of a thin film of PC2CPA.
Figure 53:
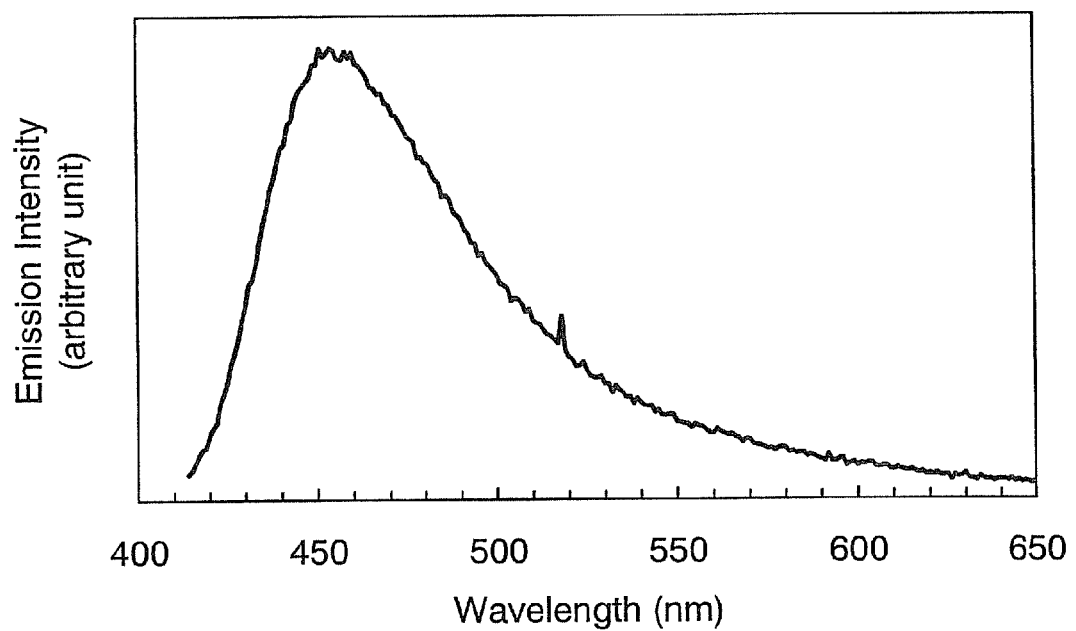
FIG. 53 illustrates an emission spectrum of a thin film of PC2CPA.

Further, a thin film of PC2CPA was similarly measured by film formation of PC2CPA by an evaporation method. The absorption spectrum and the emission spectrum are shown in FIG. 52 and FIG. 53, respectively. In each of FIG. 52 and FIG. 53, the horizontal axis indicates the wavelength (nm) and the vertical axis indicates the absorption intensity (arbitrary unit) and emission intensity (arbitrary unit).

According to FIG. 50, in the case of the toluene solution of PC2CPA, absorption was observed at wavelengths of around 307 nm, around 354 nm, around 376 nm, and around 397 nm. According to FIG. 52, in the case of the thin film of PC2CPA, absorption was observed at wavelengths of around 262 nm, around 313 nm, around 381 nm, and around 403 nm.

According to FIG. 51, the toluene solution of PC2CPA has an emission peak at 422 nm (the excitation wavelength: 397 nm). According to FIG. 53, the thin film thereof has an emission peak at 457 nm (the excitation wavelength: 398 nm).

Thus, it is found that PC2CPA is suitable for use in a light-emitting element that emits blue light in particular.

Synthesis Example 4

In Synthesis Example 4, a synthesis method of an anthracene derivative 4,4'-{9-[4-(10-phenyl-9-anthryl)phenyl]-9H-carbazol-3,6-diyl}bis(N,N-diphenylaniline) (TP2CPA) of the present invention represented by a structural formula (312) is specifically described.

(312)

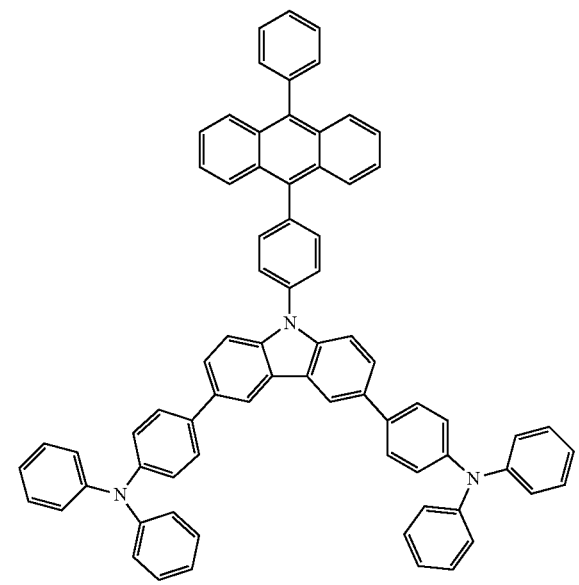

Step 1: Synthesis of 4,4'-(9H-carbazol-3,6-diyl)bis(N,N-diphenylaniline) (TP2C)

1.1 g (3.5 mmol) of 3,6-dibromocarbazole, 2.0 g (7.0 mmol) of triphenylamine-4-boronic acid, and 0.24 g (1.1 mmol) of tri(ortho-tolyl)phosphine were put into a 300 mL three-neck flask. To the mixture were added 30 mL of ethanol, 50 mL of toluene, and 10 mL (2.0 mol/L) of an aqueous solution of potassium carbonate. This mixture was stirred to be degassed while the pressure was reduced. After the degassing, 47 mg (0.21 mmol) of palladium(II) acetate was added to the mixture. This mixture was stirred at 80° C. for 3 hours under a stream of nitrogen. After the stirring, the aqueous layer of the mixture was extracted with toluene. The extract was combined with the organic layer and then washed with a saturated saline solution. Then, the obtained organic layer was dried with magnesium sulfate. After the drying, the mixture was subjected to gravity filtration. The obtained filtrate was condensed to give an oily light yellow substance. The obtained oily substance was purified by silica gel column chromatography (a developing solvent was a mixed solvent of toluene:hexane=1:1) to give an oily light yellow substance. This oily substance was recrystallized with toluene/hexane to give 1.2 g of a white powder, which was the object of the synthesis, at a yield of 51%. A synthesis scheme of Step 1 is shown in (e-1) given below.

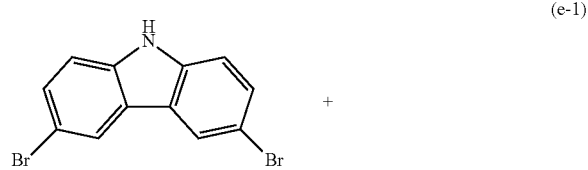

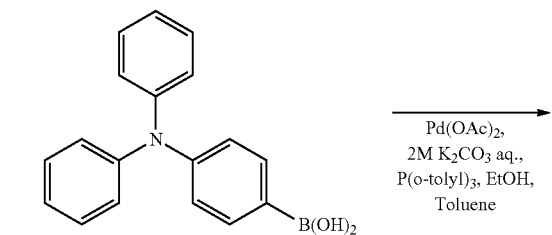

(e-1)

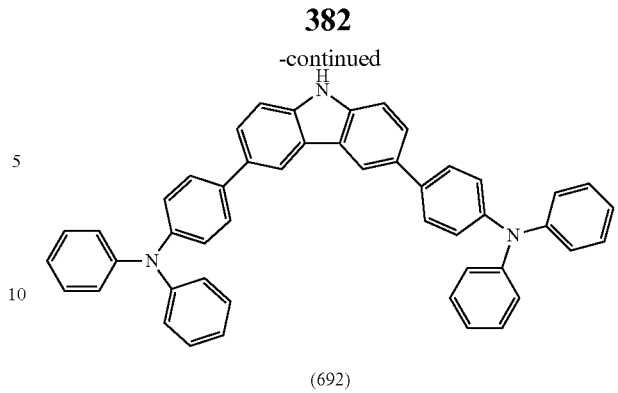

(692)

The obtained compound was analyzed by nuclear magnetic resonance (NMR) measurement, whereby it is confirmed that the compound is TP2C which is an organic compound of the present invention represented by a structural formula (692).

Figure 54A:
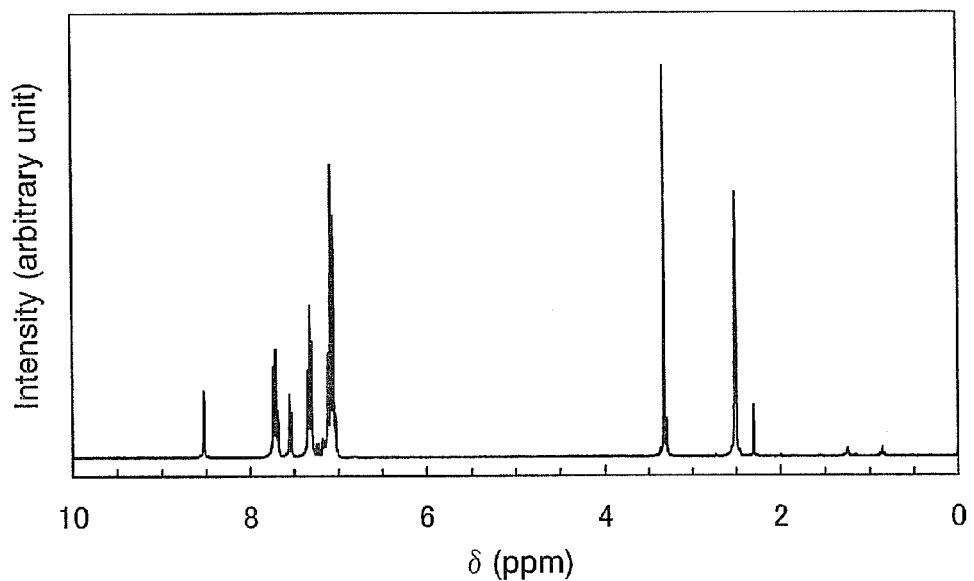
FIGS. 54A and 54B are $^1$H-NMR charts of TP2C.
Figure 54B:
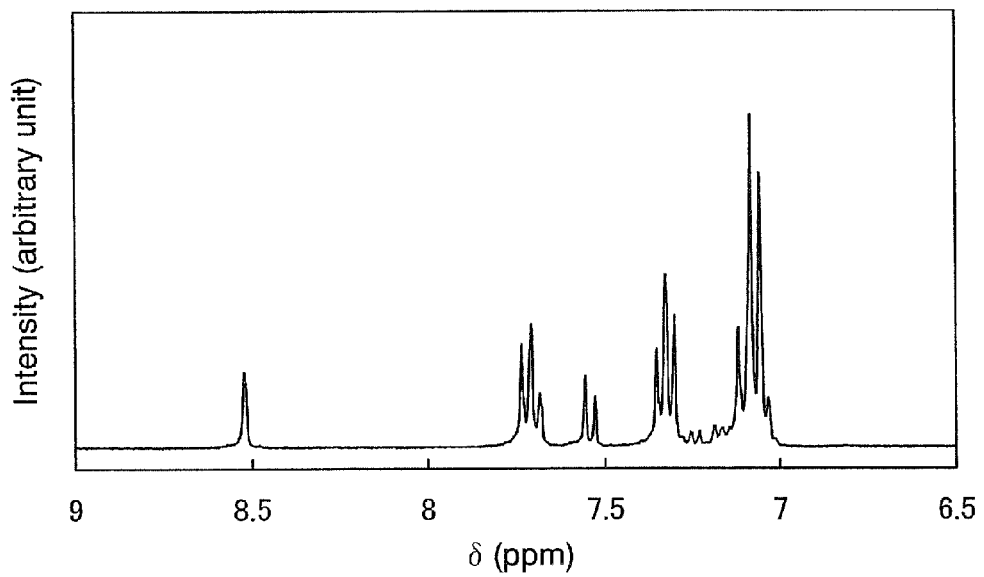

Hereinafter, the $^1$H NMR data is shown. $^1$H NMR (DMSO-$d_6$, 300 MHz): δ=7.03-7.11 (m, 16H), 7.30-7.35 (m, 8H), 7.53-7.55 (m, 2H), 7.68-7.73 (m, 6H), 8.52 (s, 2H), 11.3 (s, 1H). The $^1$H NMR charts are shown in FIGS. 54A and 54B. The range of 6.5 ppm to 9.0 ppm in FIG. 54A is expanded and shown in FIG. 54B.

Step 2: Synthesis of 4,4'-{9-[4-(10-phenyl-9-anthryl)phenyl]-9H-carbazol-3,6-diyl}bis(N,N-diphenylaniline) (TP2CPA)

0.70 g (1.7 mmol) of 9-(4-bromophenyl)-10-phenylanthracene, 1.1 g (1.7 mmol) of 4,4'-(9H-carbazol-3,6-diyl)bis(N,N-diphenylaniline) (TP2C), and 0.49 g (9.0 mmol) of sodium tert-butoxide were put into a 100 mL three-neck flask. The air in the flask was replaced with nitrogen. Then, to the mixture were added 30 mL of toluene and 0.20 mL of tri(tert-butyl)phosphine (a 10 wt % hexane solution). This mixture was stirred to be degassed while the pressure was reduced. After the degassing, 46 mg (0.080 mmol) of bis(dibenzylideneacetone)palladium(0) was added to the mixture. This mixture was stirred at 110° C. for 3 hours under a stream of nitrogen. After the stirring, the mixture was subjected to suction filtration through celite (produced by Wako Pure Chemical Industries, Ltd., Catalog No. 531-16855), alumina, and Florisil (produced by Wako Pure Chemical Industries, Ltd., Catalog No. 540-00135). The obtained filtrate was condensed to give a light yellow solid. This solid was recrystallized with toluene/hexane to give 0.70 g of a light yellow powder, which was the object of the synthesis, at a yield of 42%. A synthesis scheme of Step 2 is shown in (e-2) given below.

(e-2)

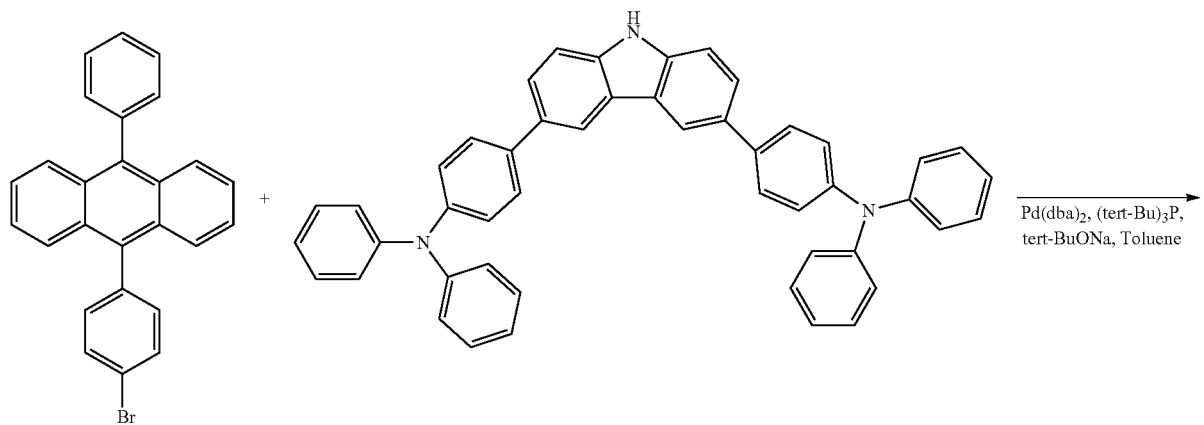

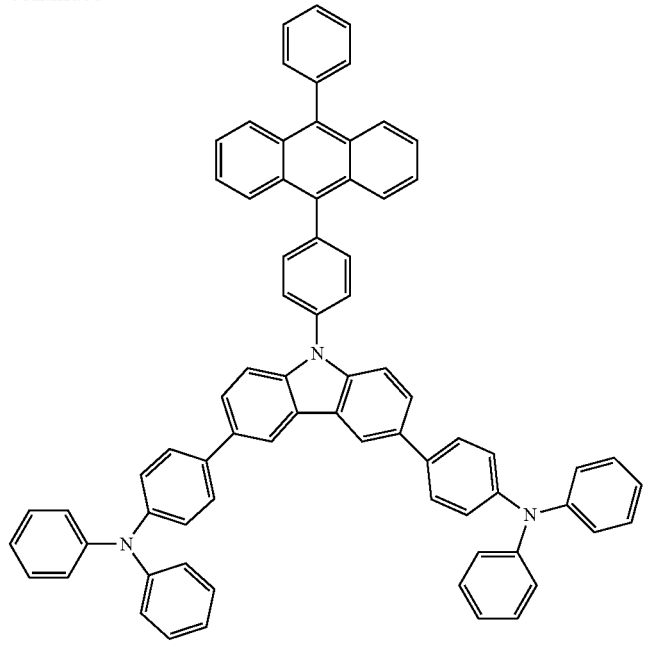

TP2CPA

The obtained compound was analyzed by nuclear magnetic resonance (NMR) measurement, whereby it is confirmed that the compound is 4,4'-{9-[4-(10-phenyl-9-anthryl)phenyl]-9H-carbazol-3,6-diyl}bis(N,N-diphenylaniline) (TP2CPA).

Figure 55A:
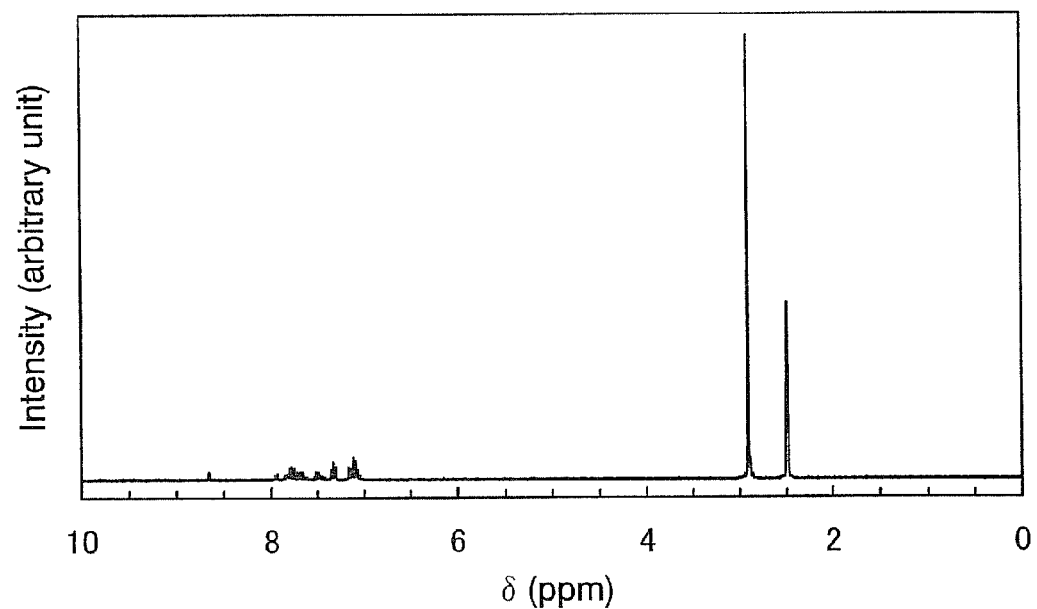
FIGS. 55A and 55B are $^1$H-NMR charts of TP2CPA.
Figure 55B:
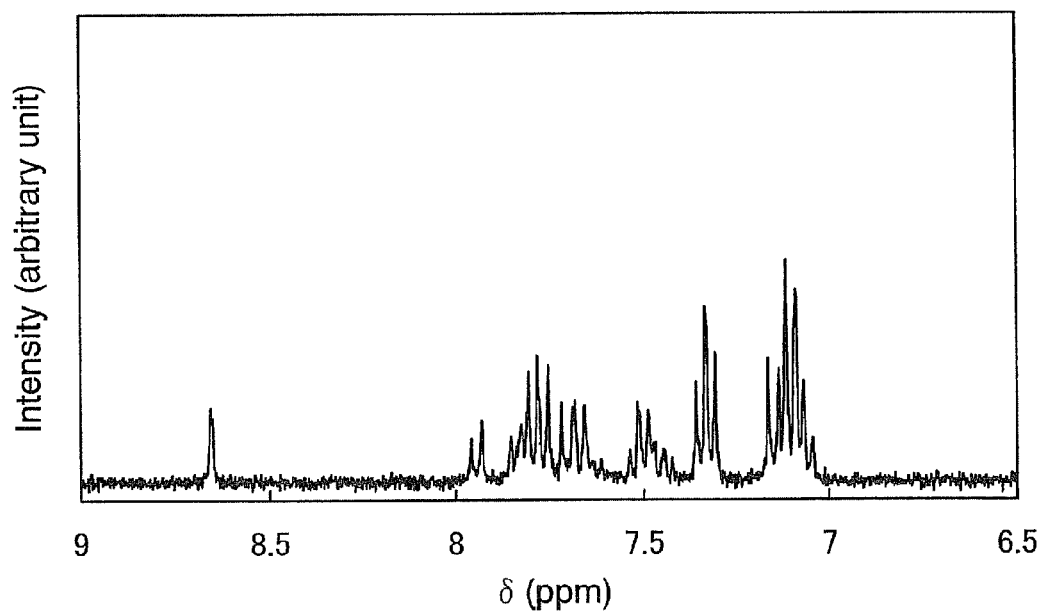

Hereinafter, the $^1$H NMR data is shown. $^1$H NMR (DMSO-$d_6$, 300 MHz): δ=7.04-7.16 (m, 17H), 7.30-7.36 (m, 8H), 7.49-7.51 (m, 5H), 7.65-7.85 (m, 17H), 7.93-7.95 (m, 2H), 8.65 (s, 2H). The $^1$H NMR charts are shown in FIGS. 55A and 55B. The range of 6.5 ppm to 9.0 ppm in FIG. 55A is expanded and shown in FIG. 55B.

Figure 56:
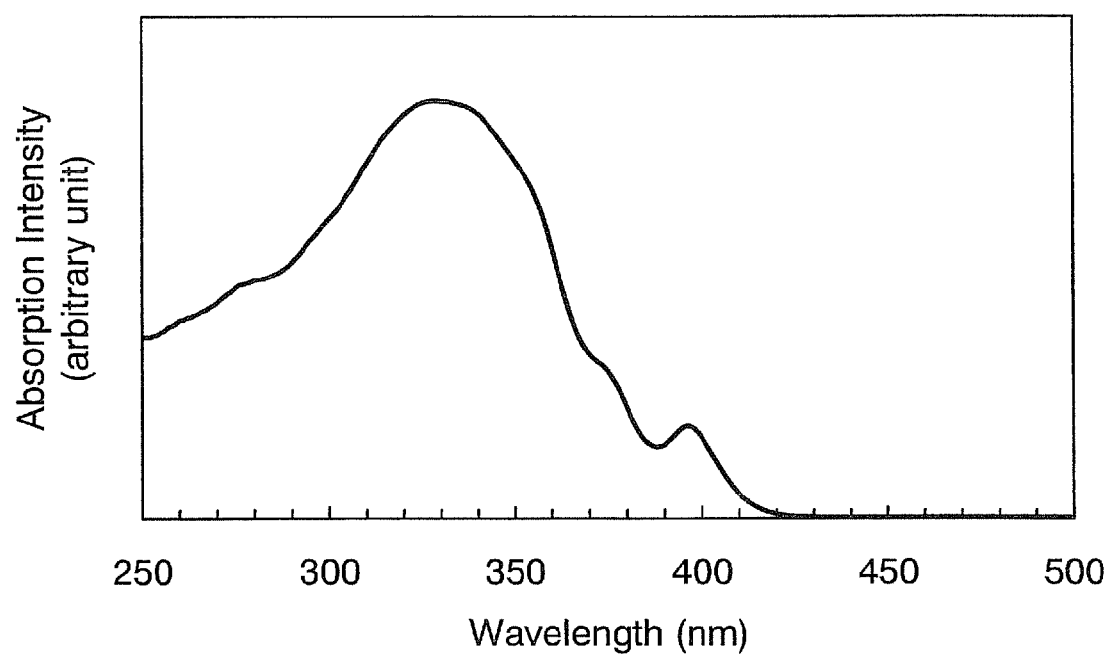
FIG. 56 illustrates an absorption spectrum of a toluene solution of TP2CPA.
Figure 57:
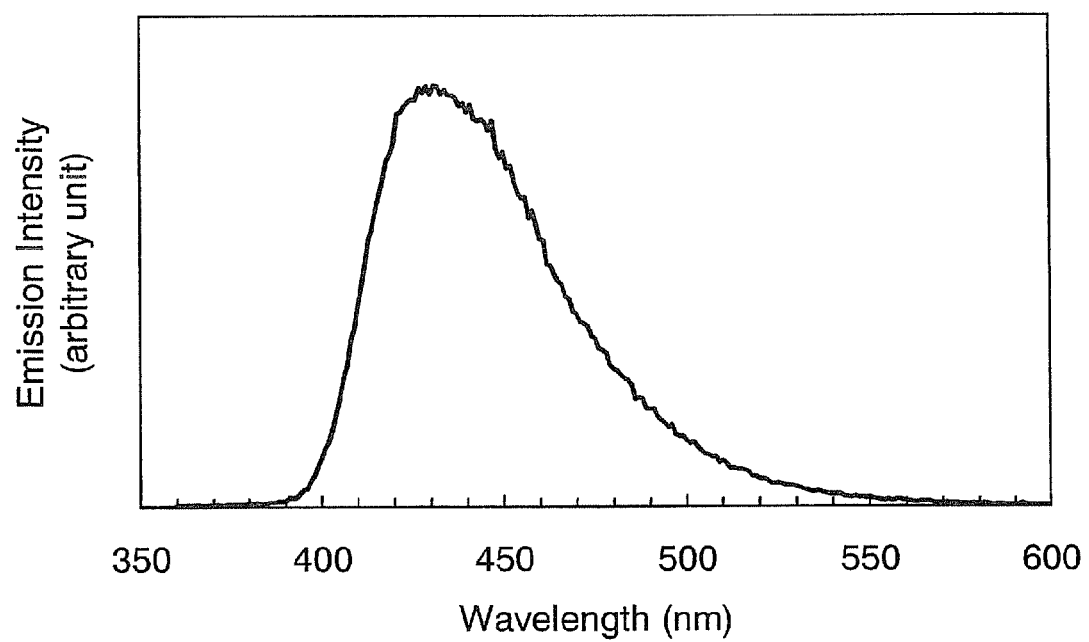
FIG. 57 illustrates an emission spectrum of a toluene solution of TP2CPA.

Next, an absorption spectrum of TP2CPA was measured at room temperature using an ultraviolet-visible spectrophotometer (V-550, manufactured by JASCO Corporation) with the use of a toluene solution. The measurement result is shown in FIG. 56. In FIG. 56, the horizontal axis indicates the wavelength (nm) and the vertical axis indicates the absorption intensity (arbitrary unit). An emission spectrum of TP2CPA was measured at room temperature using a fluorescence spectrophotometer (FS920, manufactured by Hamamatsu Photonics Corporation) with the use of a toluene solution. The measurement result is shown in FIG. 57. In FIG. 57, the horizontal axis indicates the wavelength (nm) and the vertical axis indicates the emission intensity (arbitrary unit).

Figure 58:
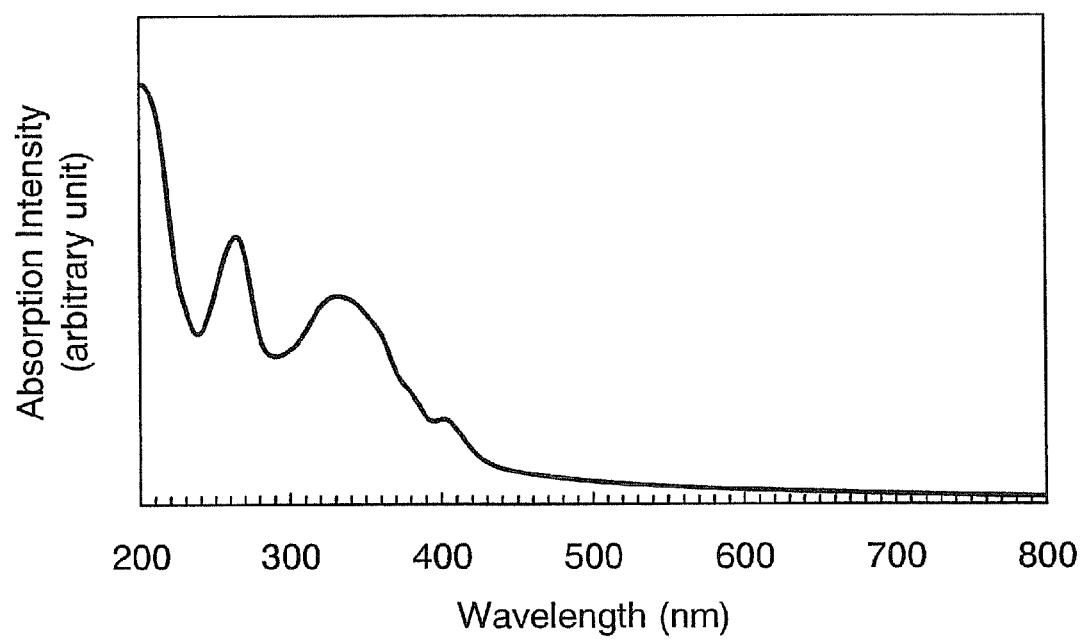
FIG. 58 illustrates an absorption spectrum of a thin film of TP2CPA.
Figure 59:
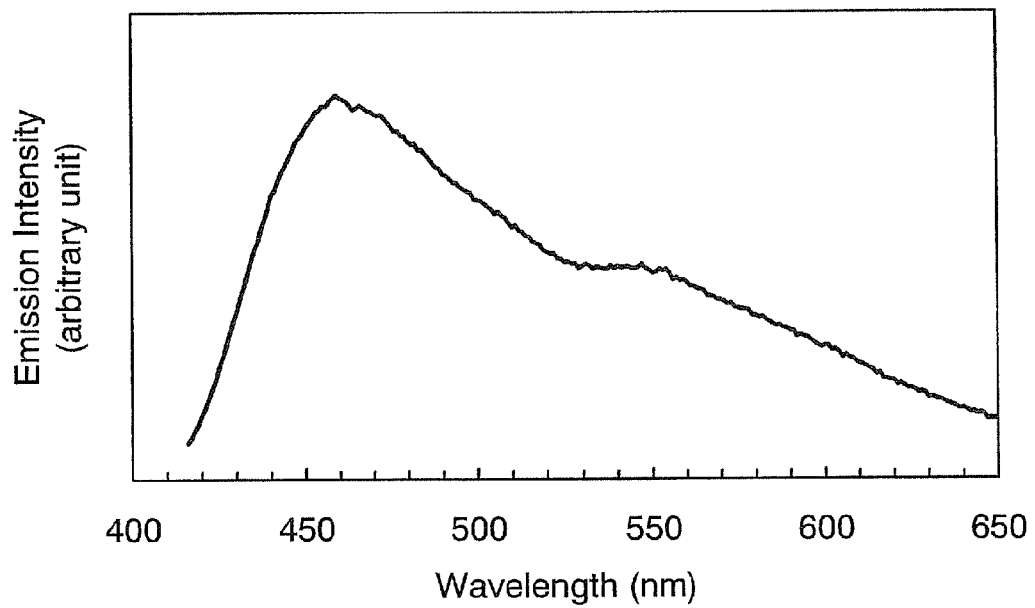
FIG. 59 illustrates an emission spectrum of a thin film of TP2CPA.

Further, a thin film of TP2CPA was similarly measured by film formation of TP2CPA by an evaporation method. The absorption spectrum and emission spectrum are shown in FIG. 58 and FIG. 59, respectively. In each of FIG. 58 and FIG. 59, the horizontal axis indicates the wavelength (nm) and the vertical axis indicates the absorption intensity (arbitrary unit) and emission intensity (arbitrary unit).

According to FIG. 56, in the case of the toluene solution of TP2CPA, absorption was observed at wavelengths of around 329 nm, around 374 nm, and around 396 nm. According to FIG. 58, in the case of the thin film of TP2CPA, absorption was observed at wavelengths of around 264 nm, around 331 nm, and around 401 nm.

According to FIG. 57, the toluene solution of TP2CPA has an emission peak at 431 nm (the excitation wavelength: 341 nm). According to FIG. 59, the thin film thereof has emission peaks at 459 nm and 546 nm (the excitation wavelength: 400 nm). Thus, it is found that TP2CPA is suitable for use in a light-emitting element that emits blue light in particular.

Synthesis Example 5

In Synthesis Example 5, a synthesis method of an anthracene derivative 3-[4-(9H-carbazol-9-yl)phenyl]-9-[4-(10-phenyl-9-anthryl)phenyl]-9H-carbazole (CPCPA) of the present invention represented by a structural formula (343) is specifically described.

(343)

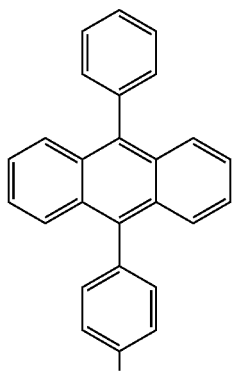

-continued

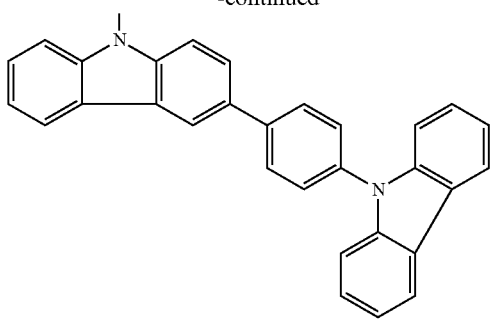

Step 1: Synthesis of 9-(4-bromophenyl)-9H-carbazole 56 g (240 mmol) of p-dibromobenzene, 31 g (180 mmol) of 9H-carbazole, 4.6 g (24 mmol) of copper(I) iodide, 66 g (480 mmol) of potassium carbonate, and 2.1 g (8 mmol) of 18-crown-6-ether were put into a 300 mL three-neck flask. The mixture was heated at about 100° C., and then 8 mL of N,N'-dimethylpropyleneurea (DMPU) was added thereto. This mixture was stirred at 180° C. for 6 hours. After the stirring, the mixture was cooled to 100° C. To the mixture was added about 200 mL of toluene, and then the mixture was cooled to room temperature. After the cooling, this mixture was subjected to suction filtration so that the precipitate was removed. The obtained filtrate was washed with dilute hydrochloric acid, a saturated sodium hydrogen carbonate solution, and a saturated saline solution in this order. The organic layer was dried with magnesium sulfate. Then, the mixture was subjected to gravity filtration. The obtained filtrate was condensed to give an oily substance. This oily substance was purified by silica gel column chromatography (a developing solvent was a mixed solvent of hexane:ether acetate=9:1), and then recrystallized with chloroform/hexane to give 21 g of a light brown plate-like crystal, which was the object of the synthesis, at a yield of 35%. A synthesis scheme of Step 1 is shown in (f-1) given below.

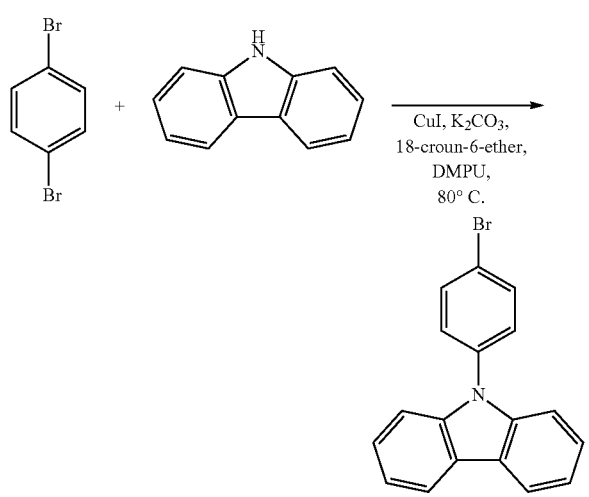

(f-1)

Step 2: Synthesis of 4-(9H-carbazol-9-yl)phenylboronic acid 21.8 g (67.5 mmol) of 9-(4-bromophenyl)-9H-carbazole was put into a 500 mL three-neck flask. The air in the flask was replaced with nitrogen. To the mixture were added 200 mL of tetrahydrofuran (THF), and then the solution was cooled to −78° C. Into this solution, 48.9 mL (74.3 mmol) of n-butyllithium (a 1.52 mol/L hexane solution) was dropped, and the solution was stirred at the same temperature for 2 hours. After the stirring, 17.4 mL (155 mmol) of trimethyl borate was added to the solution, and the solution was stirred for about 1 hour at the same temperature. Then, the mixture was stirred for 24 hours while the temperature of the solution was being increased to room temperature. Thereafter, to the solution was added about 200 mL (1.0 mol/L) of hydrochloric acid, and then the solution was stirred at room temperature for 1 hour. The organic layer of the mixture was washed with water, and then the aqueous layer was extracted with acetate ether. The extract was combined with the organic layer and then washed with a saturated saline solution. The organic layer was dried with magnesium sulfate. After the drying, the mixture was subjected to suction filtration, and then the obtained filtrate was condensed. The obtained residue was recrystallized with chloroform/hexane to give 12.8 g of a white powdered solid, which was the object of the synthesis, at a yield of 65.9%. A synthesis scheme of Step 2 is shown in (f-2) given below.

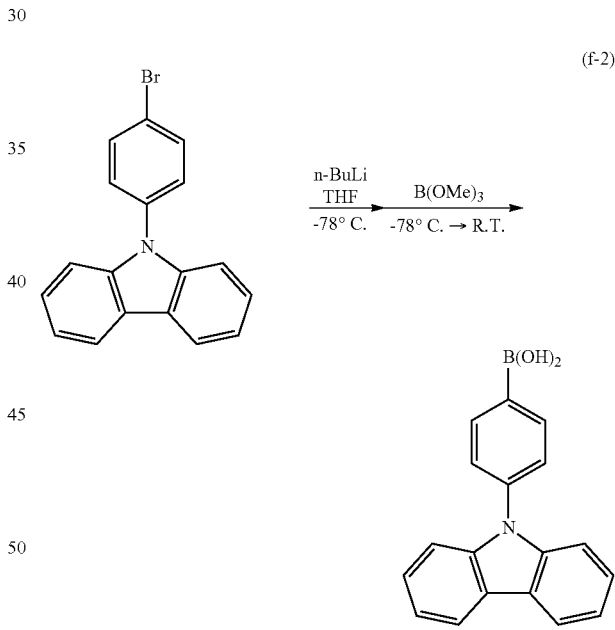

(f-2)

Step 3: Synthesis of 3-[4-(9H-carbazol-9-yl)phenyl]-9H-carbazole (CPC)

5.0 g (20 mmol) of 3-bromo-9H-carbazole, 5.8 g (20 mmol) of 4-(9H-carbazol-9-yl)phenylboronic acid, and 308 mg (1.0 mmol) of tri(ortho-tolyl)phosphine were put into a 300 mL three-neck flask. The air in the flask was replaced with nitrogen. To the mixture were added 100 mL of ethyleneglycoldimethylether and 20 mL of an aqueous solution of potassium carbonate (2.0 mol/L). This mixture was stirred to be degassed under reduced pressure. After the degassing, 46 mg (0.20 mmol) of palladium(II) acetate was added the mixture. This mixture was refluxed at 90° C. for 4.5 hours. After the reflux, the organic layer of the mixture was washed with water twice, and the aqueous layer was extracted with acetate ether. The extract was combined with the organic layer and then washed with a saturated saline solution. The obtained organic layer was dried with magnesium sulfate. After the drying, the mixture was subjected to gravity filtration. The obtained filtrate was condensed to give an oily light brown substance. The obtained oily substance was purified by silica gel column chromatography (a developing solvent was a mixed solvent of hexane:toluene=1:1) to give 5.4 g of a white powdered solid, which was the object of the synthesis, at a yield of 65%. A synthesis scheme of Step 3 is shown in (f-3) given below.

phine (a 10 wt % hexane solution). This mixture was stirred to be degassed while the pressure was reduced. After the degassing, 58 mg (0.10 mmol) of bis(dibenzylideneacetone)palladium(0) was added to the mixture. This mixture was refluxed and then cooled to room temperature. Then, to the mixture was added about 50 mL of toluene. The mixture was subjected to suction filtration through Florisil (produced by Wako Pure Chemical Industries, Ltd., Catalog No. 540-00135), celite (produced by Wako Pure Chemical Industries, Ltd., Catalog No. 531-16855), and alumina. The obtained filtrate was condensed to give a light yellow solid. This solid was recrystallized with toluene/hexane to give 2.6 g of a light yellow powdered solid, which was the object of the synthesis, at a yield of 81%. A synthesis scheme of Step 4 is shown in (f-4) given below.

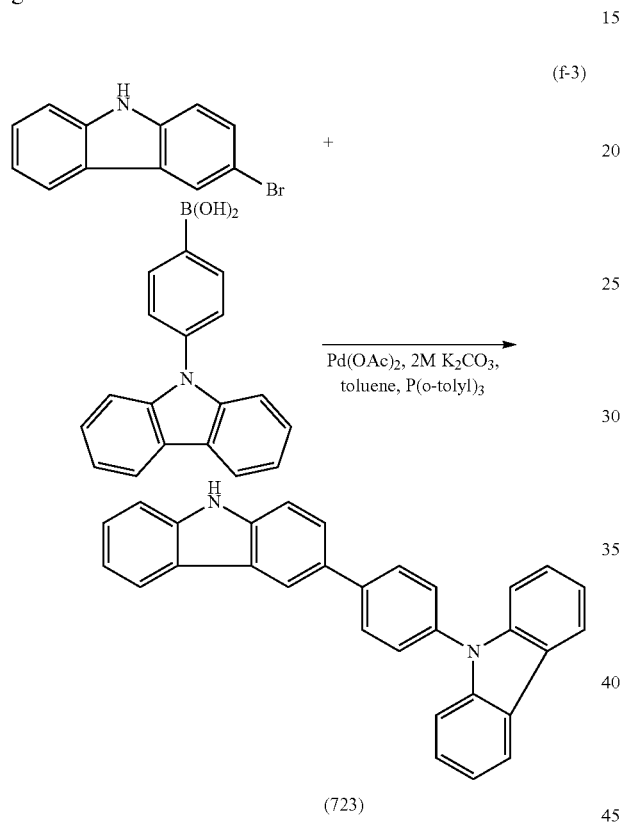

(f-3)

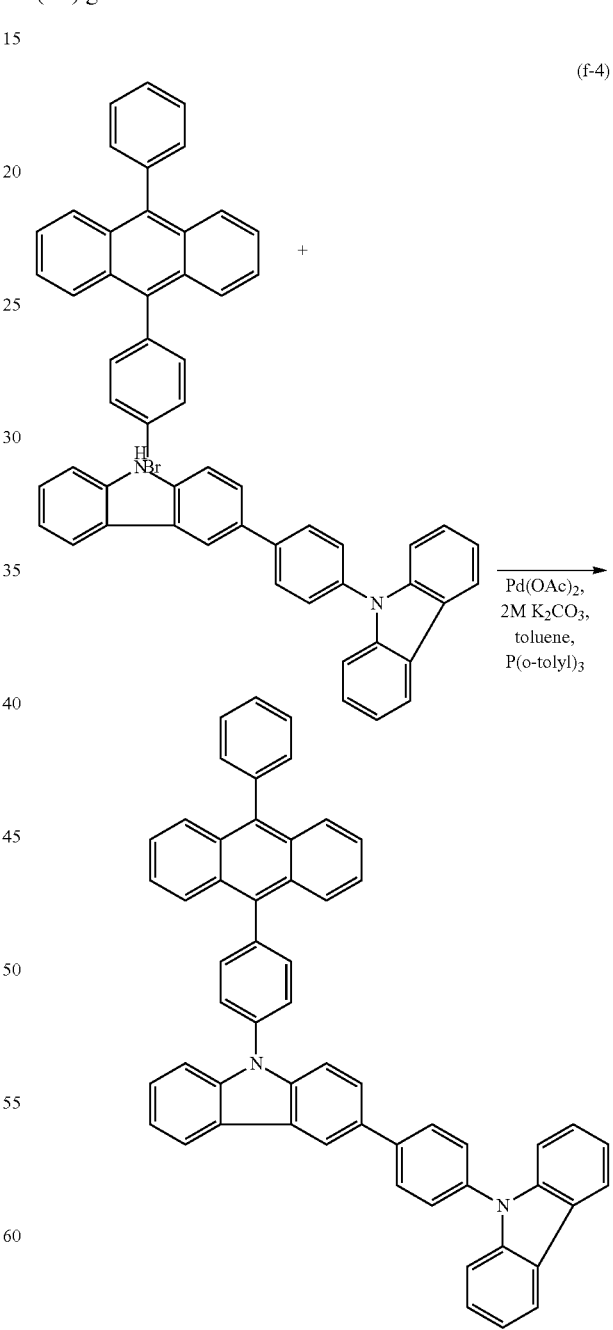

(f-4)

The obtained compound was analyzed by nuclear magnetic resonance (NMR) measurement, whereby it is confirmed that the compound is CPC which is an organic compound of the present invention represented by a structural formula (723).

Figure 60A:
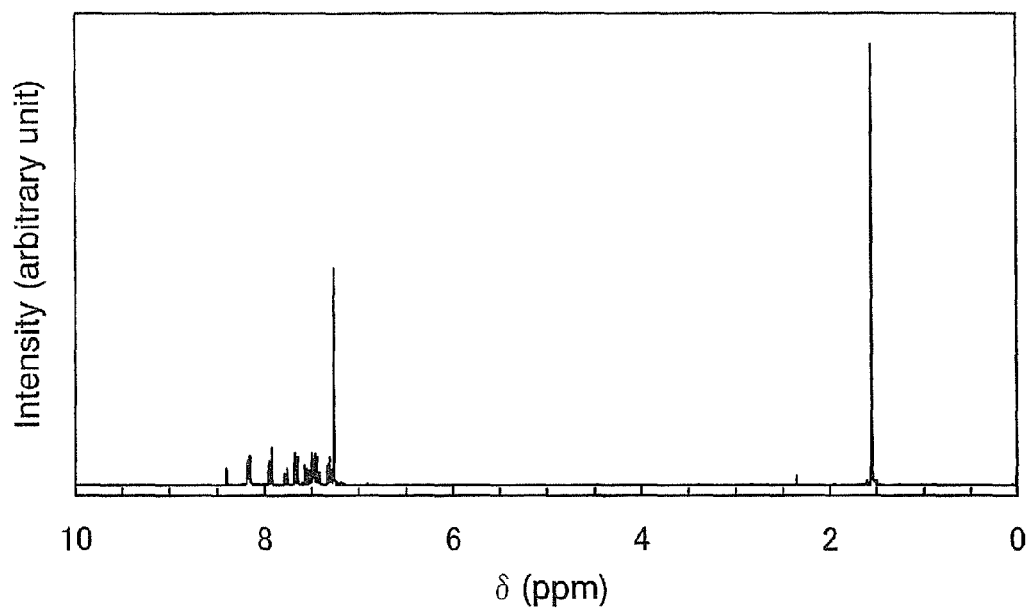
FIGS. 60A and 60B are $^1$H-NMR charts of CPC.
Figure 60B:
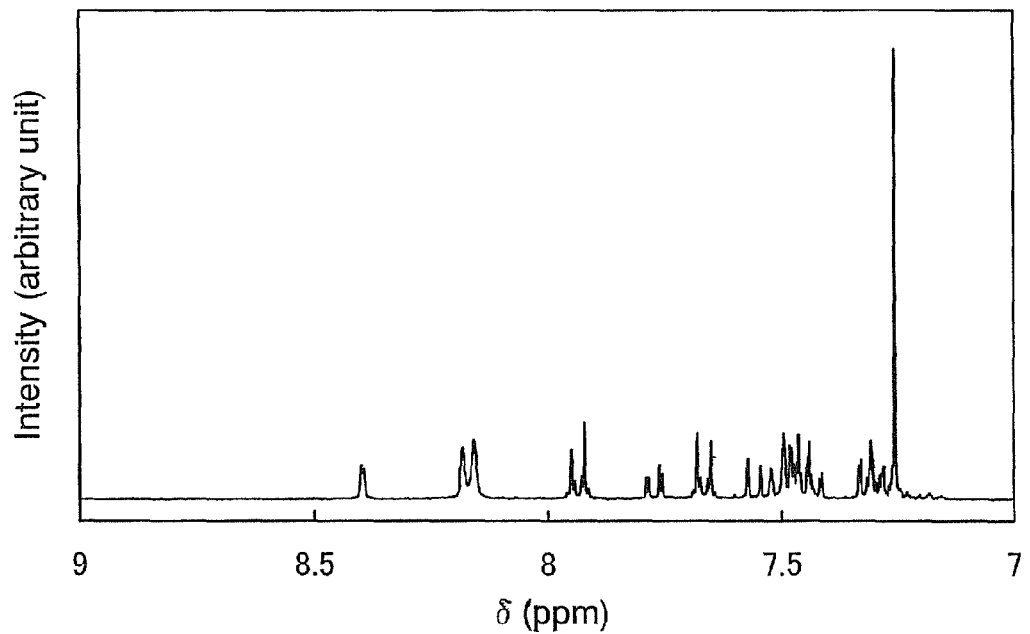

Hereinafter, the $^1$H NMR data is shown. $^1$H NMR (CDCl$_3$, 300 MHz): δ=7.27-7.33 (m, 3H), 7.14-7.58 (m, 8H), 7.67 (d, J=8.1 Hz, 2H), 7.77 (dd, J$_1$=1.7 Hz, J$_2$=8.6 Hz, 1H), 7.94 (d, J=8.4 Hz, 2H), 8.16-8.18 (m, 3H), 8.40 (d, J=12.1 Hz, 1H). The $^1$H NMR charts are shown in FIGS. 60A and 60B. The range of 7.0 ppm to 9.0 ppm in FIG. 60A is expanded and shown in FIG. 60B.

Step 4: Synthesis of 3-[4-(9H-carbazol-9-yl)phenyl]-9-[4-(10-phenyl-9-anthryl)phenyl]-9H-carbazole (CPCPA)

1.8 g (4.5 mmol) of 9-(4-bromophenyl)-10-phenylanthracene, 1.8 g (4.5 mmol) of 3-[4-(9H-carbazol-9-yl)phenyl]-9H-carbazole (CPC), and 1.1 g (10 mmol) of sodium tert-butoxide were put into a 200 mL three-neck flask. The air in the flask was replaced with nitrogen. To the mixture were added 25 mL of toluene and 0.10 mL of tri(tert-butyl)phos- The obtained compound was analyzed by nuclear magnetic resonance (NMR) measurement, whereby it is confirmed that the compound is 3-[4-(9H-carbazol-9-yl)phenyl]-9-[4-(10-phenyl-9-anthryl)phenyl]-9H-carbazole (CPCPA) which is an anthracene derivative of the present invention.

Figure 61A:
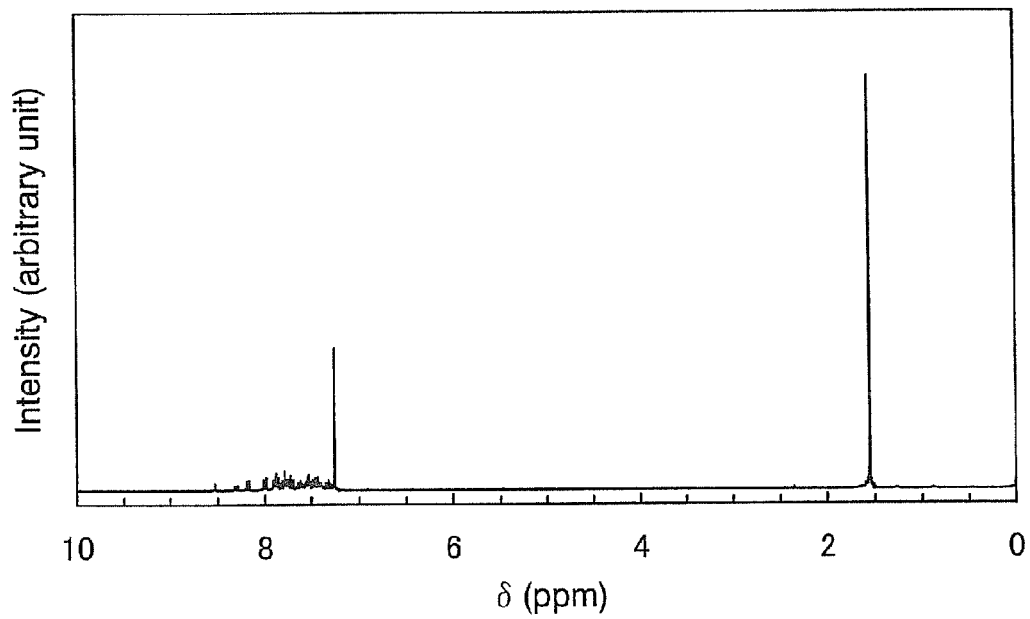
FIGS. 61A and 61B are $^1$H-NMR charts of CPCPA.
Figure 61B:
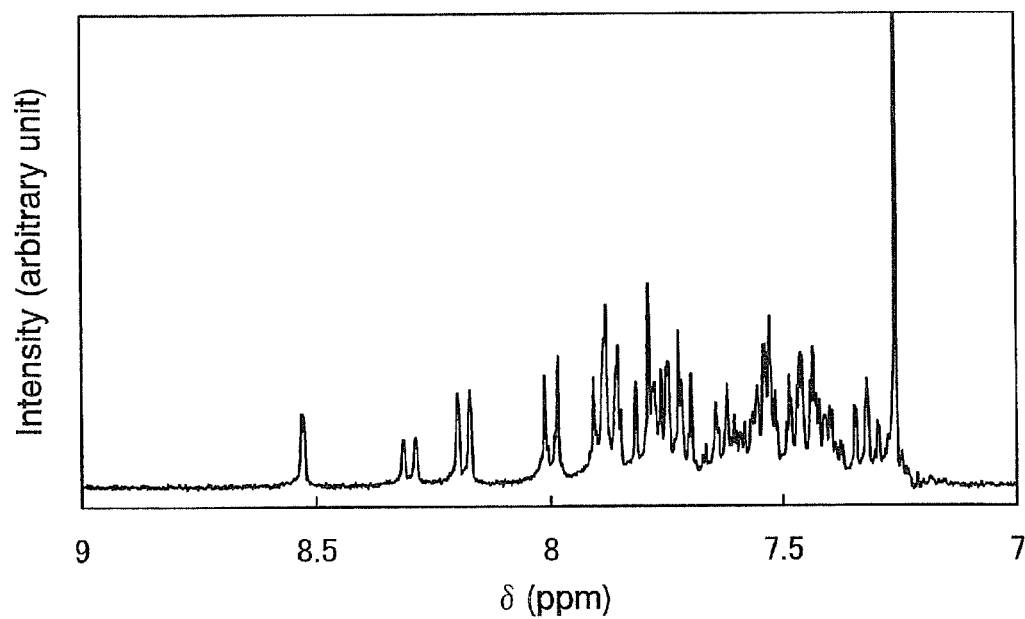

Hereinafter, the $^1$H NMR data is shown. $^1$H NMR (CDCl$_3$, 300 MHz): δ=7.30-7.91 (m, 30H), 8.00 (d, J=8.7 Hz, 2H), 8.19 (d, J=7.8 Hz, 2H), 8.30 (d, J=7.5 Hz, 1H), 8.53 (d, J=1.2 Hz, 1H). The $^1$H NMR charts are shown in FIGS. 61A and 61B. The range of 7.0 ppm to 9.0 ppm in FIG. 61A is expanded and shown in FIG. 61B.

Figure 62:
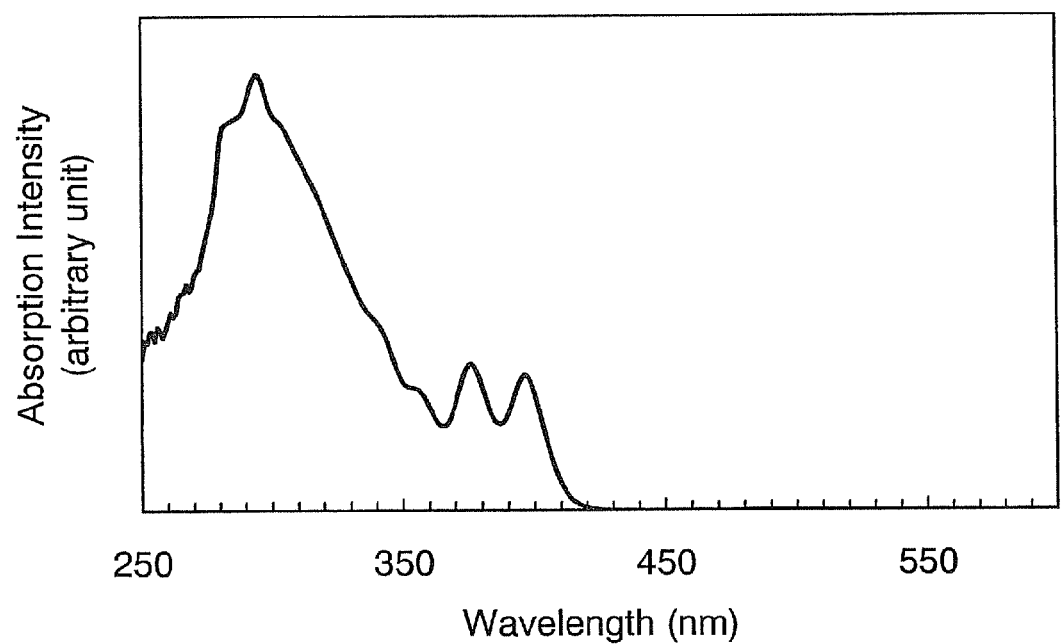
FIG. 62 illustrates an absorption spectrum of a toluene solution of CPCPA.
Figure 63:
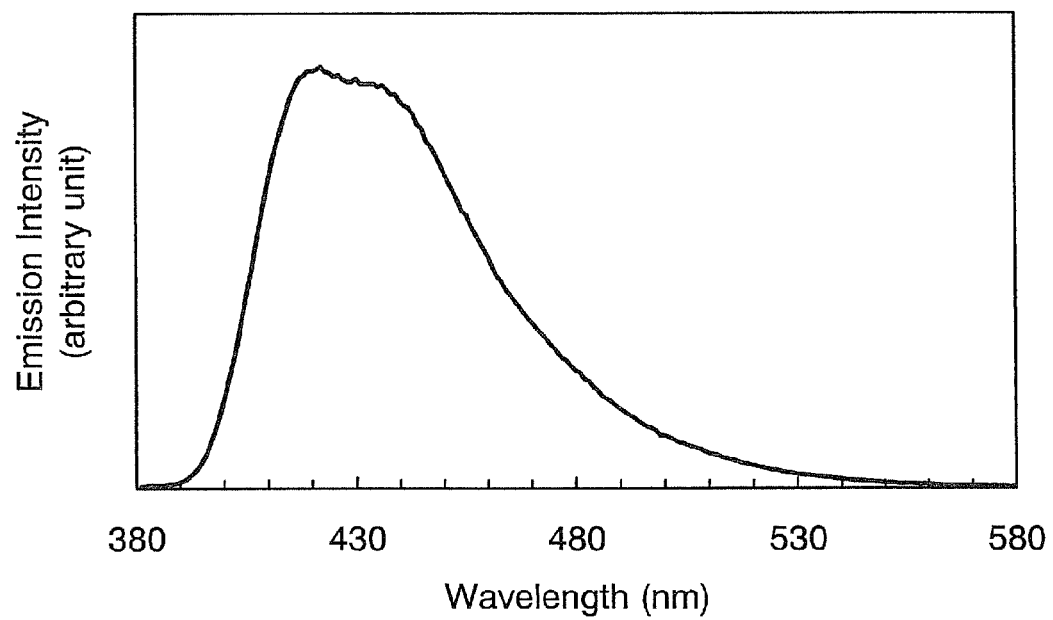
FIG. 63 illustrates an emission spectrum of a toluene solution of CPCPA.

Next, an absorption spectrum of CPCPA was measured at room temperature using an ultraviolet-visible spectrophotometer (V-550, manufactured by JASCO Corporation) with the use of a toluene solution. The measurement result is shown in FIG. 62. In FIG. 62, the horizontal axis indicates the wavelength (nm) and the vertical axis indicates the absorption intensity (arbitrary unit). An emission spectrum of CPCPA was measured at room temperature using a fluorescence spectrophotometer (FS920, manufactured by Hamamatsu Photonics Corporation) with the use of a toluene solution. The measurement result is shown in FIG. 63. In FIG. 63, the horizontal axis indicates the wavelength (nm) and the vertical axis indicates the emission intensity (arbitrary unit).

Figure 64:
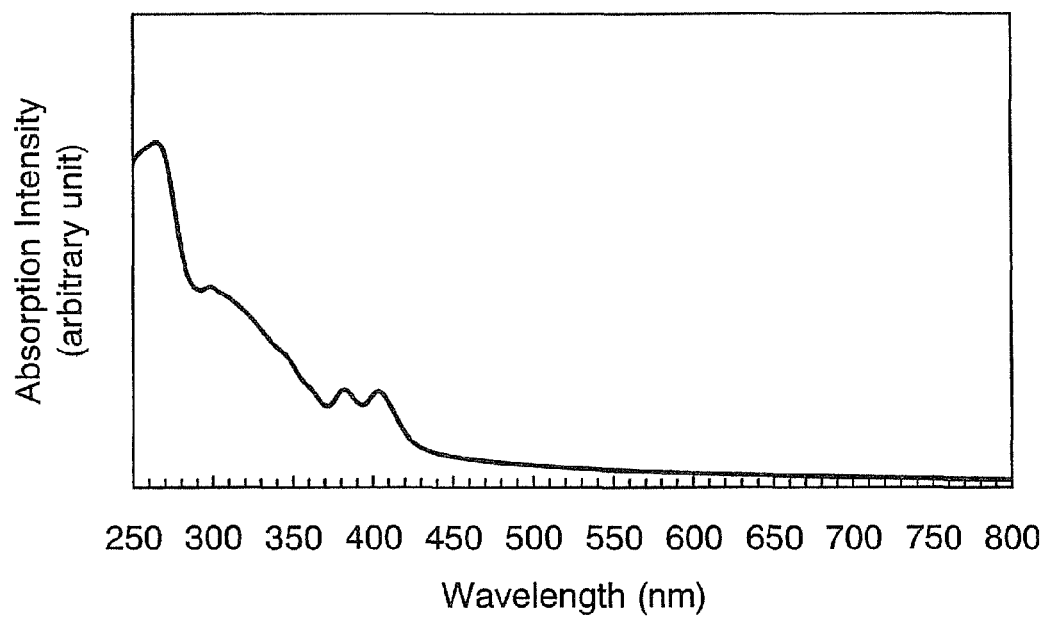
FIG. 64 illustrates an absorption spectrum of a thin film of CPCPA.
Figure 65:
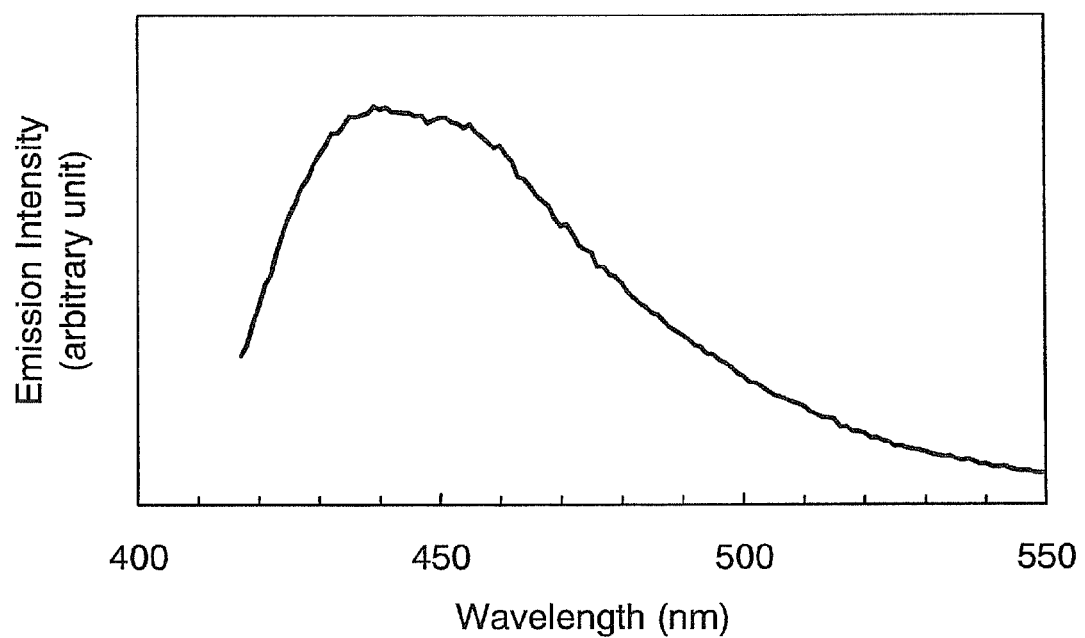
FIG. 65 illustrates an emission spectrum of a thin film of CPCPA.

Further, a thin film of CPCPA was similarly measured by film formation of CPCPA by an evaporation method. The absorption spectrum and emission spectrum are shown in FIG. 64 and FIG. 65, respectively. In each of FIG. 64 and FIG. 65, the horizontal axis indicates the wavelength (nm) and the vertical axis indicates the absorption intensity (arbitrary unit) and emission intensity (arbitrary unit).

According to FIG. 62, in the case of the toluene solution of CPCPA, absorption was observed at wavelengths of around 351 nm, around 373 nm, around and around 394 nm. According to FIG. 64, in the case of the thin film of CPCPA, absorption was observed at wavelengths of around 265 nm, around 298 nm, around 382 nm, and around 403 nm.

According to FIG. 63, the toluene solution of CPCPA has an emission peak at 424 nm (the excitation wavelength: 370 nm). According to FIG. 65, the thin film thereof has an emission peak at 440 nm (the excitation wavelength: 401 nm). Thus, it is found that CPCPA is suitable for use in a light-emitting element that emits blue light in particular.

The ionizing potential of the thin film of CPCPA was measured using a photoelectron spectrometer (AC-2, manufactured by Riken Keiki Co., Ltd) in the air and found to be 5.68 eV. As a result, the HOMO level was found to be −5.68 eV. Further, an absorption edge was obtained from a Tauc plot assuming direct transition by use of the data of the absorption spectrum of CPCPA in the thin film state, and the absorption edge was regarded as an optical energy gap. The energy gap was 2.91 eV. A LUMO level of −2.77 eV was obtained from the obtained values of the energy gap and the HOMO level.

Synthesis Example 6

In Synthesis Example 6, a synthesis method of an anthracene derivative 3-6-bis[4-(9H-carbazol-9-yl)phenyl]-9-[4-(10-phenyl-9-anthryl)phenyl]-9H-carbazole (CP2CPA) of the present invention represented by a structural formula (388) is specifically described.

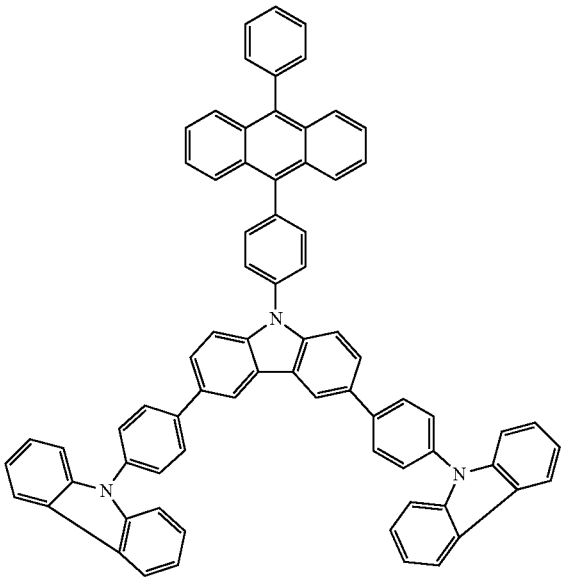

(388)

Step 1: Synthesis of 3-6-bis[4-(9H-carbazol-9-yl) phenyl]-9H-carbazole (CP2C)

1.0 g (3.1 mmol) of 3,6-dibromo-9H-carbazole, 1.8 g (6.2 mmol) of 4-(9H-carbazol-9-yl)phenylboronic acid, and 457 mg (1.5 mmol) of tri(ortho-tolyl)phosphine were put into a 300 mL three-neck flask. To the mixture were added 20 mL of ethanol, 50 mL of toluene, and 20 mL (2.0 mol/L) of an aqueous solution of potassium carbonate. This mixture was stirred to be degassed while the pressure was reduced. To the mixture was added 70 mg (0.30 mmol) of palladium(II) acetate. This mixture was refluxed at 110° C. for 5 hours, cooled to room temperature, and then left for 15 hours; accordingly a black solid was precipitated. The precipitated solid was subjected to suction filtration and then collected. The collected solid was dissolved in toluene which was heated, and this solution was subjected to filtration through celite (produced by Wako Pure Chemical Industries, Ltd., Catalog No. 531-16855), alumina, and Florisil (produced by Wako Pure Chemical Industries, Ltd., Catalog No. 540-00135). The obtained filtrate was condensed to give a white solid. The obtained solid was recrystallized with toluene/hexane to give 1.1 g of a white powder, which was the object of the synthesis, at a yield of 58%. A synthesis scheme of Step 1 is shown in (g-1) given below.

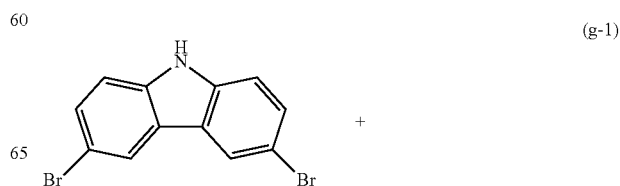

(g-1)

-continued

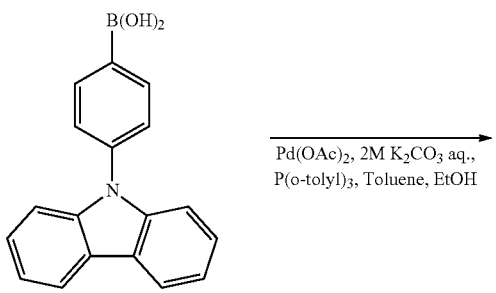

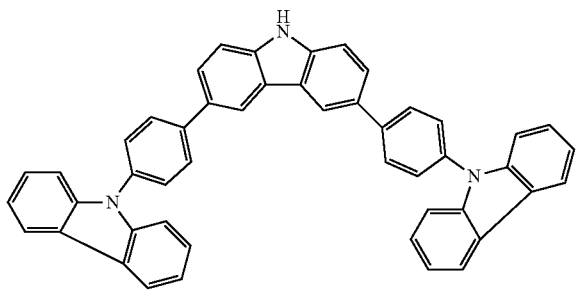

(769)

The obtained compound was analyzed by nuclear magnetic resonance (NMR) measurement, whereby it is confirmed that the compound is CP2C which is an organic compound of the present invention represented by a structural formula (769).

Figure 66A:
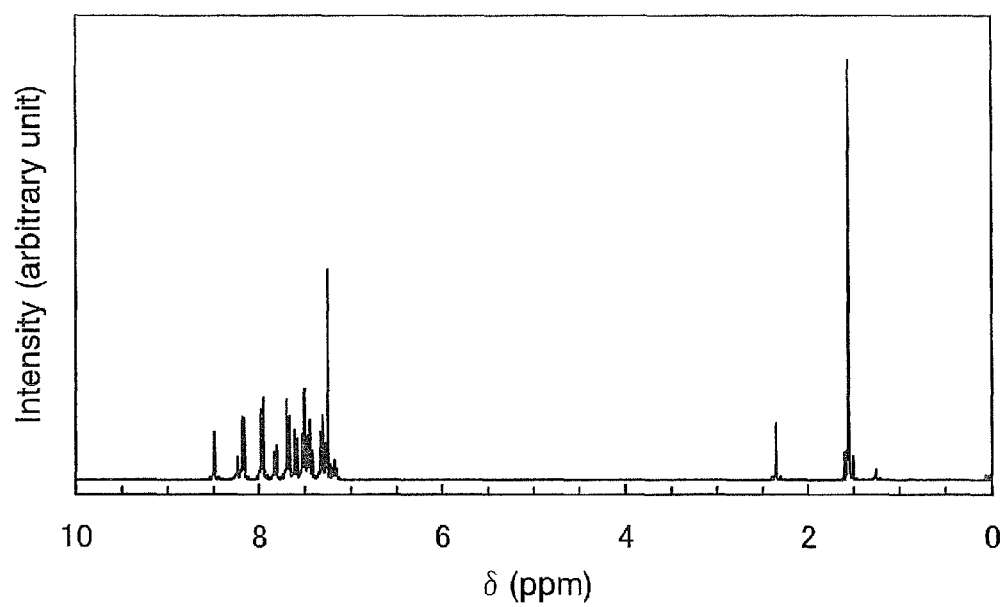
FIGS. 66A and 66B are $^1$H-NMR charts of CP2C.
Figure 66B:
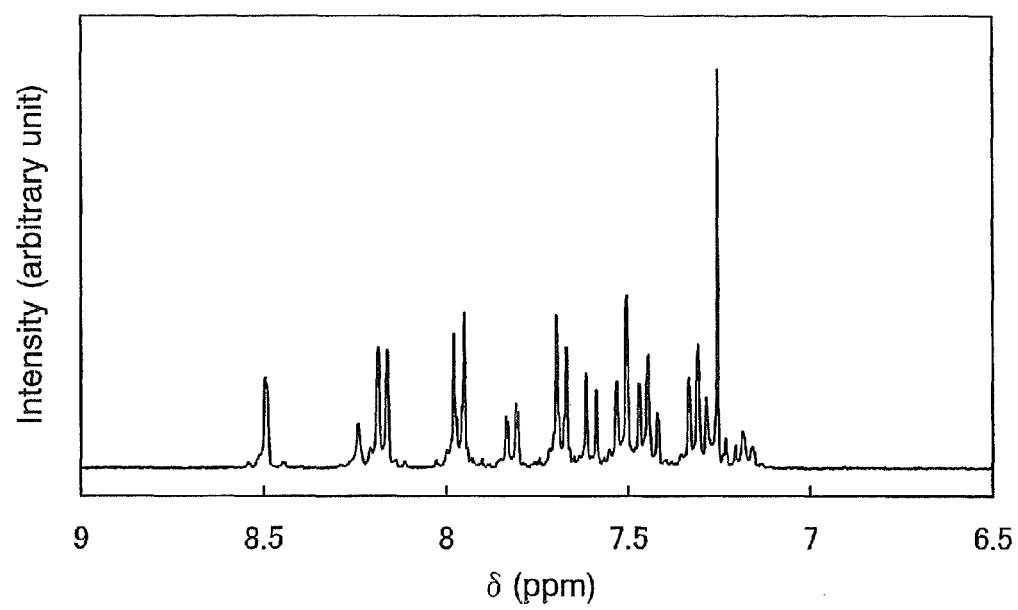

Hereinafter, the $^1$H NMR data is shown. $^1$H NMR (CDCl$_3$, 300 MHz): δ=7.29-7.34 (m, 4H), 7.42-7.53 (m, 8H), 7.60 (d, J=8.7 Hz, 2H), 7.68 (dd, J$_1$=1.5 Hz, J$_2$=6.0 Hz, 4H), 7.82 (dd, J$_1$=1.5 Hz, J$_2$=8.7 Hz, 2H), 7.96 (dd, J$_1$=1.8 Hz, J$_2$=6.3 Hz, 4H), 8.18 (d, J=7.2 Hz, 4H), 8.24 (s, 1H), 8.49 (d, J=1.5 Hz, 2H). The $^1$H NMR charts are shown in FIGS. 66A and 66B. The range of 6.5 ppm to 9.0 ppm in FIG. 66A is expanded and shown in FIG. 66B.

Step 2: Synthesis of 3-6-bis[4-(9H-carbazol-9-yl) phenyl]-9-[4-(10-phenyl-9-anthryl)phenyl]-9H-carbazole (CP2CPA)

0.63 g (1.5 mmol) of 9-(4-bromophenyl)-10-phenylanthracene, 1.0 g (1.5 mmol) of 3,6-bis[4-(9H-carbazol-9-yl)phenyl]-9H-carbazole (CP2C), and (0.50 g (4.5 mmol) of sodium tert-butoxide were put into a 200 mL three-neck flask. The air in the flask was replaced with nitrogen. To the mixture were added 20 mL of toluene and 0.10 mL of tri(tert-butyl) phosphine (a 10 wt % hexane solution). This mixture was stirred to be degassed while the pressure was reduced. After the degassing, 43 mg (0.075 mmol) of bis(dibenzylideneacetone)palladium(0) was added to the mixture. This mixture was stirred at 110° C. for 2 hours under a stream of nitrogen, cooled to room temperature, and then left for 15 hours; accordingly, a brown solid was precipitated. The precipitated solid was subjected to suction filtration and then collected. The collected solid was dissolved in 200 mL of toluene which was heated, and this mixture was subjected to filtration through celite (produced by Wako Pure Chemical Industries, Ltd., Catalog No. 531-16855), alumina, and Florisil (produced by Wako Pure Chemical Industries, Ltd., Catalog No. 540-00135). The obtained filtrate was condensed to give a white solid. The obtained solid was recrystallized with toluene/hexane to give 1.0 g of a white powder, which was the object of the synthesis, at a yield of 67%. A synthesis scheme of Step 2 is shown in (g-2) given below.

(g-2)

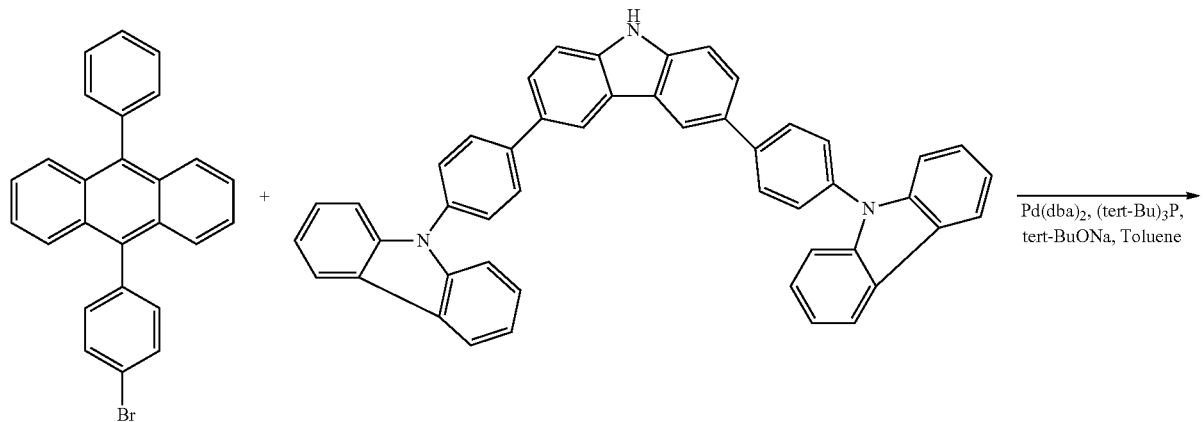

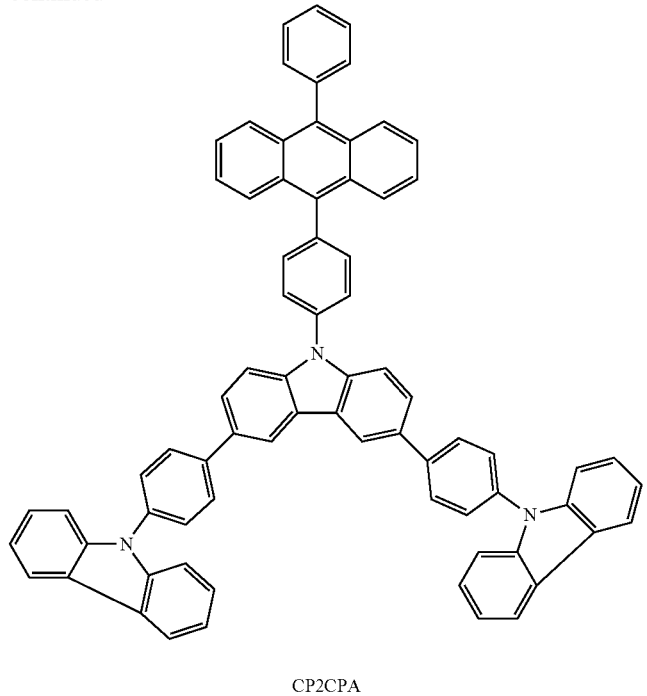

CP2CPA

The obtained compound was analyzed by nuclear magnetic resonance (NMR) measurement, whereby it is confirmed that the compound is 3,6-bis[4-(9H-carbazol-9-yl)phenyl]-9-[4-(10-phenyl-9-anthryl)phenyl]-9H-carbazole (CP2CPA) which is an anthracene derivative of the present invention.

Figure 67A:
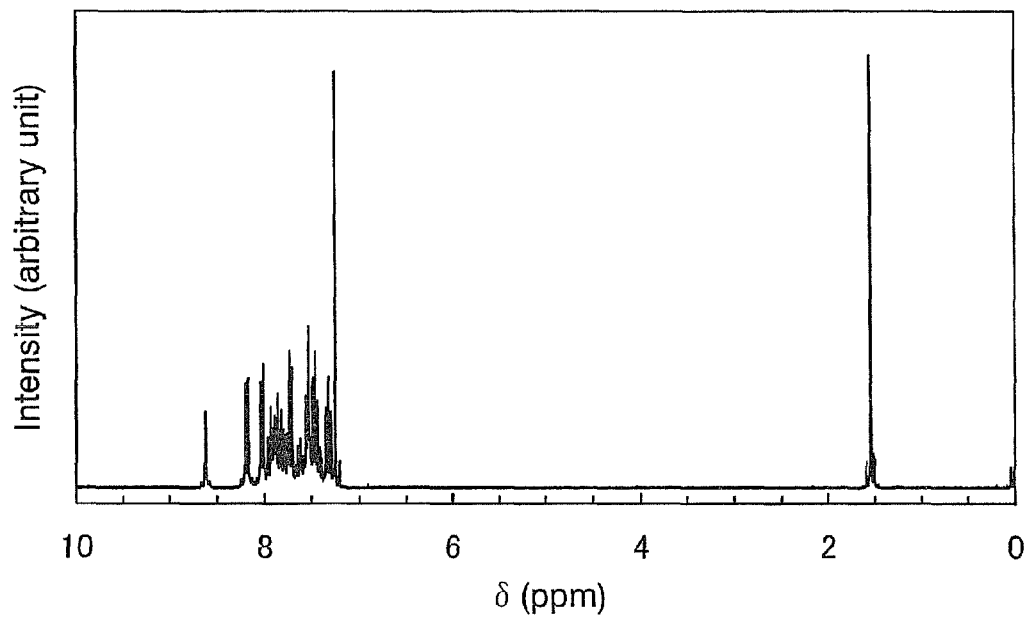
FIGS. 67A and 67B are $^1$H-NMR charts of CP2CPA.
Figure 67B:
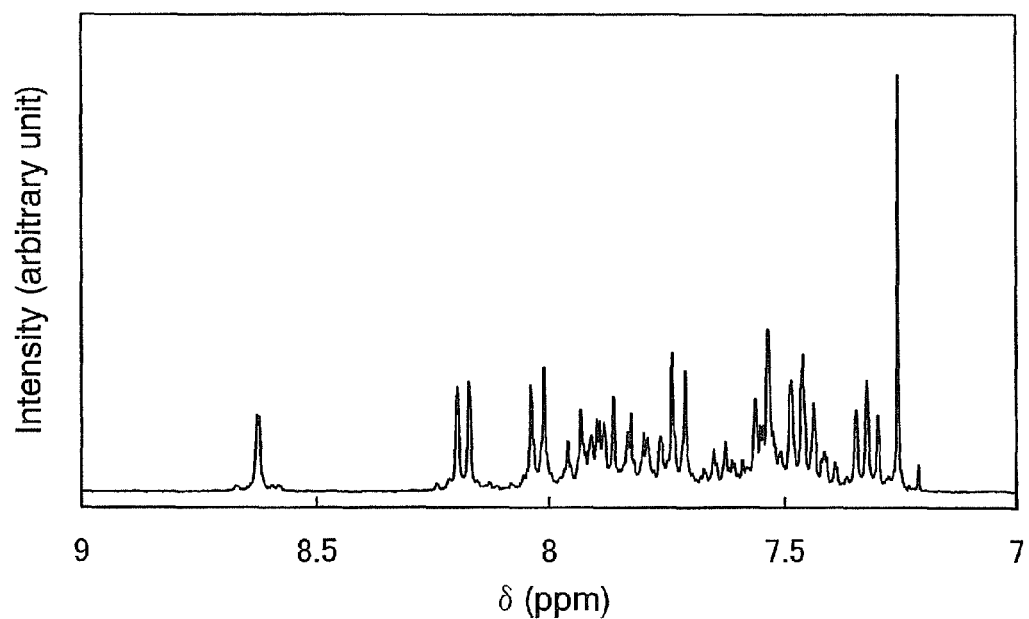

Hereinafter, the $^1$H NMR data is shown. $^1$H NMR (CDCl$_3$, 300 MHz): δ=7.30-7.96 (m, 37H), 8.02 (d, J=8.7 Hz, 4H), 8.18 (d, J=7.2 Hz, 4H), 8.62 (d, J=1.5 Hz, 2H). The $^1$H NMR charts are shown in FIGS. 67A and 67B. The range of 7.0 ppm to 9.0 ppm in FIG. 67A is expanded and shown in FIG. 67B.

Figure 68:
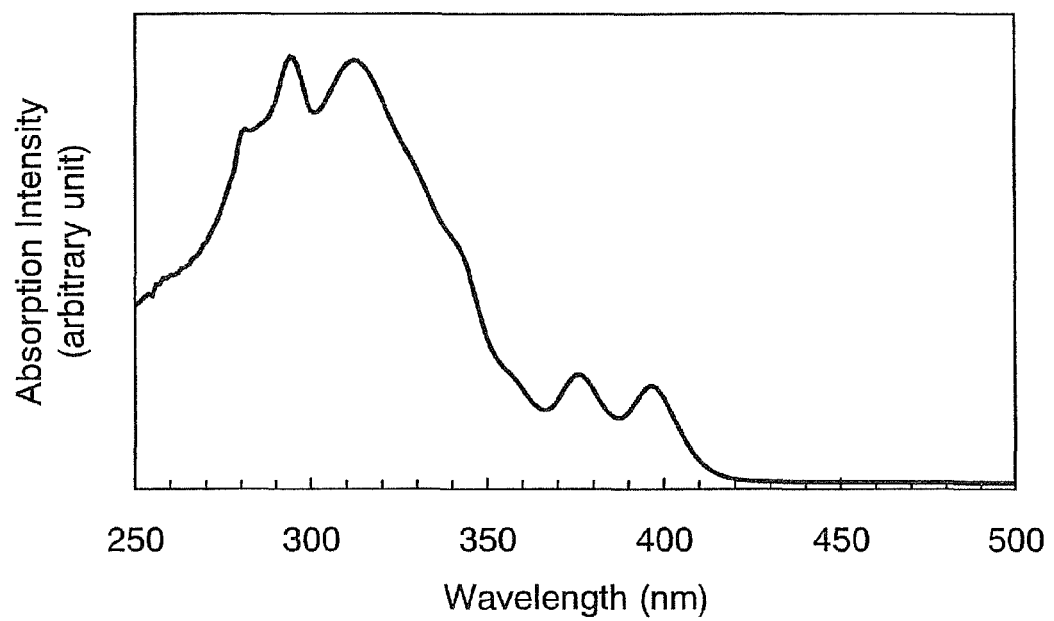
FIG. 68 illustrates an absorption spectrum of a toluene solution of CP2CPA.
Figure 69:
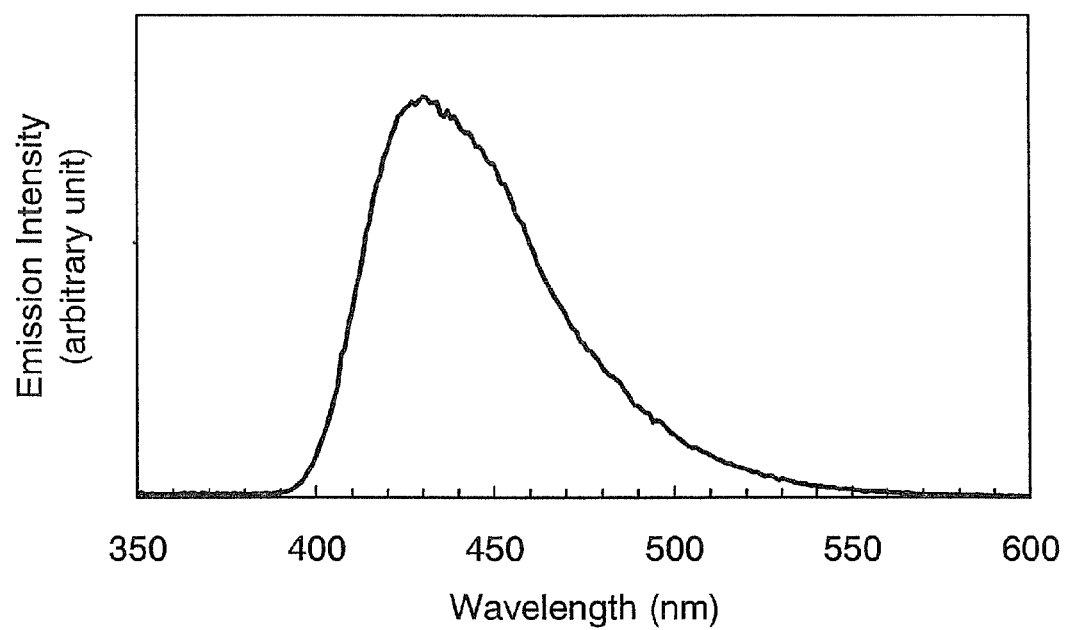
FIG. 69 illustrates an emission spectrum of a toluene solution of CP2CPA.

Next, an absorption spectrum of CP2CPA was measured at room temperature using an ultraviolet-visible spectrophotometer (V-550, manufactured by JASCO Corporation) with the use of a toluene solution. The measurement result is shown in FIG. 68. In FIG. 68, the horizontal axis indicates the wavelength (nm) and the vertical axis indicates the absorption intensity (arbitrary unit). An emission spectrum of CP2CPA was measured at room temperature using a fluorescence spectrophotometer (FS920, manufactured by Hamamatsu Photonics Corporation) with the use of a toluene solution. The measurement result is shown in FIG. 69. In FIG. 69, the horizontal axis indicates the wavelength (nm) and the vertical axis indicates the emission intensity (arbitrary unit).

Figure 70:
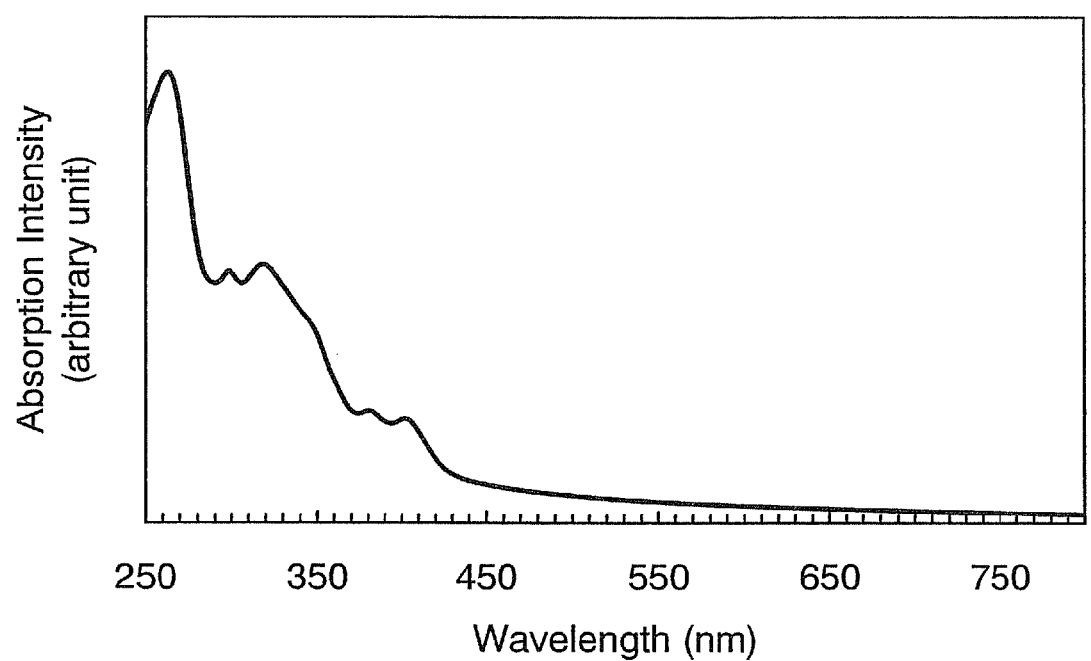
FIG. 70 illustrates an absorption spectrum of a thin film of CP2CPA.
Figure 71:
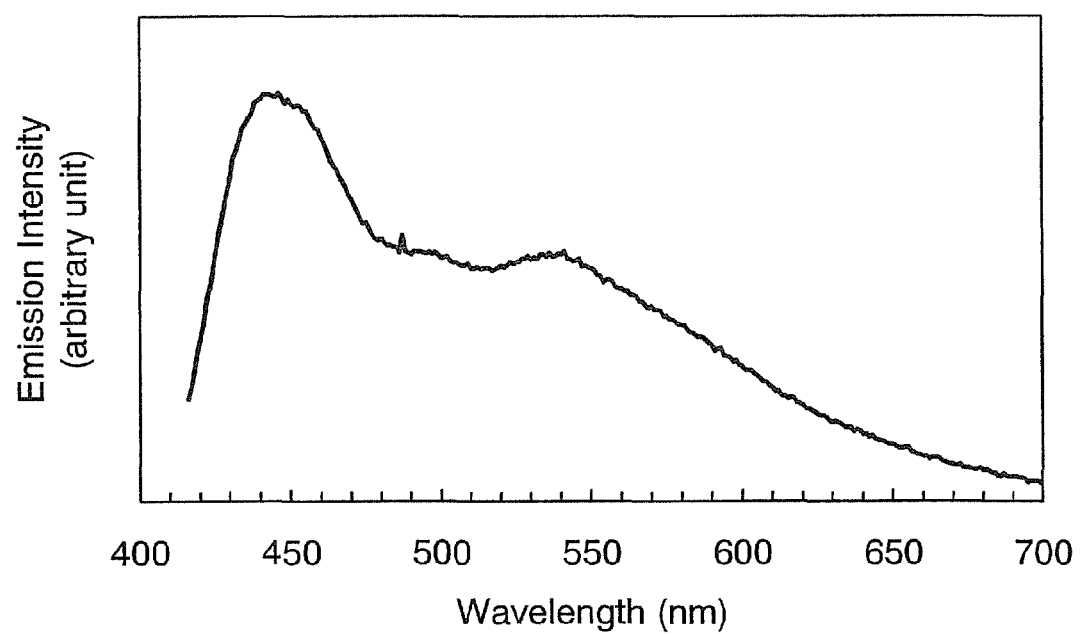
FIG. 71 illustrates an emission spectrum of a thin film of CP2CPA.

Further, a thin film of CP2CPA was similarly measured by film formation of CP2CPA by an evaporation method. The absorption spectrum and emission spectrum are shown in FIG. 70 and FIG. 71, respectively. In each of FIG. 70 and FIG. 71, the horizontal axis indicates the wavelength (nm) and the vertical axis indicates the absorption intensity (arbitrary unit) and the emission intensity (arbitrary unit).

According to FIG. 68, in the case of the toluene solution of CP2CPA, absorption was observed at wavelengths of around 294 nm, around 312 nm, around 376 nm, and around 396 nm. According to FIG. 70, in the case of the thin film of CP2CPA, absorption was observed at wavelengths of around 263 nm, around 298 nm, around 318 nm, around 380 nm, and around 402 nm.

According to FIG. 69, the toluene solution of CP2CPA has an emission peak at 423 nm (the excitation wavelength: 375 nm). According to FIG. 71, the thin film thereof has an emission peak at 444 nm and 540 nm (the excitation wavelength: 399 nm). Thus, it is found that CP2CPA is suitable for use in a light-emitting element that emits blue light in particular.

The ionizing potential of the thin film of CP2CPA was measured using a photoelectron spectrometer (AC-2, manufactured by Riken Keiki Co., Ltd) in the air and found to be 5.67 eV. As a result, the HOMO level was found to be −5.67 eV. Further, an absorption edge was obtained from a Tauc plot assuming direct transition by use of the data of the absorption spectrum of CP2CPA in the thin film state, and the absorption edge was regarded as an optical energy gap. The energy gap was 2.90 eV. A LUMO level of −2.77 eV was obtained from the obtained values of the energy gap and the HOMO level.

This application is based on Japanese Patent Application serial no. 2007-077981 filed on Mar. 23, 2007, filed with Japan Patent Office, the entire contents of which are hereby incorporated by reference.

What is claimed is:

1. A method for synthesizing a compound represented by formula 5, the method includes:

conducting a reaction according to the following scheme:

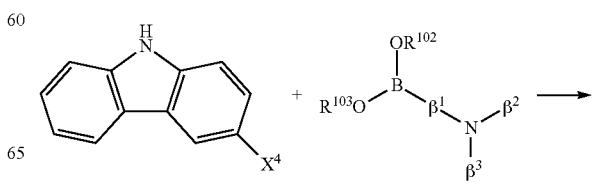

-continued

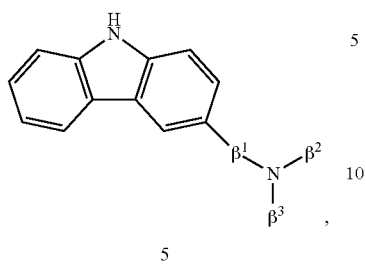

5 wherein:

X⁴ represents halogen;

$R^{102}$ and $R^{103}$ each represent hydrogen or an alkyl group having 1 to 6 carbon atoms;

$\beta^1$ represents a phenylene group; and $\beta^2$ and $\beta^3$ each represent a phenyl group.

2. The method according to claim 1,
wherein $\beta^1$ has an alkyl group having 1 to 4 carbon atoms or an aryl group having 6 to 25 carbon atoms as a substituent.

3. The method according to claim 1,
wherein $\beta^2$ has an alkyl group having 1 to 4 carbon atoms or an aryl group having 6 to 25 carbon atoms as a substituent.

4. The method according to claim 1,
wherein $R^{102}$ and $R^{103}$ are combined to form a ring.

5. The method according to claim 1,
wherein X⁴ represents bromine or a triflate group.

6. The method according to claim 1,
wherein the compound is represented by formula 149-1:

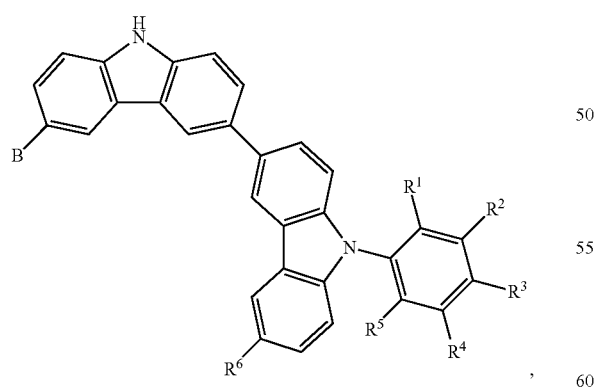

149-1 wherein:

B is hydrogen; and $R^1$ to $R^6$ each represent hydrogen, an alkyl group having 1 to 6 carbon atoms, or an aryl group having 6 to 25 carbon atoms.

7. The method according to claim 6,
wherein the compound is selected from the following compounds:

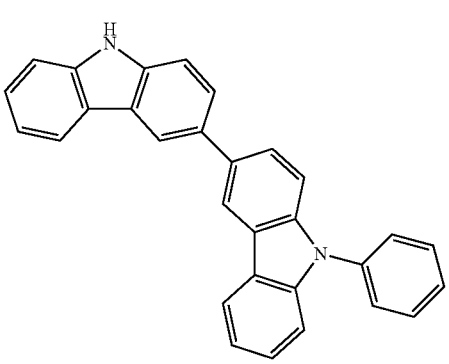

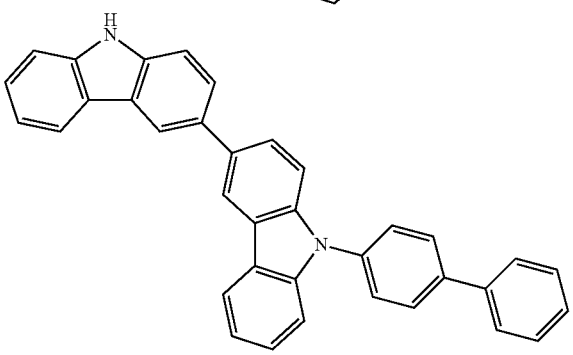

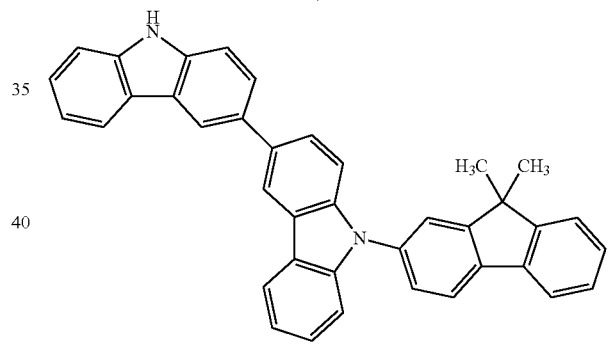

8. The method according to claim 1,
wherein the compound is represented by formula 150-1:

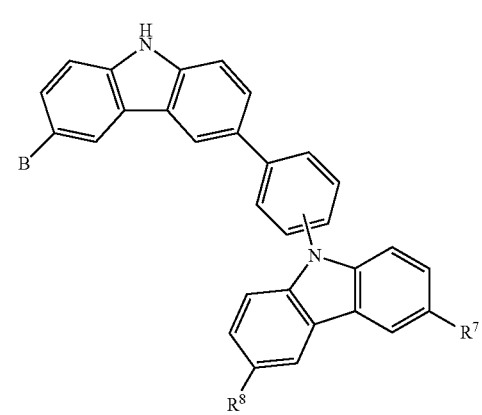

150-1 wherein:
B is hydrogen; and
R[7] and R[8] each represent hydrogen, an alkyl group having 1 to 6 carbon atoms, or an aryl group having 6 to 25 carbon atoms.

9. The method according to claim 8,
wherein the compound is selected from the following compounds:

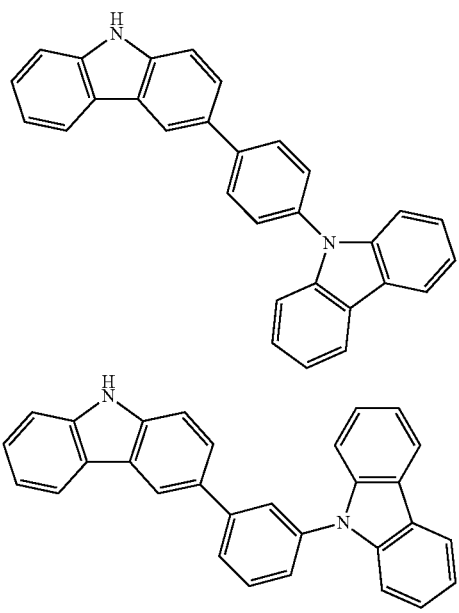

10. The method according to claim 1,
wherein the compound is represented by formula 151-1:

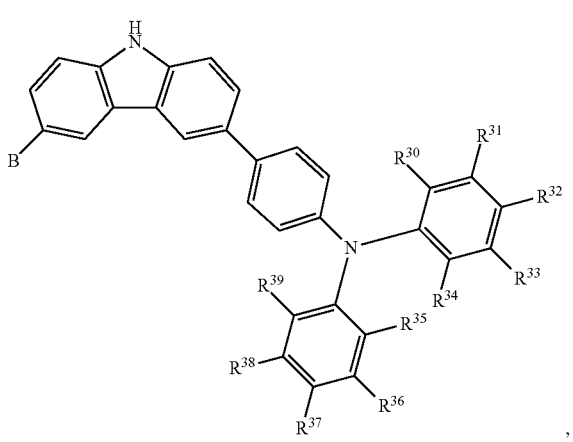

151-1 wherein:
B is hydrogen; and
R[30] to R[39] each represent hydrogen, an alkyl group having 1 to 6 carbon atoms, or an aryl group having 6 to 25 carbon atoms.

11. The method according to claim 10,
wherein the compound is selected from the following compounds:

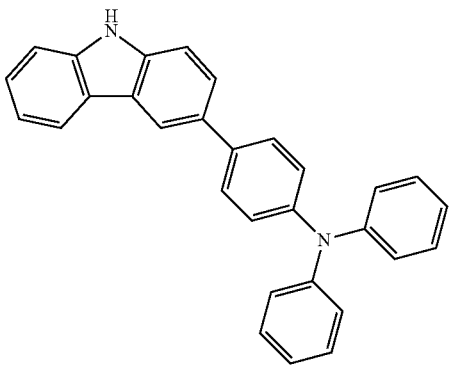

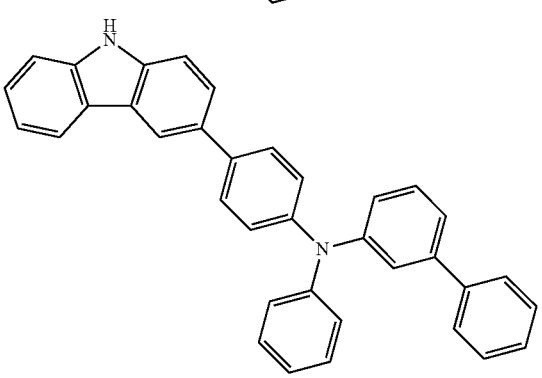

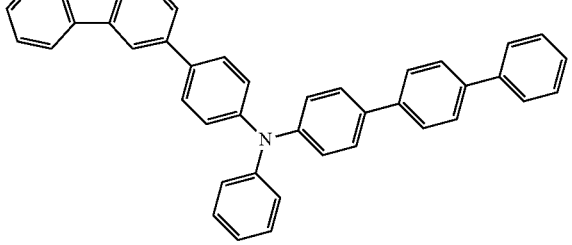

-continued

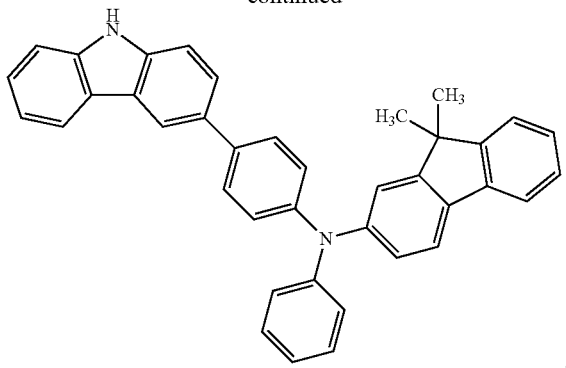

12. A method for synthesizing an organic compound, the method includes:
    conducting a reaction of an organic halide with a carbazole derivative represented by formula 5:

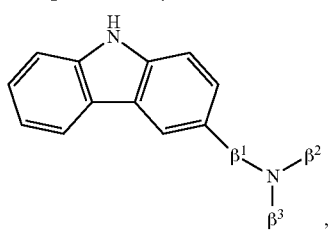

wherein:
β$^1$ represents a phenylene group; and
β$^2$ and β$^3$ each represent a phenyl group.

13. The method according to claim 12,
wherein the reaction is conducted in the presence of a metal or a metal compound.

14. The method according to claim 12,
wherein β$^1$ has an alkyl group having 1 to 4 carbon atoms or an aryl group having 6 to 25 carbon atoms as a substituent.

15. The method according to claim 12,
wherein β$^2$ has an alkyl group having 1 to 4 carbon atoms or an aryl group having 6 to 25 carbon atoms as a substituent.

16. The method according to claim 12,
wherein the carbazole derivative is represented by formula 149-1:

149-1

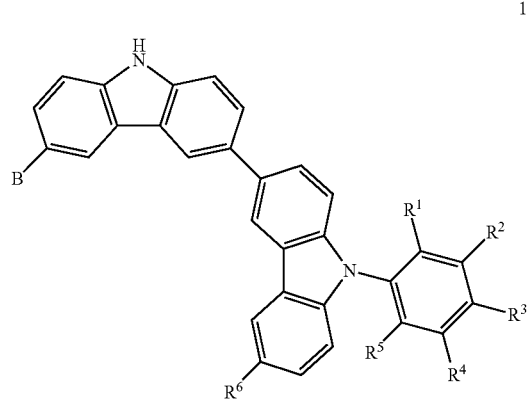

wherein:
B is hydrogen; and
R$^1$ to R$^6$ each represent hydrogen, an alkyl group having 1 to 6 carbon atoms, or an aryl group having 6 to 25 carbon atoms.

17. The method according to claim 16,
wherein the carbazole derivative is selected from the following compounds:

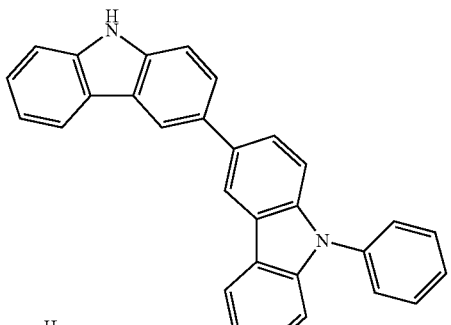

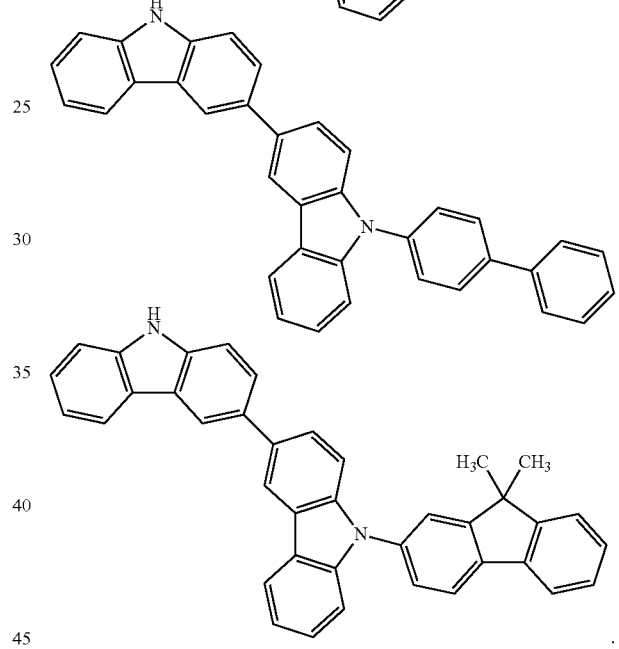

18. The method according to claim 12,
wherein the carbazole derivative is represented by formula 150-1:

150-1

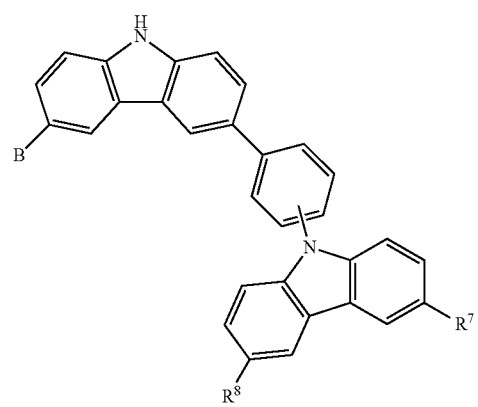

wherein:
B is hydrogen; and
R⁷ and R⁸ each represent hydrogen, an alkyl group having 1 to 6 carbon atoms, or an aryl group having 6 to 25 carbon atoms.

19. The method according to claim 18,
wherein the carbazole derivative is selected from the following compounds:

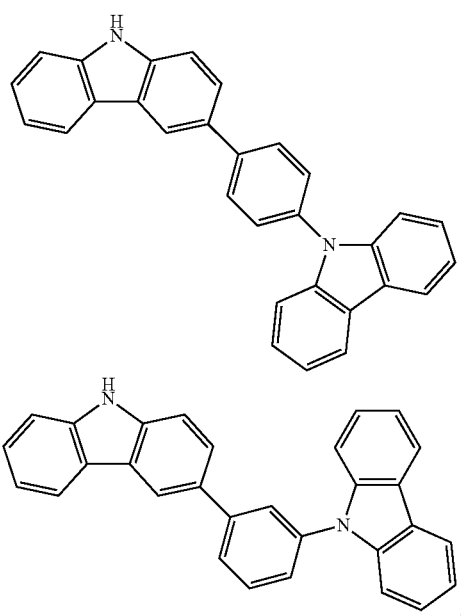

20. The method according to claim 12,
wherein the carbazole derivative is represented by formula 151-1:

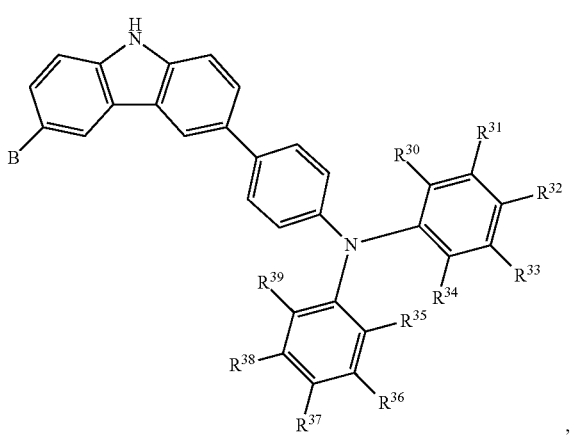

151-1 wherein:
B is hydrogen; and
R³⁰ to R³⁹ each represent hydrogen, an alkyl group having 1 to 6 carbon atoms, or an aryl group having 6 to 25 carbon atoms.

21. The method according to claim 20,
wherein the carbazole derivative is selected from the following compounds:

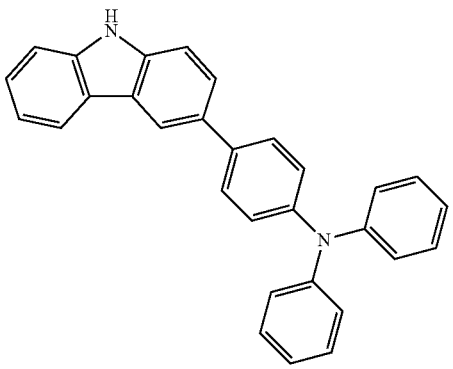

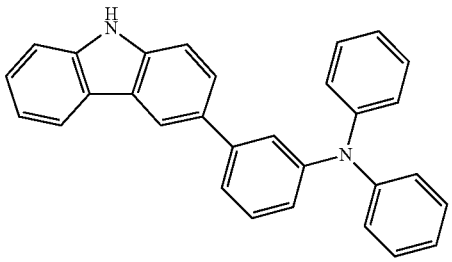

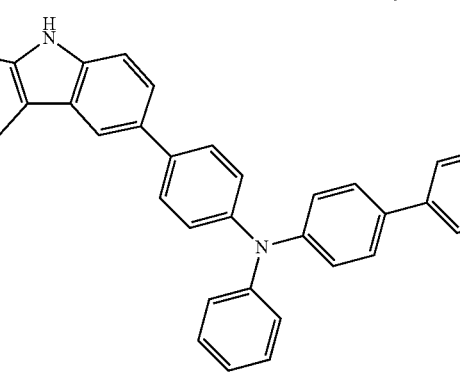

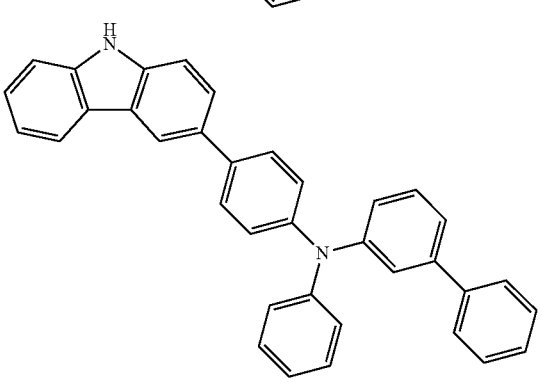

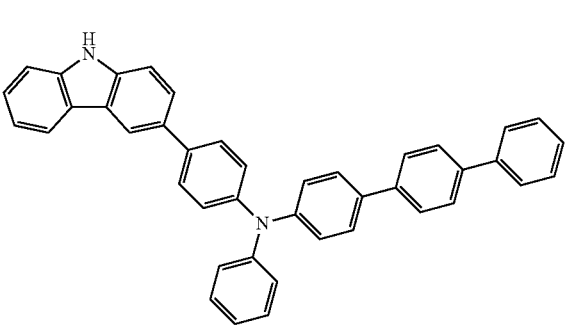

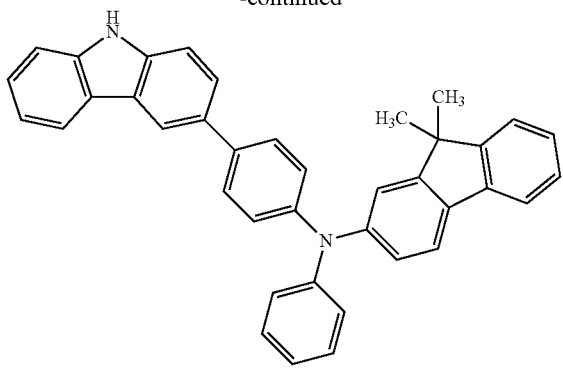

22. A method for manufacturing a light-emitting device, the method includes:
   synthesizing an organic compound by conducting a reaction of an organic halide with a carbazole derivative represented by formula 5:

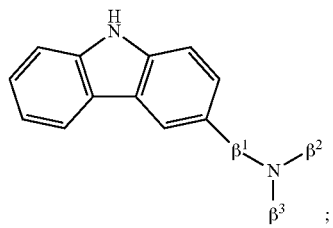

forming a film including the organic compound over a first electrode; and forming a second electrode over the film, wherein:

$\beta^1$ represents a phenylene group; and $\beta^2$ and $\beta^3$ each represent a phenyl group.

* * * * *